United States Patent
Ryu et al.

(10) Patent No.: US 11,939,334 B2
(45) Date of Patent: Mar. 26, 2024

(54) SUBSTITUTED PYRIMIDO[4,5-B][1,4]DIAZEPINES AS PLK1 DEGRADATION INDUCERS

(71) Applicant: UPPTHERA, INC., Incheon (KR)

(72) Inventors: Soo Hee Ryu, Incheon (KR); Im Suk Min, Gyeonggi-do (KR); Han Kyu Lee, Gyeonggi-do (KR); Seong Hoon Kim, Incheon (KR); Hye Guk Ryu, Incheon (KR); Keum Young Kang, Incheon (KR); Sang Youn Kim, Incheon (KR); So Hyun Chung, Incheon (KR); Jun Kyu Lee, Incheon (KR); Gibbeum Lee, Gyeonggi-do (KR)

(73) Assignee: UPPTHERA, INC., Incheon (KR)

( * ) Notice: Subject to any disclaimer, the term of this patent is extended or adjusted under 35 U.S.C. 154(b) by 0 days.

(21) Appl. No.: 18/019,034

(22) PCT Filed: Aug. 10, 2022

(86) PCT No.: PCT/KR2022/011961
§ 371 (c)(1),
(2) Date: Jan. 31, 2023

(87) PCT Pub. No.: WO2023/018236
PCT Pub. Date: Feb. 16, 2023

(65) Prior Publication Data
US 2023/0242541 A1     Aug. 3, 2023

(30) Foreign Application Priority Data

| Aug. 10, 2021 | (KR) | 10-2021-0105358 |
| Aug. 12, 2021 | (KR) | 10-2021-0106488 |
| Sep. 3, 2021 | (KR) | 10-2021-0117389 |
| Sep. 24, 2021 | (KR) | 10-2021-0126757 |
| Jan. 20, 2022 | (KR) | 10-2022-0008456 |
| Feb. 17, 2022 | (KR) | 10-2022-0020996 |
| May 3, 2022 | (KR) | 10-2022-0054880 |
| Jun. 21, 2022 | (KR) | 10-2022-0075838 |

(51) Int. Cl.
| A61K 31/519 | (2006.01) |
| A61K 47/55 | (2017.01) |
| C07D 487/04 | (2006.01) |
| C07D 519/00 | (2006.01) |

(52) U.S. Cl.
CPC ............ C07D 487/04 (2013.01); A61K 47/55 (2017.08); C07D 519/00 (2013.01)

(58) Field of Classification Search
CPC ........................... A61K 31/519; C07D 487/04
USPC ........................................ 514/262.1; 544/256
See application file for complete search history.

(56) References Cited

U.S. PATENT DOCUMENTS

| 2016/0176916 A1 | 6/2016 | Bradner et al. |
| 2020/0325130 A1 | 10/2020 | Crews et al. |

FOREIGN PATENT DOCUMENTS

| CN | 106543185 | 3/2017 |
| CN | 109879877 | 6/2019 |
| WO | WO 2009/153197 | 12/2009 |
| WO | WO 2021/061894 | 4/2021 |

OTHER PUBLICATIONS

Bolden et al., "Inducible In Vivo Silencing of Brd4 Identifies Potential Toxicities of Sustained BET Protein Inhibition," *Cell Reports*, 8(6): 1919-1929, Sep. 18, 2014.
Burslem et al., "Small-Molecule Modulation of Protein Homeostasis," *Chemical Reviews*, 117(17): 11269-11301, Aug. 4, 2017.
Gheghiani et al., "PLK1 Activation in Late G2 Sets up Commitment to Mitosis," *Cell Reports*, 19(10): 2060-2073, Jun. 6, 2017.
International Search Report and Written Opinion issued for International Application No. PCT/KR2022/011961 dated Dec. 12, 2022.
Mu et al., "Protein targeting chimeric molecules specific for dual bromodomain 4 (BRD4) and Polo-like kinase 1 (PLK1) proteins in acute myeloid leukemia cells," *Biochemical and Biophysical Research Communications*, 521(4): 833-839, Nov. 7, 2019.

*Primary Examiner* — Douglas M Willis
(74) *Attorney, Agent, or Firm* — Klarquist Sparkman, LLP

(57) ABSTRACT

The present disclosure relates to a novel PLK1 degradation inducing compound having a structure according to Formula I, a method for preparing the same, and the use thereof. The compounds of the present disclosure exhibit an effect of inducing PLK1 degradation. Therefore, the compounds of the present disclosure may be effectively utilized for preventing or treating PLK1-related diseases.

Formula I

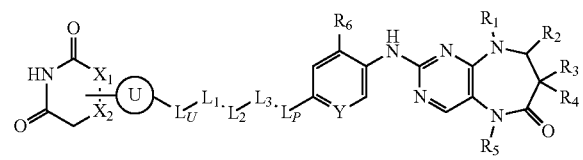

13 Claims, 1 Drawing Sheet

[Fig. 1]
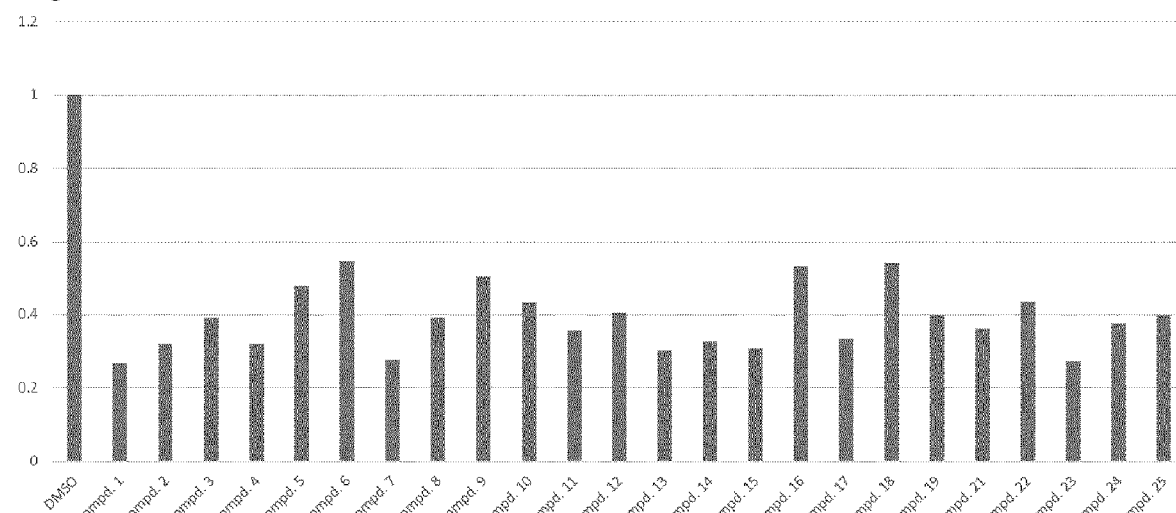
[Fig. 2]
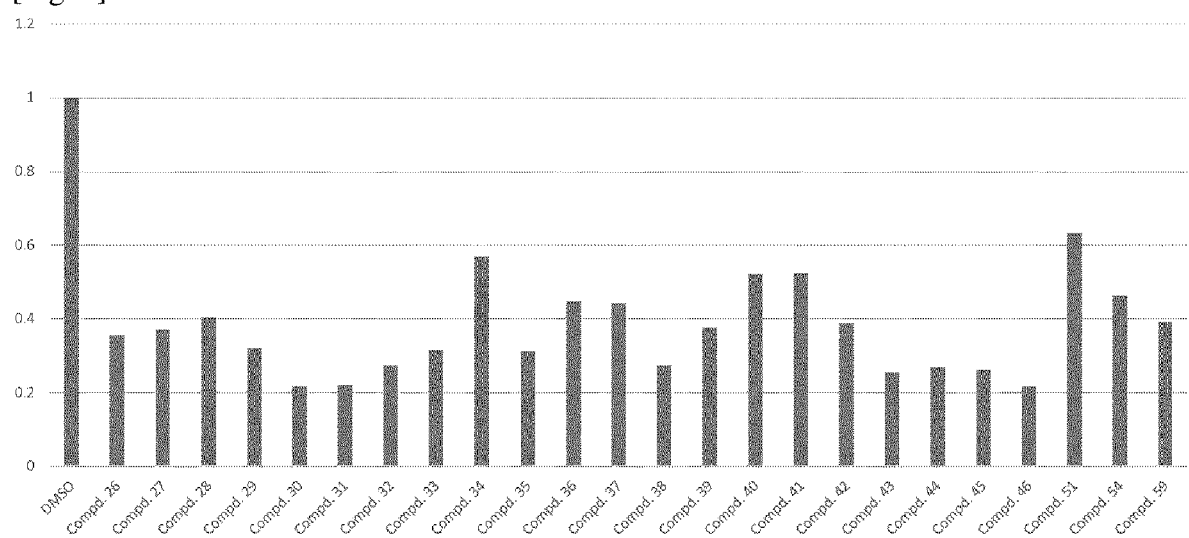

SUBSTITUTED PYRIMIDO[4,5-B][1,4]DIAZEPINES AS PLK1 DEGRADATION INDUCERS

CROSS REFERENCE TO RELATED APPLICATIONS

This is the U.S. National Stage of International Application No. PCT/KR2022/011961, filed Aug. 10, 2022, which will publish in English under PCT Article 21(2), which in turn claims the benefit of KR Patent Application No. 10-2021-0105358 filed on Aug. 10, 2021; KR Patent Application No. 10-2021-0106488 filed on Aug. 12, 2021; KR Patent Application No. 10-2021-0117389 filed on Sep. 3, 2021; KR Patent Application No. 10-2021-0126757 filed on Sep. 24, 2021; KR Patent Application No. 10-2022-0008456 filed on Jan. 20, 2022; KR Patent Application No. 10-2022-0020996 filed on Feb. 17, 2022; KR Patent Application No. 10-2022-0054880 filed on May 3, 2022; and KR Patent Application No. 10-2022-0075838 filed on Jun. 21, 2022; each of these prior applications is incorporated herein by reference in its entirety.

FIELD

The present disclosure relates to a novel PLK1 degradation inducing compound, a method for preparing the same, and the use thereof. It can specifically act on abnormal cells, etc. and can be usefully used in the treatment of various diseases through efficient degradation of PLK1.

BACKGROUND

Polo-like kinase 1 (PLK1) is a serine/threonine kinase involved in the conversion of G2/M phase during cell growth and division. PLK1 is expressed and activated in a pulse form from the S phase to the G2/M phase, and rapidly degrades as mitosis ends.

PLK1 is overexpressed in various carcinomas such as colon cancer, lung cancer, bladder cancer, and melanoma, etc., and cancer cells overexpressing PLK1 tend to show resistance to various types of anticancer drugs. As the PLK1 dependence in various carcinomas was revealed as described above, there have been attempts to develop PLK1 inhibitor compounds such as volasertib (also known as BI6727), etc.

However, the conventional PLK1 inhibitors do not sufficiently inhibit PLK1 activity at concentrations that are clinically safe. Thus, there is a problem that even if the cell cycle of cancer cells is temporarily delayed, some cancer cells eventually restart the cell cycle, which may not obtain sufficient clinical effects (see Gheghiani et al., Cell Reports, 2017, etc.). In fact, many pharmaceutical companies such as Boehringer Ingelheim, GlaxoSmithKline, etc., have attempted to develop small-molecular compound-based PLK1 inhibitors, but most of them have failed or stopped in the clinical trial stage, and thus there are no commercially available PLK1 inhibitors to date. It shows that pharmacological mechanism that follows the method of inhibiting enzyme activity by binding to the active site of PLK1 like the small molecule compound inhibitors is not sufficiently effective in the development of new drugs intended to derive anticancer effects by inhibiting PLK1 activity of cancer cells.

Recently, a proteolysis targeting chimera (PROTAC) has been proposed as a small molecule-based platform technology capable of inducing proteolysis of a target protein in the body. The PROTAC is a bifunctional compound in which a ligand molecule that binds to disease-related target protein and an E3 ubiquitin ligase binding moiety are linked by a chemical linker. Theoretically, the PROTAC compound is capable of inducing degradation of the target protein by placing the disease-related target protein near the E3 ubiquitin ligase. Based on this new mechanism different from the existing inhibitors, a lot of PROTAC compounds have been developed as therapeutic agents for cancer and inflammatory diseases, etc., and being studied with various extensibility (e.g. as payloads of ADC (Antibody-Drug Conjugates)). However, it does not show activity in all ranges of binding moieties or linkers, and in order for PROTAC to exhibit the desired level of efficacy, it is known through several studies that each binding moiety and linker must have an appropriately linked structure (see US2020-0325130A). In particular, in the case of the CRBN(Cereblon) E3 ligase targeting moiety, depending on the type of the binding moiety or the structure of the compound linked thereto, there is a risk of degrading CRBN neo-substrate (GSPT1, IKZF1/3, etc.) or showing off-target toxicity accordingly. Therefore, it is important to select appropriate binding moieties and optimize the structure of the entire compound so as not to exhibit unexpected toxicity during PROTAC drug development.

In the case of the PROTAC compound using PLK1 as a target protein, Chinese Patent Laid-Open No. 106543185 A discloses some bifunctional compounds in which a volasertib derivative compound and a binding moiety for the E3 ubiquitin ligase CRBN are linked by a chemical linker. However, the related art document merely describes some limited forms of synthesis examples of PROTAC compounds, wherein in general, the target degradation activity and selectivity of PROTAC may vary significantly depending on selection of the target protein moiety, the E3 ubiquitin ligase binding moiety, and the like (see Burslem and Crews, 2017, etc.).

Further, the PROTAC compound described in the above-described document is characterized by a compound that simultaneously degrades PLK1 and BRD4, and degrade various proteins such as other PLK family proteins and BRD4, etc.), which may cause side effects due to off-target toxicities at the time of drug development. In particular, it is known that strong inhibition of BRD4 activity inevitably accompanies on-target toxicity such as blood toxicity and gastrointestinal toxicity along with pharmacological effects. Therefore, the PROTAC compound described in the above document would expect to face greater clinical side effects as more BRD4 protein gets degraded (see Bolden et al. Cell Reports, 2014).

Moreover, according to the document published by the inventors of the above document (see Mu et al. BBRC, 2019), it can be confirmed that the PROTAC compound, which simultaneously degrades PLK1 and BRD4, has much stronger BRD4 degradation ability than PLK1 degradation ability at the cellular level, and the cell cycle thereof almost stops in the G1 phase, etc., that is, the PROTAC compound actually acts only as a BRD4 inhibitor regardless of the way that the conventional PLK1 inhibitors exert pharmacological effects.

Therefore, there is an unsatisfied demand for effective PLK1 degradation inducing compound with no or minimal side effects. (e.g. off-target toxicity)

SUMMARY

The compounds of the present disclosure exhibit an effect of inducing PLK1 degradation. Therefore, the compounds of the present disclosure may be effectively utilized for preventing or treating PLK1-related diseases.

BRIEF DESCRIPTION OF THE DRAWINGS

FIG. 1 shows the luciferase assay results by treating Compound 1 to Compound 25 of the present invention.

FIG. 2 shows the luciferase assay results by treating Compound 26 to Compound 59 of the present invention.

DETAILED DESCRIPTION

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

An object of the present disclosure is to provide novel PLK1 degradation inducing compounds. Another object of the present disclosure is to provide a method for preparing the compounds. Still another object of the present disclosure is to provide a use of the compounds.

In order to achieve the above-described objects, the present inventors made efforts to study, and as a result, found that novel PROTAC compounds of the present invention specifically act on abnormal cells overexpressing PLK1 through appropriate structural combination and optimization of E3 Ligase binder, Target binding moiety, and Linker to induce effective PLK1 degradation and minimize side effects, and completed the present invention.

Selective PLK1 Degradation Inducing Compounds

The present disclosure provides novel compounds that induce effective polo-like kinase 1 (PLK1) degradation. Specifically, the present disclosure provides a bifunctional compound in which a PLK1 binding moiety and an E3 ubiquitin ligase-binding moiety are linked by a chemical linker.

In one general aspect, there is provided a compound represented by the following Formula I, a stereoisomer thereof or a pharmaceutically acceptable salt thereof:

ULM-Linker-PTM  [Formula I]

in the Formula I above,
ULM is a moiety represented by the following Formula 1;

[Formula 1]

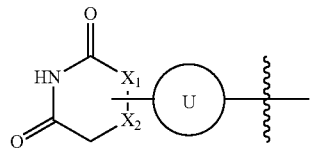

PTM is a moiety represented by the following Formula 2;

[Formula 2]

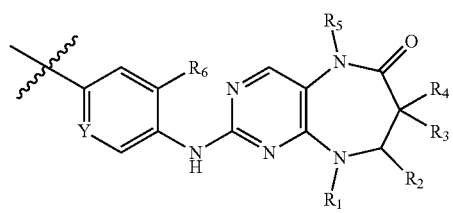

Linker is a group that chemically links ULM and PTM;
$X_1$ and $X_2$ are each independently $CH_2$, CH, or N;
ring U is phenyl or 5- to 6-membered heteroaryl linked to the $X_1$ or $X_2$ {wherein at least one H of the phenyl or 5- to 6-membered heteroaryl ring may be substituted with $R_U$};
$R_U$ is —$C_{1-4}$alkyl, —$C_{1-4}$hydroxyalkyl, —$C_{1-4}$aminoalkyl, —$C_{1-4}$haloalkyl, —$C_{1-4}$alkoxy or -halo;
Y is $CR_7$ or N;
$R_1$ is —$C_{1-4}$alkyl;
$R_2$ is —H or —$C_{1-4}$alkyl, or is linked with $R_1$ to form 5- to 6-membered ring together with N atom;
$R_3$ and $R_4$ are each independently —H, —$C_{1-4}$alkyl or -halo, or $R_3$ and $R_4$ are linked each other to form 3- to 6-membered ring;
$R_5$ is —$C_{1-4}$alkyl;
$R_6$ is —$C_{1-4}$alkyl, —$C_{1-4}$hydroxyalkyl, —$C_{1-4}$aminoalkyl, —$C_{1-4}$haloalkyl, —$C_{1-4}$alkoxy or -halo; and
$R_7$ is —H or -halo.

In one embodiment of the present disclosure,
ULM is a moiety represented by following Formula 1;

[Formula 1]

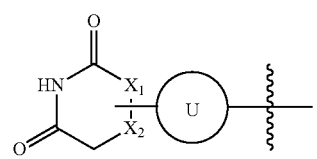

$X_1$ and $X_2$ are each independently $CH_2$, CH or N;
ring U is phenyl, pyridinyl, pyrimidinyl or pyrazolyl linked to the $X_1$ or $X_2$ {wherein at least one H of the phenyl, pyridinyl, pyrimidinyl or pyrazolyl ring may be substituted with $R_U$}; and
$R_U$ is —$C_{1-4}$alkyl, —$C_{1-4}$haloalkyl, —$C_{1-4}$alkoxy or -halo.

In one embodiment of the present disclosure,
ULM is

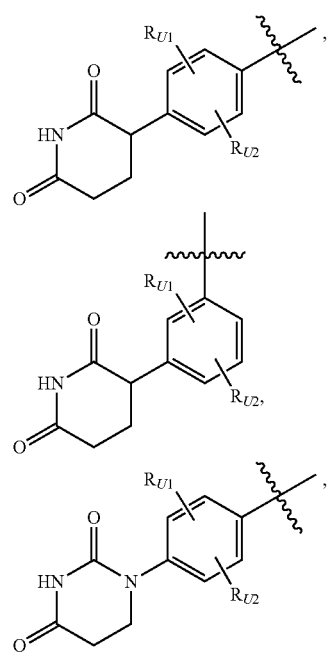

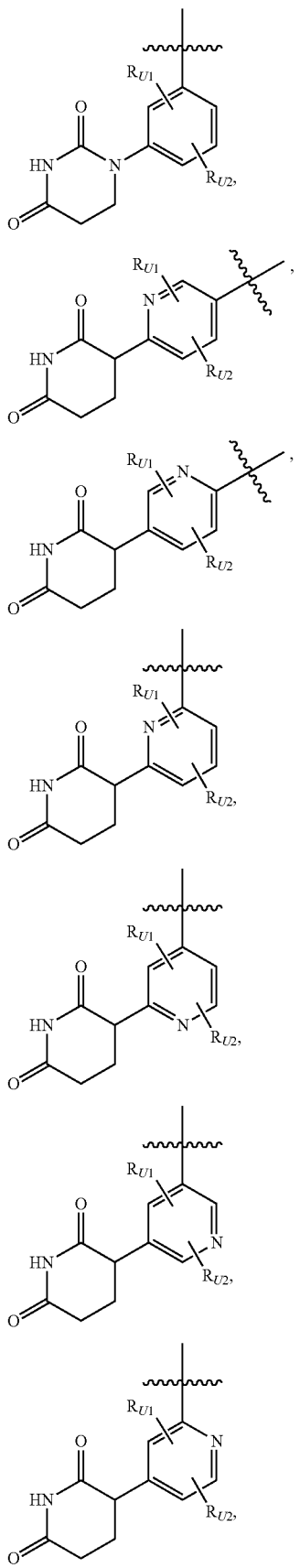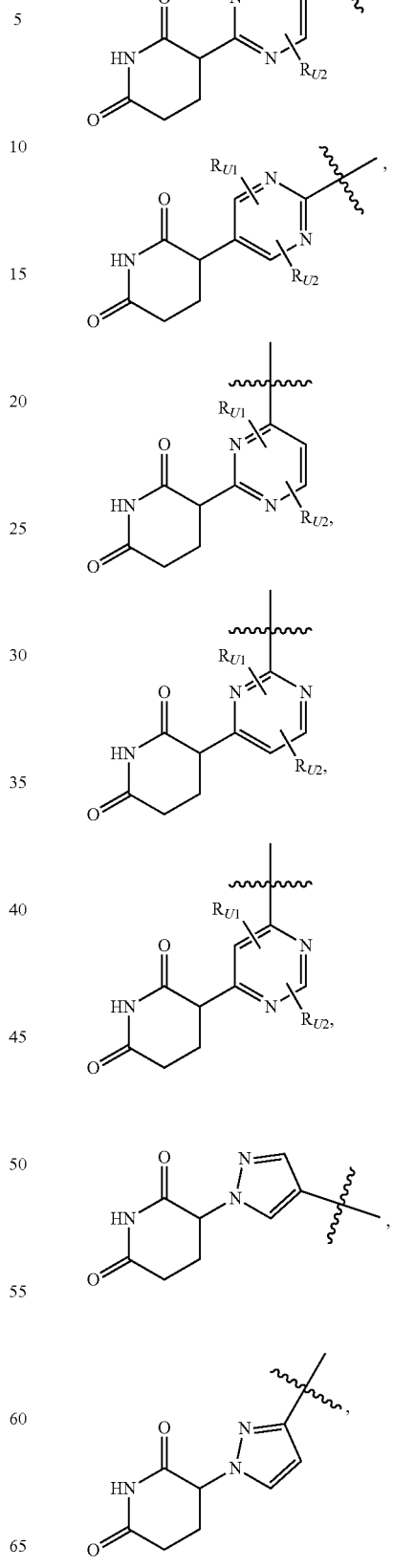

-continued
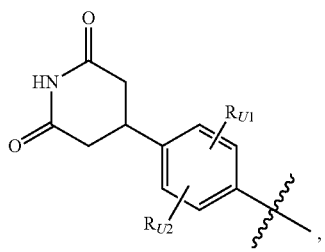
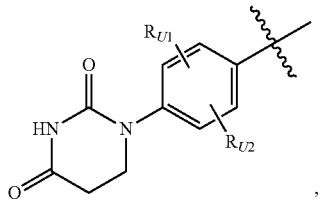
,
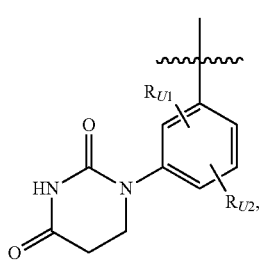
,
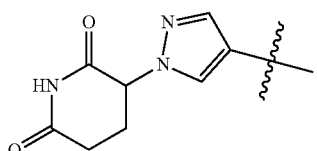
,
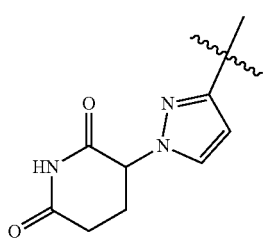
,
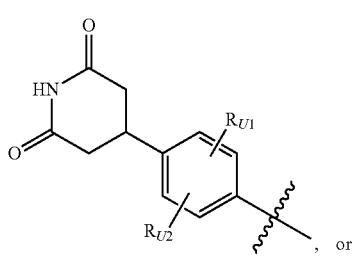
, or
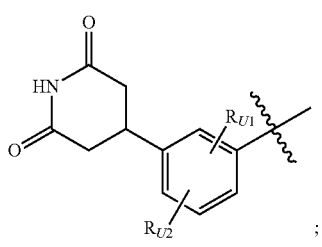
;
and
$R_{U1}$ and $R_{U2}$ are each independently —$C_{1-4}$alkyl, —$C_{1-4}$haloalkyl, —$C_{1-4}$alkoxy or -halo.
In one embodiment of the present disclosure, ULM is
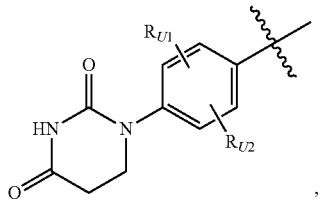
,
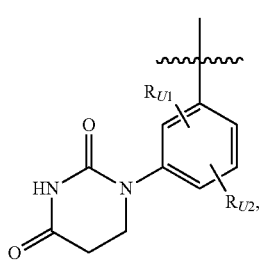
,
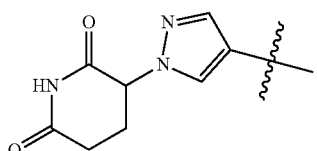
, or
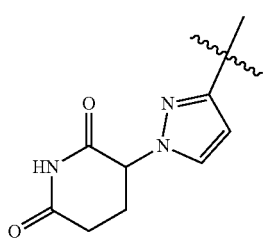
;
and
$R_{U1}$ and $R_{U2}$ are each independently —$C_{1-4}$alkyl, —$C_{1-4}$haloalkyl, —$C_{1-4}$alkoxy or -halo.

In one embodiment,
PTM is

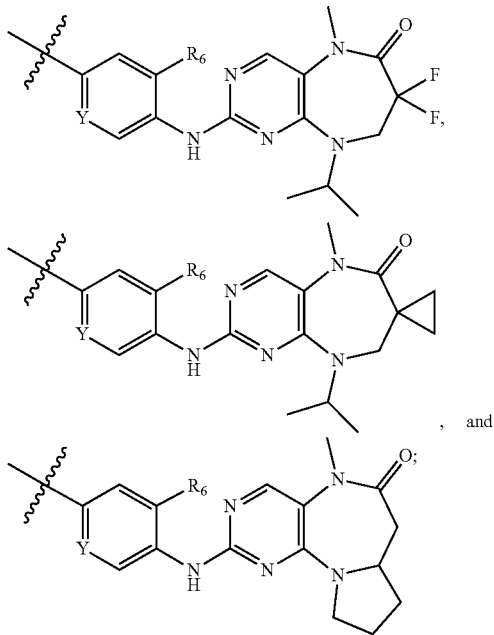

, and

Y is CH, CF or N; and
R$_6$ is —C$_{1-4}$alkyl, —C$_{1-4}$alkoxy or -halo.
In one embodiment of the present disclosure,
Linker is -L$_U$-L$_1$-L$_2$-L$_3$-L$_P$-;
L$_U$ is —(CH$_2$)x-, —(CH$_2$)x-NH—, —(CH$_2$)x-O—, —C(=O)—, phenyl or nothing (null) {wherein L$_U$ is linked with ULM [when the L$_U$ is nothing (null), L$_1$ is directly linked with ULM], and x is 0, 1, 2, 3 or 4};
L$_1$ is heterocycloalkyl or nothing (null) {wherein, when the L$_1$ is nothing (null), L$_U$ and L$_2$ are directly linked, the heterocycloalkyl contains at least one N atom in the ring, and at least one H of the heterocycloalkyl ring may be substituted with —C$_{1-4}$alkyl, —C$_{1-4}$haloalkyl, —C$_{1-4}$alkoxy, —OH, -halo or =O};
L$_2$ is —(CH$_2$)y$_1$-, —(CD$_2$)y$_1$-, —(CH$_2$)y$_2$-C(=O)—(CH$_2$)y$_3$-, —(CH$_2$)y$_2$-NH—(CH$_2$)y$_3$- or —(CH$_2$)y$_2$-N(C$_{1-4}$alkyl)-(CH$_2$)y$_3$- {wherein the y$_1$ to y$_3$ are each independently 0, 1, 2, 3, 4, 5 or 6};
L$_3$ is cycloalkyl, heterocycloalkyl or nothing (null) {wherein, when the L$_3$ is nothing (null), L$_2$ and L$_P$ are directly linked, the heterocycloalkyl contains at least one N atom in the ring, and at least one H of the cycloalkyl or heterocycloalkyl ring may be substituted with —C$_{1-4}$alkyl, —C$_{1-4}$haloalkyl or -halo}; and
L$_P$ is —(CH$_2$)p-NH—C(=O)— or —(CH$_2$)p-O—C(=O)— {wherein —(C=O)— of the L$_P$ is linked with PTM, and p is 0, 1 or 2}.
In one embodiment of the present disclosure,
L$_U$ is —(CH$_2$)x-, —(CH$_2$)x-O—, —C(=O)—, phenyl or nothing (null) {wherein L$_U$ is linked with ULM [when the L$_U$ is nothing (null), L$_1$ is directly linked with ULM], and the x is 0 or 1};
L$_1$ is 4- to 12-membered heterocycloalkyl or nothing (null) {wherein, when the L$_1$ is nothing (null), L$_U$ and L$_2$ is directly linked, the 4- to 12-membered heterocycloalkyl is single ring, bridged bicyclic ring or spiro ring, the 4- to 12-membered heterocycloalkyl contains at least one N atom in the ring, the N atom is directly linked with L$_U$ or ULM, and at least one H of the 4- to 12-membered heterocycloalkyl ring may be substituted with —C$_{1-4}$alkyl, —OH, -halo or =O};
L$_2$ is —(CH$_2$)y$_1$-, —(CH$_2$)y$_2$-C(=O)—(CH$_2$)y$_3$-, —(CH$_2$)y$_2$-NH—(CH$_2$)y$_3$- or —(CH$_2$)y$_2$- N(C$_{1-4}$alkyl)-(CH$_2$)y$_3$- {wherein the y$_1$ to y$_3$ are each independently 0, 1, 2 or 3}
L$_3$ is 4- to 6-membered cycloalkyl, 4- to 12-membered heterocycloalkyl or nothing (null) {wherein, when the L$_3$ is nothing (null), L$_2$ and L$_P$ are directly linked, the 4- to 12-membered heterocycloalkyl is single ring, bridged bicyclic ring or spiro ring, the 4- to 12-membered heterocycloalkyl contains at least one N atom in the ring, and at least one H of the 4- to 6-membered cycloalkyl or 4- to 12-membered heterocycloalkyl ring may be substituted with -halo}; and
L$_P$ is —(CH$_2$)p-NH—C(=O)— or —(CH$_2$)p-O—C(=O)— {wherein (C=O) of the L$_P$ is linked with PTM, and p is 0 or 1}.

In a certain embodiment of the present disclosure, the compound represented by Formula I is a compound that is selected from the group consisting of Compound 1 to 59.

In the present disclosure, a pharmaceutically acceptable salt refers to any organic or inorganic acid addition salt with a concentration that is relatively non-toxic, is harmless, and has effective action to patients, wherein side effects caused by this salt does not deteriorate beneficial efficacy of the compound represented by Formula I. For example, the pharmaceutically acceptable salt may be an inorganic acid such as hydrochloric acid, phosphoric acid, sulfuric acid, nitric acid, or the like, or an organic acid such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, but is not limited thereto.

Use of the Selective PLK1 Degradation Inducing Compounds

An embodiment of the present disclosure is a composition for inducing PLK1 degradation including a compound represented by Formula I or a pharmaceutically acceptable salt thereof. The Formula I is the same as defined above.

In the experimental examples of the present disclosure, it was confirmed that the compounds of the present disclosure effectively induce the protein degradation of PLK1.

The PLK1 degradation-inducing PROTAC compound of the present disclosure is capable of fundamentally degrading the target protein, PLK1 in view of the mechanism of action, thereby achieving an excellent PLK1 inhibitory effect as compared to the conventional PLK1 small molecule inhibitor that inhibits the simple activity of PLK1.

Accordingly, the composition including the compound represented by Formula I of the present disclosure or a pharmaceutically acceptable salt thereof may be effectively employed for selective degradation of PLK1.

An embodiment of the present disclosure is a composition for preventing or treating PLK1-related diseases including the compound represented by Formula I or the pharmaceutically acceptable salt thereof. An another embodiment of the present disclosure is a method for the prevention or treatment of PLK-related diseases comprising administering the composition to a subject in need thereof. The Formula I is the same as defined above.

In the present disclosure, the PLK1-related disease refers to any disease or condition capable of being treated, alleviated, delayed, inhibited or prevented from induction of degradation or inhibition of activity of PLK1. In an embodiment, the PLK1-related disease may be a cancer (malignant tumor), a benign tumor, a neurological disease, or other genetic or non-genetic diseases caused by excessive cell division.

The cancer includes all cancers capable of exhibiting prophylactic or therapeutic efficacy due to inhibition of PLK1 activity, and may be solid cancer or blood cancer. For example, the cancer may be one or more selected from the group consisting of squamous cell carcinoma, small cell lung cancer, non-small cell lung cancer, lung adenocarcinoma, lung squamous cell carcinoma, peritoneal cancer, skin cancer, skin or intraocular melanoma, rectal cancer, anal muscle cancer, esophageal cancer, small intestine cancer, endocrine cancer, parathyroid cancer, adrenal cancer, soft tissue sarcoma, urethral cancer, chronic or acute leukemia, lymphocytic lymphoma, hepatocellular carcinoma, gastrointestinal cancer, gastric cancer, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, prostate cancer, vulvar cancer, thyroid cancer, head and neck cancer, brain cancer, osteosarcoma, solid tumor, blood cancer, bone cancer, large cell lymphoma, adrenocorticoid tumor, t cell lymphoma/leukemia, neuroendocrine cancer, neuroendocrine tumor, cholangiocarcinoma, neuroblastoma, glioblastoma, glioma, and the like, but is not limited thereto. The cancer includes not only primary cancer but also metastatic cancer.

The benign tumors include all benign tumors capable of exhibiting prophylactic or therapeutic efficacy due to the inhibition of PLK1 activity, such as benign tumors in pre-cancer stages, and may be solid tumors or blood tumors. For example, the tumor may be one or more selected from the group consisting of Barrett's esophagus, colon adenoma and polyp, breast fibroadenoma and cyst, monoclonal gammopathy of undetermined significance (MGUS), monoclonal lymphocytosis, and the like, but is not limited thereto.

The neurological diseases include all neurological diseases capable of exhibiting prophylactic or therapeutic efficacy due to the inhibition of PLK1 activity, and specifically, may be one or more selected from the group consisting of central nervous system disease, neurodegenerative disease, Alzheimer's disease, Parkinson's disease, multiple sclerosis, Huntington's disease, senile dementia, epilepsy, Lou Gehrig, stroke, and nerve damage and axonal degeneration-related disorders following brain or spinal cord injury, but is not limited thereto.

The pharmaceutical composition of the present disclosure may further include one or more active ingredients exhibiting the same or similar medicinal effects in addition to the compound represented by Formula I above, or the pharmaceutically acceptable salt thereof.

An embodiment of the present disclosure is a method of degrading PLK1 by administering a compound represented by Formula I or a pharmaceutically acceptable salt thereof to mammals including humans.

Another embodiment of the present disclosure is a method of degrading PLK1 by administering the compound represented by Formula I or the pharmaceutically acceptable salt thereof to a sample in vitro. The sample may be a cell, a cell culture, a body fluid or tissue of a mammal including a human, but is not limited thereto.

The present disclosure provides synthetic methods for Compound 1 to 59 shown in the table below.

TABLE 1

| Compound | Structure |
|---|---|
| 1 | 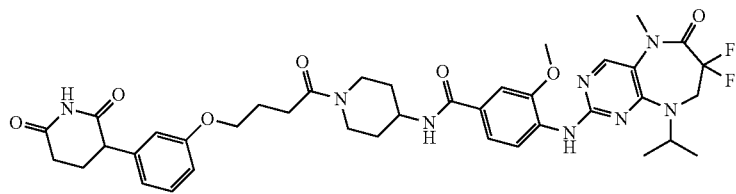 [SMILES: COc1cc(C(=O)NC2CCN(C(=O)CCCOc3cccc(C4CCC(=O)NC4=O)c3)CC2)ccc1Nc1ncc2c(n1)N(C(C)C)CC(F)(F)C(=O)N2C] |
| 2 | 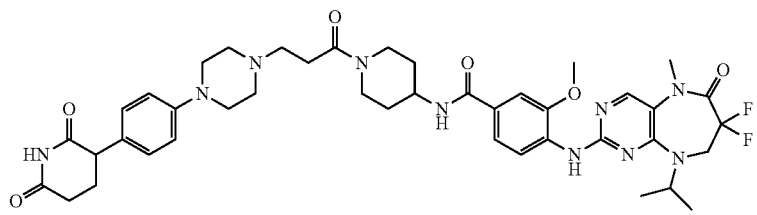 [SMILES: COc1cc(C(=O)NC2CCN(C(=O)CCN3CCN(c4ccc(C5CCC(=O)NC5=O)cc4)CC3)CC2)ccc1Nc1ncc2c(n1)N(C(C)C)CC(F)(F)C(=O)N2C] |
| 3 | 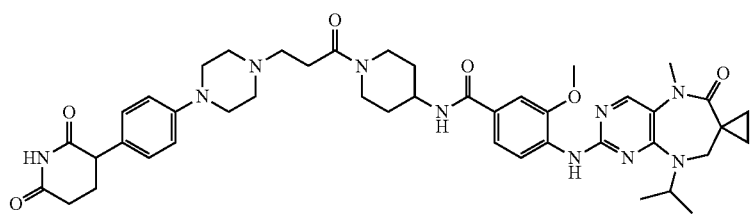 [SMILES: COc1cc(C(=O)NC2CCN(C(=O)CCN3CCN(c4ccc(C5CCC(=O)NC5=O)cc4)CC3)CC2)ccc1Nc1ncc2c(n1)N(C(C)C)CC1(CC1)C(=O)N2C] |

TABLE 1-continued

| Compound | Structure |
|---|---|
| 4 | (chemical structure) |
| 5 | (chemical structure) |
| 6 | (chemical structure) |
| 7 | (chemical structure) |
| 8 | (chemical structure) |
| 9 | (chemical structure) |
| 10 | (chemical structure) |

TABLE 1-continued
Compound Structure
11 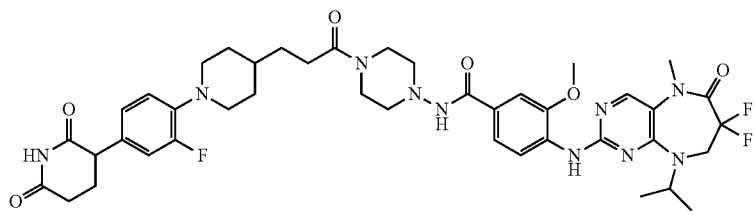 [SMILES: COc1cc(C(=O)NN2CCN(C(=O)CCC3CCN(c4ccc(C5CCC(=O)NC5=O)cc4F)CC3)CC2)ccc1Nc1ncc2c(n1)N(C(C)C)CC(F)(F)C(=O)N2C]
12 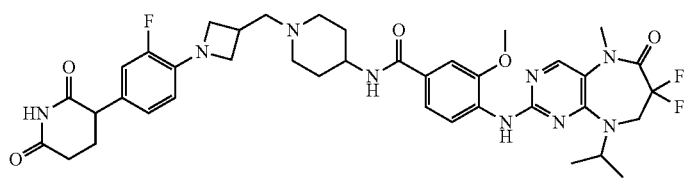 [SMILES: COc1cc(C(=O)NC2CCN(CC3CN(c4ccc(C5CCC(=O)NC5=O)cc4F)C3)CC2)ccc1Nc1ncc2c(n1)N(C(C)C)CC(F)(F)C(=O)N2C]
13 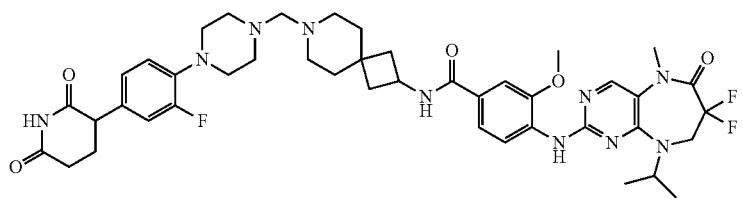 [SMILES: COc1cc(C(=O)NC2CC3(CCN(CN4CCN(c5ccc(C6CCC(=O)NC6=O)cc5F)CC4)CC3)C2)ccc1Nc1ncc2c(n1)N(C(C)C)CC(F)(F)C(=O)N2C]
14 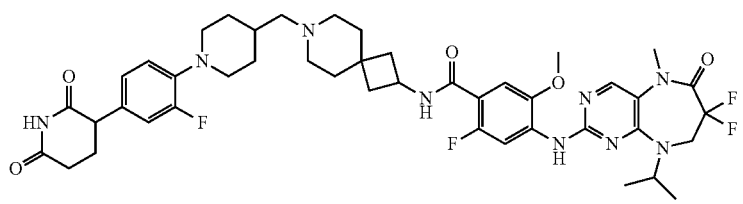 [SMILES: COc1cc(C(=O)NC2CC3(CCN(CC4CCN(c5ccc(C6CCC(=O)NC6=O)cc5F)CC4)CC3)C2)c(F)cc1Nc1ncc2c(n1)N(C(C)C)CC(F)(F)C(=O)N2C]
15 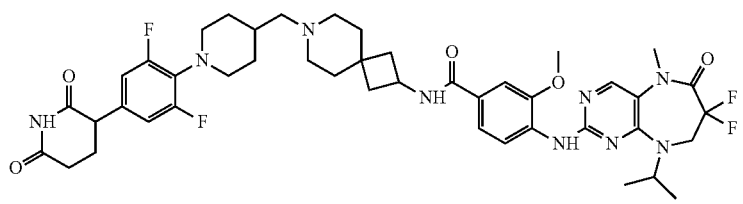 [SMILES: COc1cc(C(=O)NC2CC3(CCN(CC4CCN(c5c(F)cc(C6CCC(=O)NC6=O)cc5F)CC4)CC3)C2)ccc1Nc1ncc2c(n1)N(C(C)C)CC(F)(F)C(=O)N2C]
16 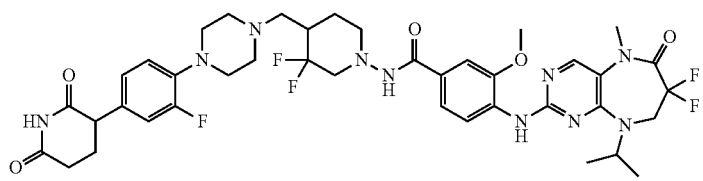 [SMILES: COc1cc(C(=O)NN2CCC(CN3CCN(c4ccc(C5CCC(=O)NC5=O)cc4F)CC3)C(F)(F)C2)ccc1Nc1ncc2c(n1)N(C(C)C)CC(F)(F)C(=O)N2C]
17 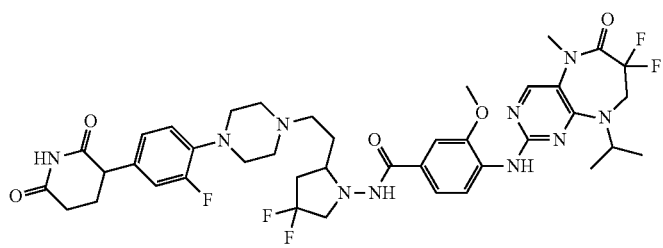 [SMILES: COc1cc(C(=O)NN2CC(F)(F)CC2CCN2CCN(c3ccc(C4CCC(=O)NC4=O)cc3F)CC2)ccc1Nc1ncc2c(n1)N(C(C)C)CC(F)(F)C(=O)N2C]

TABLE 1-continued
Compound Structure
18 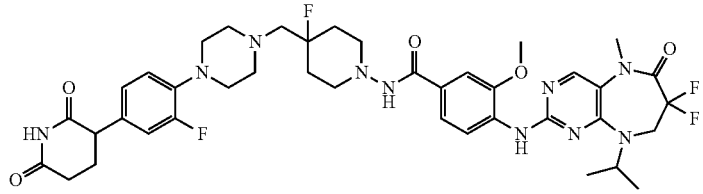 [SMILES: COc1cc(C(=O)NN2CCC(F)(CN3CCN(c4ccc(C5CCC(=O)NC5=O)cc4F)CC3)CC2)ccc1Nc1ncc2c(n1)N(C(C)C)CC(F)(F)C(=O)N2C]
19 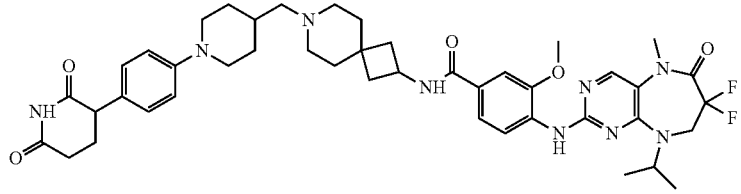 [SMILES: COc1cc(C(=O)NC2CC3(CCN(CC4CCN(c5ccc(C6CCC(=O)NC6=O)cc5)CC4)CC3)C2)ccc1Nc1ncc2c(n1)N(C(C)C)CC(F)(F)C(=O)N2C]
20 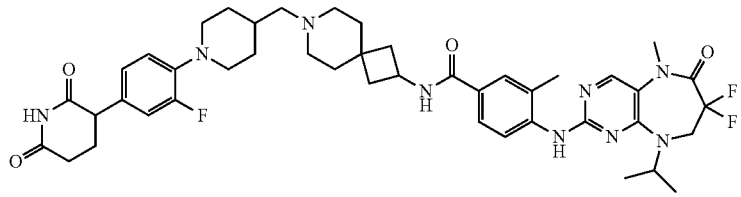 [SMILES: Cc1cc(C(=O)NC2CC3(CCN(CC4CCN(c5ccc(C6CCC(=O)NC6=O)cc5F)CC4)CC3)C2)ccc1Nc1ncc2c(n1)N(C(C)C)CC(F)(F)C(=O)N2C]
21 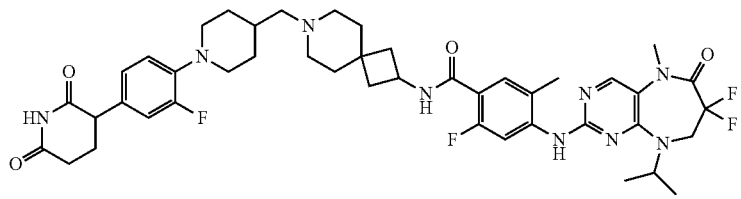 [SMILES: Cc1cc(C(=O)NC2CC3(CCN(CC4CCN(c5ccc(C6CCC(=O)NC6=O)cc5F)CC4)CC3)C2)c(F)cc1Nc1ncc2c(n1)N(C(C)C)CC(F)(F)C(=O)N2C]
22 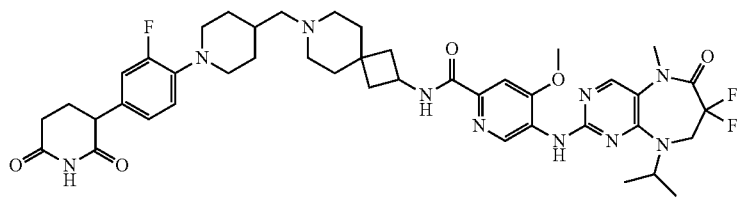 [SMILES: COc1cc(C(=O)NC2CC3(CCN(CC4CCN(c5ccc(C6CCC(=O)NC6=O)cc5F)CC4)CC3)C2)ncc1Nc1ncc2c(n1)N(C(C)C)CC(F)(F)C(=O)N2C]
23 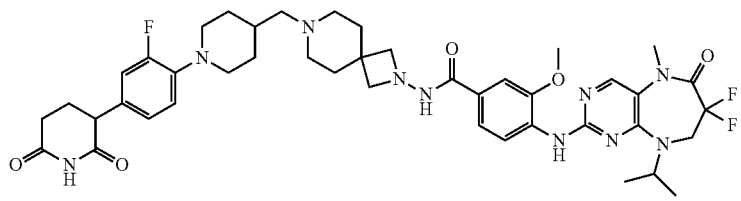 [SMILES: COc1cc(C(=O)NN2CC3(CCN(CC4CCN(c5ccc(C6CCC(=O)NC6=O)cc5F)CC4)CC3)C2)ccc1Nc1ncc2c(n1)N(C(C)C)CC(F)(F)C(=O)N2C]
24 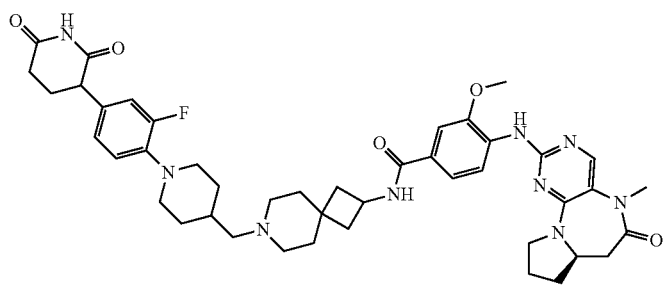 [SMILES: COc1cc(C(=O)NC2CC3(CCN(CC4CCN(c5ccc(C6CCC(=O)NC6=O)cc5F)CC4)CC3)C2)ccc1Nc1ncc2c(n1)N1CCC[C@@H]1CC(=O)N2C]

TABLE 1-continued
| Compound | Structure |
| --- | --- |
| 25 | 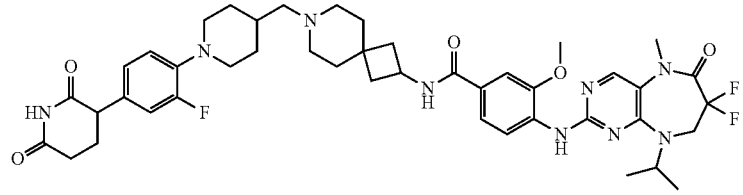 [SMILES: COc1cc(C(=O)NC2CC3(CCN(CC4CCN(c5ccc(C6CCC(=O)NC6=O)cc5F)CC4)CC3)C2)ccc1Nc1ncc2c(n1)N(C(C)C)CC(F)(F)C(=O)N2C] |
| 26 | 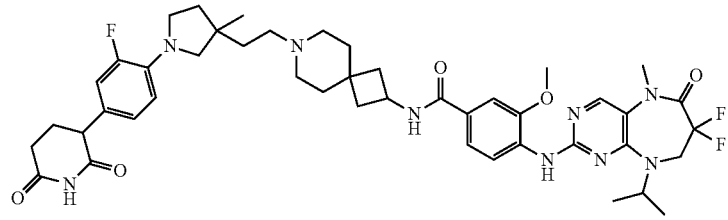 [SMILES: COc1cc(C(=O)NC2CC3(CCN(CCC4(C)CCN(c5ccc(C6CCC(=O)NC6=O)cc5F)C4)CC3)C2)ccc1Nc1ncc2c(n1)N(C(C)C)CC(F)(F)C(=O)N2C] |
| 27 | 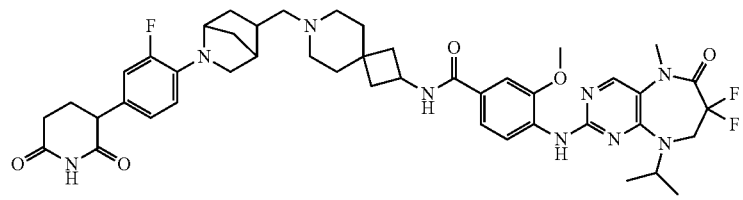 [SMILES: COc1cc(C(=O)NC2CC3(CCN(CC4CC5CC4CN5c4ccc(C5CCC(=O)NC5=O)cc4F)CC3)C2)ccc1Nc1ncc2c(n1)N(C(C)C)CC(F)(F)C(=O)N2C] |
| 28 | 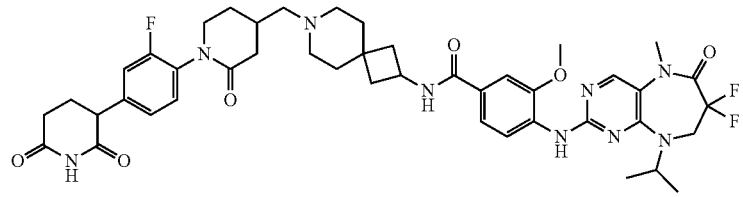 [SMILES: COc1cc(C(=O)NC2CC3(CCN(CC4CCN(c5ccc(C6CCC(=O)NC6=O)cc5F)C(=O)C4)CC3)C2)ccc1Nc1ncc2c(n1)N(C(C)C)CC(F)(F)C(=O)N2C] |
| 29 | 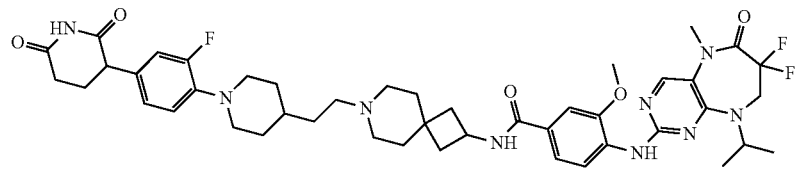 [SMILES: COc1cc(C(=O)NC2CC3(CCN(CCC4CCN(c5ccc(C6CCC(=O)NC6=O)cc5F)CC4)CC3)C2)ccc1Nc1ncc2c(n1)N(C(C)C)CC(F)(F)C(=O)N2C] |
| 30 | 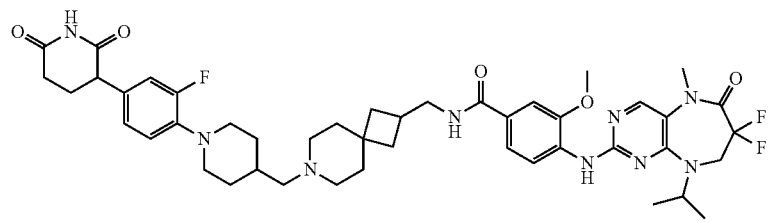 [SMILES: COc1cc(C(=O)NCC2CC3(CCN(CC4CCN(c5ccc(C6CCC(=O)NC6=O)cc5F)CC4)CC3)C2)ccc1Nc1ncc2c(n1)N(C(C)C)CC(F)(F)C(=O)N2C] |
| 31 | 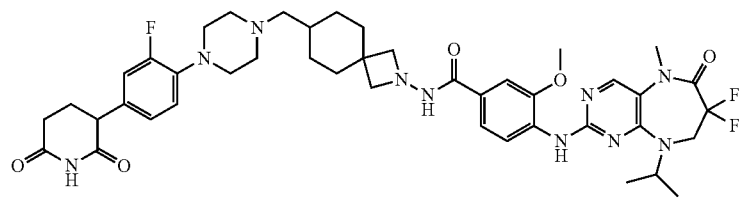 [SMILES: COc1cc(C(=O)NN2CC3(CCC(CN4CCN(c5ccc(C6CCC(=O)NC6=O)cc5F)CC4)CC3)C2)ccc1Nc1ncc2c(n1)N(C(C)C)CC(F)(F)C(=O)N2C] |

TABLE 1-continued
| Compound | Structure |
|---|---|
| 32 | 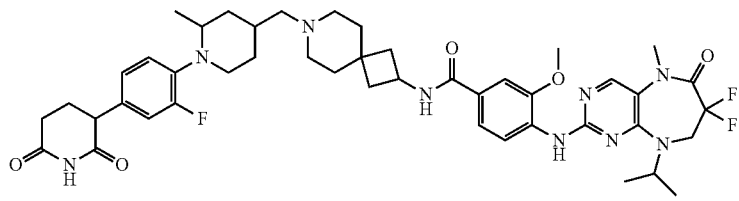 [SMILES: COc1cc(C(=O)NC2CC3(CCN(CC4CCN(c5ccc(C6CCC(=O)NC6=O)cc5F)C(C)C4)CC3)C2)ccc1Nc1ncc2c(n1)N(C(C)C)CC(F)(F)C(=O)N2C] |
| 33 | 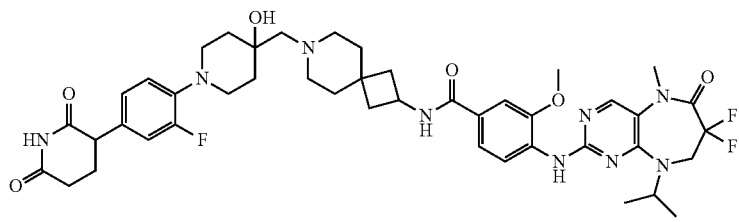 [SMILES: COc1cc(C(=O)NC2CC3(CCN(CC4(O)CCN(c5ccc(C6CCC(=O)NC6=O)cc5F)CC4)CC3)C2)ccc1Nc1ncc2c(n1)N(C(C)C)CC(F)(F)C(=O)N2C] |
| 34 | 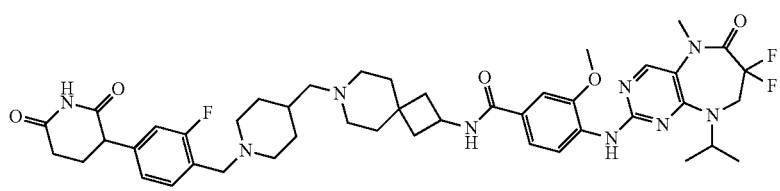 [SMILES: COc1cc(C(=O)NC2CC3(CCN(CC4CCN(Cc5ccc(C6CCC(=O)NC6=O)cc5F)CC4)CC3)C2)ccc1Nc1ncc2c(n1)N(C(C)C)CC(F)(F)C(=O)N2C] |
| 35 | 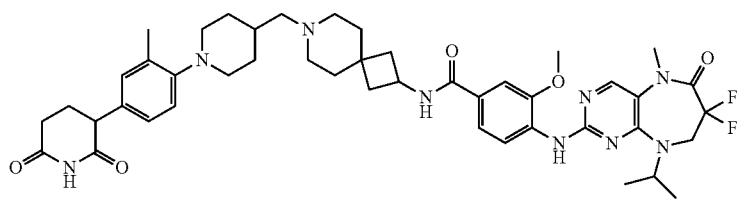 |
| 36 | 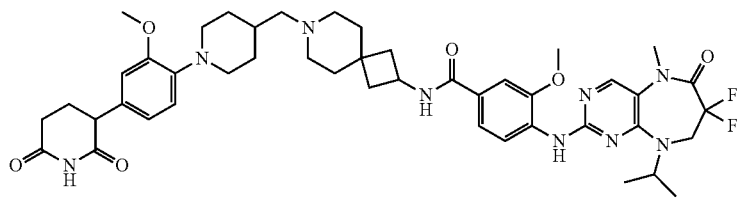 [SMILES: COc1cc(C(=O)NC2CC3(CCN(CC4CCN(c5ccc(C6CCC(=O)NC6=O)cc5OC)CC4)CC3)C2)ccc1Nc1ncc2c(n1)N(C(C)C)CC(F)(F)C(=O)N2C] |
| 37 | 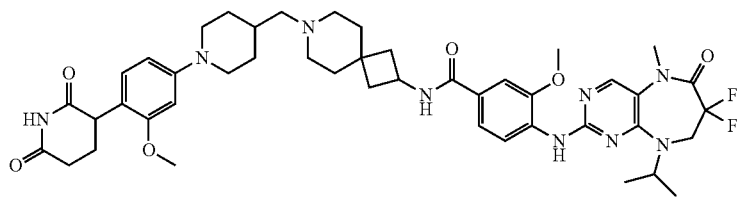 [SMILES: COc1cc(C(=O)NC2CC3(CCN(CC4CCN(c5ccc(C6CCC(=O)NC6=O)c(OC)c5)CC4)CC3)C2)ccc1Nc1ncc2c(n1)N(C(C)C)CC(F)(F)C(=O)N2C] |
| 38 | 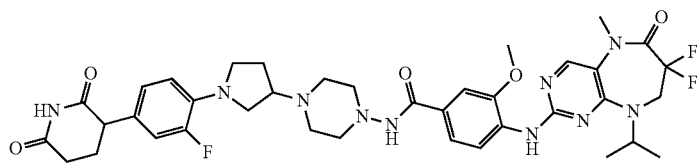 [SMILES: COc1cc(C(=O)NN2CCN(C3CCN(c4ccc(C5CCC(=O)NC5=O)cc4F)C3)CC2)ccc1Nc1ncc2c(n1)N(C(C)C)CC(F)(F)C(=O)N2C] |
| 39 | 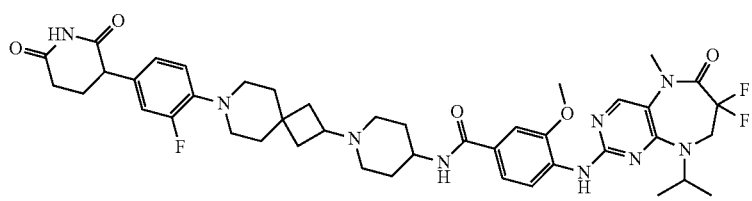 [SMILES: COc1cc(C(=O)NC2CCN(C3CC4(CCN(c5ccc(C6CCC(=O)NC6=O)cc5F)CC4)C3)CC2)ccc1Nc1ncc2c(n1)N(C(C)C)CC(F)(F)C(=O)N2C] |

TABLE 1-continued
| Compound | Structure |
|---|---|
| 40 | 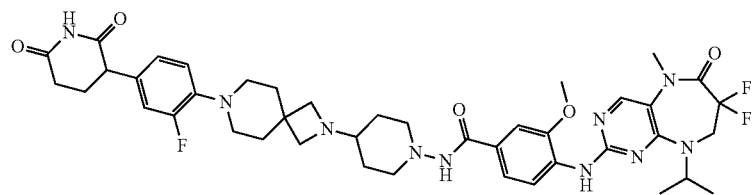 [SMILES: COc1cc(C(=O)NN2CCC(N3CC4(CCN(c5ccc(C6CCC(=O)NC6=O)cc5F)CC4)C3)CC2)ccc1Nc1ncc2c(n1)N(C(C)C)CC(F)(F)C(=O)N2C] |
| 41 | 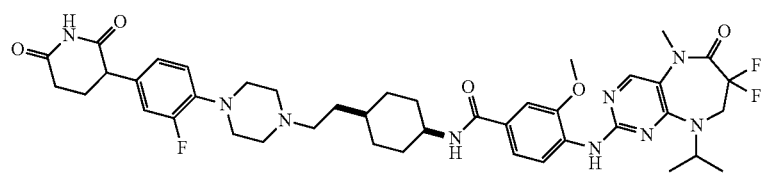<br>(cis) |
| 42 | 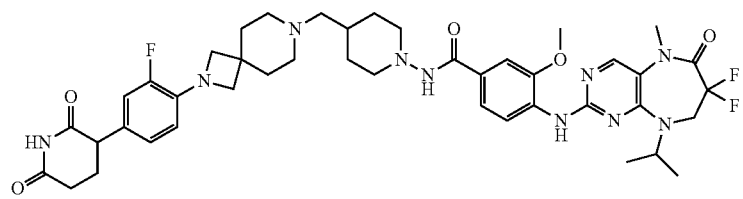 [SMILES: COc1cc(C(=O)NN2CCC(CN3CCC4(CC3)CN(c3ccc(C5CCC(=O)NC5=O)cc3F)C4)CC2)ccc1Nc1ncc2c(n1)N(C(C)C)CC(F)(F)C(=O)N2C] |
| 43 | 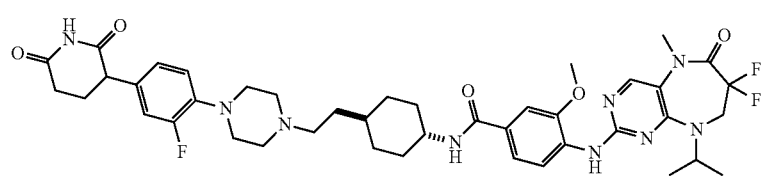<br>(trans) |
| 44 | 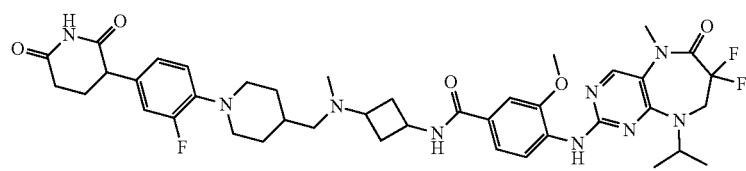 [SMILES: COc1cc(C(=O)NC2CC(N(C)CC3CCN(c4ccc(C5CCC(=O)NC5=O)cc4F)CC3)C2)ccc1Nc1ncc2c(n1)N(C(C)C)CC(F)(F)C(=O)N2C] |
| 45 | 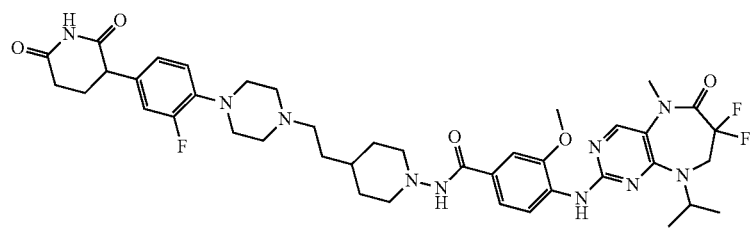 [SMILES: COc1cc(C(=O)NN2CCC(CCN3CCN(c4ccc(C5CCC(=O)NC5=O)cc4F)CC3)CC2)ccc1Nc1ncc2c(n1)N(C(C)C)CC(F)(F)C(=O)N2C] |
| 46 | 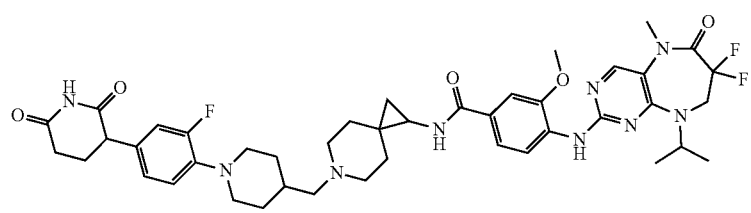 [SMILES: COc1cc(C(=O)NC2CC23CCN(CC2CCN(c4ccc(C5CCC(=O)NC5=O)cc4F)CC2)CC3)ccc1Nc1ncc2c(n1)N(C(C)C)CC(F)(F)C(=O)N2C] |

TABLE 1-continued
| Compound Structure |
|---|
| 47 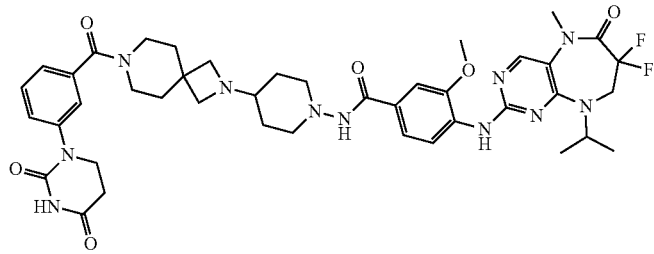 [SMILES: COc1cc(C(=O)NN2CCC(N3CC4(CCN(C(=O)c5cccc(N6CCC(=O)NC6=O)c5)CC4)C3)CC2)ccc1Nc1ncc2c(n1)N(C(C)C)CC(F)(F)C(=O)N2C] |
| 48 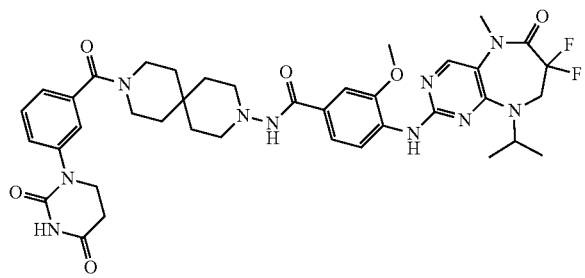 [SMILES: COc1cc(C(=O)NN2CCC3(CC2)CCN(C(=O)c2cccc(N4CCC(=O)NC4=O)c2)CC3)ccc1Nc1ncc2c(n1)N(C(C)C)CC(F)(F)C(=O)N2C] |
| 49 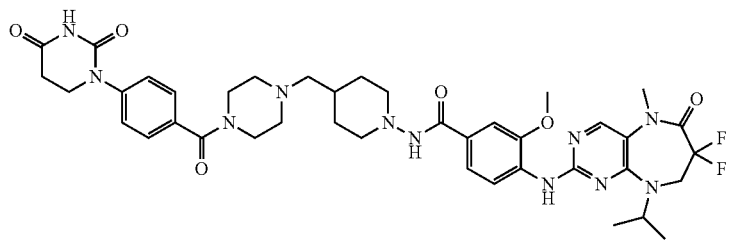 [SMILES: COc1cc(C(=O)NN2CCC(CN3CCN(C(=O)c4ccc(N5CCC(=O)NC5=O)cc4)CC3)CC2)ccc1Nc1ncc2c(n1)N(C(C)C)CC(F)(F)C(=O)N2C] |
| 50 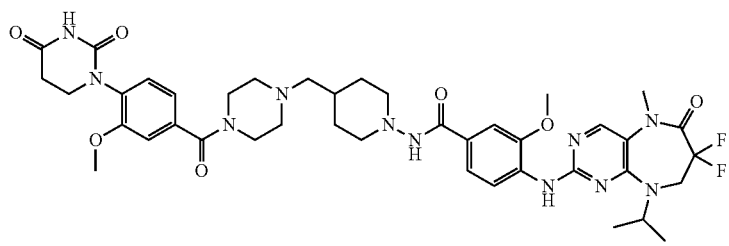 [SMILES: COc1cc(C(=O)NN2CCC(CN3CCN(C(=O)c4ccc(N5CCC(=O)NC5=O)c(OC)c4)CC3)CC2)ccc1Nc1ncc2c(n1)N(C(C)C)CC(F)(F)C(=O)N2C] |
| 51 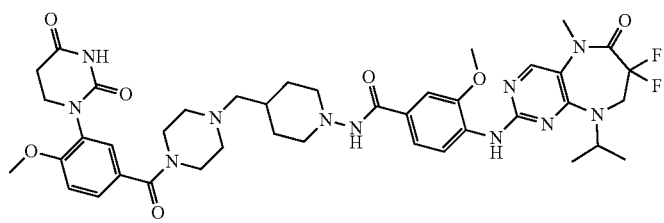 [SMILES: COc1cc(C(=O)NN2CCC(CN3CCN(C(=O)c4ccc(OC)c(N5CCC(=O)NC5=O)c4)CC3)CC2)ccc1Nc1ncc2c(n1)N(C(C)C)CC(F)(F)C(=O)N2C] |
| 52 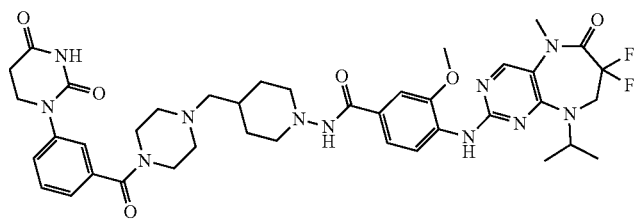 [SMILES: COc1cc(C(=O)NN2CCC(CN3CCN(C(=O)c4cccc(N5CCC(=O)NC5=O)c4)CC3)CC2)ccc1Nc1ncc2c(n1)N(C(C)C)CC(F)(F)C(=O)N2C] |

TABLE 1-continued
| Compound | Structure |
|---|---|
| 53 | 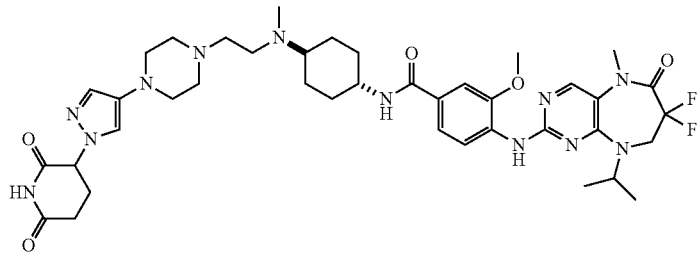 |
| 54 | 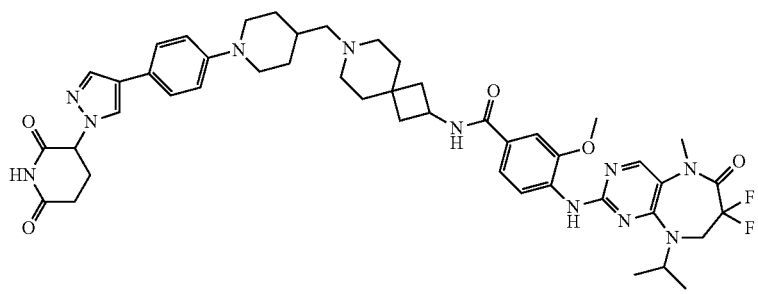 [SMILES: COc1cc(C(=O)NC2CC3(CCN(CC4CCN(c5ccc(-c6cnn(C7CCC(=O)NC7=O)c6)cc5)CC4)CC3)C2)ccc1Nc1ncc2c(n1)N(C(C)C)CC(F)(F)C(=O)N2C] |
| 55 | 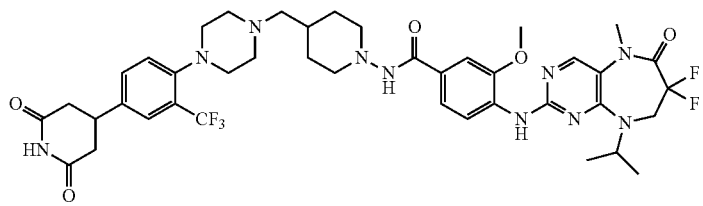 |
| 56 | 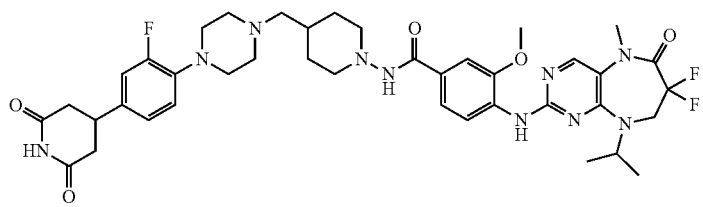 [SMILES: COc1cc(C(=O)NN2CCC(CN3CCN(c4ccc(C5CC(=O)NC(=O)C5)cc4F)CC3)CC2)ccc1Nc1ncc2c(n1)N(C(C)C)CC(F)(F)C(=O)N2C] |
| 57 | 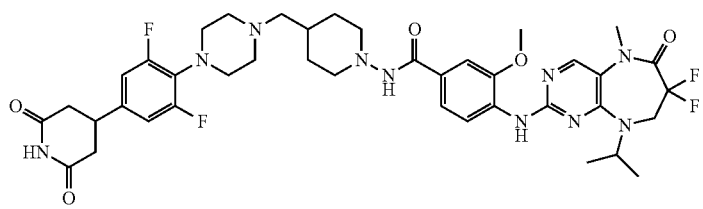 [SMILES: COc1cc(C(=O)NN2CCC(CN3CCN(c4c(F)cc(C5CC(=O)NC(=O)C5)cc4F)CC3)CC2)ccc1Nc1ncc2c(n1)N(C(C)C)CC(F)(F)C(=O)N2C] |
| 58 | 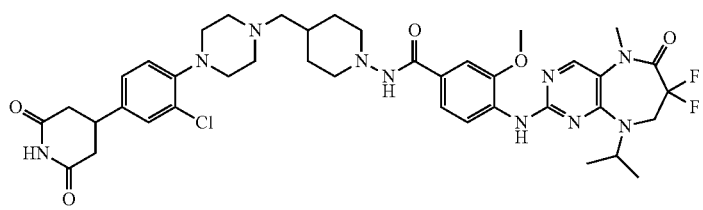 [SMILES: COc1cc(C(=O)NN2CCC(CN3CCN(c4ccc(C5CC(=O)NC(=O)C5)cc4Cl)CC3)CC2)ccc1Nc1ncc2c(n1)N(C(C)C)CC(F)(F)C(=O)N2C] |

TABLE 1-continued

Compound Structure

59

[Structure of compound 59: glutarimide-phenyl-F-pyrrolidine-piperidine-amide-methoxybenzamide-pyrimidodiazepinone with isopropyl, methyl, and gem-difluoro substituents]

The compounds of the present invention were purified according to the following method and the structure was analyzed.

Instruments
LCMS: Shimadzu LCMS-2020, Agilent 1200/G6110A, Agilent 1200/G1956A
HPLC: Agilent 1260 II LC, Agilent 1200/G6410B
NMR: BRUKER AVANCE III/400 MHz
SFC: SHIMADZU LC-30ADsf, Agilent 1260

LCMS Analysis
LCMS data were recorded with Shimadzu LCMS-2020 or Agilent 1200/G6110A or Agilent 1200/G1956A equipped with an ESI (Electron Spray Ionization) device. 0.0375% TFA in water (solvent A) and 0.01875% TFA in ACN (solvent B) or 0.025% $NH_3·H_2O$ in water (solvent A) and ACN (solvent B) were used as mobile phases. As a column, Kinetex EVO C18 (2.1×30 mm, 5 μm) or HALO C18 (3.0×30 mm, 2.7 μm) were used.

HPLC Analysis
In HPLC analysis, Agilent 1260 II LC or Agilent 1200/G6410B were used. 0.0375% TFA in water (solvent A) and 0.01875% TFA in ACN (solvent B) were used as the mobile phase. As a column, Zobrax Eclipse Plus C18 (4.6×150 mm, 3.5 μm) or YMC ODS A (4.6×150 mm, 3 μm) were used.

NMR Analysis
$^1$H NMR spectrum was recorded with Bruker AVANCE III 400 MHz/5 mm Probe (BBO).

SFC Analysis
In SFC analysis, SHIMADZU LC-30ADsf or Agilent 1260 were used. CO2 (solvent A) and 0.05% DEA in IPA+ACN (solvent B) or $CO_2$ (solvent A) and 0.05% DEA in MeOH+ACN (solvent B) or 0.05% DEA in ACN (solvent A) and 0.05% DEA in EtOH (solvent B) were used as the mobile phase. As a column, Chiralpak AD-3 (50×4.6 mm, 3 μm) or Chiralpak AS-3 (50×4.6 mm, 3 μm) or Chiralpak OJ-3 (50×4.6 mm, 3 μm) or Chiralpak IA-3 (50×4.6 mm, 3 μm) or Chiralpak OD (50×4.6 mm, 3 μm) or Chiralpak IC-3 (50×4.6 mm, 3 μm) or (S,S)Whelk-O1 (100×4.6 mm, 3.5 μm) were used.

Example 1. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-3-methoxybenzamide (Compound 1)

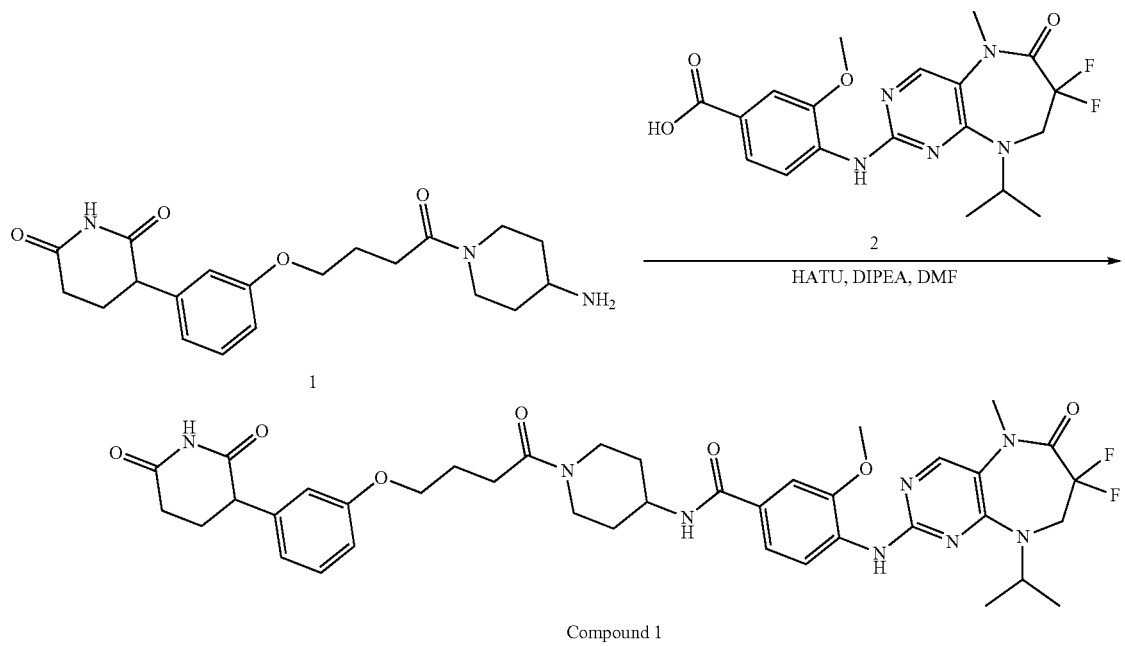

Compound 1

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (1.1 g, 2.61 mmol) in DMF (30 mL) were added HATU (1.29 g, 3.39 mmol) and DIPEA (1.69 g, 13.05 mmol, 2.27 mL), the mixture was stirred at 25° C. for 15 minutes, then 3-(3-(4-(4-aminopiperidin-1-yl)-4-oxobutoxy)phenyl)piperidine-2,6-dione (1.39 g, 3.39 mmol, HCl salt) was added and the resulting mixture was stirred at 25° C. for 1 hour. LCMS showed a peak (47%) with desired mass. The reaction mixture was combined with another batch (50 mg scale) for further work-up and purification. To the combined mixture was added CH$_3$COOH to adjust pH<7. The resulting mixture was purified by reversed-phase HPLC (0.1% FA condition, 330 g Flash Column; Welch Ultimate XB_C18 20-40 μm; 120 A; 5-60% 30 min; 60-100% 20 min @ 100 mL/min), followed by prep-HPLC (column: Waters Xbridge C18 150*50 mm*10 μm; mobile phase: [water (NH$_4$HCO$_3$)-ACN]; B %: 29%-59%, 10 min), the eluent was freeze-dried to afford 4-((7,7-difluoro-9-isopropyl-5-methyl-6-oxo-6,7,8,9-tetrahydro-5H-pyrimido[4,5-b][1,4]diazepin-2-yl)amino)-N-(1-(4-(3-(2,6-dioxopiperidin-3-yl)phenoxy)butanoyl)piperidin-4-yl)-3-methoxybenzamide (730.5 mg, 928.14 μmol, 35.56% yield, 98.7% purity) as an off-white solid. MS (M+H)$^+$=777.3.

$^1$H NMR (400 MHz, DMSO-d$_6$) δ=10.81 (s, 1H), 8.31 (d, J=8.4 Hz, 1H), 8.22 (s, 1H), 8.12 (br d, J=7.9 Hz, 1H), 7.87 (s, 1H), 7.57-7.41 (m, 2H), 7.23 (t, J=7.8 Hz, 1H), 6.84 (dd, J=2.0, 8.1 Hz, 1H), 6.82-6.73 (m, 2H), 4.88 (td, J=6.8, 13.5 Hz, 1H), 4.40 (br d, J=12.9 Hz, 1H), 4.10-3.87 (m, 9H), 3.81 (dd, J=5.0, 11.4 Hz, 1H), 3.30 (br s, 3H), 3.13 (br t, J=12.0 Hz, 1H), 2.71-2.60 (m, 2H), 2.49-2.42 (m, 3H), 2.27-2.15 (m, 1H), 2.06-2.00 (m, 1H), 1.99-1.91 (m, 2H), 1.84 (br dd, J=14.7, 16.9 Hz, 2H), 1.51-1.34 (m, 2H), 1.24 (d, J=6.6 Hz, 6H).

Example 2. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)phenyl)piperazin-1-yl)propanoyl)piperidin-4-yl)-3-methoxybenzamide (Compound 2)

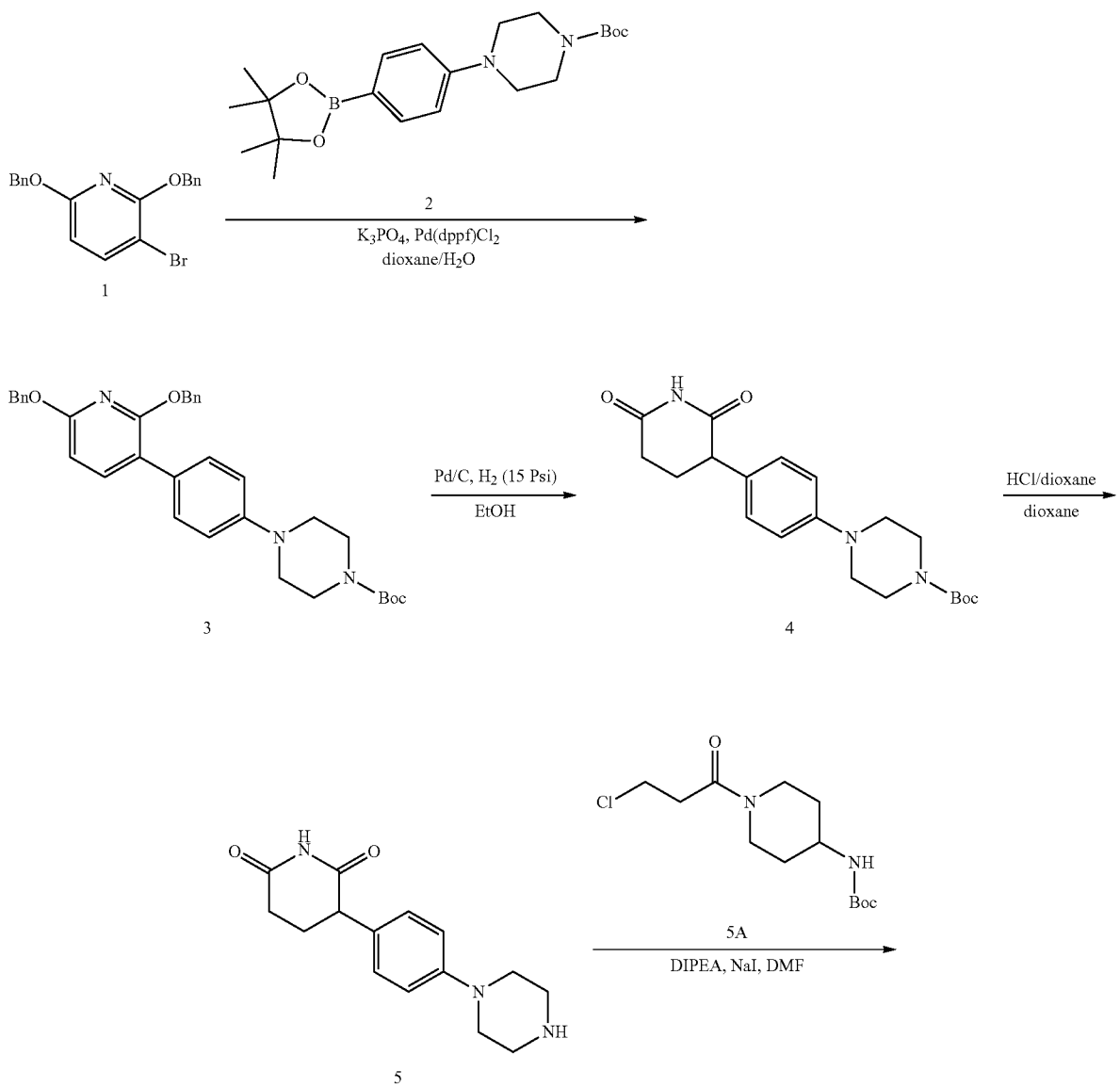

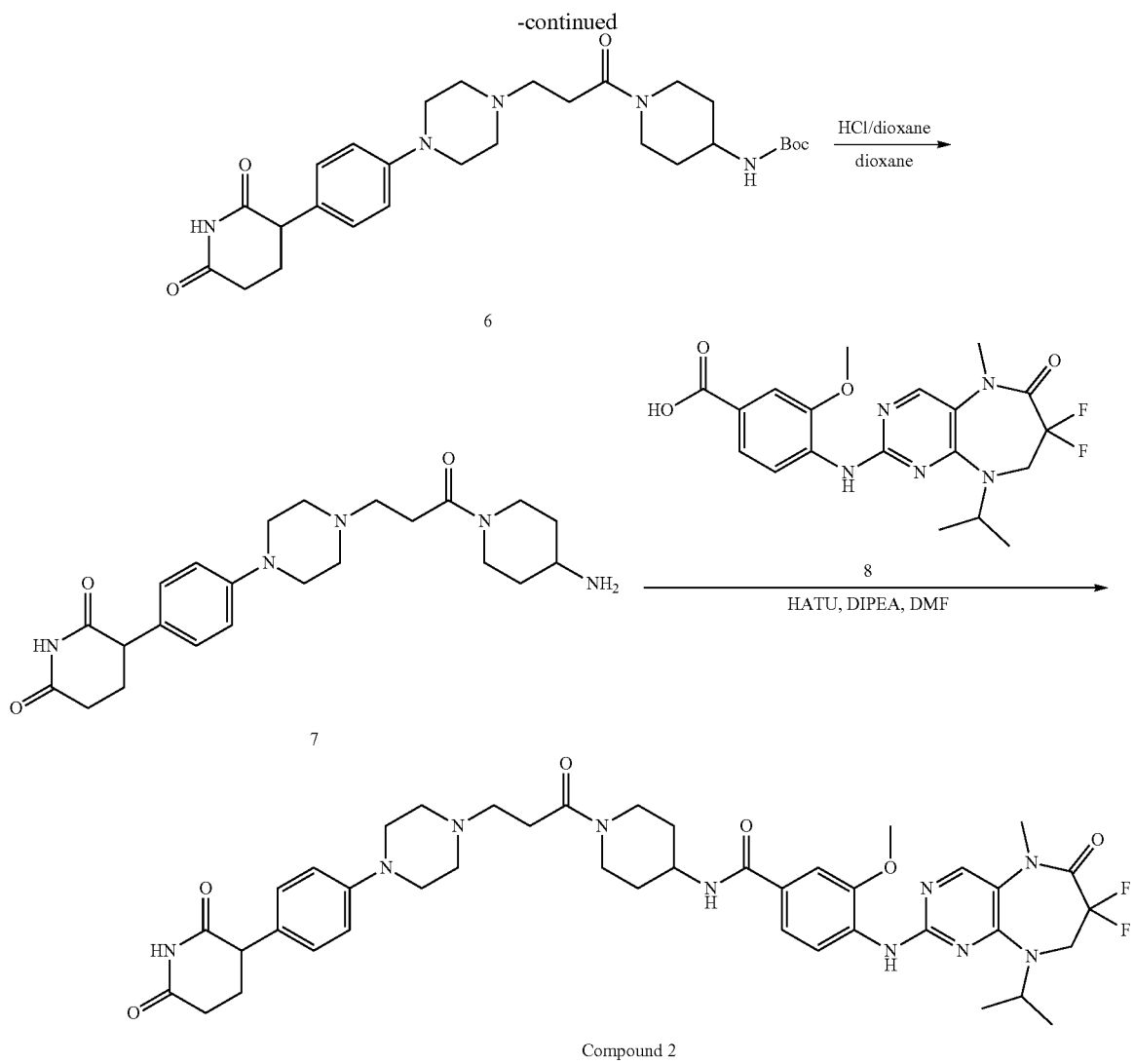

Compound 2

Step 1. Synthesis of tert-butyl 4-(4-(2,6-bis(benzyloxy)pyridin-3-yl)phenyl)piperazine-1-carboxylate (3)

To a mixture of 2,6-bis(benzyloxy)-3-bromopyridine (5 g, 13.50 mmol), tert-butyl 4-(4-(4,4,5,5-tetramethyl-1,3,2-dioxaborolan-2-yl)phenyl)piperazine-1-carboxylate (5.00 g, 12.88 mmol) and $K_3PO_4$ (8.60 g, 40.51 mmol) in dioxane (100 mL) and $H_2O$ (10 mL) was added Pd(dppf)Cl$_2$ (494.08 mg, 675.24 μmol) under $N_2$ atmosphere at 25° C. The resulting mixture was degassed and purged with $N_2$ for three times, then heated to 100° C. and stirred at 100° C. for 14 hrs. LCMS showed a main peak with desired mass. The reaction mixture was diluted with EtOAc (200 mL), dried over $Na_2SO_4$ and filtered. The filtrate was concentrated. The crude product was purified by flash silica gel chromatography (40 g silica gel column, EtOAc/petroleum ether=0-8%, 100 mL/min) to afford tert-butyl 4-(4-(2,6-bis(benzyloxy)pyridin-3-yl)phenyl)piperazine-1-carboxylate (6.5 g, 11.78 mmol, 87.25% yield, 100% purity) as a white solid. MS $(M+H)^+=552.4$ Step 2. Synthesis of tert-butyl 4-(4-(2,6-dioxopiperidin-3-yl)phenyl)piperazine-1-carboxylate (4)

A mixture of tert-butyl 4-(4-(2,6-bis(benzyloxy)pyridin-3-yl)phenyl)piperazine-1-carboxylate (6.5 g, 11.78 mmol) and Pd/C (2 g, 10% purity) in EtOH (600 mL) was degassed and purged with $H_2$ for three times, then the mixture was stirred at 25° C. for 14 h under $H_2$ (15 Psi). LCMS showed the starting material was consumed completely and a main peak with desired mass. The reaction mixture was filtered. The filter cake was washed with dioxane (400 mL). The filtrate was concentrated to afford tert-butyl 4-(4-(2,6-dioxopiperidin-3-yl)phenyl)piperazine-1-carboxylate (3.8 g, 10.18 mmol, 86.36% yield) as white solid. MS $(M+H)^+=373.9$ Step 3. Synthesis of 3-(4-(piperazin-1-yl)phenyl)piperidine-2,6-dione (5)

A solution of tert-butyl 4-(4-(2,6-dioxopiperidin-3-yl)phenyl)piperazine-1-carboxylate (3.8 g, 10.18 mmol) and HCl/dioxane (4 M, 50 mL) in dioxane (50 mL) was stirred at 25° C. for 1 h. LCMS showed the reaction was completed.

The reaction mixture was concentrated to afford 3-(4-(piperazin-1-yl)phenyl)piperidine-2,6-dione (3.5 g, crude, 2HCl salt) as a white solid. MS (M+H)⁺=274.3

Step 4. Synthesis of tert-butyl (1-(3-(4-(4-(2,6-dioxopiperidin-3-yl)phenyl)piperazin-1-yl)propanoyl)piperidin-4-yl)carbamate (6)

To a solution of 3-(4-(piperazin-1-yl)phenyl)piperidine-2,6-dione (3.5 g, 10.11 mmol, 2HCl salt) and tert-butyl (1-(3-chloropropanoyl)piperidin-4-yl)carbamate (5.88 g, 20.22 mmol) in DMF (40 mL) were added DIPEA (6.53 g, 50.54 mmol) and NaI (151.52 mg, 1.01 mmol) at 25° C. The resulting mixture was stirred at 80° C. for 14 h. LCMS showed the starting material was consumed completely and the desired mass. The reaction mixture was poured into water (150 mL), then extracted with EtOAc (50 mL×4). The combined organic layers were dried over Na₂SO₄ and concentrated. The crude product was triturated with EtOAc/petroleum ether (60 mL, 3:1) to afford tert-butyl (1-(3-(4-(4-(2,6-dioxopiperidin-3-yl)phenyl)piperazin-1-yl)propanoyl)piperidin-4-yl)carbamate (3.3 g, 5.50 mmol, 54.45% yield, 88% purity) as a brown solid. MS (M+H)⁺=528.4

¹H NMR (400 MHz, DMSO-d₆) δ=10.76 (br s, 1H), 7.05 (br d, J=8.3 Hz, 2H), 7.01-6.79 (m, 4H), 4.32-4.17 (m, 1H), 3.84-3.69 (m, 2H), 3.53-3.44 (m, 2H), 3.17-3.02 (m, 6H), 2.70-2.56 (m, 7H), 2.22-2.06 (m, 2H), 2.03-1.96 (m, 1H), 1.79-1.66 (m, 2H), 1.38 (s, 9H), 1.28-1.20 (m, 2H).

Step 5. Synthesis of 3-(4-(4-(3-(4-aminopiperidin-1-yl)-3-oxopropyl)piperazin-1-yl)phenyl)piperidine-2,6-dione (7)

A solution of tert-butyl (1-(3-(4-(4-(2,6-dioxopiperidin-3-yl)phenyl)piperazin-1-yl)propanoyl)piperidin-4-yl)carbamate (2.3 g, 4.36 mmol) and HCl/dioxane (4 M, 20 mL) in dioxane (10 mL) was stirred at 25° C. for 2 h. LCMS showed trace of the starting material remained and the desired mass. The reaction mixture was concentrated to afford 3-(4-(4-(3-(4-aminopiperidin-1-yl)-3-oxopropyl)piperazin-1-yl)phenyl)piperidine-2,6-dione (2.2 g, crude, 2HCl salt) as brown solid. MS (M+H)⁺=428.4

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)phenyl)piperazin-1-yl)propanoyl)piperidin-4-yl)-3-methoxybenzamide (Compound 2)

To a mixture of 3-(4-(4-(3-(4-aminopiperidin-1-yl)-3-oxopropyl)piperazin-1-yl)phenyl)piperidine-2,6-dione (400 mg, 799.26 μmol, 2HCl salt), 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (336.81 mg, 799.26 μmol) and DIPEA (619.80 mg, 4.80 mmol) in DMF (5 mL) was added HATU (395.08 mg, 1.04 mmol) at 25° C. The resulting mixture was stirred at 25° C. for 1 h. LCMS showed the starting material was consumed completely and the desired mass. The reaction mixture was poured into brine (20 mL). The resulting mixture was extracted with EtOAc (10 mL×3). The combined organic layers were dried over Na₂SO₄ and concentrated. The crude product was purified by flash silica gel chromatography (ISCO; 10 g SepaFlash Silica Flash Column, Eluent of 30~100% EtOAc/Petroleum ether gradient @ 60 mL/min) followed by prep-HPLC (column: Waters Xbridge 150×25 mm×5 μm; mobile phase: [water (NH₄HCO₃)-ACN]; B %: 30%-60%, 9 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(4-(4-(2,6-dioxopiperidin-3-yl)phenyl)piperazin-1-yl)propanoyl)piperidin-4-yl)-3-methoxybenzamide (47.9 mg, 56.90 μmol, 7.12% yield, 98.7% purity) as a white solid. MS (M+H)⁺=831.5

¹H NMR (400 MHz, DMSO-d₆) δ=10.78 (s, 1H), 8.31 (d, J=8.4 Hz, 1H), 8.22 (s, 1H), 8.15 (d, J=7.8 Hz, 1H), 7.88 (s, 1H), 7.53-7.47 (m, 2H), 7.04 (d, J=8.7 Hz, 2H), 6.89 (d, J=8.7 Hz, 2H), 4.88 (td, J=6.7, 13.4 Hz, 1H), 4.39 (br d, J=13.3 Hz, 1H), 4.12-3.94 (m, 4H), 3.93 (s, 3H), 3.72 (dd, J=4.9, 11.0 Hz, 1H), 3.32 (br s, 3H), 3.18-3.05 (m, 5H), 2.69-2.64 (m, 1H), 2.51-2.47 (m, 9H), 2.47-2.41 (m, 1H), 2.19-2.07 (m, 1H), 2.04-1.96 (m, 1H), 1.91-1.77 (m, 2H), 1.55-1.33 (m, 2H), 1.24 (d, J=6.7 Hz, 6H).

Example 3. Synthesis of N-(1-(3-(4-(4-(2,6-dioxopiperidin-3-yl)phenyl)piperazin-1-yl)propanoyl)piperidin-4-yl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (Compound 3)

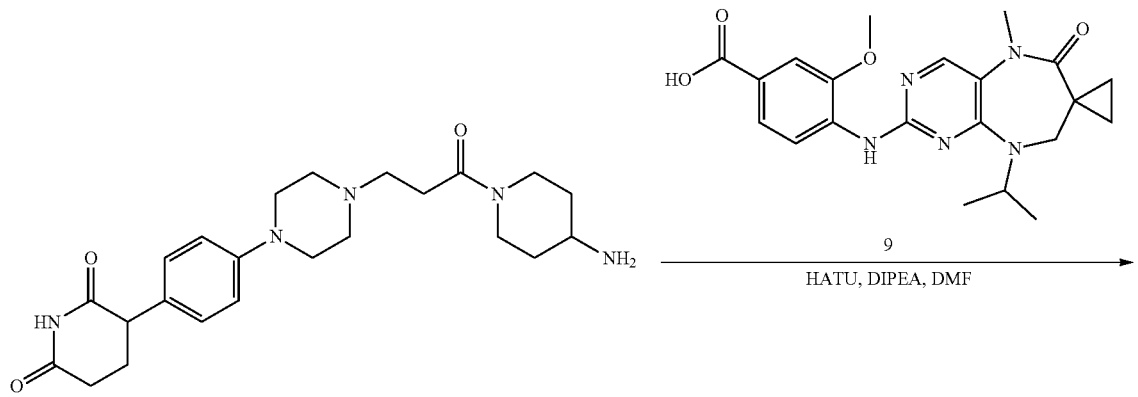

-continued

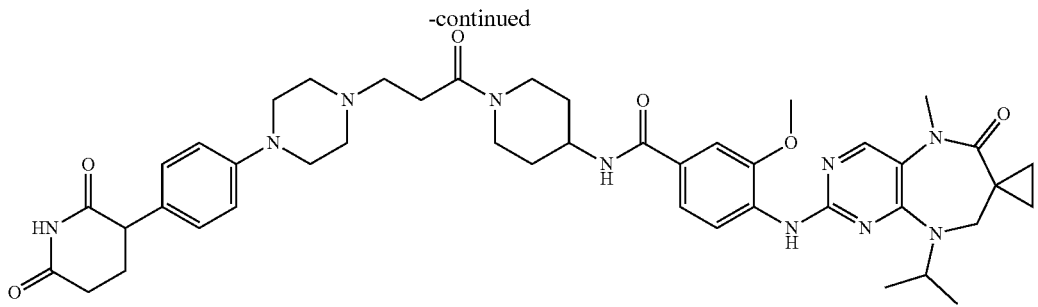

Compound 3

To a mixture of 3-(4-(4-(3-(4-aminopiperidin-1-yl)-3-oxopropyl)piperazin-1-yl)phenyl)piperidine-2,6-dione (400 mg, 799.26 μmol, 2HCl salt), 4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzoic acid (328.86 mg, 799.26 μmol) and DIPEA (619.80 mg, 4.80 mmol) in DMF (5 mL) was added HATU (395.08 mg, 1.04 mmol) at 25° C. The resulting mixture was stirred at 25° C. for 1 h. LCMS showed the starting material was consumed completely and the desired mass. The reaction mixture was poured into brine (20 mL). The resulting mixture was extracted with EtOAc (10 mL×3). The combined organic layers were dried over $Na_2SO_4$ and concentrated. The crude product was purified by flash silica gel chromatography (ISCO; 10 g SepaFlash Silica Flash Column, Eluent of 30~100% EtOAc/Petroleum ether gradient @ 60 mL/min) then followed by prep-HPLC (column: Waters Xbridge 150×25 mm×5 μm; mobile phase: [water ($NH_4HCO_3$)-ACN]; B %: 24%-57%, 9 min) and the eluent was lyophilized to afford N-(1-(3-(4-(4-(2,6-dioxopiperidin-3-yl)phenyl)piperazin-1-yl)propanoyl)piperidin-4-yl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (64.5 mg, 77.31 μmol, 9.67% yield, 98.1% purity) as a white solid. MS $(M+H)^+=821.5$ $^1H$ NMR (400 MHz, DMSO-$d_6$) δ=10.76 (s, 1H), 8.42 (d, J=8.3 Hz, 1H), 8.12 (d, J=7.7 Hz, 1H), 7.97 (s, 1H), 7.65 (s, 1H), 7.53-7.46 (m, 2H), 7.04 (d, J=8.7 Hz, 2H), 6.89 (d, J=8.8 Hz, 2H), 4.84 (td, J=6.9, 13.5 Hz, 1H), 4.39 (br d, J=12.8 Hz, 1H), 4.12-3.95 (m, 2H), 3.94 (s, 3H), 3.72 (dd, J=5.0, 10.9 Hz, 1H), 3.46 (s, 2H), 3.16 (s, 3H), 3.15-3.05 (m, 5H), 2.69-2.60 (m, 3H), 2.59-2.54 (m, 7H), 2.47-2.41 (m, 1H), 2.19-2.07 (m, 1H), 2.02-1.97 (m, 1H), 1.91-1.77 (m, 2H), 1.53-1.34 (m, 2H), 1.17 (d, J=6.6 Hz, 6H), 0.95-0.90 (m, 2H), 0.71-0.65 (m, 2H).

Example 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(4-(3-(2,6-dioxopiperidin-3-yl)phenyl)piperazin-1-yl)propanoyl)piperidin-4-yl)-3-methoxybenzamide (Compound 4)

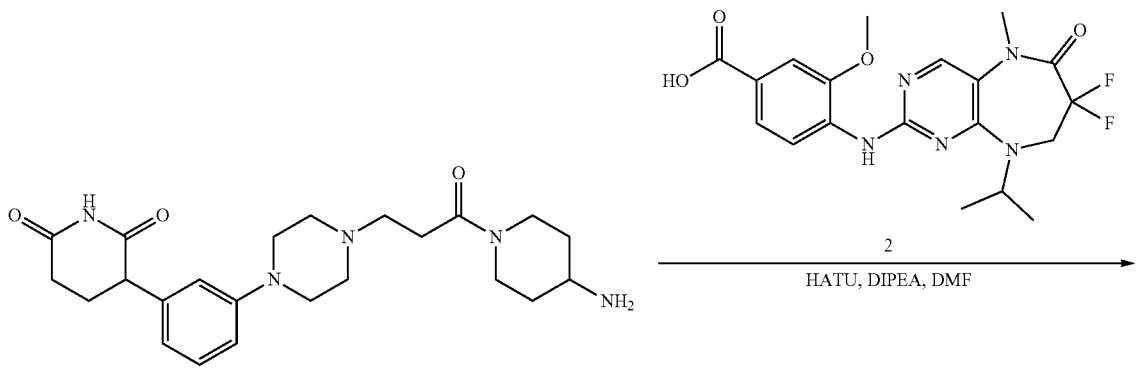

-continued

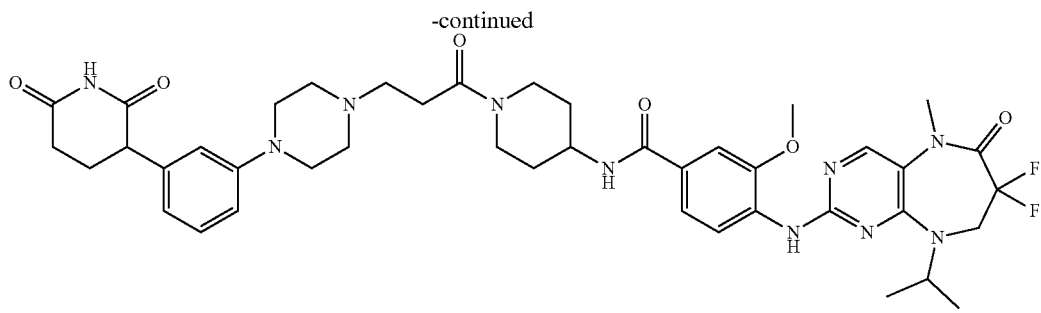

Compound 4

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (1 g, 2.37 mmol) in DMF (30 mL) were added HATU (1.17 g, 3.08 mmol) and DIPEA (1.23 g, 9.49 mmol, 1.65 mL), the mixture was stirred at 25° C. for 15 minutes, then 3-(3-(4-(3-(4-aminopiperidin-1-yl)-3-oxopropyl)piperazin-1-yl)phenyl)piperidine-2,6-dione (1.3 g, 2.80 mmol, HCl salt) was added and the resulting mixture was stirred at 25° C. for 1 hour. LCMS showed the starting material was consumed completely and 71% of desired mass was detected. To the mixture was added $CH_3COOH$ to adjust pH<7 and purified by reversed-phase HPLC (0.1% FA condition, 330 g Flash Column; Welch Ultimate XB_$C_{18}$ 20-40 μm; 120 A; 0-50% 30 min; 50-100% 20 min @100 mL/min) and re-purified by prep-HPLC (column: Waters Xbridge C18 150×50 mm×10 μm; mobile phase: [water ($NH_4HCO_3$)-ACN]; B %: 27%-57%, 10 min) and the eluent was freeze-dried to afford 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(4-(3-(2,6-dioxopiperidin-3-yl)phenyl)piperazin-1-yl)propanoyl)piperidin-4-yl)-3-methoxybenzamide (658.7 mg, 783.22 μmol, 33.00% yield, 98.8% purity) as a white solid. MS (M+H)$^+$=831.3.

$^1$H NMR (400 MHz, DMSO-d$_6$) δ=10.79 (s, 1H), 8.31 (d, J=8.3 Hz, 1H), 8.22 (s, 1H), 8.15 (br d, J=7.7 Hz, 1H), 7.88 (s, 1H), 7.59-7.43 (m, 2H), 7.15 (t, J=7.8 Hz, 1H), 6.88-6.73 (m, 2H), 6.61 (d, J=7.6 Hz, 1H), 4.97-4.78 (m, 1H), 4.39 (br d, J=12.3 Hz, 1H), 4.12-3.88 (m, 7H), 3.75 (dd, J=5.0, 11.2 Hz, 1H), 3.32 (br s, 3H), 3.20-3.06 (m, 5H), 2.68-2.53 (m, 10H), 2.44 (br t, J=4.2 Hz, 1H), 2.26-2.13 (m, 1H), 2.07-1.95 (m, 1H), 1.93-1.76 (m, 2H), 1.55-1.33 (m, 2H), 1.24 (d, J=6.7 Hz, 6H).

Example 5. Synthesis of N-(1-(3-(4-(3-(2,6-dioxopiperidin-3-yl)phenyl)piperazin-1-yl)propanoyl) piperidin-4-yl)-4-((9'-isopropyl-5'-methyl-6'-oxo-5',6',8', 9'-tetrahydrospiro[cyclopropane-1,7'-pyrimido[4,5-b][1,4]diazepin]-2'-yl)amino)-3-methoxybenzamide (Compound 5)

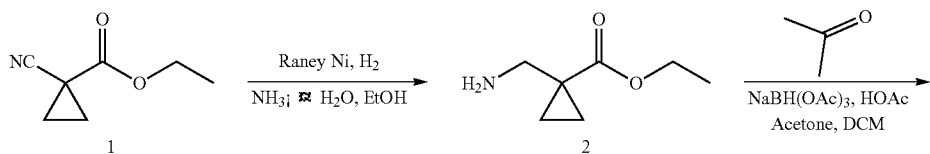

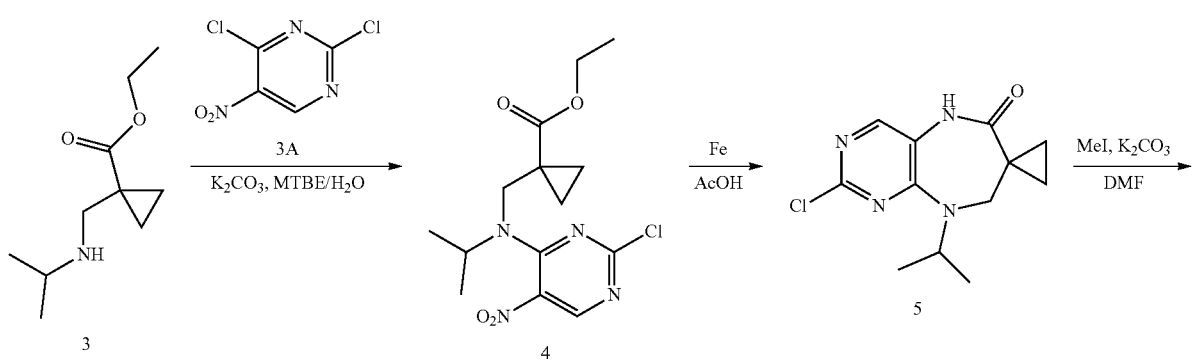

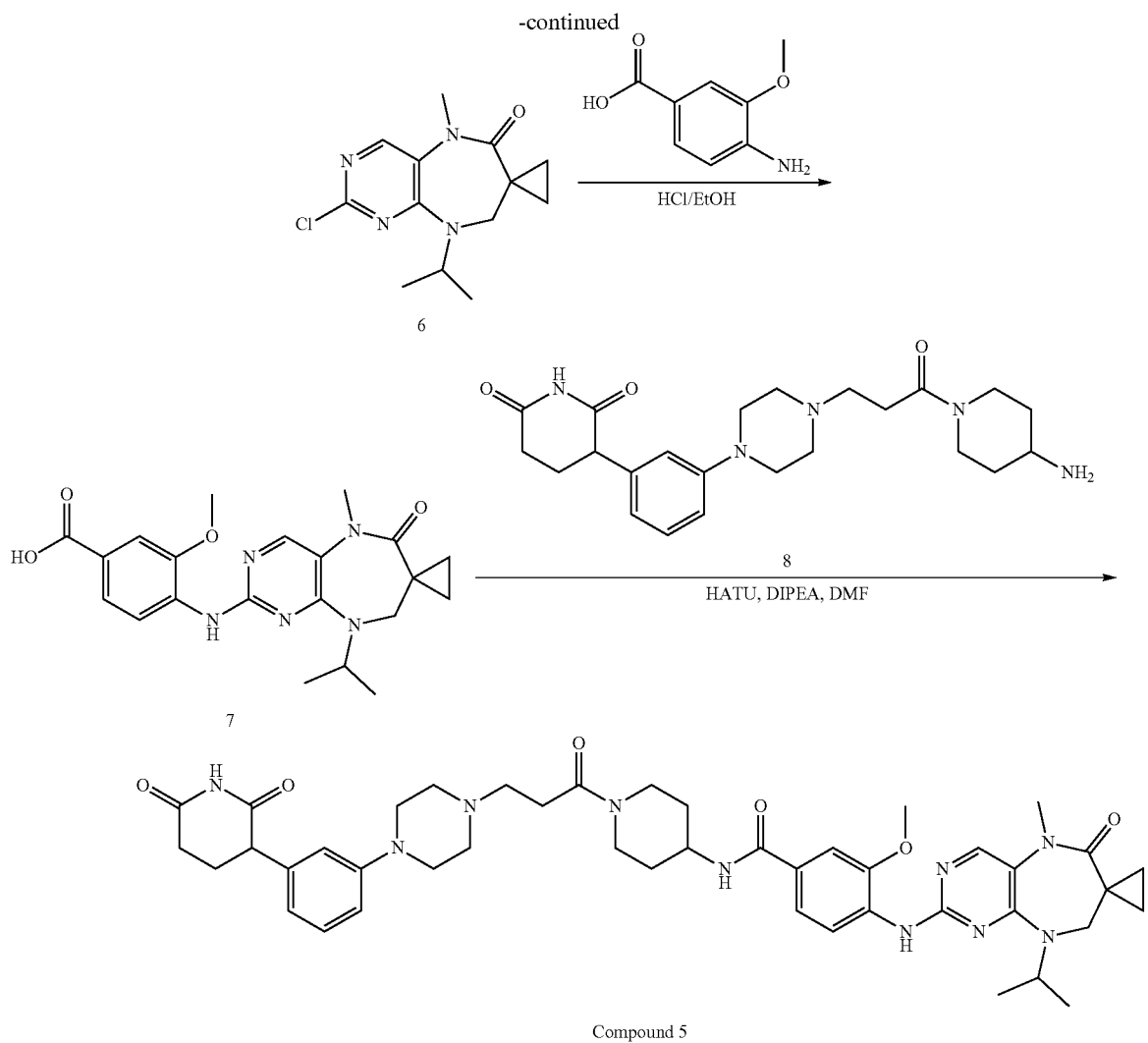

Compound 5

Step 1. Synthesis of ethyl 1-(aminomethyl)cyclopropane-1-carboxylate (2)

To a solution of ethyl 1-cyanocyclopropanecarboxylate (25 g, 179.66 mmol, 23.15 mL) in EtOH (250 mL) and NH$_3$·H$_2$O (25 mL) was added Raney-Ni (23.09 g, 269.49 mmol) under N$_2$ atmosphere. The suspension was degassed and purged with H$_2$ for 3 times. The mixture was stirred at 20° C. for 16 h under H$_2$ (50 Psi). TLC (SiO$_2$, Petroleum ether:EtOAc=3:1) indicated starting material was consumed completely and one new spot was detected. The reaction mixture was diluted with EtOH (600 mL) and filtered. The filtrate was concentrated in vacuum to afford ethyl 1-(aminomethyl)cyclopropane-1-carboxylate (18.9 g, crude) as a Colorless oil. MS (M+H)$^+$=144.1

Step 2. Synthesis of ethyl 1-((isopropylamino)methyl)cyclopropane-1-carboxylate (3)

To a solution of ethyl 1-(aminomethyl)cyclopropane-1-carboxylate (18.9 g, 132.00 mmol) and acetone (28.70 g, 494.16 mmol, 36.33 mL), AcOH (13.06 g, 217.48 mmol, 12.44 mL) in DCM (300 mL) was added NaBH(OAc)$_3$ (62.83 g, 296.45 mmol) at 20° C. and the resulting mixture was stirred at 20° C. for 16 h. The reaction mixture was quenched with NaHCO$_3$ (200 mL) and extracted with EtOAc (200 mL×3). The organic layer was washed with brine (200 mL×3), dried over Na$_2$SO$_4$, filtered. To the filtrate was added HCl (12 N) and concentrated in vacuum to afford ethyl 1-((isopropylamino)methyl)cyclopropane-1-carboxylate (6.1 g, 27.51 mmol, 20.84% yield, HCl salt) as a yellow oil. MS (M+H)$^+$=186.1

Step 3. Synthesis of ethyl 1-(((2-chloro-5-nitropyrimidin-4-yl)(isopropyl)amino)methyl)cyclopropane-1-carboxylate (4)

To a solution of ethyl 1-((isopropylamino)methyl)cyclopropane-1-carboxylate (6.1 g, 27.51 mmol, HCl salt) in MTBE (60 mL) and H$_2$O (30 mL) were added K$_2$CO$_3$ (15.21 g, 110.05 mmol) and 2,4-dichloro-5-nitro-pyrimidine (6.40 g, 33.01 mmol) at 20° C. and the resulting mixture was stirred at 20° C. for 16 h. LCMS showed starting material was consumed completely and a peak (86%) with desired mass. The reaction mixture was diluted with H$_2$O (160 mL) and extracted with EtOAc (160 mL×3). The combined organic layer was dried over Na$_2$SO$_4$, filtered and concentrated to afford ethyl 1-(((2-chloro-5-nitropyrimidin-4-yl)

(isopropyl)amino)methyl)cyclopropane-1-carboxylate (6.6 g, crude) as a yellow oil. MS (M+H)$^+$=343.1

Step 4. Synthesis of 2'-chloro-9'-isopropyl-8',9'-dihydrospiro[cyclopropane-1,7'-pyrimido[4,5-b][1,4]diazepin]-6'(5'H)-one (5)

To a solution of ethyl 1-(((2-chloro-5-nitropyrimidin-4-yl)(isopropyl)amino)methyl)cyclopropane-1-carboxylate (6.6 g, 19.25 mmol) in AcOH (60 mL) was added Fe (4.30 g, 77.02 mmol) at 20° C. and the resulting mixture was stirred at 60° C. for 2 h. LCMS showed starting material was consumed completely and a main peak (97%) with desired mass. The reaction mixture was concentrated in vacuum. The residue was diluted with H$_2$O (120 mL) and extracted with EtOAc (120 mL×3). The organic layer was dried over Na$_2$SO$_4$, filtered and concentrated to afford 2'-chloro-9'-isopropyl-8',9'-dihydrospiro[cyclopropane-1,7'-pyrimido[4,5-b][1,4]diazepin]-6'(5'H)-one (5.2 g, crude) as a yellow oil. MS (M+H)$^+$=267.1

Step 5. Synthesis of 2'-chloro-9'-isopropyl-5'-methyl-8',9'-dihydrospiro[cyclopropane-1,7'-pyrimido[4,5-b][1,4]diazepin]-6'(5'H)-one (6)

To a solution of 2'-chloro-9'-isopropyl-8',9'-dihydrospiro[cyclopropane-1,7'-pyrimido[4,5-b][1,4]diazepin]-6'(5'H)-one (5.2 g, 19.50 mmol) in DMF (60 mL) were added K$_2$CO$_3$ (8.08 g, 58.49 mmol) and MeI (4.15 g, 29.24 mmol, 1.82 mL) at 20° C. and the resulting mixture was stirred at 20° C. for 12 h. LCMS showed starting material was consumed completely and a peak (66%) with desired mass. The reaction mixture was diluted with H$_2$O (180 mL) and extracted with EtOAC (180 mL×3). The organic layer was washed with brine (180 mL×3), dried over Na$_2$SO$_4$, filtered and concentrated. The residue was purified by flash silica gel chromatography (40 g SepaFlash Silica Flash Column, Eluent of 0~25% EtOAc/Petroleum ether gradient @ 100 mL/min) to afford 2'-chloro-9'-isopropyl-5'-methyl-8',9'-dihydrospiro[cyclopropane-1,7'-pyrimido[4,5-b][1,4]diazepin]-6'(5'H)-one (3.8 g, 12.72 mmol, 65.26% yield, 94% purity) as an orange solid. MS (M+H)$^+$=281.4

Step 6. Synthesis of 4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzoic Acid (7)

To a solution of 2'-chloro-9'-isopropyl-5'-methyl-8',9'-dihydrospiro[cyclopropane-1,7'-pyrimido[4,5-b][1,4]diazepin]-6'(5'H)-one (1.8 g, 6.41 mmol) and 4-amino-3-methoxy-benzoic acid (1.29 g, 7.69 mmol) in EtOH (18 mL) and H$_2$O (6 mL) was added HCl (12 M, 1.18 mL) at 20° C. and the resulting mixture was stirred at 100° C. for 16 h. LCMS showed 12% of starting material remained and a peak (35%) with desired mass. The reaction mixture was concentrated in vacuum. The crude product was triturated with a mixture of DMF/EtOH/EtOAc (2 mL/10 mL/10 mL) at 25° C. for 0.5 h and filtered. The filter cake was dried in vacuum to afford 4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzoic acid (1.7 g, 4.13 mmol, 64.44% yield) as an off-white solid. MS (M+H)$^+$=412.3

$^1$H NMR (400 MHz, DMSO-d$_6$) δ=9.68 (br s, 1H), 8.19-8.09 (m, 2H), 7.64 (dd, J=1.3, 8.5 Hz, 1H), 7.57 (d, J=1.1 Hz, 1H), 4.94-4.75 (m, 1H), 3.94 (s, 3H), 3.64 (br s, 2H), 3.15 (s, 3H), 1.18 (br d, J=6.8 Hz, 6H), 1.07-1.01 (m, 2H), 0.80 (br s, 2H)

Step 7. Synthesis of N-(1-(3-(4-(3-(2,6-dioxopiperidin-3-yl)phenyl)piperazin-1-yl)propanoyl) piperidin-4-yl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (Compound 5)

To a solution of 4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzoic acid (700 mg, 1.70 mmol) in DMF (6 mL) were added HATU (711.57 mg, 1.87 mmol) and DIPEA (439.76 mg, 3.40 mmol, 592.67 µL). The mixture was stirred at 20° C. for 10 min, then a solution of 3-[3-[4-[3-(4-amino-1-piperidyl)-3-oxo-propyl]piperazin-1-yl]phenyl]piperidine-2,6-dione (1.03 g, 2.21 mmol, HCl salt) in DMF (6 mL) with DIPEA (439.76 mg, 3.40 mmol, 592.67 µL) was added and the resulting mixture was stirred at 20° C. for another 1 h. LCMS showed all of starting material was consumed completely and a peak (68%) with desired mass. The reaction mixture was diluted with H$_2$O (60 mL) and extracted with EtOAc (60 mL×5). The organic layer was dried over Na$_2$SO$_4$, filtered and concentrated to afford product A. The aqueous phase was concentrated in vacuum to afford product B. The product A was purified by prep-HPLC (column: Phenomenex luna C18 150×40 mm×15 µm; mobile phase: [water (FA)-ACN]; B %: 5%-35%, 10 min) and lyophilization to afford product E (620 mg) and product F (420 mg). The product B was re-purified by prep-HPLC (column: Unisil 3-100 C18 µLtra 150×50 mm×3 µm; mobile phase: [water (FA)-ACN]; B %: 5%-35%, 10 min) and lyophilization to afford product D (158 mg). Combined product D (158 mg) and product E (620 mg) and re-purified by prep-HPLC (column: Waters Xbridge C18 150×50 mm×10 µm; mobile phase: [water (NH$_4$HCO$_3$)-ACN]; B %: 25%-55%, 10 min) and lyophilization to afford N-(1-(3-(4-(3-(2,6-dioxopiperidin-3-yl)phenyl)piperazin-1-yl)propanoyl)piperidin-4-yl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (362.9 mg, 441.59 µmol, 25.96% yield, 99.9% purity) as a white solid. The product F (420 mg) was re-purified by prep-HPLC (column: Waters Xbridge C18 150×50 mm×10 µm; mobile phase: [water (NH$_4$HCO$_3$)-ACN]; B %: 25%-55%, 10 min) and lyophilization to afford N-(1-(3-(4-(3-(2,6-dioxopiperidin-3-yl)phenyl)piperazin-1-yl)propanoyl)piperidin-4-yl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (136 mg, 162.34 µmol, 9.54% yield, 98% purity) as a white solid. MS (M+H)$^+$=821.2

$^1$H NMR (400 MHz, DMSO-d$_6$) δ=10.78 (br s, 1H), 8.42 (d, J=8.4 Hz, 1H), 8.11 (d, J=7.8 Hz, 1H), 7.97 (s, 1H), 7.65 (s, 1H), 7.55-7.45 (m, 2H), 7.15 (t, J=7.9 Hz, 1H), 6.85-6.76 (m, 2H), 6.61 (d, J=7.5 Hz, 1H), 4.84 (spt, J=6.8 Hz, 1H), 4.39 (br d, J=13.3 Hz, 1H), 4.11-3.90 (m, 5H), 3.75 (dd, J=4.9, 11.2 Hz, 1H), 3.46 (s, 2H), 3.20-3.07 (m, 8H), 2.73-2.53 (m, 10H), 2.48-2.42 (m, 1H), 2.25-2.13 (m, 1H), 2.06-1.97 (m, 1H), 1.93-1.77 (m, 2H), 1.56-1.31 (m, 2H), 1.17 (d, J=6.6 Hz, 6H), 0.95-0.89 (m, 2H), 0.72-0.65 (m, 2H).

Example 6. Synthesis of N-(3-((2-(1-(3-(2,6-di-oxopiperidin-3-yl)phenyl)piperidin-4-yl)ethyl)(methyl)amino)cyclobutyl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (Compound 6)
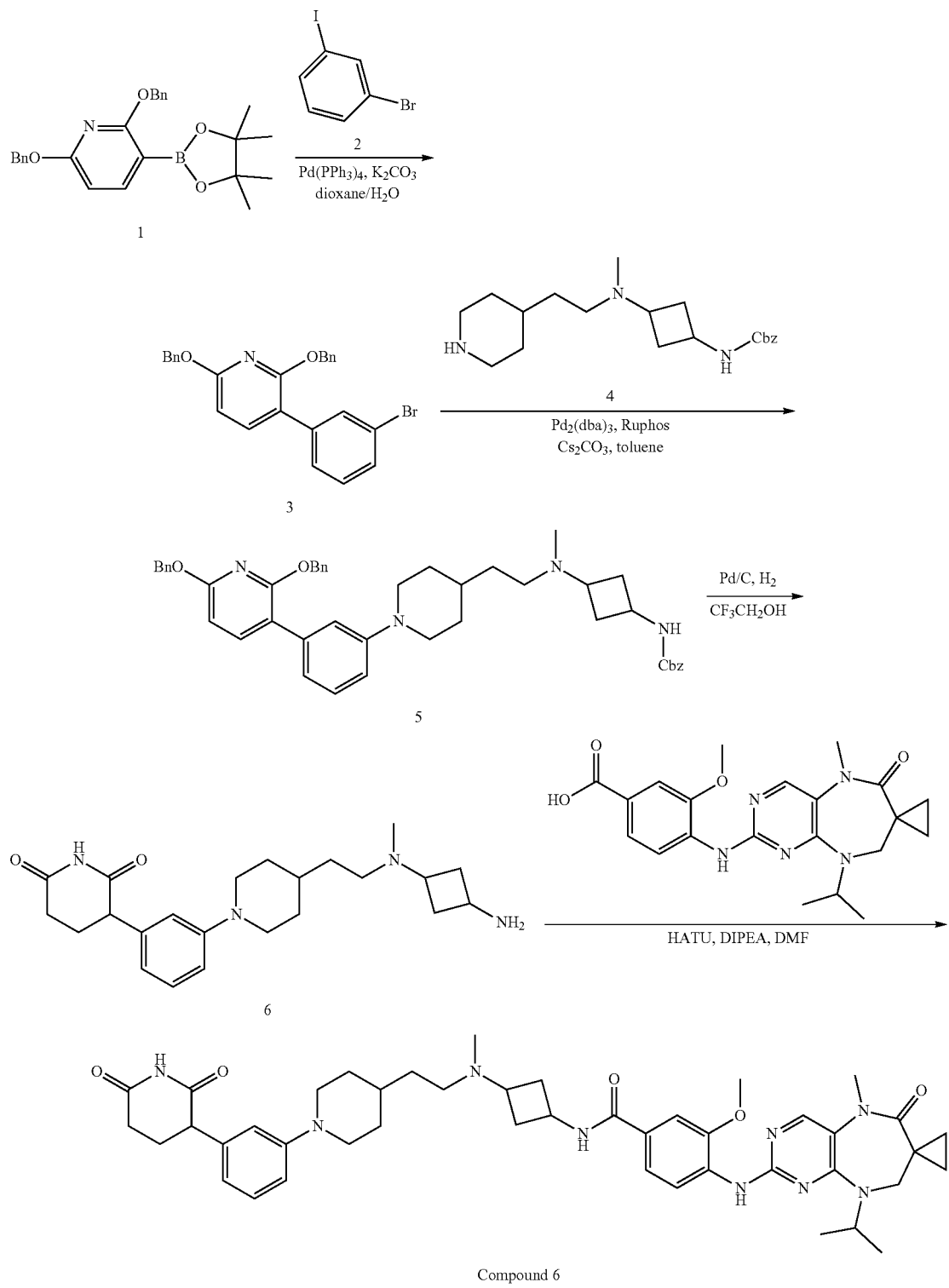

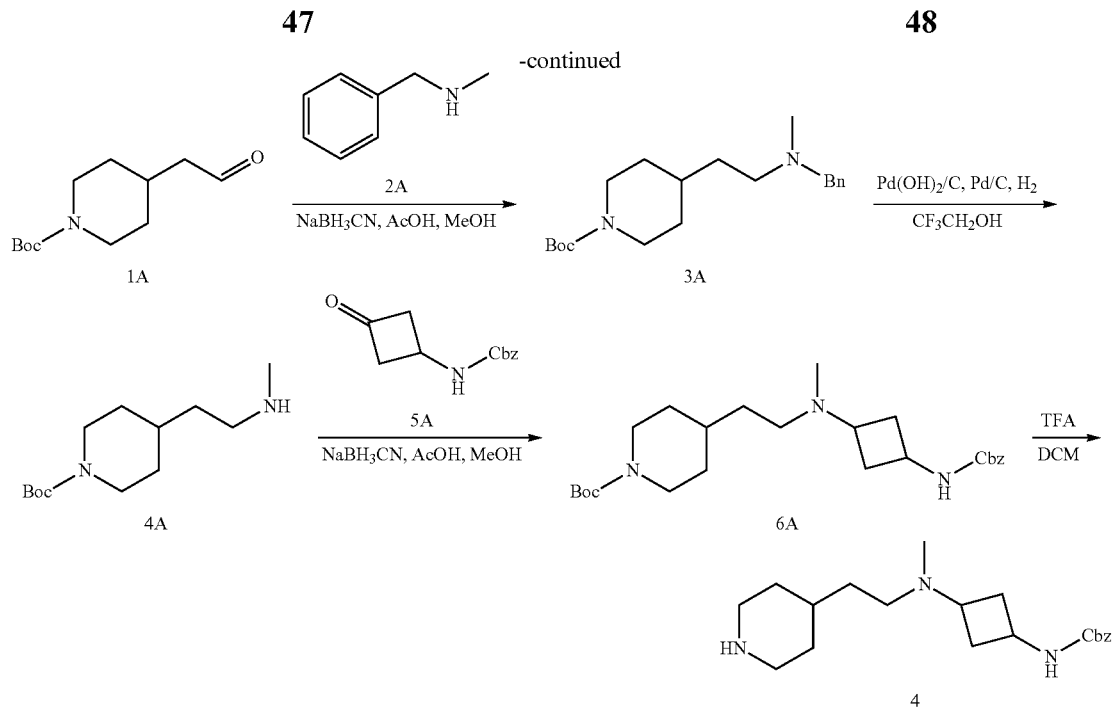

Step 1. Synthesis of 2,6-bis(benzyloxy)-3-(3-bromophenyl)pyridine (3)

To a solution of 2,6-dibenzyloxy-3-(4,4,5,5-tetramethyl-1,3,2-dioxaborolan-2-yl)pyridine (7.5 g, 17.97 mmol) and 1-bromo-3-iodo-benzene (4.07 g, 14.38 mmol, 1.83 mL) in dioxane (80 mL) and H$_2$O (20 mL) were added Pd(PPh$_3$)$_4$ (1.04 g, 898.63 μmol) and K$_2$CO$_3$ (7.45 g, 53.92 mmol) at 20° C. under N$_2$ atmosphere and the resulting mixture was stirred at 100° C. for 16 h. LCMS showed starting material was consumed completely and a peak (30%) with desired mass. The reaction mixture was combined with another batch (0.5 g scale) for work-up. The combined reaction mixture was diluted with H$_2$O (140 mL) and extracted with EtOAc (140 mL×3). The organic layer was dried over Na$_2$SO$_4$, filtered and concentrated. The residue was purified by flash silica gel chromatography (80 g SepaFlash Silica Flash Column, Eluent of 0~0% EtOAc/Petroleum ether gradient @ 100 mL/min) to afford 2,6-dibenzyloxy-3-(3-bromophenyl)pyridine (3.9 g, 8.29 mmol, 47.12% yield) as a yellow oil. MS (M+H)$^+$=446.2

Step 2. Synthesis of tert-butyl 4-(2-(benzyl(methyl)amino)ethyl)piperidine-1-carboxylate (3A)

To a solution of tert-butyl 4-(2-oxoethyl)piperidine-1-carboxylate (10 g, 43.99 mmol) and N-methyl-1-phenyl-methanamine (5.33 g, 43.99 mmol, 5.68 mL) in MeOH (160 mL) was added AcOH (2.64 g, 43.99 mmol, 2.52 mL) at 20° C. The reaction mixture was stirred at 20° C. for 0.5 h. Then NaBH$_3$CN (8.29 g, 131.98 mmol) was added slowly at 20° C. and the resulting mixture was stirred at 20° C. for 12 h. LCMS showed the starting material was consumed completely and a peak (86%) with desired mass. The reaction mixture was diluted with H$_2$O (200 mL) and extracted with EtOAc (200 mL×3). The organic layer was dried over Na$_2$SO$_4$, filtered and concentrated. The residue was purified by flash silica gel chromatography (120 g SepaFlash Silica Flash Column, Eluent of 0~100% EtOAc/Petroleum ether gradient @ 100 mL/min) to afford tert-butyl 4-(2-(benzyl (methyl)amino)ethyl)piperidine-1-carboxylate (19.1 g, 14.57 mmol, 33.12% yield, 95% purity) as a colorless oil. MS (M+H)$^+$=333.3

Step 3. Synthesis of tert-butyl 4-(2-(methylamino)ethyl)piperidine-1-carboxylate (4A)

To a solution of tert-butyl 4-(2-(benzyl(methyl)amino)ethyl)piperidine-1-carboxylate (19 g, 57.15 mmol) in CF$_3$CH$_2$OH (250 mL) were added Pd/C (2 g, 10% purity) and Pd(OH)$_2$/C (2 g, 20% purity) under N$_2$ atmosphere. The suspension was degassed and purged with H$_2$ for 3 times. The mixture was stirred at 60° C. for 16 h under H$_2$ (50 Psi). LCMS showed a peak (56%) with mass of starting material and a peak with desired mass. The reaction mixture was diluted with CF$_3$CH$_2$OH (300 mL) and filtered. The filtrate was concentrated in vacuum to afford tert-butyl 4-(2-(methylamino)ethyl)piperidine-1-carboxylate (13.7 g, crude) as a colorless oil. MS (M+H)$^+$=243.5

Step 4. Synthesis of tert-butyl 4-(2-((3-(((benzyloxy)carbonyl)amino)cyclobutyl)(methyl)amino)ethyl)piperidine-1-carboxylate (6A)

To a solution of tert-butyl 4-(2-(methylamino)ethyl)piperidine-1-carboxylate (13.7 g, 56.53 mmol) and benzyl N-(3-oxocyclobutyl)carbamate (6.20 g, 28.26 mmol) in MeOH (200 mL) was added AcOH (3.39 g, 56.53 mmol, 3.23 mL) at 20° C., the reaction mixture was stirred at 20° C. for 0.5 h, then NaBH$_3$CN (10.66 g, 169.58 mmol) was added portion-wise at 20° C. and the resulting mixture was stirred at 20° C. for another 12 h. LCMS showed the starting material was consumed completely and a peak (42%) with desired mass. The reaction mixture was diluted with H$_2$O (400 mL) and extracted with EtOAc (400 mL×3). The organic layer was washed with brine (200 mL×3), dried over Na$_2$SO$_4$, filtered and concentrated. The residue was purified by flash silica gel chromatography (120 g SepaFlash Silica Flash Column, Eluent of 0~100% EtOAc/Petroleum ether to 0~10% EtOAc:Methanol gradient @ 100 mL/min) to afford tert-butyl 4-(2-((3-(((benzyloxy)carbonyl)amino)cyclobutyl)(methyl)amino)ethyl)piperidine-1-carboxylate (7.9 g, 16.49 mmol, 29.17% yield, 93% purity) as a colorless oil. MS (M+H)$^+$=446.2

Step 5. Synthesis of benzyl (3-(methyl(2-(piperidin-4-yl)ethyl)amino)cyclobutyl)carbamate (4)

To a solution of tert-butyl 4-(2-((3-(((benzyloxy)carbonyl)amino)cyclobutyl)(methyl)amino)ethyl)piperidine-1-carboxylate (7.9 g, 17.73 mmol) in DCM (40 mL) was added TFA (12.13 g, 106.38 mmol, 7.88 mL) at 20° C. and the resulting mixture was stirred at 20° C. for 16 h. LCMS showed the starting material was consumed completely and a peak with desired mass. To this reaction mixture was added DIPEA to adjust the pH=7 at 0° C. The reaction mixture was concentrated in vacuum to afford benzyl (3-(methyl(2-(piperidin-4-yl)ethyl)amino)cyclobutyl)carbamate (6.13 g, crude) as a yellow oil. MS (M+H)$^+$=346.2

Step 6. Synthesis of benzyl (3-((2-(1-(3-(2,6-bis(benzyloxy)pyridin-3-yl)phenyl)piperidin-4-yl)ethyl)(methyl)amino)cyclobutyl)carbamate (5)

To a solution of 2,6-dibenzyloxy-3-(3-bromophenyl)pyridine (3.9 g, 8.74 mmol) and benzyl (3-(methyl(2-(piperidin-4-yl)ethyl)amino)cyclobutyl)carbamate (3.62 g, 10.49 mmol) in toluene (60 mL) were added Pd$_2$(dba)$_3$ (160.03 mg, 174.80 μmol), RuPhos (407.74 mg, 874.00 μmol) and Cs$_2$CO$_3$ (8.54 g, 26.22 mmol) at 20° C. under N$_2$ atmosphere and the resulting mixture was stirred at 100° C. for 16 h under N$_2$ atmosphere. LCMS showed 30% of starting material remained and a peak (7%) with desired mass, additional benzyl (3-(methyl(2-(piperidin-4-yl)ethyl)amino)cyclobutyl)carbamate (3.02 g, 8.74 mmol), Pd$_2$(dba)$_3$ (160.07 mg, 174.80 μmol), RuPhos (407.84 mg, 874.00 μmol) and Cs$_2$CO$_3$ (5.70 g, 17.48 mmol) was added and the resulting mixture was stirred at 100° C. for another 16 h under N$_2$. LCMS showed 24% of starting material remained and 7% peak with desired mass was detected. The reaction mixture was concentrated in vacuum. The residue was purified by flash silica gel chromatography (80 g SepaFlash Silica Flash Column, Eluent of 0~100% EtOAc/Petroleum ether gradient @ 100 mL/min) followed by prep-HPLC (column: Phenomenex luna C18 150×40 mm×15 μm; mobile phase: [water (FA)-ACN]; B %: 35%-65%, 10 min). The pH of the eluent was adjusted to ~7 with saturated NaHCO$_3$ and extracted with EtOAc (15 mL×3). The organic layer was dried over Na$_2$SO$_4$, filtered and concentrated to afford benzyl (3-((2-(1-(3-(2,6-bis(benzyloxy)pyridin-3-yl)phenyl)piperidin-4-yl)ethyl)(methyl)amino)cyclobutyl)carbamate (441 mg, 576.92 μmol, 50.57% yield, 93% purity) as a yellow oil. MS (M+H)$^+$=711.3

Step 7. Synthesis of 3-(3-(4-(2-((3-aminocyclobutyl)(methyl)amino)ethyl)piperidin-1-yl)phenyl)piperidine-2,6-dione (6)

To a solution of benzyl (3-((2-(1-(3-(2,6-bis(benzyloxy)pyridin-3-yl)phenyl)piperidin-4-yl)ethyl)(methyl)amino)cyclobutyl)carbamate (441 mg, 620.34 μmol) in CF$_3$CH$_2$OH (15 mL) was added Pd/C (120 mg, 10% purity) under N$_2$ atmosphere. The suspension was degassed and purged with H$_2$ for 3 times. The mixture was stirred at 20° C. for 16 h under H$_2$ (15 Psi). LCMS showed starting material remained and a peak with desired mass was detected, the reaction mixture was stirred at 20° C. for 16 h under H$_2$ (15 Psi). LCMS showed the starting material was consumed completely and a peak with desired mass. The reaction mixture was diluted with EtOH (30 mL) and filtered. The filtrate was concentrated in vacuum to afford 3-(3-(4-(2-((3-aminocyclobutyl)(methyl)amino)ethyl)piperidin-1-yl)phenyl)piperidine-2,6-dione (162 mg, 406.48 μmol, 65.53% yield) as a colorless oil. MS (M+H)$^+$=399.3

Step 8. Synthesis of N-(3-((2-(1-(3-(2,6-dioxopiperidin-3-yl)phenyl)piperidin-4-yl)ethyl)(methyl)amino)cyclobutyl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (Compound 6)

To a solution of 4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzoic acid (130 mg, 315.95 μmol) in DMF (3 mL) were added HATU (132.15 mg, 347.55 μmol) and DIPEA (122.50 mg, 947.86 μmol, 165.10 μL). The mixture was stirred at 20° C. for 10 min and a solution of 3-(3-(4-(2-((3-aminocyclobutyl)(methyl)amino)ethyl)piperidin-1-yl)phenyl)piperidine-2,6-dione (151.10 mg, 379.14 μmol) in DMF (3 mL) was added and the resulting mixture was stirred at 20° C. for 1 h. LCMS showed starting material was consumed completely and a peak (45%) with desired mass. The reaction mixture was diluted with H$_2$O (25 mL) and extracted with EtOAc (25 mL×3). The organic layer was washed with brine (25 mL×3), dried over Na$_2$SO$_4$, filtered and concentrated. The residue was purified by flash silica gel chromatography (10 g SepaFlash Silica Flash Column, Eluent of 0~100% EtOAc/Petroleum ether to 0~10% Dichloromethane/Methanol gradient @ 100 mL/min) and re-purified by prep-HPLC (column: Waters Xbridge 150×25 mm×5 μm; mobile phase: [water (NH$_4$HCO$_3$)-ACN]; B %: 38%-68%, 8 min), the eluent was lyophilized to afford N-(3-((2-(1-(3-(2,6-dioxopiperidin-3-yl)phenyl)piperidin-4-yl)ethyl)(methyl)amino)cyclobutyl)-4-((9'-isopropyl-5'-methyl-6'-oxo-5',6',8',9'-tetrahydrospiro[cyclopropane-1,7'-pyrimido[4,5-b][1,4]diazepin]-2'-yl)amino)-3-methoxybenzamide (73.1 mg, 91.65 μmol, 29.01% yield, 99.3% purity) as a white solid. MS (M+H)$^+$=792.4

$^1$H NMR (400 MHz, DMSO-d$_6$) δ=10.78 (s, 1H), 8.41 (br d, J=8.3 Hz, 2H), 7.97 (s, 1H), 7.64 (s, 1H), 7.57-7.46 (m, 2H), 7.13 (t, J=7.9 Hz, 1H), 6.87-6.73 (m, 2H), 6.57 (d, J=7.6 Hz, 1H), 4.89-4.78 (m, 1H), 4.21-4.08 (m, 1H), 3.94 (s, 3H), 3.74 (dd, J=5.0, 11.0 Hz, 1H), 3.65 (br d, J=11.7 Hz, 2H), 3.46 (s, 2H), 3.16 (s, 3H), 2.66-2.56 (m, 4H), 2.43 (br d, J=4.2 Hz, 3H), 2.27-2.11 (m, 3H), 2.09-1.96 (m, 4H), 1.92-1.81 (m, 2H), 1.74 (br d, J=10.8 Hz, 2H), 1.51-1.32 (m, 3H), 1.29-1.20 (m, 2H), 1.16 (d, J=6.7 Hz, 6H), 0.95-0.88 (m, 2H), 0.72-0.64 (m, 2H).

Example 7. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)methyl)(methyl)amino)cyclohexyl)-3-methoxybenzamide (Compound 7)
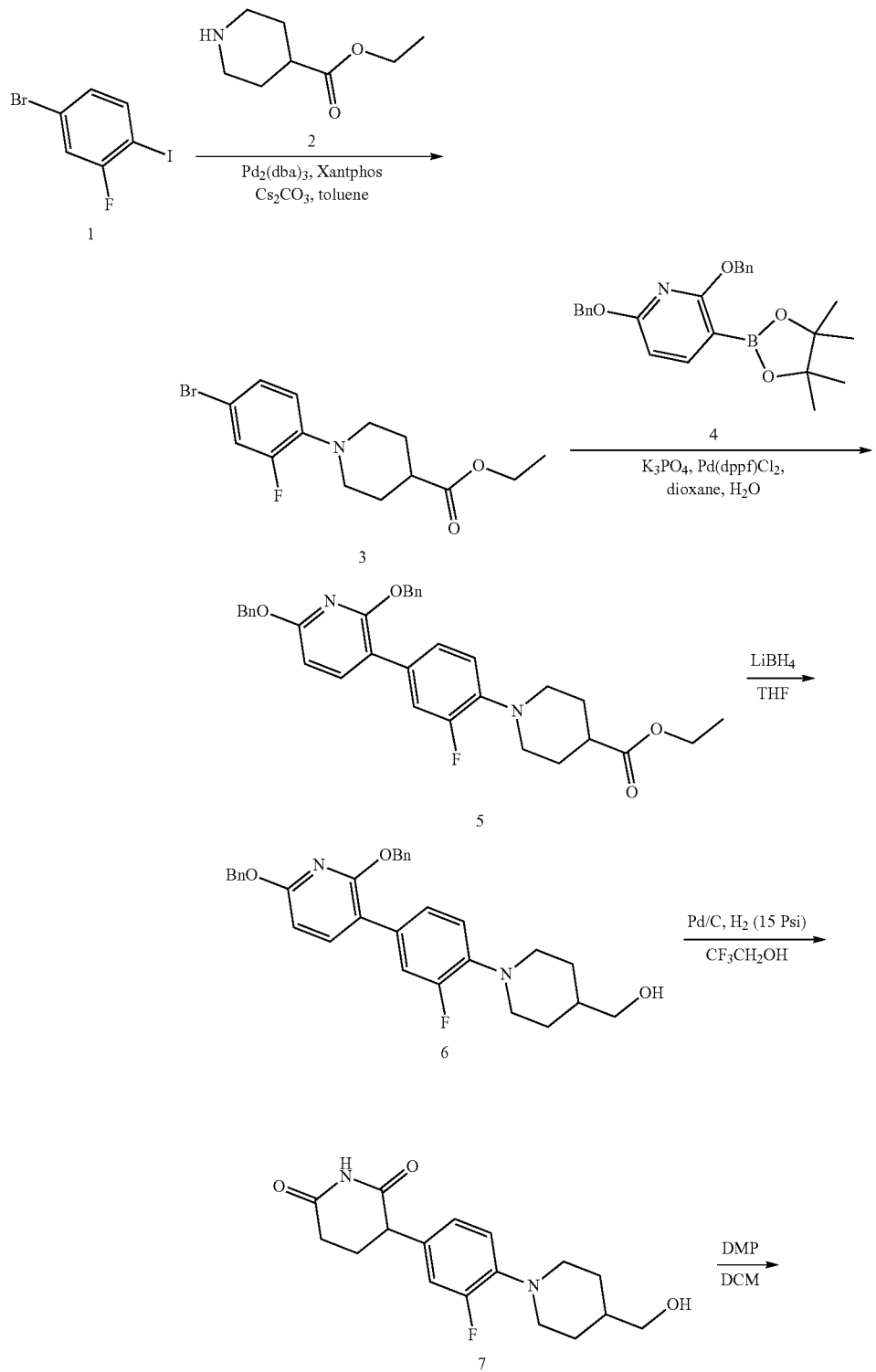

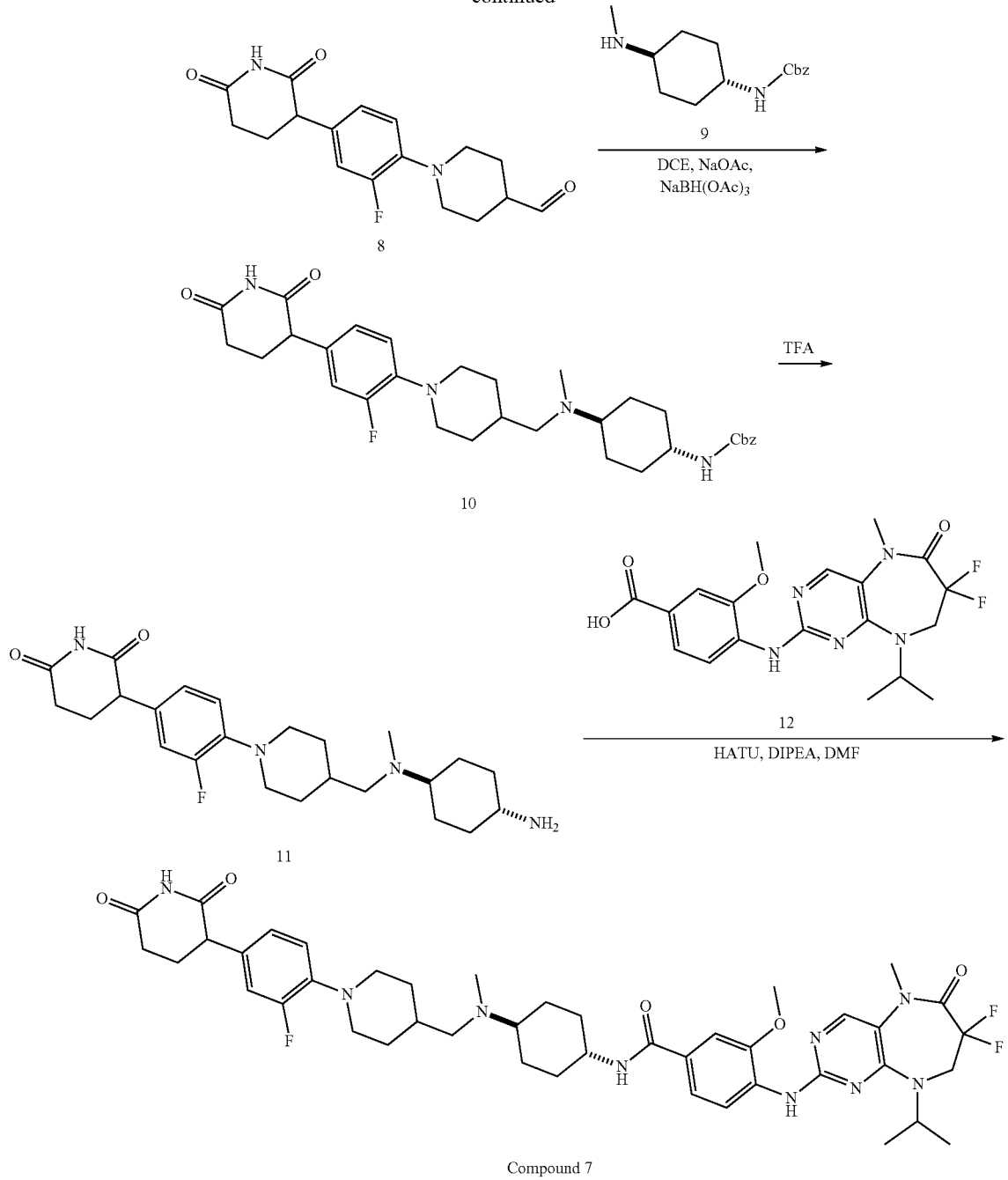

Compound 7

Step 1. Synthesis of ethyl 1-(4-bromo-2-fluorophenyl)piperidine-4-carboxylate (3)

To a solution of 4-bromo-2-fluoro-1-iodobenzene (5 g, 16.62 mmol), ethyl piperidine-4-carboxylate (2.35 g, 14.96 mmol, 2.31 mL) and Cs$_2$CO$_3$ (16.24 g, 49.85 mmol) in toluene (50 mL) were added Pd$_2$(dba)$_3$ (760.83 mg, 830.86 µmol) and Xantphos (961.50 mg, 1.66 mmol). The mixture was stirred under N$_2$ at 90° C. for 3 h. LCMS showed a main peak with desired mass. The reaction mixture was diluted with H$_2$O (50 mL), extracted with EtOAc (50 mL×3). The combined organic layers were washed with brine (100 mL×2), dried over Na$_2$SO$_4$, filtered. The filtrate was concentrated under reduced pressure. The residue was purified by flash silica gel chromatography (Biotage; 20 g SepaFlash Silica Flash Column, Eluent of 0~15% EtOAc/Petroleum ether gradient @ 40 mL/min) to afford ethyl 1-(4-bromo-2-fluorophenyl)piperidine-4-carboxylate (600 mg, 1.82 mmol, 10.94% yield) as yellow oil. MS (M+H)$^+$=330.3

Step 2. Synthesis of ethyl 1-(4-(2,6-bis(benzyloxy)pyridin-3-yl)-2-fluorophenyl)piperidine-4-carboxylate (5)

To a mixture of ethyl 1-(4-bromo-2-fluorophenyl)piperidine-4-carboxylate (600 mg, 1.82 mmol), 2,6-bis(benzyloxy)-3-(4,4,5,5-tetramethyl-1,3,2-dioxaborolan-2-yl)pyridine (1.52 g, 3.63 mmol) and $K_3PO_4$ (1.16 g, 5.45 mmol) in dioxane (12 mL) and $H_2O$ (2.4 mL) was added $Pd(dppf)Cl_2$ (132.96 mg, 181.71 µmol) at 25° C. The resulting mixture was purged and degassed with $N_2$ for three times, then the reaction mixture was heated to 90° C. and stirred at 90° C. for 4 hrs. LCMS showed a main peak with desired mass. The mixture was filtered through a pad of celite. The filtrate was concentrated in vacuum. The residue was purified by flash silica gel chromatography (Biotage; 20 g SepaFlash Silica Flash Column, Eluent of 0~10% EtOAc/Petroleum ether gradient @ 40 mL/min) to afford ethyl 1-(4-(2,6-bis(benzyloxy)pyridin-3-yl)-2-fluorophenyl)piperidine-4-carboxylate (660 mg, 1.17 mmol, 64.50% yield, 96% purity) as a yellow solid. MS $(M+H)^+$=541.3.

Step 3. Synthesis of (1-(4-(2,6-bis(benzyloxy)pyridin-3-yl)-2-fluorophenyl)piperidin-4-yl)methanol (6)

To a solution of ethyl 1-(4-(2,6-bis(benzyloxy)pyridin-3-yl)-2-fluorophenyl)piperidine-4-carboxylate (450 mg, 832.37 µmol) in THF (10 mL) was added $LiBH_4$ (37 mg, 1.70 mmol), the mixture was stirred at 20° C. for 18 h. LCMS showed a main peak with desired mass. The reaction mixture was quenched by addition of $NH_4Cl$ (10 mL) at 0° C., extracted with EtOAc (10 mL×3). The combined organic layers were dried over $Na_2SO_4$, filtered. The filtrate was concentrated under reduced pressure to afford (1-(4-(2,6-bis(benzyloxy)pyridin-3-yl)-2-fluorophenyl)piperidin-4-yl)methanol (400 mg, crude) as a colorless oil. MS $(M+H)^+$=499.3

Step 4. Synthesis of 3-(3-fluoro-4-(4-(hydroxymethyl)piperidin-1-yl)phenyl)piperidine-2,6-dione (7)

A mixture of (1-(4-(2,6-bis(benzyloxy)pyridin-3-yl)-2-fluorophenyl)piperidin-4-yl)methanol (400 mg, 802.27 µmol) and Pd/C (40 mg, 10% purity) in $CF_3CH_2OH$ (20 mL) was degassed and purged with $H_2$ for 3 times, then the mixture was stirred at 20° C. for 2 h under $H_2$ (15 Psi) atmosphere. LCMS showed a main peak with desired mass. The mixture was concentrated in vacuum to afford 3-(3-fluoro-4-(4-(hydroxymethyl)piperidin-1-yl)phenyl)piperidine-2,6-dione (200 mg, crude) as a white solid. MS $(M+H)^+$=321.2

Step 5. Synthesis of 1-(4-(2,6-dioxopiperidin-3-yl)-2-fluorophenyl)piperidine-4-carbaldehyde (8)

To a solution of 3-(3-fluoro-4-(4-(hydroxymethyl)piperidin-1-yl)phenyl)piperidine-2,6-dione (200 mg, 624.30 µmol) in DCM (1 mL) was added DMP (397.19 mg, 936.45 µmol, 289.92 µL). The mixture was stirred at 20° C. for 2 hr. TLC indicated the starting material was consumed completely. The mixture was filtered. The filtrate was concentrated under reduced pressure to afford 1-(4-(2,6-dioxopiperidin-3-yl)-2-fluorophenyl)piperidine-4-carbaldehyde (198 mg, crude) as a brown oil. MS $(M+H)^+$=319.4

Step 6. Synthesis of benzyl ((1r,4r)-4-(((1-(4-(2,6-dioxopiperidin-3-yl)-2-fluorophenyl)piperidin-4-yl)methyl)(methyl)amino)cyclohexyl)carbamate (trans) (10)

To a solution of benzyl ((1r,4r)-4-(methylamino)cyclohexyl)carbamate (trans) (100 mg, 334.66 µmol, HCl salt) in DCE (2 mL) were added 1-(4-(2,6-dioxopiperidin-3-yl)-2-fluorophenyl)piperidine-4-carbaldehyde (106.54 mg, 334.66 µmol) and NaOAc (41.18 mg, 502.00 µmol). The mixture was stirred at 25° C. for 1 hr. Then $NaBH(OAc)_3$ (355 mg, 1.67 mmol) was added, the resulting mixture was stirred at 25° C. for 15 hr. LCMS showed a peak (24%) with desired mass. The reaction mixture was quenched by addition of $NaHCO_3$ (5 mL), extracted with EtOAc (5 mL×3). The combined organic layers were washed with brine (15 mL×2), dried over $Na_2SO_4$, filtered. The filtrate was concentrated under reduced pressure. The residue was purified by flash silica gel chromatography (Biotage; 10 g SepaFlash Silica Flash Column, Eluent of 50~100% EtOAc/Petroleum ether to 20% Methanol/EtOAc gradient @ 40 mL/min) and re-purified by reversed-phase HPLC (column: Phenomenex Synergi C18 150×25 mm×10 µm; mobile phase: [water (FA)-ACN]; B %: 13%-43%, 10 min). The eluent was lyophilized to afford benzyl ((1r,4r)-4-(((1-(4-(2,6-dioxopiperidin-3-yl)-2-fluorophenyl)piperidin-4-yl)methyl)(methyl)amino)cyclohexyl)carbamate (trans) (140 mg, 222.36 µmol, 66.44% yield, 97% purity, FA salt) as a yellow solid. MS $(M+H)^+$=565.6

Step 7. Synthesis of 3-(4-(4-((((1r,4r)-4-aminocyclohexyl)(methyl)amino)methyl)piperidin-1-yl)-3-fluorophenyl)piperidine-2,6-dione (trans) (11)

A mixture of benzyl ((1r,4r)-4-(((1-(4-(2,6-dioxopiperidin-3-yl)-2-fluorophenyl)piperidin-4-yl)methyl)(methyl)amino)cyclohexyl)carbamate (trans) (70 mg, 114.62 µmol, FA) in TFA (1 mL) was stirred at 50° C. for 16 h. LCMS showed a main peak with desired mass. The mixture was concentrated in vacuum to afford 3-(4-(4-((((1r,4r)-4-aminocyclohexyl)(methyl)amino)methyl)piperidin-1-yl)-3-fluorophenyl)piperidine-2,6-dione (60 mg, crude, TFA salt) as a brown oil. MS $(M+H)^+$=431.5

Step 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)methyl)(methyl)amino)cyclohexyl)-3-methoxybenzamide (Compound 7)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (46.43 mg, 110.18 µmol) in DMF (1 mL) were added HATU (62.84 mg, 165.26 µmol), DIPEA (71.20 mg, 550.88 µmol, 95.95 µL), the mixture was stirred at 15° C. for 0.5 h, 3-(4-(4-((((1r,4r)-4-aminocyclohexyl)(methyl)amino)methyl)piperidin-1-yl)-3-fluorophenyl)piperidine-2,6-dione (60 mg, 110.18 µmol, TFA salt) was added, the mixture was stirred at 15° C. for 2 h. LCMS showed a main peak with desired mass. The reaction mixture was diluted with water (5 mL), extracted with EtOAc (10 mL×5). The combined organic layers were washed with brine (10 mL×2), dried over $Na_2SO_4$, filtered. The filtrate was concentrated under reduced pressure. The residue was purified by prep-TLC ($SiO_2$, DCM:MeOH=9:1) and re-purified by reversed-phase HPLC (column: Waters Xbridge 150×25 mm×5 µm; mobile phase: [water ($NH_4HCO_3$)-ACN]; B %: 44%-74%, 8 min). The eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-(((1-(4-(2,6-dioxopiperidin-3-yl)-2-fluorophenyl)piperidin-4-yl)methyl)(methyl)amino)cyclohexyl)-3- methoxybenzamide (34.9 mg, 41.01 μmol, 37.22% yield, 98% purity) as a white solid. MS (M+H)+=834.8
¹H NMR (400 MHz, DMSO-d₆) δ=10.81 (s, 1H), 8.30 (d, J=8.4 Hz, 1H), 8.22 (s, 1H), 8.06 (d, J=7.5 Hz, 1H), 7.87 (s, 1H), 7.54-7.44 (m, 2H), 7.05-6.90 (m, 3H), 4.94-4.81 (m, 1H), 4.11-3.98 (m, 2H), 3.93 (s, 3H), 3.85-3.68 (m, 2H), 3.41-3.35 (m, 2H), 3.30 (s, 3H), 2.69-2.58 (m, 4H), 2.35-2.26 (m, 3H), 2.25-2.12 (m, 4H), 2.04-1.95 (m, 1H), 1.94-1.87 (m, 2H), 1.85-1.73 (m, 4H), 1.58-1.47 (m, 1H), 1.43-1.32 (m, 4H), 1.29-1.17 (m, 8H).
Example 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1s,4s)-4-(((1-(4-(2,6-dioxopiperidin-3-yl)-2-fluorophenyl)piperidin-4-yl)methyl)(methyl)amino)cyclohexyl)-3-methoxybenzamide (cis) (Compound 8)
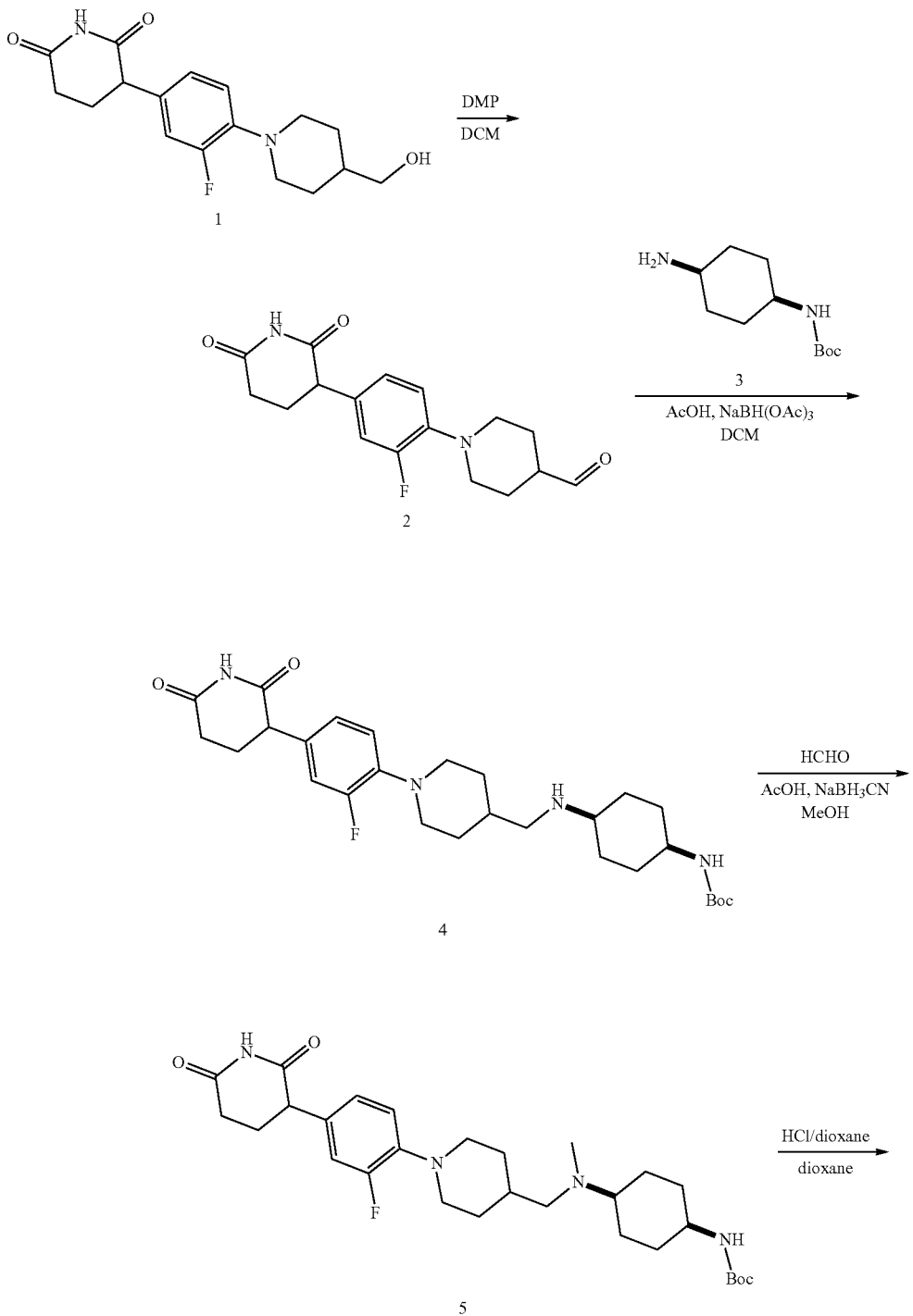

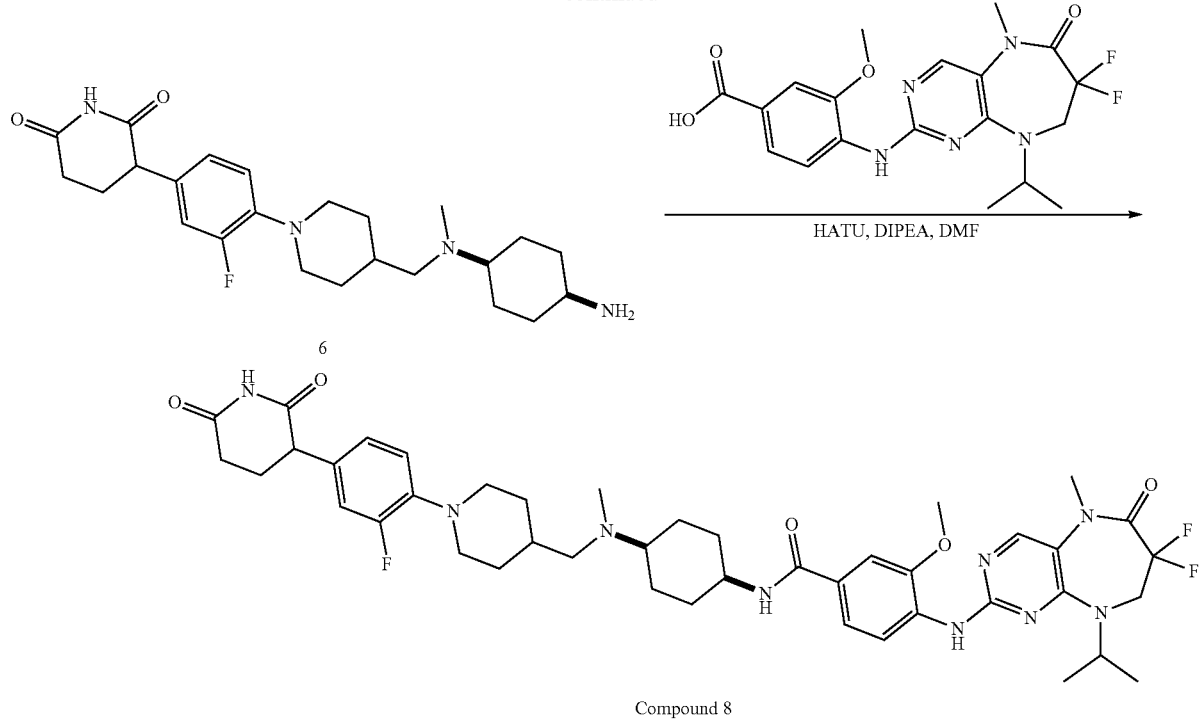

Compound 8

Step 1. Synthesis of 1-(4-(2,6-dioxopiperidin-3-yl)-2-fluorophenyl)piperidine-4-carbaldehyde (2)

To the solution of 3-(3-fluoro-4-(4-(hydroxymethyl)piperidin-1-yl)phenyl)piperidine-2,6-dione (0.5 g, 1.56 mmol) in DCM (20 mL) was added DMP (992.97 mg, 2.34 mmol) and the resulting mixture was stirred at 20° C. for 2 h. TLC (Petroleum ether/EtOAc=1/1) showed the starting material was consumed completely and new spot was formed. The mixture was filtered and the filtrate was concentrated under reduced pressure to afford 1-(4-(2,6-dioxopiperidin-3-yl)-2-fluorophenyl)piperidine-4-carbaldehyde (0.5 g, crude) as yellow oil. MS (M+H)$^+$=319.4

Step 2. Synthesis of tert-butyl ((1s,4s)-4-(((1-(4-(2,6-dioxopiperidin-3-yl)-2-fluorophenyl) piperidin-4-yl)methyl)amino)cyclohexyl)carbamate (cis) (4)

To the solution of 1-(4-(2,6-dioxopiperidin-3-yl)-2-fluorophenyl)piperidine-4-carbaldehyde (0.5 g, 1.57 mmol) and tert-butyl ((1s,4s)-4-aminocyclohexyl)carbamate (336.59 mg, 1.57 mmol) in DCM (10 mL) were added AcOH (113.18 mg, 1.88 mmol, 107.79 µL) and NaBH (OAc)$_3$ (998.65 mg, 4.71 mmol) and the resulting mixture was stirred at 20° C. for 12 h. LCMS showed a peak (19%) with desired mass. The mixture was poured into water (50 mL) and extracted with DCM (30 mL×3). The combined organic layer was washed with brine (100 mL), dried over Na$_2$SO$_4$, filtered and concentrated. The residue was purified by flash silica gel chromatography (10 g SepaFlash Silica Flash Column, Eluent of 0~10% MeOH/EtOAc gradient @ 80 mL/min) to afford tert-butyl ((1s,4s)-4-(((1-(4-(2,6-dioxopiperidin-3-yl)-2-fluorophenyl) piperidin-4-yl)methyl)amino)cyclohexyl)carbamate (cis) (0.7 g, 1.00 mmol, 63.84% yield, 74% purity) as yellow oil. MS (M+H)$^+$=517.2

Step 3. Synthesis of tert-butyl ((1s,4s)-4-(((1-(4-(2,6-dioxopiperidin-3-yl)-2-fluorophenyl)piperidin-4-yl)methyl)(methyl)amino)cyclohexyl)carbamate (cis) (5)

To the solution of tert-butyl ((1s,4s)-4-(((1-(4-(2,6-dioxopiperidin-3-yl)-2-fluorophenyl) piperidin-4-yl)methyl)amino)cyclohexyl)carbamate (cis) (0.6 g, 1.16 mmol) and formaldehyde (188.49 mg, 2.32 mmol, 172.92 µL, 37% purity) in MeOH (10 mL) were added AcOH (69.74 mg, 1.16 mmol, 66.42 µL) and NaBH$_3$CN (218.94 mg, 3.48 mmol) and the resulting mixture was stirred at 20° C. for 12 h. LCMS showed a peak (95%) with desired mass. The reaction mixture was poured into water (50 mL) and extracted with EtOAc (50 mL×3). The combined organic layer was washed with brine (100 mL), dried over Na$_2$SO$_4$, filtered and concentrated. The residue was purified by flash silica gel chromatography (20 g SepaFlash Silica Flash Column, Eluent of 0~10% MeOH/EtOAc gradient @ 80 mL/min) to afford tert-butyl ((1s,4s)-4-(((1-(4-(2,6-dioxopiperidin-3-yl)-2-fluorophenyl)piperidin-4-yl)methyl)(methyl)amino)cyclohexyl)carbamate (cis) (0.5 g, 942.20 µmol, 81.13% yield) as yellow oil. MS (M+H)$^+$=531.4

Step 4. Synthesis of 3-(4-(4-((((1s,4s)-4-aminocyclohexyl)(methyl)amino)methyl)piperidin-1-yl)-3-fluorophenyl)piperidine-2,6-dione (cis) (6)

To the solution of tert-butyl ((1s,4s)-4-(((1-(4-(2,6-dioxopiperidin-3-yl)-2-fluorophenyl) piperidin-4-yl)methyl)(methyl)amino)cyclohexyl)carbamate (cis) (0.2 g, 376.88 µmol) in dioxane (5 mL) was added HCl/dioxane (4 M, 5 mL) and the mixture was stirred at 20° C. for 2 h. LCMS showed a major peak (100%) with desired mass. The mixture was concentrated to afford 3-(4-(4-((((1s,4s)-4-aminocyclohexyl)(methyl)amino)methyl)piperidin-1-yl)-3-fluorophenyl) piperidine-2,6-dione (cis) (200 mg, 370.41 μmol, 98.28% yield, 3HCl) as yellow oil. MS (M+H)+=431.2.

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1s,4s)-4-(((1-(4-(2,6-dioxopiperidin-3-yl)-2-fluorophenyl)piperidin-4-yl)methyl)(methyl)amino)cyclohexyl)-3-methoxybenzamide (cis) (Compound 8)

To the solution of 3-(4-(4-((((1s,4s)-4-aminocyclohexyl)(methyl)amino)methyl)piperidin-1-yl)-3-fluorophenyl)piperidine-2,6-dione (cis) (0.2 g, 370.41 μmol, 3HCl) and 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (156.09 mg, 370.41 μmol) in DMF (5 mL) were added HATU (169.01 mg, 444.49 μmol) and DIPEA (287.24 mg, 2.22 mmol, 387.11 μL). The resulting mixture was stirred at 20° C. for 12 h. LCMS showed a peak with desired mass. The mixture was poured into water (50 mL) and extracted with EtOAc (30 mL×3). The combined organic layer was washed with brine (50 mL), dried over Na$_2$SO$_4$, filtered and concentrated. The resulting mixture was purified by prep-HPLC (column: Waters Xbridge C18 150*50 mm*10 μm; mobile phase: [water (NH$_4$HCO$_3$)-ACN]; B %: 45%-75%, 10 min) and re-purified by prep-HPLC (column: Unisil 3-100 C18 μLtra 150*50 mm*3 μm; mobile phase: [water (FA)-ACN]; B %: 16%-46%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-((1s,4s)-4-(((1-(4-(2,6-dioxopiperidin-3-yl)-2-fluorophenyl)piperidin-4-yl)methyl)(methyl)amino)cyclohexyl)-3-methoxybenzamide (cis) (55.8 mg, 64.90 μmol, 17.52% yield, 97% purity) as a white solid. MS (M+H)+=834.6

$^1$H NMR (400 MHz, DMSO-d$_6$) δ=10.81 (s, 1H), 8.32-8.29 (m, 1H), 8.22-8.21 (m, 1H), 7.99 (br d, J=7.3 Hz, 1H), 7.88 (s, 1H), 7.52 (br d, J=8.7 Hz, 1H), 7.48 (d, J=1.6 Hz, 1H), 7.02-6.93 (m, 3H), 4.93-4.85 (m, 1H), 4.04 (br t, J=13.5 Hz, 2H), 3.95 (s, 4H), 3.79 (dd, J=4.8, 11.7 Hz, 1H), 3.33 (s, 5H), 2.69-2.59 (m, 4H), 2.30-2.26 (m, 3H), 2.23-2.14 (m, 4H), 2.04-1.97 (m, 1H), 1.87-1.79 (m, 6H), 1.60-1.46 (m, 5H), 1.32-1.24 (m, 8H).

Example 9. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(4-(2,6-dioxopiperidin-3-yl)-2-fluorophenyl)piperazin-1-yl)ethyl)(methyl)amino)cyclohexyl)-3-methoxybenzamide (trans) (Compound 9)

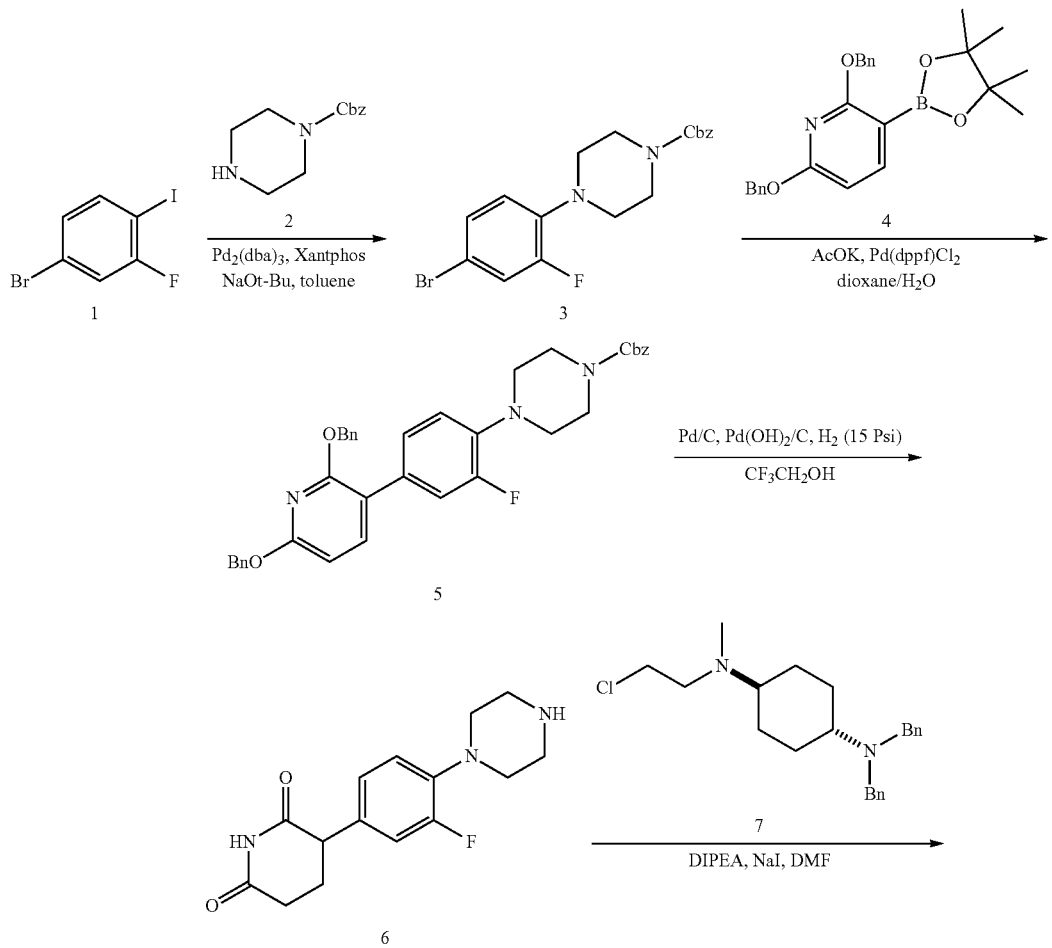

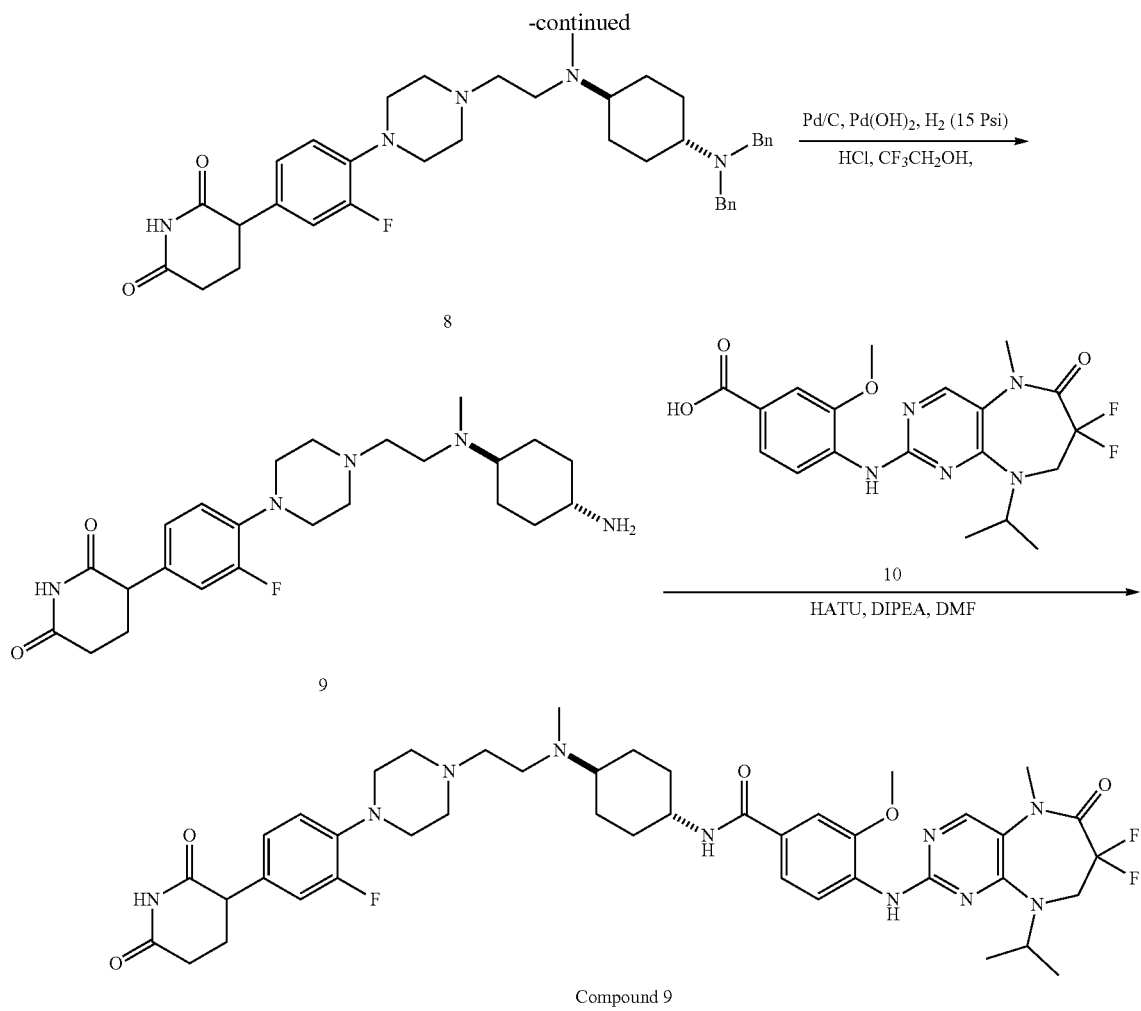

Compound 9

Step 1. Synthesis of benzyl 4-(4-bromo-2-fluorophenyl)piperazine-1-carboxylate (3)

To a mixture of 4-bromo-2-fluoro-1-iodobenzene (25 g, 83.09 mmol), benzyl piperazine-1-carboxylate (18.30 g, 83.09 mmol, 16.05 mL) and t-BuONa (2 M, 124.63 mL) in toluene (500 mL) were added Pd$_2$(dba)$_3$ (3.80 g, 4.15 mmol) and Xantphos (4.81 g, 8.31 mmol) at 25° C. The resulting mixture was degassed and purged with N$_2$ for three times, heated to 80° C. and stirred for 3 h under N$_2$ atmosphere. TLC (Petroleum ether/EtOAc=10/1) showed that 4-bromo-2-fluoro-1-iodobenzene was consumed and new spots were formed. The reaction mixture was filtered and concentrated. The residue was purified by flash silica gel chromatography (120 g silica gel column, EtOAc/petroleum ether=0-7%, 100 mL/min) to afford benzyl 4-(4-bromo-2-fluorophenyl)piperazine-1-carboxylate (27 g, 68.66 mmol, 82.64% yield) as a yellow solid. MS (M+H)$^+$=394.3

Step 2. Synthesis of benzyl 4-(4-(2,6-bis(benzyloxy)pyridin-3-yl)-2-fluorophenyl)piperazine-1-carboxylate (5)

A mixture of benzyl 4-(4-bromo-2-fluorophenyl)piperazine-1-carboxylate (15 g, 38.14 mmol), 2,6-bis(benzyloxy)-3-(4,4,5,5-tetramethyl-1,3,2-dioxaborolan-2-yl)pyridine (39.79 g, 95.36 mmol), KOAc (11.23 g, 114.43 mmol) and Pd(dppf)Cl$_2$ (2.79 g, 3.81 mmol) in H$_2$O (60 mL) and dioxane (300 mL) was stirred at 100° C. for 14 h under the protection of N$_2$. LCMS showed a peak (26%) with desired mass. The mixture was concentrated and the residue was purified by flash silica gel chromatography (120 g SepaFlash Silica Flash Column, Eluent of 0~20% EtOAc/Petroleum ether gradient @ 100 mL/min) to afford benzyl 4-(4-(2,6-bis(benzyloxy)pyridin-3-yl)-2-fluorophenyl) piperazine-1-carboxylate (11 g, 17.86 mmol, 46.82% yield, 98% purity) as yellow oil. MS (M+H)$^+$=604.2

Step 3. Synthesis of 3-(3-fluoro-4-(piperazin-1-yl)phenyl)piperidine-2,6-dione (6)

To a solution of benzyl 4-(4-(2,6-bis(benzyloxy)pyridin-3-yl)-2-fluorophenyl)piperazine-1-carboxylate (11 g, 18.22 mmol) in CF$_3$CH$_2$OH (200 mL) were added Pd/C (1.1 g, 10% purity) and Pd(OH)$_2$/C (1.1 g, 20% purity) at 25° C. under the protection of N$_2$. The resulting mixture was degassed and purged with H$_2$ for three times, then stirred at 45° C. for 14 h under H$_2$ (15 Psi). LCMS showed a peak (71%) with desired mass. The reaction mixture was filtered and washed with CF$_3$CH$_2$OH (200 mL) and the filtrate was concentrated to afford 3-(3-fluoro-4-(piperazin-1-yl)phenyl)piperidine-2,6-dione (5.7 g, crude) as yellow oil. MS (M+H)$^+$=292.1

Step 4. Synthesis of 3-(4-(4-(2-(((1r,4r)-4-(dibenzylamino)cyclohexyl)(methyl)amino)ethyl)piperazin-1-yl)-3-fluorophenyl)piperidine-2,6-dione (trans) (8)

To the solution of 3-(3-fluoro-4-(piperazin-1-yl)phenyl)piperidine-2,6-dione (3 g, 10.30 mmol) and (1r,4r)-N1,N1-dibenzyl-N4-(2-chloroethyl)-N4-methylcyclohexane-1,4-diamine (4.11 g, 9.27 mmol, 0.9 eq, 2HCl salt) in DMF (50 mL) was added NaI (154.36 mg, 1.03 mmol) and DIPEA (6.65 g, 51.49 mmol, 8.97 mL) and the resulting mixture was stirred at 50° C. for 12 h. LCMS showed a peak (56% under 254 nm) with desired mass. The mixture was concentrated and the residue was purified by flash silica gel chromatography (40 g SepaFlash Silica Flash Column, Eluent of 0~100% EtOAc/Petroleum ether-MeOH/EtOAc/NH$_4$OH=1/5/0.005 gradient @ 80 mL/min) to afford 3-(4-(4-(2-(((1r,4r)-4-(dibenzylamino)cyclohexyl)(methyl)amino)ethyl)piperazin-1-yl)-3-fluorophenyl)piperidine-2,6-dione (2 g, 2.17 mmol, 21.10% yield, 68% purity) as yellow oil. MS (M+H)$^+$=626.5

Step 5. Synthesis of 3-(4-(4-(2-(((1r,4r)-4-aminocyclohexyl)(methyl)amino)ethyl)piperazin-1-yl)-3-fluorophenyl)piperidine-2,6-dione (trans) (9)

To a solution of 3-(4-(4-(2-(((1r,4r)-4-(dibenzylamino)cyclohexyl)(methyl)amino)ethyl)piperazin-1-yl)-3-fluorophenyl)piperidine-2,6-dione (2.0 g, 3.20 mmol) in CF$_3$CH$_2$OH (100 mL) was added Pd/C (0.2 g, 10% purity), Pd(OH)$_2$/C (0.2 g, 20% purity) and HCl (1 M, 3.20 mL) under N$_2$ atmosphere, the resulting mixture was degassed and purged with H$_2$ for three times, then the mixture was stirred at 50-55° C. for 12 h under H$_2$ (15 psi) atmosphere. LCMS showed a peak (65%) with desired mass. The suspension was filtered through a pad of Celite and the filter cake was washed with CF$_3$CH$_2$OH (200 mL). The filtrate was concentrated to dryness to afford 3-(4-(4-(2-(((1r,4r)-4-aminocyclohexyl)(methyl)amino)ethyl)piperazin-1-yl)-3-fluorophenyl)piperidine-2,6-dione (1.9 g, crude, 4HCl salt) as yellow oil. MS (M+H)$^+$=446.3

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(4-(2,6-dioxopiperidin-3-yl)-2-fluorophenyl)piperazin-1-yl)ethyl)(methyl)amino)cyclohexyl)-3-methoxybenzamide (trans) (Compound 9)

To the solution of 3-(4-(4-(2-(((1r,4r)-4-aminocyclohexyl)(methyl)amino)ethyl)piperazin-1-yl)-3-fluorophenyl)piperidine-2,6-dione (1.80 g, 3.04 mmol 4HCl salt) and 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (1.15 g, 2.74 mmol) in DMF (30 mL) were added HATU (1.39 g, 3.65 mmol) and DIPEA (2.36 g, 18.26 mmol, 3.18 mL) and the resulting mixture was stirred at 20° C. for 12 h. LCMS showed that a peak (61%) with desired mass. The reaction mixture was poured into water (150 mL) and extracted with EtOAc (100 mL×3). The combined organic layer was washed with brine (200 mL), dried over Na$_2$SO$_4$, filtered and concentrated. The residue was purified by prep-HPLC (column: Phenomenex luna C18 150×40 mm×15 μm; mobile phase: [water (TFA)-ACN]; B %: 8%-38%, 10 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(4-(2,6-dioxopiperidin-3-yl)-2-fluorophenyl)piperazin-1-yl)ethyl)(methyl)amino)cyclohexyl)-3-methoxybenzamide (1.2 g, 1.18 mmol, 38.90% yield, 98% purity, TFA salt) as a white solid. MS (M+H)$^+$=849.4.

$^1$H NMR (400 MHz, DMSO-d$_6$) δ=10.82 (s, 1H), 8.36-8.28 (m, 1H), 8.23 (s, 1H), 8.07 (br d, J=7.6 Hz, 1H), 7.88 (s, 1H), 7.56-7.46 (m, 2H), 7.07-6.92 (m, 3H), 4.93-4.83 (m, 1H), 4.05 (br t, J=13.6 Hz, 2H), 3.94 (s, 3H), 3.81 (dd, J=4.8, 11.8 Hz, 1H), 3.75 (br dd, J=1.7, 4.3 Hz, 1H), 3.33 (s, 3H), 3.06-2.95 (br s, 4H), 2.71-2.56 (m, 8H), 2.47-2.43 (m, 2H), 2.31-2.12 (m, 5H), 2.05-1.97 (m, 1H), 1.94-1.88 (m, 2H), 1.83-1.76 (m, 2H), 1.43-1.32 (m, 4H), 1.25 (d, J=6.8, 6H).

Example 10. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(4-(2,6-dioxopiperidin-3-yl)-2,6-difluorophenyl)piperazin-1-yl)ethyl)(methyl)amino)cyclohexyl)-3-methoxybenzamide(trans) (Compound 10)

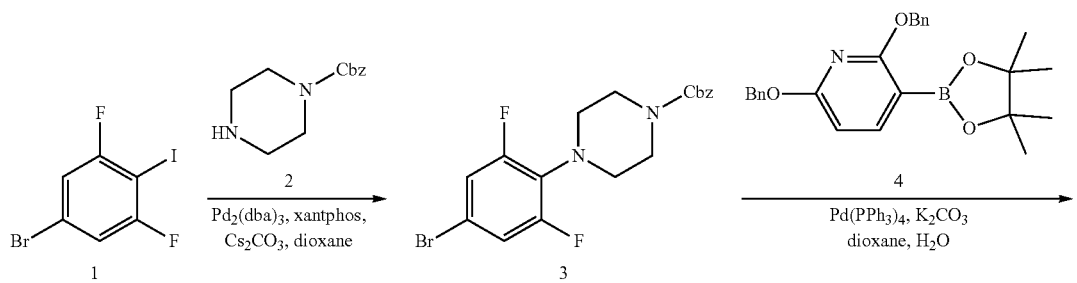

-continued
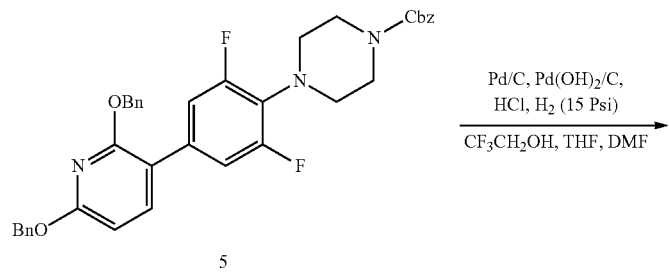
5
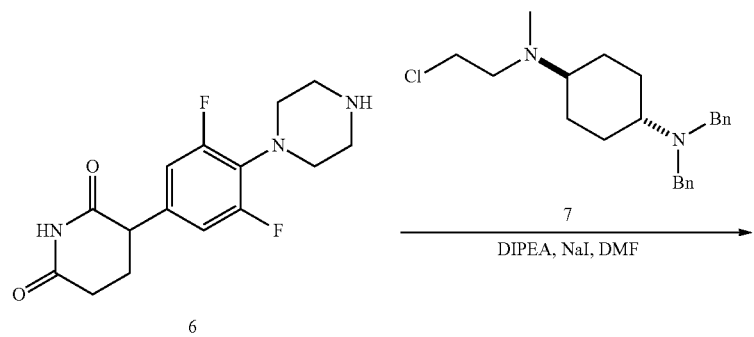
6
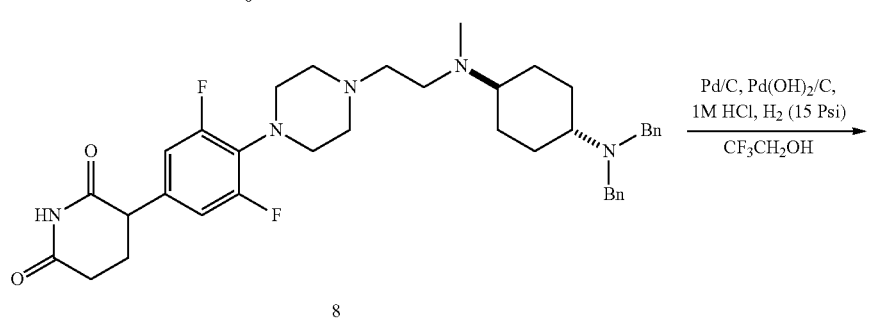
8
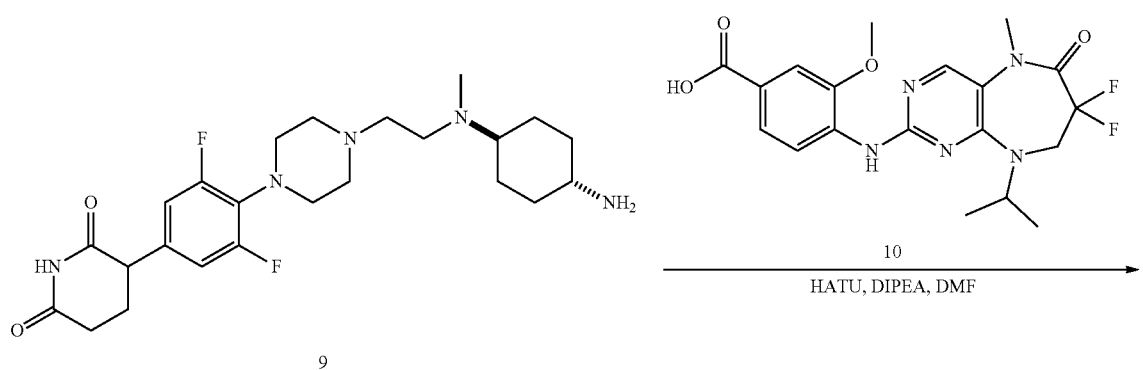
9
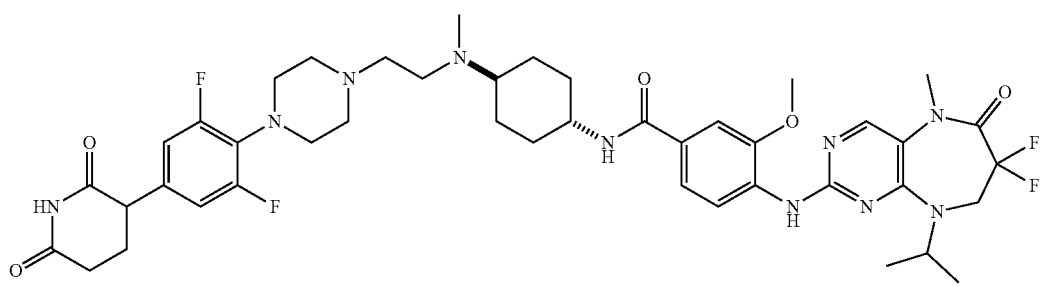
Compound 10

Step 1. Synthesis of benzyl 4-(4-bromo-2,6-difluorophenyl)piperazine-1-carboxylate (3)

To a solution of 5-bromo-1,3-difluoro-2-iodobenzene (10 g, 31.36 mmol) and benzyl piperazine-1-carboxylate (7.25 g, 32.93 mmol, 6.36 mL) in dioxane (150 mL) was added $Cs_2CO_3$ (20.43 g, 62.72 mmol), $Pd_2(dba)_3$ (574.33 mg, 627.19 µmol) and Xantphos (544.35 mg, 940.78 µmol) and the mixture was stirred at 100° C. for 14 h under $N_2$ atmosphere. LCMS showed a peak (41%) with desired mass. The mixture was filtered and the filter cake was washed with EtOAc (100 mL). The filtrate was concentrated under reduced pressure. The residue was purified by flash silica gel chromatography (120 g SepaFlash Silica Flash Column, Eluent of 10~15% EtOAc/Petroleum ether gradient @ 50 mL/min) to afford benzyl 4-(4-bromo-2,6-difluorophenyl)piperazine-1-carboxylate (6.2 g, 14.17 mmol, 45.19% yield, 94% purity) as yellow oil. MS $(M+H)^+$=411.1

Step 2. Synthesis of benzyl 4-(4-(2,6-bis(benzyloxy)pyridin-3-yl)-2,6-difluorophenyl)piperazine-1-carboxylate (5)

To a solution of benzyl 4-(4-bromo-2,6-difluorophenyl)piperazine-1-carboxylate (3.5 g, 8.51 mmol) and 2,6-bis(benzyloxy)-3-(4,4,5,5-tetramethyl-1,3,2-dioxaborolan-2-yl)pyridine (3.91 g, 9.36 mmol) in dioxane (30 mL) and $H_2O$ (15 mL) were added $K_2CO_3$ (3.53 g, 25.53 mmol) and $Pd(PPh_3)_4$ (196.70 mg, 170.22 µmol) and the mixture was stirred at 100° C. for 14 h under $N_2$ atmosphere. LCMS showed a peak (53%) with desired mass. The mixture was diluted with $H_2O$ (30 mL) and extracted with EtOAc (20 mL×3), the combined organic layer was washed with brine (10 mL×3), dried over $Na_2SO_4$ and filtered. The filtrate was concentrated under reduced pressure. The residue was purified by flash silica gel chromatography (40 g SepaFlash Silica Flash Column, Eluent of 15~20% EtOAc/Petroleum ether gradient @ 80 mL/min) to afford benzyl 4-(4-(2,6-bis(benzyloxy)pyridin-3-yl)-2,6-difluorophenyl)piperazine-1-carboxylate (2.65 g, 3.92 mmol, 46.08% yield, 92% purity) as yellow oil. MS $(M+H)^+$=622.3

Step 3. Synthesis of 3-(3,5-difluoro-4-(piperazin-1-yl)phenyl)piperidine-2,6-dione (6)

To a solution of benzyl 4-(4-(2,6-bis(benzyloxy)pyridin-3-yl)-2,6-difluorophenyl)piperazine-1-carboxylate (2.65 g, 4.26 mmol) and HCl (12 M, 358.65 µL) in $CF_3CH_2OH$ (50 mL) and THF (50 mL) were added Pd/C (0.15 g, 10% purity) and $Pd(OH)_2$/C (0.15 g, 20% purity) under $N_2$ atmosphere and the mixture was degassed and purged with $N_2$ for 3 times, then the suspension was stirred at 50° C. under $H_2$ (15 Psi) for 34 h. LCMS showed no reaction. DMF (10 mL) was added and the resulting mixture was stirred at 50° C. under $H_2$ (15 Psi) for 14 h. LCMS showed no reaction. Additional DMF (40 mL) was added and the mixture was stirred at 50° C. under $H_2$ (15 Psi) for 14 h. LCMS showed a major peak (94%) with desired mass. The mixture was diluted with THF (50 mL) and filtered. The filter cake was washed with THF (30 mL), DMF (100 mL) and MeOH (200 mL). The filtrate was concentrated under reduced pressure to afford 3-(3,5-difluoro-4-(piperazin-1-yl)phenyl)piperidine-2,6-dione (1.2 g, crude, HCl salt) as a yellow solid. MS $(M+H)^+$=310.2

Step 4. Synthesis of 3-(4-(4-(2-(((1r,4r)-4-(dibenzylamino)cyclohexyl)(methyl)amino)ethyl)piperazin-1-yl)-3,5-difluorophenyl)piperidine-2,6-dione(trans) (8)

To a solution of 3-(3,5-difluoro-4-(piperazin-1-yl)phenyl)piperidine-2,6-dione (1.1 g, 3.18 mmol, HCl salt) in DMF (20 mL) were added NaI (23.84 mg, 159.06 µmol), DIPEA (2.08 g, 16.08 mmol, 2.8 mL) and (1r,4r)-N1,N1-dibenzyl-N4-(2-chloroethyl)-N4-methylcyclohexane-1,4-diamine (trans) (1.27 g, 2.86 mmol, 2HCl salt) and the mixture was stirred at 50° C. for 14 h. LCMS showed a peak (85%) with desired mass. The mixture was diluted with $H_2O$ (40 mL) and extracted with EtOAc (20 mL×3), the combined organic layer was washed with brine (10 mL×3), dried over $Na_2SO_4$ and filtered. The filtrate was concentrated under reduced pressure. The residue was purified by flash silica gel chromatography (12 g SepaFlash Silica Flash Column, Eluent of 0~20% EtOAc/Petroleum ether gradient @ 60 mL/min) to afford 3-(4-(4-(2-(((1r,4r)-4-(dibenzylamino)cyclohexyl)(methyl)amino)ethyl)piperazin-1-yl)-3,5-difluorophenyl)piperidine-2,6-dione(trans) (1.25 g, 1.65 mmol, 51.88% yield, 85% purity) as a yellow solid. MS $(M+H)^+$=644.2

Step 5. Synthesis of 3-(4-(4-(2-(((1r,4r)-4-aminocyclohexyl)(methyl)amino)ethyl)piperazin-1-yl)-3,5-difluorophenyl)piperidine-2,6-dione(trans) (9)

To a solution of 3-(4-(4-(2-(((1r,4r)-4-(dibenzylamino)cyclohexyl)(methyl)amino)ethyl)piperazin-1-yl)-3,5-difluorophenyl)piperidine-2,6-dione(trans) (1.05 g, 1.63 mmol) and HCl (1 M, 1.63 mL) in $CF_3CH_2OH$ (20 mL) were added Pd/C (100 mg, 10% purity) and $Pd(OH)_2$/C (100 mg, 20% purity) at $N_2$ atmosphere and the suspension was degassed and purged with $H_2$ for 3 times and the resulting mixture was stirred at 50° C. for 28 h under $H_2$ (15 Psi). LCMS showed a peak (30%) with mass of starting material and a peak (54%) with desired mass. The mixture was stirred at 50° C. under $H_2$ (15 Psi) for another 14 h. LCMS showed 91% of desired mass. The mixture was diluted with $CF_3CH_2OH$ (50 mL) and filtered. The filter cake was washed with THF (30 mL), DMF (100 mL) and $CF_3CH_2OH$ (50 mL). The filtrate was concentrated under reduced pressure to afford 3-(4-(4-(2-(((1r,4r)-4-aminocyclohexyl)(methyl)amino)ethyl)piperazin-1-yl)-3,5-difluorophenyl)piperidine-2,6-dione(trans) (830 mg, crude, 3HCl) as yellow solid. MS $(M+H)^+$=464.3

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(4-(2,6-dioxopiperidin-3-yl)-2,6-difluorophenyl)piperazin-1-yl)ethyl)(methyl)amino)cyclohexyl)-3-methoxybenzamide(trans) (Compound 10)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (470 mg, 1.12 mmol) and HATU (508.90 mg, 1.34 mmol) in DMF (7 mL) was added DIPEA (348.74 mg, 2.70 mmol, 470.00 µL) and the mixture was stirred at 20° C. for 15 min. Then a solution of 3-(4-(4-(2-(((1r,4r)-4-aminocyclohexyl)(methyl)amino)ethyl)piperazin-1-yl)-3,5-difluorophenyl)piperidine-2,6-dione (780 mg, 1.36 mmol, 3HCl) and DIPEA (697.46 mg, 5.40 mmol, 939.98 µL) in DMF (8 mL) was added and the mixture was stirred at 20° C. for 1 h. LCMS showed the desired mass was detected. The mixture was diluted with $H_2O$ (30 mL) and extracted with EtOAc (10 mL×3). The combined organic layer was washed with brine (10 mL×2), dried over $Na_2SO_4$ and filtered. The filtrate was concentrated under reduced pressure. The residue was purified by flash silica gel chromatography (12 g SepaFlash Silica Flash Column, Eluent of 20~30% MeOH/EtOAc gradient @ 50 m/min), then re-purified by prep-HPLC (column: Waters Xbridge C18 150×50 mm×10 µm; mobile phase: [water (NH₄HCO₃)-ACN]; B %: 40%-70%, 10 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(4-(2,6-dioxopiperidin-3-yl)-2,6-difluorophenyl)piperazin-1-yl)ethyl)(methyl)amino)cyclohexyl)-3-methoxybenzamide (346.7 mg, 383.91 μmol, 34.42% yield, 96% purity) as a white solid. MS (M+H)⁺=867.5

¹H NMR (400 MHz, DMSO-d₆) δ=10.85 (s, 1H), 8.30 (dd, J=2.9, 8.3 Hz, 1H), 8.22 (s, 1H), 8.06 (br d, J=7.8 Hz, 1H), 7.87 (s, 1H), 7.52-7.46 (m, 2H), 6.99-6.90 (m, 2H), 4.92-4.84 (m, 1H), 4.10-3.99 (m, 2H), 3.93 (s, 3H), 3.83 (dd, J=4.7, 12.4 Hz, 1H), 3.79-3.66 (m, 1H), 3.30 (s, 3H), 3.13-3.06 (m, 4H), 2.66-2.53 (m, 8H), 2.44-2.36 (m, 2H), 2.29-2.16 (m, 5H), 2.03-1.95 (m, 1H), 1.93-1.86 (m, 2H), 1.80-1.73 (m, 2H), 1.42-1.31 (m, 4H), 1.24 (d, J=6.6 Hz, 6H).

Example 11. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(1-(4-(2,6-dioxopiperidin-3-yl)-2-fluorophenyl)piperidin-4-yl)propanoyl)piperazin-1-yl)-3-methoxybenzamide (Compound 11)

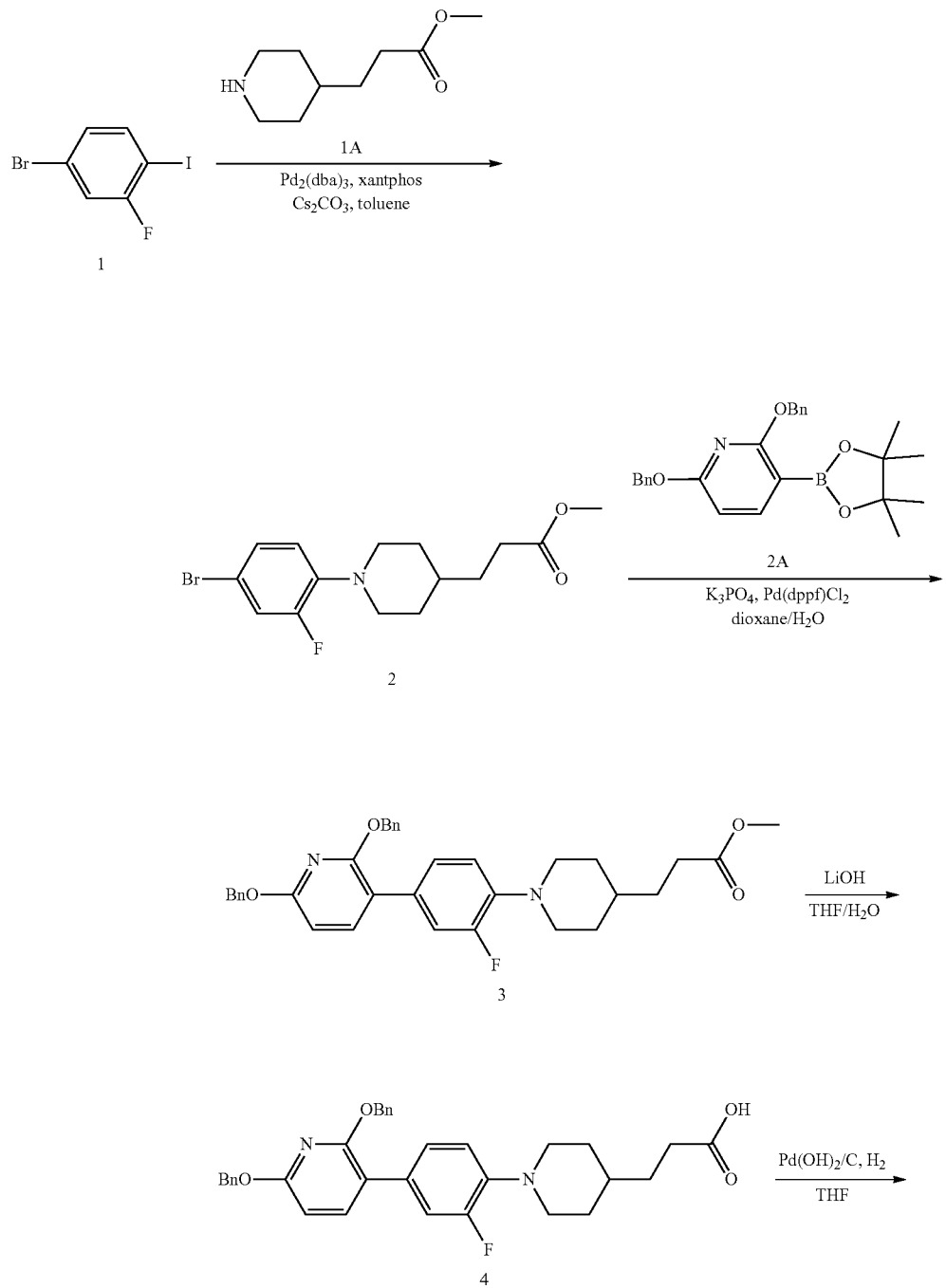

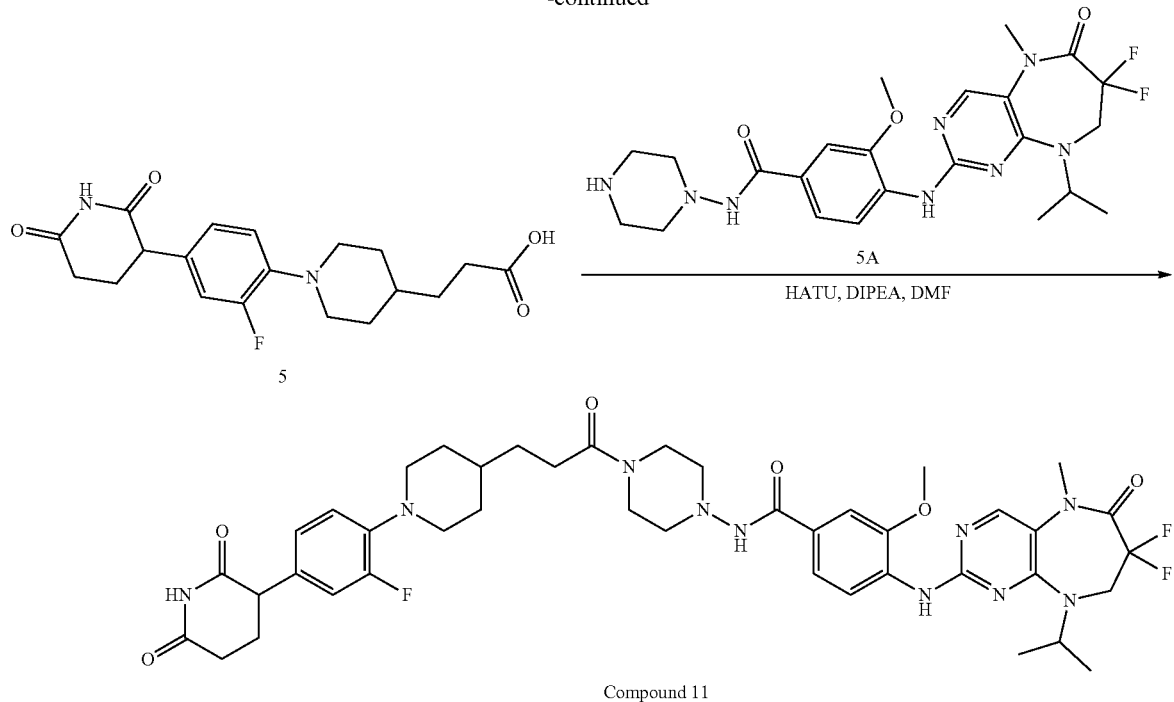

Compound 11

Step 1. Synthesis of methyl 3-(1-(4-bromo-2-fluorophenyl)piperidin-4-yl)propanoate (2)

To a solution of 4-bromo-2-fluoro-1-iodobenzene (750 mg, 2.49 mmol), methyl 3-(piperidin-4-yl)propanoate (491.81 mg, 2.37 mmol, HCl) and Cs$_2$CO$_3$ (2.44 g, 7.48 mmol) in toluene (10 mL) were added Pd$_2$(dba)$_3$ (114.12 mg, 124.63 μmol) and Xantphos (144.23 mg, 249.26 μmol) was added at 25° C. The mixture was stirred under N$_2$ at 90° C. for 12 h. LCMS showed a peak (45%) with desired mass. The mixture was diluted with EtOAc (30 mL) and washed with brine (10 mL×3), dried over Na$_2$SO$_4$, filtered and concentrated under reduced pressure to give a residue. The residue was purified by flash silica gel chromatography (10 g SepaFlash Silica Flash Column, Eluent of 0~30% EtOAc/Petroleum ether gradient @ 60 mL/min) to afford methyl 3-(1-(4-bromo-2-fluorophenyl)piperidin-4-yl)propanoate (250 mg, crude) as yellow oil, which was used for the next step directly. MS (M+H)$^+$=344.0

Step 2. Synthesis of methyl 3-(1-(4-(2,6-bis(benzyloxy)pyridin-3-yl)-2-fluorophenyl)piperidin-4-yl)propanoate (3)

To a mixture of 2,6-bis(benzyloxy)-3-(4,4,5,5-tetramethyl-1,3,2-dioxaborolan-2-yl)pyridine (333.39 mg, 798.91 μmol), methyl 3-(1-(4-bromo-2-fluorophenyl)piperidin-4-yl)propanoate (250 mg, 726.28 μmol) and K$_3$PO$_4$ (462.50 mg, 2.18 mmol) in dioxane (5 mL) and H$_2$O (1 mL) was added Pd(dppf)Cl$_2$ (53.14 mg, 72.63 μmol) at 25° C. The resulting mixture was purged and degassed with N$_2$ for three times, heated to 90° C. and stirred for 12 hrs. LCMS showed the starting material was consumed completely and a peak (34%) with desired mass. The mixture was diluted with EtOAc (50 mL) dried over Na$_2$SO$_4$ and concentrated. The residue was purified by flash silica gel chromatography (12 g SepaFlash Silica Flash Column, Eluent of 0~15% EtOAc/Petroleum ether gradient @ 60 mL/min) to afford methyl 3-(1-(4-(2,6-bis(benzyloxy)pyridin-3-yl)-2-fluorophenyl)piperidin-4-yl)propanoate (150 mg, 262.33 μmol, 36.12% yield, 97% purity) as yellow oil, which was used for the next step directly. MS (M+H)$^+$=555.6

Step 3. Synthesis of 3-(1-(4-(2,6-bis(benzyloxy)pyridin-3-yl)-2-fluorophenyl)piperidin-4-yl)propanoic Acid (4)

A mixture of methyl 3-(1-(4-(2,6-bis(benzyloxy)pyridin-3-yl)-2-fluorophenyl)piperidin-4-yl)propanoate (150 mg, 270.44 μmol) and LiOH·H$_2$O (34.05 mg, 811.32 μmol) in THF (2 mL) and H$_2$O (2 mL) was stirred at 50° C. for 5 hr. LCMS showed the starting material was consumed completely, and a main peak with desired mass. The mixture was adjusted the pH=3 with 1 N HCl and then the mixture was diluted with H$_2$O (10 mL) and extracted with EtOAc (10 mL×3), the combined organic layer was washed with H$_2$O (10 mL), dried over Na$_2$SO$_4$ and filtered. The filtrate was concentrated under reduced pressure to afford 3-(1-(4-(2,6-bis(benzyloxy)pyridin-3-yl)-2-fluorophenyl)piperidin-4-yl)propanoic acid (150 mg, 260.81 μmol, 96.44% yield, 94% purity) as yellow solid, which was used for the next step directly. MS (M+H)$^+$=541.3

Step 4. Synthesis of 3-(1-(4-(2,6-dioxopiperidin-3-yl)-2-fluorophenyl)piperidin-4-yl)propanoic Acid (5)

To a solution of 3-(1-(4-(2,6-bis(benzyloxy)pyridin-3-yl)-2-fluorophenyl)piperidin-4-yl)propanoic acid (146 mg, 270.06 μmol) in THF (5 mL) was added Pd(OH)$_2$/C (50 mg, 20% purity). The mixture was stirred at 30° C. under H$_2$ (15 psi) for 12 hr. LCMS showed the starting material was consumed completely and a peak (54%) with desired mass. The reaction mixture was filtered through a celite pad and the filtrate was concentrated to afford 3-(1-(4-(2,6-dioxopiperidin-3-yl)-2-fluorophenyl)piperidin-4-yl)propanoic acid (97 mg, crude) as white solid, which was used for the next step directly. MS (M+H)$^+$=363.1

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(1-(4-(2,6-dioxopiperidin-3-yl)-2-fluorophenyl)piperidin-4-yl)propanoyl)piperazin-1-yl)-3-methoxybenzamide (Compound 11)

To a solution of 3-(1-(4-(2,6-dioxopiperidin-3-yl)-2-fluorophenyl)piperidin-4-yl)propanoic acid (60 mg, 165.57 μmol) in DMF (2 mL) was added HATU (94.43 mg, 248.36 μmol) and DIPEA (64.19 mg, 496.71 μmol, 86.51 μL). The mixture was stirred at 25° C. for 10 min. To the mixture was added 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(piperazin-1-yl)benzamide (84.90 mg, 156.93 μmol, HCl). The mixture was stirred at 25° C. for 2 h. LCMS showed the 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(piperazin-1-yl)benzamide was consumed completely and a main peak with desired mass. The mixture was diluted with EtOAc (20 mL) dried over Na$_2$SO$_4$ and concentrated. The residue was purified by flash silica gel chromatography (4 g SepaFlash Silica Flash Column, Eluent of 0~100% EtOAc/Petroleum ether gradient @ 50 mL/min; Eluent of 0~50% Methanol/EtOAc @ 50 mL/min) to give crude product. The crude product was purified by prep-HPLC (column: Waters Xbridge 150×25 mm×5 μm; mobile phase: [water (NH$_4$HCO$_3$)-ACN]; B %: 36%-66%, 8 min) and lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(1-(3-(1-(4-(2,6-dioxopiperidin-3-yl)-2-fluorophenyl)piperidin-4-yl)propanoyl)piperazin-1-yl)-3-methoxybenzamide (57 mg, 65.13 μmol, 39.34% yield, 97% purity) as white solid. MS (M+H)$^+$=849.1

$^1$H NMR (400 MHz, DMSO-d$_6$) δ=10.80 (s, 1H), 9.43 (s, 1H), 8.31 (d, J=8.3 Hz, 1H), 8.22 (s, 1H), 7.89 (s, 1H), 7.48-7.38 (m, 2H), 7.05-6.90 (m, 3H), 4.95-4.80 (m, 1H), 4.03 (t, J=13.6 Hz, 2H), 3.93 (s, 3H), 3.79 (dd, J=4.9, 11.8 Hz, 1H), 3.64-3.50 (m, 4H), 3.32 (s, 3H), 3.32-3.30 (m, 2H), 2.97-2.81 (m, 4H), 2.69-2.57 (m, 4H), 2.39 (t, J=7.6 Hz, 2H), 2.27-2.12 (m, 1H), 2.05-1.94 (m, 1H), 1.78 (d, J=11.9 Hz, 2H), 1.56-1.46 (m, 2H), 1.45-1.26 (m, 4H), 1.24 (d, J=6.8 Hz, 6H)

Example 12. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-((1-(4-(2,6-dioxopiperidin-3-yl)-2-fluorophenyl)azetidin-3-yl)methyl)piperidin-4-yl)-3-methoxybenzamide (Compound 12)

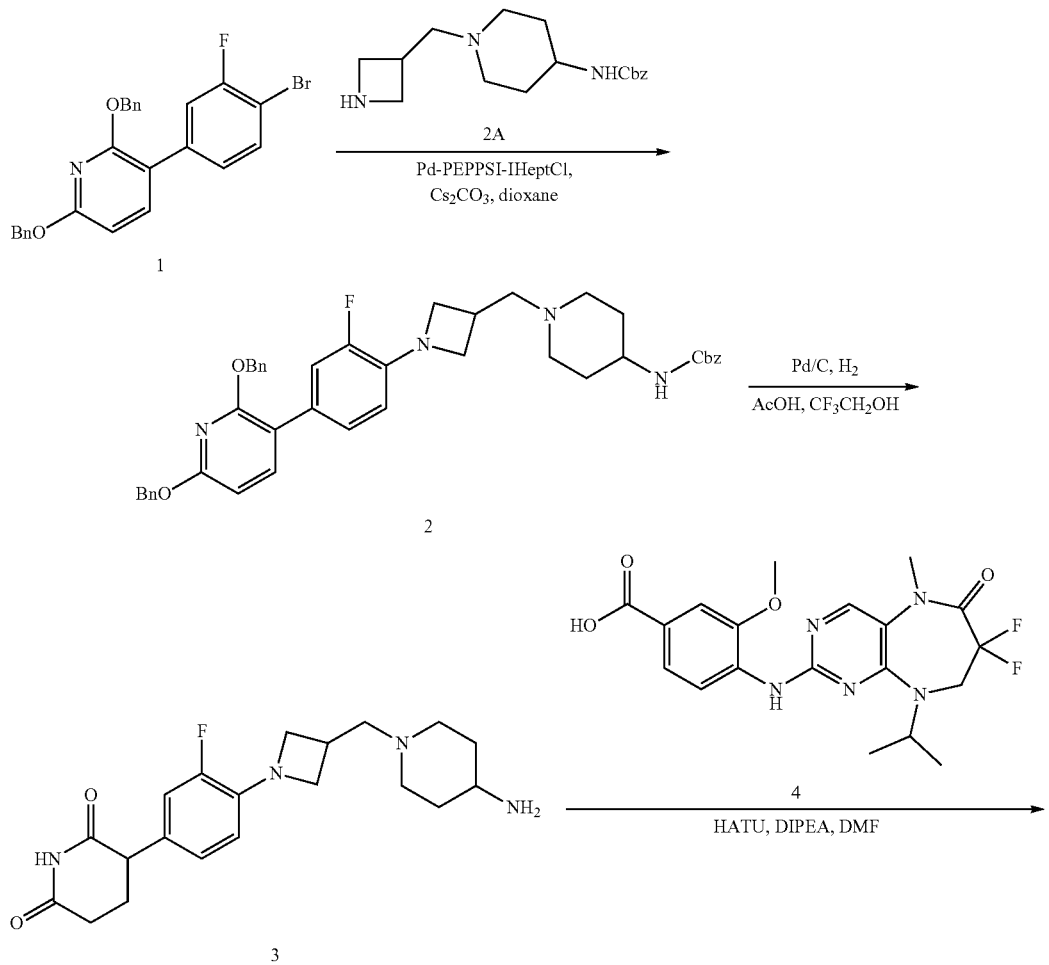

-continued

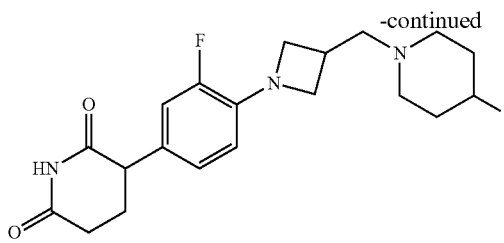

Compound 12

Step 1. Synthesis of benzyl (1-((1-(4-(2,6-bis(benzyloxy)pyridin-3-yl)-2-fluorophenyl)azetidin-3-yl)methyl)piperidin-4-yl)carbamate (2)

To a solution of 2,6-dibenzyloxy-3-(4-bromo-3-fluorophenyl)pyridine (600 mg, 1.29 mmol) in dioxane (12 mL) were added benzyl N-[1-(azetidin-3-ylmethyl)-4-piperidyl]carbamate (2.43 g, 5.81 mmol, TFA salt), $Cs_2CO_3$ (2.53 g, 7.75 mmol) and Pd-PEPPSI-IHeptCl (62.85 mg, 64.61 µmol) at 20° C. under $N_2$ and the resulting mixture was stirred at 100° C. for 16 h under $N_2$. LCMS showed starting material was consumed completely and a peak (50%) with desired mass. The reaction mixture was filtered and the filtrate was concentrated in vacuum. The residue was purified by flash silica gel chromatography (12 g SepaFlash Silica Flash Column, Eluent of 0~100% EtOAc/Petroleum ether gradient @ 100 mL/min) to afford benzyl (1-((1-(4-(2,6-bis(benzyloxy)pyridin-3-yl)-2-fluorophenyl)azetidin-3-yl)methyl)piperidin-4-yl)carbamate (1.3 g, crude) as an orange oil. MS $(M+H)^+=687.2$ Step 2. Synthesis of 3-(4-(3-((4-aminopiperidin-1-yl)methyl)azetidin-1-yl)-3-fluorophenyl) piperidine-2,6-dione (3)

To a solution of benzyl (1-((1-(4-(2,6-bis(benzyloxy)pyridin-3-yl)-2-fluorophenyl)azetidin-3-yl)methyl)piperidin-4-yl)carbamate (0.7 g, 1.02 mmol) in $CF_3CH_2OH$ (10 mL) and AcOH (1 mL) was added Pd/C (0.3 g, 10% purity) under $N_2$ atmosphere. The suspension was degassed and purged with $H_2$ for 3 times. The mixture was stirred at 20° C. for 16 h under $H_2$ (15 Psi). LCMS showed the starting material was consumed completely and a peak with desired mass. The reaction mixture was diluted with EtOAc:THF=1:1 (30 mL) and filtered, the filtrate was concentrated in vacuum to afford 3-(4-(3-((4-aminopiperidin-1-yl)methyl)azetidin-1-yl)-3-fluorophenyl)piperidine-2,6-dione (648 mg, crude) as a yellow oil. MS $(M+H)^+=375.4$ Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-((1-(4-(2,6-dioxopiperidin-3-yl)-2-fluorophenyl)azetidin-3-yl)methyl)piperidin-4-yl)-3-methoxybenzamide (Compound 12)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (100 mg, 237.31 µmol) in DMF (3 mL) were added HATU (99.25 mg, 261.04 µmol) and DIPEA (61.34 mg, 474.61 µmol, 82.67 µL). The mixture was stirred at 20° C. for 10 min and a solution of 3-(4-(3-((4-aminopiperidin-1-yl)methyl)azetidin-1-yl)-3-fluorophenyl)piperidine-2,6-dione (266.58 mg, 711.92 µmol) with DIPEA (122.68 mg, 949.22 µmol, 165.34 µL) in DMF (3 mL) was added and the resulting mixture was stirred at 20° C. for 1 h. LCMS showed starting material was consumed completely and a peak (56%) with desired mass. The reaction mixture was diluted with $H_2O$ (15 mL) and extracted with EtOAc (15 mL×3). The organic layer was washed with brine (15 mL×3), dried over $Na_2SO_4$, filtered and concentrated. The residue was purified by prep-TLC ($SiO_2$, DCM:MeOH=20:1) followed by prep-HPLC (column: Waters Xbridge 150×25 mm×5 µm; mobile phase: [water ($NH_4HCO_3$)-ACN]; B %: 33%-68%, 9 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(1-((1-(4-(2,6-dioxopiperidin-3-yl)-2-fluorophenyl)azetidin-3-yl)methyl)piperidin-4-yl)-3-methoxybenzamide (23 mg, 28.68 µmol, 12.09% yield, 97% purity) as a white solid. MS $(M+H)^+=778.2$ $^1$H NMR (400 MHz, DMSO-$d_6$) δ=10.78 (s, 1H), 8.30 (br d, J=8.3 Hz, 1H), 8.22 (s, 1H), 8.09 (br d, J=7.9 Hz, 1H), 7.87 (s, 1H), 7.55-7.45 (m, 2H), 6.96-6.82 (m, 2H), 6.49 (t, J=9.0 Hz, 1H), 4.94-4.82 (m, 1H), 4.09-3.97 (m, 4H), 3.94 (s, 3H), 3.83-3.69 (m, 2H), 3.54 (br t, J=6.1 Hz, 2H), 3.32 (s, 3H), 2.96-2.80 (m, 3H), 2.65-2.55 (m, 3H), 2.45 (br s, 1H), 2.16 (dq, J=3.4, 12.1 Hz, 1H), 2.08-1.94 (m, 3H), 1.77 (br d, J=11.0 Hz, 2H), 1.64-1.51 (m, 2H), 1.24 (d, J=6.6 Hz, 6H).

Example 13. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (Compound 13)

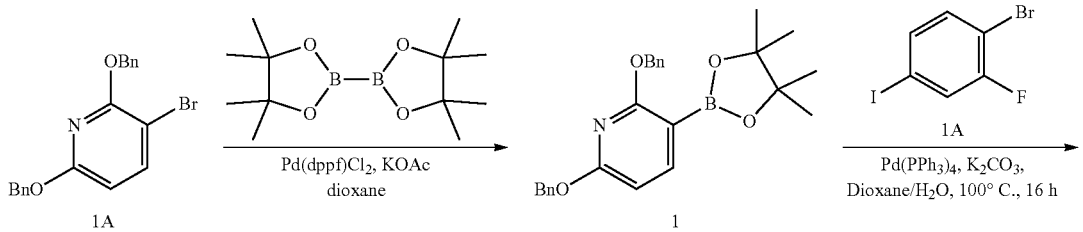

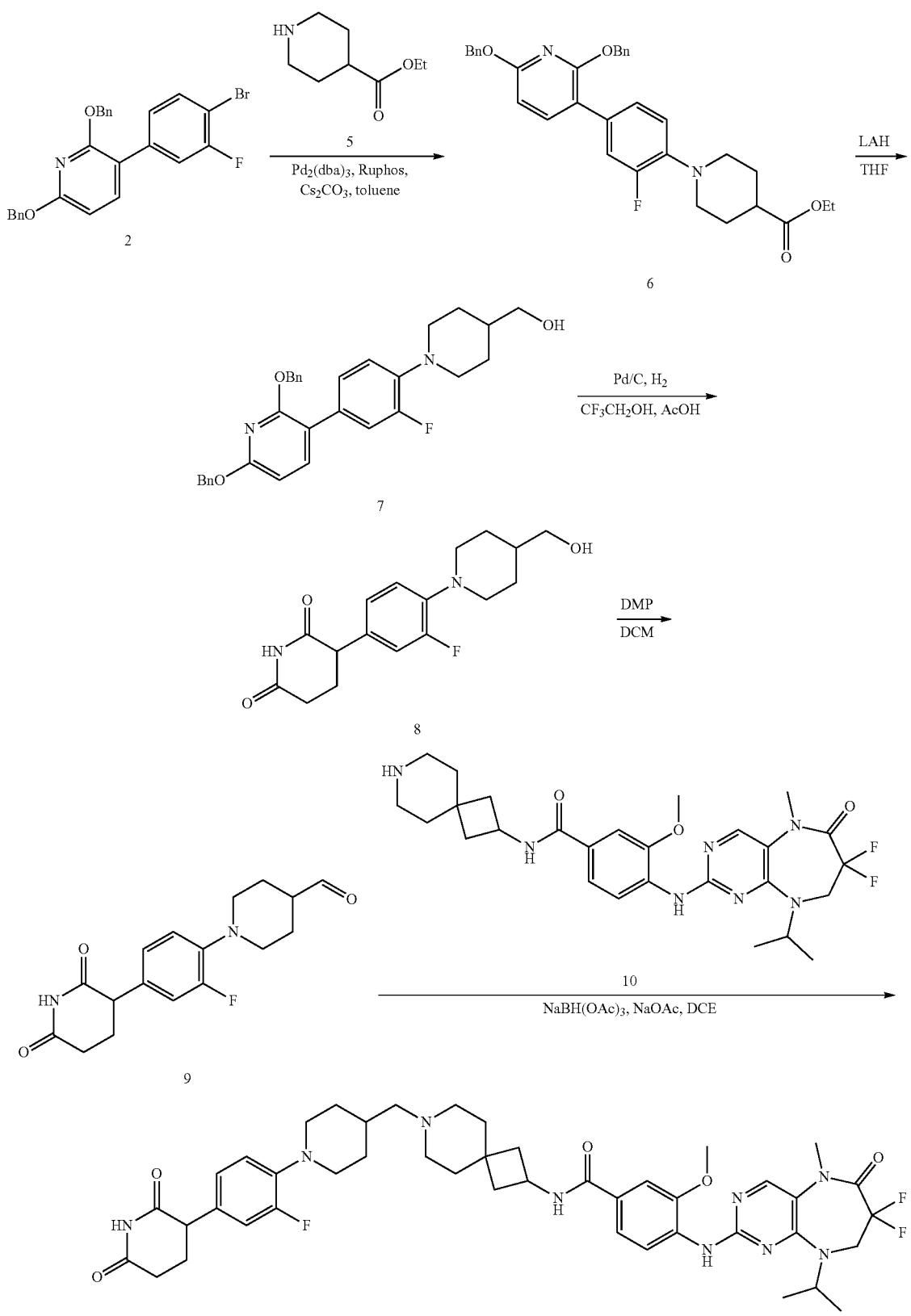

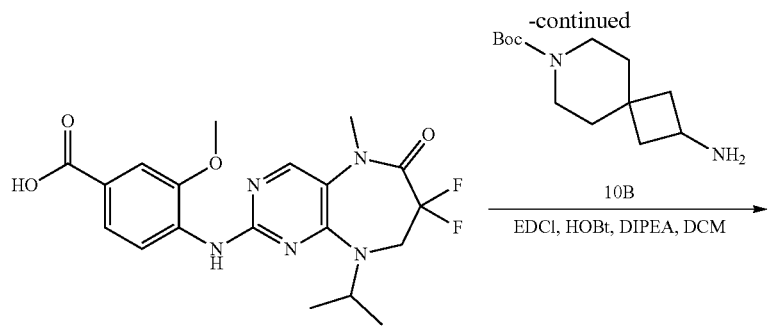

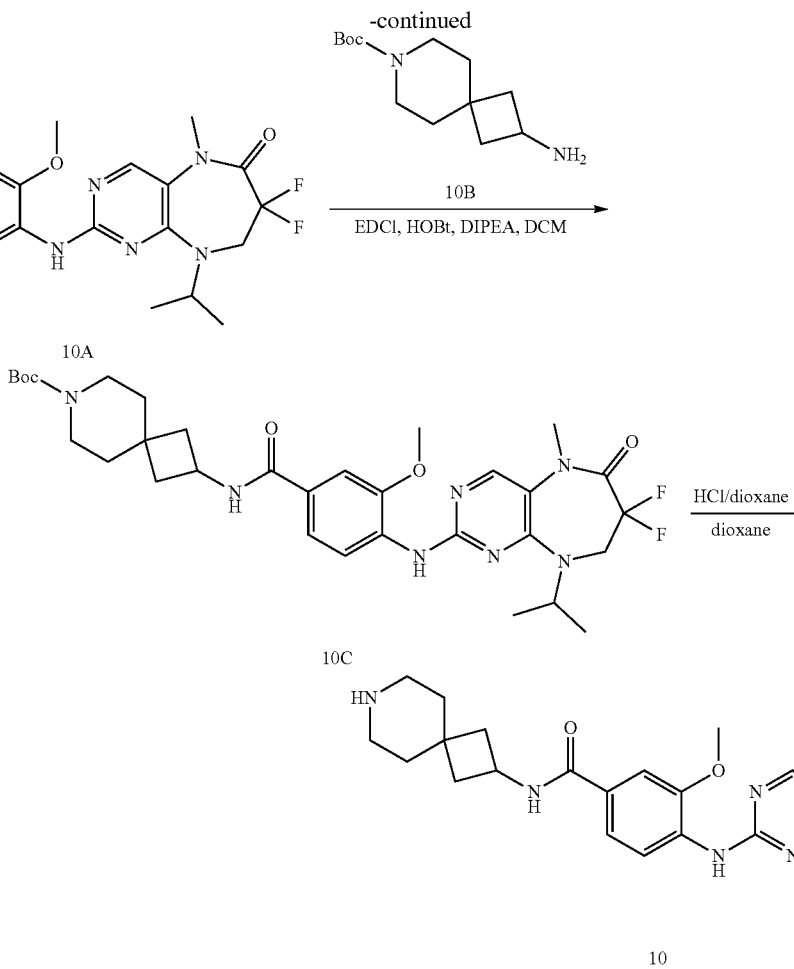

Step 1. Synthesis of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-7-azaspiro[3.5]nonane-7-carboxylate (10C)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (3 g, 7.12 mmol) in DMF (50 mL) was added EDCI (2.10 g, 10.95 mmol), HOBt (900.00 mg, 6.66 mmol), DIPEA (4.45 g, 34.45 mmol, 6.00 mL) and tert-butyl 2-amino-7-azaspiro[3.5]nonane-7-carboxylate (1.90 g, 7.91 mmol) at 25° C. The resulting mixture was stirred at 25° C. for 16 hr under $N_2$ atmosphere. LCMS showed a peak (85%) with desired mass. The reaction mixture was diluted with $H_2O$ (30 mL), and extracted with EtOAc (80 mL×2). The combined organic layers were washed with brine (60 mL×3), dried over anhydrous $Na_2SO_4$, filtered and the filtrate was concentrated under reduced pressure. The residue was purified by flash silica gel chromatography (Biotage; 40 g SepaFlash Silica Flash Column, Eluent of 40~100% EtOAc:Petroleum ether gradient, 80 mL/min) to afford tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-7-azaspiro[3.5]nonane-7-carboxylate (3.6 g, 5.59 mmol, 78.56% yield) as a light yellow solid. MS (M+H)⁺=644.2.

Step 2. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (10)

To a solution of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-7-azaspiro[3.5]nonane-7-carboxylate (3.6 g, 5.59 mmol) in dioxane (40 mL) was added HCl/dioxane (4 M, 60 mL), the mixture was stirred at 20° C. for 2 hr. LCMS showed a main peak with desired mass. The reaction mixture was filtered and the filtrate was concentrated under reduced pressure to afford 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (3.2 g, crude, HCl salt) as a light yellow solid. MS (M+H)⁺=544.2.

¹H NMR (400 MHz, DMSO-d₆) δ=9.98 (s, 1H), 9.30-9.12 (m, 2H), 8.96-8.81 (m, J=7.0 Hz, 1H), 8.44 (s, 1H), 8.01-7.92 (m, 1H), 7.74-7.64 (m, 1H), 7.64-7.57 (m, 1H), 5.00-4.86 (m, 1H), 4.47-4.38 (m, 1H), 4.35-4.23 (m, 2H), 3.98-3.91 (m, 3H), 3.33 (s, 3H), 3.01-2.87 (m, 4H), 2.28-2.20 (m, 2H), 2.04-1.96 (m, 2H), 1.84-1.74 (m, 4H), 1.33-1.21 (m, 6H).

Step 3. Synthesis of 2,6-bis(benzyloxy)-3-(4,4,5,5-tetramethyl-1,3,2-dioxaborolan-2-yl)pyridine (1)

A mixture of 2,6-bis(benzyloxy)-3-bromopyridine (20 g, 54.02 mmol), 4,4,4',4',5,5,5',5'-octamethyl-2,2'-bi(1,3,2-dioxaborolane) (20.58 g, 81.03 mmol), Pd(dppf)Cl$_2$ (4.41 g, 5.40 mmol), and KOAc (7.58 g, 108.04 mmol) in dioxane (500 mL) was degassed and purged with N$_2$ for 3 times, and then the mixture was stirred at 100° C. for 16 hr under N$_2$ atmosphere. LCMS showed a peak (32%) with desired mass. The reaction mixture was diluted with water (500 mL) and extracted with EtOAc (500 mL). The combined organic layers were washed with bine (300 mL×2), dried over Na$_2$SO$_4$, filtered and concentrated under reduced pressure. The residue was purified by flash silica gel chromatography (320 g SepaFlash Silica Flash Column, Eluent of 0~10% EtOAc/Petroleum ether gradient @ 100 mL/min) to afford 2,6-bis(benzyloxy)-3-(4,4,5,5-tetramethyl-1,3,2-dioxaborolan-2-yl)pyridine (26 g, crude) as a yellow oil. MS (M+H)$^+$=418.2.

Step 4. Synthesis of 2,6-bis(benzyloxy)-3-(4-bromo-3-fluorophenyl)pyridine (2)

A mixture of 2,6-bis(benzyloxy)-3-(4,4,5,5-tetramethyl-1,3,2-dioxaborolan-2-yl)pyridine (8 g, 19.17 mmol), 1-bromo-2-fluoro-4-iodobenzene (4.8 g, 15.95 mmol), Pd(PPh$_3$)$_4$ (1.6 g, 1.38 mmol) and K$_2$CO$_3$ (8.0 g, 57.88 mmol) in dioxane (80 mL) and H$_2$O (20 mL) was degassed and purged with N$_2$ for 3 times, then the mixture was stirred at 100° C. for 16 hr under N$_2$ atmosphere. LCMS showed a peak (41%) with desired mass. The reaction mixture was filtered. The filtrate was diluted with H$_2$O (50 mL), and extracted with EtOAc (120 mL×2). The combined organic layers were washed with brine (60 mL×3), dried over anhydrous Na$_2$SO$_4$, filtered and the filtrate was concentrated under reduced pressure. The residue was purified by flash silica gel chromatography (Biotage; 120 g SepaFlash Silica Flash Column, Eluent of 0~10% EtOAc:Petroleum ether gradient, 60 mL/min) to afford two batches of product.

Batch 1: 2,6-bis(benzyloxy)-3-(4-bromo-3-fluorophenyl)pyridine (2.4 g, 5.17 mmol, 26.96% yield) was obtained as a light yellow oil.

Batch 2: 2,6-bis(benzyloxy)-3-(4-bromo-3-fluorophenyl)pyridine (4.2 g, 9.05 mmol, 47.18% yield) was obtained as a light yellow oil. MS (M+H)$^+$=465.1.

Step 5. Synthesis of ethyl 1-(4-(2,6-bis(benzyloxy)pyridin-3-yl)-2-fluorophenyl)piperidine-4-carboxylate (6)

A mixture of 2,6-bis(benzyloxy)-3-(4-bromo-3-fluorophenyl)pyridine (4.2 g, 9.05 mmol), ethyl piperidine-4-carboxylate (3.82 g, 24.31 mmol, 3.75 mL), Pd$_2$(dba)$_3$ (1.60 g, 1.75 mmol), RuPhos (800 mg, 1.71 mmol) and Cs$_2$CO$_3$ (9 g, 27.62 mmol) in Tol. (150 mL) was degassed and purged with N$_2$ for 3 times, and then the mixture was stirred at 100° C. for 16 hr under N$_2$ atmosphere. LCMS showed a peak (25%) with desired mass. The reaction mixture was filtered and the filtrate was concentrated under reduced pressure. The residue was purified by flash silica gel chromatography (Biotage; 120 g SepaFlash Silica Flash Column, Eluent of 2~20% EtOAc:Petroleum ether gradient, 80 mL/min). Compound ethyl 1-(4-(2,6-bis(benzyloxy)pyridin-3-yl)-2-fluorophenyl)piperidine-4-carboxylate (2.7 g, 4.99 mmol, 55.21% yield) was obtained as a light yellow oil. MS (M+H)$^+$=541.1

Step 6. Synthesis of (1-(4-(2,6-bis(benzyloxy)pyridin-3-yl)-2-fluorophenyl)piperidin-4-yl)methanol (7)

To a mixture of LAH (360 mg, 9.49 mmol) in THF (30 mL) was added ethyl 1-(4-(2,6-bis(benzyloxy)pyridin-3-yl)-2-fluorophenyl)piperidine-4-carboxylate (3.50 g, 6.47 mmol) in THF (40 mL) at 0° C., and then the mixture was stirred at 25° C. for 2 hr under N$_2$ atmosphere. LCMS showed main peak with desired mass. The reaction mixture was quenched with H$_2$O (4 mL) and NaOH solution (15%, 6 mL) at 0° C., then Na$_2$SO$_4$ (30 g) was added, then the suspension was filtered and the filtrate was concentrated under reduced pressured. Compound (1-(4-(2,6-bis(benzyloxy)pyridin-3-yl)-2-fluorophenyl)piperidin-4-yl)methanol (3.0 g, crude) was obtained as a light yellow solid. MS (M+H)$^+$=499.2.

Step 7. Synthesis of 3-(3-fluoro-4-(4-(hydroxymethyl)piperidin-1-yl)phenyl)piperidine-2,6-dione (8)

To a solution of (1-(4-(2,6-bis(benzyloxy)pyridin-3-yl)-2-fluorophenyl)piperidin-4-yl)methanol (3 g, 6.02 mmol) in CF$_3$CH$_2$OH (150 mL) was added HOAc (315.00 mg, 5.25 mmol, 300 uL) and Pd/C (800 mg, 6.02 mmol, 10% purity) under N$_2$ atmosphere, the mixture was degassed and purged with H$_2$ for several times, then the mixture was stirred at 20° C. for 16 hr under H$_2$ atmosphere (15 Psi). LCMS showed main peak with desired mass. The reaction mixture was filtered and the filtrate was concentrated under reduced pressure. Compound 3-(3-fluoro-4-(4-(hydroxymethyl)piperidin-1-yl)phenyl)piperidine-2,6-dione (1.9 g, crude) was obtained as a light yellow oil. MS (M+H)$^+$=321.1.

Step 8. Synthesis of 1-(4-(2,6-dioxopiperidin-3-yl)-2-fluorophenyl)piperidine-4-carbaldehyde (9)

To a solution of 3-(3-fluoro-4-(4-(hydroxymethyl)piperidin-1-yl)phenyl)piperidine-2,6-dione (1.90 g, 5.93 mmol) in DCM (100 mL) was added DMP (3.80 g, 8.96 mmol, 2.77 mL). The mixture was stirred at 20° C. for 2 hr. LCMS showed main peak with the desired mass was detected. The reaction mixture was filtered and the filtrate was concentrated under reduced pressure to give a residue. Compound 1-(4-(2,6-dioxopiperidin-3-yl)-2-fluorophenyl)piperidine-4-carbaldehyde (1.80 g, crude) was obtained as a yellow oil. MS (M+H)$^+$=319.1

Step 9. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (Compound 13)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (2.6 g, 4.48 mmol, HCl salt) in DCE (100 mL) was added 1-(4-(2,6-dioxopiperidin-3-yl)-2-fluorophenyl)piperidine-4-carbaldehyde (1.80 g, 5.65 mmol) and NaOAc (500 mg, 6.10 mmol). The mixture was stirred at 25° C. for 1 hr. Then NaBH(OAc)$_3$ (5.0 g, 23.59 mmol) was added to the mixture at 25° C., the mixture was stirred at 25° C. for 15 hr. LCMS showed a peak (41%) with desired mass. The reaction mixture was diluted with H$_2$O (30 mL) at 0° C., and adjusted pH ~9 with NaHCO$_3$ (sat. aq) at 0° C., then extracted with EtOAc (80 mL×3). The combined organic layers were washed with brine (100 mL×2), dried over anhydrous Na$_2$SO$_4$, filtered. The filtrate was concentrated under reduced pressure. The residue was purified by flash silica gel chromatography (Biotage; 20 g SepaFlash Silica Flash Column, Eluent of 2~20% Methanol:Dichloromethane ether gradient, 50 mL/min). The product was triturated with MTBE and CH$_3$CN at 20° C. for 1 hr 4 times followed by lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (501.9 mg, 578.47 μmol, 12.91% yield, 97.5% purity) as a white solid. The mother liquor was concentrated under reduced pressure, the residue was purified by prep-HPLC (column: Waters Xbridge C18 150*50 mm*10 μm; mobile phase: [water (NH$_4$HCO$_3$)-ACN]; B %: 42%-72%, 10 min; Column Temp: 30° C.) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methoxybenzamide (694 mg, 812.18 μmol, 18.12% yield, 99% purity) as a white solid. MS (M+H)$^+$=846.4

$^1$H NMR (400 MHz, DMSO-d$_6$) δ 10.82 (s, 1H), 8.49-8.39 (m, 1H), 8.35-8.26 (m, 1H), 8.22 (s, 1H), 7.88 (s, 1H), 7.55-7.44 (m, 2H), 7.03-6.90 (m, 3H), 4.93-4.82 (m, 1H), 4.48-4.32 (m, 1H), 4.04 (t, J=13.5 Hz, 2H), 3.94 (s, 3H), 3.83-3.73 (m, 1H), 3.37-3.32 (m, 5H), 2.69-2.57 (m, 3H), 2.47-2.43 (m 1H), 2.35-2.10 (m, 9H), 2.03-1.96 (m, 1H), 1.85-1.73 (m, 4H), 1.65-1.49 (m, 5H), 1.28-1.18 (m, 8H).

Example 14. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methoxybenzamide (Compound 14)

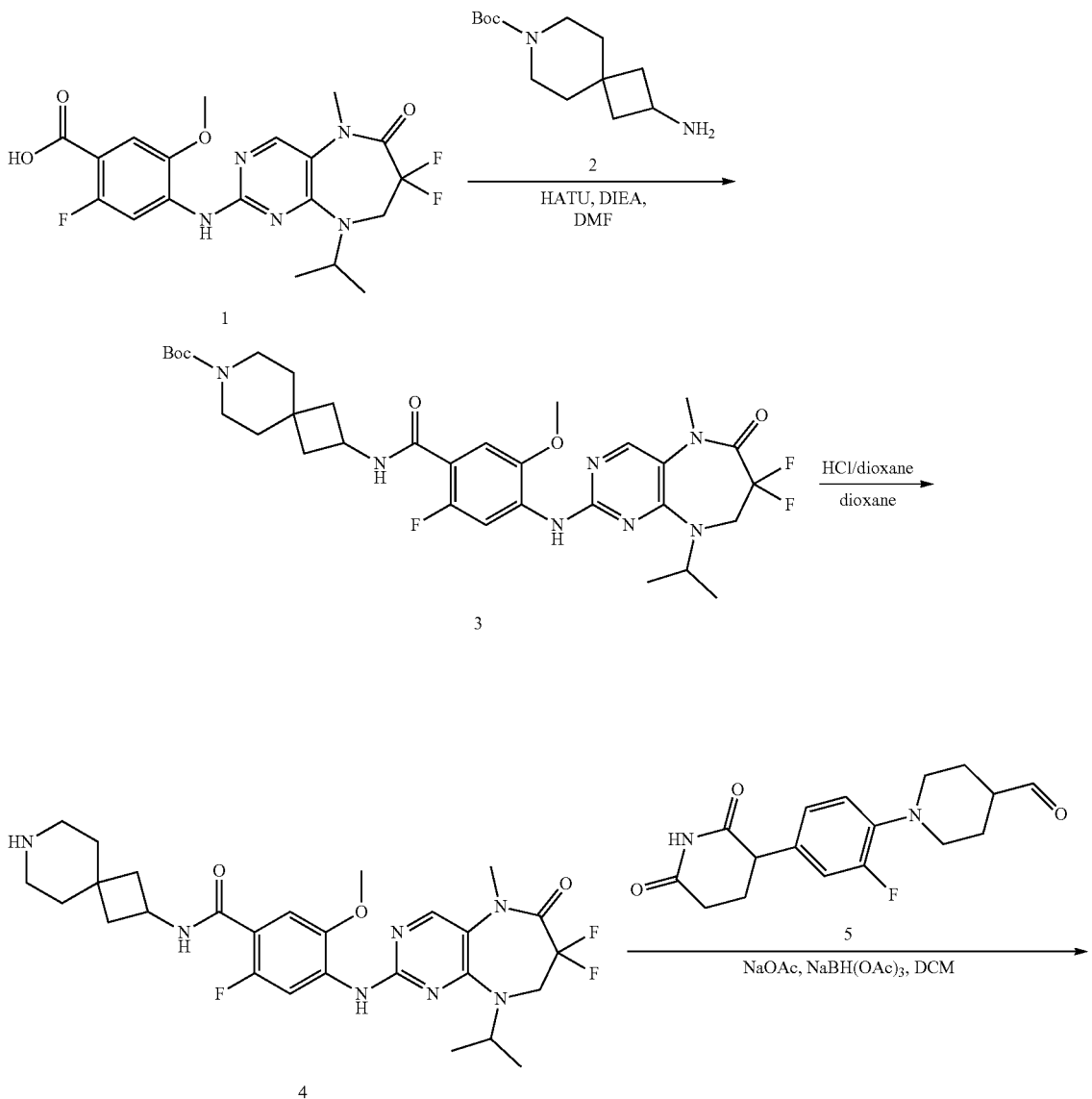

-continued

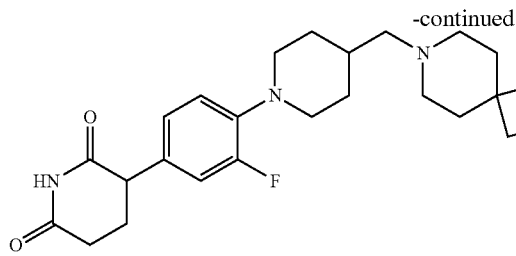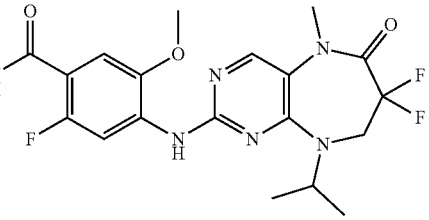

Compound 14

Step 1. Synthesis of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzamido)-7-azaspiro[3.5]nonane-7-carboxylate (3)

To the solution of 4-((7,7-difluoro-9-isopropyl-5-methyl-6-oxo-6,7,8,9-tetrahydro-5H-pyrimido [4,5-b][1,4]diazepin-2-yl)amino)-2-fluoro-5-methoxybenzoic acid (1 g, 2.28 mmol) and tert-butyl 2-amino-7-azaspiro[3.5]nonane-7-carboxylate (546.99 mg, 2.28 mmol) in DMF (20 mL) were added HATU (1.04 g, 2.73 mmol) and DIPEA (882.43 mg, 6.83 mmol, 1.19 mL) and the resulting mixture was stirred at 20° C. for 12 h. LCMS showed a peak (79%) with desired mass, the mixture was poured into water (100 mL) and extracted with EtOAc (50 mL×3). The combined organic layer was washed with brine (50 mL), dried over Na$_2$SO$_4$, filtered and concentrated in vacuum. The residue was purified by flash silica gel chromatography (20 g SepaFlash Silica Flash Column, Eluent of 0~100% EtOAc/Petroleum ether gradient @ 80 mL/min) to afford tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzamido)-7-azaspiro[3.5]nonane-7-carboxylate (1.5 g, 2.24 mmol, 98.61% yield, 99% purity) as a yellow solid. MS (M+H)$^+$=662.6

Step 2. Synthesis of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxy-N-(7-azaspiro[3.5]nonan-2-yl)benzamide (4)

To the solution of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxybenzamido)-7-azaspiro[3.5]nonane-7-carboxylate (1.5 g, 2.27 mmol) in dioxane (10 mL) was added HCl/dioxane (4 M, 10 mL) and the resulting mixture was stirred at 20° C. for 2 h. LCMS showed a peak (100%) with desired mass, the mixture was concentrated under reduced pressure to afford 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxy-N-(7-azaspiro[3.5]nonan-2-yl)benzamide (1.3 g, 2.17 mmol, 95.89% yield, HCl salt) as a yellow solid. MS (M+H)$^+$=562.2

Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methoxybenzamide (Compound 14)

To a solution of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methoxy-N-(7-azaspiro[3.5]nonan-2-yl)benzamide (1.3 g, 2.17 mmol HCl salt) in DCM (20 mL) was added 1-(4-(2,6-dioxopiperidin-3-yl)-2-fluorophenyl)piperidine-4-carbaldehyde (691.98 mg, 2.17 mmol) and NaOAc (267.48 mg, 3.26 mmol), the mixture was stirred at 20° C. for 1 h. Then NaBH (OAc)$_3$ (2.30 g, 10.87 mmol) was added to the mixture at 20° C., the resulting mixture was stirred at 20° C. for 15 h. LCMS showed a peak (29%) with desired mass, the mixture was poured into water (100 mL) and extracted with DCM (50 mL×3). The combined organic layer was washed with brine (50 mL), dried over Na$_2$SO$_4$, filtered and concentrated. The residue was purified by flash silica gel chromatography (20 g SepaFlash Silica Flash Column, Eluent of 0~30% MeOH/EtOAc gradient @ 80 mL/min) to afford 0.75 g of crude product. The crude product was triturated with DMF (5 mL) and MeOH (2 mL) to afford 4-((7,7-difluoro-9-isopropyl-5-methyl-6-oxo-6,7,8, 9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methoxybenzamide (203 mg, 225.57 μmol, 10.38% yield, 96% purity) as a white solid. The mother liquor was re-purified by prep-HPLC (column: Waters Xbridge C18 150*50 mm*10 um; mobile phase: [water (NH$_4$HCO$_3$)-ACN]; B %: 45%-75%, 10 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methoxybenzamide (271.3 mg, 301.47 μmol, 13.87% yield, 96% purity) as a white solid. MS (M+H)$^+$=864.5.

$^1$H NMR (400 MHz, DMSO-d$_6$) δ=10.80 (s, 1H), 8.31-8.24 (m, 2H), 8.21 (dd, J=3.3, 7.4 Hz, 1H), 7.96 (s, 1H), 7.19 (d, J=6.8 Hz, 1H), 7.03-6.92 (m, 3H), 4.97-4.83 (m, 1H), 4.44-4.31 (m, 1H), 4.06 (t, J=13.4 Hz, 2H), 3.91 (s, 3H), 3.79 (dd, J=4.8, 11.8 Hz, 1H), 3.33 (s, 2H), 3.29 (s, 3H), 2.68-2.58 (m, 3H), 2.49-2.43 (m, 1H), 2.32-2.09 (m, 9H), 2.03-1.96 (m, 1H), 1.82-1.74 (m, 4H), 1.62-1.49 (m, 5H), 1.28-1.19 (m, 8H).

Example 15. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2,6-difluorophenyl)piperidin-4-yl)methyl)-7-azaspiro[3.5]nonan-2-yl)-3-methoxybenzamide (Compound 15)

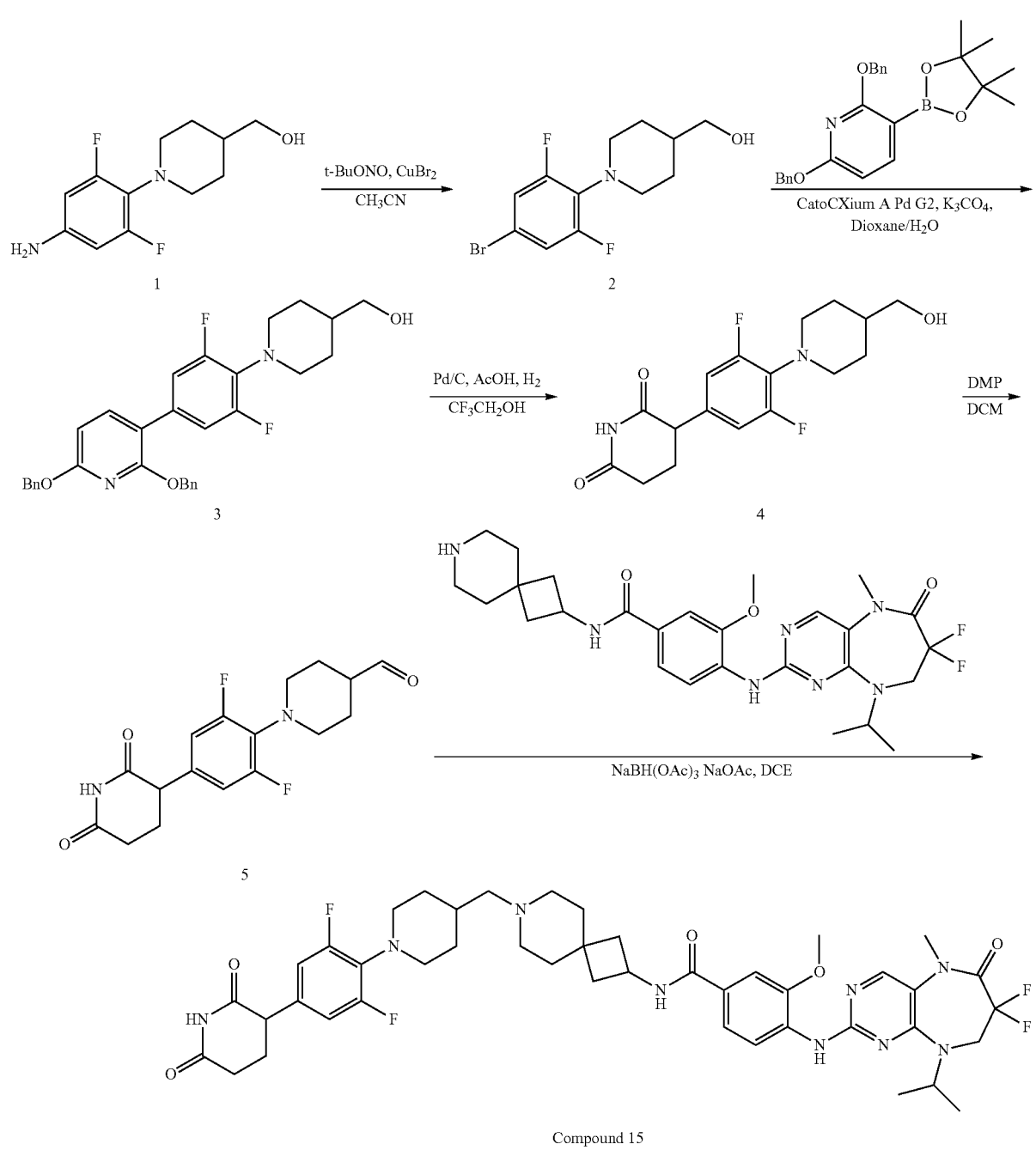

Compound 15

Step 1. Synthesis of (1-(4-bromo-2,6-difluorophenyl)piperidin-4-yl)methanol (2)

To a mixture of (1-(4-amino-2,6-difluorophenyl)piperidin-4-yl)methanol (3.4 g, 14.03 mmol) in CH$_3$CN (50 mL) was added tert-butyl nitrite (2.25 g, 21.86 mmol, 2.6 mL) at 0° C., and then the mixture was stirred at 0° C. for 0.5 h and then CuBr$_2$ (2.7 g, 12.09 mmol, 566.04 μL) was added at 0° C., the mixture was stirred at 25° C. for 3.5 h under N$_2$ atmosphere. LCMS showed a main peak with the desired mass. The reaction mixture was filtered and the filtrate was concentrated under reduced pressure. The residue was diluted with EtOAc (80 mL) and then added H$_2$O (20 mL) added at 0° C., then saturated NaHCO$_3$ (20 mL) was added to the water layers to adjust pH=9 at 0° C., the combined water layers was extracted with EtOAc 120 mL (40 mL×3), then the combined organic layers dried over $Na_2SO_4$, filtered and the filtrate was concentrated under reduced pressure. The residue was purified by flash silica gel chromatography (Biotage; 40 g SepaFlash Silica Flash Column, Eluent of 10~50% EtOAc:Petroleum ether gradient, 80 mL/min) to afford (1-(4-bromo-2,6-difluorophenyl)piperidin-4-yl) methanol (900 mg, 2.94 mmol, 20.95% yield) as a light yellow oil. MS $(M+H)^+$=306

Step 2. Synthesis of (1-(4-(2,6-bis(benzyloxy)pyridin-3-yl)-2,6-difluorophenyl)piperidin-4-yl) methanol (3)

A mixture of (1-(4-bromo-2,6-difluorophenyl)piperidin-4-yl)methanol (800 mg, 2.61 mmol), 2,6-bis(benzyloxy)-3-(4,4,5,5-tetramethyl-1,3,2-dioxaborolan-2-yl)pyridine (1.31 g, 3.14 mmol), CataCXium A Pd $G_2$ (300 mg, 448.68 µmol) and $K_3PO_4$ (1.66 g, 7.84 mmol) in dioxane (25 mL) and $H_2O$ (5 mL) was degassed and purged with $N_2$ for 3 times, and then the mixture was stirred at 50° C. for 16 hr under $N_2$ atmosphere. LCMS showed 40% peak with the desired mass was detected. The reaction mixture was filtered and to the filtrate was added $H_2O$ (10 mL), the mixture was extracted with EtOAc (40 mL×2), the combined organic layers were washed with brine 90 mL (30 mL×3), dried over $Na_2SO_4$, filtered and the filtrate was concentrated under reduced pressure. The residue was purified by flash silica gel chromatography (Biotage; 40 g SepaFlash Silica Flash Column, Eluent of 10~50% EtOAc:Petroleum ether gradient, 80 mL/min) to afford (1-(4-(2,6-bis(benzyloxy)pyridin-3-yl)-2,6-difluorophenyl)piperidin-4-yl)methanol (1.1 g, 2.13 mmol, 81.49% yield) as a light yellow oil. MS $(M+H)^+$=517.2

Step 3. Synthesis of 3-(3,5-difluoro-4-(4-(hydroxymethyl)piperidin-1-yl)phenyl) piperidine-2,6-dione (4)

To a solution of (1-(4-(2,6-bis(benzyloxy)pyridin-3-yl)-2,6-difluorophenyl)piperidin-4-yl)methanol (1.1 g, 2.13 mmol) in $CF_3CH_2OH$ (50 mL) was added $CH_3COOH$ (100 mg, 1.67 mmol, 95.24 µL) and Pd/C (400 mg, 2.13 mmol, 10% purity) under $N_2$ atmosphere, then the mixture was stirred at 20° C. for 16 hr under $H_2$ atmosphere (15 Psi). LCMS showed main peak with the desired mass was detected and no peak with the starting material was remained. The reaction mixture was filtered and the filtrate was concentrated under reduced pressure to afford 3-(3,5-difluoro-4-(4-(hydroxymethyl)piperidin-1-yl)phenyl)piperidine-2,6-dione (560 mg, crude) as a light yellow oil. MS $(M+H)^+$=339.1

$^1$H NMR (400 MHz, DMSO-$d_6$) δ=11.28-10.15 (m, 1H), 6.99-6.83 (m, 2H), 3.89-3.76 (m, 2H), 3.35-3.26 (m, 2H), 3.20-3.12 (m, 2H), 3.04-2.99 (m, 2H), 2.69-2.57 (m, 1H), 2.29-2.17 (m, 1H), 2.06-1.96 (m, 1H), 1.76-1.68 (m, 2H), 1.53-1.44 (m, 1H), 1.30-1.20 (m, 3H).

Step 4. Synthesis of 1-(4-(2,6-dioxopiperidin-3-yl)-2,6-difluorophenyl)piperidine-4-carbaldehyde (5)

To a solution of 3-(3,5-difluoro-4-(4-(hydroxymethyl)piperidin-1-yl)phenyl)piperidine-2,6-dione (200 mg, 591.11 µmol) in DCM (10 mL) was added DMP (380 mg, 895.93 µmol, 277.37 µL). The mixture was stirred at 20° C. for 2 hr. LCMS showed a main peak with the desired mass was detected. The reaction mixture was filtered and the filtrate was concentrated under reduced pressure to afford 1-(4-(2,6-dioxopiperidin-3-yl)-2,6-difluorophenyl)piperidine-4-carbaldehyde (180 mg, crude) as a light yellow oil. MS $(M+H)^+$=337.1

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2,6-difluorophenyl)piperidin-4-yl)methyl)-7-azaspiro[3.5]nonan-2-yl)-3-methoxybenzamide (Compound 15)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (220 mg, 379.27 µmol, HCl) in DCE (10 mL) was added 1-(4-(2,6-dioxopiperidin-3-yl)-2,6-difluorophenyl)piperidine-4-carbaldehyde (160 mg, 475.72 µmol) and NaOAc (60 mg, 731.44 µmol) The mixture was stirred at 25° C. for 1 hr. Then NaBH$(OAc)_3$ (460 mg, 2.17 mmol) was added to the mixture at 25° C., the mixture was stirred at 25° C. for 15 hr. LCMS showed 40% peak with the desired mass. To the reaction mixture was diluted with $H_2O$ (10 mL) at 0° C., then saturated $NaHCO_3$ (aq, 15 mL) was added to the water layers to adjust pH=9 at 0° C., the combined water layers was extracted with EtOAc 60 mL (20 mL×3), then the combined organic layers were washed with brine 60 mL (30 mL×2), dried over $Na_2SO_4$, filtered and the filtrate was concentrated under reduced pressure. The residue was purified by prep-HPLC (column: Phenomenex Synergi Polar-RP 100×25 mm×4 um; mobile phase: [water (TFA)-ACN]; B %: 33%-53%, 7 min; Column Temp: 30° C.) followed by lyophilization to give the crude product. The crude product was diluted with DMF (2 mL) and adjust pH=7~8 with DIPEA (0.15 mL). Then the mixture was filtered and the filtrate was re-purified by prep-HPLC (column: Waters Xbridge 150×25 mm×5 um; mobile phase: [water (NH$_4$HCO$_3$)-ACN]; B %: 47%-77%, 9 min; Column Temp: 30° C.) followed by lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2,6-difluorophenyl)piperidin-4-yl)methyl)-7-azaspiro[3.5]nonan-2-yl)-3-methoxybenzamide (37.4 mg, 40.69 µmol, 10.73% yield, 94% purity) as a white solid. MS $(M+H)^+$=864.4

$^1$H NMR (400 MHz, DMSO-$d_6$) δ=10.85 (s, 1H), 8.47-8.36 (m, 1H), 8.35-8.27 (m, 1H), 8.23 (s, 1H), 7.88 (s, 1H), 7.57-7.44 (m, 2H), 7.01-6.84 (m, 2H), 4.96-4.81 (m, 1H), 4.49-4.31 (m, 1H), 4.09-3.98 (m, 2H), 3.95 (s, 3H), 3.88-3.78 (m, 1H), 3.30 (s, 3H), 3.18-3.10 (m, 2H), 3.05-2.96 (m, 2H), 2.71-2.54 (m, 2H), 2.35-2.22 (m, 4H), 2.21-2.07 (m, 5H), 2.03-1.96 (m, 1H), 1.85-1.78 (m, 2H), 1.77-1.69 (m, 2H), 1.68-1.52 (m, 5H), 1.29-1.23 (m, 6H), 1.22-1.11 (m, 2H).

Example 16. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-3-yl)-2-fluorophenyl)piperazin-1-yl)methyl)-3,3-difluoropiperidin-1-yl)-3-methoxybenzamide (Compound 16)

Step 1. Synthesis of (3,3-difluoro-1-nitrosopiperidin-4-yl)methanol (2)

To a solution of (3,3-difluoro-4-piperidyl)methanol (4 g, 21.32 mmol HCl salt) and NaNO₂ (2.94 g, 42.64 mmol) in H₂O (50 mL) was added AcOH (3.20 g, 53.30 mmol) drop-wise at 0° C. The resulting solution was stirred at 20°

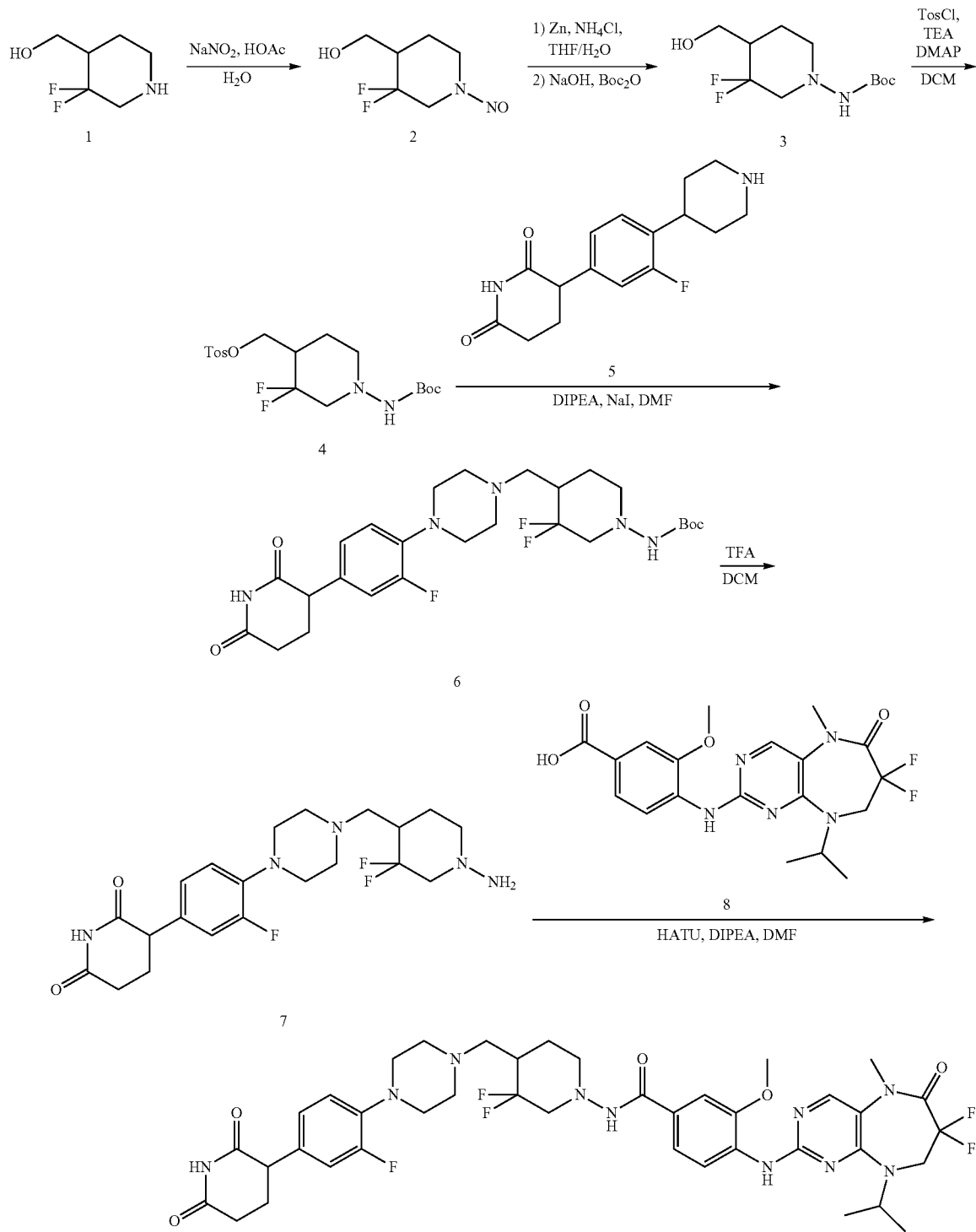

Compound 16

C. for 12 hrs. LCMS showed the starting material was consumed completely and a main peak with desired mass. The reaction solution was neutralized by solid NaHCO$_3$. The resulting mixture was extracted with EtOAc (40 mL×5). The combined organic layers were dried over Na$_2$SO$_4$, filtered. The filtrate was concentrated to afford (3,3-difluoro-1-nitrosopiperidin-4-yl)methanol (3.8 g, 20.67 mmol, 96.96% yield, 98% purity) as yellow oil. MS (M+H)$^+$=181.2

Step 2. Synthesis of tert-butyl (3,3-difluoro-4-(hydroxymethyl)piperidin-1-yl)carbamate (3)

To a mixture of (3,3-difluoro-1-nitrosopiperidin-4-yl)methanol (3.8 g, 21.09 mmol) and NH$_4$Cl (11.28 g, 210.93 mmol) in THF (40 mL) and H$_2$O (40 mL) was added Zn (6.21 g, 95.00 mmol) in portions at 0° C. The resulting mixture was stirred at 20° C. for 14 hrs. LCMS showed the starting material was consumed completely and the desired mass. The reaction mixture was filtered through a celite pad. To the filtrate was added NaOH (4.22 g, 105.47 mmol) and Boc$_2$O (11.51 g, 52.73 mmol). The resulting mixture was stirred at 20° C. for 14 hrs. LCMS showed trace of the starting material remained and the desired mass. The reaction mixture was filtered. The filtrate was extracted with EtOAc (300 mL×3). The combined organic layers were dried over Na$_2$SO$_4$, filtered. The filtrate was concentrated in vacuum. The crude product was triturated with petroleum ether (20 mL) to afford 6 g of the product as a white solid. 1 g of the crude product was further purified by flash silica gel chromatography (10 g silica gel column, EtOAc/petroleum ether=10-50%, 100 mL/min) to afford tert-butyl (3,3-difluoro-4-(hydroxymethyl)piperidin-1-yl)carbamate (500 mg, crude) as a white solid. Another 5 g of crude product was kept in hand. MS (M−56+H)$^+$=211.4

Step 3. Synthesis of (1-((tert-butoxycarbonyl)amino)-3,3-difluoropiperidin-4-yl)methyl 4-methylbenzenesulfonate (4)

To a solution of tert-butyl (3,3-difluoro-4-(hydroxymethyl)piperidin-1-yl)carbamate (2 g, 7.51 mmol) and TosCl (2.15 g, 11.27 mmol) in DCM (30 mL) were added TEA (2.28 g, 22.53 mmol) and DMAP (91.76 mg, 751.08 µmol) at 20° C. The resulting mixture was stirred at 20° C. for 14 hrs. LCMS showed the starting material was consumed completely and the desired mass. The reaction solution was diluted with DCM (20 mL) and washed with brine (20 mL), the organic layer was dried over Na$_2$SO$_4$, filtered. The filtrate was concentrated. The residue was purified by flash silica gel chromatography (20 g silica gel chromatography, EtOAc/petroleum ether=10-30%, 60 mL/min) to afford (1-((tert-butoxycarbonyl)amino)-3,3-difluoropiperidin-4-yl)methyl 4-methylbenzenesulfonate (700 mg, crude) as yellow solid. MS (M+Na)$^+$=443.1

Step 4. Synthesis of tert-butyl (4-((4-(4-(2,6-dioxopiperidin-3-yl)-2-fluorophenyl)piperazin-1-yl)methyl)-3,3-difluoropiperidin-1-yl)carbamate (6)

To a solution of 3-(3-fluoro-4-piperazin-1-yl-phenyl)piperidine-2,6-dione (350 mg, 1.07 mmol HCl salt) and (1-((tert-butoxycarbonyl)amino)-3,3-difluoropiperidin-4-yl)methyl 4-methylbenzenesulfonate (400.83 mg, 953.29 µmol) in DMF (5 mL) were added DIPEA (691.43 mg, 5.35 mmol) and NaI (32.08 mg, 214.00 µmol) at 20° C. The resulting mixture was stirred at 70° C. for 1 h. LCMS showed the starting material remained and the desired mass. The reaction solution was stirred at 70° C. for another 13 hrs. LCMS showed the starting material was consumed completely and the desired mass. The reaction mixture was poured into water (15 mL) and extracted with EtOAc (10 mL×4). The combined organic layers were dried over Na$_2$SO$_4$, filtered. The filtrate was concentrated in vacuum. The crude product was purified prep-TLC (pure ethyl acetate, Rf=0.4) to afford tert-butyl (4-((4-(4-(2,6-dioxopiperidin-3-yl)-2-fluorophenyl)piperazin-1-yl)methyl)-3,3-difluoropiperidin-1-yl)carbamate (70 mg, 125.84 µmol, 11.76% yield, 97% purity). MS (M+H)$^+$=540.3

$^1$H NMR (400 MHz, CDCl$_3$) δ=7.99 (s, 1H), 6.96-6.87 (m, 3H), 6.12 (br s, 1H), 3.72 (dd, J=5.2, 9.8 Hz, 1H), 3.38-3.20 (m, 2H), 3.18-3.01 (m, 6H), 2.78-2.62 (m, 5H), 2.59-2.47 (m, 2H), 2.47-2.37 (m, 1H), 2.32-2.19 (m, 2H), 2.03-1.96 (m, 1H), 1.71-1.57 (m, 2H), 1.46 (s, 9H).

Step 5. Synthesis of 3-(4-(4-((1-amino-3,3-difluoropiperidin-4-yl)methyl)piperazin-1-yl)-3-fluorophenyl)piperidine-2,6-dione (7)

To a solution of tert-butyl (4-((4-(4-(2,6-dioxopiperidin-3-yl)-2-fluorophenyl)piperazin-1-yl)methyl)-3,3-difluoropiperidin-1-yl)carbamate (50 mg, 92.66 µmol) in DCM (1 mL) was added TFA (10.57 mg, 92.66 µmol) at 20° C. The resulting solution was stirred at 20° C. for 20 mins. LCMS showed the starting material was consumed completely and the desired mass. The reaction solution was concentrated to afford 3-(4-(4-((1-amino-3,3-difluoropiperidin-4-yl)methyl)piperazin-1-yl)-3-fluorophenyl)piperidine-2,6-dione (60 mg, crude, 2TFA salt) as yellow oil. MS (M+H)$^+$=440.3

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-3-yl)-2-fluorophenyl)piperazin-1-yl)methyl)-3,3-difluoropiperidin-1-yl)-3-methoxybenzamide (Compound 16)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (37.88 mg, 89.89 µmol), DIPEA (69.70 mg, 539.31 µmol) and HATU (37.59 mg, 98.87 µmol) in DMF (2 mL) was added 3-(4-(4-((1-amino-3,3-difluoropiperidin-4-yl)methyl)piperazin-1-yl)-3-fluorophenyl)piperidine-2,6-dione (60 mg, 89.89 µmol, 2TFA salt) at 20° C. The resulting mixture was stirred at 20° C. for 30 mins. LCMS showed the starting material was consumed completely and the desired mass. The reaction solution was poured into water (10 mL) and extracted with EtOAc (5 mL×4). The combined organic layers were dried over Na$_2$SO$_4$, filtered. The filtrate was concentrated. The crude product was further purified by prep-HPLC (column: Phenomenex C18 75×30 mm×3 µm; mobile phase: [water (FA)-ACN]; B %: 12%-42%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-3-yl)-2-fluorophenyl)piperazin-1-yl)methyl)-3,3-difluoropiperidin-1-yl)-3-methoxybenzamide (12.8 mg, 14.73 µmol, 16.39% yield, 97% purity) as a white solid. MS (M+H)$^+$=843.2

$^1$H NMR (400 MHz, CDCl$_3$) δ=8.48 (d, J=8.4 Hz, 1H), 8.04 (s, 1H), 7.97 (s, 1H), 7.74 (s, 1H), 7.70 (br s, 1H), 7.38 (br s, 1H), 7.26-7.20 (m, 1H), 6.95-6.88 (m, 3H), 4.98 (td, J=6.4, 13.0 Hz, 1H), 3.98 (s, 3H), 3.88 (t, J=13.0 Hz, 2H), 3.72 (dd, J=5.2, 9.8 Hz, 1H), 3.68-3.54 (m, 1H), 3.51-3.35 (m, 5H), 3.32-3.24 (m, 1H), 3.17-3.07 (m, 4H), 2.83-2.72 (m, 4H), 2.72-2.66 (m, 1H), 2.62-2.54 (m, 1H), 2.53-2.45 (m, 1H), 2.30-2.18 (m, 2H), 2.15-2.03 (m, 2H), 1.75-1.70 (m, 1H), 1.33 (d, J=6.8 Hz, 6H).

Example 17. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(2-(2-(4-(4-(2,6-dioxopiperidin-3-yl)-2-fluorophenyl)piperazin-1-yl)ethyl)-4,4-difluoropyrrolidin-1-yl)-3-methoxybenzamide (Compound 17)

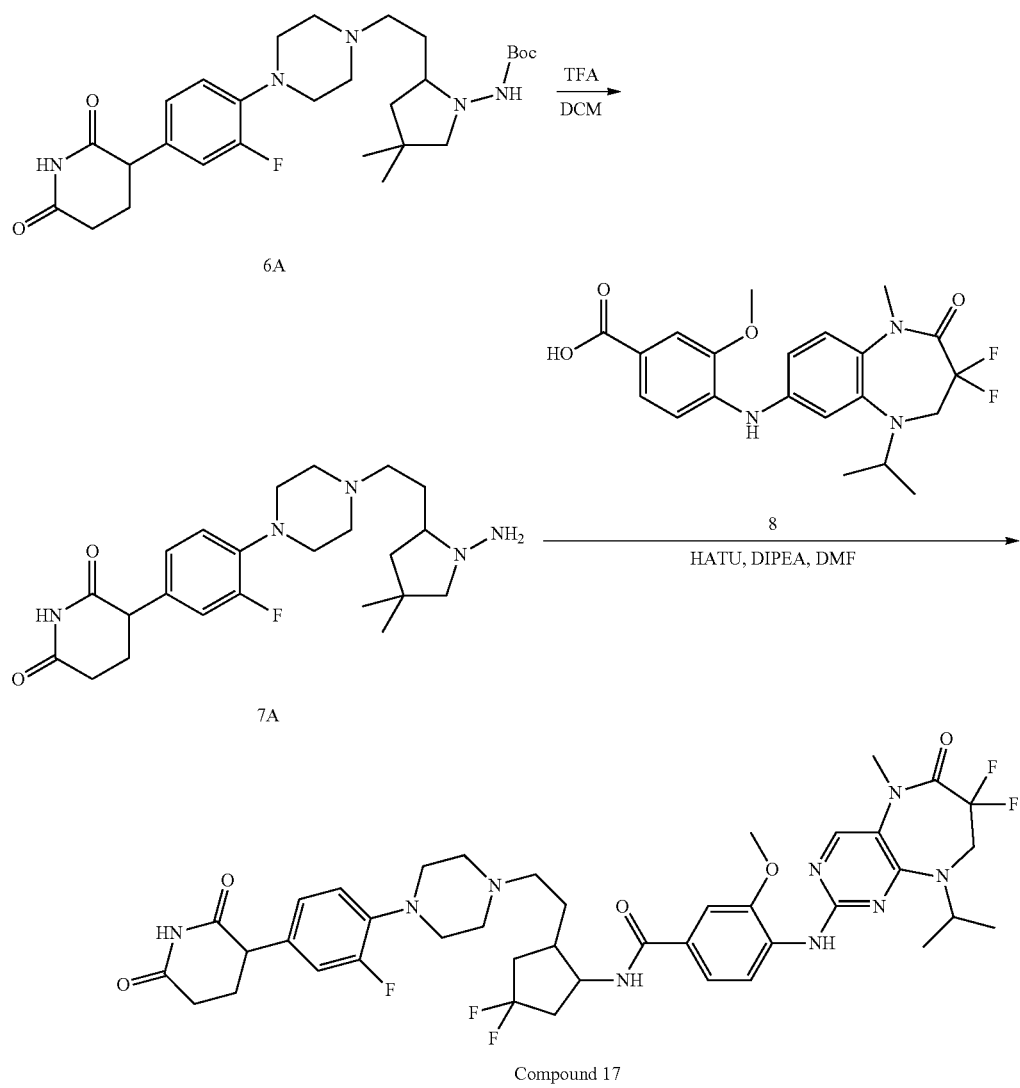

Step 1. Synthesis of 3-(4-(4-(2-(1-amino-4,4-difluoropyrrolidin-2-yl)ethyl)piperazin-1-yl)-3-fluorophenyl)piperidine-2,6-dione (7A)

To a solution of tert-butyl (2-(2-(4-(4-(2,6-dioxopiperidin-3-yl)-2-fluorophenyl)piperazin-1-yl)ethyl)-4,4-difluoropyrrolidin-1-yl)carbamate (110 mg, 203.86 μmol) in DCM (1 mL) was added TFA (0.678 g, 5.943 mmol) at 20° C. The resulting solution was stirred at 20° C. for 20 mins. LCMS showed the starting material was consumed completely and the desired mass. The reaction solution was concentrated to afford 3-(4-(4-(2-(1-amino-4,4-difluoropyrrolidin-2-yl)ethyl)piperazin-1-yl)-3-fluorophenyl)piperidine-2,6-dione (130 mg, crude, 2TFA salt) as yellow oil. MS (M+H)$^+$=440.3

Step 2. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(2-(2-(4-(4-(2,6-dioxopiperidin-3-yl)-2-fluorophenyl)piperazin-1-yl)ethyl)-4,4-difluoropyrrolidin-1-yl)-3-methoxybenzamide (Compound 17)

To a solution of 4-[(7,7-difluoro-9-isopropyl-5-methyl-6-oxo-8H-pyrimido[4, 5-b][1, 4]diazepin-2-yl)amino]-3-methoxy-benzoic acid (37.88 mg, 89.89 μmol), DIPEA (139.40 mg, 1.08 mmol) and HATU (54.68 mg, 143.82 μmol) in DMF (2 mL) was added 3-(4-(4-(2-(1-amino-4,4-difluoropyrrolidin-2-yl)ethyl)piperazin-1-yl)-3-fluorophenyl)piperidine-2,6-dione (120 mg, 179.77 μmol, 2TFA salt) at 20° C. The resulting mixture was stirred at 20° C. for 30 mins. LCMS showed the starting material was consumed completely and the desired mass. The reaction solution was poured into water (10 mL) and extracted with EtOAc (5 mL×4). The combined organic layers were dried over $Na_2SO_4$, filtered. The filtrate was concentrated in vacuum. The crude product was further purified by prep-HPLC (column: Phenomenex C18 75×30 mm×3 μm; mobile phase: [water (FA)-ACN]; B %: 15%-45%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(2-(2-(4-(4-(2,6-dioxopiperidin-3-yl)-2-fluorophenyl)piperazin-1-yl)ethyl)-4,4-difluoropyrrolidin-1-yl)-3-methoxybenzamide (12.5 mg, 14.43 μmol, 8.03% yield, 97.3% purity) as a white solid. MS $(M+H)^+=843.2$ $^1H$ NMR (400 MHz, $CDCl_3$) δ=8.49 (d, J=8.4 Hz, 1H), 8.04 (s, 1H), 7.96 (s, 1H), 7.75 (s, 1H), 7.41 (s, 1H), 7.21-7.24 (m, 2H), 6.96-6.89 (m, 3H), 5.02-4.93 (m, 1H), 3.98 (s, 3H), 3.88 (br t, J=13.0 Hz, 2H), 3.83-3.75 (m, 1H), 3.72 (dd, J=5.4, 9.9 Hz, 1H), 3.66-3.60 (m, 1H), 3.58-3.47 (m, 1H), 3.41 (s, 3H), 3.20-3.08 (m, 5H), 2.81-2.65 (m, 7H), 2.60-2.50 (m, 2H), 2.31-2.19 (m, 2H), 2.05-1.97 (m, 1H), 1.90-1.85 (m, 1H), 1.33 (d, J=6.8 Hz, 6H).

Example 18. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-3-yl)-2-fluorophenyl)piperazin-1-yl)methyl)-4-fluoropiperidin-1-yl)-3-methoxybenzamide (Compound 18)

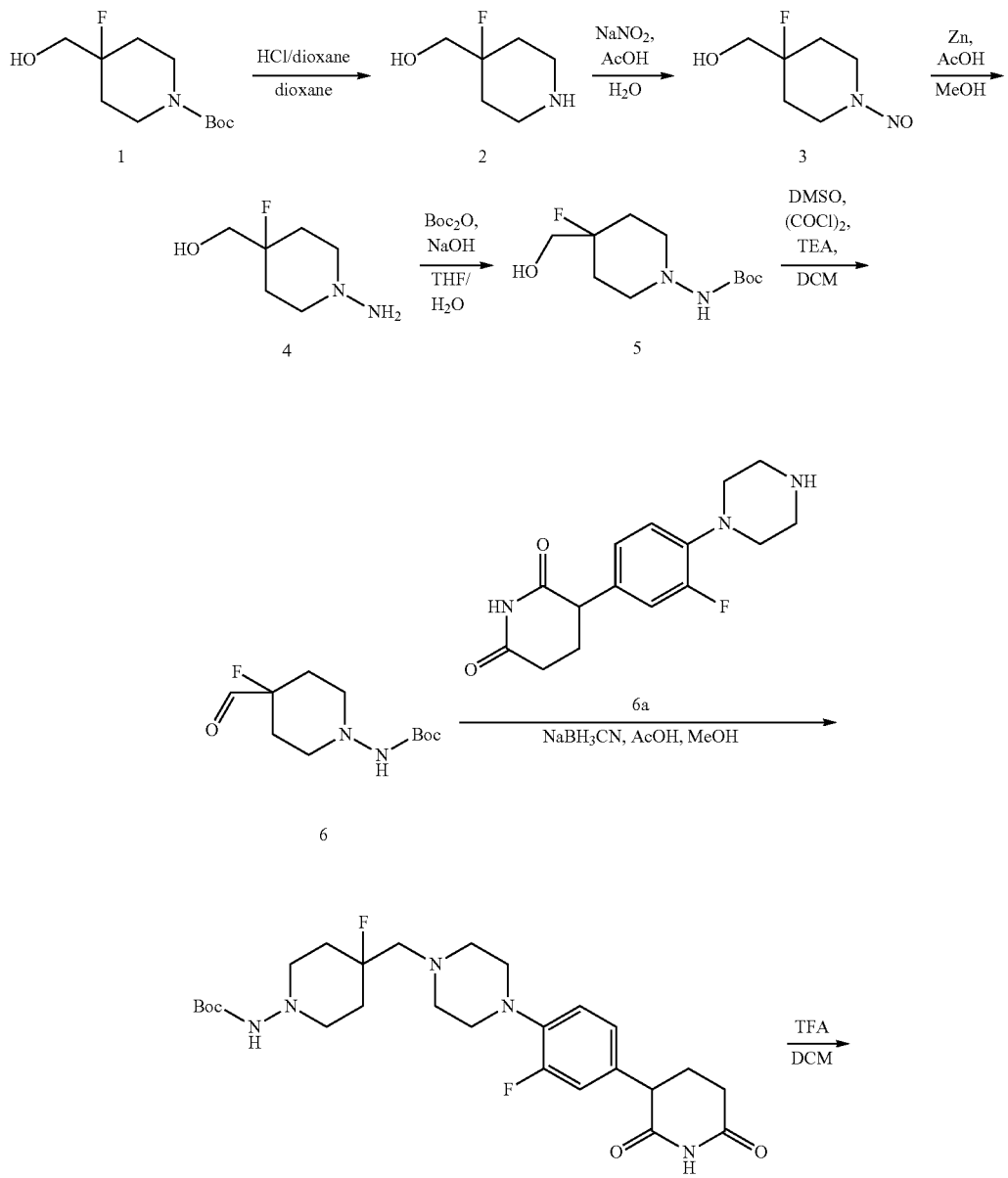

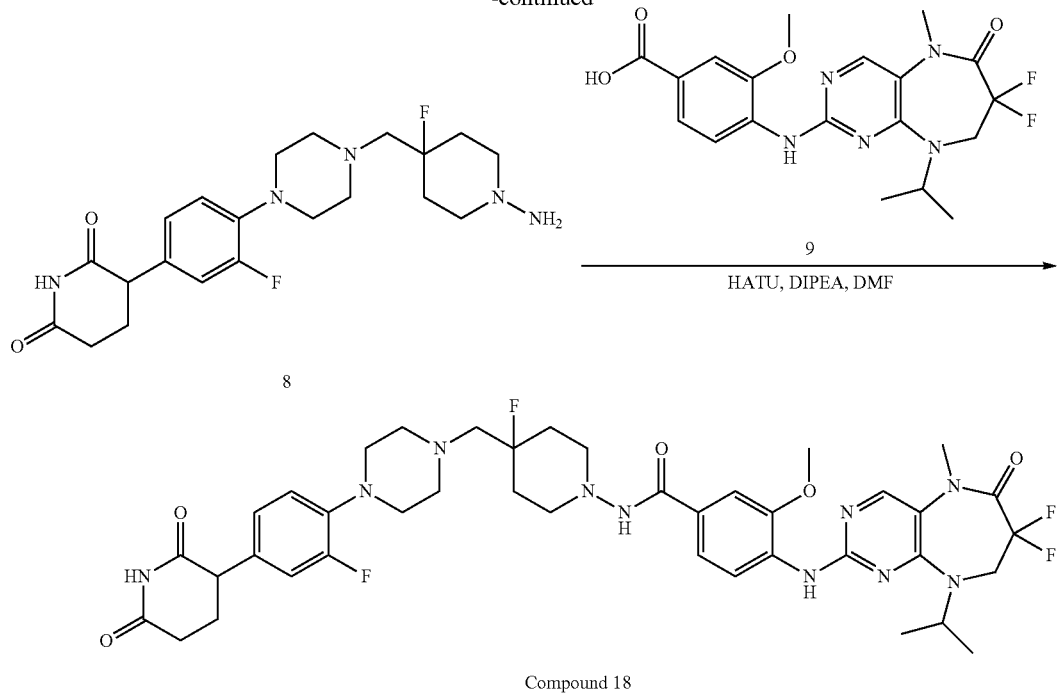

Compound 18

Step 1. Synthesis of (4-fluoropiperidin-4-yl)methanol (2)

To a solution of tert-butyl 4-fluoro-4-(hydroxymethyl) piperidine-1-carboxylate (3 g, 12.86 mmol) in dioxane (5 mL) was added HCl/dioxane (4 M, 30.00 mL) at 25° C. The mixture was stirred at 25° C. for 1 hr. LCMS showed the starting material was consumed completely and a peak (30%) with desired mass. The reaction mixture was concentrated under reduced pressure to afford (4-fluoropiperidin-4-yl)methanol (2.1 g, 12.38 mmol, 96.27% yield, 100% purity, HCl salt) as a white solid, which was used for the next step directly. MS (M+H)$^+$=134.2

Step 2. Synthesis of (4-fluoro-1-nitrosopiperidin-4-yl)methanol (3)

To a solution of (4-fluoropiperidin-4-yl)methanol (2.1 g, 12.38 mmol, HCl salt) in H$_2$O (20 mL) was added NaNO$_2$ (1.28 g, 18.57 mmol) portion wise at 0° C., then AcOH (1.49 g, 24.76 mmol, 1.42 mL) was added drop-wise at 0° C. The resulting mixture was allowed to warm to 25° C. slowly and stirred at 25° C. for 12 h. LCMS showed the starting material was consumed completely and a main peak with desired mass. The reaction mixture was adjust pH to 8 with solid NaHCO$_3$ and extracted with EtOAc/methanol (10:1, 150 mL×5). The combined organic layers were dried over Na$_2$SO$_4$, filtered and concentrated to afford (4-fluoro-1-nitrosopiperidin-4-yl)methanol (2 g, crude) as a yellow solid, which was used for the next step directly. MS (M+H)$^+$=163.3

Step 3. Synthesis of (1-amino-4-fluoropiperidin-4-yl)methanol (4)

To a solution of (4-fluoro-1-nitrosopiperidin-4-yl)methanol (2 g, 12.33 mmol) in MeOH (20 mL) was added Zn (3.23 g, 49.33 mmol) followed by AcOH (2.96 g, 49.33 mmol, 2.82 mL) at 0° C. The resulting mixture was allowed to warm to slowly and stirred at 25° C. for 2 h. LCMS showed the starting material was consumed completely and a peak (66%) with desired mass. The reaction mixture was filtered through a celite pad and the filter cake was washed with THF (100 mL). The combined filtrate was concentrated to afford (1-amino-4-fluoropiperidin-4-yl)methanol (5.6 g, crude) as a yellow solid, which was used for the next step directly. MS (M+H)$^+$=149.2

Step 4. Synthesis of tert-butyl (4-fluoro-4-(hydroxymethyl)piperidin-1-yl)carbamate (5)

A mixture of (1-amino-4-fluoropiperidin-4-yl)methanol (5.6 g, 37.79 mmol), Boc$_2$O (16.50 g, 75.58 mmol, 17.36 mL) and NaOH (6.05 g, 151.17 mmol) in H$_2$O (50 mL) and THF (50 mL) was stirred at 25° C. for 12 hr. LCMS showed the starting material was consumed completely and a peak (29%) with desired mass. The reaction mixture was filtered and the filtrate was extracted with EtOAc (30 mL×6). The combined organic phase was washed with brine (10 mL×3), dried over Na$_2$SO$_4$, filtered and concentrated under reduced pressure. The crude product was triturated with Petroleum ether:EtOAc=10:1 (50 mL) and stirred for 0.5 h. Then the mixture was filtered. The filter cake was collected and dried in vacuo to afford tert-butyl (4-fluoro-4-(hydroxymethyl)piperidin-1-yl)carbamate (1.2 g, 4.83 mmol, 12.79% yield) as a white solid, which was used for the next step directly. MS (M−56+H)$^+$=193.1

Step 5. Synthesis of tert-butyl (4-fluoro-4-formylpiperidin-1-yl)carbamate (6)

To a solution of DMSO (125.87 mg, 1.61 mmol, 125.87 μL) in DCM (5 mL) was added a solution of oxalyl chloride (132.91 mg, 1.05 mmol, 91.66 μL) in DCM (5 mL) dropwise at −65° C. The mixture was stirred at −65° C. for 10 min. Then a solution of tert-butyl (4-fluoro-4-(hydroxymethyl)piperidin-1-yl)carbamate (0.2 g, 805.50 µmol) in DCM (5 mL) was added drop-wise at −65° C. The mixture was stirred at −65° C. for 20 min, and TEA (407.54 mg, 4.03 mmol, 560.57 µL) was added drop-wise at −65° C. and the resulting mixture was warmed to 20° C. slowly and stirred at 20° C. for 30 min. LCMS showed the starting material was consumed completely. The mixture was diluted with DCM (50 mL), and washed with brine (10 mL×3), the organic layer was dried over $Na_2SO_4$, filtered. The filtrate was concentrated under reduced pressure to afford tert-butyl (4-fluoro-4-formylpiperidin-1-yl)carbamate (180 mg, crude) as colorless oil, which was used for the next step directly. MS $(M+H)^+$=247.3

Step 6. Synthesis of tert-butyl (4-((4-(4-(2,6-dioxopiperidin-3-yl)-2-fluorophenyl)piperazin-1-yl)methyl)-4-fluoropiperidin-1-yl)carbamate (7)

To a solution of tert-butyl (4-fluoro-4-formylpiperidin-1-yl)carbamate (169.08 mg, 686.53 µmol), 3-(3-fluoro-4-(piperazin-1-yl)phenyl)piperidine-2,6-dione (100 mg, 343.27 µmol) in MeOH (10 mL) was added HOAc (10.31 mg, 171.63 µmol, 9.82 µL) and the mixture was stirred at 25° C. for 30 min. Then $NaBH_3CN$ (43.14 mg, 686.53 µmol) was added and the mixture was stirred at 25° C. for another 12 h. LCMS showed the starting material was consumed completely and a main peak with desired mass. The reaction mixture was concentrated. The crude product was dissolved in EtOAc (50 mL) and washed with saturated $NaHCO_3$ (20 mL). The organic layer was separated and dried over $Na_2SO_4$, filtered. The filtrate was concentrated under reduced pressure. The residue was purified by flash silica gel chromatography (4 g SepaFlash Silica Flash Column, Eluent of 0~100% EtOAc/Petroleum ether gradient @ 60 mL/min) to afford tert-butyl (4-((4-(4-(2,6-dioxopiperidin-3-yl)-2-fluorophenyl)piperazin-1-yl)methyl)-4-fluoropiperidin-1-yl)carbamate (110 mg, crude) as a white sold, which was used for the next step directly. MS $(M+H)^+$=522.2

Step 7. Synthesis of 3-(4-(4-((1-amino-4-fluoropiperidin-4-yl)methyl)piperazin-1-yl)-3-fluorophenyl)piperidine-2,6-dione (8)

To a solution of tert-butyl (4-((4-(4-(2,6-dioxopiperidin-3-yl)-2-fluorophenyl)piperazin-1-yl)methyl)-4-fluoropiperidin-1-yl)carbamate (110 mg, 210.89 µmol) in DCM (5 mL) was added TFA (1.54 g, 13.51 mmol, 1 mL) at 25° C. The resulting mixture was stirred at 25° C. for 2 hr. LCMS showed the starting material was consumed completely and a main peak with desired mass. The mixture was concentrated under reduced pressure to afford 3-(4-(4-((1-amino-4-fluoropiperidin-4-yl)methyl)piperazin-1-yl)-3-fluorophenyl)piperidine-2,6-dione (112 mg, crude, TFA salt) as yellow oil, which was used for the next step directly. MS $(M+H)^+$=422.2

Step 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-3-yl)-2-fluorophenyl)piperazin-1-yl)methyl)-4-fluoropiperidin-1-yl)-3-methoxybenzamide (Compound 18)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (95 mg, 225.44 µmol) in DMF (2 mL) were added HATU (102.86 mg, 270.53 µmol) and DIPEA (87.41 mg, 676.32 µmol, 117.80 µL). The mixture was stirred at 25° C. for 10 min. Then 3-(4-(4-((1-amino-4-fluoropiperidin-4-yl)methyl)piperazin-1-yl)-3-fluorophenyl)piperidine-2,6-dione (108.65 mg, 202.90 µmol, TFA salt) was added and the resulting mixture was stirred at 25° C. for 1 h. LCMS showed the 3-(4-(4-((1-amino-4-fluoropiperidin-4-yl)methyl)piperazin-1-yl)-3-fluorophenyl)piperidine-2,6-dione was consumed completely and a peak (~63%) with desired mass. The reaction mixture was concentrated under reduced pressure. The residue was purified by flash silica gel chromatography (4 g SepaFlash Silica Flash Column, Eluent of 0~100% EtOAc/Petroleum ether gradient @ 60 mL/min; Eluent of 0~50% Methanol/EtOAc @ 60 mL/min) followed by prep-HPLC (column: Waters Xbridge 150×25 mm×5 µm; mobile phase: [water ($NH_4HCO_3$)-ACN]; B %: 39%-69%, 9 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-3-yl)-2-fluorophenyl)piperazin-1-yl)methyl)-4-fluoropiperidin-1-yl)-3-methoxybenzamide (23.9 mg, 28.39 µmol, 12.60% yield, 98% purity) as a white solid. MS $(M+H)^+$=825.5

$^1$H NMR (400 MHz, DMSO-$d_6$) δ=10.81 (s, 1H), 9.33 (s, 1H), 8.31 (dd, J=3.0, 8.3 Hz, 1H), 8.22 (s, 1H), 7.88 (s, 1H), 7.49-7.41 (m, 2H), 7.07-6.93 (m, 3H), 4.94-4.82 (m, 1H), 4.04 (br t, J=13.6 Hz, 2H), 3.93 (s, 3H), 3.80 (dd, J=4.8, 11.8 Hz, 1H), 3.30 (s, 3H), 3.05-2.86 (m, 8H), 2.85-2.50 (m, 8H), 2.27-2.13 (m, 1H), 2.05-1.71 (m, 5H), 1.24 (d, J=6.8 Hz, 6H).

Example 19. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)phenyl)piperidin-4-yl)methyl)-7-azaspiro[3.5]nonan-2-yl)-3-methoxybenzamide (Compound 19)

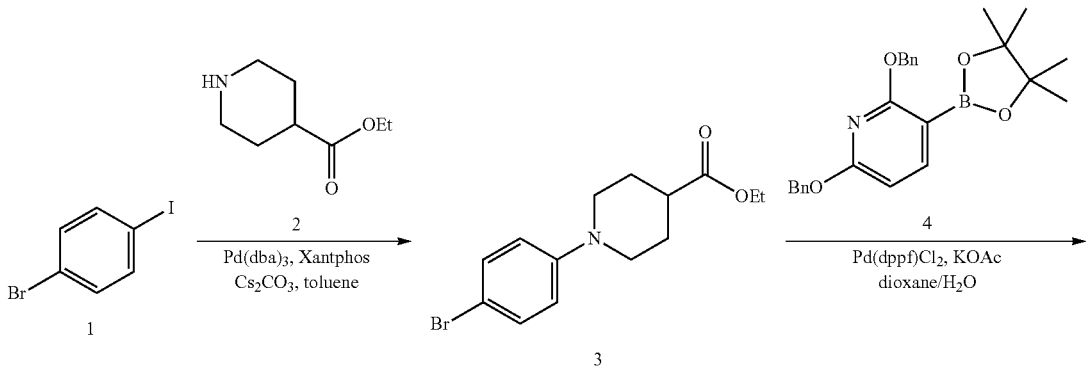

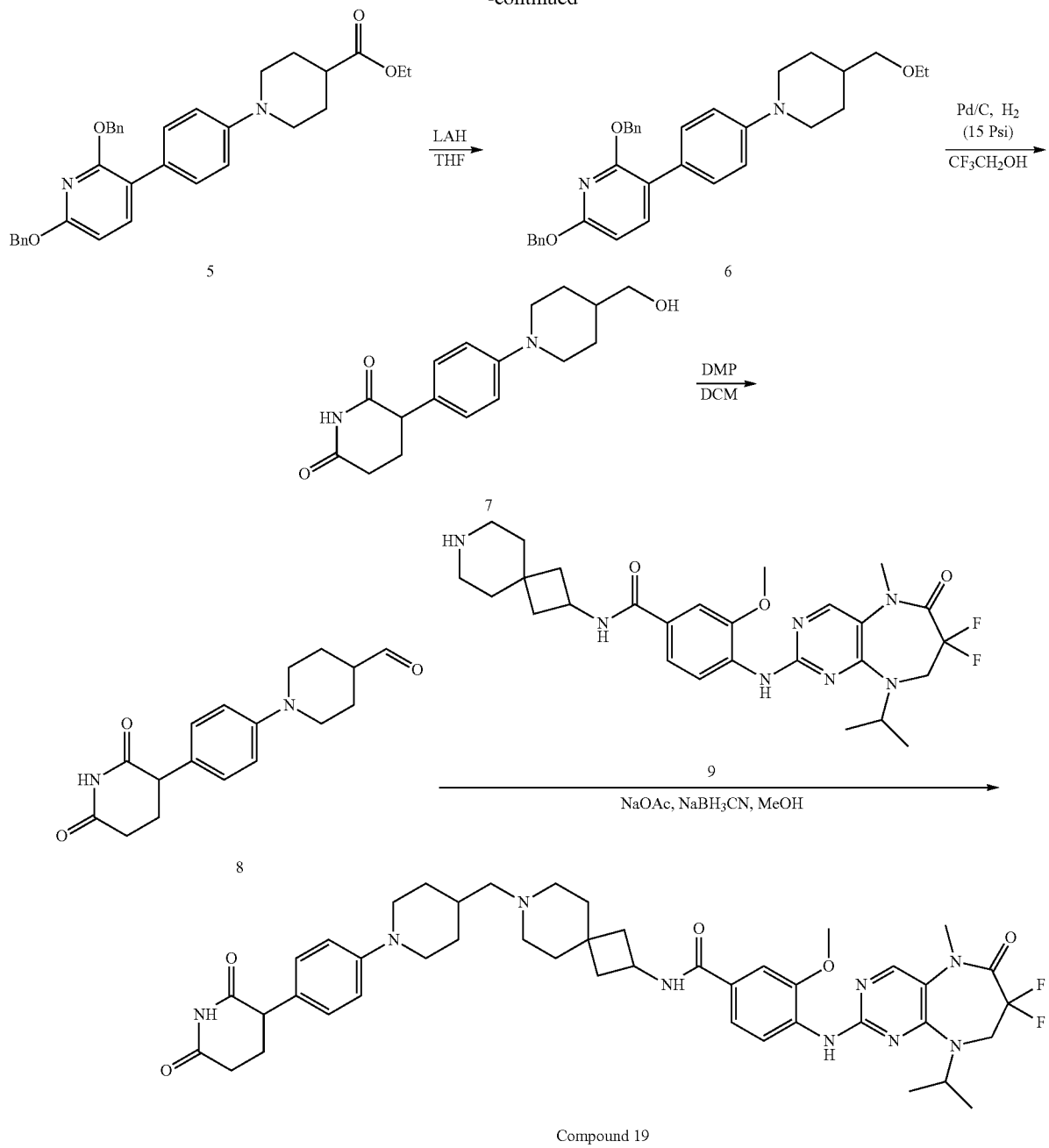

Compound 19

Step 1. Synthesis of ethyl 1-(4-bromophenyl)piperidine-4-carboxylate (3)

To a solution of 1-bromo-4-iodo-benzene (5 g, 17.67 mmol) and ethyl piperidine-4-carboxylate (2.50 g, 15.91 mmol) in toluene (50 mL) was added Pd$_2$(dba)$_3$ (809.21 mg, 883.69 µmol), Xantphos (613.58 mg, 1.06 mmol) and Cs$_2$CO$_3$ (17.28 g, 53.02 mmol) under N$_2$ atmosphere. The mixture was stirred at 90° C. for 2 h under N$_2$ atmosphere. LCMS showed the desired mass. The reaction mixture was filtered and concentrated under reduced pressure. The residue was purified by flash silica gel chromatography (ISCO; 40 g SepaFlash Silica Flash Column, Eluent of 0~30% EtOAc/Petroleum ether gradient @ 100 mL/min) to afford ethyl 1-(4-bromophenyl)piperidine-4-carboxylate (1.7 g, 3.27 mmol, 18.49% yield, 60% purity) as a light yellow solid. MS (M+H)$^+$=312.3

Step 2. Synthesis of ethyl 1-(4-(2,6-bis(benzyloxy)pyridin-3-yl)phenyl)piperidine-4-carboxylate (5)

To a solution of ethyl 1-(4-bromophenyl)piperidine-4-carboxylate (1 g, 3.20 mmol) and 2,6-bis(benzyloxy)-3-(4,4,5,5-tetramethyl-1,3,2-dioxaborolan-2-yl)pyridine (1.20 g, 2.88 mmol) in dioxane (10 mL) and H$_2$O (2 mL) were added KOAc (943.07 mg, 9.61 mmol) and Pd(dppf)Cl$_2$ (234.37 mg, 320.31 µmol) under N$_2$ atmosphere. The mixture was stirred at 100° C. for 16 h under N$_2$ atmosphere. LCMS showed the desired Mass. The reaction mixture was concentrated under reduced pressure. The residue was diluted with EtOAc (20 mL), dried over $Na_2SO_4$, filtered and concentrated under reduced pressure. The residue was purified by flash silica gel chromatography (ISCO; 40 g SepaFlash Silica Flash Column, Eluent of 0~30% EtOAc/Petroleum ether gradient @ 80 mL/min) to afford ethyl 1-(4-(2,6-bis(benzyloxy)pyridin-3-yl)phenyl)piperidine-4-carboxylate (280 mg, 482.17 μmol, 15.05% yield, 90% purity) as a yellow solid. MS $(M+H)^+$=523.5

Step 3. Synthesis of (1-(4-(2,6-bis(benzyloxy)pyridin-3-yl)phenyl)piperidin-4-yl)methanol (6)

To the suspension of $LiAlH_4$ (14.52 mg, 382.68 μmol) in THF (3 mL) was added a solution of ethyl 1-(4-(2,6-bis(benzyloxy)pyridin-3-yl)phenyl)piperidine-4-carboxylate (0.1 g, 191.34 μmol) in THF (3 mL) dropwise at 0° C. under $N_2$ atmosphere. The reaction mixture was stirred at 20° C. for 1 h. LCMS showed the desired Mass. The reaction mixture was combined another batch (0.18 g scale) for further work-up. The combined reaction mixture was quenched by addition of $H_2O$ (0.4 mL), 15% NaOH aq. (0.4 mL) and $H_2O$ (1.2 mL), the suspension was diluted with THF (50 mL), then dried over $Na_2SO_4$, filtered. The filtrate was concentrated under reduced pressure to afford (1-(4-(2,6-bis(benzyloxy)pyridin-3-yl)phenyl)piperidin-4-yl)methanol (250 mg, 520.19 μmol, 93.96% yield, 96% purity) as a yellow solid. MS $(M+H)^+$=481.5

Step 4. Synthesis of 3-(4-(4-(hydroxymethyl)piperidin-1-yl)phenyl)piperidine-2,6-dione (7)

To a solution of (1-(4-(2,6-bis(benzyloxy)pyridin-3-yl)phenyl)piperidin-4-yl)methanol (250 mg, 520.19 μmol) in $CF_3CH_2OH$ (5 mL) was added Pd/C (55.36 mg, 52.02 μmol, 10% purity) under $N_2$ atmosphere. The reaction mixture was degassed and purged with $H_2$ for 3 times, then the mixture was stirred at 20° C. for 16 h under $H_2$ (15 psi). LCMS showed the desired mass. The reaction mixture was filtered. The filtrate was concentrated under reduced pressure to afford 3-(4-(4-(hydroxymethyl)piperidin-1-yl)phenyl)piperidine-2,6-dione (150 mg, crude) as a yellow solid. MS $(M+H)^+$=303.2

Step 5. Synthesis of 1-(4-(2,6-dioxopiperidin-3-yl)phenyl)piperidine-4-carbaldehyde (8)

To a solution of 3-(4-(4-(hydroxymethyl)piperidin-1-yl)phenyl)piperidine-2,6-dione (100 mg, 330.72 μmol) in DCM (1 mL) was added DMP (210.41 mg, 496.09 μmol). The mixture was stirred at 20° C. for 2 h. The reaction mixture was filtered. The filtrate was concentrated under reduced pressure to afford 1-(4-(2,6-dioxopiperidin-3-yl)phenyl)piperidine-4-carbaldehyde (100 mg, crude) as a yellow oil.

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)phenyl)piperidin-4-yl)methyl)-7-azaspiro[3.5]nonan-2-yl)-3-methoxybenzamide (Compound 19)

To a solution of 1-[4-(2,6-dioxo-3-piperidyl) phenyl]piperidine-4-carbaldehyde (50 mg, 166.47 μmol) in MeOH (1 mL) were added 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (77.25 mg, 133.18 μmol, HCl salt) and NaOAc (20.48 mg, 249.71 μmol). The mixture was stirred at 20° C. for 1 hr. Then $NaBH_3CN$ (52.31 mg, 832.36 μmol) was added at 20° C. and the resulting mixture was stirred at 20° C. for 3 h. LCMS showed the desired mass. The reaction mixture was combined with another batch (50 mg scale) for further work-up. The combined reaction mixture was concentrated under reduced pressure. The residue was purified by flash silica gel chromatography (ISCO; 12 g SepaFlash Silica Flash Column, Eluent of 0~100% EtOAc/Petroleum ether to 0~100% MeOH/EtOAc gradient @ 80 mL/min) followed by prep-HPLC (column: Waters Xbridge 150×25 mm×5 μm; mobile phase: [water ($NH_4HCO_3$)-ACN]; B %: 47%-77%, 8 min) to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)phenyl)piperidin-4-yl)methyl)-7-azaspiro[3.5]nonan-2-yl)-3-methoxybenzamide (17.8 mg, 20.21 μmol, 12.14% yield, 94% purity) as a white solid. MS $(M+H)^+$=828.8

$^1$H NMR (400 MHz, DMSO-$d_6$) δ=10.76 (br d, J=3.2 Hz, 1H), 8.42 (br d, J=7.2 Hz, 1H), 8.33-8.27 (m, 1H), 8.22 (s, 1H), 7.88 (s, 1H), 7.53-7.47 (m, 2H), 7.02 (d, J=8.6 Hz, 2H), 6.87 (d, J=8.8 Hz, 2H), 4.88 (td, J=6.9, 13.4 Hz, 1H), 4.45-4.34 (m, 1H), 4.04 (br t, J=13.5 Hz, 2H), 3.94 (s, 3H), 3.71 (dd, J=5.0, 10.8 Hz, 1H), 3.64 (br d, J=12.1 Hz, 2H), 3.30 (s, 3H), 2.65-2.57 (m, 3H), 2.45-2.41 (m, 1H), 2.31-2.06 (m, 9H), 2.05-1.96 (m, 1H), 1.85-1.72 (m, 4H), 1.68-1.49 (m, 5H), 1.24 (d, J=6.7 Hz, 6H), 1.21-1.11 (m, 2H).

Example 20. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methylbenzamide (Compound 20)

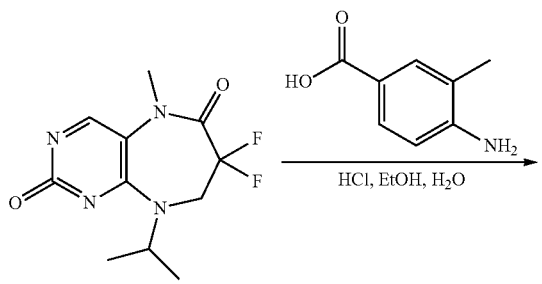

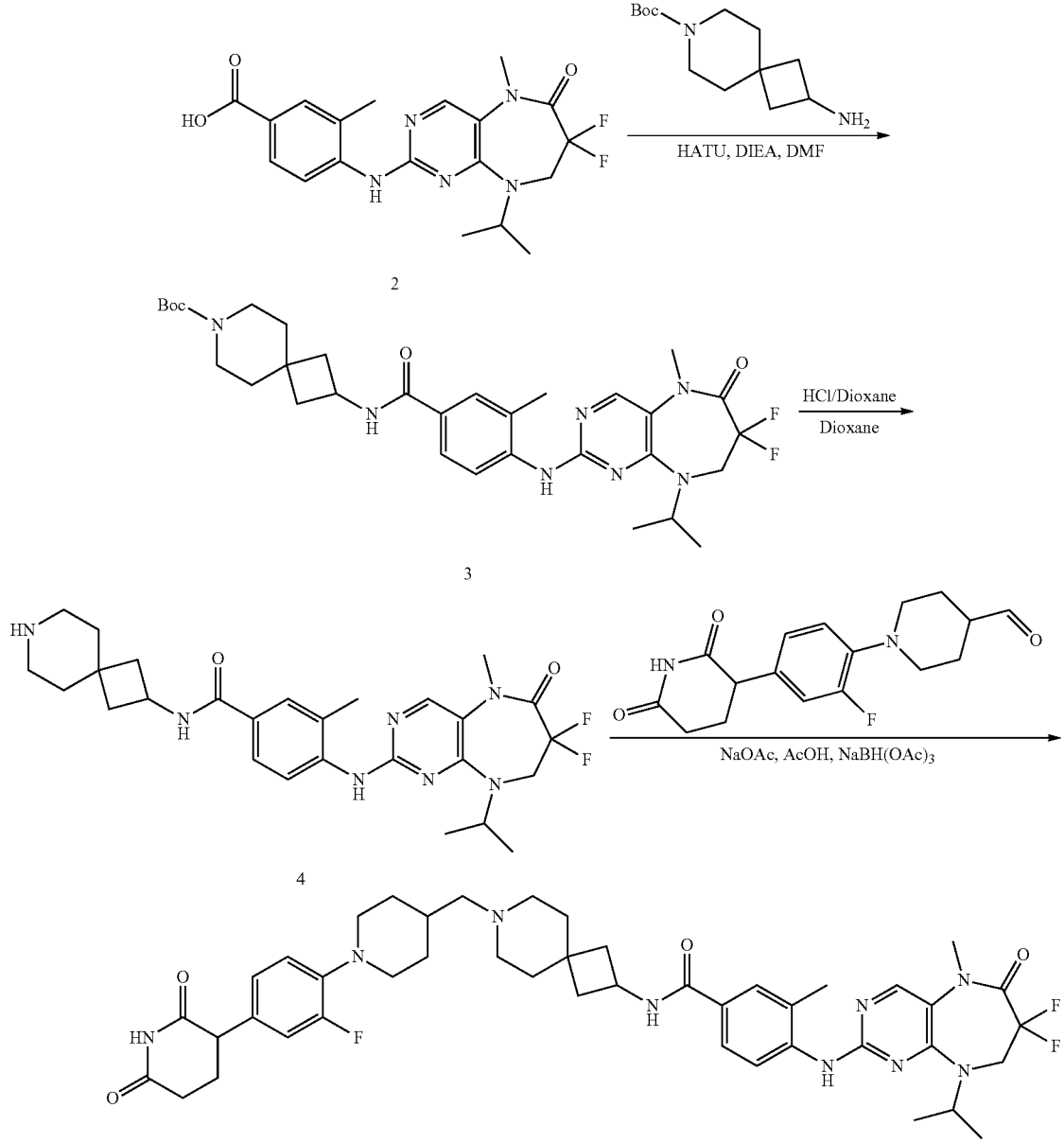

Compound 20

Step 1. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methylbenzoic Acid (2)

To a mixture of 2-chloro-7,7-difluoro-9-isopropyl-5-methyl-5,7,8,9-tetrahydro-6H-pyrimido[4,5-b][1,4]diazepin-6-one (1 g, 3.44 mmol) in EtOH (8 mL) and H$_2$O (32 mL) were added HCl (12 M, 602.00 μL) and 4-amino-3-methylbenzoic acid (520.00 mg, 3.44 mmol). The mixture was stirred at 100° C. for 16 hr. LCMS showed a main peak with desired mass. The mixture was concentrated under vacuum to remove EtOH and then filtered. The filter cake was concentrated under vacuum to afford 4-((7,7-difluoro-9-isopropyl-5-methyl-6-oxo-6,7,8,9-tetrahydro-5H-pyrimido[4,5-b][1,4]diazepin-2-yl)amino)-3-methylbenzoic acid (620 mg, crude) as a yellow powder. MS (M+H)$^+$=406.3.

Step 2. Synthesis of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-3-methylbenzamido)-7-azaspiro[3.5]nonane-7-carboxylate (3)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methylbenzoic acid (200 mg, 493.34 μmol) in DMF (3 mL) were added HATU (281.38 mg, 740.01 μmol) and DIPEA (191.28 mg, 1.48 mmol, 257.79 μL), then tert-butyl 2-amino-7-azaspiro[3.5]nonane-7-carboxylate (130.43 mg, 542.68 μmol) was added. The mixture was stirred at 20° C. for 16 hr. LCMS showed the starting material was consumed completely and the desired mass. The mixture was diluted with water (3 mL) and extracted with EtOAc (5 mL×3). The organic layer was dried over $Na_2SO_4$, filtered and concentrated under vacuum. The crude product was purified by flash silica gel chromatography (Biotage, 4 g SepaFlash Silica Flash Column, Eluent of 15~100% EtOAc/Petroleum ether gradient @ 20 mL/min) to afford tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-3-methylbenzamido)-7-azaspiro[3.5]nonane-7-carboxylate (230 mg, 359.08 μmol, 72.78% yield, 98% purity) as an orange powder. MS (M+H)$^+$=628.7

Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methyl-N-(7-azaspiro[3.5]nonan-2-yl)benzamide (4)

To a solution of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-3-methylbenzamido)-7-azaspiro[3.5]nonane-7-carboxylate (100 mg, 159.31 μmol) in dioxane (2 mL) was added HCl/dioxane (4 M, 2 mL), the mixture was stirred at 20° C. for 1 hr. LCMS showed main peak with desired mass. The reaction mixture was concentrated under vacuum to afford 4-((7,7-difluoro-9-isopropyl-5-methyl-6-oxo-6,7,8,9-tetrahydro-5H-pyrimido[4,5-b][1,4]diazepin-2-yl)amino)-3-methyl-N-(7-azaspiro[3.5]nonan-2-yl)benzamide (110 mg, crude, HCl) as a white powder. MS (M+H)$^+$=528.3

Step 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methylbenzamide (Compound 20)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methyl-N-(7-azaspiro[3.5]nonan-2-yl)benzamide (100 mg, 177.28 μmol, HCl) in DCE (2 mL) was added AcONa (14.54 mg, 177.28 μmol). The mixture was stirred at 20° C. for 0.5 h. Then 1-(4-(2,6-dioxopiperidin-3-yl)-2-fluorophenyl)piperidine-4-carbaldehyde (67.72 mg, 212.74 μmol) and AcOH (10.65 mg, 177.28 μmol, 10.14 μL) were added and stirred for 0.5 h. Then NaBH(OAc)$_3$ (56.36 mg, 265.92 μmol) was added. The resulting mixture was stirred at 20° C. for 17 hr. LCMS showed desired mass. The mixture was diluted with water (10 mL), extracted with EtOAc (15 mL×3). The organic layer was dried over $Na_2SO_4$, filtered and concentrated under vacuum. The crude product was purified by flash silica gel chromatography (Biotage, 4 g SepaFlash Silica Flash Column, Eluent of 4~100% EtOAc/Petroleum ether gradient @ 20 mL/min) to afford the product, which was further purified by Prep-HPLC (column: Waters Xbridge 150×25 mm×5 μm; mobile phase: [water (NH$_4$HCO$_3$)-ACN]; B %: 40%-70%, 9 min) and lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-3-methylbenzamide (5.2 mg, 6.16 μmol, 3.47% yield, 98.3% purity) as a white powder. MS (M+H)$^+$=830.4
$^1$H NMR (400 MHz, DMSO-d$_6$) δ=ppm 10.82 (s, 1H), 8.52 (s, 1H), 8.41 (d, J=7.58 Hz, 1H), 8.16 (d, J=0.86 Hz, 1H), 7.77-7.83 (m, 1H), 7.70 (s, 1H), 7.66 (d, J=8.31 Hz, 1H), 6.91-7.06 (m, 3H), 4.68-4.83 (m, 1H), 4.34-4.47 (m, 1H), 3.99 (t, J=13.57 Hz, 2H), 3.80 (dd, J=11.92, 4.58 Hz, 1H), 3.33-3.31 (m, 5H), 2.59-2.70 (m, 4H), 2.32-2.34 (m, 1H), 2.33-2.31 (m, 4H), 2.20-2.26 (m, 2H), 2.10-2.19 (m, 5H), 2.02-1.98 (m, 1H), 1.74-1.84 (m, 4H), 1.50-1.65 (m, 5H), 1.21-1.30 (m, 2H), 1.16 (d, J=6.72 Hz, 6H).

Example 21. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methylbenzamide (Compound 21)

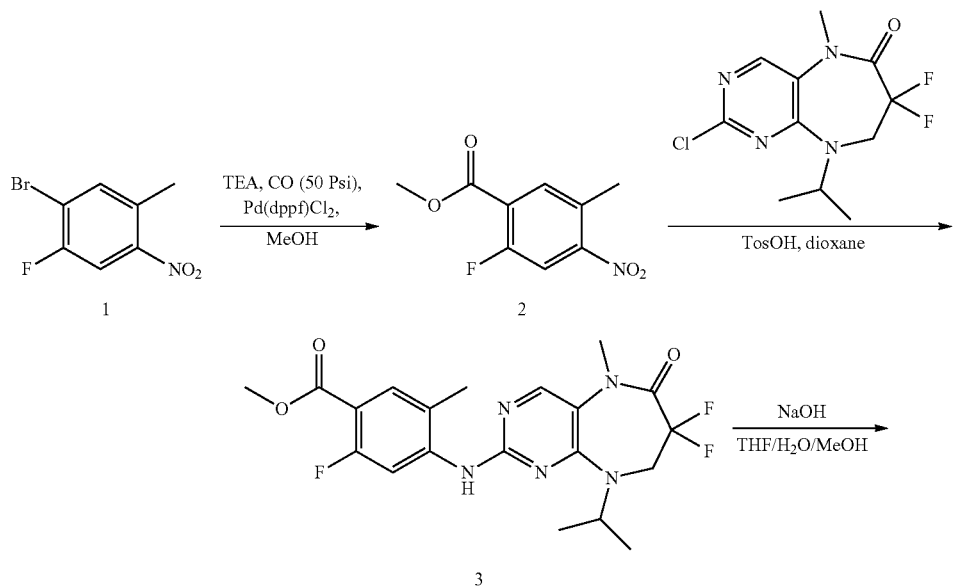

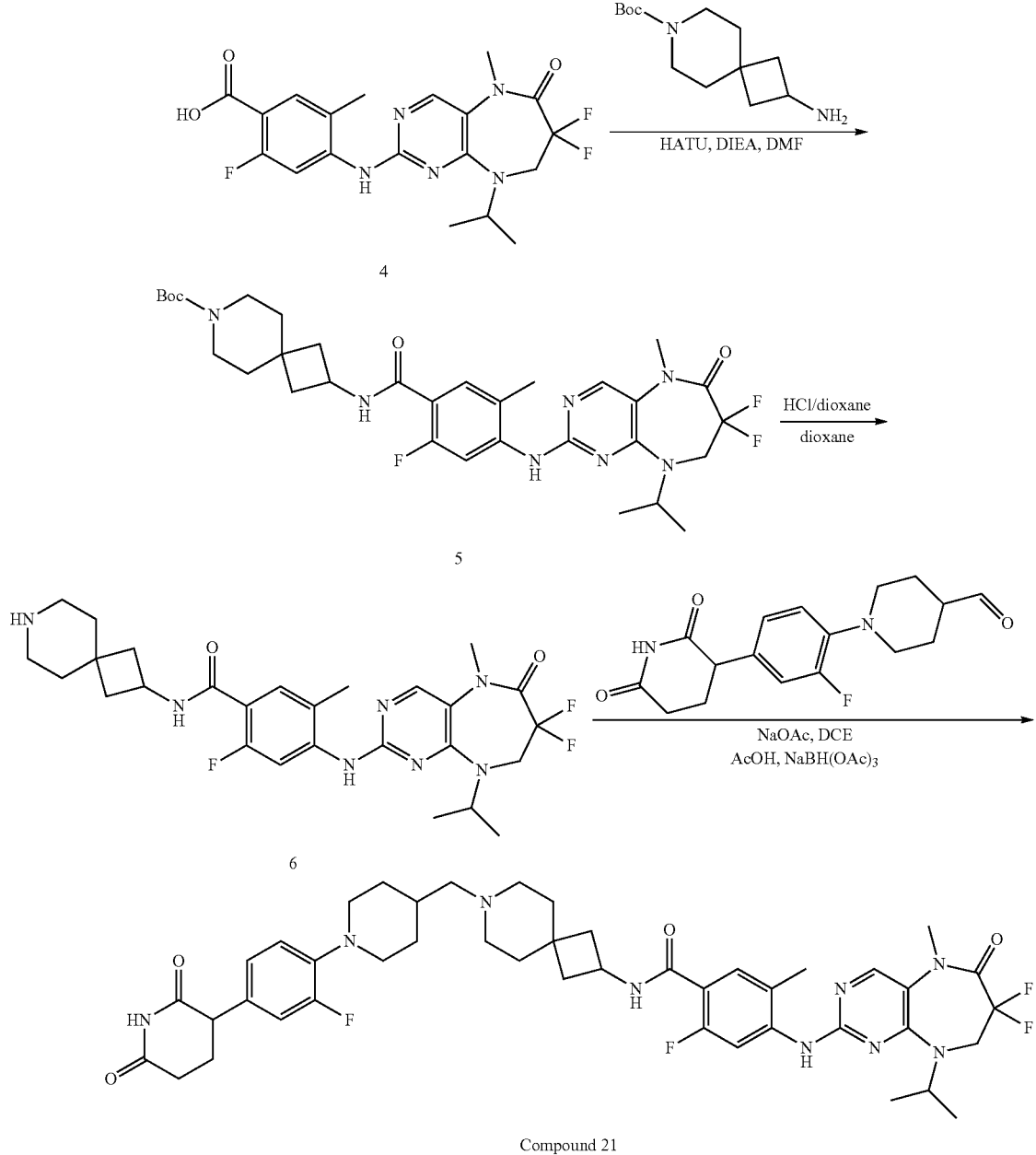

Compound 21

Step 1. Synthesis of methyl 4-amino-2-fluoro-5-methylbenzoate (2)

To a solution of 1-bromo-2-fluoro-5-methyl-4-nitrobenzene (1.5 g, 6.41 mmol) in MeoH (10 mL) were added Pd(dppf)Cl₂ (469.00 mg, 640.96 µmol) and TEA (1.95 g, 19.23 mmol, 2.68 mL). The mixture was degassed by N₂ for 3 times, then CO was bubbled into the mixture. The reaction mixture was stirred under CO (50 Psi) at 80° C. for 16 h. LCMS showed the desired mass. The mixture was diluted with water (3 mL) and extracted with EtOAc (5 mL×3). The organic layer was dried over Na₂SO₄, filtered and concentrated under vacuum. The crude product was purified by flash silica gel chromatography (Biotage, 4 g SepaFlash Silica Flash Column, Eluent of 4~50% EtOAc/Petroleum ether gradient @ 15 mL/min) to afford methyl 4-amino-2-fluoro-5-methylbenzoate (300 mg, 1.56 mmol, 24.27% yield, 95% purity) as a yellow solid. MS (M+H)⁺=184.1

Step 2. Synthesis of methyl 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzoate (3)

To a solution of methyl 4-amino-2-fluoro-5-methylbenzoate (300 mg, 1.64 mmol) in dioxane (10 mL) were added 2-chloro-7,7-difluoro-9-isopropyl-5-methyl-5, 7, 8, 9-tetrahydro-6H-pyrimido[4, 5-b][1, 4]diazepin-6-one (476.09 mg, 1.64 mmol) and TsOH. H₂O (934.58 mg, 4.91 mmol). The mixture was stirred at 100° C. for 16 hr. LCMS showed the desired mass. The mixture was diluted with water (3 mL) and extracted with EtOAc (5 mL×3). The organic layer was dried over Na$_2$SO$_4$, filtered and concentrated under vacuum. The crude product was purified by flash silica gel chromatography (Biotage, 4 g SepaFlash Silica Flash Column, Eluent of 20~98% EtOAc/Petroleum ether gradient @ 20 mL/min) to afford methyl 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzoate (190 mg, 395.28 μmol, 24.14% yield, 91% purity) as a yellow powder. MS (M+H)$^+$=438.4

Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzoic Acid (4)

To a solution of methyl 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzoate (190 mg, 434.37 μmol) in H$_2$O (3 mL), THF (3 mL) and MeOH (3 mL) was added NaOH (2 M, 1.52 mL). The mixture was stirred at 20° C. for 2 hr. LCMS showed the starting material consumed completely. The reaction mixture was concentrated under vacuum to remove the organic solvents, then adjusted pH to 1~2 by 1N HCl. The resulting mixture was filtered. The filtrate was concentrated to afford 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzoic acid (150 mg, crude, Li) as a yellow powder. MS (M+H)$^+$=424.4

Step 4. Synthesis of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzamido)-7-azaspiro[3.5]nonane-7-carboxylate (5)

To a solution of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzoic acid (150 mg, 348.57 μmol, Li) in DMF (2 mL) were added HATU (198.81 mg, 522.86 μmol) and DIPEA (135.15 mg, 1.05 mmol, 182.14 μL), then tert-butyl 2-amino-7-azaspiro[3.5]nonane-7-carboxylate (92.15 mg, 383.43 μmol) was added. The mixture was stirred at 15° C. for 16 hr. LCMS showed the desired mass. The mixture was diluted with water (3 mL) and extracted with EtOAc (5 mL×3). The organic layer was dried over Na$_2$SO$_4$, filtered and concentrated under vacuum. The crude product was purified by flash silica gel chromatography (Biotage, 4 g SepaFlash Silica Flash Column, Eluent of 4~100% EtOAc/Petroleum ether gradient @ 25 mL/min) to afford tert-butyl 2-(4-((7,7-difluoro-9-isopropyl-5-methyl-6-oxo-6, 7, 8, 9-tetrahydro-5H-pyrimido[4, 5-b][1, 4]diazepin-2-yl) amino)-2-fluoro-5-methylbenzamido)-7-azaspiro[3.5]nonane-7-carboxylate (240 mg, 334.51 μmol, 95.97% yield, 90% purity) as colorless oil. MS (M+H)$^+$=646.7

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methyl-N-(7-azaspiro[3.5]nonan-2-yl)benzamide (6)

To a solution of tert-butyl 2-(4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methylbenzamido)-7-azaspiro[3.5]nonane-7-carboxylate (240 mg, 371.68 μmol) in dioxane (4 mL) was added HCl/dioxane (4 M, 4 mL). The mixture was stirred at 20° C. for 1 hr. LCMS showed main peak with desired mass. The mixture was concentrated under vacuum to afford 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methyl-N-(7-azaspiro[3.5]nonan-2-yl)benzamide (220 mg, crude, HCl) as yellow oil. MS (M+H)$^+$=546.3

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methylbenzamide (Compound 21)

To a solution of 4-((7,7-difluoro-9-isopropyl-5-methyl-6-oxo-6,7,8,9-tetrahydro-5H-pyrimido[4,5-b][1,4]diazepin-2-yl)amino)-2-fluoro-5-methyl-N-(7-azaspiro[3.5]nonan-2-yl)benzamide (220 mg, 377.97 μmol, HCl) in DCE (2 mL) was added NaOAc (37.21 mg, 453.56 μmol) and stirred at 20° C. for 0.5 h. Then 1-(4-(2,6-dioxopiperidin-3-yl)-2-fluorophenyl)piperidine-4-carbaldehyde (144.39 mg, 453.56 μmol), AcOH (11.35 mg, 188.98 μmol, 10.81 μL) and NaBH(OAc)$_3$ (120.16 mg, 566.95 μmol) were added. The mixture was stirred at 20° C. for 15.5 hrs. LCMS showed the desired mass. The mixture was diluted with water (3 mL) and extracted with EtOAc (5 mL×3). The organic layer was dried over Na$_2$SO$_4$, filtered and concentrated under vacuum. The crude product was purified by flash silica gel chromatography (Biotage, 4 g SepaFlash Silica Flash Column, Eluent of 4~98% EtOAc/Petroleum ether gradient @ 20 mL/min) to afford the desired product, which was further purified by Prep-HPLC (column: Waters Xbridge 150×25 mm×5 μm; mobile phase: [water (NH$_4$HCO$_3$)-ACN]; B %: 40%-70%, 9 min) and lyophilized to afford 4-((7,7-difluoro-9-isopropyl-5-methyl-6-oxo-6,7,8,9-tetrahydro-5H-pyrimido[4,5-b][1, 4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-2-fluoro-5-methylbenzamide (24.3 mg, 27.00 μmol, 7.14% yield, 94.2% purity) as a white powder. MS (M+H)$^+$=848.4

$^1$H NMR (400 MHz, DMSO-d$_6$) δ=10.82 (s, 1H), 8.54 (s, 1H), 8.26 (dd, J=7.34, 2.57 Hz, 1H), 8.21 (s, 1H), 7.81-7.89 (m, 1H), 7.42 (d, J=8.31 Hz, 1H), 6.92-7.04 (m, 3H), 4.85 (dt, J=13.24, 6.65 Hz, 1H), 4.31-4.41 (m, 1H), 4.03 (t, J=13.57 Hz, 2H), 3.80 (dd, J=11.80, 4.71 Hz, 1H), 3.30-3.33 (m, 5H), 2.54-2.71 (m, 4H), 2.32-2.35 (m, 1H), 2.26-2.29 (m, 4H), 2.21-2.25 (m, 2H), 2.10-2.18 (m, 5H), 1.95-2.02 (m, 1H), 1.73-1.81 (m, 4H), 1.49-1.64 (m, 5H), 1.23-1.30 (m, 2H), 1.21 (d, J=6.72 Hz, 6H).

Example 22. Synthesis of 5-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-4-methoxypicolinamide (Compound 22)
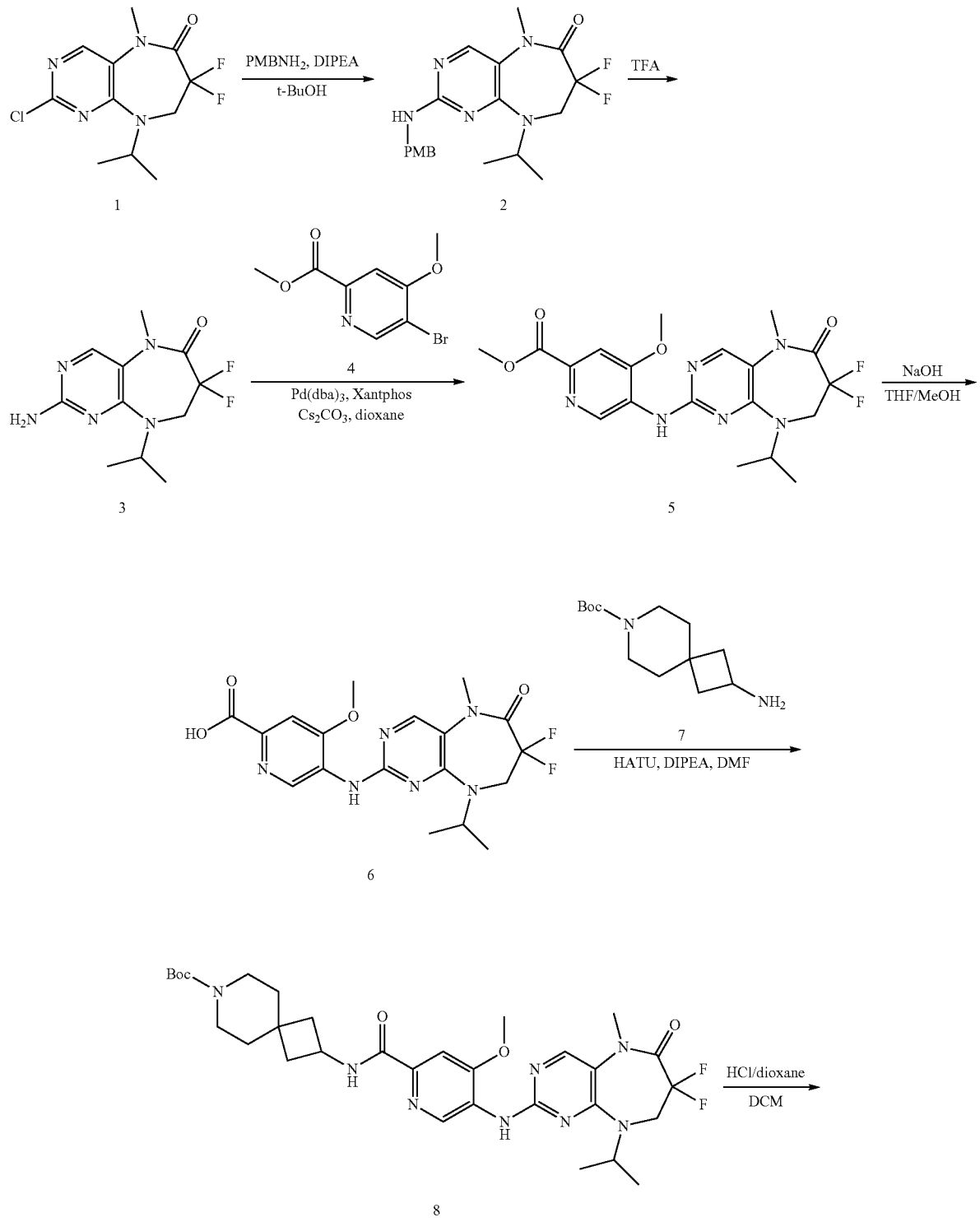

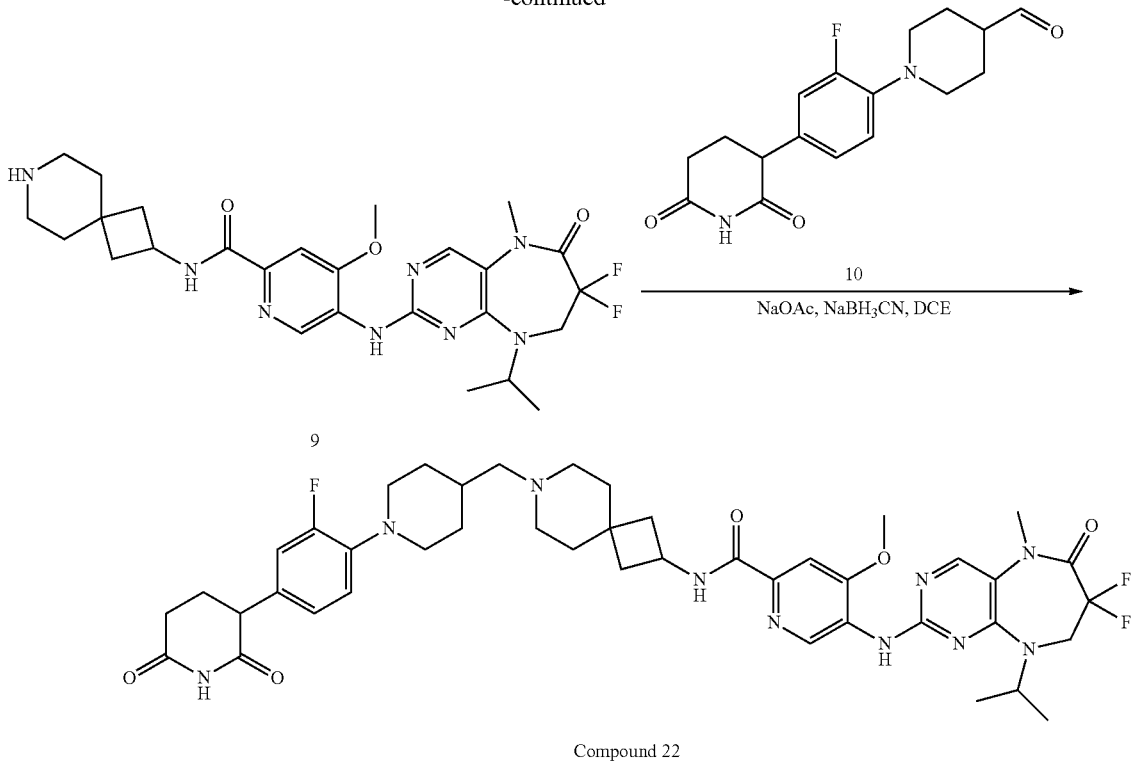

Compound 22

Step 1. Synthesis of 7,7-difluoro-9-isopropyl-2-((4-methoxybenzyl)amino)-5-methyl-5,7,8,9-tetrahydro-6H-pyrimido[4,5-b][1,4]diazepin-6-one (2)

To a solution of 2-chloro-7,7-difluoro-9-isopropyl-5-methyl-5,7,8,9-tetrahydro-6H-pyrimido[4,5-b][1,4]diazepin-6-one (2 g, 6.88 mmol) in t-BuOH (20 mL) were added (4-methoxyphenyl) methanamine (943.79 mg, 6.88 mmol, 890.37 μL), DIPEA (1.78 g, 13.76 mmol, 2.40 mL), the mixture was stirred at 100° C. for 16 h. LCMS showed a main peak with desired mass. The mixture was concentrated in vacuum to give a residue. The residue was triturated with MTBE:EtOAc=1:1 (10 mL) at 15° C. for 10 min to afford 7,7-difluoro-9-isopropyl-2-((4-methoxybenzyl)amino)-5-methyl-5,7,8,9-tetrahydro-6H-pyrimido[4,5-b][1,4]diazepin-6-one (1.9 g, 4.85 mmol, 70.55% yield) as a yellow solid. MS (M+H)$^+$=392.0

Step 2. Synthesis of 2-amino-7,7-difluoro-9-isopropyl-5-methyl-5,7,8,9-tetrahydro-6H-pyrimido[4,5-b][1,4]diazepin-6-one (3)

A mixture of 7,7-difluoro-9-isopropyl-2-((4-methoxybenzyl)amino)-5-methyl-5,7,8,9-tetrahydro-6H-pyrimido[4,5-b][1,4]diazepin-6-one (1.9 g, 4.85 mmol) in TFA (10 mL) was stirred at 20° C. for 16 h. LCMS showed a main peak with desired mass. The mixture was concentrated in vacuum to remove most of the solvent. The residue was diluted with EtOAc (30 mL), washed with saturated Na$_2$CO$_3$ solution (20 mL×2), the organic phase was dried over Na$_2$SO$_4$, filtered. The filtrate was concentrated in vacuum to afford a residue. The residue was purified by flash silica gel chromatography (Biotage; 20 g SepaFlash Silica Flash Column, Eluent of 50~100% EtOAc/Petroleum ether gradient @ 40 mL/min) to afford 2-amino-7,7-difluoro-9-isopropyl-5-methyl-5,7,8,9-tetrahydro-6H-pyrimido[4,5-b][1,4]diazepin-6-one (1 g, 3.65 mmol, 75.56% yield, 99% purity) as a yellow solid. MS (M+H)$^+$=272.0

Step 3. Synthesis of methyl 5-((7,7-difluoro-9-isopropyl-5-methyl-6-oxo-6,7,8,9-tetrahydro-5H-pyrimido[4,5-b][1,4]diazepin-2-yl)amino)-4-methoxypicolinate (5)

To a solution of 2-amino-7,7-difluoro-9-isopropyl-5-methyl-5,7,8,9-tetrahydro-6H-pyrimido[4,5-b][1,4]diazepin-6-one (500 mg, 1.84 mmol) and methyl 5-bromo-4-methoxypicolinate (453.54 mg, 1.84 mmol) in dioxane (10 mL) were added Pd$_2$(dba)$_3$ (168.79 mg, 184.32 μmol), Xantphos (106.65 mg, 184.32 μmol) and Cs$_2$CO$_3$ (1.80 g, 5.53 mmol), and the resulting mixture was degassed and purged with N$_2$ for 3 times, and then the mixture was stirred at 100° C. for 16 h. LCMS showed a main peak with desired mass. The mixture was filtered through a pad of celite. The filtrate was concentrated in vacuum to give a residue. The residue was purified by flash silica gel chromatography (Biotage; 12 g SepaFlash Silica Flash Column, Eluent of 50~100% EtOAc/Petroleum ether gradient @ 80 mL/min) to afford methyl 5-((7,7-difluoro-9-isopropyl-5-methyl-6-oxo-6,7,8,9-tetrahydro-5H-pyrimido[4,5-b][1,4]diazepin-2-yl)amino)-4-methoxypicolinate (630 mg, 1.37 mmol, 74.40% yield, 95% purity) as a yellow solid. MS (M+H)$^+$=437.1

Step 4. Synthesis of 5-((7,7-difluoro-9-isopropyl-5-methyl-6-oxo-6,7,8,9-tetrahydro-5H-pyrimido[4,5-b][1,4]diazepin-2-yl)amino)-4-methoxypicolinic Acid (6)

To a solution of methyl 5-((7,7-difluoro-9-isopropyl-5-methyl-6-oxo-6,7,8,9-tetrahydro-5H-pyrimido[4,5-b][1,4]

diazepin-2-yl)amino)-4-methoxypicolinate (200 mg, 458.28 μmol) in THF (2 mL) and MeOH (2 mL) was added NaOH (2 M, 2 mL), the mixture was stirred at 20° C. for 16 h. LCMS showed a main peak with desired hydrous mass. The mixture was adjusted to pH=2 using HCl (12 M) and concentrated in vacuum at 70° C. to afford 5-((7,7-difluoro-9-isopropyl-5-methyl-6-oxo-6,7,8,9-tetrahydro-5H-pyrimido[4,5-b][1,4]diazepin-2-yl)amino)-4-methoxypicolinic acid (190 mg, crude) as a white solid. MS (M+H)$^+$=423.2

Step 5. Synthesis of tert-butyl 2-(5-((7,7-difluoro-9-isopropyl-5-methyl-6-oxo-6,7,8,9-tetrahydro-5H-pyrimido[4,5-b][1,4]diazepin-2-yl)amino)-4-methoxypicolinamido)-7-azaspiro[3.5]nonane-7-carboxylate (8)

To a solution of 5-((7,7-difluoro-9-isopropyl-5-methyl-6-oxo-6,7,8,9-tetrahydro-5H-pyrimido[4,5-b][1,4]diazepin-2-yl)amino)-4-methoxypicolinic acid (190 mg, 449.83 μmol) in DMF (5 mL) were added HATU (256.56 mg, 674.74 μmol), DIPEA (290.68 mg, 2.25 mmol, 391.76 μL), the mixture was stirred at 20° C. for 0.5 h. Then tert-butyl 2-amino-7-azaspiro[3.5]nonane-7-carboxylate (108.11 mg, 449.83 μmol) was added, the resulting mixture was stirred at 20° C. for 2 h. LCMS showed a main peak with desired mass. The reaction mixture was diluted with water (15 mL), extracted with EtOAc (10 mL×3). The combined organic layers were washed with brine (20 mL×2), dried over Na$_2$SO$_4$, filtered. The filtrate was concentrated in vacuum to give a residue. The residue was purified by flash silica gel chromatography (Biotage; 12 g SepaFlash Silica Flash Column, Eluent of 20~100% EtOAc/Petroleum ether gradient @ 40 mL/min) to afford tert-butyl 2-(5-((7,7-difluoro-9-isopropyl-5-methyl-6-oxo-6,7,8,9-tetrahydro-5H-pyrimido[4,5-b][1,4]diazepin-2-yl)amino)-4-methoxypicolinamido)-7-azaspiro[3.5]nonane-7-carboxylate (280 mg, 356.13 μmol, 79.17% yield, 82% purity) as a yellow solid. MS (M+H)$^+$=645.4

Step 6. Synthesis of 5-((7,7-difluoro-9-isopropyl-5-methyl-6-oxo-6,7,8,9-tetrahydro-5H-pyrimido[4,5-b][1,4]diazepin-2-yl)amino)-4-methoxy-N-(7-azaspiro[3.5]nonan-2-yl)picolinamide (9)

To a solution of tert-butyl 2-(5-((7,7-difluoro-9-isopropyl-5-methyl-6-oxo-6,7,8,9-tetrahydro-5H-pyrimido[4,5-b][1,4]diazepin-2-yl)amino)-4-methoxypicolinamido)-7-azaspiro[3.5]nonane-7-carboxylate (150 mg, 232.66 μmol) in DCM (5 mL) was added HCl/dioxane (4 M, 2 mL), the mixture was stirred at 20° C. for 0.5 h. LCMS showed a main peak with desired mass. The mixture was concentrated in vacuum to afford 5-((7,7-difluoro-9-isopropyl-5-methyl-6-oxo-6,7,8,9-tetrahydro-5H-pyrimido[4,5-b][1,4]diazepin-2-yl)amino)-4-methoxy-N-(7-azaspiro[3.5]nonan-2-yl)picolinamide (130 mg, crude, HCl) as a white solid. MS (M+H)$^+$=545.3

Step 7. Synthesis of 5-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-4-methoxypicolinamide (Compound 22)

To a solution of 5-((7,7-difluoro-9-isopropyl-5-methyl-6-oxo-6,7,8,9-tetrahydro-5H-pyrimido[4,5-b][1,4]diazepin-2-yl)amino)-4-methoxy-N-(7-azaspiro[3.5]nonan-2-yl)picolinamide (130 mg, crude, HCl) in DCE (2 mL) were added 1-(4-(2,6-dioxopiperidin-3-yl)-2-fluorophenyl)piperidine-4-carbaldehyde (85.47 mg, 268.48 μmol) and NaOAc (27.53 mg, 335.60 μmol). The mixture was stirred at 25° C. for 1 hr. Then NaBH(OAc)$_3$ (237.32 mg, 1.12 mmol) was added to the mixture at 25° C., the resulting mixture was stirred at 25° C. for 15 hr. LCMS showed a main peak with desired mass. The reaction mixture was quenched by addition NaHCO$_3$ (10 mL), extracted with EtOAc (10 mL×3). The combined organic layers were washed with brine (20 mL×2), dried over Na$_2$SO$_4$, filtered. The filtrate was concentrated in vacuum to give a residue. The residue was purified by prep-TLC (SiO$_2$, DCM:MeOH=9:1) and re-purified by prep-HPLC (column: Waters Xbridge 150*25 mm*5 μm; mobile phase: [water (NH$_4$HCO$_3$)-ACN]; B %: 43%-78%, 8 min). The eluent was lyophilized to afford 5-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)piperidin-4-yl)methyl)-7-azaspiro[3.5]nonan-2-yl)-4-methoxypicolinamide (43.4 mg, 50.22 μmol, 22.45% yield, 98% purity) as a white solid. MS (M+H)$^+$=847.5

$^1$H NMR (400 MHz, DMSO-d$_6$) δ=10.81 (s, 1H), 9.12 (s, 1H), 8.76 (d, J=8.3 Hz, 1H), 8.23-8.17 (m, 2H), 7.64 (s, 1H), 7.05-6.91 (m, 3H), 4.88-4.74 (m, 1H), 4.49-4.37 (m, 1H), 4.09-3.93 (m, 5H), 3.84-3.75 (m, 1H), 3.32 (s, 3H), 3.31-3.29 (m, 2H), 2.71-2.57 (m, 3H), 2.49-2.41 (m, 2H), 2.37-2.25 (m, 2H), 2.24-2.17 (m, 2H), 2.16-2.08 (m, 4H), 2.04-1.96 (m, 1H), 1.95-1.87 (m, 2H), 1.82-1.72 (m, 2H), 1.68-1.51 (m, 5H), 1.30-1.14 (m, 8H).

Example 23. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((7-((1-(4-(2,6-dioxopiperidin-3-yl)-2-fluorophenyl)piperidin-4-yl)methyl)-2,7-diazaspiro[3.5]nonan-2-yl)-3-methoxybenzamide (Compound 23)

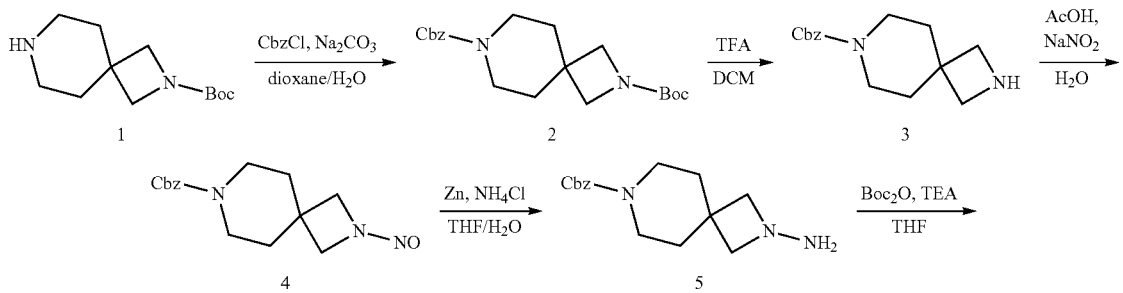

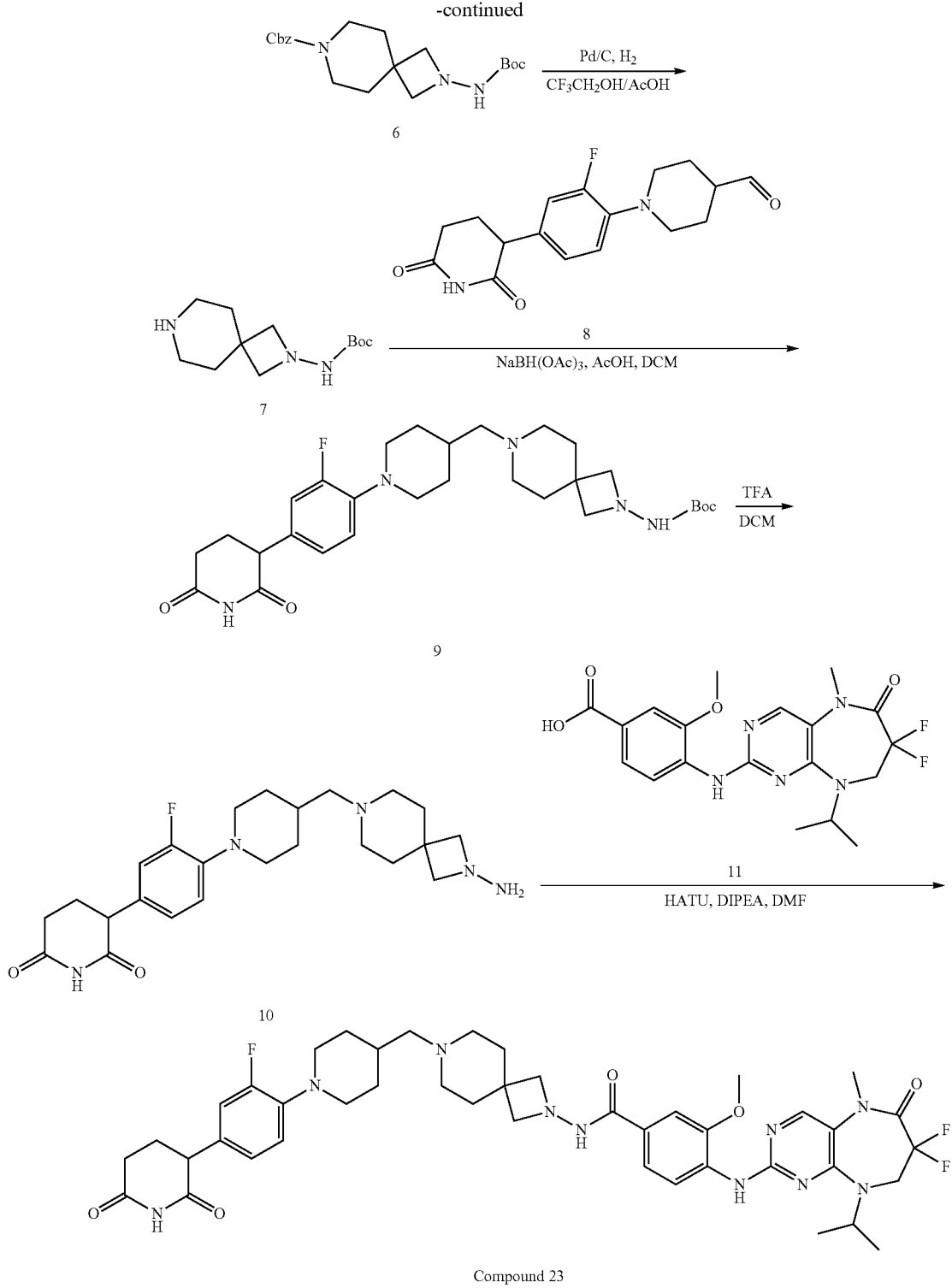

Compound 23

Step 1. Synthesis of 7-benzyl 2-(tert-butyl) 2,7-diazaspiro[3.5]nonane-2,7-dicarboxylate (2)

To a solution of tert-butyl 2,7-diazaspiro[3.5]nonane-2-carboxylate (10 g, 44.19 mmol) in dioxane (100 mL) and H$_2$O (20 mL) were added Na$_2$CO$_3$ (14.05 g, 132.56 mmol) and CbzCl (9.05 g, 53.02 mmol, 7.54 mL) at 0° C. and the resulting mixture was stirred at 20° C. for 3 h. LCMS showed starting material was consumed completely and a peak (40%) with desired mass. The reaction mixture was diluted with H$_2$O (200 mL) and extracted with EtAOc (150 mL×3). The combined organic layer was dried over Na$_2$SO$_4$, filtered and concentrated. The residue was purified by flash silica gel chromatography (80 g SepaFlash Silica Flash Column, Eluent of 0~20% EtOAc/Petroleum ether gradient @ 100 mL/min) to afford 7-benzyl 2-(tert-butyl) 2,7-diazaspiro[3.5]nonane-2,7-dicarboxylate (17.1 g, 40.33 mmol, 91.26% yield, 85% purity) as a yellow oil. MS $(M+H)^+$ =361.4

Step 2. Synthesis of benzyl
2,7-diazaspiro[3.5]nonane-7-carboxylate (3)

To a solution of 7-benzyl 2-(tert-butyl) 2,7-diazaspiro[3.5]nonane-2,7-dicarboxylate (10 g, 23.58 mmol, 85% purity) in DCM (20 mL) was added TFA (13.44 g, 117.91 mmol, 8.73 mL) at 20° C. and the resulting mixture was stirred at 20° C. for 13 h. LCMS showed trace starting material remained and a peak (71%) with desired mass. The reaction mixture was concentrated in vacuum to afford benzyl 2,7-diazaspiro[3.5]nonane-7-carboxylate (8.9 g, crude, TFA salt) as a yellow oil. MS $(M+H)^+$=261.1

Step 3. Synthesis of benzyl 2-nitroso-2,7-diazaspiro
[3.5]nonane-7-carboxylate (4)

To a solution of benzyl 2,7-diazaspiro[3.5]nonane-7-carboxylate (8.9 g, 34.19 mmol) in $H_2O$ (100 mL) was added $NaNO_2$ (7.08 g, 102.56 mmol) at 0° C., then AcOH (8.21 g, 136.75 mmol, 7.82 mL) was added drop-wise at 0° C. and the resulting mixture was stirred at 20° C. for 4 h. LCMS showed starting material was consumed completely and a peak (75%) with desired mass. Added saturated $NaHCO_3$ (80 mL) to this reaction mixture at 0° C. to adjust the pH=8 and extracted with EtOAc (100 mL×3). The combined organic layer was dried over $Na_2SO_4$, filtered and concentrated in vacuum to afford benzyl 2-nitroso-2,7-diazaspiro[3.5]nonane-7-carboxylate (9.4 g, crude) as a yellow oil. MS $(M+H)^+$=290.4

Step 4. Synthesis of benzyl 2-amino-2,7-diazaspiro
[3.5]nonane-7-carboxylate (5)

To a solution of benzyl 2-nitroso-2,7-diazaspiro[3.5]nonane-7-carboxylate (9.4 g, 32.49 mmol) in THF (200 mL) and $H_2O$ (20 mL) was added $NH_4Cl$ (6.95 g, 129.96 mmol) at 0° C., then Zn (8.50 g, 129.96 mmol) was added slowly at 0° C. and the resulting mixture was stirred at 20° C. for 1 h. TLC ($SiO_2$, Petroleum ether:EtOAc=1:1) indicated starting material was consumed completely and one major new spot was formed. The reaction mixture was diluted with THF (400 mL) and filtered. The filtrate was concentrated in vacuum to afford benzyl 2-amino-2,7-diazaspiro[3.5]nonane-7-carboxylate (9 g, crude) as a yellow oil. MS $(M+H)^+$=276.4

Step 5. Synthesis of benzyl 2-((tert-butoxycarbonyl)
amino)-2,7-diazaspiro[3.5]nonane-7-carboxylate (6)

To a solution of benzyl 2-amino-2,7-diazaspiro[3.5]nonane-7-carboxylate (8.9 g, 32.32 mmol) in THF (100 mL) was added TEA (9.81 g, 96.97 mmol, 13.50 mL) and $(Boc)_2O$ (10.58 g, 48.48 mmol, 11.14 mL) at 20° C. and the resulting mixture was stirred at 20° C. for 12 h. LCMS showed 8% of starting material remained and a peak (47%) with desired mass. The reaction mixture was concentrated in vacuum. The residue was purified by flash silica gel chromatography (80 g SepaFlash Silica Flash Column, Eluent of 0~33% EtOAc/Petroleum ether gradient @ 100 mL/min) to afford benzyl 2-((tert-butoxycarbonyl)amino)-2,7-diazaspiro[3.5]nonane-7-carboxylate (6.4 g, 17.05 mmol, 52.74% yield) as a yellow oil. MS $(M+H)^+$=376.4

Step 6. Synthesis of tert-butyl
(2,7-diazaspiro[3.5]nonan-2-yl)carbamate (7)

To a solution of benzyl 2-((tert-butoxycarbonyl)amino)-2,7-diazaspiro[3.5]nonane-7-carboxylate (3.4 g, 9.06 mmol) in $CF_3CH_2OH$ (50 mL) and AcOH (5 mL) was added Pd/C (1 g, 10% purity) under $N_2$ atmosphere. The suspension was degassed and purged with $H_2$ for 3 times. The mixture was stirred at 20° C. for 12 h under $H_2$ (15 Psi). LCMS showed starting material was consumed completely and a peak with desired mass. The reaction mixture was diluted with $CF_3CH_2OH$ (150 mL) and filtered. The filtrate was concentrated in vacuum to afford tert-butyl (2,7-diazaspiro[3.5]nonan-2-yl)carbamate (2.8 g, crude, HOAC salt) as a yellow oil. MS $(M+H)^+$=242.2

Step 7. Synthesis of tert-butyl (7-((1-(4-(2,6-dioxopiperidin-3-yl)-2-fluorophenyl)piperidin-4-yl)
methyl)-2,7-diazaspiro[3.5]nonan-2-yl)carbamate
(9)

To a solution of 1-(4-(2,6-dioxopiperidin-3-yl)-2-fluorophenyl)piperidine-4-carbaldehyde (600 mg, 1.88 mmol) and tert-butyl (2,7-diazaspiro[3.5]nonan-2-yl)carbamate (1.14 g, 3.77 mmol, HOAC salt) in DCM (10 mL) was added AcOH (113.18 mg, 1.88 mmol, 107.79 µL), then $NaBH(OAc)_3$ (1.20 g, 5.65 mmol) was added slowly at 20° C. and the resulting mixture was stirred at 20° C. for 1 h. LCMS showed starting material was consumed completely and a peak (55%) with desired mass. The reaction mixture was diluted with $H_2O$ (30 mL) and extracted with DCM (20 mL×3). The combined organic layer was washed with saturated $NaHCO_3$ (20 mL×3), dried over $Na_2SO_4$, filtered and concentrated. The residue was purified by flash silica gel chromatography (20 g SepaFlash Silica Flash Column, Eluent of 0~100% EtOAc/Petroleum ether gradient @ 100 mL/min) to afford tert-butyl (7-((1-(4-(2,6-dioxopiperidin-3-yl)-2-fluorophenyl)piperidin-4-yl)methyl)-2,7-diazaspiro[3.5]nonan-2-yl)carbamate (622 mg, 1.14 mmol, 60.70% yield) as a yellow solid. MS $(M+H)^+$=544.4

Step 8. Synthesis of 3-(4-(4-((2-amino-2,7-diazaspiro[3.5]nonan-7-yl)methyl)piperidin-1-yl)-3-fluorophenyl)piperidine-2,6-dione (10)

To a solution of tert-butyl (7-((1-(4-(2,6-dioxopiperidin-3-yl)-2-fluorophenyl)piperidin-4-yl)methyl)-2,7-diazaspiro[3.5]nonan-2-yl)carbamate (622 mg, 1.14 mmol) in DCM (3 mL) was added TFA (652.25 mg, 5.72 mmol, 423.54 µL) at 20° C. and the resulting mixture was stirred at 20° C. for 0.5 h. LCMS showed starting material was consumed completely and a peak with desired mass. The reaction mixture was concentrated in vacuum to afford 3-(4-(4-((2-amino-2,7-diazaspiro[3.5]nonan-7-yl)methyl)piperidin-1-yl)-3-fluorophenyl)piperidine-2,6-dione (638 mg, crude, TFA salt) as a yellow solid. MS $(M+H)^+$=444.4

Step 9. Synthesis of 4-((7,7-difluoro-9-isopropyl-5-methyl-6-oxo-6,7,8,9-tetrahydro-5H-pyrimido[4,5-b]
[1,4]diazepin-2-yl)amino)-N-(7-((1-(4-(2,6-dioxopiperidin-3-yl)-2-fluorophenyl)piperidin-4-yl)methyl)-
2,7-diazaspiro[3.5]nonan-2-yl)-3-methoxybenzamide
(Compound 23)

To a solution of 4-((7,7-difluoro-9-isopropyl-5-methyl-6-oxo-6,7,8,9-tetrahydro-5H-pyrimido[4,5-b][1,4]diazepin-2- yl)amino)-3-methoxybenzoic acid (450 mg, 1.07 mmol) in DMF (4 mL) were added HATU (446.64 mg, 1.17 mmol) and DIPEA (276.03 mg, 2.14 mmol, 372.01 μL). The mixture was stirred at 20° C. for 10 min and a solution of 3-(4-(4-((2-amino-2,7-diazaspiro[3.5]nonan-7-yl)methyl) piperidin-1-yl)-3-fluorophenyl)piperidine-2,6-dione (625.20 mg, 1.12 mmol, TFA salt) in DMF (4 mL) with DIPEA (414.05 mg, 3.20 mmol, 558.01 μL) was added and the resulting mixture was stirred at 20° C. for 1 h. LCMS showed starting material was consumed completely and a peak (44%) with desired mass. The reaction mixture was diluted with H$_2$O (20 mL) and extracted with EtOAc (20 mL×3). The combined organic layer was washed with brine (20 mL×3), dried over Na$_2$SO$_4$, filtered and concentrated. The residue was purified by flash silica gel chromatography (25 g SepaFlash Silica Flash Column, Eluent of 0~100% EtOAc/Petroleum ether gradient @ 100 mL/min) to afford product A (426 mg) and product B (207 mg). The product A was triturated with mix solution (10 mL, EtOAc:Methanol=10:1) at 20° C. for 12 h and filtered. The filter cake was dried in vacuum to afford 4-((7,7-difluoro-9-isopropyl-5-methyl-6-oxo-6,7,8,9-tetrahydro-5H-pyrimido[4,5-b][1,4] diazepin-2-yl)amino)-N-(7-((1-(4-(2,6-dioxopiperidin-3-yl)-2-fluorophenyl)piperidin-4-yl)methyl)-2,7-diazaspiro [3.5]nonan-2-yl)-3-methoxybenzamide (291.1 mg, 332.37 μmol, 31.12% yield, 96.7% purity) as a white solid. MS (M+H)$^+$=847.4

$^1$H NMR (400 MHz, DMSO-d$_6$) δ=10.81 (s, 1H), 9.48 (s, 1H), 8.30 (br d, J=8.4 Hz, 1H), 8.22 (s, 1H), 7.88 (s, 1H), 7.45-7.38 (m, 2H), 7.03-6.91 (m, 3H), 4.87 (td, J=6.7, 13.4 Hz, 1H), 4.03 (br t, J=13.5 Hz, 2H), 3.93 (s, 3H), 3.79 (dd, J=4.7, 11.6 Hz, 1H), 3.61-3.45 (m, 4H), 3.33-3.25 (m, 5H), 2.65-2.56 (m, 3H), 2.45-2.34 (m, 1H), 2.31-2.22 (m, 3H), 2.19 (br dd, J=3.6, 12.6 Hz, 1H), 2.13 (br d, J=6.4 Hz, 2H), 1.99 (td, J=4.3, 8.7 Hz, 1H), 1.86-1.53 (m, 8H), 1.24 (d, J=6.6 Hz, 8H).

Example 24. Synthesis of N-(7-((1-(4-(2,6-dioxopiperidin-3-yl)-2-fluorophenyl)piperidin-4-yl)methyl)-7-azaspiro[3.5]nonan-2-yl)-3-methoxy-4-(((R)-5-methyl-6-oxo-6,7,7a,8,9,10-hexahydro-5H-pyrimido [5,4-b]pyrrolo[1,2-d][1,4]diazepin-2-yl)amino) benzamide (Compound 24)

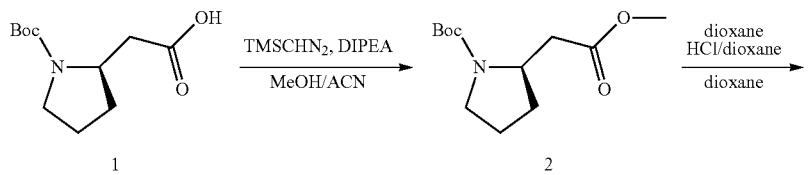

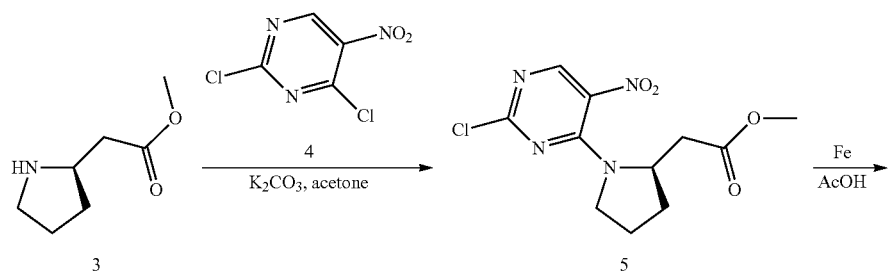

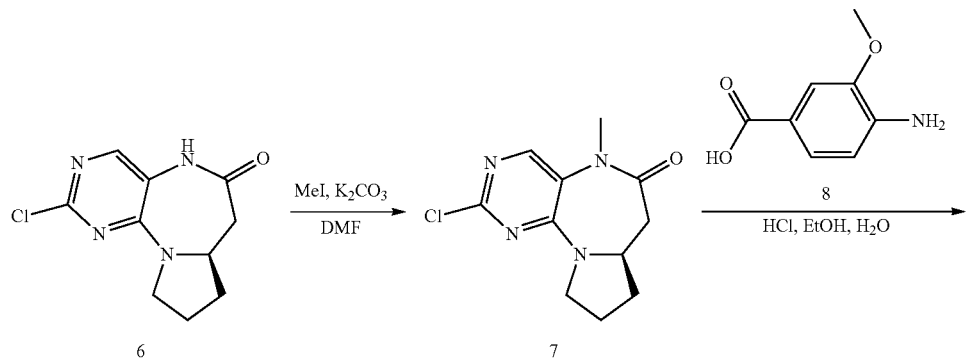

-continued
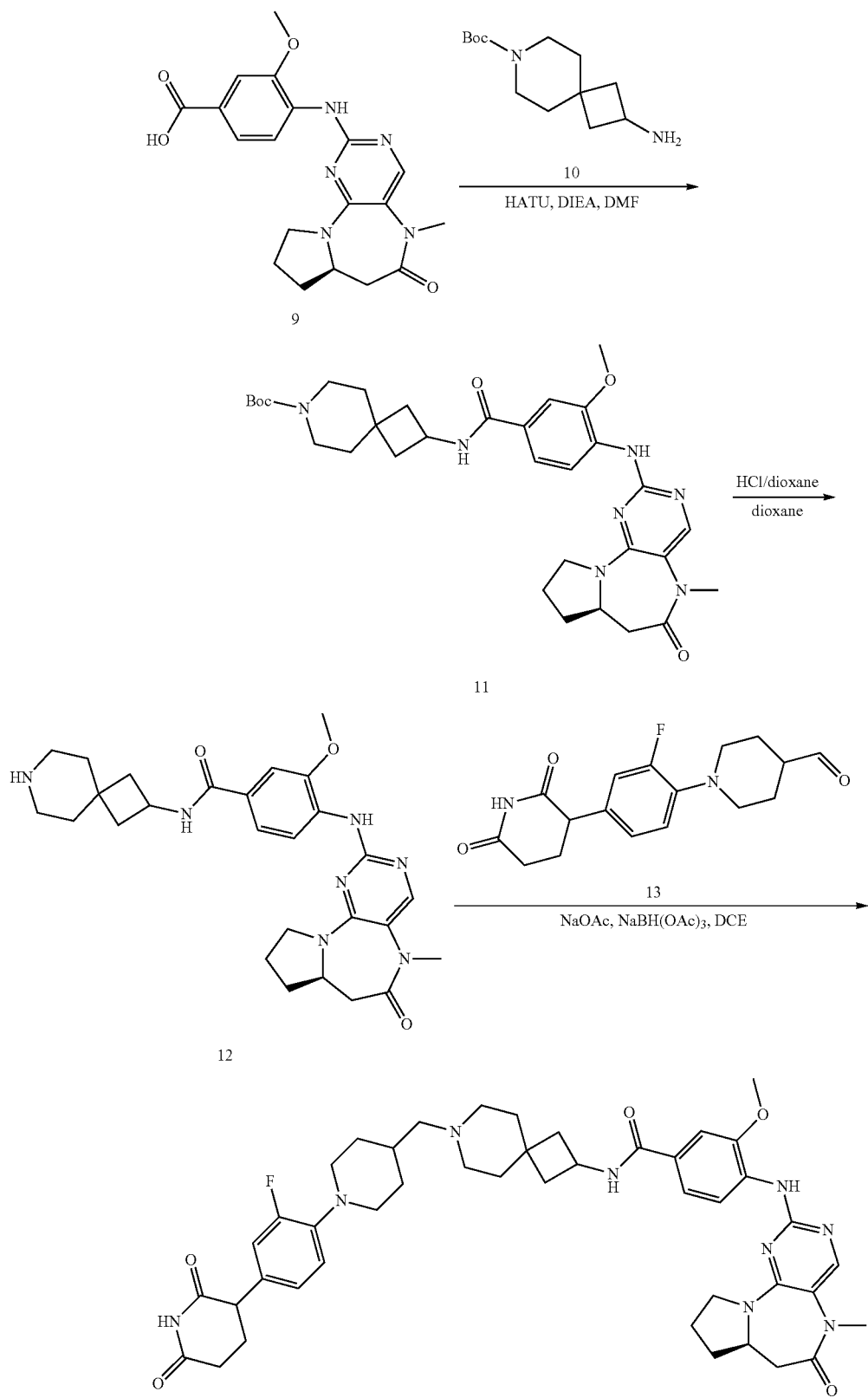
Compound 24

Step 1. Synthesis of tert-butyl (R)-2-(2-methoxy-2-oxoethyl)pyrrolidine-1-carboxylate (2)

To a solution of (R)-2-(1-(tert-butoxycarbonyl)pyrrolidin-2-yl)acetic acid (3 g, 13.08 mmol) and DIPEA (1.86 g, 14.39 mmol, 2.51 mL) in MeOH (50 mL) and MeCN (50 mL) was added TMSCHN$_2$ (2 M, 13.08 mL) at 0° C. The mixture was stirred at 20° C. for 3 hr. LCMS showed the desired Mass. The reaction mixture was concentrated under reduced pressure. The residue was purified by flash silica gel chromatography (ISCO; 20 g SepaFlash Silica Flash Column, Eluent of 0~30% EtOAc/Petroleum ether gradient @100 mL/min) to afford tert-butyl (R)-2-(2-methoxy-2-oxoethyl)pyrrolidine-1-carboxylate (2 g, 7.81 mmol, 59.68% yield, 95% purity) as a colorless oil. MS (M−100+H)$^+$=144.3

Step 2. Synthesis of methyl (R)-2-(pyrrolidin-2-yl)acetate (3)

To a solution of tert-butyl (R)-2-(2-methoxy-2-oxoethyl)pyrrolidine-1-carboxylate (2 g, 8.22 mmol) in dioxane (10 mL) was added HCl/dioxane (4 M, 10 mL). The mixture was stirred at 20° C. for 2 hr. LCMS showed the desired Mass. The reaction mixture was concentrated under reduced pressure to afford methyl (R)-2-(pyrrolidin-2-yl)acetate (1.5 g, crude, HCl salt) as a colorless oil. MS (M+H)$^+$=144.1

Step 3. Synthesis of methyl (R)-2-(1-(2-chloro-5-nitropyrimidin-4-yl)pyrrolidin-2-yl)acetate (5)

To a solution of 2,4-dichloro-5-nitropyrimidine (1.78 g, 9.18 mmol) and methyl (R)-2-(pyrrolidin-2-yl)acetate (1.5 g, 8.35 mmol, HCl salt) in acetone (30 mL) was added K$_2$CO$_3$ (6.92 g, 50.10 mmol) at 0° C., the mixture was stirred at 20° C. for 16 h. LCMS showed the desired Mass. The reaction mixture was diluted with H$_2$O (50 mL) and adjust pH=8 by adding HCl (1 M), then extracted with EtOAc (20 mL×3). The combined organic Layers were dried over Na$_2$SO$_4$, filtered and concentrated under reduced pressure. The residue was purified by flash silica gel chromatography (ISCO; 40 g SepaFlash Silica Flash Column, Eluent of 0~40% EtOAc/Petroleum ether gradient @ 100 mL/min) to afford methyl (R)-2-(1-(2-chloro-5-nitropyrimidin-4-yl)pyrrolidin-2-yl)acetate (2.4 g, 7.98 mmol, 95.59% yield, 100% purity) as a colorless oil. MS (M+H)$^+$=301.0

Step 4. Synthesis of (R)-2-chloro-7a,8,9,10-tetrahydro-5H-pyrimido[5,4-b]pyrrolo[1,2-d][1,4]diazepin-6(7H)-one (6)

To a solution of methyl (R)-2-(1-(2-chloro-5-nitropyrimidin-4-yl)pyrrolidin-2-yl)acetate (2.4 g, 7.98 mmol) in HOAc (20 mL) was added Fe (2.23 g, 39.91 mmol), the suspension was stirred at 60° C. for 4 h. LCMS showed the desired Mass The reaction mixture was diluted with H$_2$O (100 mL), extracted with EtOAc (30 mL×3). The combined organic Layers were dried over Na$_2$SO$_4$, filtered and concentrated under reduced pressure. The residue was purified by flash silica gel chromatography (ISCO; 20 g SepaFlash Silica Flash Column, Eluent of 50~100% EtOAc/Petroleum ether gradient @ 100 mL/min) to afford (R)-2-chloro-7a,8,9,10-tetrahydro-5H-pyrimido[5,4-b]pyrrolo[1,2-d][1,4]diazepin-6(7H)-one (1.3 g, 5.45 mmol, 69.09% yield, 96% purity) as a red solid. MS (M+H)$^+$=239.1

$^1$H NMR (400 MHz, DMSO-d$_6$) δ=9.76 (br s, 1H), 7.76 (s, 1H), 3.99 (dt, J=5.6, 9.9 Hz, 1H), 3.65-3.52 (m, 2H), 2.83 (dd, J=10.1, 14.9 Hz, 1H), 2.60 (br d, J=14.9 Hz, 1H), 2.18 (td, J=5.7, 11.6 Hz, 1H), 1.94 (td, J=6.1, 12.1 Hz, 1H), 1.88-1.74 (m, 1H), 1.67-1.54 (m, 1H)

Step 5. Synthesis of (R)-2-chloro-5-methyl-7a,8,9,10-tetrahydro-5H-pyrimido[5,4-b]pyrrolo[1,2-d][1,4]diazepin-6(7H)-one (7)

To a solution of (R)-2-chloro-7a,8,9,10-tetrahydro-5H-pyrimido[5,4-b]pyrrolo[1,2-d][1,4]diazepin-6(7H)-one (1.3 g, 5.45 mmol) in DMF (10 mL) were added K$_2$CO$_3$ (1.51 g, 10.89 mmol) and MeI (850.42 mg, 5.99 mmol), the suspension was stirred at 20° C. for 16 h. LCMS showed the starting material was consumed completely and a peak with desired mass. The reaction mixture was diluted with H$_2$O (100 mL) and extracted with EtOAc (20 mL×3). The combined organic Layers were washed with brine (20 mL), dried over Na$_2$SO$_4$, filtered and concentrated under reduced pressure. The residue was purified by flash silica gel chromatography (ISCO; 12 g SepaFlash Silica Flash Column, Eluent of 0~100% EtOAc/Petroleum ether gradient @ 100 mL/min) to afford (R)-2-chloro-5-methyl-7a,8,9,10-tetrahydro-5H-pyrimido[5,4-b]pyrrolo[1,2-d][1,4]diazepin-6(7H)-one (0.95 g, 3.61 mmol, 66.26% yield, 96% purity) as a gray solid. MS (M+H)$^+$=253.3

Step 6. Synthesis of (R)-3-methoxy-4-((5-methyl-6-oxo-6,7,7a,8,9,10-hexahydro-5H-pyrimido[5,4-b]pyrrolo[1,2-d][1,4]diazepin-2-yl)amino)benzoic Acid (9)

To a solution of (R)-2-chloro-5-methyl-7a,8,9,10-tetrahydro-5H-pyrimido[5,4-b]pyrrolo[1,2-d][1,4]diazepin-6(7H)-one (0.85 g, 3.36 mmol) and 4-amino-3-methoxybenzoic acid (787.19 mg, 4.71 mmol) in EtOH (2 mL) and H$_2$O (8 mL) was added HCl (12 M, 560.61 μL), the mixture was stirred at 100° C. for 16 h. LCMS showed the desired Mass. The reaction mixture was concentrated under reduced pressure. The residue was triturated with a mixture solvent (EtOAC:ACN:EtOH:DMF=30:15:15:5, 5 mL) for 10 minutes, the suspension was filtered and the filter cake was washed with a mixture solvent (EtOAC:ACN:EtOH:DMF=30:15:15:5, 3 mL). The filter cake was collected and dried to afford (R)-3-methoxy-4-((5-methyl-6-oxo-6,7,7a,8,9,10-hexahydro-5H-pyrimido[5,4-b]pyrrolo[1,2-d][1,4]diazepin-2-yl)amino)benzoic acid (1.3 g, 2.95 mmol, 87.70% yield, 87% purity) as a light brown solid. MS (M+H)$^+$=384.4

Step 7. Synthesis of tert-butyl (R)-2-(3-methoxy-4-((5-methyl-6-oxo-6,7,7a,8,9,10-hexahydro-5H-pyrimido[5,4-b]pyrrolo[1,2-d][1,4]diazepin-2-yl)amino)benzamido)-7-azaspiro[3.5]nonane-7-carboxylate (11)

A solution of (R)-3-methoxy-4-((5-methyl-6-oxo-6,7,7a,8,9,10-hexahydro-5H-pyrimido[5,4-b]pyrrolo[1,2-d][1,4]diazepin-2-yl)amino)benzoic acid (500 mg, 1.30 mmol), HATU (743.80 mg, 1.96 mmol) and DIPEA (505.65 mg, 3.91 mmol, 681.46 μL in DMF (10 mL) was stirred at 20° C. for 20 min, then tert-butyl 2-amino-7-azaspiro[3.5]nonane-7-carboxylate (344.78 mg, 1.43 mmol) was added and the resulting mixture was stirred at 20° C. for 16 h. LCMS showed the desired mass. The reaction mixture was diluted with H$_2$O (100 mL) and extracted with EtOAc (20 mL×3). The combined organic Layers were washed with brine (20 mL), dried over Na$_2$SO$_4$, filtered and concentrated under reduced pressure. The residue was purified by flash silica gel chromatography (ISCO; 12 g SepaFlash Silica Flash Column, Eluent of 0~100% EtOAc/Petroleum ether to 0~100% MeOH/EtOAc gradient @ 80 mL/min) to afford tert-butyl (R)-2-(3-methoxy-4-((5-methyl-6-oxo-6,7,7a,8,9,10-hexahydro-5H-pyrimido[5,4-b]pyrrolo[1,2-d][1,4]diazepin-2-yl)amino)benzamido)-7-azaspiro[3.5]nonane-7-carboxylate (700 mg, 878.28 μmol, 67.35% yield, 76% purity) as a brown solid. MS (M+H)⁺=606.6.

Step 8. Synthesis of (R)-3-methoxy-4-((5-methyl-6-oxo-6,7,7a,8,9,10-hexahydro-5H-pyrimido[5,4-b]pyrrolo[1,2-d][1,4]diazepin-2-yl)amino)-N-(7-azaspiro[3.5]nonan-2-yl)benzamide (12)

To a solution of tert-butyl (R)-2-(3-methoxy-4-((5-methyl-6-oxo-6,7,7a,8,9,10-hexahydro-5H-pyrimido[5,4-b]pyrrolo[1,2-d][1,4]diazepin-2-yl)amino)benzamido)-7-azaspiro[3.5]nonane-7-carboxylate (700 mg, 1.16 mmol) in dioxane (3 mL) was added HCl/dioxane (4 M, 2 mL), the mixture was stirred at 20° C. for 1 h. LCMS showed the desired Mass. The reaction mixture was concentrated under reduced pressure to afford (R)-3-methoxy-4-((5-methyl-6-oxo-6,7,7a,8,9,10-hexahydro-5H-pyrimido[5,4-b]pyrrolo[1,2-d][1,4]diazepin-2-yl)amino)-N-(7-azaspiro[3.5]nonan-2-yl)benzamide (600 mg, crude) as a yellow solid. MS (M+H)⁺=506.5

Step 9. Synthesis of N-(7-((1-(4-(2,6-dioxopiperidin-3-yl)-2-fluorophenyl)piperidin-4-yl)methyl)-7-azaspiro[3.5]nonan-2-yl)-3-methoxy-4-(((R)-5-methyl-6-oxo-6,7,7a,8,9,10-hexahydro-5H-pyrimido[5,4-b]pyrrolo[1,2-d][1,4]diazepin-2-yl)amino)benzamide (Compound 24)

To a solution of 1-(4-(2,6-dioxopiperidin-3-yl)-2-fluorophenyl)piperidine-4-carbaldehyde (50 mg, 157.06 μmol) in DCE (2 mL) was added (R)-3-methoxy-4-((5-methyl-6-oxo-6,7,7a,8,9,10-hexahydro-5H-pyrimido[5,4-b]pyrrolo[1,2-d][1,4]diazepin-2-yl)amino)-N-(7-azaspiro[3.5]nonan-2-yl)benzamide (85.14 mg, 157.06 μmol, HCl salt) and NaOAc (19.33 mg, 235.60 μmol). The mixture was stirred at 20° C. for 1 hr. Then NaBH(OAc)₃ (166.44 mg, 785.32 μmol) was added at 20° C. and the resulting mixture was stirred at 20° C. for 3 h. LCMS showed the desired mass. The reaction mixture was concentrated under reduced pressure. The residue was purified by flash silica gel chromatography (ISCO; 12 g SepaFlash Silica Flash Column, Eluent of 0~100% EtOAc/Petroleum ether to 0~100% MeOH/EtOAc gradient @ 80 mL/min) followed by prep-HPLC (column: Phenomenex Synergi C18 150×25 mm×10 μm; mobile phase: [water (FA)-ACN]; B %: 5%-35%, 10 min) to afford N-(7-((1-(4-(2,6-dioxopiperidin-3-yl)-2-fluorophenyl)piperidin-4-yl)methyl)-7-azaspiro[3.5]nonan-2-yl)-3-methoxy-4-(((R)-5-methyl-6-oxo-6,7,7a,8,9,10-hexahydro-5H-pyrimido[5,4-b]pyrrolo[1,2-d][1,4]diazepin-2-yl)amino)benzamide (18.3 mg, 20.92 μmol, 13.32% yield, 95% purity, 0.5FA) as a white solid. MS (M+H)⁺=808.6

¹H NMR (400 MHz, CD₃Cl) δ=8.56 (d, J=8.4 Hz, 1H), 8.01 (br s, 1H), 7.93 (s, 1H), 7.74 (s, 1H), 7.43 (s, 1H), 7.29 (br s, 1H), 6.97-6.86 (m, 3H), 6.21 (br d, J=7.2 Hz, 1H), 4.60-4.51 (m, 1H), 4.02-3.91 (m, 5H), 3.74-3.67 (m, 2H), 3.45 (br d, J=12.1 Hz, 2H), 3.33 (s, 3H), 2.80-2.57 (m, 11H), 2.56-2.40 (m, 5H), 2.30-2.20 (m, 3H), 2.10 (td, J=6.3, 12.5 Hz, 1H), 1.93-1.85 (m, 4H), 1.80-1.72 (m, 4H), 1.68-1.57 (m, 1H), 1.53-1.41 (m, 2H)

Example 25. Synthesis of 7-((1-(4-(2,6-dioxopiperidin-3-yl)-2-fluorophenyl)piperidin-4-yl)methyl)-7-azaspiro[3.5]nonan-2-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (Compound 25)

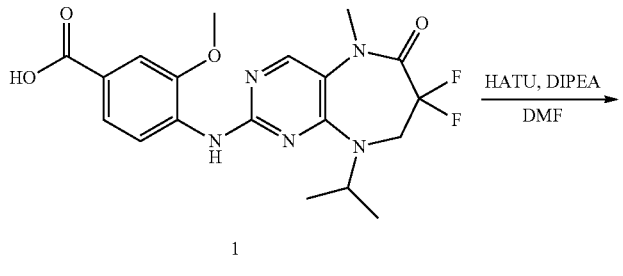

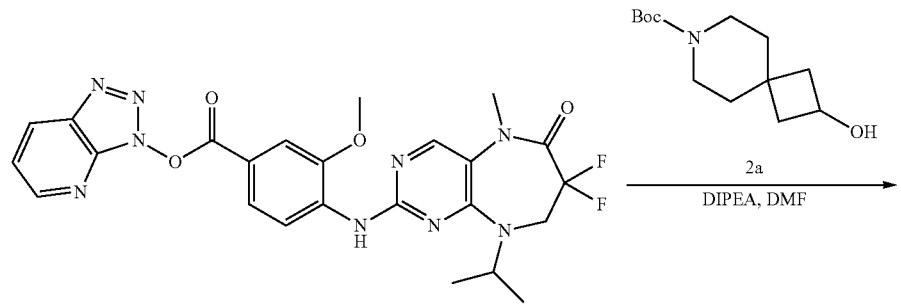

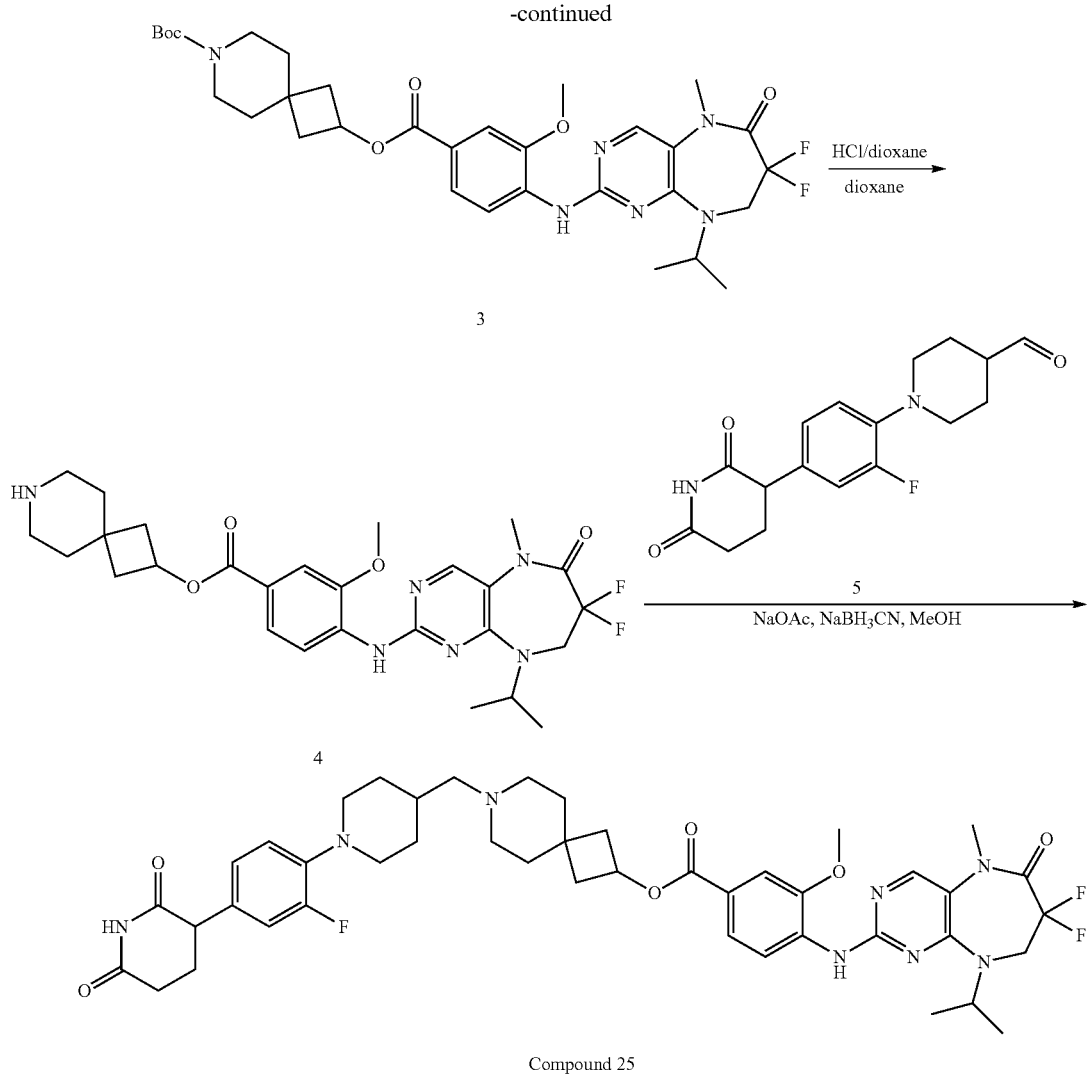

Compound 25

Step 1. Synthesis of 3H-[1,2,3]triazolo[4,5-b]pyridin-3-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (2)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (0.5 g, 1.19 mmol) in DMF (2 mL) was added HATU (541.38 mg, 1.42 mmol) and DIPEA (460.04 mg, 3.56 mmol, 620.00 μL). The mixture was stirred at 25° C. for 2 hr. LCMS showed the starting material was consumed completely, and a main peak with desired mass. The mixture was poured into brine (80 mL) and extracted with EtOAc (30 mL×5). The combined organic phase was washed with brine (10 mL×3), dried over Na$_2$SO$_4$, filtered and concentrated under reduced pressure to give a residue. The crude product was treated with MTBE (20 mL) and stirred for 0.5 h. Then the mixture was filtered. The filter cake was collected and dried, to afford 3H-[1,2,3]triazolo[4,5-b]pyridin-3-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (0.6 g, crude) as brown solid, which was used for the next step directly. MS (M+H)$^+$=540.2

Step 2. Synthesis of tert-butyl 2-((4-((7,7-difluoro-9-isopropyl-5-methyl-6-oxo-6,7,8,9-tetrahydro-5H-pyrimido[4,5-b][1,4]diazepin-2-yl)amino)-3-methoxybenzoyl)oxy)-7-azaspiro[3.5]nonane-7-carboxylate (3)

A mixture of 3H-[1,2,3]triazolo[4,5-b]pyridin-3-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (0.6 g, 1.11 mmol), tert-butyl 2-hydroxy-7-azaspiro[3.5]nonane-7-carboxylate (268.39 mg, 1.11 mmol) and DIPEA (718.67 mg, 5.56 mmol, 968.56 μL) in DMF (10 mL) was stirred at 80° C. for 12 h. LCMS showed the starting material was consumed completely and a peak (19%) with desired mass. The mixture was poured into brine (50 mL) and extracted with EtOAc (20 mL×3). The combined organic phase was washed with brine (10 mL×3), dried over Na$_2$SO$_4$, filtered and concentrated under reduced pressure to give a residue. The residue was purified by flash silica gel chromatography (12 g SepaFlash Silica Flash Column, Eluent of 0~50% EtOAc/Petroleum ether gradient @ 60 mL/min) and re-purified by prep-HPLC (column: Phenomenex luna C18 150×40 mm×15 um; mobile phase: [water (FA)-ACN]; B %: 68%-98%, 10 min) and lyophilized to afford tert-butyl 2-((4-((7,7-difluoro-9-isopropyl-5-methyl-6-oxo-6,7,8,9-tetrahydro-5H-pyrimido[4,5-b][1,4]diazepin-2-yl)amino)-3-methoxybenzoyl)oxy)-7-azaspiro[3.5]nonane-7-carboxylate (0.15 g, 232.66 μmol, 20.92% yield, 100% purity) as white solid. MS (M+H)$^+$=645.5

Step 3. Synthesis of 7-azaspiro[3.5]nonan-2-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (4)

To a solution of tert-butyl 2-((4-((7,7-difluoro-9-isopropyl-5-methyl-6-oxo-6,7,8,9-tetrahydro-5H-pyrimido[4,5-b][1,4]diazepin-2-yl)amino)-3-methoxybenzoyl)oxy)-7-azaspiro[3.5]nonane-7-carboxylate (0.15 g, 232.66 μmol) in dioxane (1 mL) was added HCl/dioxane (4 M, 15.00 mL) at 25° C. The resulting mixture was stirred at 25° C. for 0.5 hr. LCMS showed the starting material was consumed completely, and a main peak with desired mass. The mixture solution was concentrated under reduced pressure to afford 7-azaspiro[3.5]nonan-2-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (0.15 g, crude, HCl) as white solid, which was used for the next step directly. MS (M+H)$^+$=545.3

Step 4. Synthesis of 7-((1-(4-(2,6-dioxopiperidin-3-yl)-2-fluorophenyl)piperidin-4-yl)methyl)-7-azaspiro[3.5]nonan-2-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (Compound 25)

A mixture of 7-azaspiro[3.5]nonan-2-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (145 mg, 249.55 μmol, HCl) and NaOAc (20.47 mg, 249.55 μmol) in MeOH (2 mL) was stirred at 25° C. for 20 min. To the mixture was added 1-(4-(2,6-dioxopiperidin-3-yl)-2-fluorophenyl)piperidine-4-carbaldehyde (111.22 mg, 349.37 μmol) and AcOH (14.99 mg, 249.55 μmol, 14.27 μL) at 25° C. The resulting mixture was stirred at 25° C. for 30 min. To reaction mixture was added NaBH$_3$CN (47.04 mg, 748.64 μmol) at 25° C., The mixture was stirred at 25° C. for 1 h. LCMS showed the starting material was consumed completely, and a peak (~40%) with desired mass. The reaction solution was concentrated to remove the organic solvent. The crude product was dissolved with EtOAc (50 mL) and washed with saturated NaHCO$_3$ (20 mL) and HCl (20 mL, 0.2M), dried over Na$_2$SO$_4$, filtered and concentrated under reduced pressure to give a residue. The residue was purified by prep-HPLC (column: Waters Xbridge C18 150× 50 mm×10 μm; mobile phase: [water (NH$_4$HCO$_3$)-ACN]; B %: 57%-87%, 10 min) and lyophilized to give crude product. The crude product was purified by prep-HPLC (column: Phenomenex Synergi C18 150×25 mm×10 μm; mobile phase: [water (FA)-ACN]; B %: 19%-49%, 10 min) and lyophilized to afford 7-((1-(4-(2,6-dioxopiperidin-3-yl)-2-fluorophenyl)piperidin-4-yl)methyl)-7-azaspiro[3.5]nonan-2-yl 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoate (92.1 mg, 106.96 μmol, 42.86% yield, 99% purity, 0.12FA) as white solid. MS (M+H)$^+$=847.4

$^1$H NMR (400 MHz, DMSO-d$_6$) δ=10.80 (s, 1H), 8.42 (d, J=8.6 Hz, 1H), 8.24 (s, 1H), 8.19 (s, 0.12H), 7.98 (s, 1H), 7.62 (dd, J=1.4, 8.6 Hz, 1H), 7.50 (d, J=1.6 Hz, 1H), 7.05-6.87 (m, 3H), 5.13 (q, J=7.2 Hz, 1H), 4.89 (q, J=6.7 Hz, 1H), 4.04 (t, J=13.4 Hz, 2H), 3.95 (s, 3H), 3.79 (dd, J=5.0, 11.7 Hz, 1H), 3.32-3.23 (m, 5H), 2.70-2.57 (m, 3H), 2.40-2.07 (m, 10H), 2.05-1.95 (m, 1H), 1.88 (dd, J=6.8, 12.5 Hz, 2H), 1.77 (d, J=12.8 Hz, 2H), 1.68-1.55 (m, 5H), 1.29-1.15 (m, 8H).

Example 26. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)-3-methylpyrrolidin-3-yl)ethyl)-7-azaspiro[3.5]nonan-2-yl)-3-methoxybenzamide (Compound 26)

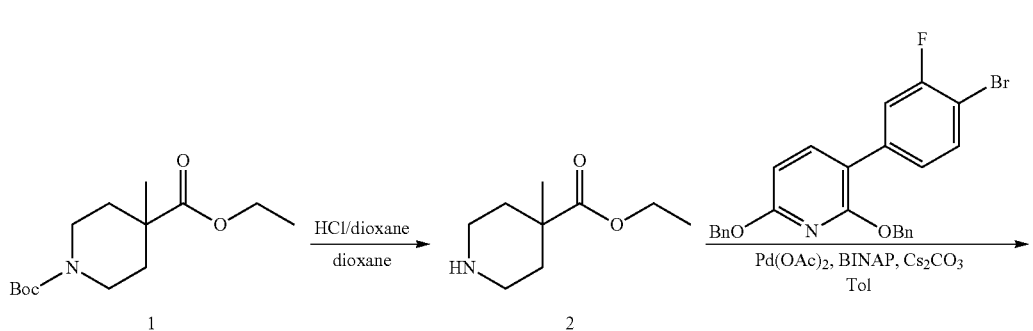

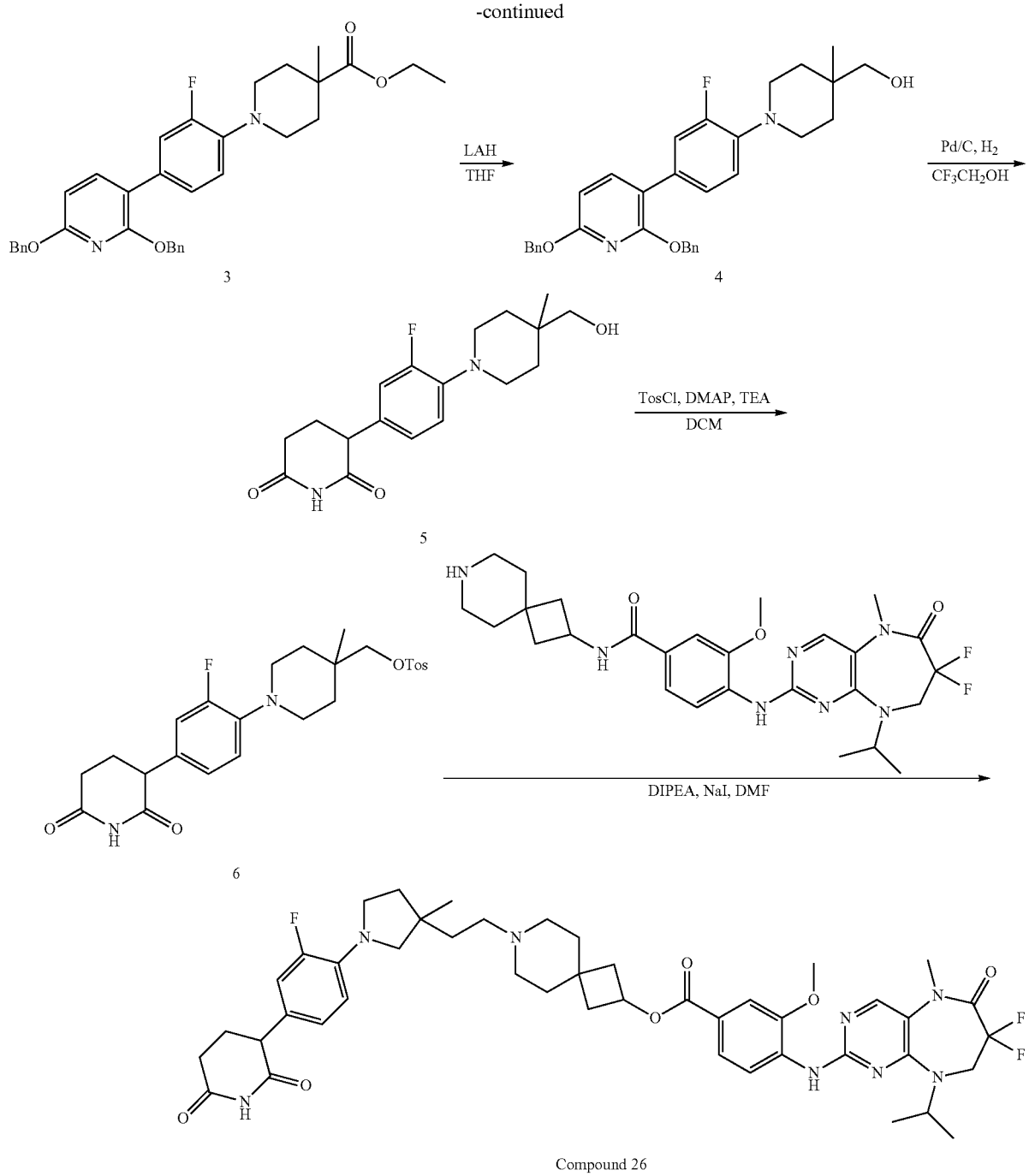

Compound 26

Step 1. Synthesis of ethyl 4-methylpiperidine-4-carboxylate (2)

To a solution of 1-(tert-butyl) 4-ethyl 4-methylpiperidine-1,4-dicarboxylate (1 g, 3.69 mmol) in dioxane (10 mL) was added HCl/dioxane (4 M, 921.31 μL), the mixture was stirred at 20° C. for 1 hr. LCMS showed main peak with desired mass, the mixture was concentrated under vacuum to afford ethyl 4-methylpiperidine-4-carboxylate (2.2 g, crude, HCl salt) as white powder. MS (M+H)$^+$=172.1

Step 2. Synthesis of ethyl 1-(4-(2,6-bis(benzyloxy)pyridin-3-yl)-2-fluorophenyl)-4-methylpiperidine-4-carboxylate (3)

To a solution of ethyl 4-methylpiperidine-4-carboxylate (0.5 g, crude, HCl salt) and 2,6-bis(benzyloxy)-3-(4-bromo-3-fluorophenyl)pyridine (1.86 g, 2.41 mmol, 60% purity) in Toluene (20 mL) were added Cs$_2$CO$_3$ (2.35 g, 7.22 mmol), Pd(OAc)$_2$ (81.07 mg, 361.10 μmol) and BINAP (449.70 mg, 722.21 μmol), the mixture was stirred at 80° C. for 16 hr under N$_2$ atmosphere. LCMS showed the desired mass, the mixture was diluted with water (30 mL), extracted with EtOAc (20 mL×3). The organic layer was dried over Na₂SO₄, filtered and concentrated under vacuum. The crude product was purified by flash silica gel chromatography (Biotage, 25 g SepaFlash Silica Flash Column, Eluent of 4~25% EtOAc/Petroleum ether gradient @ 20 mL/min) to afford ethyl 1-(4-(2,6-bis(benzyloxy)pyridin-3-yl)-2-fluorophenyl)-4-methylpiperidine-4-carboxylate (1.1 g, 1.71 mmol, 70.85% yield, 86% purity) as yellow oil. MS (M+H)⁺=555.3

Step 3. Synthesis of (1-(4-(2,6-bis(benzyloxy)pyridin-3-yl)-2-fluorophenyl)-4-methylpiperidin-4-yl)methanol (4)

To a solution of ethyl 1-(4-(2,6-bis(benzyloxy)pyridin-3-yl)-2-fluorophenyl)-4-methylpiperidine-4-carboxylate (1.1 g, 1.98 mmol) in THF (4 mL) was added LiAlH₄ (105.38 mg, 2.78 mmol) at 0° C., the mixture was stirred at 0° C. for 1 hr. LCMS showed a main peak with desired mass. The reaction mixture was quenched with H₂O (0.2 mL), NaOH (15%, 0.2 mL) and H₂O (0.6 mL), then filtered and dried over Na₂SO₄. The filtrate was concentrated under vacuum to afford (1-(4-(2,6-bis(benzyloxy)pyridin-3-yl)-2-fluorophenyl)-4-methylpiperidin-4-yl)methanol (1 g, crude) as yellow oil. MS (M+H)⁺=513.3

Step 4. Synthesis of 3-(3-fluoro-4-(4-(hydroxymethyl)-4-methylpiperidin-1-yl)phenyl)piperidine-2,6-dione (5)

To a solution of (1-(4-(2,6-bis(benzyloxy)pyridin-3-yl)-2-fluorophenyl)-4-methylpiperidin-4-yl)methanol (1 g, 1.95 mmol) in CF₃CH₂OH (4 mL) was added Pd/C (2.69 g, 10% purity) under N₂ atmosphere, the suspension was degassed and purged with H₂ for 3 times, then the reaction mixture was stirred at 20° C. for 16 hr under 15 psi of H₂. LCMS showed a main peak with desired mass. The mixture was filtered, the filtrate was concentrated under vacuum to afford 3-(3-fluoro-4-(4-(hydroxymethyl)-4-methylpiperidin-1-yl)phenyl)piperidine-2,6-dione (620 mg, crude) as a gray powder. MS (M+H)⁺=335.1

Step 5. Synthesis of (1-(4-(2,6-dioxopiperidin-3-yl)-2-fluorophenyl)-4-methylpiperidin-4-yl)methyl 4-methylbenzenesulfonate (6)

To a solution of 3-(3-fluoro-4-(4-(hydroxymethyl)-4-methylpiperidin-1-yl)phenyl)piperidine-2,6-dione (200 mg, 598.11 μmol) in DCM (10 mL) were added TosCl (171.04 mg, 897.17 μmol) and TEA (181.57 mg, 1.79 mmol, 249.75 μL) followed by DMAP (14.61 mg, 119.62 μmol), the mixture was stirred at 20° C. for 2 hr. LCMS showed a main peak with desired mass, the mixture was diluted with water (30 mL), extracted with EtOAc (15 mL×3). The organic layer was dried over Na₂SO₄, filtered and concentrated under vacuum. The crude product was purified by flash silica gel chromatography (Biotage, 4 g SepaFlash Silica Flash Column, Eluent of 4~51% EtOAc/Petroleum ether gradient @ 20 mL/min) to afford (1-(4-(2,6-dioxopiperidin-3-yl)-2-fluorophenyl)-4-methylpiperidin-4-yl)methyl 4-methylbenzenesulfonate (60 mg, 110.53 μmol, 18.48% yield, 90% purity) as yellow oil. MS (M+H)⁺=489.2

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)-3-methylpyrrolidin-3-yl)ethyl)-7-azaspiro[3.5]nonan-2-yl)-3-methoxybenzamide (Compound 26)

To a solution of (1-(4-(2,6-dioxopiperidin-3-yl)-2-fluorophenyl)-4-methylpiperidin-4-yl)methyl 4-methylbenzenesulfonate (60 mg, 122.81 μmol) in DMF (8 mL) were added 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (71.24 mg, 122.81 μmol, HCl salt), DIPEA (47.62 mg, 368.42 μmol, 64.17 μL) and NaI (3.68 mg, 24.56 μmol), the mixture was stirred at 80° C. for 16 hr. LCMS showed a main peak with desired mass. The mixture was diluted with water (3 mL), extracted with EtOAc (5 mL×3). The organic layer was dried over Na₂SO₄, filtered and concentrated under vacuum. The crude product was purified by Prep-HPLC (column: Waters Xbridge C18 150*50 mm*10 μm; mobile phase: [water (NH₄HCO₃)-ACN]; B %: 42%-72%, 10 min) to afford 4-((7,7-difluoro-9-isopropyl-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)-3-methylpyrrolidin-3-yl)ethyl)-7-azaspiro[3.5]nonan-2-yl)-3-methoxybenzamide (23 mg, 24.10 μmol, 19.62% yield, 90.1% purity) as a white powder. MS (M+H)⁺=860.4

¹H NMR (400 MHz, DMSO-d₆) δ=10.77 (s, 1H), 8.42 (d, J=7.4 Hz, 1H), 8.35-8.28 (m, 1H), 8.23 (s, 1H), 7.88 (s, 1H), 7.53-7.48 (m, 2H), 6.93 (dd, J=1.8, 15.3 Hz, 1H), 6.84 (dd, J=1.6, 8.3 Hz, 1H), 6.63 (t, J=9.1 Hz, 1H), 4.89 (td, J=6.5, 13.4 Hz, 1H), 4.46-4.35 (m, 1H), 4.05 (t, J=13.6 Hz, 2H), 3.95 (s, 3H), 3.73 (dd, J=4.9, 11.4 Hz, 1H), 3.42 (t, J=7.9 Hz, 2H), 3.30 (s, 3H), 3.22-3.17 (m, 1H), 3.07 (d, J=8.8 Hz, 1H), 2.70-2.59 (m, 2H), 2.38-2.10 (m, 10H), 2.02-1.96 (m, 1H), 1.83-1.69 (m, 3H), 1.62-1.50 (m, 6H), 1.25 (d, J=6.8 Hz, 6H), 1.05 (s, 3H).

Example 27. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-(((1R,4R,5S)-2-(4-(2,6-dioxopiperidin-3-yl)-2-fluorophenyl)-2-azabicyclo[2.2.1]heptan-5-yl)methyl)-7-azaspiro[3.5]nonan-2-yl)-3-methoxybenzamide (trans) (Compound 27)

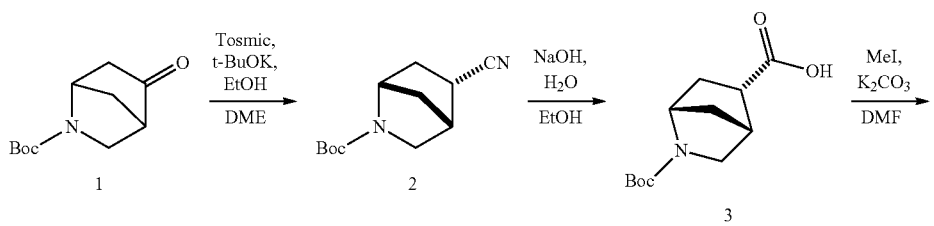

-continued
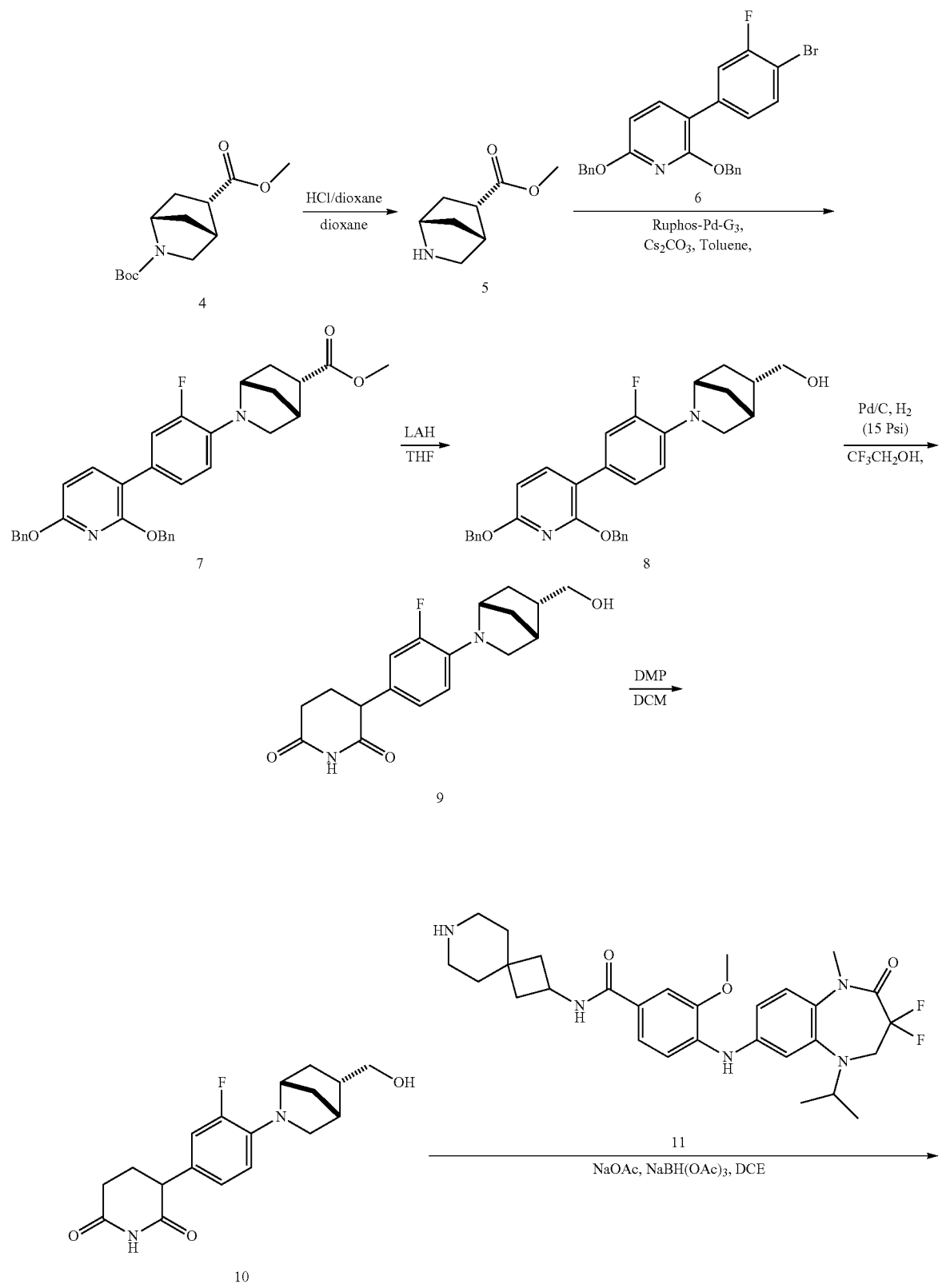

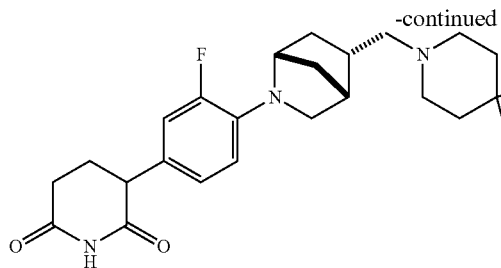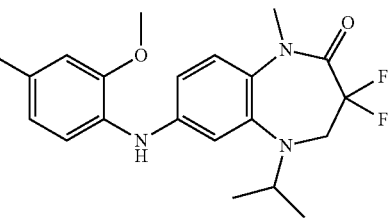

Compound 27

Step 1. Synthesis of tert-butyl (1S,4R,5S)-5-cyano-2-azabicyclo[2.2.1]heptane-2-carboxylate (trans) (2)

To a solution of tert-butyl 5-oxo-2-azabicyclo[2.2.1]heptane-2-carboxylate (1.8 g, 8.52 mmol) and 1-(isocyanomethylsulfonyl)-4-methyl-benzene (2.16 g, 11.08 mmol) in DME (50 mL) and EtOH (511 mg, 11.09 mmol) was added t-BuOK (1 M, 21.30 mL) at −10° C. The mixture was stirred at 20° C. for 3 hr. TLC (Petroleum ether:EtOAc=2:1) indicated the starting material was consumed completely and two new spots with lower polarity. The reaction mixture was quenched by addition aq. Sat NH₄Cl (100 mL) at 0° C., and extracted with EtOAc (50 mL×2). The combined organic layers were washed with brine (100 mL), dried over Na₂SO₄, filtered. The filtrate was concentrated in vacuum to give a residue. The residue was purified by flash silica gel chromatography (ISCO; 12 g SepaFlash Silica Flash Column, Eluent of 0~18% EtOAc/Petroleum ether gradient @ 50 mL/min) to afford tert-butyl (1S,4R,5R)-5-cyano-2-azabicyclo[2.2.1]heptane-2-carboxylate (trans) (700 mg, 3.15 mmol, 36.96% yield) as a yellow oil and tert-butyl (1S,4R,5S)-5-cyano-2-azabicyclo[2.2.1]heptane-2-carboxylate (cis) (650 mg, 2.92 mmol, 34.32% yield) as a yellow oil. MS (M+H)⁺=223.3

Step 2. Synthesis of (1S,4R,5S)-2-(tert-butoxycarbonyl)-2-azabicyclo[2.2.1]heptane-5-carboxylic acid (trans) (3)

To a solution of tert-butyl (1S,4R,5S)-5-cyano-2-azabicyclo[2.2.1]heptane-2-carboxylate (trans) (600 mg, 2.70 mmol) in EtOH (20 mL) and H₂O (2 mL) was added NaOH (539.85 mg, 13.50 mmol), the mixture was stirred at 80° C. for 16 h. TLC (Petroleum ether:EtOAc=2:1) indicated the starting material was consumed completely. The reaction mixture was concentrated under reduced pressure to remove ethanol. The residue was diluted with water 10 mL, acidified with 1N HCl to pH=6, extracted with EtOAc (30 mL×2). The combined organic layers were washed with brine (60 mL), dried over Na₂SO₄, filtered. The filtrate was concentrated in vacuum to afford (1S,4R,5S)-2-(tert-butoxycarbonyl)-2-azabicyclo[2.2.1]heptane-5-carboxylic acid (trans) (630 mg, crude) as a yellow solid. MS (M+H)⁺=242.1

Step 3. Synthesis of 2-(tert-butyl) 5-methyl (1S,4R,5S)-2-azabicyclo[2.2.1]heptane-2,5-dicarboxylate (trans) (4)

To a solution of (1S,4R,5S)-2-(tert-butoxycarbonyl)-2-azabicyclo[2.2.1]heptane-5-carboxylic acid (trans) (630 mg, 2.61 mmol) in DMF (10 mL) were added MeI (400 mg, 2.82 mmol, 175.44 μL) and K₂CO₃ (541.29 mg, 3.92 mmol). The mixture was stirred at 20° C. for 16 hr. TLC (Petroleum ether:EtOAc=1:1) indicated the starting material was consumed completely, one major new spot with lower polarity. The reaction mixture was diluted with brine (30 mL) at 0° C., extracted with EtOAc (40 mL×3). The combined organic layers were washed with brine (80 mL×3), dried over Na₂SO₄, filtered. The filtrate was concentrated in vacuum to give a residue. The residue was purified by flash silica gel chromatography (Biotage; 12 g SepaFlash Silica Flash Column, Eluent of 0~20% EtOAc/Petroleum ether gradient @ 80 mL/min) to afford 2-(tert-butyl) 5-methyl (1S,4R,5S)-2-azabicyclo[2.2.1]heptane-2,5-dicarboxylate (trans) (550 mg, 2.15 mmol, 82.51% yield) as a yellow oil. MS (M+H)⁺=256.1

Step 4. Synthesis of methyl (1S,4R,5S)-2-azabicyclo[2.2.1]heptane-5-carboxylate (trans) (5)

To a solution of 2-(tert-butyl) 5-methyl (1S,4R,5S)-2-azabicyclo[2.2.1]heptane-2,5-dicarboxylate (trans) (550 mg, 2.15 mmol) in dioxane (5 mL) was added HCl/dioxane (4 M, 5 mL), the mixture was stirred at 20° C. for 1 h. TLC indicated the starting material was consumed completely. The mixture was concentrated in vacuum to afford methyl (1S,4R,5S)-2-azabicyclo[2.2.1]heptane-5-carboxylate (trans) (400 mg, crude, HCl) as a white solid. MS (M+H)⁺=156.1

Step 5. Synthesis of methyl (1S,4R,5S)-2-(4-(2,6-bis(benzyloxy)pyridin-3-yl)-2-fluorophenyl)-2-azabicyclo[2.2.1]heptane-5-carboxylate (trans) (7)

To a solution of 2,6-bis(benzyloxy)-3-(4-bromo-3-fluorophenyl)pyridine (896.41 mg, 1.93 mmol) and methyl (1S,4R,5S)-2-azabicyclo[2.2.1]heptane-5-carboxylate (trans) (370 mg, crude, HCl) in toluene (18 mL) were added Cs₂CO₃ (1.89 g, 5.79 mmol), RuPhos Pd G₃ (161.46 mg, 193.06 μmol), the mixture was stirred at 100° C. for 16 h. LCMS showed a peak (45%) with desired mass. The mixture was filtered through a pad of celite. The filtrate was concentrated in vacuum to give a residue. The residue was purified by flash silica gel chromatography (Biotage; 20 g SepaFlash Silica Flash Column, Eluent of 0~50% EtOAc/Petroleum ether gradient @ 40 mL/min) to afford methyl (1S,4R,5S)-2-(4-(2,6-bis(benzyloxy)pyridin-3-yl)-2-fluorophenyl)-2-azabicyclo[2.2.1]heptane-5-carboxylate (trans) (410 mg, 761.22 μmol, 39.43% yield) as a yellow solid. MS (M+H)⁺=539.2

Step 6. Synthesis of ((1S,4R,5S)-2-(4-(2,6-bis(benzyloxy)pyridin-3-yl)-2-fluorophenyl)-2-azabicyclo[2.2.1]heptan-5-yl)methanol (trans) (8)

To a suspension of methyl (1S,4R,5S)-2-(4-(2,6-bis(benzyloxy)pyridin-3-yl)-2-fluorophenyl)-2-azabicyclo[2.2.1]

heptane-5-carboxylate (trans) (360 mg, 668.39 μmol) in THF (10 mL) was added LAH (50 mg, 1.32 mmol) at 0° C., the mixture was stirred at 15° C. for 2 hours. LCMS showed a main peak with desired mass. The reaction mixture was quenched by addition H$_2$O (0.2 mL), NaOH (15% aq, 0.2 mL) and H$_2$O (0.6 mL), the mixture was dried over Na$_2$SO$_4$, filtered. The filtrate was concentrated in vacuum to give a residue. The residue was purified by flash silica gel chromatography (Biotage; 20 g SepaFlash Silica Flash Column, Eluent of 20~80% EtOAc/Petroleum ether gradient @ 40 mL/min) to afford ((1S,4R,5S)-2-(4-(2,6-bis(benzyloxy)pyridin-3-yl)-2-fluorophenyl)-2-azabicyclo[2.2.1]heptan-5-yl)methanol (trans) (340 mg, 539.37 μmol, 80.70% yield, 81% purity) as a yellow solid. MS (M+H)$^+$=511.3

Step 7. Synthesis of 3-(3-fluoro-4-((1S,4R,5S)-5-(hydroxymethyl)-2-azabicyclo[2.2.1]heptan-2-yl)phenyl)piperidine-2,6-dione (trans) (9)

A mixture of ((1S,4R,5S)-2-(4-(2,6-bis(benzyloxy)pyridin-3-yl)-2-fluorophenyl)-2-azabicyclo[2.2.1]heptan-5-yl)methanol (trans) (140 mg, 274.19 μmol) and Pd/C (14 mg, 10% purity) in CF$_3$CH$_2$OH (5 mL) was degassed and purged with H$_2$ for 3 times, and then the mixture was stirred at 20° C. for 2 h under H$_2$ (15 Psi) atmosphere. LCMS showed a peak with desired mass. The mixture was filtered through a pad of celite. The filtrate was concentrated in vacuum to afford 3-(3-fluoro-4-((1S,4R,5S)-5-(hydroxymethyl)-2-azabicyclo[2.2.1]heptan-2-yl)phenyl)piperidine-2,6-dione (trans) (90 mg, crude) as a yellow oil. MS (M+H)$^+$=333.1

Step 8. Synthesis of (1S,4R,5S)-2-(4-(2,6-dioxopiperidin-3-yl)-2-fluorophenyl)-2-azabicyclo[2.2.1]heptane-5-carbaldehyde (trans) (10)

To a solution of 3-(3-fluoro-4-((1S,4R,5S)-5-(hydroxymethyl)-2-azabicyclo[2.2.1]heptan-2-yl)phenyl)piperidine-2,6-dione (trans) (90 mg, crude) in DCM (2 mL) was added DMP (137.82 mg, 324.94 μmol, 100.60 μL), the mixture was stirred at 20° C. for 1 h. TLC indicated the starting material was consumed completely and a new spots with lower polarity was detected. The mixture was filtered through a pad of celite. The filtrate was concentrated in vacuum to afford (1S,4R,5S)-2-(4-(2,6-dioxopiperidin-3-yl)-2-fluorophenyl)-2-azabicyclo[2.2.1]heptane-5-carbaldehyde (trans) (90 mg, crude) as a brown oil. MS (M+H)$^+$=331.1

Step 9. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-(((1R,4R,5S)-2-(4-(2,6-dioxopiperidin-3-yl)-2-fluorophenyl)-2-azabicyclo[2.2.1]heptan-5-yl)methyl)-7-azaspiro[3.5]nonan-2-yl)-3-methoxybenzamide (trans) (Compound 27)

To a solution of (1S,4R,5S)-2-(4-(2,6-dioxopiperidin-3-yl)-2-fluorophenyl)-2-azabicyclo[2.2.1]heptane-5-carbaldehyde (trans) (90 mg, 272.44 μmol) and 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (148.10 mg, 255.31 μmol, HCl) in DCE (2 mL) was added NaOAc (22.35 mg, 272.44 μmol), the mixture was stirred at 20° C. for 0.5 h, NaBH(OAc)$_3$ (173.22 mg, 817.31 μmol) was added, the resulting mixture was stirred at 20° C. for 1 h. LCMS showed a peak (34%) with desired mass. The reaction mixture was quenched with NaHCO$_3$ (10 mL), extracted with EtOAc (10 mL×3). The combined organic layers were washed with brine (20 mL×2), dried over Na$_2$SO$_4$, filtered. The filtrate was concentrated in vacuum to give a residue. The residue was purified by prep-TLC (SiO$_2$, DCM:MeOH=9:1) and re-purified by reversed-phase HPLC (column: Waters Xbridge 150*25 mm*5 μm; mobile phase: [water (NH$_4$HCO$_3$)-ACN]; B %: 47%-77%, 8 min). The eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-(((1R,4R,5S)-2-(4-(2,6-dioxopiperidin-3-yl)-2-fluorophenyl)-2-azabicyclo[2.2.1]heptan-5-yl)methyl)-7-azaspiro[3.5]nonan-2-yl)-3-methoxybenzamide (trans) (57.3 mg, 62.78 μmol, 23.04% yield, 94% purity) as a yellow solid. MS (M+H)$^+$=858.6

$^1$H NMR (400 MHz, DMSO-d$_6$) δ=10.77 (s, 1H), 8.40 (d, J=7.2 Hz, 1H), 8.32-8.27 (m, 1H), 8.22 (s, 1H), 7.87 (s, 1H), 7.54-7.45 (m, 2H), 6.93-6.87 (m, 1H), 6.81 (d, J=8.1 Hz, 1H), 6.65-6.59 (t, J=9.1 Hz, 1H), 4.94-4.82 (m, 1H), 4.45-4.33 (m, 1H), 4.10-3.99 (m, 3H), 3.93 (s, 3H), 3.74-3.67 (m, 1H), 3.61-3.54 (m, 1H), 3.30 (s, 3H), 2.84-2.77 (m, 1H), 2.76-2.69 (m, 1H), 2.65-2.59 (m, 2H), 2.40-2.35 (m, 2H), 2.27-2.22 (m, 2H), 2.17-2.11 (m, 3H), 2.05-1.97 (m, 2H), 1.86-1.76 (m, 4H), 1.61-1.50 (m, 6H), 1.31-1.17 (m, 8H).

Example 28. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-2-oxopiperidin-4-yl)methyl)-7-azaspiro[3.5]nonan-2-yl)-3-methoxybenzamide (Compound 28)

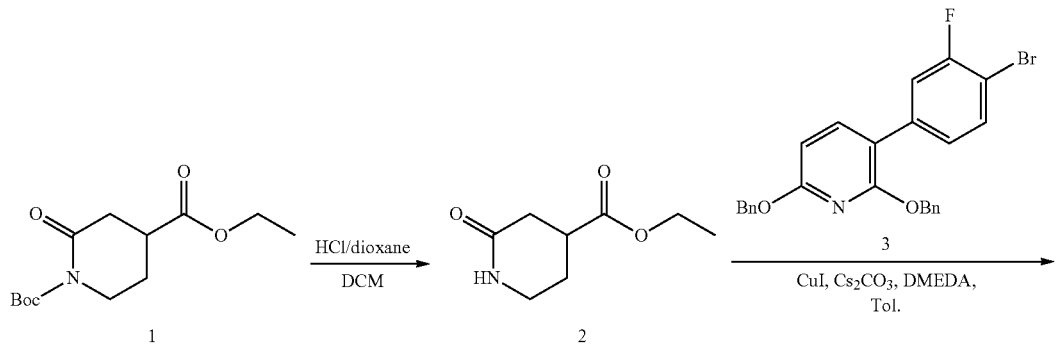

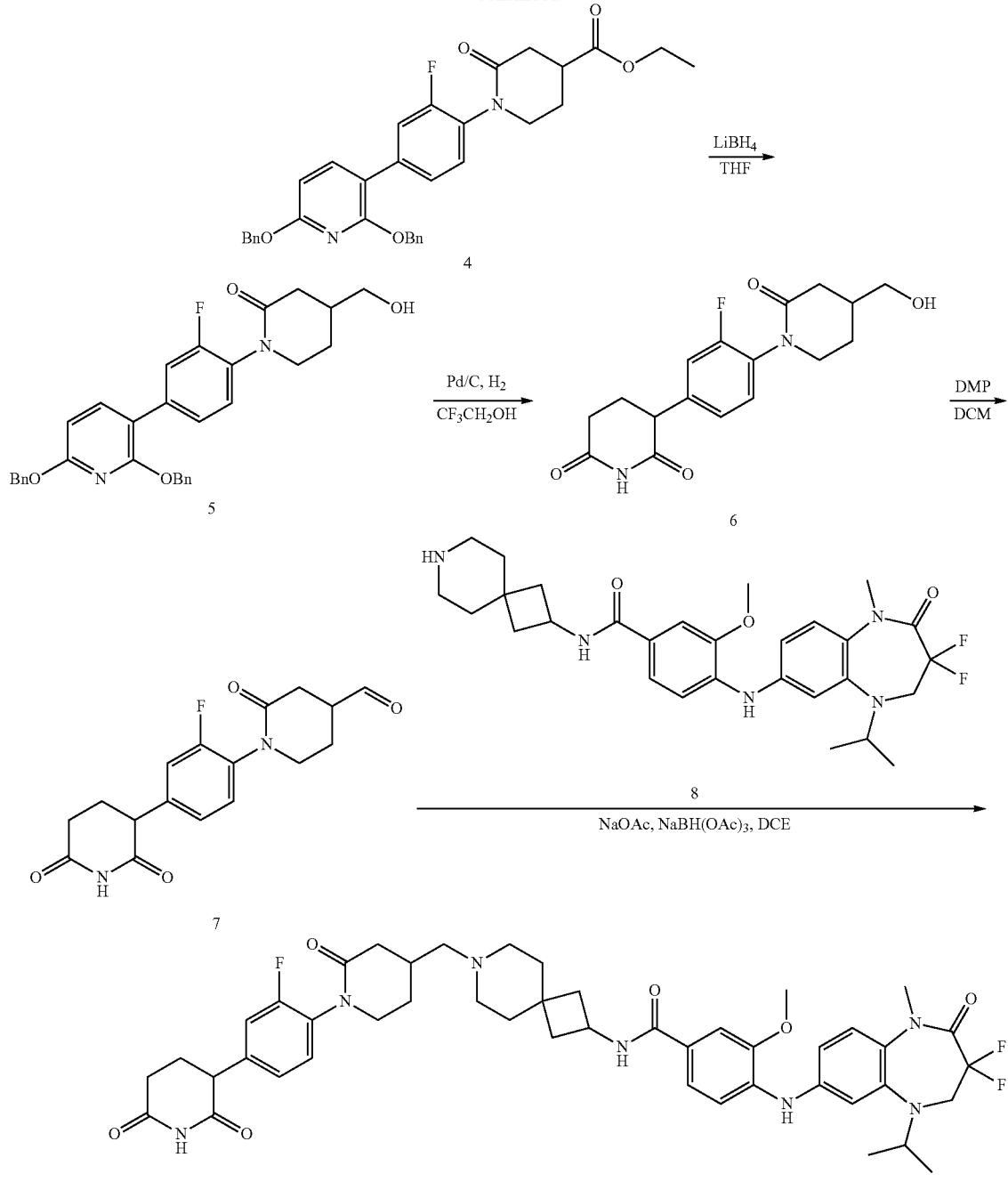

Compound 28

Step 1. Synthesis of ethyl 2-oxopiperidine-4-carboxylate (2)

To a solution of 1-(tert-butyl) 4-ethyl 2-oxopiperidine-1,4-dicarboxylate (2 g, 7.37 mmol) in DCM (10 mL) was added HCl/dioxane (4 M, 3 mL), the mixture was stirred at 20° C. for 1 h. TLC (Petroleum ether:EtOAc=3:1) indicated the starting material was consumed completely and one major new spot with larger polarity. The mixture was concentrated in vacuum to afford ethyl 2-oxopiperidine-4-carboxylate (1.26 g, crude) as a white solid. MS $(M+H)^+=172.1$.

Step 2. Synthesis of ethyl 1-(4-(2,6-bis(benzyloxy) pyridin-3-yl)-2-fluorophenyl)-2-oxopiperidine-4-carboxylate (4)

To a solution of 2,6-bis(benzyloxy)-3-(4-bromo-3-fluorophenyl)pyridine (1.68 g, 3.61 mmol), ethyl 2-oxopiperidine-4-carboxylate (500 mg, crude) and CuI (458.57 mg, 2.41 mmol) in Tol. (20 mL) were added DMEDA (212.26 mg, 2.41 mmol, 259.16 μL) and $Cs_2CO_3$ (1.57 g, 4.82 mmol) under $N_2$, the resulting mixture was stirred at 100° C. for 16 h. LCMS showed a main peak with desired mass. The mixture was filtered through a pad of celite. The filtrate was concentrated in vacuum to give a residue. The residue was purified by flash silica gel chromatography (Biotage; 20 g SepaFlash Silica Flash Column, Eluent of 20~100% EtOAc/Petroleum ether to 10% Methanol/EtOAc gradient @ 40 mL/min) to afford ethyl 1-(4-(2,6-bis(benzyloxy)pyridin-3-yl)-2-fluorophenyl)-2-oxopiperidine-4-carboxylate (500 mg, 901.54 µmol, 37.44% yield) as a yellow solid. MS (M+H)$^+$=555.2.

Step 3. Synthesis of 1-(4-(2,6-bis(benzyloxy)pyridin-3-yl)-2-fluorophenyl)-4-(hydroxymethyl)piperidin-2-one (5)

To a suspension of ethyl 1-(4-(2,6-bis(benzyloxy)pyridin-3-yl)-2-fluorophenyl)-2-oxopiperidine-4-carboxylate (400 mg, 721.23 µmol) in THF (8 mL) was added LiBH$_4$ (2 M, 734.50 µL) dropwise at 0° C., the mixture was stirred at 20° C. for 6 hours. LCMS showed a peak (17%) with desired mass and 76% of the starting material was remained. The mixture was stirred at 20° C. for 16 h. LCMS showed a main peak with desired mass. The reaction mixture was quenched by addition NH$_4$Cl (10 mL) at 0° C., extracted with EtOAc (10 mL×3). The combined organic layers were washed with brine (20 mL×2), dried over Na$_2$SO$_4$, filtered. The filtrate was concentrated in vacuum to give a residue. The residue was purified by flash silica gel chromatography (Biotage; 20 g SepaFlash Silica Flash Column, Eluent of 20~100% EtOAc/Petroleum ether gradient @ 80 mL/min) to afford 1-(4-(2,6-bis(benzyloxy)pyridin-3-yl)-2-fluorophenyl)-4-(hydroxymethyl)piperidin-2-one (300 mg, 561.87 µmol, 77.90% yield, 96% purity) as a yellow oil. MS (M+H)$^+$=513.3.

Step 4. Synthesis of 3-(3-fluoro-4-(4-(hydroxymethyl)-2-oxopiperidin-1-yl)phenyl)piperidine-2,6-dione (6)

A mixture of 1-(4-(2,6-bis(benzyloxy)pyridin-3-yl)-2-fluorophenyl)-4-(hydroxymethyl)piperidin-2-one (200 mg, 390.19 µmol) and Pd/C (20 mg, 10% purity) in CF$_3$CH$_2$OH (10 mL) was degassed and purged with H$_2$ for 3 times, then the mixture was stirred at 20° C. for 12 h under H$_2$ (15 Psi) atmosphere. LCMS showed a main peak with desired mass. The mixture was filtered through a pad of celite. The filtrate was concentrated in vacuum to afford 3-(3-fluoro-4-(4-(hydroxymethyl)-2-oxopiperidin-1-yl)phenyl)piperidine-2,6-dione (130 mg, crude) as a white solid. MS (M+H)$^+$=335.1.

Step 5. Synthesis of 1-(4-(2,6-dioxopiperidin-3-yl)-2-fluorophenyl)-2-oxopiperidine-4-carbaldehyde (7)

To a solution of 3-(3-fluoro-4-(4-(hydroxymethyl)-2-oxopiperidin-1-yl)phenyl)piperidine-2,6-dione (130 mg, crude) in DCM (2 mL) was added DMP (197.90 mg, 466.59 µmol, 144.45 µL), the mixture was stirred at 20° C. for 1 h. TLC indicated the starting material was consumed completely and a new spot was detected. The mixture was filtered through a pad of celite. The filtrate was concentrated in vacuum to afford 1-(4-(2,6-dioxopiperidin-3-yl)-2-fluorophenyl)-2-oxopiperidine-4-carbaldehyde (130 mg, crude) as a brown oil, which was used into the next step directly. MS (M+H)$^+$=333.3.

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-2-oxopiperidin-4-yl)methyl)-7-azaspiro[3.5]nonan-2-yl)-3-methoxybenzamide (Compound 28)

To a solution of 1-(4-(2,6-dioxopiperidin-3-yl)-2-fluorophenyl)-2-oxopiperidine-4-carbaldehyde (130 mg, crude) and 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (212.65 mg, 366.59 µmol, HCl) in DCE (2 mL) was added NaOAc (32.09 mg, 391.18 µmol), the mixture was stirred at 20° C. for 0.5 h, NaBH(OAc)$_3$ (248.72 mg, 1.17 mmol) was added, the mixture was stirred at 20° C. for 1 h. LCMS showed a main peak with desired mass. The reaction mixture was quenched by addition NaHCO$_3$ (5 mL), extracted with EtOAc (10 mL×3). The combined organic layers were washed with brine (20 mL×2), dried over Na$_2$SO$_4$, filtered. The filtrate was concentrated in vacuum to give a residue. The residue was purified by prep-TLC (SiO$_2$, DCM: MeOH=9:1) and re-purified by reversed-phase HPLC (column: Waters Xbridge 150*25 mm*5 um; mobile phase: [water (NH$_4$HCO$_3$)-ACN]; B %: 38%-68%, 8 min). The eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-2-oxopiperidin-4-yl)methyl)-7-azaspiro[3.5]nonan-2-yl)-3-methoxybenzamide (50.8 mg, 58.48 µmol, 14.95% yield, 99% purity) as a white solid. MS (M+H)$^+$=860.6.

$^1$H NMR (400 MHz, DMSO-d$_6$) δ=10.87 (s, 1H), 8.42 (d, J=7.6 Hz, 1H), 8.33-8.28 (m, 1H), 8.22 (s, 1H), 7.88 (s, 1H), 7.53-7.47 (m, 2H), 7.34-7.28 (m, 1H), 7.21-7.17 (m, 1H), 7.12-7.07 (m, 1H), 4.94-4.82 (m, 1H), 4.47-4.33 (m, 1H), 4.04 (t, J=13.4 Hz, 2H), 3.96-3.87 (m, 4H), 3.63-3.54 (m, 1H), 3.53-3.46 (m, 1H), 3.30 (s, 3H), 2.73-2.62 (m, 2H), 2.57-2.54 (m, 2H), 2.35-2.32 (m, 1H), 2.29-2.13 (m, 8H), 2.10-1.97 (m, 3H), 1.87-1.76 (m, 2H), 1.66-1.52 (m, 5H), 1.24 (d, J=6.7 Hz, 6H).

Example 29. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)piperidin-4-yl)ethyl)-7-azaspiro[3.5]nonan-2-yl)-3-methoxybenzamide (Compound 29)

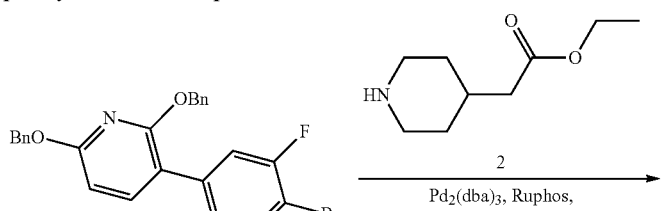

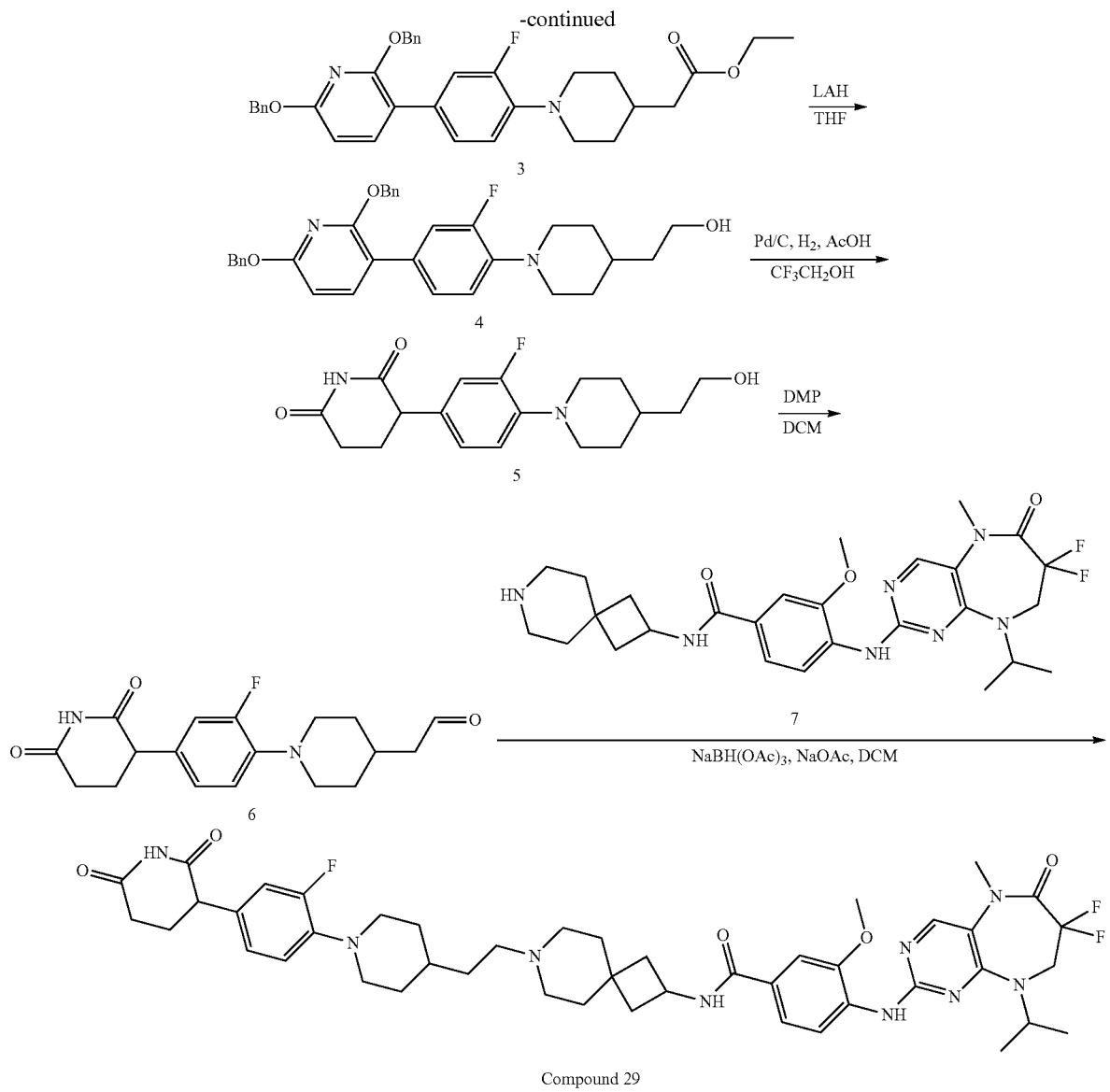

Step 1. Synthesis of ethyl 2-(1-(4-(2,6-bis(benzyloxy)pyridin-3-yl)-2-fluorophenyl)piperidin-4-yl)acetate (3)

To the solution of 2,6-bis(benzyloxy)-3-(4-bromo-3-fluorophenyl)pyridine (2 g, 4.31 mmol) and ethyl 2-(piperidin-4-yl)acetate (737.57 mg, 4.31 mmol) in toluene (50 mL) was added RuPhos (401.99 mg, 861.46 μmol), Pd₂(dba)₃ (394.43 mg, 430.73 μmol) and Cs₂CO₃ (4.21 g, 12.92 mmol) and the resulting mixture was stirred at 100° C. for 12 h under N₂. LCMS showed a peak (45%) with desired mass, the mixture was filtered and concentrated. The residue was purified by flash silica gel chromatography (20 g SepaFlash Silica Flash Column, Eluent of 0~20% EtOAc/Petroleum ether gradient @ 80 mL/min) to afford ethyl 2-(1-(4-(2,6-bis(benzyloxy)pyridin-3-yl)-2-fluorophenyl)piperidin-4-yl)acetate (0.7 g, 1.10 mmol, 25.49% yield, 87% purity) as a yellow solid. MS (M+H)⁺=555.3

Step 2. Synthesis of 2-(1-(4-(2,6-bis(benzyloxy)pyridin-3-yl)-2-fluorophenyl)piperidin-4-yl)ethanol (4)

To the suspension of LAH (100 mg, 2.64 mmol) in THF (10 mL) was added ethyl 2-(1-(4-(2,6-bis(benzyloxy)pyridin-3-yl)-2-fluorophenyl)piperidin-4-yl)acetate (700 mg, 1.26 mmol) in THF (5 mL) at 20° C. and the resulting mixture was stirred at 20° C. for 2 h. LCMS showed a peak (79%) with desired mass. The reaction mixture was quenched with H₂O (0.1 mL), NaOH solution (15%, 0.1 mL) and H₂O (0.3 mL) at 0° C., then the mixture was filtered and the filtrate was concentrated to afford 2-(1-(4-(2,6-bis(benzyloxy)pyridin-3-yl)-2-fluorophenyl)piperidin-4-yl)ethanol (0.6 g, 1.17 mmol, 92.74% yield) as yellow oil. MS (M+H)⁺=513.2

Step 3. Synthesis of 3-(3-fluoro-4-(4-(2-hydroxyethyl)piperidin-1-yl)phenyl)piperidine-2,6-dione (5)

To the solution of 2-(1-(4-(2,6-bis(benzyloxy)pyridin-3-yl)-2-fluorophenyl)piperidin-4-yl)ethanol (0.6 g, 1.17 mmol) in CF$_3$CH$_2$OH (20 mL) was added AcOH (70.29 mg, 1.17 mmol, 66.94 µL) and Pd/C (100 mg, 10% purity) under N$_2$ atmosphere, Then the mixture was stirred at 20-25° C. for 16 h under H$_2$ atmosphere (15 Psi). LCMS showed that reactant 1 was consumed, the mixture was filtered and concentrated to afford crude product (0.5 g, crude) as a black solid. The 400 mg of crude product was purified by flash silica gel chromatography (10 g SepaFlash Silica Flash Column, Eluent of 0~60% EtOAc/Petroleum ether gradient @ 80 mL/min) to afford 3-(3-fluoro-4-(4-(2-hydroxyethyl) piperidin-1-yl)phenyl)piperidine-2,6-dione (60 mg, 179.43 µmol, 15.33% yield, 100% purity) as a white solid. MS (M+H)$^+$=335.2

Step 4. Synthesis of 2-(1-(4-(2,6-dioxopiperidin-3-yl)-2-fluorophenyl)piperidin-4-yl)acetaldehyde (6)

To a solution of 3-(3-fluoro-4-(4-(2-hydroxyethyl)piperidin-1-yl)phenyl)piperidine-2,6-dione (60 mg, 179.43 µmol) in DCM (3 mL) was added DMP (114.16 mg, 269.15 µmol, 83.33 µL) and the mixture was stirred at 20° C. for 2 h. TLC (EtOAc:Petroleum ether=2:1) showed that 3-(3-fluoro-4-(4-(2-hydroxyethyl)piperidin-1-yl)phenyl)piperidine-2,6-dione was consumed completely and new spot formed, the mixture was filtered and the filtrate was concentrated under reduced pressure to afford 2-(1-(4-(2,6-dioxopiperidin-3-yl)-2-fluorophenyl) piperidin-4-yl)acetaldehyde (60 mg, crude) was obtained as yellow oil. MS (M+H)$^+$=333.4

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)piperidin-4-yl)ethyl)-7-azaspiro[3.5]nonan-2-yl)-3-methoxybenzamide (Compound 29)

To a solution of 2-(1-(4-(2,6-dioxopiperidin-3-yl)-2-fluorophenyl) piperidin-4-yl)acetaldehyde (59 mg, 177.51 µmol) in DCM (5 mL) was added 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (92.67 mg, 159.76 µmol, HCl) and NaOAc (21.84 mg, 266.27 µmol) and the mixture was stirred at 20° C. for 1 h. Then NaBH(OAc)$_3$ (188.11 mg, 887.57 µmol) was added to the mixture at 20° C., the mixture was stirred at 20° C. for 15 h. LCMS showed a peak (24%) with desired mass. The mixture was poured into water (20 mL) and extracted with DCM (10 mL×3), the combined organic layer was washed with brine (20 mL), dried over Na$_2$SO$_4$, filtered and concentrated. The residue was purified by prep-HPLC (column: Phenomenex luna C18 150*25 mm*10 µm; mobile phase: [water (FA)-ACN]; B %: 18%-48%, 10 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-(2-(1-(4-(2,6-dioxopiperidin-3-yl)-2-fluorophenyl)piperidin-4-yl)ethyl)-7-azaspiro[3.5]nonan-2-yl)-3-methoxybenzamide (13.6 mg, 14.71 µmol, 8.29% yield, 93% purity) as a white solid. MS (M+H)$^+$=860.4.

$^1$H NMR (400 MHz, DMSO-d$_6$) δ=10.81 (s, 1H), 8.43 (d, J=7.4 Hz, 1H), 8.31-8.27 (m, 1H), 8.23 (s, 1H), 7.89 (s, 1H), 7.54-7.48 (m, 2H), 7.06-6.91 (m, 3H), 4.96-4.82 (m, 1H), 4.48-4.33 (m, 1H), 4.05 (t, J=13.6 Hz, 2H), 3.95 (s, 3H), 3.80 (dd, J=4.8, 11.6 Hz, 1H), 3.30-3.26 (m, 5H), 2.70-2.57 (m, 3H), 2.48-2.45 (m, 1H), 2.39-2.28 (m, 5H), 2.26-2.10 (m, 5H), 2.09-2.00 (m, 1H), 1.85-1.73 (m, 4H), 1.64-1.53 (m, 4H), 1.45-1.39 (m, 2H), 1.38-1.30 (m, 2H), 1.25 (d, J=6.6 Hz, 6H).

Example 30. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((7-((1-(4-(2,6-dioxopiperidin-3-yl)-2-fluorophenyl)piperidin-4-yl)methyl)-7-azaspiro[3.5]nonan-2-yl)methyl)-3-methoxybenzamide (Compound 30)

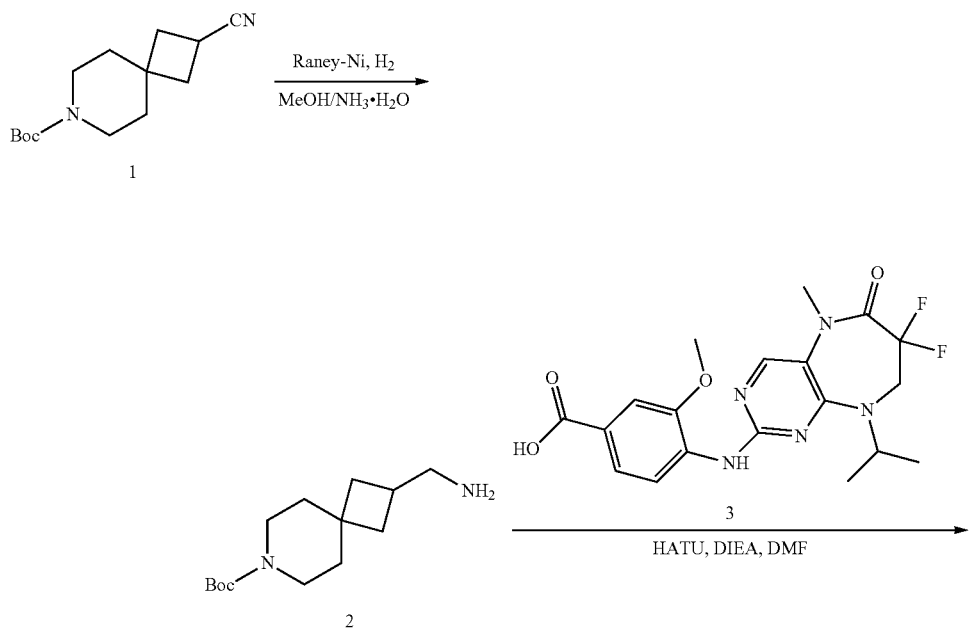

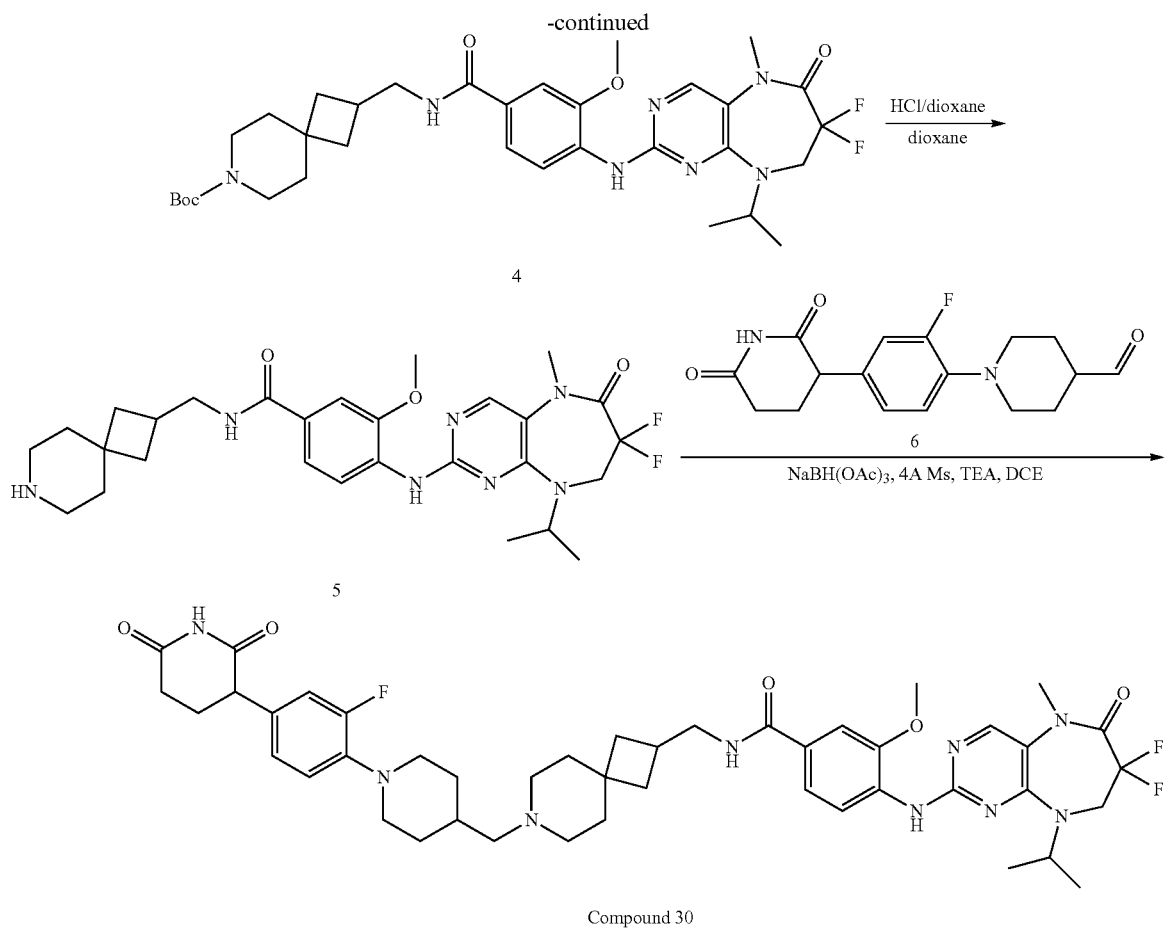

Compound 30

Step 1. Synthesis of tert-butyl 2-(aminomethyl)-7-azaspiro[3.5]nonane-7-carboxylate (2)

To a solution of tert-butyl 2-cyano-7-azaspiro[3.5]nonane-7-carboxylate (0.5 g, 2.00 mmol) in MeOH (10 mL) and NH$_3$·H$_2$O (1 mL) was added Raney-Ni (342.24 mg, 3.99 mmol) under N$_2$ atmosphere. The suspension was degassed and purged with H$_2$ for 3 times. The mixture was stirred at 25° C. for 12 h under H$_2$ (50 Psi). LCMS showed starting material was consumed completely and a peak (69%) with desired mass. The reaction mixture was diluted with MeOH (100 mL) and filtered. The filtrate was concentrated in vacuum to afford tert-butyl 2-(aminomethyl)-7-azaspiro[3.5]nonane-7-carboxylate (512 mg, crude) as a yellow oil. MS (M−56+H)$^+$=199.1

Step 2. Synthesis of tert-butyl 2-((4-(((7,7-difluoro-9-isopropyl-5-methyl-6-oxo-6,7,8,9-tetrahydro-5H-pyrimido[4,5-b][1,4]diazepin-2-yl)amino)-3-methoxybenzamido)methyl)-7-azaspiro[3.5]nonane-7-carboxylate (4)

To a solution of 4-(((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (600 mg, 1.42 mmol) in DMF (4 mL) were added HATU (595.52 mg, 1.57 mmol) and DIPEA (552.06 mg, 4.27 mmol, 744.02 µL). The mixture was stirred at 20° C. for 10 min and a solution of tert-butyl 2-(aminomethyl)-7-azaspiro[3.5]nonane-7-carboxylate (507.05 mg, 1.99 mmol) in DMF (4 mL) was added and the resulting mixture was stirred at 20° C. for 1 h. LCMS showed all starting material was consumed completely and a peak (69%) with desired mass. The reaction mixture was diluted with H$_2$O (15 mL) and extracted with EtOAc (15 mL×3). The organic layer was washed with brine (15 mL×3), dried over Na$_2$SO, filtered and concentrated. The residue was purified by flash silica gel chromatography (10 g SepaFlash Silica Flash Column, Eluent of 0~80% EtOAc/Petroleum ether gradient @ 100 mL/min) to afford tert-butyl 2-((4-(((7,7-difluoro-9-isopropyl-5-methyl-6-oxo-6,7,8,9-tetrahydro-5H-pyrimido[4,5-b][1,4]diazepin-2-yl)amino)-3-methoxybenzamido)methyl)-7-azaspiro[3.5]nonane-7-carboxylate (916 mg, 1.39 mmol, 97.81% yield) as an orange solid. MS (M+H)$^+$=658.3

Step 3. Synthesis of N-((7-azaspiro[3.5]nonan-2-yl)methyl)-4-(((7,7-difluoro-9-isopropyl-5-methyl-6-oxo-6,7,8,9-tetrahydro-5H-pyrimido[4,5-b][1,4]diazepin-2-yl)amino)-3-methoxybenzamide (5)

To a solution of tert-butyl 2-((4-(((7,7-difluoro-9-isopropyl-5-methyl-6-oxo-6,7,8,9-tetrahydro-5H-pyrimido[4,5-b][1,4]diazepin-2-yl)amino)-3-methoxybenzamido)methyl)-7-azaspiro[3.5]nonane-7-carboxylate (916 mg, 1.39 mmol) in dioxane (4 mL) was added HCl/dioxane (4 M, 12 mL) at 20° C. and the resulting mixture was stirred at 20° C. for 1 h. LCMS showed starting material was consumed completely and a peak (76%) with desired mass. The reaction mixture was concentrated in vacuum to afford N-((7-azaspiro[3.5]nonan-2-yl)methyl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (830 mg, crude, HCl salt) as a yellow solid. MS (M+H)$^+$=558.4

Step 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((7-((1-(4-(2,6-dioxopiperidin-3-yl)-2-fluorophenyl)piperidin-4-yl)methyl)-7-azaspiro[3.5]nonan-2-yl)methyl)-3-methoxybenzamide (Compound 30)

To a solution of N-((7-azaspiro[3.5]nonan-2-yl)methyl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (223.95 mg, 376.95 μmol, HCl salt) in DCE (8 mL) were added TEA (476.79 mg, 4.71 mmol, 655.84 μL) and 1-(4-(2,6-dioxopiperidin-3-yl)-2-fluorophenyl)piperidine-4-carbaldehyde (150 mg, 471.19 μmol), 4 Å MS (100 mg) at 20° C. Then NaBH(OAc)$_3$ (299.59 mg, 1.41 mmol) was slowly added at 20° C. and the resulting mixture was stirred at 20° C. for 12 h. LCMS showed 1-(4-(2,6-dioxopiperidin-3-yl)-2-fluorophenyl)piperidine-4-carbaldehyde was consumed completely and a peak (32%) with desired mass. The reaction mixture was filtered and the filtrate was concentrated in vacuum. The residue was purified by prep-HPLC (column: Phenomenex Synergi Polar-RP 100*25 mm*4 μm; mobile phase: [water (TFA)-ACN]; B %: 33%-53%, 7 min) and re-purified by prep-HPLC (column: Phenomenex C18 75*30 mm*3 μm; mobile phase: [water (FA)-ACN]; B %: 15%-45%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-((7-((1-(4-(2,6-dioxopiperidin-3-yl)-2-fluorophenyl)piperidin-4-yl)methyl)-7-azaspiro[3.5]nonan-2-yl)methyl)-3-methoxybenzamide (56.9 mg, 62.86 μmol, 13.34% yield, 95% purity) as a white solid. MS (M+H)$^+$=860.4

$^1$H NMR (400 MHz, DMSO-d$_6$) δ=10.80 (s, 1H), 8.36-8.28 (m, 2H), 8.22-8.17 (m, 1H), 7.88 (s, 1H), 7.54-7.45 (m, 2H), 7.06-6.88 (m, 3H), 4.94-4.82 (m, 1H), 4.03 (br t, J=13.5 Hz, 2H), 3.93 (s, 3H), 3.78 (dd, J=4.8, 11.8 Hz, 1H), 3.32 (s, 4H), 3.31-3.26 (m, 4H), 2.66-2.56 (m, 3H), 2.48-2.44 (m, 1H), 2.41-2.11 (m, 7H), 2.04-1.94 (m, 1H), 1.87-1.71 (m, 4H), 1.68-1.59 (m, 1H), 1.55 (br s, 2H), 1.52-1.42 (m, 4H), 1.24 (d, J=6.7 Hz, 8H).

Example 31. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((4-(4-(2,6-dioxopiperidin-3-yl)-2-fluorophenyl)piperazin-1-yl)methyl)-2-azaspiro[3.5]nonan-2-yl)-3-methoxybenzamide (Compound 31)

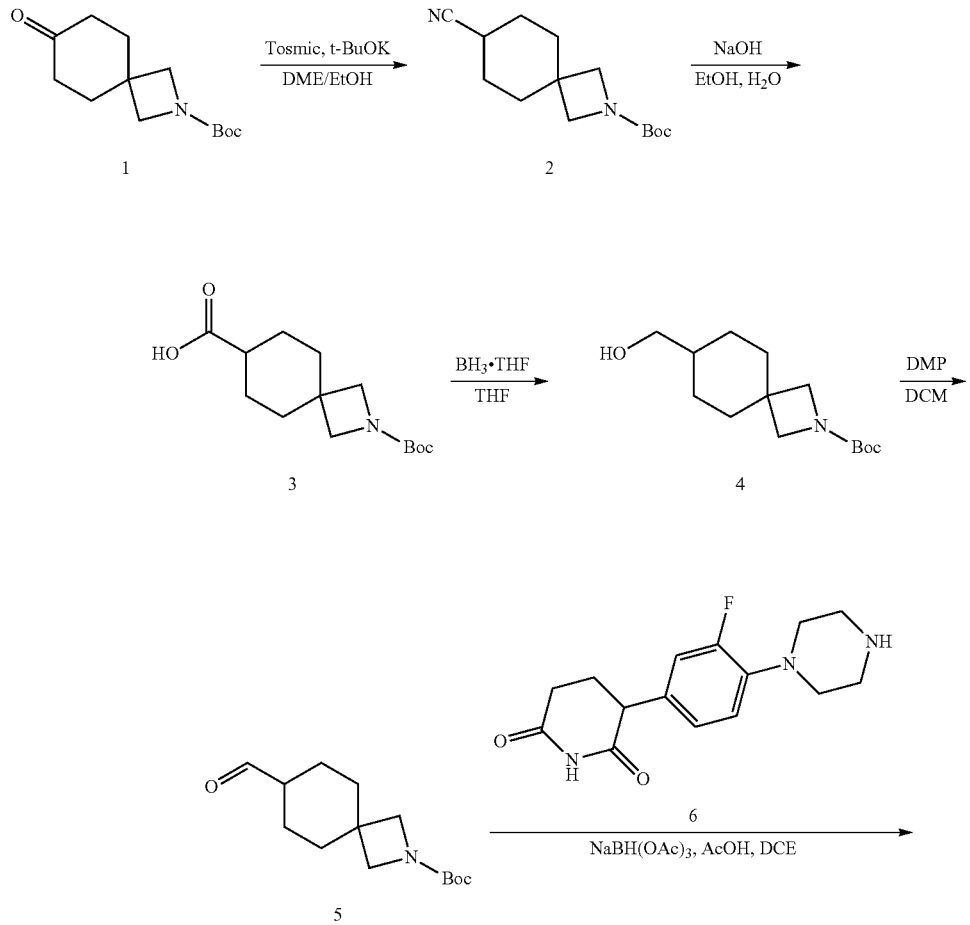

161 162
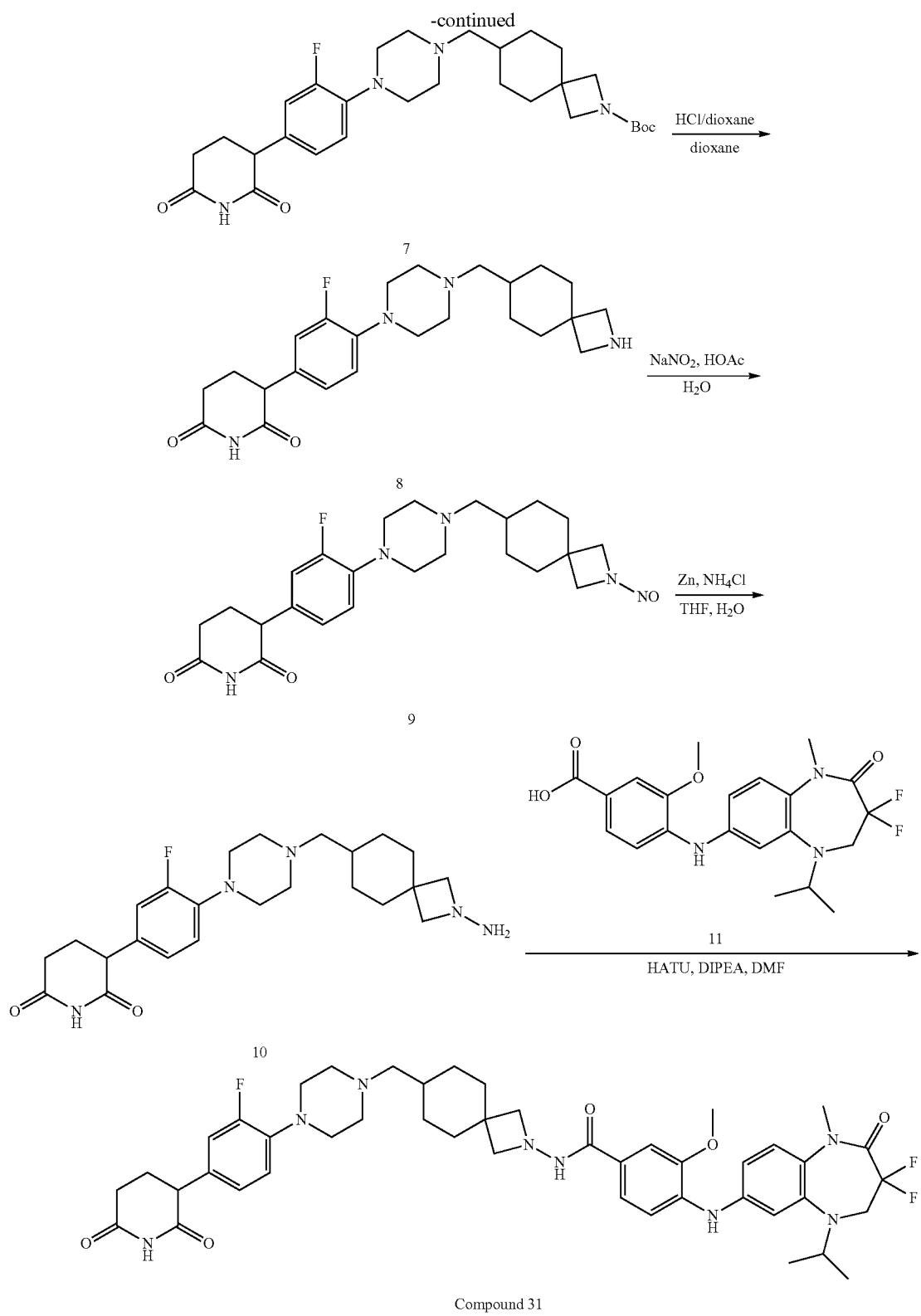
Compound 31
Step 1. Synthesis of tert-butyl 7-cyano-2-azaspiro[3.5]nonane-2-carboxylate (2)
To a solution of tert-butyl 7-oxo-2-azaspiro[3.5]nonane-2-carboxylate (1.35 g, 5.64 mmol) and 1-(isocyanomethyl-sulfonyl)-4-methyl-benzene (1.43 g, 7.33 mmol) in DME (20 mL) and EtOH (337.85 mg, 7.33 mmol) was added t-BuOK (1 M, 14.10 mL) at −10° C. The mixture was stirred at 20° C. for 3 h. TLC (Petroleum ether:EtOAc=2:1, Rf=0.66) indicated the starting material was consumed completely and one new spot was formed. The reaction mixture was quenched by addition of aq. sat NH₄Cl (30 mL) at 0° C., then extracted with EtOAc (50 mL×2). The combined organic layers were washed with brine (20 mL), dried over Na₂SO₄, filtered and concentrated under reduced pressure. The residue was purified by flash silica gel chromatography (ISCO; 12 g SepaFlash Silica Flash Column, Eluent of 0~25% EtOAc/Petroleum ether gradient @ 50 mL/min) to afford tert-butyl 7-cyano-2-azaspiro[3.5]nonane-2-carboxylate (1.4 g, 5.59 mmol, 99.14% yield) as colorless oil. MS (M+H)$^+$=251.3

$^1$H NMR (400 MHz, CDCl₃) δ=3.60 (d, J=14.5 Hz, 4H), 2.63 (br s, 1H), 1.97-1.64 (m, 9H), 1.45 (s, 9H)

Step 2. Synthesis of 2-(tert-butoxycarbonyl)-2-azaspiro[3.5]nonane-7-carboxylic Acid (3)

To a solution of tert-butyl 7-cyano-2-azaspiro[3.5]nonane-2-carboxylate (1.4 g, 5.59 mmol) in EtOH (15 mL) was added a solution of NaOH (939.47 mg, 23.49 mmol) in H₂O (1.5 mL). The mixture was stirred at 80° C. for 16 h. TLC (Petroleum ether:EtOAc=1:1) indicated the starting material was consumed completely and one main spot was formed. The reaction mixture was concentrated under reduced pressure to remove ethanol. The residue was diluted with water (15 mL), acidified with 1N HCl to pH=6. The resulting mixture was extracted with EtOAc (50 mL×3), the combined organic layers were washed with brine (20 mL), dried over Na₂SO₄, filtered and concentrated under reduced pressure to afford 2-(tert-butoxycarbonyl)-2-azaspiro[3.5]nonane-7-carboxylic acid (1.15 g, 4.27 mmol, 76.35% yield) as a yellow solid. MS (M+H)$^+$=270.3

Step 3. Synthesis of tert-butyl 7-(hydroxymethyl)-2-azaspiro[3.5]nonane-2-carboxylate (4)

To a solution of 2-(tert-butoxycarbonyl)-2-azaspiro[3.5]nonane-7-carboxylic acid (950 mg, 3.53 mmol) in THF (20 mL) was added BH₃·THF (1 M, 7.05 mL) at 0° C. under N₂ atmosphere. The mixture was stirred at 20° C. for 3 h. TLC (Petroleum ether:EtOAc=1:1, Rf=0.32) indicated the starting material was consumed completely and two new spots were formed. The reaction mixture was quenched by addition of aq. sat NH₄Cl (20 mL) at 0° C., then extracted with EtOAc (50 mL×2). The combined organic layers were washed with brine (20 mL), dried over Na₂SO₄, filtered and concentrated under reduced pressure. The residue was purified by flash silica gel chromatography (ISCO; 20 g SepaFlash Silica Flash Column, Eluent of 0~40% EtOAc/Petroleum ether gradient @ 50 mL/min) to afford tert-butyl 7-(hydroxymethyl)-2-azaspiro[3.5]nonane-2-carboxylate (600 mg, 2.35 mmol, 66.62% yield) as a white solid. MS (M+H)$^+$=256.4

Step 4. Synthesis of tert-butyl 7-formyl-2-azaspiro[3.5]nonane-2-carboxylate (5)

To a solution of tert-butyl 7-(hydroxymethyl)-2-azaspiro[3.5]nonane-2-carboxylate (600 mg, 2.35 mmol) in DCM (10 mL) was added DMP (1.20 g, 2.82 mmol, 872.94 µL). The mixture was stirred at 20° C. for 1 h. TLC (Petroleum ether:EtOAc=2:1, Rf=0.61) indicated the starting material was consumed completely and one main new spot with lower polarity was formed. The reaction mixture was filtered and the filtrate was concentrated to afford tert-butyl 7-formyl-2-azaspiro[3.5]nonane-2-carboxylate (600 mg, crude) as a red solid. MS (M+H)$^+$=254.3

Step 5. Synthesis of tert-butyl 7-((4-(4-(2,6-dioxopiperidin-3-yl)-2-fluorophenyl)piperazin-1-yl) methyl)-2-azaspiro[3.5]nonane-2-carboxylate (7)

To a solution of tert-butyl 7-formyl-2-azaspiro[3.5] nonane-2-carboxylate (600 mg, 2.37 mmol) and 3-(3-fluoro-4-(piperazin-1-yl)phenyl)piperidine-2,6-dione (689.96 mg, 2.37 mmol) in DCE (15 mL) was added HOAc (142.23 mg, 2.37 mmol, 135.45 µL). The mixture was stirred at 20° C. for 1 h. Then NaBH(OAc)₃ (2.51 g, 11.84 mmol) was added and the mixture was stirred at 20° C. for 16 h. LCMS showed the desired mass. The mixture was diluted with water (30 mL) and extracted with EtOAc (15 mL×3). The combined organic layer was washed with brine (10 mL), dried over Na₂SO₄ and filtered. The filtrate was concentrated under reduced pressure. The residue was purified by flash silica gel chromatography (5 g SepaFlash Silica Flash Column, Eluent of 70~100% EtOAc/Petroleum ether gradient @ 50 mL/min) to afford tert-butyl 7-((4-(4-(2,6-dioxopiperidin-3-yl)-2-fluorophenyl)piperazin-1-yl)methyl)-2-azaspiro[3.5] nonane-2-carboxylate (430 mg, 813.38 µmol, 28.67% yield) as a yellow solid. MS (M+H)$^+$=529.6

Step 6. Synthesis of 3-(4-(4-((2-azaspiro[3.5]nonan-7-yl)methyl)piperazin-1-yl)-3-fluorophenyl)piperidine-2,6-dione (8)

To a solution of tert-butyl 7-((4-(4-(2,6-dioxopiperidin-3-yl)-2-fluorophenyl)piperazin-1-yl)methyl)-2-azaspiro[3.5] nonane-2-carboxylate (380 mg, 718.80 µmol) in dioxane (5 mL) was added HCl/dioxane (4 M, 5 mL) and the mixture was stirred at 20° C. for 1 h. LCMS showed a peak (43%) with desired mass. The mixture was concentrated under reduced pressure to afford 3-(4-(4-((2-azaspiro[3.5]nonan-7-yl)methyl)piperazin-1-yl)-3-fluorophenyl)piperidine-2,6-dione (0.38 g, crude, HCl salt) as a yellow solid. MS (M+H)$^+$=429.5

Step 7. Synthesis of 3-(3-fluoro-4-(4-((2-nitroso-2-azaspiro[3.5]nonan-7-yl)methyl)piperazin-1-yl)phenyl)piperidine-2,6-dione (9)

To a solution of 3-(4-(4-((2-azaspiro[3.5]nonan-7-yl) methyl)piperazin-1-yl)-3-fluorophenyl)piperidine-2,6-dione (0.38 g, 817.20 µmol, HCl salt) in H₂O (8 mL) was added NaNO₂ (226 mg, 3.28 mmol) followed by AcOH (245.37 mg, 4.09 mmol, 233.91 µL) at 0° C. and the mixture was stirred at 20° C. for 14 h. LCMS showed 27% of the desired mass and 19% of the starting material remained. NaNO₂ (169.15 mg, 2.45 mmol) was added at 20° C., then AcOH (294.00 mg, 4.90 mmol, 280 µL) was added and the mixture was stirred at 20° C. for 1 h. LCMS showed 52% of the desired mass and 8% of the starting material remained. The mixture was stirred at 20° C. for 1 h. The mixture was quenched with NaHCO₃ (20 mL) and extracted with EtOAc (10 mL×3). The combined organic layer was concentrated under reduced pressure. The crude was diluted with MTBE (5 mL) and EtOAc (5 mL), then filtered. The filter cake was washed with EtOAc (3 mL) and the filter cake was collected and dried under reduced pressure to afford 3-(3-fluoro-4-(4-((2-nitroso-2-azaspiro[3.5]nonan-7-yl)methyl)piperazin-1-yl)phenyl)piperidine-2,6-dione (150 mg, crude) as yellow solid. MS (M+H)$^+$=458.5

Step 8. Synthesis of 3-(4-(4-((2-amino-2-azaspiro[3.5]nonan-7-yl)methyl)piperazin-1-yl)-3-fluorophenyl)piperidine-2,6-dione (10)

To a solution of 3-(3-fluoro-4-(4-((2-nitroso-2-azaspiro[3.5]nonan-7-yl)methyl)piperazin-1-yl)phenyl)piperidine-2,6-dione (0.11 g, 240.42 μmol) in THF (3 mL) and H$_2$O (3 mL) was added NH$_4$Cl (128 mg, 2.39 mmol), then Zn (150 mg, 2.29 mmol) was added slowly at 0° C. and the mixture was stirred at 20° C. for 2.5 h. LCMS showed the starting material was consumed and a peak with desired mass. The mixture was filtered and the filter cake was washed with THF (20 mL) and MeOH (10 mL). The filtrate was concentrated under reduced pressure. The crude was diluted with THF (5 mL) and MeOH (5 mL), then filtered. The filter cake was washed with MeOH (5 mL). The combined filtrate was concentrated under reduced pressure to afford 3-(4-(4-((2-amino-2-azaspiro[3.5]nonan-7-yl)methyl)piperazin-1-yl)-3-fluorophenyl)piperidine-2,6-dione (150 mg, crude) as a yellow solid. MS (M+H)$^+$=444.2

Step 9. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((4-(4-(2,6-dioxopiperidin-3-yl)-2-fluorophenyl)piperazin-1-yl)methyl)-2-azaspiro[3.5]nonan-2-yl)-3-methoxybenzamide (Compound 31)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (150 mg, 355.96 μmol) in DMF (2 mL) were added HATU (162.42 mg, 427.15 μmol) and DIPEA (230.03 mg, 1.78 mmol, 310.01 μL) and the mixture was stirred at 20° C. for 30 min. Then a solution of 3-(4-(4-((2-amino-2-azaspiro[3.5]nonan-7-yl)methyl)piperazin-1-yl)-3-fluorophenyl)piperidine-2,6-dione (150 mg, 338.18 μmol) in DMF (2 mL) was added and the mixture was stirred at 20° C. for 2 h. LCMS showed the desired mass. The mixture was diluted with water (10 mL) and extracted with EtOAc (10 mL×3). The combined organic layer was washed with brine (10 mL×3), dried over Na$_2$SO$_4$ and filtered. The filtrate was concentrated under reduced pressure. The residue was purified by flash silica gel chromatography (12 g SepaFlash Silica Flash Column, Eluent of 30% MeOH/EtOAc gradient @ 50 m/min), then re-purified by prep-TLC (Dichloromethane:Methanol=10:1) to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((4-(4-(2,6-dioxopiperidin-3-yl)-2-fluorophenyl)piperazin-1-yl)methyl)-2-azaspiro[3.5]nonan-2-yl)-3-methoxybenzamide (10 mg, 10.27 μmol, 2.89% yield, 87% purity) as a white solid. MS (M+H)$^+$=847.1

$^1$H NMR (400 MHz, DMSO-d$_6$) δ=10.84-10.80 (m, 1H), 9.47 (s, 1H), 8.31-8.27 (m, 1H), 8.22 (s, 1H), 7.88 (s, 1H), 7.44-7.40 (m, 2H), 7.05-6.99 (m, 1H), 6.98-6.94 (m, 2H), 4.92-4.83 (m, 1H), 4.04 (br t, J=13.2 Hz, 2H), 3.93 (s, 3H), 3.83-3.76 (m, 1H), 3.54-3.46 (m, 4H), 3.32 (s, 3H), 3.31-3.29 (m, 4H), 3.02-2.97 (m, 4H), 2.65-2.59 (m, 1H), 2.47-2.43 (m, 1H), 2.21-2.10 (m, 3H), 2.03-1.92 (m, 3H), 1.75-1.66 (m, 2H), 1.52-1.35 (m, 3H), 1.24 (d, J=6.6 Hz, 6H), 0.94-0.79 (m, 2H).

Example 32. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-2-methylpiperidin-4-yl)methyl)-7-azaspiro[3.5]nonan-2-yl)-3-methoxybenzamide (Compound 32)

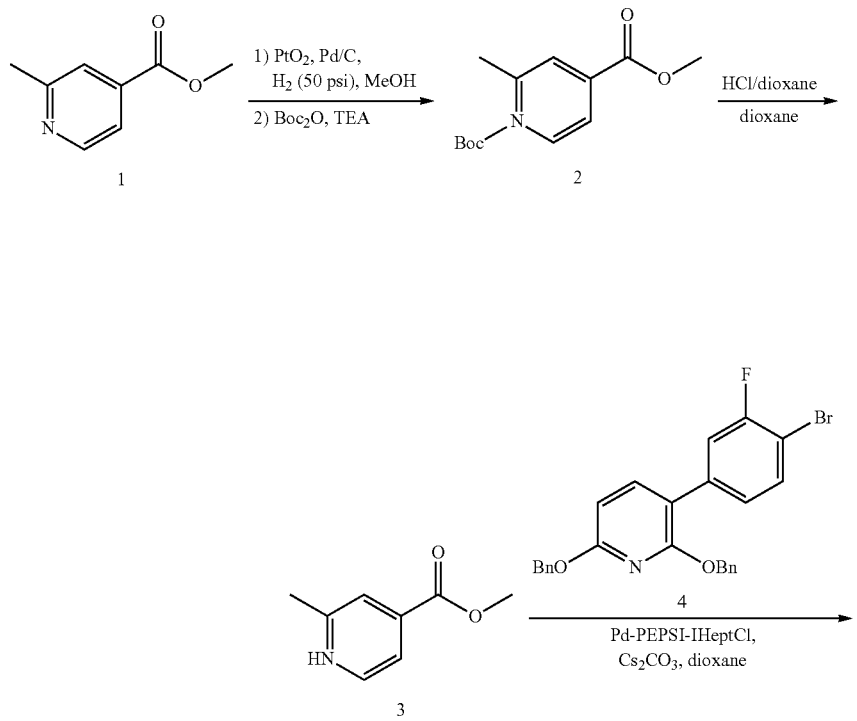

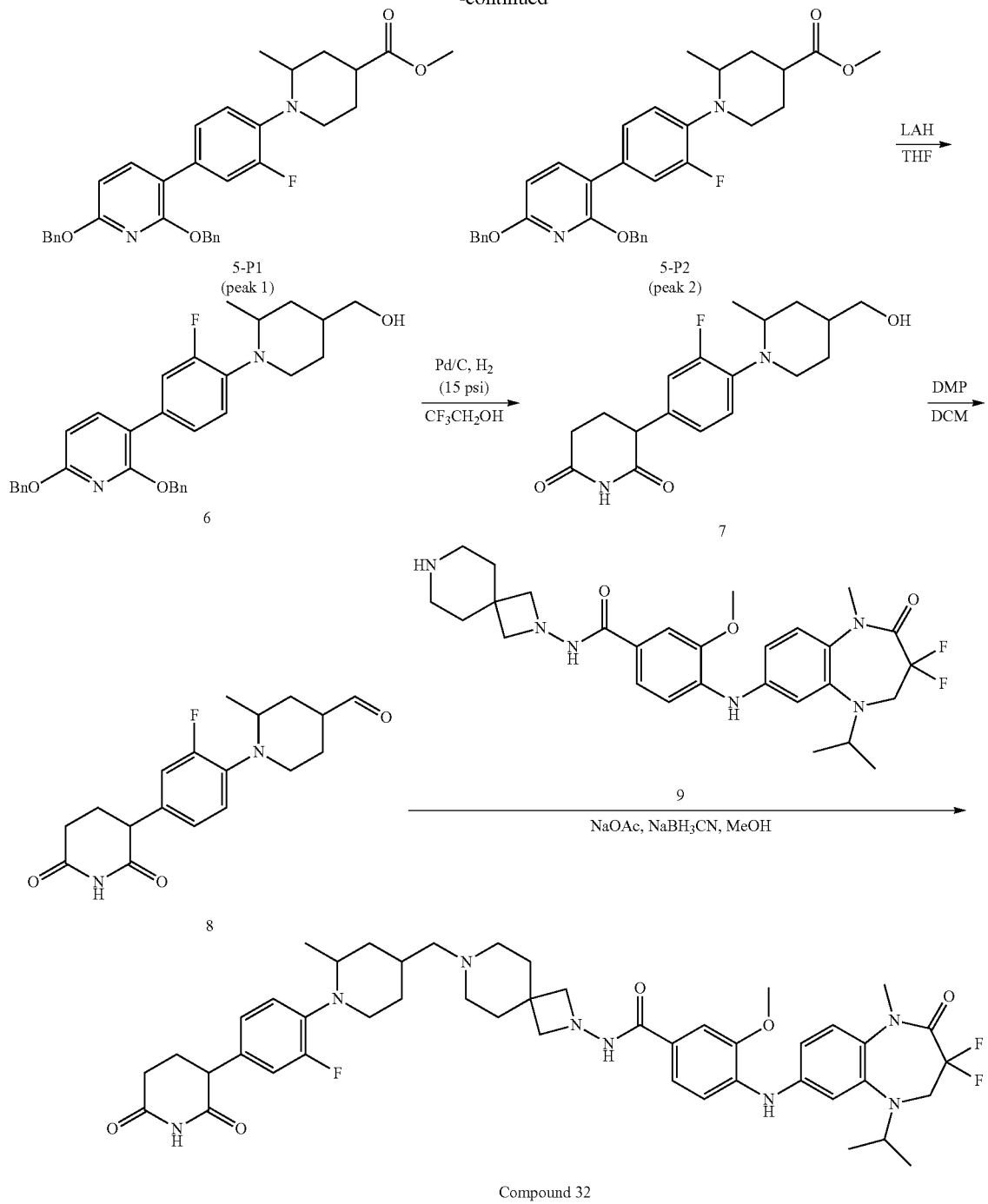

Compound 32

Step 1. Synthesis of 1-(tert-butyl) 4-methyl 2-methylpiperidine-1,4-dicarboxylate (2)

To a solution of methyl 2-methylisonicotinate (4 g, 26.46 mmol) in MeOH (50 mL) were added PtO$_2$ (600.88 mg, 2.65 mmol) and Pd/C (1 g, 10% purity) under N$_2$ atmosphere at 15° C. The suspension was degassed under vacuum and purged with H$_2$ for several times. The mixture was stirred under H$_2$ (50 Psi) at 50° C. for 32 h. Then Boc$_2$O (8.66 g, 39.69 mmol, 9.12 mL) and TEA (5.36 g, 52.92 mmol, 7.37 mL) were added and the resulting mixture was stirred at 15° C. for 16 h. LCMS showed the starting material was consumed completely and a peak (50%) with desired mass. The suspension was filtered and the filter cake was washed with EtOAc (200 mL), the filtrate was concentrated in vacuum. The residue was purified by flash silica gel chromatography (40 g SepaFlash Silica Flash Column, Eluent of 4~10% EtOAc/Petroleum ether gradient @ 100 mL/min) to afford 1-(tert-butyl) 4-methyl 2-methylpiperidine-1,4-dicarboxylate (4.25 g, 16.52 mmol, 62.42% yield) as a colorless oil. MS (M−56+H)$^+$=202.0

Step 2. Synthesis of methyl 2-methylpiperidine-4-carboxylate (3)

To a solution of 1-(tert-butyl) 4-methyl 2-methylpiperidine-1,4-dicarboxylate (3.5 g, 13.60 mmol) in dioxane (10 mL) was added HCl/dioxane (4 M, 20 mL) and the mixture was stirred at 15° C. at 2 h. TLC (SiO$_2$, Petroleum ether: EtOAc=5:1) indicated the starting material was consumed completely and a new spot was formed. The reaction mixture was concentrated in vacuum to afford methyl 2-methylpiperidine-4-carboxylate (3.2 g, HCl salt) as a white solid. MS (M−56+H)$^+$=158.1

Step 3. Synthesis of methyl 1-(4-(2,6-bis(benzyloxy)pyridin-3-yl)-2-fluorophenyl)-2-methylpiperidine-4-carboxylate (5-P1 & 5-P2)

A mixture of methyl 2-methylpiperidine-4-carboxylate (3.1 g, 16.01 mmol, HCl salt), 2,6-bis(benzyloxy)-3-(4-bromo-3-fluorophenyl)pyridine (4.46 g, 9.60 mmol), Cs$_2$CO$_3$ (15.65 g, 48.02 mmol), and Pd-PEPPSI-IHeptCl (202.42 mg, 208.09 µmol) in dioxane (100 mL) was stirred at 100° C. for 24 h at N$_2$ atmosphere. LCMS showed a peak (33%) with desired mass. The mixture was filtered and the filter cake was washed with EtOAc (400 mL), the filtrate was concentrated in vacuum. The residue was purified by flash silica gel chromatography (20 g SepaFlash Silica Flash Column, Eluent of 4~7% EtOAc/Petroleum ether gradient @ 200 mL/min) followed by prep-HPLC (column: Phenomenex luna C18 150*40 mm*15 µm; mobile phase: [water (TFA)-ACN]; B %: 48%-78%, 10 min) to afford two batches of the eluents (peak 1 and peak 2). Two batches of the eluents were freeze-dried respectively to afford methyl 1-(4-(2,6-bis(benzyloxy)pyridin-3-yl)-2-fluorophenyl)-2-methylpiperidine-4-carboxylate (peak 1) (329 mg, 608.56 µmol, 3.80% yield) as a yellow oil and methyl 1-(4-(2,6-bis(benzyloxy)pyridin-3-yl)-2-fluorophenyl)-2-methylpiperidine-4-carboxylate (peak 2) (175 mg, 323.70 µmol, 2.02% yield) as a brown oil. The peak 1 was used in the next step. MS (M+H)$^+$=541.4.

Step 4. Synthesis of (1-(4-(2,6-bis(benzyloxy)pyridin-3-yl)-2-fluorophenyl)-2-methylpiperidin-4-yl)methanol (6)

To a solution of LAH (105.31 mg, 2.77 mmol) in THF (8 mL) was added a solution of methyl 1-(4-(2,6-bis(benzyloxy)pyridin-3-yl)-2-fluorophenyl)-2-methylpiperidine-4-carboxylate (500 mg, 924.86 µmol) in THF (8 mL) dropwise at 0° C., the mixture was stirred at 15° C. for 2 h. LCMS showed starting material was consumed completely and a main peak (94%) with desired mass. The reaction mixture was diluted with THF (20 mL) at 20° C. The reaction mixture was quenched with H$_2$O (0.1 mL), NaOH (15% aq, 0.1 mL) and H$_2$O (0.3 mL), the suspension was dried over Na$_2$SO$_4$, filtered and concentrated in vacuum to afford (1-(4-(2,6-bis(benzyloxy)pyridin-3-yl)-2-fluorophenyl)-2-methylpiperidin-4-yl)methanol (375 mg) as a gray oil. MS (M+H)$^+$=513.4.

Step 5. Synthesis of 3-(3-fluoro-4-(4-(hydroxymethyl)-2-methylpiperidin-1-yl)phenyl)piperidine-2,6-dione (7)

To a solution of (1-(4-(2,6-bis(benzyloxy)pyridin-3-yl)-2-fluorophenyl)-2-methylpiperidin-4-yl)methanol (375 mg, 731.55 µmol) in CF$_3$CH$_2$OH (15 mL) and THF (6 mL) was added Pd/C (150 mg, 10% purity) under N$_2$ atmosphere. The suspension was degassed under vacuum and purged with H$_2$ for several times. The mixture was stirred at 15° C. for 16 h under H$_2$ (15 psi). LCMS showed the starting material was consumed completely and desired mass was detected. The suspension was filtered and the filter cake was washed with CF$_3$CH$_3$OH (100 mL) and THF (100 mL), the filtrate was concentrated in vacuum to afford 3-(3-fluoro-4-(4-(hydroxymethyl)-2-methylpiperidin-1-yl)phenyl)piperidine-2,6-dione (420 mg) as a purple gum. MS (M+H)$^+$=335.3

Step 6. Synthesis of 1-(4-(2,6-dioxopiperidin-3-yl)-2-fluorophenyl)-2-methylpiperidine-4-carbaldehyde (8)

To a solution of 3-(3-fluoro-4-(4-(hydroxymethyl)-2-methylpiperidin-1-yl)phenyl)piperidine-2,6-dione (420 mg, 1.26 mmol) in DCM (20 mL) was added DMP (799.11 mg, 1.88 mmol, 583.29 µL) at 0° C., the mixture was stirred at 15° C. for 2 h. LCMS showed the starting material was consumed completely. The reaction mixture was filtered and the filter cake was washed with DCM (10 mL), the filtrate was concentrated in vacuum at 30° C. to afford 1-(4-(2,6-dioxopiperidin-3-yl)-2-fluorophenyl)-2-methylpiperidine-4-carbaldehyde (410 mg) as a brown oil. MS (M+H)$^+$=333.1

Step 7. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-2-methylpiperidin-4-yl)methyl)-7-azaspiro[3.5]nonan-2-yl)-3-methoxybenzamide (Compound 32)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (429.33 mg, 740.14 µmol, HCl salt) in MeOH (10 mL) was added NaOAc (404.78 mg, 4.93 mmol), then 1-(4-(2,6-dioxopiperidin-3-yl)-2-fluorophenyl)-2-methylpiperidine-4-carbaldehyde (410 mg, 1.23 mmol) was added and the mixture was stirred at 15° C. for 30 minutes. NaBH$_3$CN (232.56 mg, 3.70 mmol) was added and the resulting mixture was stirred at 15° C. for 16 h. LCMS showed the desired mass. The reaction mixture was filtered and the filtrate was concentrated in vacuum. The residue was purified by flash silica gel chromatography (12 g SepaFlash Silica Flash Column, Eluent of 1~50% EtOAc/Petroleum ether gradient @ 100 mL/min) followed by flash silica gel chromatography (12 g SepaFlash Silica Flash Column, Eluent of 30~100% MeOH/EtOAc gradient @ 80 mL/min) to afford the product A (0.2 g, 20% purity) and the product B (0.2 g, crude). The crude A (0.2 g, 20% purity) was purified by prep-HPLC (column: Phenomenex C18 75*30 mm*3 µm; mobile phase: [water (FA)-ACN]; B %: 10%-40%, 7 min) and the eluent was lyophilized to afford product C (26 mg, 84% purity, FA). The crude B (0.2 g, crude) was purified by prep-HPLC (column: Phenomenex Synergi Polar-RP 100*25 mm*4 um; mobile phase: [water (TFA)-ACN]; B %: 24%-44%, 7 min) and the eluent was lyophilized to afford to afford a product D (28 mg, 82% purity, TFA). The product C (26 mg, 84% purity, FA) and D (28 mg, 82% purity, TFA) was combined and diluted with water (10 mL), adjusted the pH=7 with aq. sat NaHCO$_3$, then extracted with DCM (10 mL×3). The combined organic layer was washed with brine (10 mL×3), dried over Na$_2$SO$_4$ and filtered. The filtrate was concentrated under reduced pressure. The crude was purified by prep-TLC (Dichloromethane:Methanol=8/1) to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-2-methylpiperidin-4-yl)methyl)-7-azaspiro[3.5]nonan-2-yl)-3-methoxybenzamide (18.8 mg, 21.21 µmol, 33.77% yield, 97% purity) as a white solid. MS (M+H)⁺=860.6.

¹H NMR (400 MHz, DMSO-d₆) δ=10.83 (s, 1H), 8.44-8.39 (m, 1H), 8.32-8.28 (m, 1H), 8.21 (s, 1H), 7.87 (s, 1H), 7.52-7.46 (m, 2H), 7.22-7.17 (m, 1H), 7.06-7.01 (m, 1H), 7.00-6.96 (m, 1H), 4.92-4.83 (m, 1H), 4.44-4.35 (m, 1H), 4.03 (br t, J=13.5 Hz, 2H), 3.93 (s, 3H), 3.86-3.80 (m, 1H), 3.29 (s, 3H), 3.05-2.92 (m, 2H), 2.70-2.61 (m, 1H), 2.44-2.36 (m, 2H), 2.27-1.96 (m, 9H), 1.87-1.49 (m, 10H), 1.27-1.20 (m, 7H), 0.99-0.88 (m, 1H), 0.85 (br d, J=5.3 Hz, 3H).

Example 33. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-4-hydroxypiperidin-4-yl)methyl)-7-azaspiro[3.5]nonan-2-yl)-3-methoxybenzamide (Compound 33)

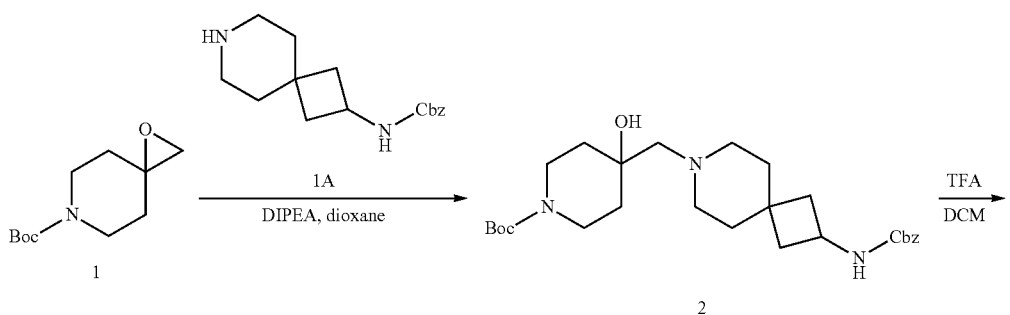

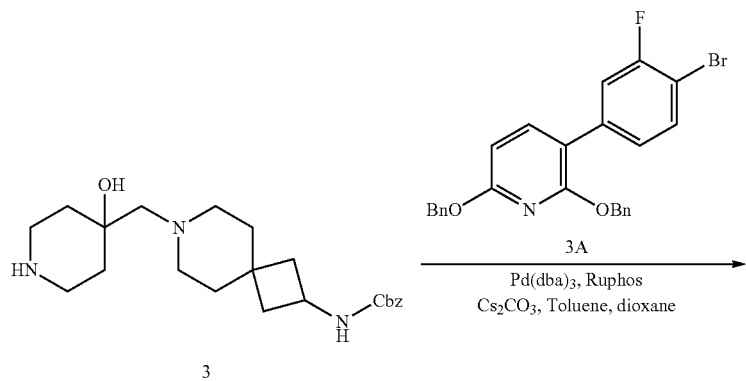

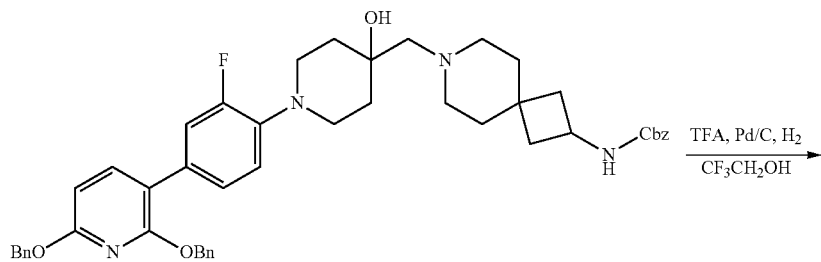

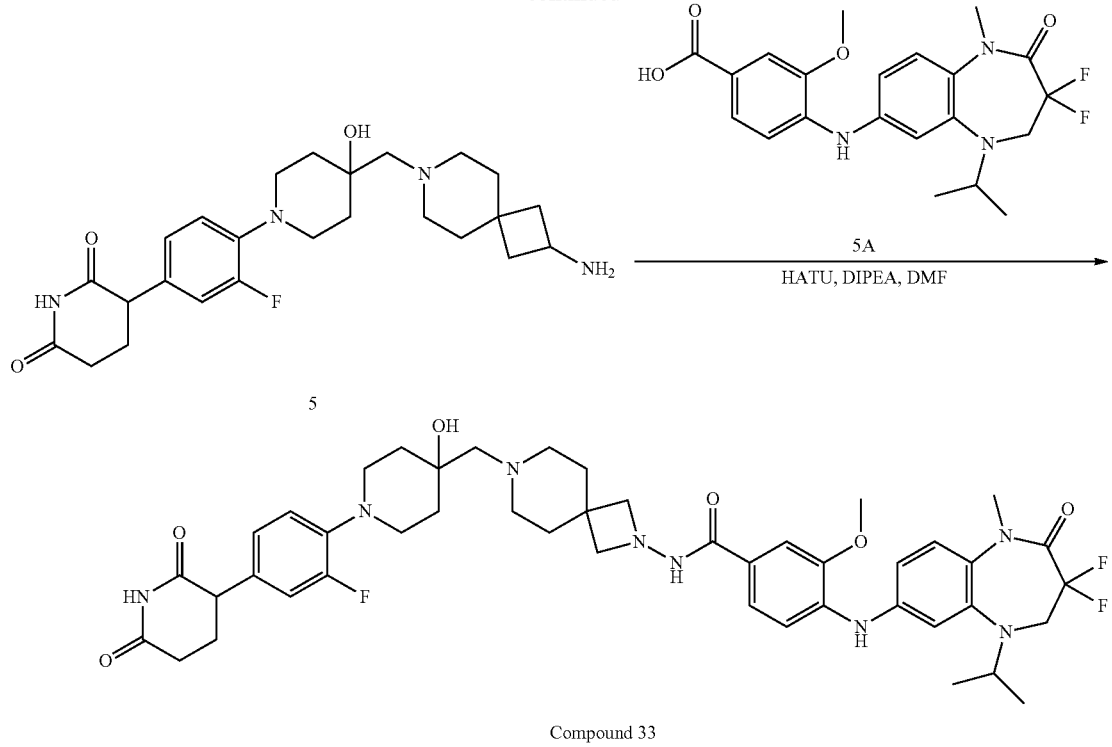

Compound 33

Step 1. Synthesis of tert-butyl 4-((2-(((benzyloxy)carbonyl)amino)-7-azaspiro[3.5]nonan-7-yl)methyl)-4-hydroxypiperidine-1-carboxylate (2)

To a solution of tert-butyl 1-oxa-6-azaspiro[2.5]octane-6-carboxylate (2.33 g, 10.93 mmol) in dioxane (25 mL) were added DIPEA (2.36 g, 18.22 mmol, 3.17 mL) and benzyl (7-azaspiro[3.5]nonan-2-yl)carbamate (1 g, 3.64 mmol). The mixture was stirred at 100° C. for 16 h. LCMS showed a main peak with desired mass. The reaction mixture was diluted with water 50 mL and extracted with EtOAc (50 mL×3), the combined organic layers were washed with 25 mL×3), dried over Na$_2$SO$_4$, filtered and concentrated under reduced pressure. The residue was purified by flash silica gel chromatography (40 g SepaFlash Silica Flash Column, Eluent of 0~90% EtOAc/Petroleum ether gradient @ 60 mL/min) to afford tert-butyl 4-((2-(((benzyloxy)carbonyl)amino)-7-azaspiro[3.5]nonan-7-yl)methyl)-4-hydroxypiperidine-1-carboxylate (800 mg, 1.33 mmol, 36.46% yield, 81% purity) as a brown solid. MS (M+H)$^+$=488.3.

Step 2. Synthesis of benzyl (7-((4-hydroxypiperidin-4-yl)methyl)-7-azaspiro[3.5]nonan-2-yl) carbamate (3)

To a solution of tert-butyl 4-((2-(((benzyloxy)carbonyl)amino)-7-azaspiro[3.5]nonan-7-yl)methyl)-4-hydroxypiperidine-1-carboxylate (700 mg, 1.44 mmol) in DCM (20 mL) was added TFA (3.08 g, 27.01 mmol, 2.00 mL). The mixture was stirred at 25° C. for 2 h. LCMS showed a peak with desired mass. The reaction mixture was concentrated to afford benzyl (7-((4-hydroxypiperidin-4-yl)methyl)-7-azaspiro[3.5]nonan-2-yl) carbamate (1 g, crude, TFA) as yellow oil. MS (M+H)$^+$=387.3.

Step 3. Synthesis of benzyl (7-((1-(4-(2,6-bis(benzyloxy)pyridin-3-yl)-2-fluorophenyl)-4-hydroxypiperidin-4-yl)methyl)-7-azaspiro[3.5]nonan-2-yl)carbamate (4)

The mixture of benzyl (7-((4-hydroxypiperidin-4-yl)methyl)-7-azaspiro[3.5]nonan-2-yl)carbamate (800 mg, crude, TFA), 2,6-bis(benzyloxy)-3-(4-bromo-3-fluorophenyl)pyridine (958.57 mg, 2.06 mmol), Pd$_2$(dba)$_3$ (189.04 mg, 206.44 μmol), Cs$_2$CO$_3$ (2.02 g, 6.19 mmol) and RuPhos (192.67 mg, 412.89 μmol) in toluene (3 mL) and dioxane (0.5 mL) was degassed and purged with N$_2$ for 3 times, and the mixture was stirred at 100° C. for 16 h under N$_2$ atmosphere. LCMS showed a peak desired mass. The reaction mixture was concentrated under reduced pressure to give a residue. The residue was purified by flash silica gel chromatography (20 g SepaFlash Silica Flash Column, Eluent of 50~70% EtOAc/Petroleum ether gradient @ 40 mL/min) to afford benzyl (7-((1-(4-(2,6-bis(benzyloxy)pyridin-3-yl)-2-fluorophenyl)-4-hydroxypiperidin-4-yl)methyl)-7-azaspiro[3.5]nonan-2-yl)carbamate (200 mg, 259.43 μmol, 12.57% yield) as yellow oil. MS (M+H)$^+$=771.5

Step 4. Synthesis of 3-(4-(4-((2-amino-7-azaspiro[3.5]nonan-7-yl)methyl)-4-hydroxypiperidin-1-yl)-3-fluorophenyl)piperidine-2,6-dione (5)

To the solution of benzyl (7-((1-(4-(2,6-bis(benzyloxy)pyridin-3-yl)-2-fluorophenyl)-4-hydroxypiperidin-4-yl)methyl)-7-azaspiro[3.5]nonan-2-yl)carbamate (140 mg, 181.60 μmol) in CF$_3$CH$_2$OH (5 mL) were added TFA (41.41 mg, 363.20 μmol, 26.89 μL) and Pd/C (14 mg, 10% purity) under N$_2$ atmosphere. The suspension was degassed and purged with H$_2$ for 3 times. The mixture was stirred under H₂ (15 Psi) at 20-25° C. for 12 h. LCMS showed a main peak with desired mass. The suspension was filtered through a pad of Celite and the filter cake was washed with CF₃CH₂OH (20 mL). The combined filtrates were concentrated to dryness to afford 3-(4-(4-((2-amino-7-azaspiro[3.5] nonan-7-yl)methyl)-4-hydroxypiperidin-1-yl)-3-fluorophenyl)piperidine-2,6-dione (100 mg, 174.64 μmol, 96.17% yield, TFA) as a yellow solid MS (M+H)⁺=459.3.

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-4-hydroxypiperidin-4-yl)methyl)-7-azaspiro[3.5]nonan-2-yl)-3-methoxybenzamide (Compound 33)

To the solution of 3-(4-(4-((2-amino-7-azaspiro[3.5] nonan-7-yl)methyl)-4-hydroxypiperidin-1-yl)-3-fluorophenyl)piperidine-2,6-dione (70 mg, 122.25 μmol, TFA) and 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (51.52 mg, 122.25 μmol) in DMF (5 mL) were added HATU (55.78 mg, 146.70 μmol) and DIPEA (47.40 mg, 366.75 μmol, 63.88 μL) and the resulting mixture was stirred at 20° C. for 1 h. LCMS showed a peak (35%) with desired mass. The mixture was poured into water (100 mL) and extracted with DCM (50 mL×3), the combined organic layers were washed with brine (50 mL), dried over Na₂SO₄, filtered and concentrated. The residue was purified by prep-HPLC (column: Unisil 3-100 C18 μLtra 150*50 mm*3 μm; mobile phase: [water (FA)-ACN]; B %: 14%-44%, 7 min) and the eluent was lyophilized to afford crude product. The crude product was re-purified by prep-HPLC (column: Waters Xbridge C18 150*50 mm*10 μm; mobile phase: [water (NH₄HCO₃)-ACN]; B %: 40%-70%, 10 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorophenyl)-4-hydroxypiperidin-4-yl)methyl)-7-azaspiro[3.5]nonan-2-yl)-3-methoxybenzamide (19 mg, 21.60 μmol, 17.67% yield, 98% purity) as a white solid. MS (M+H)⁺=862.4.

¹H NMR (400 MHz, DMSO-d₆) δ=10.82 (s, 1H), 8.42 (d, J=6.8 Hz, 1H), 8.36-8.29 (m, 1H), 8.23 (s, 1H), 7.89 (s, 1H), 7.56-7.45 (m, 2H), 7.06-6.89 (m, 3H), 4.95-4.82 (m, 1H), 4.46-4.33 (m, 1H), 4.11-4.00 (m, 3H), 3.95 (s, 3H), 3.80 (dd, J=3.0, 10.7 Hz, 1H), 3.36-3.28 (m, 5H), 3.13-2.89 (m, 4H), 2.68-2.59 (m, 1H), 2.48-2.41 (m, 3H), 2.27-2.12 (m, 5H), 2.08-1.97 (m, 1H), 1.85-1.78 (m, 2H), 1.76-1.67 (m, 2H), 1.64-1.51 (m, 6H), 1.25 (d, J=5.7 Hz, 6H).

Example 34. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorobenzyl)piperidin-4-yl)methyl)-7-azaspiro[3.5]nonan-2-yl)-3-methoxybenzamide (Compound 34)

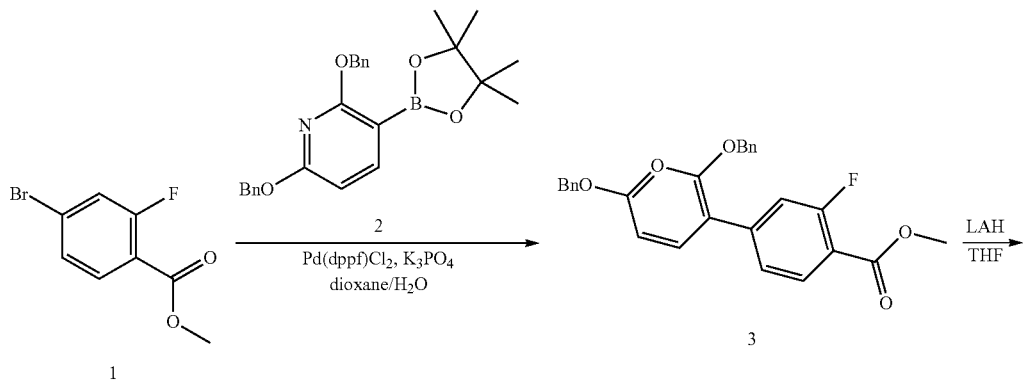

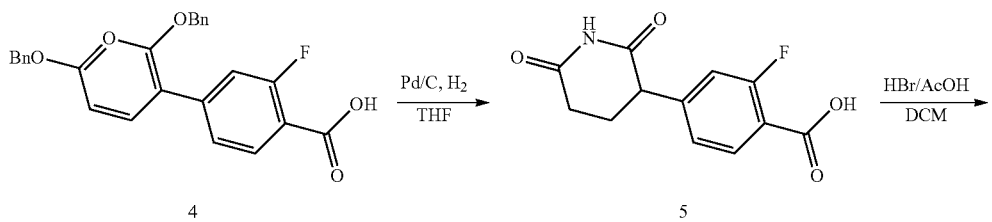

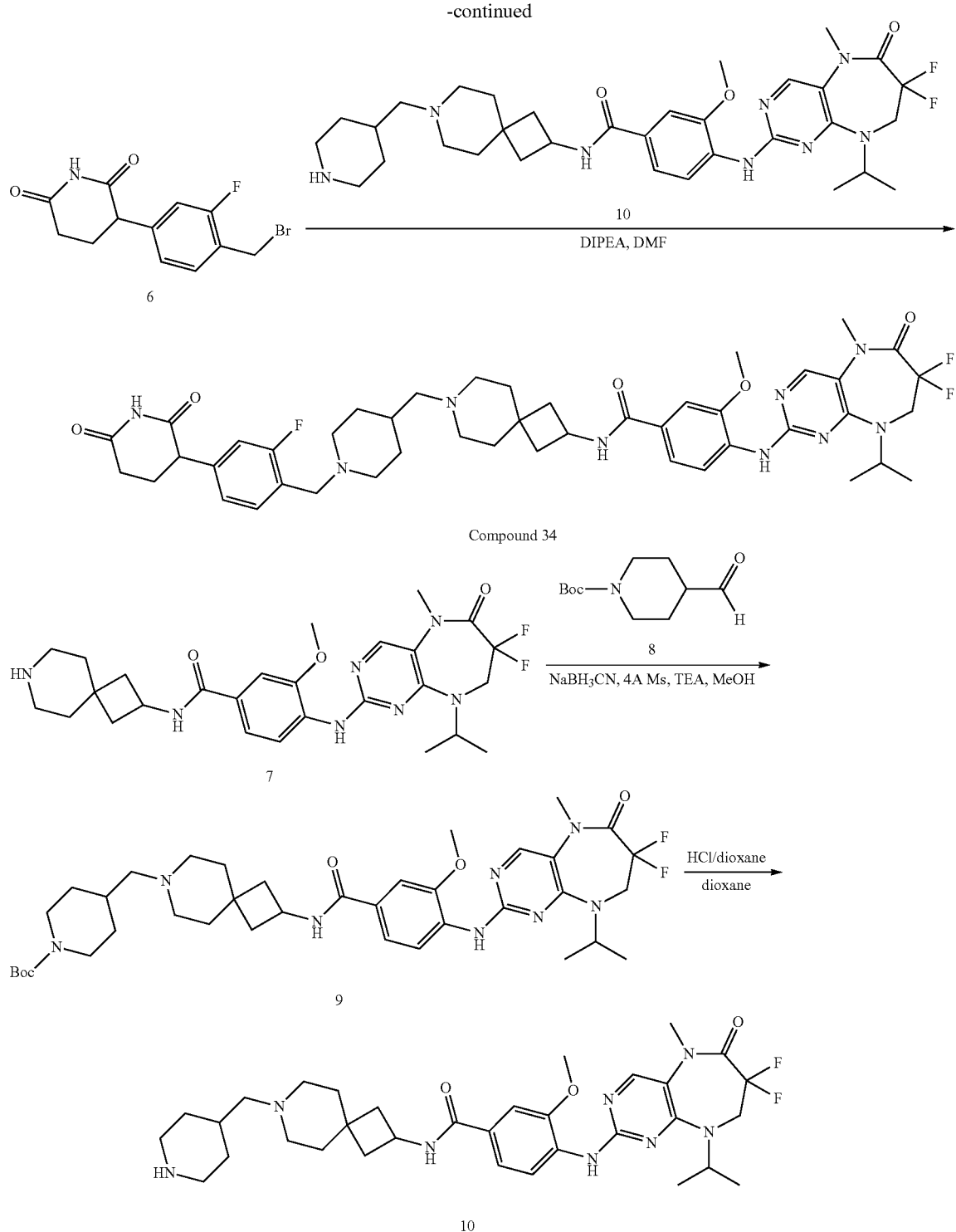

Step 1. Synthesis of methyl 4-(2,6-bis(benzyloxy) pyridin-3-yl)-2-fluorobenzoate (3)

To a solution of methyl 4-bromo-2-fluorobenzoate (3 g, 12.87 mmol) and 2,6-bis(benzyloxy)-3-(4,4,5,5-tetramethyl-1,3,2-dioxaborolan-2-yl)pyridine (5.37 g, 12.87 mmol) in dioxane (100 mL) and H$_2$O (20 mL) were added Pd(dppf)Cl$_2$ (941.98 mg, 1.29 mmol) and K$_3$PO$_4$ (8.20 g, 38.62 mmol) at 20° C. under N$_2$ and the resulting mixture was stirred at 100° C. for 12 h under N$_2$. LCMS showed starting material was consumed completely and a peak (45%) with desired mass. The reaction mixture was concentrated in vacuum. The residue was purified by flash silica gel chromatography (80 g SepaFlash Silica Flash Column, Eluent of 0~5% EtOAc/Petroleum ether gradient @ 100 mL/min) to afford methyl 4-(2,6-bis(benzyloxy)pyridin-3- yl)-2-fluorobenzoate (2.5 g, 5.47 mmol, 42.48% yield, 97% purity) as a white solid. MS (M+H)⁺=444.2

Step 2. Synthesis of (4-(2,6-bis(benzyloxy)pyridin-3-yl)-2-fluorophenyl)methanol (4)

To a suspension of LAH (427.93 mg, 11.27 mmol) in THF (20 mL) was added a solution of methyl 4-(2,6-bis(benzyloxy)pyridin-3-yl)-2-fluorobenzoate (2.5 g, 5.64 mmol) in THF (10 mL) drop-wise at 20° C. under $N_2$ atmosphere and the resulting mixture was stirred at 20° C. for 2 h. LCMS showed starting material was consumed completely and a peak (92%) with desired mass. The reaction mixture was quenched with $H_2O$ (0.45 mL), aq.NaOH (15%, 0.45 mL) and $H_2O$ (1.35 mL). The reaction mixture was dried over $Na_2SO_4$ and filtered. The filtrate was concentrated in vacuum to afford (4-(2,6-bis(benzyloxy)pyridin-3-yl)-2-fluorophenyl)methanol (2.3 g, crude) as a white solid. MS (M+H)⁺=416.3

Step 3. Synthesis of 3-(3-fluoro-4-(hydroxymethyl)phenyl)piperidine-2,6-dione (5)

To a solution of (4-(2,6-bis(benzyloxy)pyridin-3-yl)-2-fluorophenyl)methanol (2.3 g, 5.54 mmol) in THF (30 mL) was added Pd/C (1 g, 10% purity) under $N_2$ atmosphere. The suspension was degassed and purged with $H_2$ for 3 times. The mixture was stirred at 20° C. for 12 h under $H_2$ (15 Psi). LCMS showed starting material was consumed completely and a peak with desired mass. The reaction mixture was diluted with THF (100 mL) and filtered. The filtrate was concentrated in vacuum to afford 3-(3-fluoro-4-(hydroxymethyl)phenyl)piperidine-2,6-dione (1.8 g, crude) as a yellow oil. MS (M+H)⁺=238.1

Step 4. Synthesis of 3-(4-(bromomethyl)-3-fluorophenyl)piperidine-2,6-dione (6)

To a solution of 3-(3-fluoro-4-(hydroxymethyl)phenyl)piperidine-2,6-dione (0.6 g, 2.53 mmol) in DCM (6 mL) was added HBr/AcOH (2 mL, 33% purity) at 20° C. and the resulting mixture was stirred at 20° C. for 12 h. LCMS showed starting material was consumed completely and a peak with desired mass. The reaction mixture was concentrated in vacuum to afford 3-(4-(bromomethyl)-3-fluorophenyl)piperidine-2,6-dione (760 mg, crude) as a yellow oil. MS (M+H)⁺=300.2

Step 5. Synthesis of tert-butyl 4-((2-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-7-azaspiro[3.5]nonan-7-yl)methyl)piperidine-1-carboxylate (9)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (300 mg, 517.18 µmol, HCl salt) in MeOH (10 mL) were added TEA (523.33 mg, 5.17 mmol, 719.85 µL) and 4 A MS (200 mg), tert-butyl 4-formylpiperidine-1-carboxylate (165.45 mg, 775.77 µmol) at 20° C. Then NaBH₃CN (97.50 mg, 1.55 mmol) was added at 20° C. and the resulting mixture was stirred at 20° C. for 2 h. LCMS showed all starting material was consumed completely and a peak (71%) with desired mass. The reaction mixture was filtered and the filtrate was concentrated in vacuum. The residue was purified by flash silica gel chromatography (10 g SepaFlash Silica Flash Column, Eluent of 0~100% EtOAc/Petroleum ether to 0~15% Dichloromethane/Methanol gradient @ 100 mL/min) to afford tert-butyl 4-((2-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-7-azaspiro[3.5]nonan-7-yl)methyl)piperidine-1-carboxylate (352 mg, 475.11 µmol, 91.87% yield) as a white solid. MS (M+H)⁺=741.3

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-(piperidin-4-ylmethyl)-7-azaspiro[3.5]nonan-2-yl)benzamide (10)

To a solution of tert-butyl 4-((2-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-7-azaspiro[3.5]nonan-7-yl)methyl)piperidine-1-carboxylate (352 mg, 475.11 µmol) in dioxane (2 mL) was added HCl/dioxane (4 M, 9.71 mL) at 20° C. and the resulting mixture was stirred at 20° C. for 1 hr. LCMS showed starting material was consumed completely and a peak (87%) with desired mass. The reaction mixture was concentrated in vacuum to afford 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-(piperidin-4-ylmethyl)-7-azaspiro[3.5]nonan-2-yl)benzamide (322 mg, crude, HCl salt) as a white solid. MS (M+H)⁺=641.3

Step 7. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorobenzyl)piperidin-4-yl)methyl)-7-azaspiro[3.5]nonan-2-yl)-3-methoxybenzamide (Compound 34)

To a solution of 3-(4-(bromomethyl)-3-fluorophenyl)piperidine-2,6-dione (500 mg, 1.67 mmol) and 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-(piperidin-4-ylmethyl)-7-azaspiro[3.5]nonan-2-yl)benzamide (322 mg, 475.47 µmol, HCl salt) in DMF (6 mL) was added DIPEA (645.95 mg, 5.00 mmol, 870.55 µL) at 20° C. and the resulting mixture was stirred at 20° C. for 2 h. LCMS showed all starting material was consumed completely and a peak (32%) with desired mass. The reaction mixture was diluted with $H_2O$ (20 mL) and extracted with EtOAc (20 mL×3). The organic layer was washed with brine (20 mL×3), dried over $Na_2SO_4$, filtered and concentrated. The residue was purified by flash silica gel chromatography (10 g SepaFlash Silica Flash Column, Eluent of 0~100% EtOAc/Petroleum ether 0~50% Dichloromethane/EtOH gradient @100 mL/min) and re-purified by prep-HPLC (column: Phenomenex Synergi Polar-RP 100*25 mm*4 µm; mobile phase: [water (TFA)-ACN]; B %: 22%-42%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-fluorobenzyl)piperidin-4-yl)methyl)-7-azaspiro[3.5]nonan-2-yl)-3-methoxybenzamide (146.5 mg, 129.26 µmol, 7.76% yield, 96% purity, 2TFA) as a white solid. MS (M+H)⁺=860.4

¹H NMR (400 MHz, DMSO-d₆) δ=10.91 (s, 1H), 10.02-9.84 (m, 1H), 9.41-9.26 (m, 1H), 8.52 (br d, J=7.2 Hz, 1H), 8.30-8.20 (m, 1H), 8.15 (s, 1H), 7.58-7.53 (m, 1H), 7.53-7.48 (m, 1H), 7.29 (d, J=11.1 Hz, 1H), 7.22 (d, J=7.9 Hz, 1H), 4.94-4.83 (m, 1H), 4.46-4.39 (m, 1H), 4.34 (br s, 2H), 4.07 (br t, J=13.3 Hz, 2H), 3.99 (br dd, J=4.8, 12.1 Hz, 1H), 3.94 (s, 3H), 3.52-3.35 (m, 4H), 3.32 (s, 3H), 3.26-3.15 (m, 1H), 3.10-2.75 (m, 6H), 2.74-2.65 (m, 1H), 2.58-2.52 (m, 1H), 2.43-2.34 (m, 1H), 2.30-2.21 (m, 1H), 2.20-2.10 (m, 1H), 2.05 (td, J=4.1, 8.2 Hz, 1H), 2.02-1.91 (m, 4H), 1.90-1.75 (m, 4H), 1.43 (q, J=11.1 Hz, 2H), 1.24 (d, J=6.7 Hz, 6H).
Example 35. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methylphenyl)piperidin-4-yl)methyl)-7-azaspiro[3.5]nonan-2-yl)-3-methoxybenzamide (Compound 35)
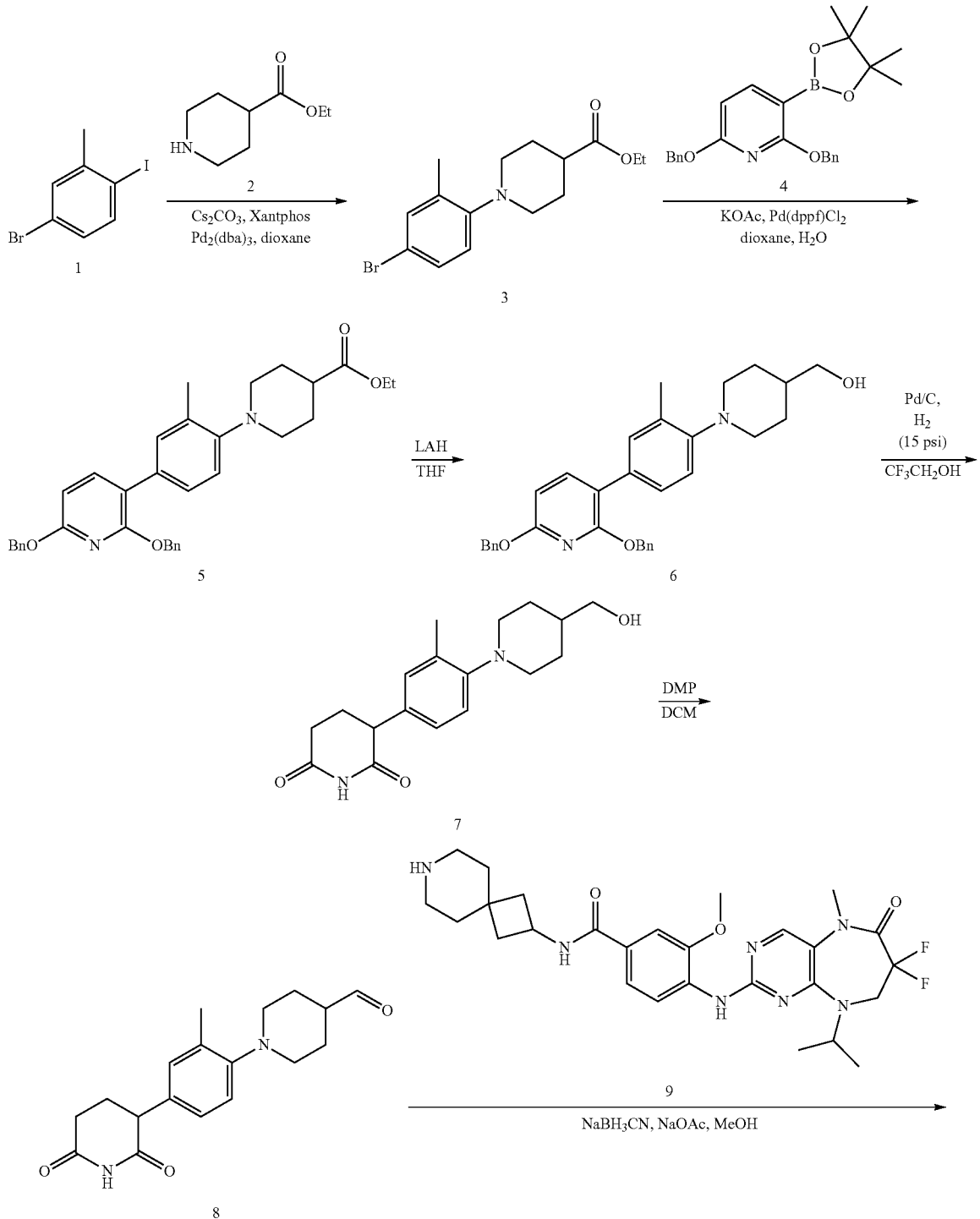

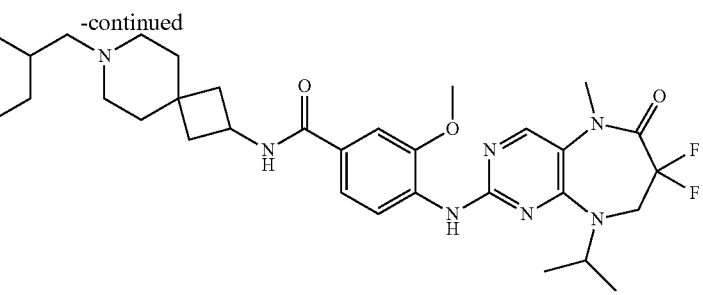

Compound 35

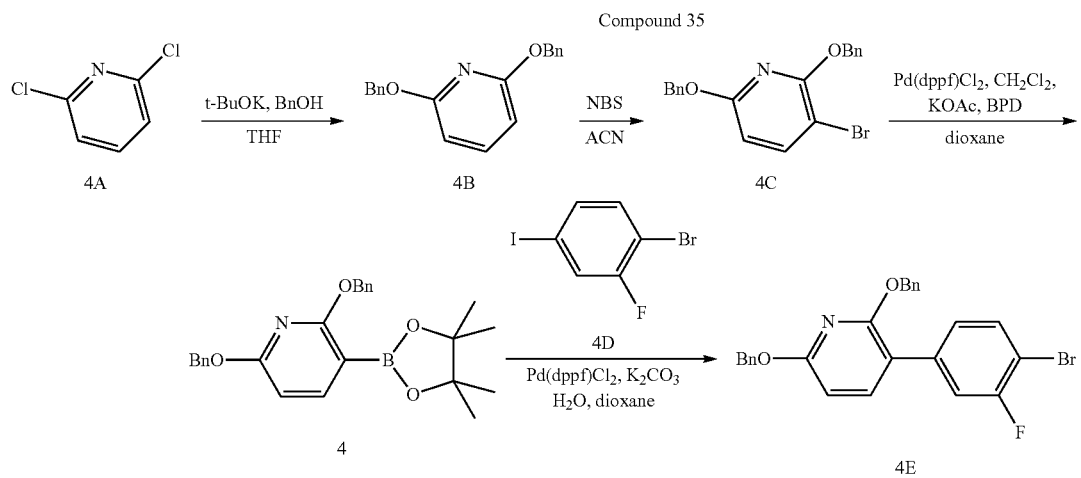

Step 1. Synthesis of ethyl 1-(4-bromo-2-methylphenyl)piperidine-4-carboxylate (3)

A mixture of 4-bromo-1-iodo-2-methylbenzene (25.8 g, 86.89 mmol), ethyl piperidine-4-carboxylate (13.66 g, 86.89 mmol, 13.39 mL), Xantphos (1.76 g, 3.04 mmol), $Pd_2(dba)_3$ (2.39 g, 2.61 mmol) and $Cs_2CO_3$ (42.47 g, 130.33 mmol) in dioxane (300 mL) was stirred at 80° C. for 16 hours under $N_2$ atmosphere. TLC ($SiO_2$, Petroleum ether:EtOAc=20:1) indicated 4-bromo-1-iodo-2-methylbenzene remained and one major new spot with larger polarity was detected. The mixture was filtered and the filter cake was washed with EtOAc (500 mL), the filtrate was concentrated in vacuum. The residue was purified by flash silica gel chromatography (330 g SepaFlash Silica Flash Column, Eluent of 0~3% EtOAc/Petroleum ether gradient @ 100 mL/min), the eluent was concentrated in vacuum to afford ethyl 1-(4-bromo-2-methylphenyl)piperidine-4-carboxylate (2.2 g, 6.74 mmol, 7.76% yield) as a light yellow oil. MS $(M+H)^+=326.0$.

Step 2. Synthesis of 2,6-bis(benzyloxy)pyridine (4B)

To a solution of t-BuOK (576.26 g, 5.14 mol) in THF (2 L) was added dropwise phenylmethanol (222.14 g, 2.05 mol, 213.59 mL) at 0° C., the mixture was stirred at 0° C. for 0.5 hours, then 2,6-dichloropyridine (152 g, 1.03 mol) was added at 0° C. over a period of 0.5 hours. The resulting mixture was stirred at 75° C. for 65 hours. LCMS showed 20% of 2-(benzyloxy)-6-chloropyridine and a peak (68%) with desired mass. The mixture was poured into $H_2O$ (1 L) and extracted with EtOAc (1 L×3). The combined organic layers were concentrated in vacuum to remove most of the THF, the suspension was diluted with EtOAc (1.5 L) and the mixture was washed with $H_2O$ (1 L×2). The organic layer was concentrated in vacuum. The residue was triturated with petroleum ether (300 mL) at 15° C. for 10 minutes, the suspension was filtered and the filter cake was collected and dried to afford 2,6-bis(benzyloxy)pyridine (243.3 g, 804.21 mmol, 78.30% yield) as a white solid. MS $(M+H)^+=292.1$.

Step 3. Synthesis of 2,6-bis(benzyloxy)-3-bromopyridine (4C)

To a solution of 2,6-bis(benzyloxy)pyridine (234.3 g, 804.21 mmol) in ACN (1.5 L) was added NBS (143.14 g, 804.21 mmol), the mixture was stirred at 80° C. for 3 hours. LCMS showed trace starting material remained and a peak (83%) with desired mass. The reaction mixture was concentrated in vacuum to remove most of the solvent. The residue was diluted with EtOAc (1.5 L) and washed with $H_2O$ (1.2 L×2). The organic layer was dried over $Na_2SO_4$, filtered and concentrated in vacuum. The residue was triturated with petroleum ether (300 mL) at 15° C. for 10 minutes, the suspension was filtered and the filter cake was collected and dried to afford 2,6-bis(benzyloxy)-3-bromopyridine (295.3 g, 797.59 mmol, 99.18% yield) as a white solid. MS $(M+H)^+=370.0, 372.0$.

Step 4. Synthesis of 2,6-bis(benzyloxy)-3-(4,4,5,5-tetramethyl-1,3,2-dioxaborolan-2-yl)pyridine (4)

To a solution of 2,6-bis(benzyloxy)-3-bromopyridine (100 g, 270.10 mmol) in dioxane (1.5 L) were added BPD (102.88 g, 405.14 mmol), KOAc (53.02 g, 540.19 mmol) and $Pd(dppf)Cl_2 \cdot CH_2Cl_2$ (4.41 g, 5.40 mmol), the mixture was stirred at 100° C. for 36 hours under $N_2$ atmosphere. LCMS showed 2,6-bis(benzyloxy)-3-bromopyridine consumed completely and a peak (38%) with desired mass.

The reaction mixture was filtered and the filter cake was washed with EtOAc (700 mL). The combined filtrates was concentrated in vacuum. The residue was purified by column chromatography (SiO$_2$, Petroleum ether/EtOAc=50/1 to 10/1) to afford 2,6-bis(benzyloxy)-3-(4,4,5,5-tetramethyl-1,3,2-dioxaborolan-2-yl)pyridine (80.2 g, 192.19 mmol, 71.15% yield) as a light green solid. MS (M+H)$^+$=418.0.

Step 5. Synthesis of 2,6-bis(benzyloxy)-3-(4-bromo-3-fluorophenyl)pyridine (4E)

To a solution of 1-bromo-2-fluoro-4-iodobenzene (7 g, 23.26 mmol) and 2,6-bis(benzyloxy)-3-(4,4,5,5-tetramethyl-1,3,2-dioxaborolan-2-yl)pyridine (10 g, 23.96 mmol) in dioxane (80 mL) and H$_2$O (15 mL) were added K$_2$CO$_3$ (6.43 g, 46.53 mmol) and Pd(dppf)Cl$_2$ (1.70 g, 2.33 mmol) under N$_2$ atmosphere, the mixture was stirred at 100° C. for 16 hours under N$_2$ atmosphere. LCMS showed the 1-bromo-2-fluoro-4-iodobenzene was consumed completely and a peak (43%) with desired mass. The reaction mixture was concentrated in vacuum to remove most of the dioxane. The residue was diluted with H$_2$O (250 mL) and extracted with EtOAc (150 mL×4). The combined organic layers were dried over Na$_2$SO$_4$, filtered and concentrated. The residue was purified by flash silica gel chromatography (330 g SepaFlash Silica Flash Column, Eluent of 0~4% EtOAc/Petroleum ether gradient @ 100 mL/min) to afford 2,6-bis(benzyloxy)-3-(4-bromo-3-fluorophenyl)pyridine (6.14 g, 13.22 mmol, 56.84% yield) as a light yellow solid. MS (M+H)$^+$=464.0.

Step 6. Synthesis of ethyl 1-(4-(2,6-bis(benzyloxy)pyridin-3-yl)-2-methylphenyl)piperidine-4-carboxylate (5)

To a solution of ethyl 1-(4-bromo-2-methylphenyl)piperidine-4-carboxylate (2.2 g, 6.74 mmol), 2,6-bis(benzyloxy)-3-(4,4,5,5-tetramethyl-1,3,2-dioxaborolan-2-yl)pyridine (3.94 g, 9.44 mmol) and KOAc (1.99 g, 20.23 mmol) in dioxane (60 mL) and H$_2$O (10 mL) was added Pd(dppf)Cl$_2$ (246.72 mg, 337.19 µmol), the mixture was stirred at 100° C. for 16 hours under N$_2$ atmosphere. LCMS showed ethyl 1-(4-bromo-2-methylphenyl)piperidine-4-carboxylate was consumed completely and a peak (40%) with desired mass. The mixture was combined with another batch (460 mg scale) and concentrated in vacuum to remove most of the solvent. The residue was purified by flash silica gel chromatography (40 g SepaFlash Silica Flash Column, Eluent of 0~4% EtOAc/Petroleum ether gradient @ 100 mL/min) to afford ethyl 1-(4-(2,6-bis(benzyloxy)pyridin-3-yl)-2-methylphenyl)piperidine-4-carboxylate (1.95 g, 3.63 mmol, 53.88% yield) as a light brown oil. MS (M+H)$^+$=537.3.

Step 7. Synthesis of (1-(4-(2,6-bis(benzyloxy)pyridin-3-yl)-2-methylphenyl)piperidin-4-yl)methanol (6)

To a suspension of LAH (141.45 mg, 3.73 mmol) in THF (10 mL) was added a solution of ethyl 1-(4-(2,6-bis(benzyloxy)pyridin-3-yl)-2-methylphenyl)piperidine-4-carboxylate (1 g, 1.86 mmol) in THF (10 mL) dropwise at 0° C., the mixture was stirred at 15° C. for 4 hours. LCMS showed trace starting material remained and a peak (87%) with desired mass. The reaction mixture was diluted with THF (20 mL) at 20° C. and the resulting mixture was quenched with H$_2$O (0.2 mL), NaOH solution (15% aq, 0.2 mL) and H$_2$O (0.6 mL), the suspension was dried over Na$_2$SO$_4$, filtered and concentrated in vacuum to afford (1-(4-(2,6-bis(benzyloxy)pyridin-3-yl)-2-methylphenyl)piperidin-4-yl)methanol (890 mg) as a white solid. MS (M+H)$^+$=495.2.

Step 8. Synthesis of 3-(4-(4-(hydroxymethyl)piperidin-1-yl)-3-methylphenyl)piperidine-2,6-dione (7)

To a solution of (1-(4-(2,6-bis(benzyloxy)pyridin-3-yl)-2-methylphenyl)piperidin-4-yl)methanol (890 mg, 1.80 mmol) in CF$_3$CH$_2$OH (20 mL) was added Pd/C (100 mg, 10% purity) under N$_2$ atmosphere, the suspension was degassed and purged with H$_2$ for several times, the mixture was stirred at 15° C. for 32 hours under H$_2$ (15 psi). LCMS showed the starting material was consumed completely. The reaction mixture was filtered, the filter cake was washed with CF$_3$CH$_2$OH (60 mL). The combined filtrates was concentrated in vacuum to afford 3-(4-(4-(hydroxymethyl)piperidin-1-yl)-3-methylphenyl)piperidine-2,6-dione (625 mg) as a green solid. MS (M+H)$^+$=317.2.

Step 9. Synthesis of 1-(4-(2,6-dioxopiperidin-3-yl)-2-methylphenyl)piperidine-4-carbaldehyde (8)

To a solution of 3-(4-(4-(hydroxymethyl)piperidin-1-yl)-3-methylphenyl)piperidine-2,6-dione (420 mg, 1.33 mmol) in DCM (10 mL) was added DMP (731.94 mg, 1.73 mmol, 534.26 µL) at 0° C., the mixture was stirred at 15° C. for 2 hours. LCMS showed trace starting material remained and desired mass. The reaction mixture was filtered. The filter cake was washed with DCM (20 mL). The combined filtrates was concentrated in vacuum at 20° C. to afford 1-(4-(2,6-dioxopiperidin-3-yl)-2-methylphenyl)piperidine-4-carbaldehyde (410 mg) as a brown oil, which was used directly. MS (M+H)$^+$=315.2.

Step 10. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methylphenyl)piperidin-4-yl)methyl)-7-azaspiro[3.5]nonan-2-yl)-3-methoxybenzamide (Compound 35)

To mixture of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (302.60 mg, 521.67 µmol, HCl salt) and NaOAc (320.96 mg, 3.91 mmol) in MeOH (10 mL) was added 1-(4-(2,6-dioxopiperidin-3-yl)-2-methylphenyl)piperidine-4-carbaldehyde (410 mg, 1.30 mmol), the mixture was stirred at 15° C. for 30 minutes, then NaBH$_3$CN (245.87 mg, 3.91 mmol) was added and the resulting mixture was stirred at 15° C. for 16 hours. LCMS showed 1-(4-(2,6-dioxopiperidin-3-yl)-2-methylphenyl)piperidine-4-carbaldehyde was consumed completely and a peak (52%) with desired mass. The reaction mixture was combined with another batch (200 mg scale) and diluted with H$_2$O (50 mL), then extracted with EtOAc (50 mL×4). The combined organic layers were dried over Na$_2$SO$_4$, filtered and concentrated in vacuum. The residue was purified by prep-HPLC (column: Phenomenex luna C18 150×25 mm×10 µm; mobile phase: [water (FA)-ACN]; B %: 13%-43%, 10 min), two batches of the eluents were freeze-dried to afford two batches of the crude product. Batch 1: LCMS indicated the crude product 1, the crude product 1 was purified by prep-HPLC (column: Waters Xbridge 150×25 mm×5 m; mobile phase: [water (NH$_4$HCO$_3$)-ACN]; B %: 52%-82%, 8 min) to afford the eluent 1. Batch 2: LCMS indicated the crude product 2, the crude product 2 was purified by prep-HPLC (column: Waters Xbridge 150×25 mm×5 μm; mobile phase: [water (NH₄HCO₃)-ACN]; B %: 46%-76%, 8 min) to afford the eluent 2, two batches of the eluents were combined and freeze-dried to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methylphenyl)piperidin-4-yl)methyl)-7-azaspiro[3.5]nonan-2-yl)-3-methoxybenzamide (50.8 mg, 57.92 μmol, 4.44% yield) as an off-white solid. MS (M+H)⁺=842.1.

¹H NMR (400 MHz, CDCl₃) δ=8.47 (d, J=8.3 Hz, 1H), 8.04 (s, 1H), 8.01-7.91 (m, 1H), 7.74 (s, 1H), 7.45 (d, J=1.7 Hz, 1H), 7.25 (br d, J=1.8 Hz, 1H), 7.03-6.94 (m, 3H), 6.18 (br d, J=7.2 Hz, 1H), 5.05-4.91 (m, 1H), 4.64-4.48 (m, 1H), 3.98 (s, 3H), 3.94-3.83 (m, 2H), 3.72 (dd, J=5.3, 9.1 Hz, 1H), 3.41 (s, 3H), 3.11 (br d, J=12.0 Hz, 2H), 2.77-2.69 (m, 1H), 2.67-2.56 (m, 3H), 2.48-2.31 (m, 5H), 2.30-2.25 (m, 5H), 2.25-2.16 (m, 3H), 1.83 (br d, J=12.2 Hz, 2H), 1.71 (br d, J=7.7 Hz, 4H), 1.67 (br s, 3H), 1.41-1.30 (m, 8H).

Example 36. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methoxyphenyl)piperidin-4-yl)methyl)-7-azaspiro[3.5]nonan-2-yl)-3-methoxybenzamide (Compound 36)

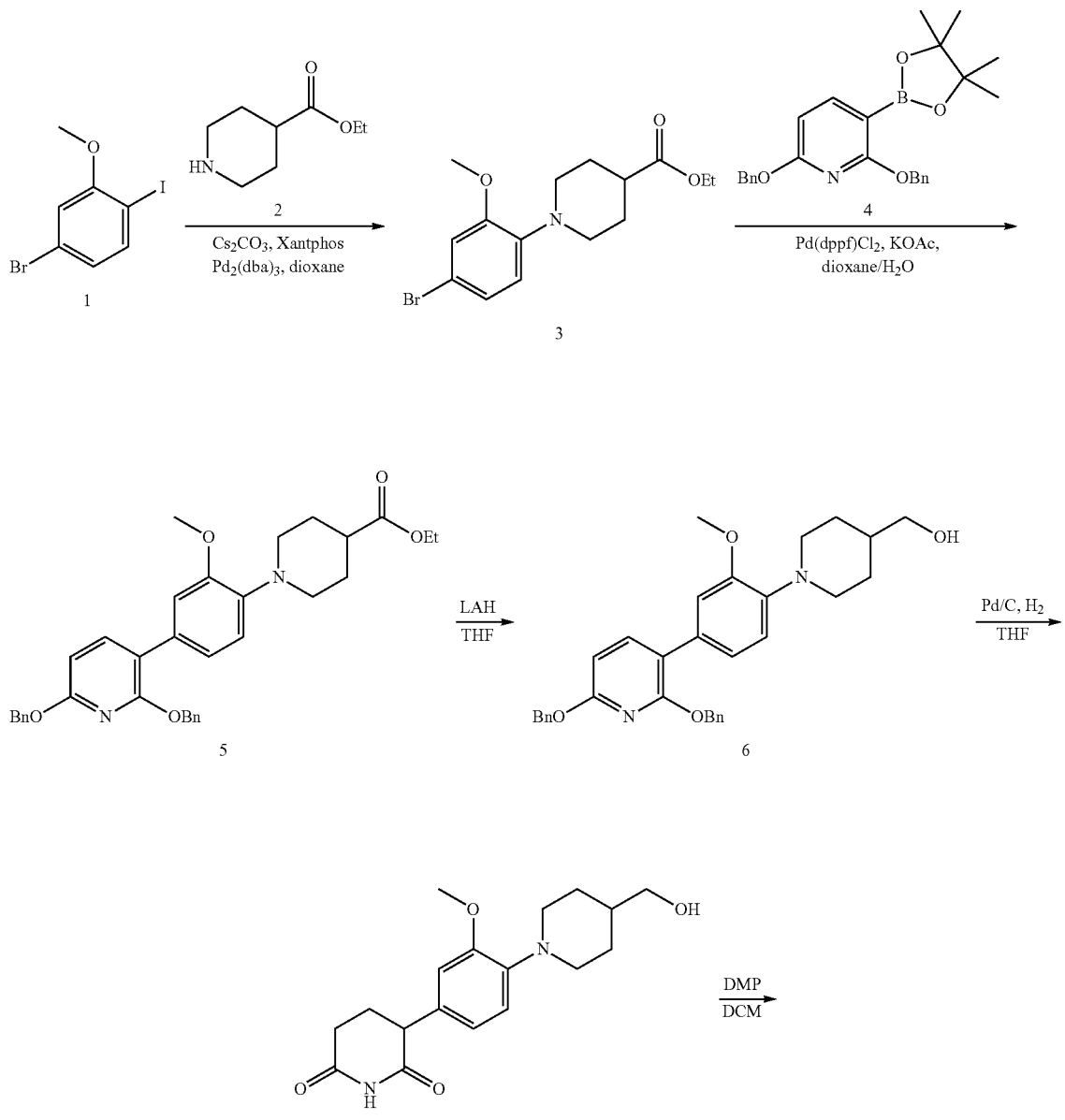

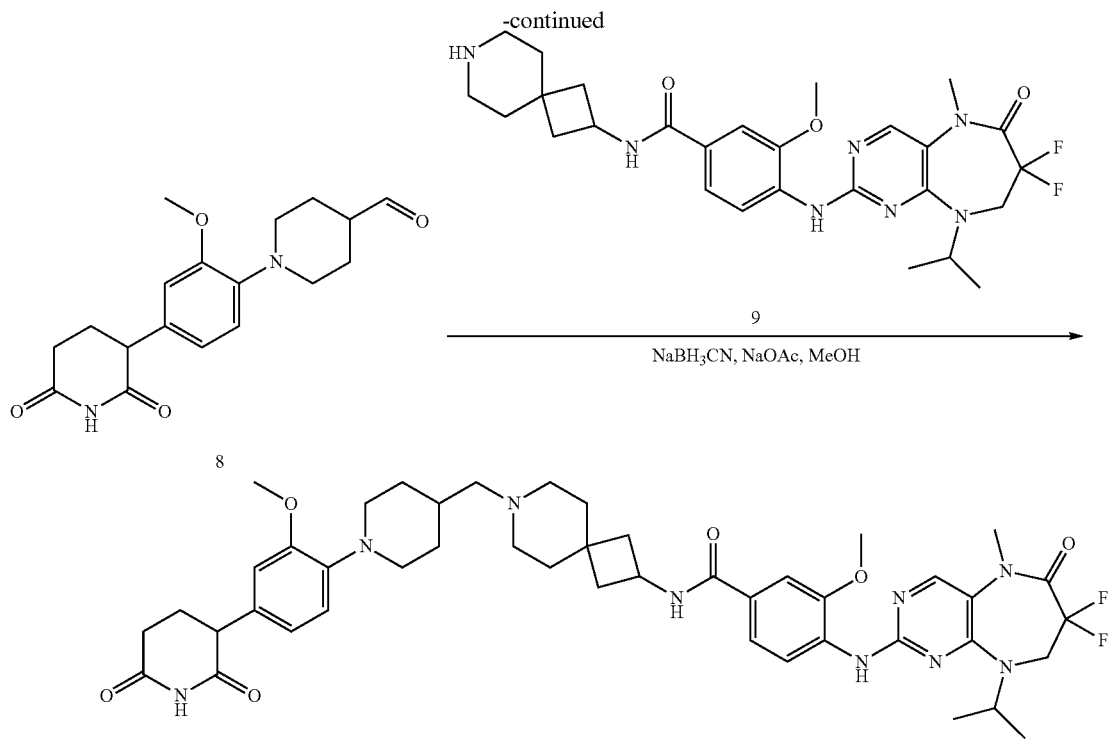

Compound 36

Step 1. Synthesis of ethyl 1-(4-bromo-2-methoxyphenyl)piperidine-4-carboxylate (3)

To a solution of 4-bromo-1-iodo-2-methoxybenzene (10 g, 31.96 mmol) and ethyl piperidine-4-carboxylate (5.02 g, 31.96 mmol, 4.93 mL) in dioxane (100 mL) was added $Pd_2(dba)_3$ (877.88 mg, 958.68 μmol) Xantphos (647.16 mg, 1.12 mmol) and $Cs_2CO_3$ (15.62 g, 47.93 mmol) at 20° C. under $N_2$ and the resulting mixture was stirred at 80° C. for 16 h. LCMS showed a peak (18%) with desired mass. The reaction mixture was filtered and the filtrate was concentrated in vacuum. The residue was purified by flash silica gel chromatography (80 g SepaFlash Silica Flash Column, Eluent of 0~5% EtOAc/Petroleum ether gradient @ 100 mL/min) to afford ethyl 1-(4-bromo-2-methoxyphenyl)piperidine-4-carboxylate (3.1 g, 9.06 mmol, 28.35% yield) as a yellow oil. MS $(M+H)^+$=342.1, 344.1

Step 2. Synthesis of ethyl 1-(4-(2,6-bis(benzyloxy)pyridin-3-yl)-2-methoxyphenyl)piperidine-4-carboxylate (5)

To a solution of ethyl 1-(4-bromo-2-methoxyphenyl)piperidine-4-carboxylate (3.1 g, 9.06 mmol) and 2,6-bis(benzyloxy)-3-(4,4,5,5-tetramethyl-1,3,2-dioxaborolan-2-yl)pyridine (5.29 g, 12.68 mmol) in dioxane (60 mL) and $H_2O$ (10 mL) were added KOAc (2.67 g, 27.17 mmol) and $Pd(dppf)Cl_2$ (331.40 mg, 452.92 μmol) at 20° C. under $N_2$ and the resulting mixture was stirred at 100° C. for 12 h under $N_2$. LCMS showed all starting material was consumed completely and a peak (45%) with desired mass. The reaction mixture was diluted with $H_2O$ (60 mL) and extracted with EtOAc (60 mL×3). The organic layer was dried over $Na_2SO_4$, filtered and concentrated. The residue was purified by flash silica gel chromatography (40 g SepaFlash Silica Flash Column, Eluent of 0~33% EtOAc/Petroleum ether gradient @ 100 mL/min) to afford ethyl 1-(4-(2,6-bis(benzyloxy)pyridin-3-yl)-2-methoxyphenyl)piperidine-4-carboxylate (1.9 g, 3.44 mmol, 37.98% yield) as a yellow solid. MS $(M+H)^+$=553.3

Step 3. Synthesis of (1-(4-(2,6-bis(benzyloxy)pyridin-3-yl)-2-methoxyphenyl)piperidin-4-yl)methanol (6)

To a suspension of LAH (260.97 mg, 6.88 mmol) in THF (20 mL) at 20° C. under $N_2$ atmosphere was added a solution of ethyl 1-(4-(2,6-bis(benzyloxy)pyridin-3-yl)-2-methoxyphenyl)piperidine-4-carboxylate (1.9 g, 3.44 mmol) in THF (10 mL) drop-wise at 20° C. and the resulting mixture was stirred at 20° C. for 2 h. TLC ($SiO_2$, Petroleum ether: EtOAc=2:1) indicated starting material was consumed completely and one new spot was formed. The reaction mixture was diluted with THF (50 mL). Then the resulting mixture was quenched with $H_2O$ (0.3 mL), NaOH (15% aq, 0.3 mL) and $H_2O$ (0.9 mL) and filtered. The filtrate was dried over $Na_2SO_4$ and concentrated to afford (1-(4-(2,6-bis(benzyloxy)pyridin-3-yl)-2-methoxyphenyl)piperidin-4-yl)methanol (1.7 g, crude) as a light yellow solid. MS $(M+H)^+$=511.6

Step 4. Synthesis of 3-(4-(4-(hydroxymethyl)piperidin-1-yl)-3-methoxyphenyl)piperidine-2,6-dione (7)

To a solution of (1-(4-(2,6-bis(benzyloxy)pyridin-3-yl)-2-methoxyphenyl)piperidin-4-yl)methanol (1.7 g, 3.33 mmol) in THF (20 mL) was added Pd/C (0.8 g, 10% purity) under $N_2$ atmosphere. The suspension was degassed and purged with $H_2$ for 3 times. The mixture was stirred at 20° C. for 12 h under $H_2$ (15 Psi). LCMS showed starting material was consumed completely and a peak with desired mass. The reaction mixture was diluted with THF (60 mL) and filtered. The filtrate was concentrated in vacuum to afford 3-(4-(4-(hydroxymethyl)piperidin-1-yl)-3-methoxyphenyl)piperidine-2,6-dione (1.2 g, crude) as a white solid. MS (M+H)$^+$=333.3

Step 5. Synthesis of 1-(4-(2,6-dioxopiperidin-3-yl)-2-methoxyphenyl)piperidine-4-carbaldehyde (8)

To a solution of 3-(4-(4-(hydroxymethyl)piperidin-1-yl)-3-methoxyphenyl)piperidine-2,6-dione (300 mg, 902.55 μmol) in DCM (10 mL) was added DMP (574.21 mg, 1.35 mmol, 419.13 μL) at 20° C. and the resulting mixture was stirred at 20° C. for 1 h. LCMS showed starting material was consumed completely and a peak (77%) with mass of hydrate. The reaction mixture was concentrated in vacuum to afford 1-(4-(2,6-dioxopiperidin-3-yl)-2-methoxyphenyl)piperidine-4-carbaldehyde (300 mg, crude) as a purple oil. MS (M+H)$^+$=349.2

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methoxyphenyl)piperidin-4-yl)methyl)-7-azaspiro[3.5]nonan-2-yl)-3-methoxybenzamide (Compound 36)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (379.25 mg, 653.80 μmol, HCl salt) in MeOH (10 mL) was added NaOAc (201.13 mg, 2.45 mmol). Then 1-(4-(2,6-dioxopiperidin-3-yl)-2-methoxyphenyl)piperidine-4-carbaldehyde (270 mg, 817.25 μmol) was added followed by NaBH$_3$CN (154.07 mg, 2.45 mmol) at 20° C. and the reaction mixture was stirred at 20° C. for 12 h. LCMS showed 1-(4-(2,6-dioxopiperidin-3-yl)-2-methoxyphenyl)piperidine-4-carbaldehyde was consumed completely and a peak with desired mass. The reaction mixture was diluted with H$_2$O (15 mL) and extracted with EtOAc (15 mL×3). The organic layer was dried over Na$_2$SO$_4$, filtered and concentrated. The residue was purified by flash silica gel chromatography (10 g SepaFlash Silica Flash Column, Eluent of 0~100% EtOAc/Petroleum ether to 0~20% Dichloromethane/Methanol gradient @ 100 mL/min) followed by prep-HPLC (column: 3_Phenomenex Luna C18 75*30 mm*3 μm; mobile phase: [water (TFA)-ACN]; B %: 16%-36%, 9 min) and the eluent was lyophilized to afford pure product B and impure product C. The impure product C was re-purified by prep-HPLC (column: 3_Phenomenex Luna C18 75*30 mm*3 μm; mobile phase: [water (TFA)-ACN]; B %: 15%-35%, 9 min) and the eluent was lyophilized to afford product D. The product B and the product D was combined and lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-2-methoxyphenyl)piperidin-4-yl)methyl)-7-azaspiro[3.5]nonan-2-yl)-3-methoxybenzamide (24.1 mg, 23.31 μmol, 2.85% yield, 94% purity, TFA) as an off-white solid. MS (M+H)$^+$=858.4

$^1$H NMR (400 MHz, DMSO-d$_6$) δ=10.82 (s, 1H), 9.04-8.91 (m, 1H), 8.51 (br d, J=7.1 Hz, 1H), 8.29-8.14 (m, 2H), 7.55-7.47 (m, 2H), 7.10-6.97 (m, 1H), 6.91 (br s, 1H), 6.79 (br d, J=7.8 Hz, 1H), 4.89 (td, J=6.7, 13.4 Hz, 1H), 4.47-4.40 (m, 1H), 4.30-3.95 (m, 2H), 3.94 (s, 3H), 3.83-3.79 (m, 4H), 3.43 (br d, J=7.6 Hz, 4H), 3.32 (s, 3H), 3.06 (br s, 2H), 3.01-2.92 (m, 1H), 2.90-2.77 (m, 2H), 2.65-2.61 (m, 1H), 2.44-2.34 (m, 2H), 2.31-2.11 (m, 3H), 2.06-1.94 (m, 4H), 1.91-1.75 (m, 6H), 1.56-1.40 (m, 2H), 1.24 (d, J=6.6 Hz, 6H).

Example 37. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-3-methoxyphenyl)piperidin-4-yl)methyl)-7-azaspiro[3.5]nonan-2-yl)-3-methoxybenzamide (Compound 37)

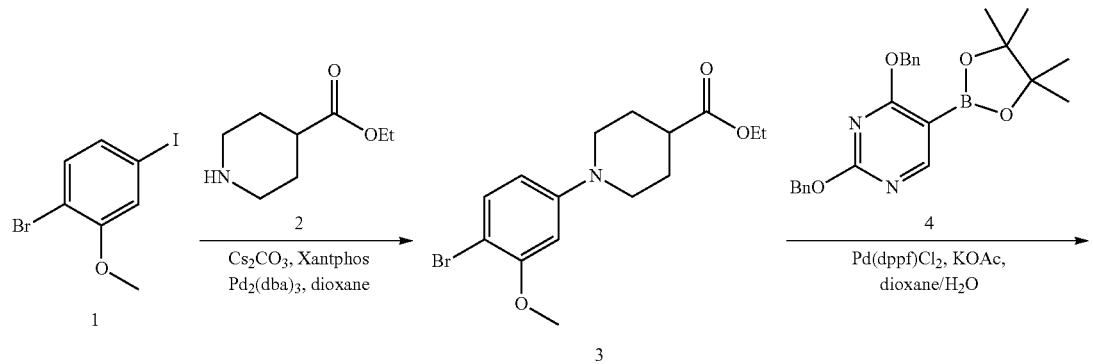

193
194
-continued
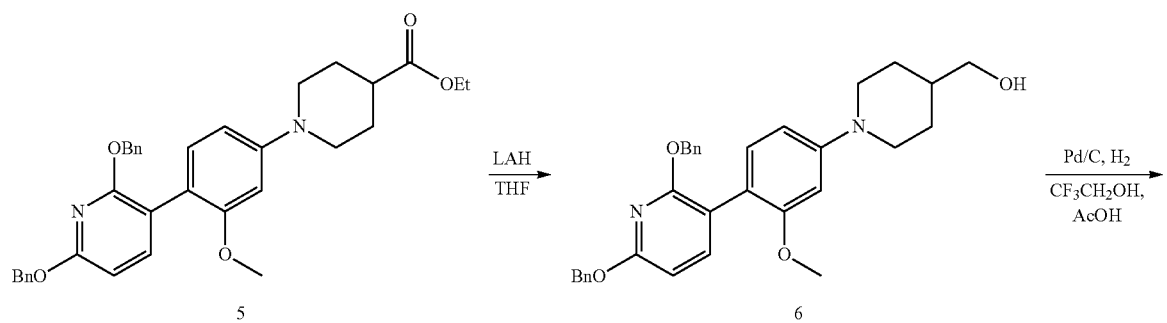
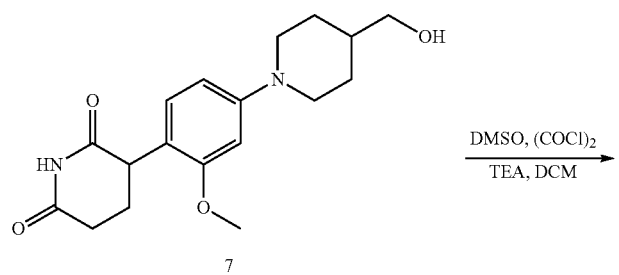
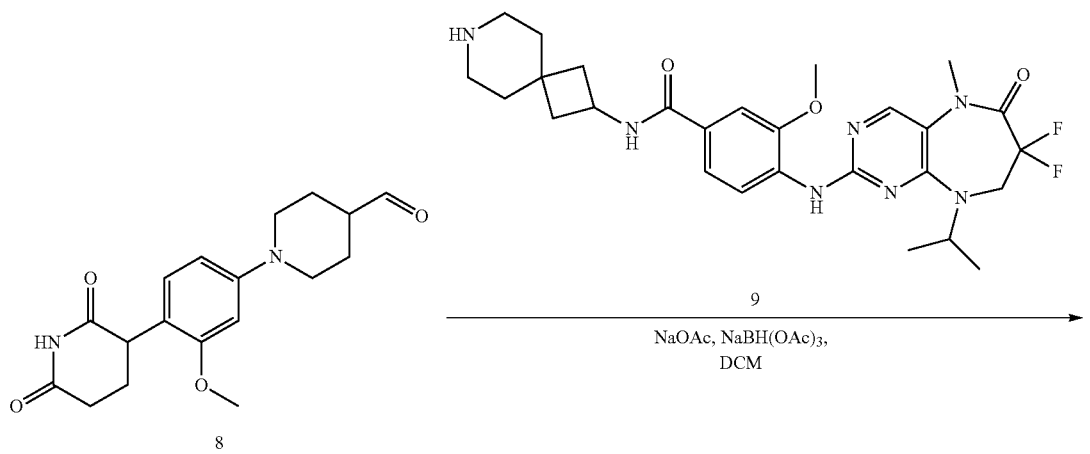
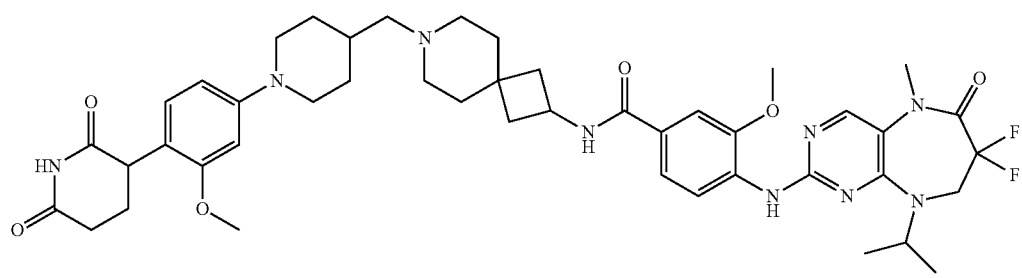
Compound 37

Step 1. Synthesis of ethyl 1-(4-bromo-3-methoxyphenyl)piperidine-4-carboxylate (3)

To a solution of 1-bromo-4-iodo-2-methoxybenzene (3 g, 9.59 mmol) and ethyl piperidine-4-carboxylate (1.51 g, 9.59 mmol, 1.48 mL) in toluene (50 mL) were added $Cs_2CO_3$ (9.37 g, 28.76 mmol), $Pd_2(dba)_3$ (175.58 mg, 191.74 µmol) and Xantphos (166.41 mg, 287.60 µmol) and the mixture was stirred at 100° C. for 14 h under $N_2$. LCMS showed a peak (93%) with desired mass. The reaction mixture was filtered and concentrated under reduced pressure. The residue was purified by flash silica gel chromatography (40 g SepaFlash Silica Flash Column, Eluent of 0~30% EtOAc/Petroleum ether gradient @ 80 mL/min) to afford ethyl 1-(4-bromo-3-methoxyphenyl)piperidine-4-carboxylate (1.4 g, 4.09 mmol, 42.67% yield) as yellow oil. MS $(M+H)^+=342.2$ Step 2. Synthesis of ethyl 1-(4-(2,6-bis(benzyloxy)pyridin-3-yl)-3-methoxyphenyl)piperidine-4-carboxylate (5)

To the solution of ethyl 1-(4-bromo-3-methoxyphenyl)piperidine-4-carboxylate (1.4 g, 4.09 mmol) and 2,6-bis(benzyloxy)-3-(4,4,5,5-tetramethyl-1,3,2-dioxaborolan-2-yl)pyridine (2.22 g, 5.32 mmol) in dioxane (50 mL) and $H_2O$ (10 mL) was added $K_3PO_4$ (2.61 g, 12.27 mmol) and $Pd(dppf)Cl_2$ (299.33 mg, 409.08 µmol) and the resulting mixture was stirred at 90° C. for 12 h. LCMS showed a peak (65%) with desired mass, the mixture was concentrated. The residue was purified by flash silica gel chromatography (40 g SepaFlash Silica Flash Column, Eluent of 0~10% EtOAc/Petroleum ether gradient @ 100 mL/min) to afford ethyl 1-(4-(2,6-bis(benzyloxy)pyridin-3-yl)-3-methoxyphenyl)piperidine-4-carboxylate (1.5 g, 2.71 mmol, 66.35% yield, 100% purity) as a white solid. MS $(M+H)^+=553.3$ Step 3. Synthesis of (1-(4-(2,6-bis(benzyloxy)pyridin-3-yl)-3-methoxyphenyl)piperidin-4-yl) methanol (6)

To the suspension of LAH (0.2 g, 5.27 mmol) in THF (30 mL) was added ethyl 1-(4-(2,6-bis(benzyloxy)pyridin-3-yl)-3-methoxyphenyl)piperidine-4-carboxylate (1.5 g, 2.71 mmol) in THF (10 mL) at 20° C. and the resulting mixture was stirred at 20° C. for 2 h. LCMS showed a peak (91%) with desired mass. The reaction mixture was quenched with $H_2O$ (0.2 mL), NaOH solution (15%, 0.2 mL) and $H_2O$ (0.6 mL) at 0° C., then the mixture was filtered and the filtrate was concentrated under reduced pressured to afford (1-(4-(2,6-bis(benzyloxy)pyridin-3-yl)-3-methoxyphenyl)piperidin-4-yl) methanol (1.3 g, 2.55 mmol, 93.80% yield) as a yellow solid. MS $(M+H)^+=511.3$ Step 4. Synthesis of 3-(4-(4-(hydroxymethyl)piperidin-1-yl)-2-methoxyphenyl)piperidine-2,6-dione (7)

To a solution of (1-(4-(2,6-bis(benzyloxy)pyridin-3-yl)-3-methoxyphenyl)piperidin-4-yl) methanol (500 mg, 979.20 µmol) in $CF_3CH_2OH$ (10 mL) was added AcOH (58.80 mg, 979.20 µmol, 56.00 µL) and Pd/C (50 mg, 10% purity) under $N_2$ atmosphere and the mixture was stirred at 20-25° C. for 12 h under $H_2$ atmosphere (15 Psi). LCMS showed a peak with desired mass. The suspension was filtered through a pad of Celite and the filter cake was washed with $CF_3CH_2OH$ (20 mL), the combined filtrates were concentrated to afford 3-(4-(4-(hydroxymethyl)piperidin-1-yl)-2-methoxyphenyl)piperidine-2,6-dione (0.4 g, crude) as a yellow solid. MS $(M+H)^+=333.2$.

Step 5. Synthesis of 1-(4-(2,6-dioxopiperidin-3-yl)-3-methoxyphenyl)piperidine-4-carbaldehyde (8)

To a solution of DMSO (47.01 mg, 601.70 µmol, 47.01 µL) in DCM (1 mL) was added a solution of $(COCl)_2$ (57.28 mg, 451.27 µmol, 39.50 µL) in DCM (1 mL) drop-wise at −70° C. The mixture was stirred at 70° C. for 10 mins. Then a solution of 3-(4-(4-(hydroxymethyl)piperidin-1-yl)-2-methoxyphenyl)piperidine-2,6-dione (100 mg, 300.85 µmol) in DCM (2 mL) was added drop-wise at −70° C. The mixture was stirred at −70° C. for 20 mins. Then TEA (152.21 mg, 1.50 mmol, 209.37 µL) was added drop-wise at −70° C. The resulting mixture was stirred at 20° C. for 10 mins. TLC (Petroleum ether/EtOAc=1/1) showed that 3-(4-(4-(hydroxymethyl)piperidin-1-yl)-2-methoxyphenyl)piperidine-2,6-dione was consumed completely and new spot formed, the mixture was filtered and the filtrate was concentrated under reduced pressure to afford 1-(4-(2,6-dioxopiperidin-3-yl)-3-methoxyphenyl)piperidine-4-carbaldehyde (100 mg, crude) as yellow oil.

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-3-methoxyphenyl)piperidin-4-yl)methyl)-7-azaspiro[3.5]nonan-2-yl)-3-methoxybenzamide (Compound 37)

To the solution of 1-(4-(2,6-dioxopiperidin-3-yl)-3-methoxyphenyl)piperidine-4-carbaldehyde (100 mg, 302.68 µmol) and 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(7-azaspiro[3.5]nonan-2-yl)benzamide (105.35 mg, 181.61 µmol, HCl) in DCM (3 mL) was added NaOAc (37.25 mg, 454.03 µmol) and $NaBH(OAc)_3$ (192.45 mg, 908.05 µmol) and the resulting mixture was stirred at 20° C. for 12 h. LCMS showed a peak (53%) with desired mass, the mixture was poured into water (20 mL) and extracted with DCM (10 mL×3), the combined organic layer was washed with brine (20 mL), dried over $Na_2SO_4$, filtered and concentrated. The residue was purified by prep-HPLC (column: Unisil 3-100 C18 Ultra 150*50 mm*3 µm; mobile phase: [water (FA)-ACN]; B %: 13%-43%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(2,6-dioxopiperidin-3-yl)-3-methoxyphenyl)piperidin-4-yl)methyl)-7-azaspiro[3.5]nonan-2-yl)-3-methoxybenzamide (25.8 mg, 28.27 µmol, 9.34% yield, 92% purity) as a white solid. MS $(M+H)^+=858.5$.

$^1$H NMR (400 MHz, DMSO-$d_6$) δ=10.68 (s, 1H), 8.43 (d, J=7.2 Hz, 1H), 8.34-8.29 (m, 1H), 8.24-8.20 (m, 1H), 7.89 (s, 1H), 7.53-7.49 (m, 2H), 6.91 (d, J=8.6 Hz, 1H), 6.53 (d, J=2.0 Hz, 1H), 6.48-6.42 (m, 1H), 4.94-4.85 (m, 1H), 4.46-4.37 (m, 1H), 4.05 (t, J=13.5 Hz, 2H), 3.95 (s, 3H), 3.80-3.76 (m, 1H), 3.72 (s, 3H), 3.70-3.66 (m, 2H), 3.33-3.31 (m, 3H), 2.67-2.60 (m, 3H), 2.45-2.39 (m, 2H), 2.32-2.22 (m, 3H), 2.19-2.13 (m, 5H), 1.87-1.76 (m, 5H), 1.63-1.54 (m, 5H), 1.26-1.18 (m, 8H).

Example 38. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(1-(4-(2,6-dioxopiperidin-3-yl)-2-fluorophenyl)pyrrolidin-3-yl)piperazin-1-yl)-3-methoxybenzamide (Compound 38)

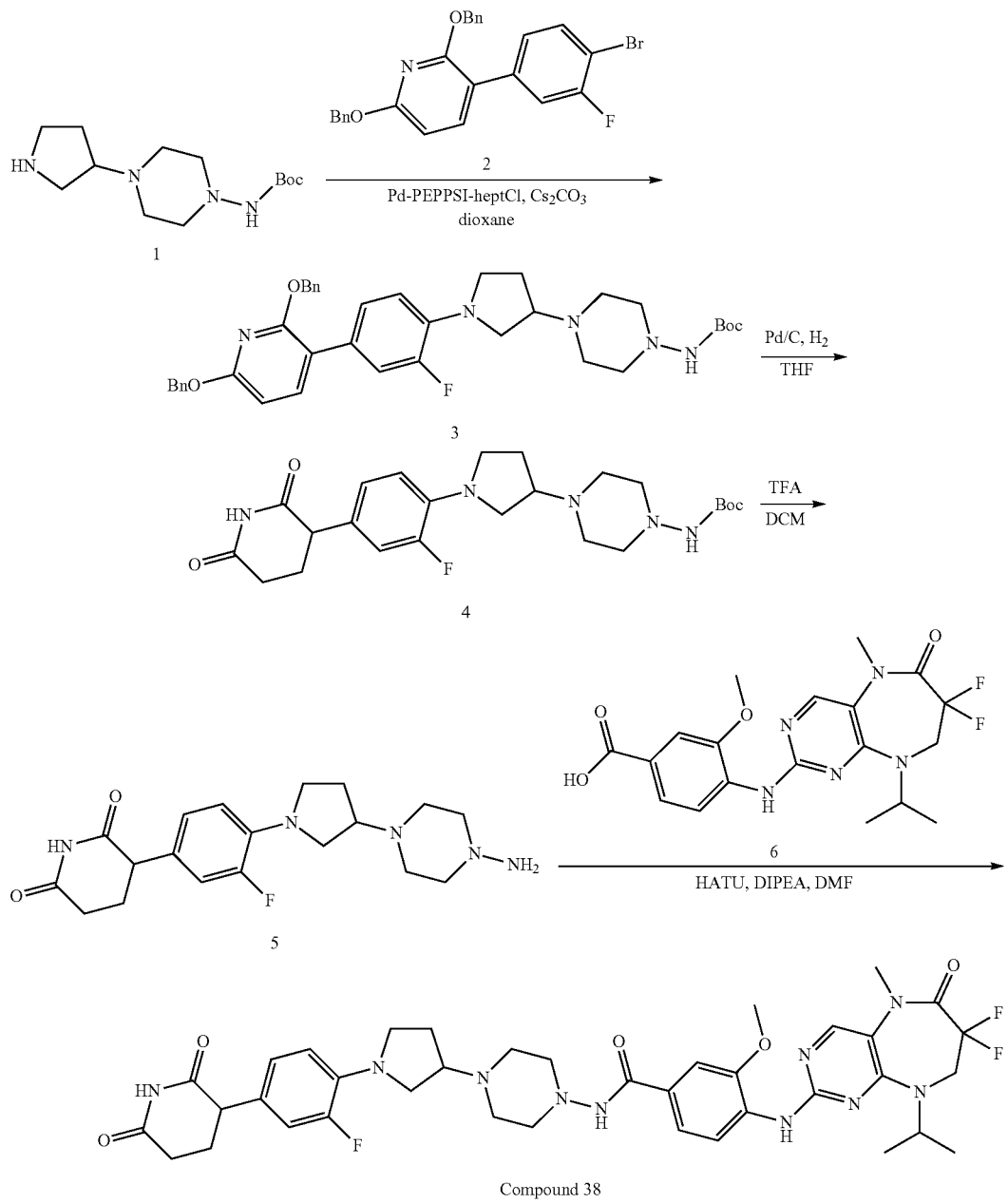

Compound 38

Step 1. Synthesis of tert-butyl (4-(1-(4-(2,6-bis(benzyloxy)pyridin-3-yl)-2-fluorophenyl)pyrrolidin-3-yl)piperazin-1-yl)carbamate (3)

To a solution of 2,6-bis(benzyloxy)-3-(4-bromo-3-fluorophenyl)pyridine (250 mg, 538.42 µmol) and tert-butyl (4-(pyrrolidin-3-yl)piperazin-1-yl)carbamate (174.69 mg, 646.10 µmol) in dioxane (5 mL) were added Pd-PEPPSI-heptCl (26.19 mg, 26.92 µmol) and $Cs_2CO_3$ (526.28 mg, 1.62 mmol) at 20° C. under $N_2$ atmosphere and the resulting mixture was stirred at 100° C. for 12 h under $N_2$ atmosphere. LCMS showed starting material was consumed completely and a peak (32%) with desired mass. The reaction mixture was concentrated in vacuum. The residue was purified by flash silica gel chromatography (10 g SepaFlash Silica Flash Column, Eluent of 0~100% EtOAc/Petroleum ether gradient @ 100 mL/min) to afford tert-butyl (4-(1-(4-(2,6-bis(benzyloxy)pyridin-3-yl)-2-fluorophenyl)pyrrolidin-3-yl)piperazin-1-yl)carbamate (175 mg, 262.32 μmol, 48.72% yield, 98% purity) as a colorless oil. MS (M+H)⁺=654.3

Step 2. Synthesis of tert-butyl (4-(1-(4-(2,6-dioxopiperidin-3-yl)-2-fluorophenyl)pyrrolidin-3-yl)piperazin-1-yl)carbamate (4)

To a solution of tert-butyl (4-(1-(4-(2,6-bis(benzyloxy)pyridin-3-yl)-2-fluorophenyl)pyrrolidin-3-yl)piperazin-1-yl)carbamate (175 mg, 267.67 μmol) in THF (8 mL) was added Pd/C (50 mg, 10% purity) under N₂ atmosphere. The suspension was degassed and purged with H₂ for 3 times. The mixture was stirred at 20° C. for 12 h under H₂ (15 Psi). LCMS showed starting material was consumed completely and a peak (62%) with desired mass. The reaction mixture was diluted with THF (10 mL) and filtered. The filtrate was concentrated in vacuum to afford tert-butyl (4-(1-(4-(2,6-dioxopiperidin-3-yl)-2-fluorophenyl)pyrrolidin-3-yl)piperazin-1-yl)carbamate (56 mg, 117.76 μmol, 43.99% yield) as a white solid. MS (M+H)⁺=476.2

Step 3. Synthesis of 3-(4-(3-(4-aminopiperazin-1-yl)pyrrolidin-1-yl)-3-fluorophenyl)piperidine-2,6-dione (5)

To a solution of tert-butyl (4-(1-(4-(2,6-dioxopiperidin-3-yl)-2-fluorophenyl)pyrrolidin-3-yl)piperazin-1-yl)carbamate (56 mg, 117.76 μmol) in DCM (1 mL) was added TFA (67.14 mg, 588.79 μmol, 43.59 μL) at 20° C. and the resulting mixture was stirred at 20° C. for 20 min. LCMS showed starting material was consumed completely and a peak (75%) with desired mass. The reaction mixture was concentrated in vacuum to afford 3-(4-(3-(4-aminopiperazin-1-yl)pyrrolidin-1-yl)-3-fluorophenyl)piperidine-2,6-dione (60 mg, crude, TFA) as a yellow oil. MS (M+H)⁺=376.2

Step 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(1-(4-(2,6-dioxopiperidin-3-yl)-2-fluorophenyl)pyrrolidin-3-yl)piperazin-1-yl)-3-methoxybenzamide (Compound 38)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (50 mg, 118.65 μmol) in DMF (1 mL) were added HATU (49.63 mg, 130.52 μmol) and DIPEA (30.67 mg, 237.31 μmol, 41.33 μL). The mixture was stirred at 20° C. for 10 min and a solution of 3-(4-(3-(4-aminopiperazin-1-yl)pyrrolidin-1-yl)-3-fluorophenyl)piperidine-2,6-dione (58.08 mg, 118.65 μmol, TFA salt) in DMF (1 mL) with DIPEA (46.01 mg, 355.96 μmol, 62.00 μL) was added and the resulting mixture was stirred at 20° C. for 1 h. LCMS showed starting material was consumed completely and a peak (80%) with desired mass. The reaction mixture was diluted with H₂O (12 mL) and extracted with EtOAc (12 mL×3). The organic layer was dried over Na₂SO₄, filtered and concentrated. The residue was purified by prep-HPLC (column: Phenomenex Synergi Polar-RP 100*25 mm*4 μm; mobile phase: [water (TFA)-ACN]; B %: 27%-47%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-(1-(4-(2,6-dioxopiperidin-3-yl)-2-fluorophenyl)pyrrolidin-3-yl)piperazin-1-yl)-3-methoxybenzamide (56.3 mg, 52.00 μmol, 43.83% yield, 93% purity, 2TFA) as a white solid. MS (M+H)⁺=779.4

¹H NMR (400 MHz, CD₃CN) δ=9.58 (br s, 1H), 8.70 (s, 1H), 8.27 (br s, 1H), 8.07 (br d, J=8.2 Hz, 1H), 7.93 (s, 1H), 7.47-7.36 (m, 2H), 6.98-6.89 (m, 2H), 6.80-6.72 (m, 1H), 4.96 (td, J=6.7, 13.3 Hz, 1H), 4.00 (br t, J=12.3 Hz, 2H), 3.93 (s, 3H), 3.91-3.85 (m, 1H), 3.79 (br d, J=10.1 Hz, 1H), 3.70 (dd, J=5.5, 11.1 Hz, 1H), 3.66-3.59 (m, 2H), 3.54 (br s, 2H), 3.42-3.15 (m, 10H), 2.69-2.54 (m, 2H), 2.46-2.27 (m, 2H), 2.24-2.09 (m, 2H), 1.23 (d, J=6.7 Hz, 6H).

Example 39. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(7-(4-(2,6-dioxopiperidin-3-yl)-2-fluorophenyl)-7-azaspiro[3.5]nonan-2-yl)piperidin-4-yl)-3-methoxybenzamide (Compound 39)

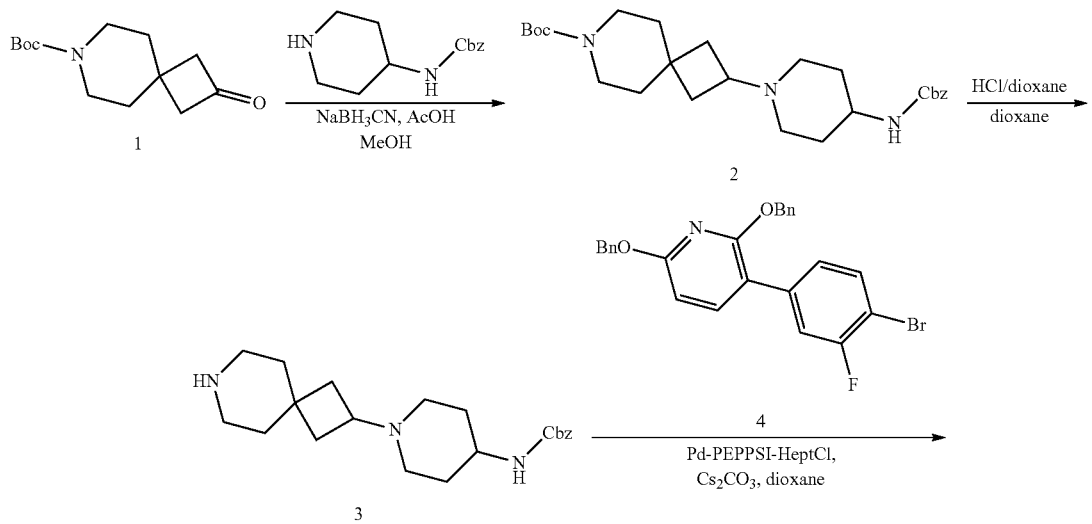

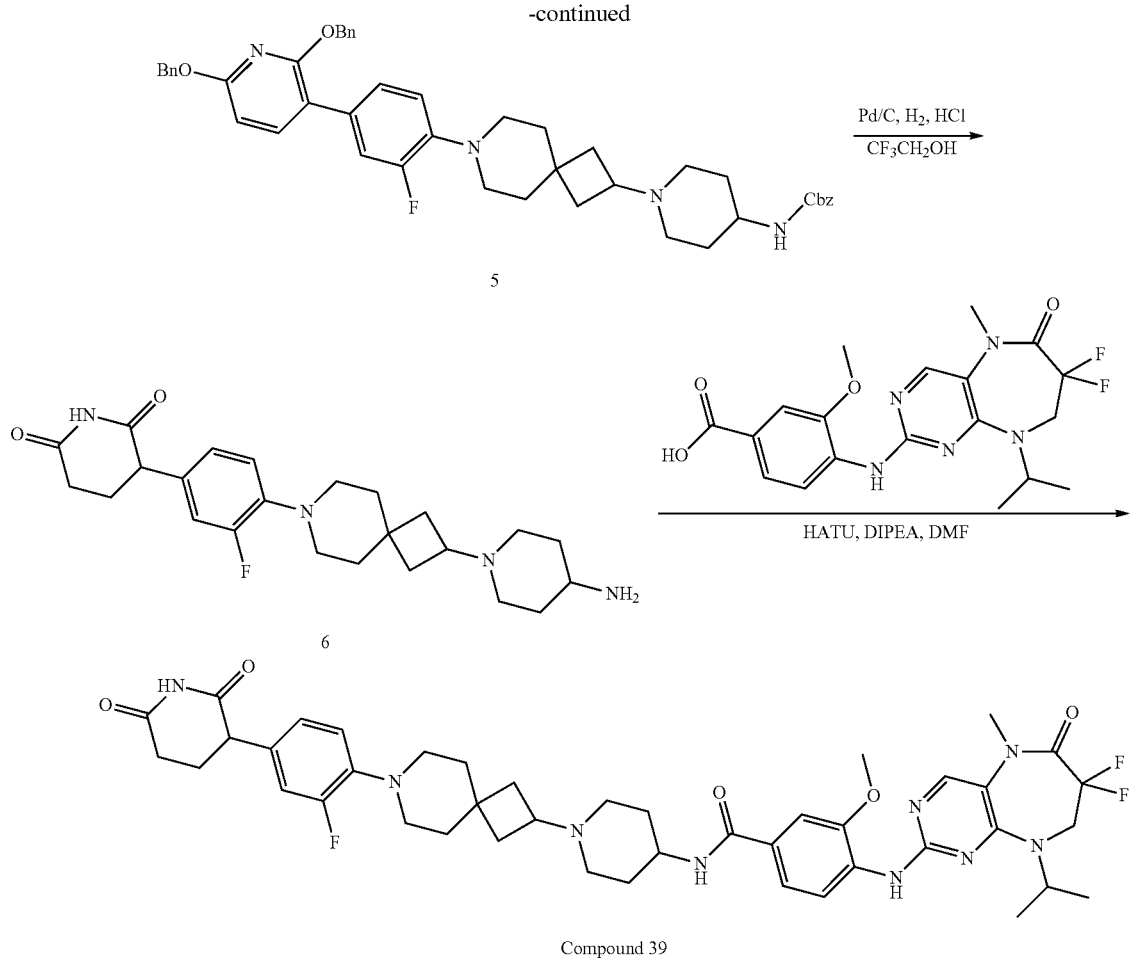

Compound 39

Step 1. Synthesis of tert-butyl 2-(4-(((benzyloxy)carbonyl)amino)piperidin-1-yl)-7-azaspiro[3.5]nonane-7-carboxylate (2)

To a solution of tert-butyl 2-oxo-7-azaspiro[3.5]nonane-7-carboxylate (600 mg, 2.51 mmol) and benzyl piperidin-4-ylcarbamate (587.42 mg, 2.51 mmol) in MeOH (8 mL) was added AcOH (150.56 mg, 2.51 mmol, 143.39 μL) at 0° C. Then NaBH$_3$CN (472.67 mg, 7.52 mmol) was added slowly at 0° C. The mixture was stirred at 20° C. for 16 hr. LCMS showed starting material was consumed completely and a peak (80%) with desired mass. The reaction mixture was concentrated in vacuum. The residue was purified by flash silica gel chromatography (25 g SepaFlash Silica Flash Column, Eluent of 0~100% EtOAc/Petroleum ether gradient @ 100 mL/min) and re-purified by prep-HPLC (column: Phenomenex luna C18 150×40 mm×15 μm; mobile phase: [water (HCl)-ACN]; B %: 22%-52%, 10 min) and the eluent was lyophilized to afford tert-butyl 2-(4-(((benzyloxy)carbonyl)amino)piperidin-1-yl)-7-azaspiro[3.5]nonane-7-carboxylate (560 mg, 1.13 mmol, 45.21% yield, 100% purity, HCl salt) as a white solid. MS (M+H)$^+$=458.3

Step 2. Synthesis of benzyl (1-(7-azaspiro[3.5]nonan-2-yl)piperidin-4-yl)carbamate (3)

To a solution of tert-butyl 2-(4-(((benzyloxy)carbonyl)amino)piperidin-1-yl)-7-azaspiro[3.5]nonane-7-carboxylate (160 mg, 349.65 μmol) in dioxane (6 mL) was added HCl/dioxane (4 M, 4.00 mL). The mixture was stirred at 20° C. for 1 hr under N$_2$ atmosphere. LCMS showed a main peak with desired mass. The reaction mixture was concentrated under reduced pressure to afford benzyl (1-(7-azaspiro[3.5]nonan-2-yl)piperidin-4-yl)carbamate (137 mg, crude, HCl salt) as a light yellow solid. MS (M+H)$^+$=358.2

Step 3. Synthesis of benzyl (1-(7-(4-(2,6-bis(benzyloxy)pyridin-3-yl)-2-fluorophenyl)-7-azaspiro[3.5]nonan-2-yl)piperidin-4-yl)carbamate (5)

A mixture of 2,6-bis(benzyloxy)-3-(4-bromo-3-fluorophenyl)pyridine (180 mg, 387.66 μmol), benzyl (1-(7-azaspiro[3.5]nonan-2-yl)piperidin-4-yl)carbamate (137 mg, 383.23 μmol, HCl salt), Pd-PEPPSI-IHeptCl (22.50 mg, 23.13 μmol) and Cs$_2$CO$_3$ (675.00 mg, 2.07 mmol) in dioxane (8 mL) was degassed and purged with N$_2$ for 3 times, then the mixture was stirred at 100° C. for 16 hr under N$_2$ atmosphere. LCMS showed a peak (27%) with the desired mass. The reaction mixture was filtered and the filtrate was concentrated under reduced pressure. The residue was purified by flash silica gel chromatography (Biotage; 10 g SepaFlash Silica Flash Column, Eluent of 0~25% Methanol:Dichloromethane gradient, 60 mL/min) to afford benzyl (1-(7-(4-(2,6-bis(benzyloxy)pyridin-3-yl)-2-fluorophenyl)-7-azaspiro[3.5]nonan-2-yl)piperidin-4-yl)carbamate (200 mg, 269.94 μmol, 69.63% yield) as a yellow solid. MS (M+H)$^+$=741.3

¹H NMR (400 MHz, DMSO-$d_6$) δ=7.81 (d, J=8.2 Hz, 1H), 7.50-7.36 (m, 17H), 7.29 (d, J=7.7 Hz, 1H), 7.12-7.03 (m, 1H), 6.59 (d, J=8.1 Hz, 1H), 5.47 (s, 2H), 5.42 (s, 2H), 5.06 (s, 2H), 3.67-3.63 (m, 1H), 3.04-2.92 (m, 4H), 2.80-2.74 (m, 1H), 2.05-1.97 (m, 2H), 1.80-1.71 (m, 6H), 1.67-1.62 (m, 2H), 1.61-1.54 (m, 2H), 1.42 (s, 4H).

Step 4. Synthesis of 3-(4-(2-(4-aminopiperidin-1-yl)-7-azaspiro[3.5]nonan-7-yl)-3-fluorophenyl)piperidine-2,6-dione (6)

To a solution of benzyl (1-(7-(4-(2,6-bis(benzyloxy)pyridin-3-yl)-2-fluorophenyl)-7-azaspiro[3.5]nonan-2-yl)piperidin-4-yl)carbamate (70 mg, 94.48 μmol) in $CF_3CH_2OH$ (5 mL) was added HCl (1 M, 105.00 μL) and Pd/C (30 mg, 10% purity) under $N_2$ atmosphere, the suspension was degassed and purged with $H_2$ 3 times. Then the mixture was stirred at 20° C. for 16 hr under $H_2$ atmosphere (15 Psi). LCMS showed reactant was consumed completely and one main peak with desired mass. The reaction mixture was filtered and the filtrate was concentrated under reduced pressure to afford 3-(4-(2-(4-aminopiperidin-1-yl)-7-azaspiro[3.5]nonan-7-yl)-3-fluorophenyl)piperidine-2,6-dione (43 mg, crude, HCl salt) as a yellow oil. MS (M+H)⁺=429.2

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(7-(4-(2,6-dioxopiperidin-3-yl)-2-fluorophenyl)-7-azaspiro[3.5]nonan-2-yl)piperidin-4-yl)-3-methoxybenzamide (Compound 39)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (40 mg, 94.92 μmol) in DMF (2 mL) were added HATU (65 mg, 170.95 μmol), DIPEA (74.20 mg, 574.11 μmol, 100 μL) and 3-(4-(2-(4-aminopiperidin-1-yl)-7-azaspiro[3.5]nonan-7-yl)-3-fluorophenyl)piperidine-2,6-dione (43 mg, 92.47 μmol, HCl salt) at 20° C. The mixture was stirred at 20° C. for 16 hr. LCMS showed a peak (69%) with desired mass. The reaction mixture was diluted with $H_2O$ (10 mL), then extracted with EtOAc (20 mL×2). The combined organic layers were washed with brine (20 mL×3), dried over $Na_2SO_4$, filtered and the filtrate was concentrated under reduced pressure. The residue was combined with another batch (45 mg scale) for purification. The combined residue was purified by flash silica gel chromatography (Biotage; 10 g SepaFlash Silica Flash Column, Eluent of 0~25% Methanol:Dichloromethane gradient, 60 mL/min) and repurified prep-HPLC (column: Phenomenex Synergi C18 150×25 mm×10 μm; mobile phase: [water (FA)-ACN]; B %: 12%-42%, 7 min; Column Temp: 30° C.), the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(1-(7-(4-(2,6-dioxopiperidin-3-yl)-2-fluorophenyl)-7-azaspiro[3.5]nonan-2-yl)piperidin-4-yl)-3-methoxybenzamide (52.0 mg, 59.03 μmol, 62.18% yield, 96% purity, 0.3FA) as a white solid. MS (M+H)⁺=832.1

¹H NMR (400 MHz, DMSO-$d_6$) δ=10.81 (s, 1H), 8.31 (d, J=8.3 Hz, 1H), 8.22 (s, 1H), 8.14-8.07 (m, 1H), 7.88 (s, 1H), 7.57-7.38 (m, 2H), 7.08-6.81 (m, 3H), 4.96-4.79 (m, 1H), 4.04 (t, J=13.5 Hz, 2H), 3.94 (s, 3H), 3.83-3.73 (m, 2H), 3.33 (s, 3H), 2.98-2.90 (m, 2H), 2.89-2.76 (m, 4H), 2.76-2.69 (m, 1H), 2.67-2.57 (m, 1H), 2.54-2.52 (m, 1H), 2.24-2.13 (m, 1H), 2.04-1.91 (m, 3H), 1.90-1.74 (m, 4H), 1.73-1.66 (m, 2H), 1.65-1.42 (m, 6H), 1.25 (d, J=6.7 Hz, 6H).

Example 40. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(7-(4-(2,6-dioxopiperidin-3-yl)-2-fluorophenyl)-2,7-diazaspiro[3.5]nonan-2-yl)piperidin-1-yl)-3-methoxybenzamide (Compound 40)

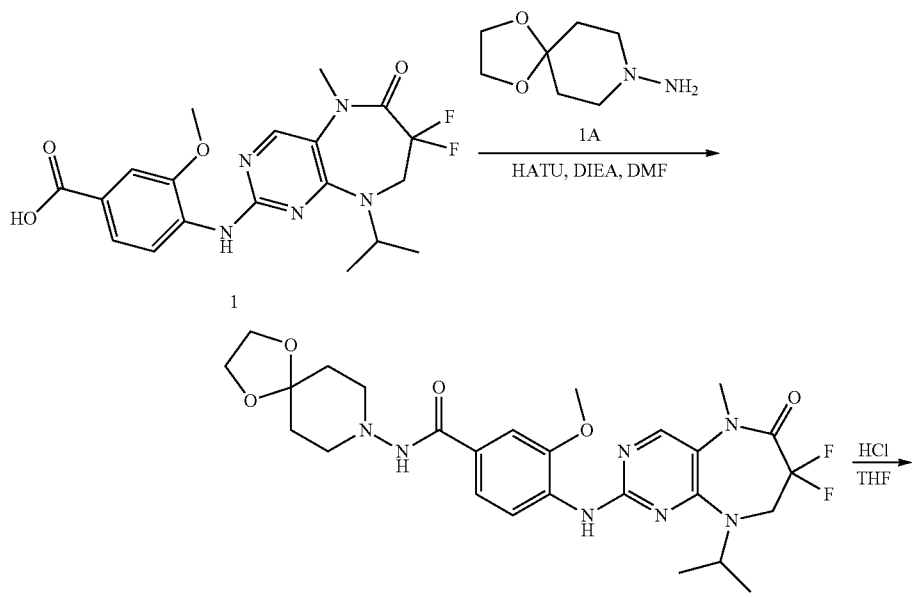

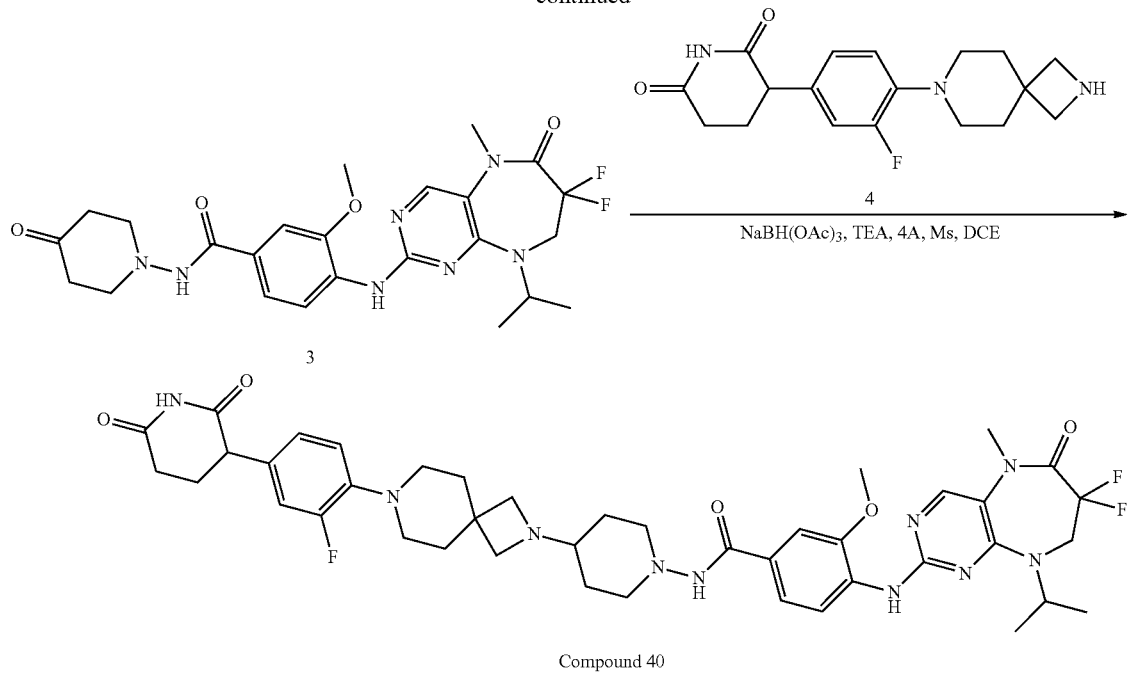

Compound 40

Step 1. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(1,4-dioxa-8-azaspiro[4.5]decan-8-yl)benzamide (2)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (5.33 g, 12.64 mmol) in DMF (15 mL) were added HATU (5.29 g, 13.91 mmol) and DIPEA (4.90 g, 37.93 mmol, 6.61 mL). The mixture was stirred at 20° C. for 10 min and a solution of 1,4-dioxa-8-azaspiro[4.5]decan-8-amine (2 g, 12.64 mmol) in DMF (15 mL) was added and the resulting mixture was stirred at 20° C. for 0.5 h. LCMS showed starting material was consumed completely and 72% of peak with desired mass. The reaction mixture was diluted with H$_2$O (100 mL) and extracted with EtOAc (100 mL×3). The organic layer was washed with brine (100 mL×3), dried over Na$_2$SO$_4$, filtered and concentrated. The residue was purified by flash silica gel chromatography (80 g SepaFlash Silica Flash Column, Eluent of 0~100% EtOAc/Petroleum ether gradient @ 100 mL/min) to afford 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(1,4-dioxa-8-azaspiro[4.5]decan-8-yl)benzamide (3.6 g, 6.28 mmol, 49.69% yield, 98% purity) as a light yellow solid. MS (M+H)$^+$=562.3

Step 2. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(4-oxopiperidin-1-yl)benzamide (3)

Two batches: to a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(1,4-dioxa-8-azaspiro[4.5]decan-8-yl)benzamide (200 mg, 356.14 μmol) in THF (2 mL) was added HCl (2 M, 890.35 μL) at 20° C. and the resulting mixture was stirred at 60° C. for 16 h. Batch 1, LCMS showed 31% of starting material remained and 61% peak with desired mass was detected. Batch 2, LCMS showed 16% of starting material remained and 80% peak with desired mass was detected. Two batches was combined and diluted with saturated Na$_2$CO$_3$ (15 mL) to this reaction mixture at 20° C. to adjust the pH=8 and extracted with EtOAc (15 mL×3). The organic layer was dried over Na$_2$SO$_4$, filtered and concentrated to afford 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(4-oxopiperidin-1-yl)benzamide (348 mg, crude) as a yellow solid. MS (M+H)$^+$=518.3

Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(7-(4-(2,6-dioxopiperidin-3-yl)-2-fluorophenyl)-2,7-diazaspiro[3.5]nonan-2-yl)piperidin-1-yl)-3-methoxybenzamide (Compound 40)

To a solution of 3-(3-fluoro-4-(2,7-diazaspiro[3.5]nonan-7-yl)phenyl)piperidine-2,6-dione (321.55 mg, 874.16 μmol, HCl) in DCE (10 mL) were added 4 A MS (700 mg), TEA (680.42 mg, 6.72 mmol, 935.93 μL) and 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(4-oxopiperidin-1-yl)benzamide (348 mg, 672.43 μmol). Then NaBH(OAc)$_3$ (427.55 mg, 2.02 mmol) was slowly added at 20° C. and the resulting mixture was stirred at 20° C. for 12 h. LCMS showed all starting material was consumed completely and 39% of peak with desired mass. The reaction mixture was filtered and the filtrate was concentrated in vacuum. The residue was purified by prep-HPLC (column: Phenomenex Synergi Polar-RP 100*25 mm*4 μm; mobile phase: [water (TFA)-ACN]; B %: 27%-47%, 7 min) followed by lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-(4-(7-(4-(2,6-dioxopiperidin- 3-yl)-2-fluorophenyl)-2,7-diazaspiro[3.5]nonan-2-yl)piperidin-1-yl)-3-methoxybenzamide (276.8 mg, 245.24 µmol, 36.47% yield, 94% purity, 2TFA) as a white solid. MS (M+H)$^+$=833.4

$^1$H NMR (400 MHz, DMSO-d$_6$) δ=10.81 (s, 1H), 10.13-10.01 (m, 1H), 9.53 (s, 1H), 8.36 (s, 1H), 8.26-8.18 (m, 1H), 7.48-7.41 (m, 2H), 7.08-6.91 (m, 3H), 4.91-4.88 (m, 1H), 4.10 (t, J=13.3 Hz, 2H), 4.06-3.95 (m, 4H), 3.93 (s, 3H), 3.84-3.77 (m, 1H), 3.36-3.23 (m, 4H), 3.10 (d, J=9.0 Hz, 2H), 3.01 (s, 2H), 2.93-2.80 (m, 4H), 2.70-2.60 (m, 1H), 2.48-2.41 (m, 2H), 2.25-2.13 (m, 1H), 2.04-1.95 (m, 4H), 1.91 (s, 2H), 1.57-1.42 (m, 2H), 1.24 (d, J=6.7 Hz, 6H)

Example 41. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1s,4s)-4-(2-(4-(4-(2,6-dioxopiperidin-3-yl)-2-fluorophenyl)piperazin-1-yl)ethyl)cyclohexyl)-3-methoxybenzamide (cis) (Compound 41)

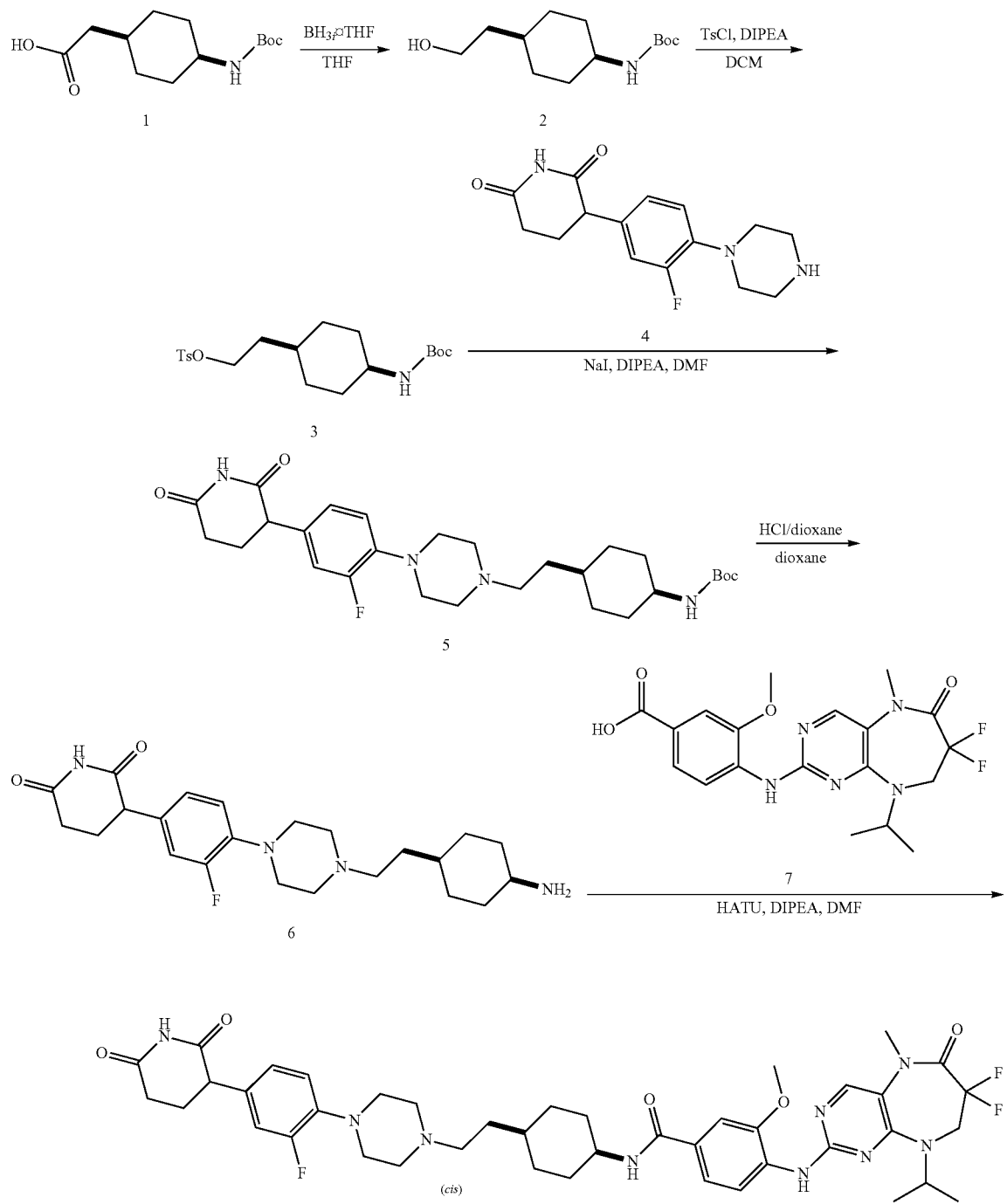

Compound 41

Step 1. Synthesis of tert-butyl ((1s,4s)-4-(2-hydroxyethyl)cyclohexyl)carbamate (cis) (2)

To a solution of 2-((1s,4s)-4-((tert-butoxycarbonyl)amino)cyclohexyl)acetic acid (cis) (0.5 g, 1.94 mmol) in THF (10 mL) was added BH$_3$·THF (1 M, 5 mL) at 0° C. and the mixture was stirred at 20° C. for 2 h. TLC (Petroleum ether:EtOAc=1:1) showed the starting material was consumed and the new spot was formed. The mixture was quenched with water (20 mL) at 0° C. and extracted with EtOAc (10 mL×3). The combined organic layer was washed with water (10 mL), dried over Na$_2$SO$_4$ and filtered. The filtrate was concentrated under reduced pressure to afford tert-butyl ((1s,4s)-4-(2-hydroxyethyl)cyclohexyl)carbamate (cis) (480 mg, crude) as yellow oil. MS (M+H)$^+$=244.4

Step 2. Synthesis of 2-((1s,4s)-4-((tert-butoxycarbonyl)amino)cyclohexyl)ethyl 4-methylbenzenesulfonate (cis) (3)

To a solution of tert-butyl ((1s,4s)-4-(2-hydroxyethyl)cyclohexyl)carbamate (cis) (480 mg, 1.97 mmol) in DCM (10 mL) were added DIPEA (764.81 mg, 5.92 mmol, 1.03 mL) and TosCl (451.27 mg, 2.37 mmol) and the mixture was stirred at 20° C. for 14 h. LCMS showed a peak (48%) with desired mass. The mixture was diluted with water (10 mL) and extracted with EtOAc (10 mL). The organic layer was washed with water (10 mL), dried over Na$_2$SO$_4$ and filtered. The filtrate was concentrated under reduced pressure. The residue was purified by flash silica gel chromatography (5 g SepaFlash Silica Flash Column, Eluent of 7~22% EtOAc/Petroleum ether gradient @ 50 mL/min) to afford 2-((1s,4s)-4-((tert-butoxycarbonyl)amino)cyclohexyl)ethyl 4-methylbenzenesulfonate (cis) (480 mg, 1.17 mmol, 59.38% yield, 97% purity) as yellow oil. MS (M−100+H)$^+$=298.1

Step 3. Synthesis of tert-butyl ((1s,4s)-4-(2-(4-(4-(2,6-dioxopiperidin-3-yl)-2-fluorophenyl)piperazin-1-yl)ethyl)cyclohexyl)carbamate (cis) (5)

To a solution of 2-((1s,4s)-4-((tert-butoxycarbonyl)amino)cyclohexyl)ethyl 4-methylbenzenesulfonate (cis) (480 mg, 1.21 mmol) and 3-(3-fluoro-4-(piperazin-1-yl)phenyl)piperidine-2,6-dione (0.3 g, 1.03 mmol) in DMF (6 mL) were added DIPEA (400.68 mg, 3.10 mmol, 540 µL) and NaI (15.44 mg, 103.00 µmol) and the mixture was stirred at 60° C. for 14 h. LCMS showed a peak (53%) with desired mass. The mixture was diluted with water (20 mL) and extracted with EtOAc (10 mL). The combined organic layer was washed with brine (10 mL×3), dried over Na$_2$SO$_4$ and filtered. The filtrate was concentrated under reduced pressure. The residue was purified by flash silica gel chromatography (5 g SepaFlash Silica Flash Column, Eluent of 70~90% EtOAc/Petroleum ether gradient @ 50 mL/min) to afford tert-butyl ((1s,4s)-4-(2-(4-(4-(2,6-dioxopiperidin-3-yl)-2-fluorophenyl)piperazin-1-yl)ethyl)cyclohexyl)carbamate (cis) (0.2 g, 329.05 µmol, 31.95% yield, 85% purity) as a yellow solid. MS (M+H)$^+$=517.5

Step 4. Synthesis of 3-(4-(4-(2-((1s,4s)-4-aminocyclohexyl)ethyl)piperazin-1-yl)-3-fluorophenyl)piperidine-2,6-dione (cis) (6)

To a solution of tert-butyl ((1s,4s)-4-(2-(4-(4-(2,6-dioxopiperidin-3-yl)-2-fluorophenyl)piperazin-1-yl)ethyl)cyclohexyl)carbamate (cis) (0.15 g, 246.78 µmol, 85% purity) in dioxane (2 mL) was added HCl/dioxane (4 M, 5 mL) and the mixture was stirred at 20° C. for 0.5 h. LCMS showed the starting material was consumed and desired mass. The mixture was concentrated under reduced pressure to afford 3-(4-(4-(2-((1s,4s)-4-aminocyclohexyl)ethyl)piperazin-1-yl)-3-fluorophenyl)piperidine-2,6-dione (cis) (110 mg, crude, HCl salt) as yellow oil. MS (M+H)$^+$=417.5

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1s,4s)-4-(2-(4-(4-(2,6-dioxopiperidin-3-yl)-2-fluorophenyl)piperazin-1-yl)ethyl)cyclohexyl)-3-methoxybenzamide (cis) (Compound 41)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (90 mg, 213.58 µmol) and HATU (97.45 mg, 256.29 µmol) in DMF (1.5 mL) was added DIPEA (44.52 mg, 344.47 µmol, 60 µL) and the mixture was stirred at 20° C. for 15 min. Then a solution of 3-(4-(4-(2-((1s,4s)-4-aminocyclohexyl)ethyl)piperazin-1-yl)-3-fluorophenyl)piperidine-2,6-dione (cis) (110 mg, 242.83 µmol, HCl salt) and DIPEA (89.04 mg, 688.93 µmol, 120 µL) in DMF (1.5 mL) was added and the mixture was stirred at 20° C. for 2 h. LCMS showed a peak (64%) with desired mass. The mixture was diluted with water (10 mL) and extracted with EtOAc (10 mL×3). The combined organic layer was washed with brine (10 mL×3), dried over Na$_2$SO$_4$ and filtered. The filtrate was concentrated under reduced pressure. The crude was purified by prep-HPLC (column: Phenomenex Synergi Polar-RP 100*25 mm*4 µm; mobile phase: [water (TFA)-ACN]; B %: 32%-52%, 7 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-((1s,4s)-4-(2-(4-(4-(2,6-dioxopiperidin-3-yl)-2-fluorophenyl)piperazin-1-yl)ethyl)cyclohexyl)-3-methoxybenzamide (cis) (54.8 mg, 48.11 µmol, 22.53% yield, 92% purity, 2TFA salt) as a yellow solid. MS (M+H)$^+$=820.1

$^1$H NMR (400 MHz, DMSO-d$_6$) δ=10.83 (s, 1H), 9.47-9.45 (m, 1H), 8.27-8.14 (m, 3H), 8.02-7.94 (m, 1H), 7.53-7.47 (m, 2H), 7.13-7.00 (m, 3H), 4.93-4.85 (m, 1H), 4.12-4.01 (m, 3H), 3.94 (s, 3H), 3.86-3.82 (m, 1H), 3.62-3.58 (m, 2H), 3.55-3.49 (m, 2H), 3.32 (s, 3H), 3.27-3.15 (m, 4H), 3.07-2.99 (m, 2H), 2.68-2.61 (m, 2H), 2.26-2.15 (m, 1H), 2.03-1.95 (m, 1H), 1.76-1.47 (m, 11H), 1.24 (d, J=6.7 Hz, 6H).

Example 42. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((2-(4-(2,6-dioxopiperidin-3-yl)-2-fluorophenyl)-2,7-diazaspiro[3.5]nonan-7-yl)methyl)piperidin-1-yl)-3-methoxybenzamide (Compound 42)
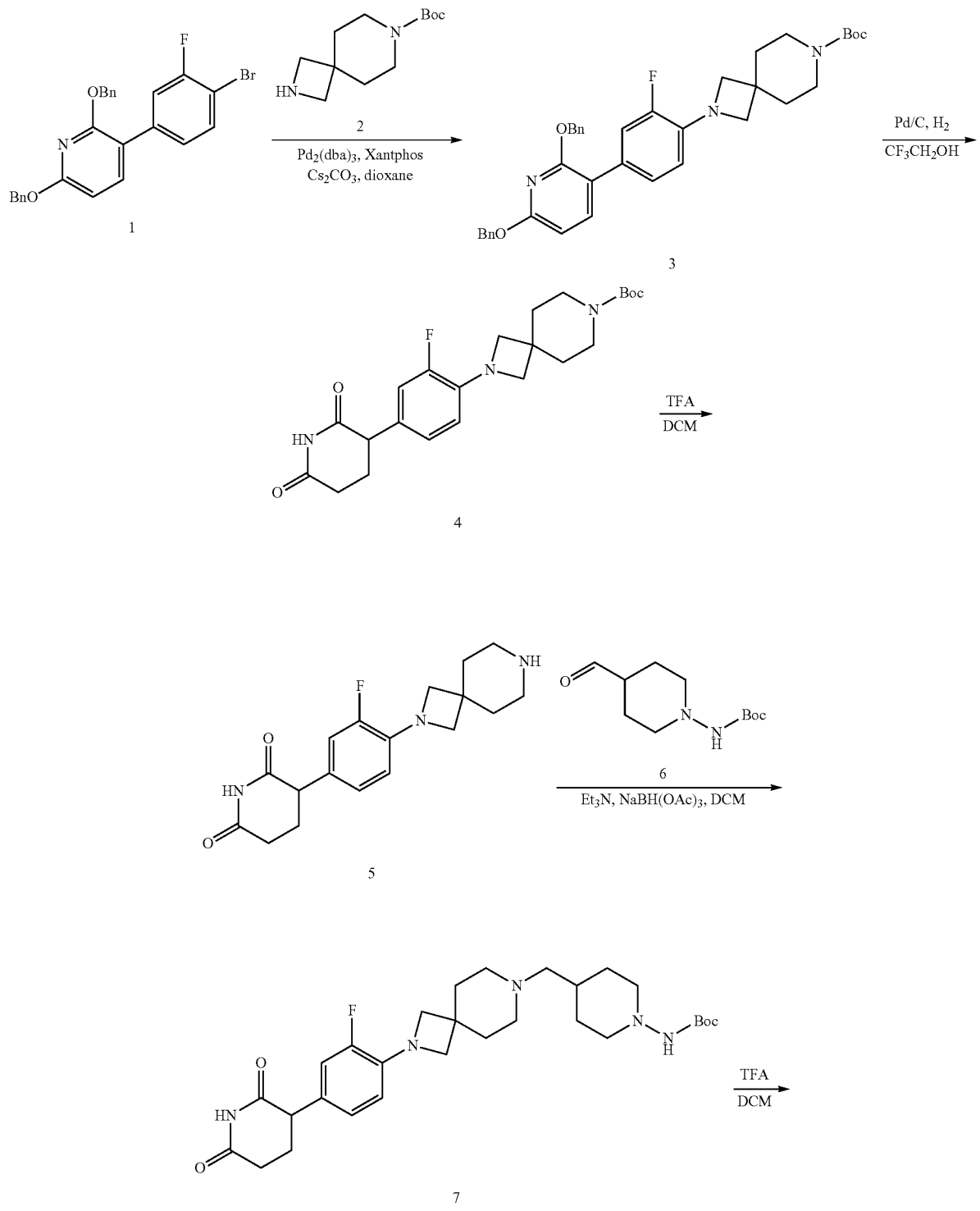

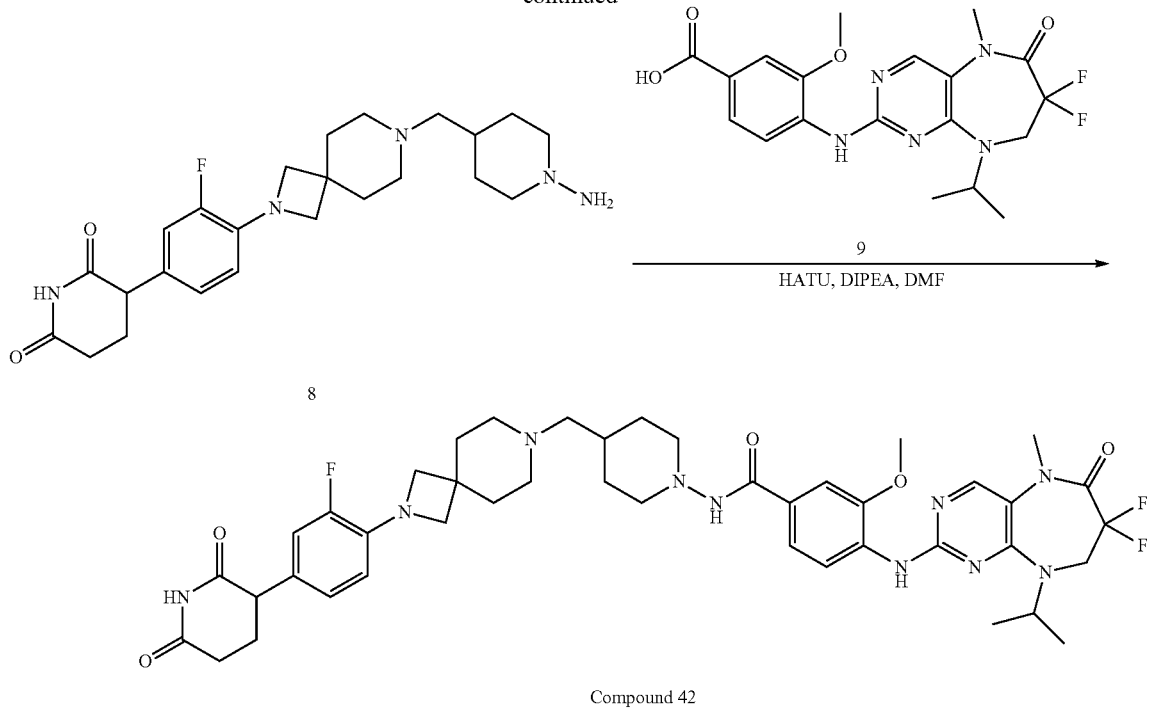

Compound 42

Step 1. Synthesis of tert-butyl 2-(4-(2,6-bis(benzyloxy)pyridin-3-yl)-2-fluorophenyl)-2,7-diazaspiro[3.5]nonane-7-carboxylate (3)

To a solution of 2,6-bis(benzyloxy)-3-(4-bromo-3-fluorophenyl)pyridine (1.5 g, 3.23 mmol) and tert-butyl 2,7-diazaspiro[3.5]nonane-7-carboxylate; hydrochloride (848.89 mg, 3.23 mmol) in dioxane (20 mL) were added Pd$_2$(dba)$_3$ (295.82 mg, 323.05 µmol), Xantphos (373.84 mg, 646.10 µmol) and Cs$_2$CO$_3$ (3.16 g, 9.69 mmol) at 20° C. under N$_2$. The mixture was stirred at 100° C. for 12 h. LCMS showed a peak (28%) with desired mass. The mixture was poured into water (50 mL) and extracted with EtOAc (50 mL×3), the combined organic layer was washed with brine (100 mL), dried over Na$_2$SO$_4$, filtered and concentrated. The residue was purified by flash silica gel chromatography (20 g SepaFlash Silica Flash Column, Eluent of 0~20% EtOAc/Petroleum ether gradient @ 80 mL/min) to afford tert-butyl 2-(4-(2,6-bis(benzyloxy)pyridin-3-yl)-2-fluorophenyl)-2,7-diazaspiro[3.5]nonane-7-carboxylate (0.7 g, 1.15 mmol, 35.54% yield, 100% purity) as yellow oil. MS (M+H)$^+$=610.4

Step 2. Synthesis of tert-butyl 2-(4-(2,6-dioxopiperidin-3-yl)-2-fluorophenyl)-2,7-diazaspiro[3.5]nonane-7-carboxylate (4)

To a solution of tert-butyl 2-(4-(2,6-bis(benzyloxy)pyridin-3-yl)-2-fluorophenyl)-2,7-diazaspiro [3.5]nonane-7-carboxylate (0.7 g, 1.15 mmol) in CF$_3$CH$_2$OH (20 mL) was added Pd/C (100 mg, 1.15 mmol, 10% purity) under N$_2$ atmosphere, the suspension was degassed and purged with H$_2$ for 3 times, the mixture was stirred under H$_2$ (15 Psi) at 20-25° C. for 12 h. LCMS showed that a peak with desired mass. The suspension was filtered through a pad of Celite and the filter cake was washed with CF$_3$CH$_2$OH (50 mL), the combined filtrates were concentrated to dryness to afford tert-butyl 2-(4-(2,6-dioxopiperidin-3-yl)-2-fluorophenyl)-2,7-diazaspiro[3.5]nonane-7-carboxylate (450 mg, 1.01 mmol, 88.11% yield, 97% purity) as a yellow solid. MS (M-Boc+H)$^+$=332.2

$^1$H NMR (400 MHz, CDCl$_3$) δ=7.83 (s, 1H), 6.79-6.70 (m, 2H), 6.36 (t, J=8.9 Hz, 1H), 3.69-3.58 (m, 4H), 3.62-3.56 (m, 1H), 3.34-3.30 (m, 4H), 2.71-2.54 (m, 2H), 2.23-2.08 (m, 2H), 1.72-1.67 (m, 4H), 1.39 (s, 9H)

Step 3. Synthesis of 3-(3-fluoro-4-(2,7-diazaspiro[3.5]nonan-2-yl)phenyl)piperidine-2,6-dione (5)

To the solution of tert-butyl 2-(4-(2,6-dioxopiperidin-3-yl)-2-fluorophenyl)-2,7-diazaspiro [3.5]nonane-7-carboxylate (250 mg, 579.38 µmol) in DCM (2 mL) was added TFA (1.54 g, 13.51 mmol, 1 mL) and the resulting mixture was stirred at 20° C. for 12 h. LCMS showed that 87% desired mass was detected. The mixture was concentrated to dryness to afford 3-(3-fluoro-4-(2,7-diazaspiro[3.5]nonan-2-yl)phenyl)piperidine-2,6-dione (250 mg, crude, TFA) as yellow oil. MS (M+H)$^+$=332.2

Step 4. Synthesis of tert-butyl (4-((2-(4-(2,6-dioxopiperidin-3-yl)-2-fluorophenyl)-2,7-diazaspiro[3.5]nonan-7-yl)methyl)piperidin-1-yl)carbamate (7)

To a solution of 3-(3-fluoro-4-(2,7-diazaspiro[3.5]nonan-2-yl)phenyl)piperidine-2,6-dione (200 mg, crude, TFA) in DCM (10 mL) were added tert-butyl (4-formylpiperidin-1-yl)carbamate (200 mg, 876.09 µmol) and Et$_3$N (90.87 mg, 898.06 µmol, 125.00 µL). The mixture was stirred at 20° C. for 1 h, then NaBH(OAc)$_3$ (285.50 mg, 1.35 mmol) was added to the mixture at 20° C., the mixture was stirred at 20° C. for 15 h. LCMS showed a peak (52%) with desired mass. The mixture was poured into water (50 mL) and extracted with DCM (50 mL×3), the combined organic layer was washed with brine (100 mL), dried over Na$_2$SO$_4$, filtered and concentrated. The residue was purified by flash silica gel chromatography (10 g SepaFlash Silica Flash Column, Eluent of 0~10% MeOH/EtOAc gradient @ 80 mL/min) to afford tert-butyl (4-((2-(4-(2,6-dioxopiperidin-3-yl)-2-fluorophenyl)-2,7-diazaspiro[3.5]nonan-7-yl)methyl)piperidin-1-yl)carbamate (0.1 g, 183.93 μmol, 40.96% yield, N/A purity) as yellow oil. MS (M+H)$^+$=544.1.

Step 5. Synthesis of 3-(4-(7-((1-aminopiperidin-4-yl)methyl)-2,7-diazaspiro[3.5]nonan-2-yl)-3-fluorophenyl)piperidine-2,6-dione (8)

To the solution of tert-butyl (4-((2-(4-(2,6-dioxopiperidin-3-yl)-2-fluorophenyl)-2,7-diazaspiro [3.5]nonan-7-yl) methyl)piperidin-1-yl)carbamate (0.1 g, 183.93 μmol) in DCM (2 mL) was added TFA (770.00 mg, 6.75 mmol, 0.5 mL) and the resulting mixture was stirred at 20° C. for 12 h. LCMS showed a peak (62%) with desired mass, the mixture was concentrated to afford 3-(4-(7-((1-aminopiperidin-4-yl) methyl)-2,7-diazaspiro[3.5]nonan-2-yl)-3-fluorophenyl)piperidine-2,6-dione (0.1 g, crude, TFA) as yellow oil. MS (M+H)$^+$=444.3.

Step 6. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((2-(4-(2,6-dioxopiperidin-3-yl)-2-fluorophenyl)-2,7-diazaspiro[3.5]nonan-7-yl)methyl)piperidin-1-yl)-3-methoxybenzamide (Compound 42)

To the solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (75.58 mg, 179.35 μmol, 1 eq) in DMF (2 mL) was added HATU (75.01 mg, 197.28 μmol) and DIPEA (92.72 mg, 717.39 μmol, 124.96 μL) and the mixture was stirred at 20° C. for 0.5 h, 3-(4-(7-((1-aminopiperidin-4-yl)methyl)-2,7-diazaspiro [3.5]nonan-2-yl)-3-fluorophenyl)piperidine-2,6-dione (0.1 g, crude, TFA) was added and the resulting mixture was stirred at 20° C. for 0.5 h. LCMS showed a main peak with desired mass, the mixture was poured into water (20 mL) and extracted with EtOAc (20 mL×3), the combined organic layer was washed with brine (50 mL), dried over Na$_2$SO$_4$, filtered and concentrated. The residue was purified prep-HPLC (column: Waters Xbridge C18 150*50 mm*10 μm; mobile phase: [water (NH$_4$HCO$_3$)-ACN]; B %: 38%-68%, 10 min) and the eluent was lyophilized to afford 4-((7,7-difluoro-9-isopropyl-5-methyl-6-oxo-6,7,8,9-tetrahydro-5H-pyrimido [4,5-b][1,4]diazepin-2-yl)amino)-N-(4-((2-(4-(2,6-dioxopiperidin-3-yl)-2-fluorophenyl)-2,7-diazaspiro [3.5]nonan-7-yl)methyl)piperidin-1-yl)-3-methoxybenzamide (19 mg, 20.64 μmol, 11.51% yield, 92% purity) as a yellow solid. MS (M+H)$^+$=847.4.

$^1$H NMR (400 MHz, DMSO-d$_6$) δ=10.78 (s, 1H), 9.27 (s, 1H), 8.30 (d, J=8.1 Hz, 1H), 8.23 (s, 1H), 7.88 (s, 1H), 7.47-7.42 (m, 2H), 6.93 (dd, J=1.6, 13.9 Hz, 1H), 6.86 (dd, J=1.7, 8.1 Hz, 1H), 6.55-6.45 (m, 1H), 4.94-4.83 (m, 1H), 4.04 (t, J=13.6 Hz, 2H), 3.94 (s, 3H), 3.77-3.71 (m, 1H), 3.65-3.60 (m, 4H), 3.31-3.30 (m, 7H), 3.05-2.99 (m, 2H), 2.80-2.71 (m, 2H), 2.65-2.58 (m, 1H), 2.47-2.44 (m, 2H), 2.36-2.31 (m, 2H), 2.19-2.11 (m, 3H), 2.03-1.93 (m, 2H), 1.80-1.70 (m, 4H), 1.56-1.47 (m, 1H), 1.25 (d, J=6.8 Hz, 6H).

Example 43. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-(2-(4-(4-(2,6-dioxopiperidin-3-yl)-2-fluorophenyl)piperazin-1-yl)ethyl)cyclohexyl)-3-methoxybenzamide (trans) (Compound 43)

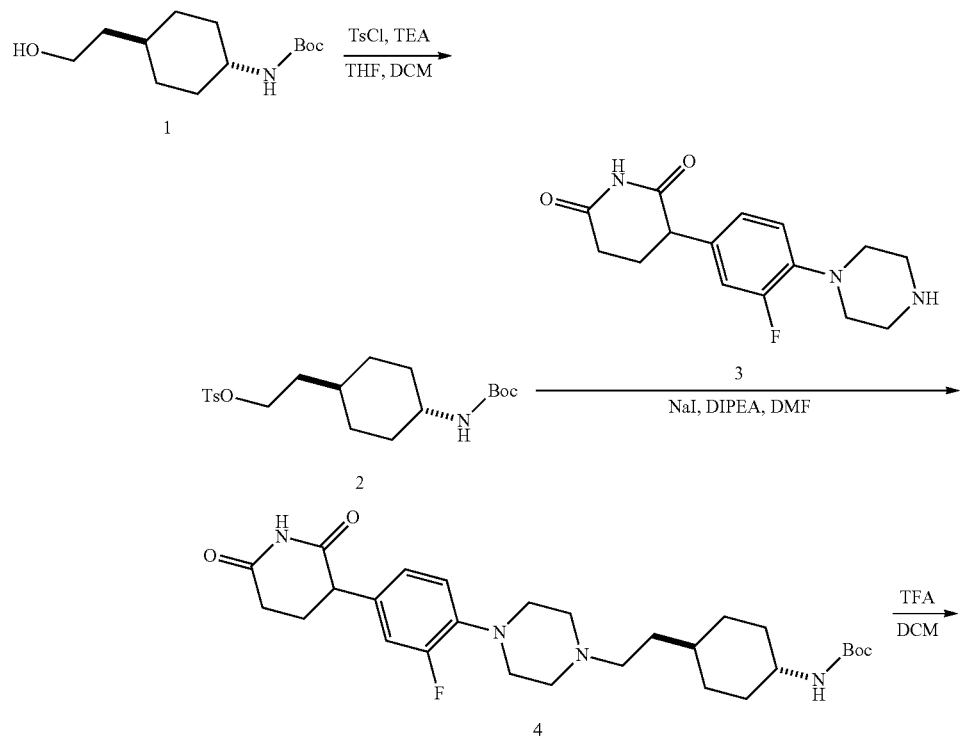

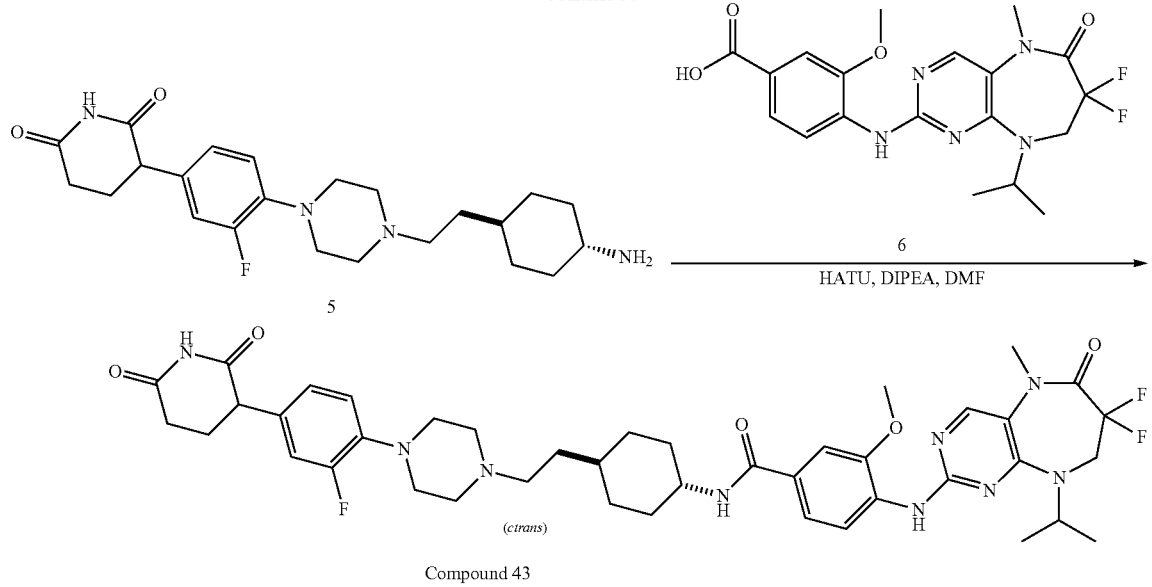

Compound 43

Step 1. Synthesis of 2-((1r,4r)-4-((tert-butoxycarbonyl)amino)cyclohexyl)ethyl 4-methylbenzenesulfonate (trans) (2)

To a solution of tert-butyl ((1r,4r)-4-(2-hydroxyethyl)cyclohexyl)carbamate (200 mg, 821.89 µmol) in THF (2 mL) were added TEA (249.50 mg, 2.47 mmol, 343.19 µL) and a solution of TosCl (235.04 mg, 1.23 mmol) in DCM (2 mL) at 0° C. The mixture was stirred at 20° C. for 16 hours. TLC (Petroleum ether:EtOAc=2:1, Rf=0.72) indicated 15% of tert-butyl ((1r,4r)-4-(2-hydroxyethyl)cyclohexyl)carbamate was remained and one major new spot with lower polarity. The reaction mixture was quenched by water (20 mL) at 0° C., and then extracted with EtOAc (30 mL×2). The combined organic layers were washed with brine (20 mL), dried over $Na_2SO_4$, filtered and concentrated under reduced pressure. The residue was purified by flash silica gel chromatography (ISCO; 12 g SepaFlash Silica Flash Column, Eluent of 0~30% EtOAc/Petroleum ether gradient @ 50 mL/min) to give 2-((1r,4r)-4-((tert-butoxycarbonyl)amino)cyclohexyl)ethyl 4-methylbenzenesulfonate (280 mg, 704.35 µmol, 85.70% yield) as colorless oil. MS $(M+H)^+$=358.5

Step 2. Synthesis of tert-butyl ((1r,4r)-4-(2-(4-(4-(2,6-dioxopiperidin-3-yl)-2-fluorophenyl)piperazin-1-yl)ethyl)cyclohexyl)carbamate (trans) (4)

To a solution of 2-((1r,4r)-4-((tert-butoxycarbonyl)amino)cyclohexyl)ethyl 4-methylbenzenesulfonate (170 mg, 427.64 µmol) and 3-(3-fluoro-4-(piperazin-1-yl)phenyl)piperidine-2,6-dione (124.58 mg, 427.64 µmol) in DMF (2 mL) was added DIPEA (110.54 mg, 855.29 µmol, 148.98 µL) and NaI (32.05 mg, 213.82 µmol). The mixture was stirred at 60° C. for 16 hr. LC-MS showed 32% of 3-(3-fluoro-4-(piperazin-1-yl)phenyl)piperidine-2,6-dione remained, several new peaks were shown on LC-MS and 34% of desired compound was detected. The reaction mixture was quenched by water (20 mL) at 0° C., and extracted with EtOAc (50 mL×2). The combined organic layers were washed with brine (30 mL), dried over $Na_2SO_4$, filtered and concentrated under reduced pressure to give a residue. The residue was purified by flash silica gel chromatography (ISCO; 12 g SepaFlash Silica Flash Column, Eluent of 0~100% EtOAc/Petroleum ether gradient @ 50 mL/min) to give tert-butyl ((1r,4r)-4-(2-(4-(4-(2,6-dioxopiperidin-3-yl)-2-fluorophenyl)piperazin-1-yl)ethyl)cyclohexyl)carbamate (60 mg, 91.75 µmol, 21.45% yield, 79% purity) as a white solid. MS $(M+H)^+$=517.3

Step 3. Synthesis of 3-(4-(4-(2-((1r,4r)-4-aminocyclohexyl)ethyl)piperazin-1-yl)-3-fluorophenyl)piperidine-2,6-dione (trans) (5)

To a solution of tert-butyl ((1r,4r)-4-(2-(4-(4-(2,6-dioxopiperidin-3-yl)-2-fluorophenyl)piperazin-1-yl)ethyl)cyclohexyl)carbamate (60 mg, 91.75 µmol, 79% purity) in DCM (1 mL) was added TFA (364.98 mg, 3.20 mmol, 237.00 µL). The mixture was stirred at 20° C. for 0.5 hr. LC-MS showed tert-butyl ((1r,4r)-4-(2-(4-(4-(2,6-dioxopiperidin-3-yl)-2-fluorophenyl)piperazin-1-yl)ethyl)cyclohexyl)carbamate was consumed completely and one peak (70%) with desired mass. The reaction mixture was concentrated under reduced pressure to remove solvent to give 3-(4-(4-(2-((1r,4r)-4-aminocyclohexyl)ethyl)piperazin-1-yl)-3-fluorophenyl)piperidine-2,6-dione (48 mg, 90.47 µmol, 98.61% yield, TFA) as yellow oil, it was used into the next step without further purification. MS $(M+H)^+$=417.1

Step 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-(2-(4-(4-(2,6-dioxopiperidin-3-yl)-2-fluorophenyl)piperazin-1-yl)ethyl)cyclohexyl)-3-methoxybenzamide (trans) (Compound 43)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (34.31 mg, 81.42 µmol) in DMF (1 mL) was added HATU (51.60 mg, 135.71 µmol) and DIPEA (35.08 mg, 271.41 µmol, 47.28 µL). The mixture was stirred at 20° C. for 1 hour, then 3-(4-(4-(2-((1r,4r)-4- aminocyclohexyl)ethyl)piperazin-1-yl)-3-fluorophenyl)piperidine-2,6-dione (48 mg, 90.47 μmol, TFA) was added, the mixture was stirred at 20° C. for 16 hours. LC-MS showed 3-(4-(4-(2-((1r,4r)-4-aminocyclohexyl)ethyl)piperazin-1-yl)-3-fluorophenyl)piperidine-2,6-dione was consumed completely and one peak (34%) with desired mass. The reaction mixture was quenched by water (20 mL) at 25° C., and extracted with EtOAc (50 mL×2). The combined organic layers were washed with brine (30 mL), dried over Na₂SO₄, filtered and concentrated under reduced pressure to give a residue. The residue was purified by prep-HPLC (column: Phenomenex Synergi Polar-RP 100*25 mm*4 μm; mobile phase: [water (TFA)-ACN]; B %: 30%-50%, 10 min) and re-purified by prep-HPLC (column: Waters Xbridge 150*25 mm*5 μm; mobile phase: [water (NH₄HCO₃)-ACN]; B %: 45%-75%, 8 min) and followed by lyophilization to give 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-(2-(4-(4-(2,6-dioxopiperidin-3-yl)-2-fluorophenyl)piperazin-1-yl)ethyl)cyclohexyl)-3-methoxybenzamide (20 mg, 23.90 μmol, 26.42% yield, 98% purity) as a white solid. MS (M+H)⁺=820.3

¹H NMR (400 MHz, DMSO-d₆) δ=10.80 (s, 1H), 8.30 (d, J=8.3 Hz, 1H), 8.22 (s, 1H), 8.04 (d, J=7.7 Hz, 1H), 7.86 (s, 1H), 7.55-7.45 (m, 2H), 7.07-6.91 (m, 3H), 4.90-4.84 (m, 1H), 4.03 (t, J=13.6 Hz, 2H), 3.93 (s, 3H), 3.84-3.71 (m, 2H), 3.36 (s, 3H), 3.30 (s, 3H), 3.07-2.93 (m, 4H), 2.72-2.58 (m, 2H), 2.47-2.46 (m, 1H), 2.39-2.30 (m, 3H), 2.25-2.13 (m, 1H), 2.05-1.94 (m, 1H), 1.90-1.74 (m, 4H), 1.43-1.29 (m, 4H), 1.24 (d, J=6.7 Hz, 6H), 1.11-0.98 (m, 2H).

Example 44. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(3-(((1-(4-(2,6-dioxopiperidin-3-yl)-2-fluorophenyl)piperidin-4-yl)methyl)(methyl)amino)cyclobutyl)-3-methoxybenzamide (Compound 44)

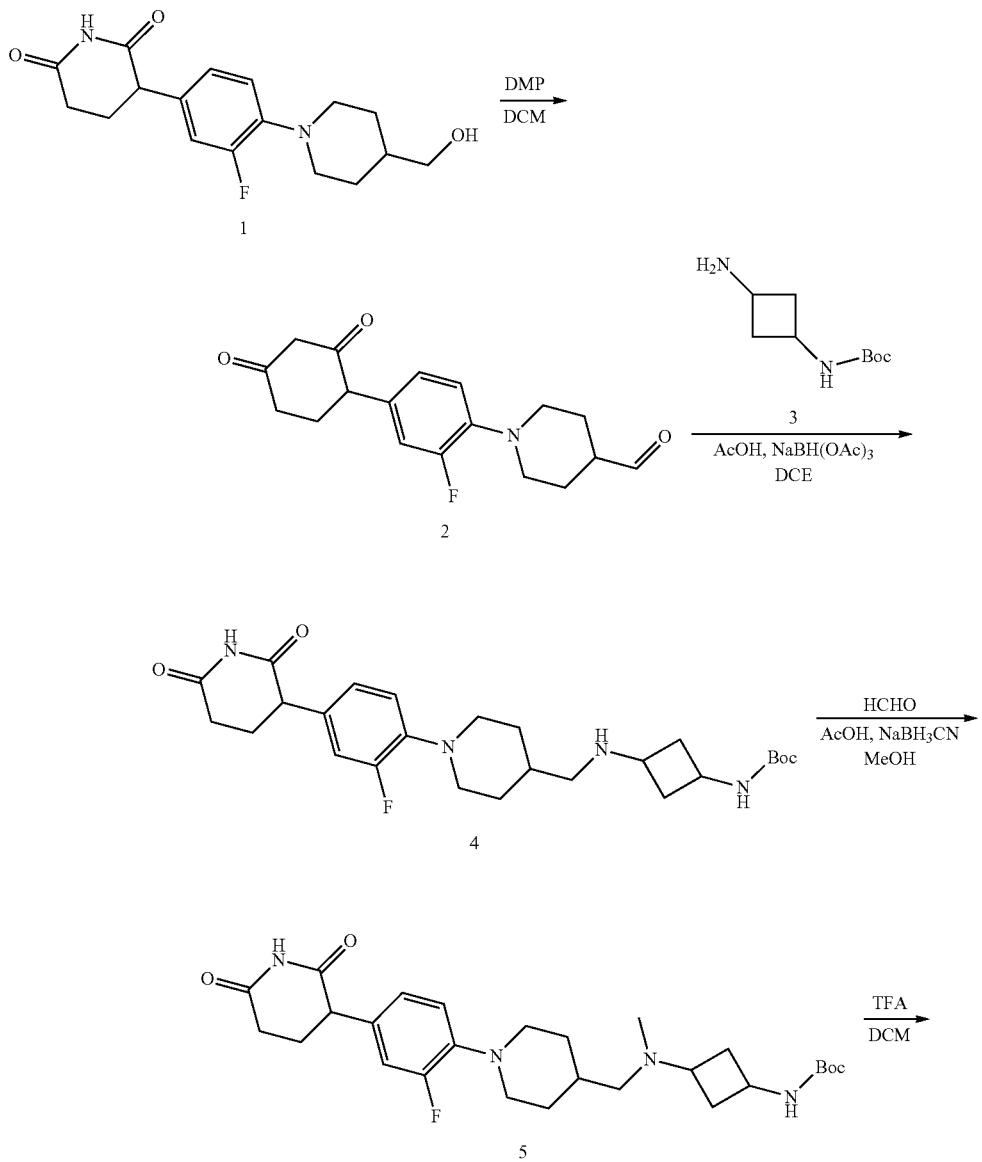

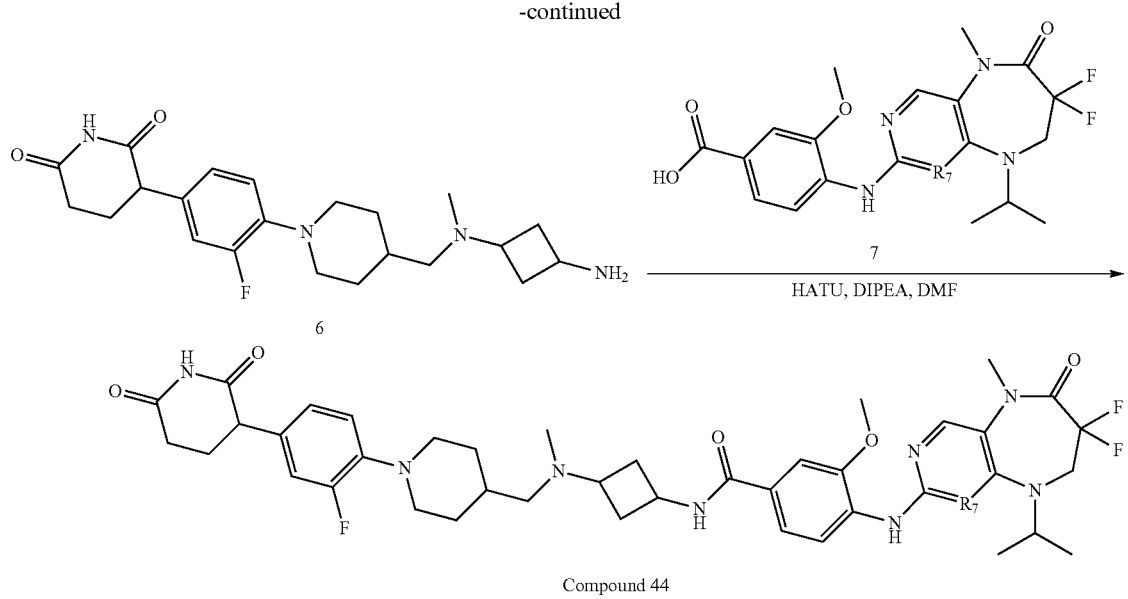

Compound 44

Step 1. Synthesis of 1-(4-(2,6-dioxopiperidin-3-yl)-2-fluorophenyl)piperidine-4-carbaldehyde (2)

To a solution of 3-(3-fluoro-4-(4-(hydroxymethyl)piperidin-1-yl)phenyl)piperidine-2,6-dione (210 mg, 655.52 µmol) in DCM (2 mL) was added DMP (361.44 mg, 852.17 µmol) at 0° C. The mixture was stirred at 20° C. for 3 hr. LC-MS showed 3-(3-fluoro-4-(4-(hydroxymethyl)piperidin-1-yl)phenyl)piperidine-2,6-dione was consumed completely and a peak with desired mass. The reaction mixture was filtered and the filtrate was concentrated to give 1-(4-(2,6-dioxopiperidin-3-yl)-2-fluorophenyl)piperidine-4-carbaldehyde (208 mg, crude) as yellow solid, it was used into the next step without further purification. MS (M+H)$^+$=319.0

Step 2. Synthesis of tert-butyl (3-(((1-(4-(2,6-dioxopiperidin-3-yl)-2-fluorophenyl)piperidin-4-yl)methyl)amino)cyclobutyl)carbamate (4)

To a solution of 1-(4-(2,6-dioxopiperidin-3-yl)-2-fluorophenyl)piperidine-4-carbaldehyde (208 mg, 653.39 µmol) and tert-butyl (3-aminocyclobutyl)carbamate (121.69 mg, 653.39 µmol) in DCE (4 mL) was added HOAc (39.24 mg, 653.39 µmol, 37.37 µL). The mixture was stirred at 20° C. for 1 hour. Then NaBH(OAc)$_3$ (692.40 mg, 3.27 mmol) was added at 0° C., the mixture was stirred at 20° C. for 16 hours. LC-MS showed 1-(4-(2,6-dioxopiperidin-3-yl)-2-fluorophenyl)piperidine-4-carbaldehyde was consumed completely and one peak (36%) with desired mass. The reaction mixture was quenched by water (30 mL) at 0° C., and then extracted with EtOAc (40 mL×2). The combined organic layers were washed with brine (20 mL), dried over Na$_2$SO$_4$, filtered and concentrated under reduced pressure to give a residue. The residue was purified by flash silica gel chromatography (ISCO; 12 g SepaFlash Silica Flash Column, Eluent of 0~100% EtOAc/Petroleum ether to EtOAc/MeOH=10:1 gradient @ 50 mL/min) to give tert-butyl (3-(((1-(4-(2,6-dioxopiperidin-3-yl)-2-fluorophenyl)piperidin-4-yl)methyl)amino)cyclobutyl)carbamate (200 mg, 409.34 µmol, 62.65% yield) as a yellow solid. MS (M+H)$^+$=489.1

Step 3. Synthesis of tert-butyl (3-(((1-(4-(2,6-dioxopiperidin-3-yl)-2-fluorophenyl)piperidin-4-yl)methyl)(methyl)amino)cyclobutyl)carbamate (5)

To a solution of tert-butyl (3-(((1-(4-(2,6-dioxopiperidin-3-yl)-2-fluorophenyl)piperidin-4-yl)methyl)amino)cyclobutyl)carbamate (150 mg, 307.00 µmol) and HCHO (124.57 mg, 1.54 mmol, 114.28 µL, 37% purity) in MeOH (2 mL) was added HOAc (18.44 mg, 307.00 µmol, 17.56 µL). The mixture was stirred at 20° C. for 1 hour, then NaBH$_3$CN (57.88 mg, 921.01 µmol) was added. The mixture was stirred at 20° C. for another 16 hours. LC-MS showed tert-butyl (3-(((1-(4-(2,6-dioxopiperidin-3-yl)-2-fluorophenyl)piperidin-4-yl)methyl)amino)cyclobutyl)carbamate was consumed completely and one peak (47%) with desired mass. The reaction mixture was quenched by addition aqueous saturated NaHCO$_3$ (20 mL) at 0° C., and then extracted with EtOAc (40 mL×2). The combined organic layers were washed with brine (30 mL), dried over Na$_2$SO$_4$, filtered and concentrated under reduced pressure to give tert-butyl (3-(((1-(4-(2,6-dioxopiperidin-3-yl)-2-fluorophenyl)piperidin-4-yl)methyl)(methyl)amino)cyclobutyl)carbamate (150 mg, 220.84 µmol, 71.93% yield, 74% purity) as a yellow solid, it was used into the next step without further purification. MS (M+H)$^+$=503.5

Step 4. Synthesis of 3-(4-(4-(((3-aminocyclobutyl)(methyl)amino)methyl)piperidin-1-yl)-3-fluorophenyl)piperidine-2,6-dione (6)

To a solution of tert-butyl tert-butyl (3-(((1-(4-(2,6-dioxopiperidin-3-yl)-2-fluorophenyl)piperidin-4-yl)methyl)(methyl)amino)cyclobutyl)carbamate (150 mg, 220.84 µmol, 74% purity) in DCM (1 mL) was added TFA (1.07 g, 9.37 mmol, 693.75 µL). The mixture was stirred at 20° C. for 0.5 hr. LC-MS showed tert-butyl (3-(((1-(4-(2,6-dioxopiperidin-3-yl)-2-fluorophenyl)piperidin-4-yl)methyl)(methyl)amino)cyclobutyl)carbamate was consumed completely and one peak (94%) with desired mass. The reaction mixture was concentrated under reduced pressure to remove solvent to 3-(4-(4-(((3-aminocyclobutyl)(methyl)amino)methyl)piperidin-1-yl)-3-fluorophenyl)piperidine-2,6-dione (100 mg, 193.60 μmol, 87.66% yield, TFA) as yellow oil. MS (M+H)⁺=403.2

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(3-(((1-(4-(2,6-dioxopiperidin-3-yl)-2-fluorophenyl)piperidin-4-yl)methyl)(methyl)amino)cyclobutyl)-3-methoxybenzamide (Compound 44)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (73.42 mg, 174.24 μmol) in DMF (1 mL) was added HATU (110.42 mg, 290.40 μmol) and DIPEA (125.11 mg, 968.00 μmol, 168.61 μL). The mixture was stirred at 20° C. for 1 hour. Then 3-(4-(4-(((3-aminocyclobutyl)(methyl)amino)methyl)piperidin-1-yl)-3-fluorophenyl)piperidine-2,6-dione (100 mg, 193.60 μmol, TFA) was added, the mixture was stirred at 20° C. for 2 hours. LC-MS showed 3-(4-(4-(((3-aminocyclobutyl)(methyl)amino)methyl)piperidin-1-yl)-3-fluorophenyl)piperidine-2,6-dione was consumed completely and one peak (32%) with desired mass was detected. The reaction mixture was quenched by aqueous saturated NaHCO₃ (20 mL) at 0° C., and then extracted with EtOAc (40 mL×2). The combined organic layers were washed with brine (30 mL), dried over Na₂SO₄, filtered and concentrated under reduced pressure to give a residue. The residue was purified by prep-HPLC (column: 3_Phenomenex Luna C18 75*30 mm*3 μm; mobile phase: [water (TFA)-ACN]; B %: 19%-39%, 9 min) and re-purified by prep-HPLC (column: Waters Xbridge 150*25 mm*5 μm; mobile phase: [water (NH₄HCO₃)-ACN]; B %: 41%-71%, 8 min) and followed by lyophilization to give 4-((7,7-difluoro-9-isopropyl-5-methyl-6-oxo-6,7,8,9-tetrahydro-5H-pyrimido[4,5-b][1,4]diazepin-2-yl)amino)-N-(3-(((1-(4-(2,6-dioxopiperidin-3-yl)-2-fluorophenyl)piperidin-4-yl)methyl)(methyl)amino)cyclobutyl)-3-methoxybenzamide (35 mg, 42.13 μmol, 21.76% yield, 97% purity) as a white solid. MS (M+H)⁺=806.4

¹H NMR (400 MHz, DMSO-d₆) δ=10.80 (s, 1H), 8.55-8.41 (m, 1H), 8.35-8.27 (m, 1H), 8.22 (s, 1H), 7.93-7.81 (m, 1H), 7.59-7.46 (m, 2H), 7.05-6.91 (m, 3H), 4.95-4.81 (m, 1H), 4.40-4.26 (m, 1H), 4.13-3.97 (m, 2H), 3.96-3.89 (m, 3H), 3.81-3.77 (m, 1H), 3.33-3.32 (m, 2H), 3.29-3.28 (m, 6H), 2.98-2.91 (m, 1H), 2.65-2.59 (m, 2H), 2.41-2.39 (m, 1H), 2.22-2.12 (m, 4H), 2.10-2.07 (m, 3H), 2.05-1.95 (m, 2H), 1.86-1.79 (m, 2H), 1.63-1.51 (m, 1H), 1.33-1.19 (m, 8H).

Example 45. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(2-(4-(4-(2,6-dioxopiperidin-3-yl)-2-fluorophenyl)piperazin-1-yl)ethyl)piperidin-1-yl)-3-methoxybenzamide (Compound 45)

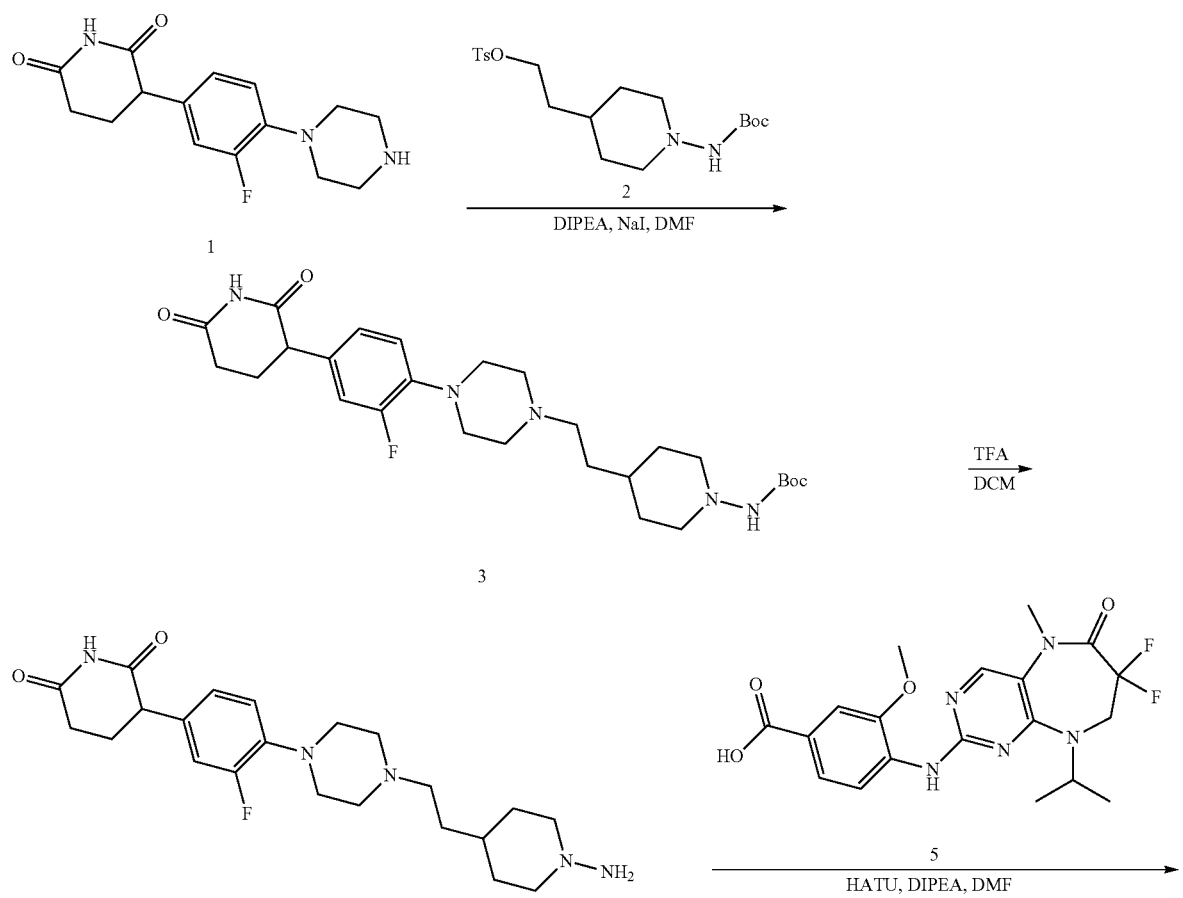

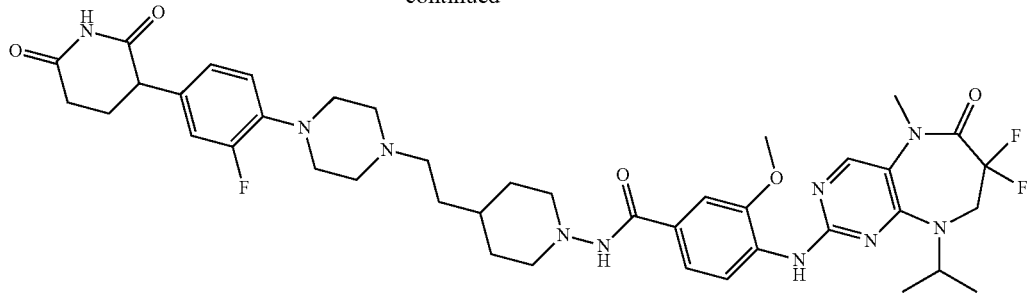

Compound 45

Step 1. Synthesis of tert-butyl (4-(2-(4-(4-(2,6-di-oxopiperidin-3-yl)-2-fluorophenyl)piperazin-1-yl)ethyl)piperidin-1-yl)carbamate (3)

To a solution of 3-(3-fluoro-4-(piperazin-1-yl)phenyl)piperidine-2,6-dione (100 mg, 343.27 μmol) in DMF (2 mL) were added 2-(1-((tert-butoxycarbonyl)amino)piperidin-4-yl)ethyl 4-methylbenzenesulfonate (136.80 mg, 343.27 μmol), DIPEA (133.09 mg, 1.03 mmol, 179.37 μL), and NaI (5.15 mg, 34.33 μmol), and the resulting mixture was stirred at 20° C. for 34 h. LCMS showed a peak (49%) with desired mass. The reaction mixture was diluted with H$_2$O (8 mL), extracted with EtOAc (10 mL×3). The combined organic layers were washed with brine (20 mL×3), dried over Na$_2$SO$_4$, filtered. The filtrate was concentrated in vacuum. The residue was purified by flash silica gel chromatography (Biotage; 20 g SepaFlash Silica Flash Column, Eluent of 20~100% EtOAc/Petroleum ether to 10% Methanol/EtOAc gradient @ 80 mL/min) to afford tert-butyl (4-(2-(4-(4-(2,6-dioxopiperidin-3-yl)-2-fluorophenyl)piperazin-1-yl)ethyl)piperidin-1-yl)carbamate (150 mg, 289.78 μmol, 84.42% yield) as a yellow solid. MS (M+H)$^+$=518.4.

Step 2. Synthesis of 3-(4-(4-(2-(1-aminopiperidin-4-yl)ethyl)piperazin-1-yl)-3-fluorophenyl)piperidine-2,6-dione (4)

To a solution of tert-butyl (4-(2-(4-(4-(2,6-dioxopiperidin-3-yl)-2-fluorophenyl)piperazin-1-yl)ethyl)piperidin-1-yl)carbamate (150 mg, 289.78 μmol) in DCM (2 mL) was added TFA (770.00 mg, 6.75 mmol, 500.00 μL), the mixture was stirred at 20° C. for 1 h. LCMS showed a main peak with desired mass. The mixture was concentrated in vacuum to afford 3-(4-(4-(2-(1-aminopiperidin-4-yl)ethyl)piperazin-1-yl)-3-fluorophenyl)piperidine-2,6-dione (120 mg, crude, TFA) as a brown oil. MS (M+H)$^+$=418.2.

Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(2-(4-(4-(2,6-dioxopiperidin-3-yl)-2-fluorophenyl)piperazin-1-yl)ethyl)piperidin-1-yl)-3-methoxybenzamide (Compound 45)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (95.13 mg, 225.76 μmol) and HATU (128.76 mg, 338.64 μmol) in DMF (2 mL) was added DIPEA (87.53 mg, 677.27 μmol, 117.97 μL), the mixture was stirred at 20° C. for 1 h. 3-(4-(4-(2-(1-aminopiperidin-4-yl)ethyl)piperazin-1-yl)-3-fluorophenyl)piperidine-2,6-dione (120 mg, 225.76 μmol, TFA) was added, the resulting mixture was stirred at 20° C. for 16 h. LCMS showed a peak (33%) with desired mass. The reaction mixture was diluted with H$_2$O (10 mL), extracted with EtOAc (10 mL×3). The combined organic layers were washed with brine (20 mL×2), dried over Na$_2$SO$_4$, filtered. The filtrate was concentrated under reduced pressure to give a residue. The residue was purified by prep-TLC (SiO$_2$, DCM:MeOH=10:1) and re-purified by prep-HPLC (column: Waters Xbridge 150*25 mm*5 μm; mobile phase: [water (NH$_4$HCO$_3$)-ACN]; B %: 35%-65%, 8 min). The eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-(2-(4-(4-(2,6-dioxopiperidin-3-yl)-2-fluorophenyl)piperazin-1-yl)ethyl)piperidin-1-yl)-3-methoxybenzamide (56.8 mg, 67.81 μmol, 30.04% yield, 98% purity) as a white solid. MS (M+H)$^+$=821.4.

$^1$H NMR (400 MHz, DMSO-d$_6$) δ=10.81 (s, 1H), 9.23 (s, 1H), 8.33-8.27 (m, 1H), 8.22 (s, 1H), 7.87 (s, 1H), 7.46-7.39 (m, 2H), 7.06-6.93 (m, 3H), 4.96-4.79 (m, 1H), 4.03 (t, J=13.6 Hz, 2H), 3.93 (s, 3H), 3.82-3.77 (m, 1H), 3.30 (s, 3H), 3.03-2.96 (m, 6H), 2.75-2.65 (m, 7H), 2.36-2.33 (m, 2H), 2.25-2.13 (m, 2H), 2.04-1.97 (m, 1H), 1.75-1.68 (m, 2H), 1.46-1.40 (m, 2H), 1.34-1.28 (m, 3H), 1.24 (d, J=6.6 Hz, 6H).

Example 46. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(6-((1-(4-(2,6-dioxopiperidin-3-yl)-2-fluorophenyl)piperidin-4-yl)methyl)-6-azaspiro[2.5]octan-1-yl)-3-methoxybenzamide (Compound 46)
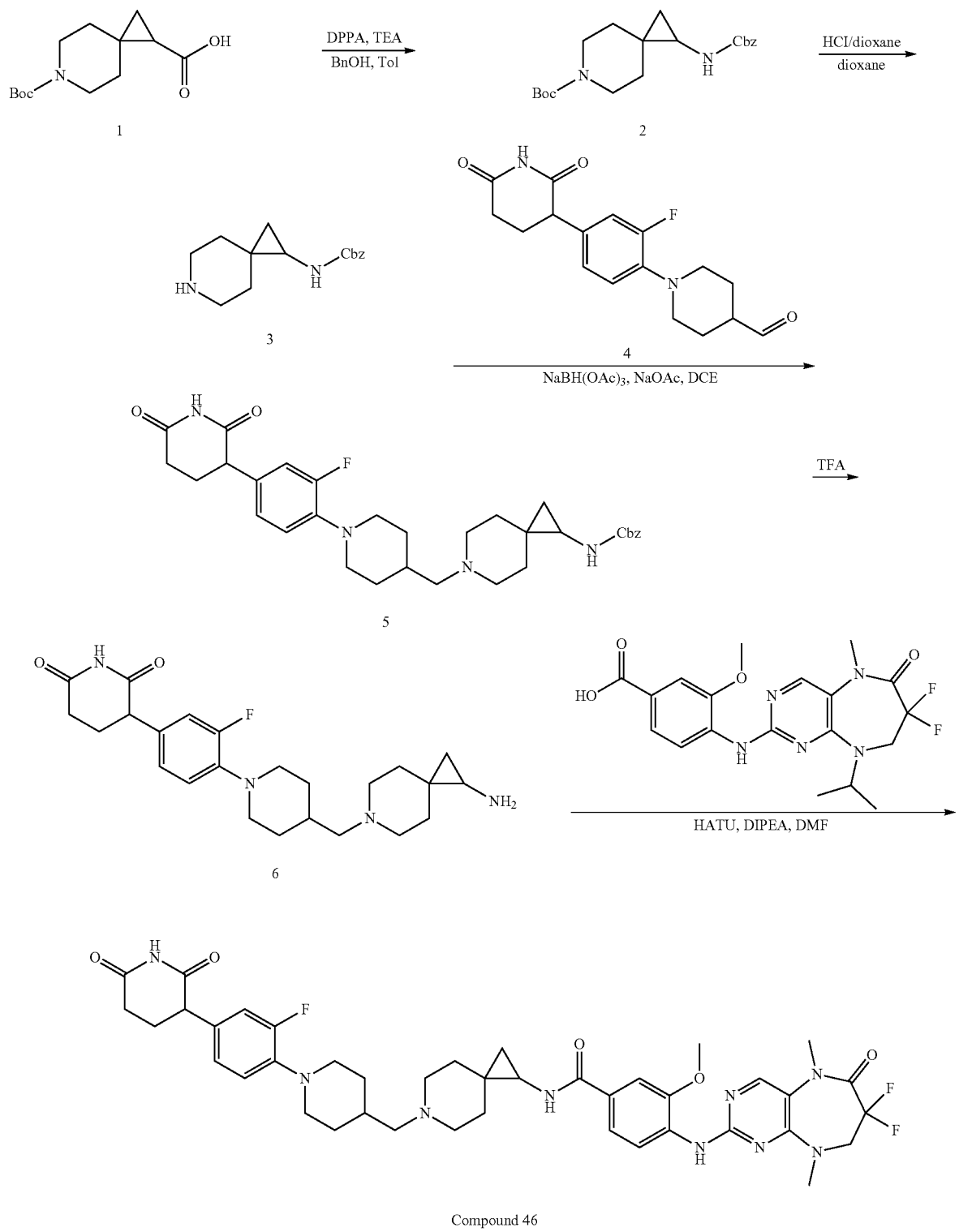

Step 1. Synthesis of tert-butyl 1-(((benzyloxy)carbonyl)amino)-6-azaspiro[2.5]octane-6-carboxylate (2)

To a mixture of 6-(tert-butoxycarbonyl)-6-azaspiro[2.5]octane-1-carboxylic acid (1 g, 3.92 mmol) in toluene (20 mL) were added TEA (799.70 mg, 7.90 mmol, 1.1 mL) and DPPA (1.65 g, 6.00 mmol, 1.3 mL) at 0° C. and then the mixture was stirred at 110° C. for 1 hr under $N_2$ atmosphere, then BnOH (832.00 mg, 7.69 mmol, 800 µL) was added to the mixture at 25° C., the resulting mixture was stirred at 110° C. for 15 h under $N_2$ atmosphere. LCMS showed the acid was consumed completely and one peak with mass [M−55] was detected. The reaction mixture was concentrated under reduced pressure. The residue was purified by flash silica gel chromatography (Biotage; 10 g SepaFlash Silica Flash Column, Eluent of 10~33% EtOAc:Petroleum ether gradient, 60 mL/min) to afford tert-butyl 1-(((benzyloxy)carbonyl)amino)-6-azaspiro[2.5]octane-6-carboxylate (1.4 g, 3.88 mmol, 99.16% yield) was obtained as a light yellow oil. MS $(M+1)^+=361.0$

Step 2. Synthesis of benzyl (6-azaspiro[2.5]octan-1-yl)carbamate (3)

To a solution of tert-butyl 1-(((benzyloxy)carbonyl)amino)-6-azaspiro[2.5]octane-6-carboxylate (600 mg, 1.66 mmol) in dioxane (10 mL) were added HCl/dioxane (4 M, 10 mL). The mixture was stirred at 20° C. for 1 h under $N_2$ atmosphere. LCMS showed a main peak with desired mass and no peak with reactant 1 was detected. The reaction mixture was concentrated under reduced pressure to afford benzyl (6-azaspiro[2.5]octan-1-yl)carbamate (300 mg, crude, HCl) as a yellow oil. MS $(M+H)^+=261.1$

Step 3. Synthesis of benzyl (6-((1-(4-(2,6-dioxopiperidin-3-yl)-2-fluorophenyl)piperidin-4-yl)methyl)-6-azaspiro[2.5]octan-1-yl)carbamate (5)

To a solution of 1-(4-(2,6-dioxopiperidin-3-yl)-2-fluorophenyl)piperidine-4-carbaldehyde (150 mg, 471.19 µmol) in DCE (5 mL) was added benzyl (6-azaspiro[2.5]octan-1-yl)carbamate (140 mg, crude, HCl) and NaOAc (121.21 mg, 1.48 mmol). The mixture was stirred at 20° C. for 1 hr. Then $NaBH(OAc)_3$ (499.32 mg, 2.36 mmol) was added to the mixture at 0° C., the mixture was stirred at 20° C. for 15 hr. LCMS showed 13% peak with the desired mass and no peak with the starting material. To the reaction mixture was added $H_2O$ (10 mL) at 0° C., then $NaHCO_3$ (sat. aq, 15 mL) was added to the water layers at 0° C. to pH=9, the combined water layers was extracted with EtOAc 120 mL (40 mL×3), then the combined organic layers were washed with brine 120 mL (60 mL×2), dried over anhydrous $Na_2SO_4$, filtered and the filtrate was concentrated under reduced pressure. The residue was purified by flash silica gel chromatography (Biotage; 10 g SepaFlash Silica Flash Column, Eluent of 0~20% Methanol:Dichloromethane gradient, 60 mL/min) to afford benzyl (6-((1-(4-(2,6-dioxopiperidin-3-yl)-2-fluorophenyl)piperidin-4-yl)methyl)-6-azaspiro[2.5]octan-1-yl)carbamate (260 mg, 462.08 µmol, 98.07% yield) as a yellow solid. MS $(M+H)^+=563.1$

Step 4. Synthesis of 3-(4-(4-((1-amino-6-azaspiro[2.5]octan-6-yl)methyl)piperidin-1-yl)-3-fluorophenyl)piperidine-2,6-dione (6)

A solution of benzyl (6-((1-(4-(2,6-dioxopiperidin-3-yl)-2-fluorophenyl)piperidin-4-yl)methyl)-6-azaspiro[2.5]octan-1-yl)carbamate (120 mg, 213.27 µmol) in TFA (2 mL) was stirred at 60° C. for 5 h under $N_2$ atmosphere. LCMS showed benzyl (6-((1-(4-(2,6-dioxopiperidin-3-yl)-2-fluorophenyl)piperidin-4-yl)methyl)-6-azaspiro[2.5]octan-1-yl)carbamate was consumed completely and 32% peak with desired mass. The reaction mixture was concentrated under reduced pressure to afford 3-(4-(4-((1-amino-6-azaspiro[2.5]octan-6-yl)methyl)piperidin-1-yl)-3-fluorophenyl)piperidine-2,6-dione (115 mg, crude, TFA) as a yellow oil. MS $(M+H)^+=429.4$

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(6-((1-(4-(2,6-dioxopiperidin-3-yl)-2-fluorophenyl)piperidin-4-yl)methyl)-6-azaspiro[2.5]octan-1-yl)-3-methoxybenzamide (Compound 46)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (80 mg, 189.84 µmol) in DMF (3 mL) were added HATU (108.28 mg, 284.77 µmol), DIPEA (148.40 mg, 1.15 mmol, 200.00 µL) and 3-(4-(4-((1-amino-6-azaspiro[2.5]octan-6-yl)methyl)piperidin-1-yl)-3-fluorophenyl)piperidine-2,6-dione (115 mg, crude, TFA) at 20° C. The mixture was stirred at 20° C. for 16 h under $N_2$ atmosphere. LCMS showed 28% peak with the desired mass. To the reaction mixture was added $H_2O$ (10 mL), the mixture was extracted with EtOAc 50 mL (25 mL×2), the combined organic layers were washed with brine (20 mL×3), dried over $Na_2SO_4$, filtered and the filtrate was concentrated under reduced pressure. The residue was purified by flash silica gel chromatography (Biotage; 10 g SepaFlash Silica Flash Column, Eluent of 0~25% Methanol:Dichloromethane gradient, 60 mL/min). The product was repurified prep-HPLC (column: Phenomenex Synergi C18 150×25 mmx 10 um; mobile phase: [water (FA)-ACN]; B %: 12%-42%, 7 min; Column Temp: 30° C.) followed by lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-(6-((1-(4-(2,6-dioxopiperidin-3-yl)-2-fluorophenyl)piperidin-4-yl)methyl)-6-azaspiro[2.5]octan-1-yl)-3-methoxybenzamide (50.3 mg, 56.21 µmol, 29.61% yield, 94% purity, 0.2FA) was obtained as a white solid. MS $(M+H)^+=832.2$ $^1$H NMR (400 MHz, DMSO-$d_6$) δ=10.82 (s, 1H), 8.30 (d, J=8.3 Hz, 1H), 8.23-8.19 (m, 2H), 8.18-8.17 (m, 0.2H), 7.88 (s, 1H), 7.58-7.46 (m, 2H), 7.05-6.89 (m, 3H), 4.92-4.83 (m, 1H), 4.03 (t, J=13.6 Hz, 2H), 3.96-3.91 (m, 3H), 3.81-3.75 (m, 1H), 3.43-3.31 (m, 6H), 2.73-2.56 (m, 6H), 2.44-2.33 (m, 2H), 2.25-2.11 (m, 3H), 2.03-1.94 (m, 1H), 1.85-1.72 (m, 2H), 1.68-1.56 (m, 1H), 1.54-1.32 (m, 4H), 1.30-1.19 (m, 8H), 0.76-0.62 (m, 2H).

Example 47. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(7-(3-(2,4-dioxotetrahydropyrimidin-1(2H)-yl)benzoyl)-2,7-diazaspiro[3.5]nonan-2-yl)piperidin-1-yl)-3-methoxybenzamide (Compound 47)

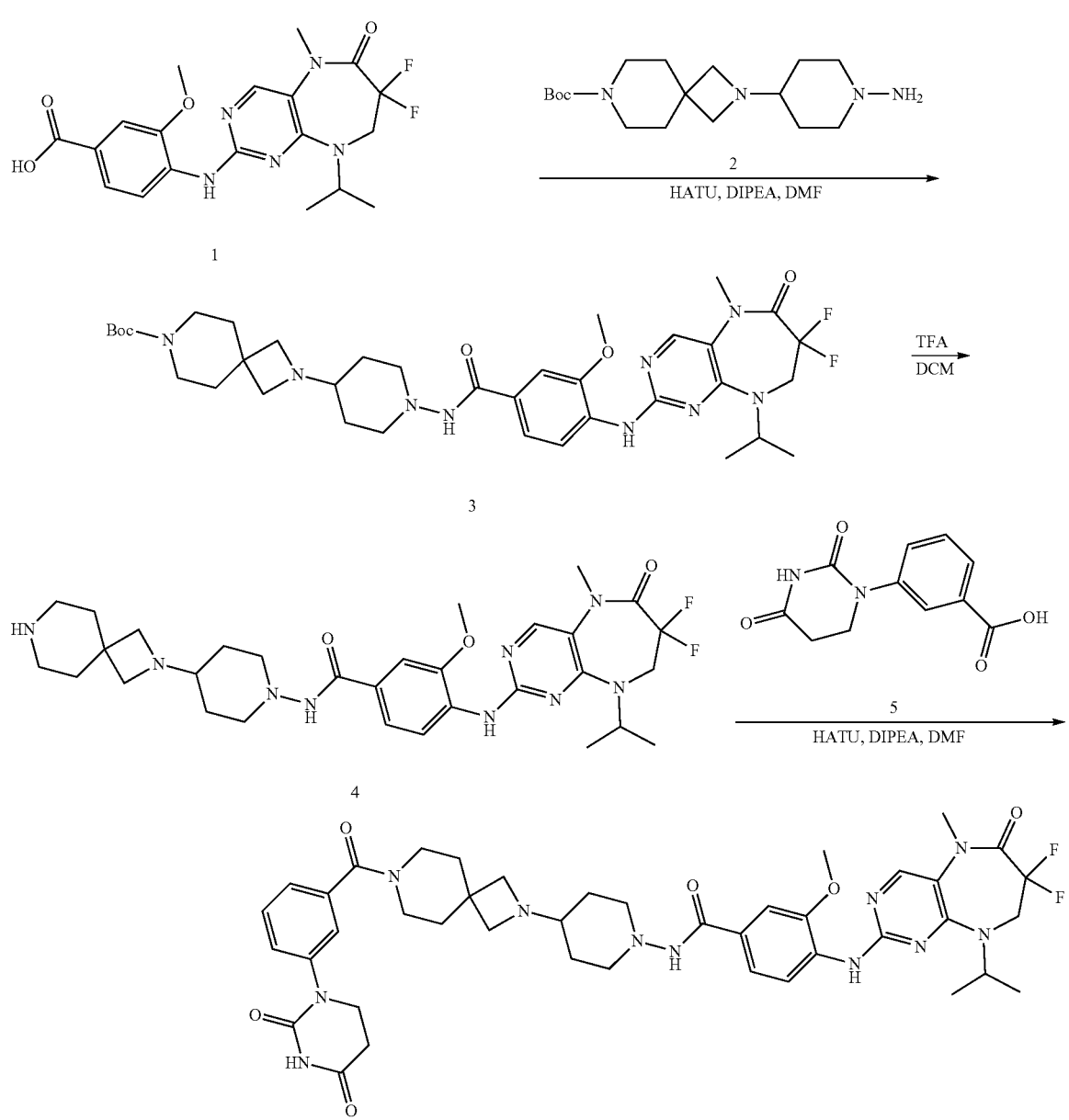

Step 1. Synthesis of tert-butyl 2-(1-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)piperidin-4-yl)-2,7-diazaspiro[3.5]nonane-7-carboxylate (3)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (500 mg, 1.19 mmol) in DMF (3 mL) were added HATU (496.27 mg, 1.31 mmol) and DIPEA (306.70 mg, 2.37 mmol, 413.34 μL), the mixture was stirred at 20° C. for 10 min and a solution of tert-butyl 2-(1-aminopiperidin-4-yl)-2,7-diazaspiro[3.5]nonane-7-carboxylate (577.47 mg, 1.78 mmol) and DIPEA (613.40 mg, 4.75 mmol, 826.69 μL) in DMF (3 mL) was added and the resulting mixture was stirred at 20° C. for 1 h. LCMS showed starting material was consumed completely and 35% peak with desired mass was detected. The reaction mixture was diluted with H$_2$O (15 mL) and extracted with EtOAc (15 mL×3). The organic layer was washed with brine (15 mL×3), dried over Na$_2$SO$_4$, filtered and concentrated. The residue was purified by flash silica gel chromatography (12 g SepaFlash Silica Flash Column, Eluent of 0~100% EtOAc/Petroleum ether gradient @ 100 mL/min) to afford product A (368 mg) with 82% purity by LCMS. The product A was dissolved in DMF (4 mL) and re-purified by prep-HPLC (column: Waters Xbridge 150*25 mm*5 μm; mobile phase: [water (NH$_4$HCO$_3$)-ACN]; B %: 46%-76%, 8 min), and the eluent was lyophilized to afford tert-butyl 2-(1-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)piperidin-4-yl)-2,7-diazaspiro[3.5]nonane-7-carboxylate (32 mg, 41.33 μmol, 3.48% yield, 94% purity) as a white solid. MS (M+H)$^+$=728.3

Step 2. Synthesis of N-(4-(2,7-diazaspiro[3.5]nonan-2-yl)piperidin-1-yl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (4)

To a solution of tert-butyl 2-(1-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)piperidin-4-yl)-2,7-diazaspiro[3.5]nonane-7-carboxylate (31 mg, 42.59 μmol) in DCM (1 mL) was added TFA (14.57 mg, 127.77 μmol, 9.46 μL) at 20° C. and the resulting mixture was stirred at 20° C. for 1 h. LCMS showed starting material was consumed completely and 93% peak with desired mass was detected. The reaction mixture was concentrated in vacuum to afford N-(4-(2,7-diazaspiro[3.5]nonan-2-yl)piperidin-1-yl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (76 mg, crude, TFA) as a yellow oil. MS (M+H)$^+$=628.3

Step 3. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-(7-(3-(2,4-dioxotetrahydropyrimidin-1(2H)-yl)benzoyl)-2,7-diazaspiro[3.5]nonan-2-yl)piperidin-1-yl)-3-methoxybenzamide (Compound 47)

To a solution of 3-(2,4-dioxohexahydropyrimidin-1-yl)benzoic acid (20 mg, 85.39 μmol) in DMF (2 mL) were added HATU (35.72 mg, 93.93 μmol) and DIPEA (22.07 mg, 170.79 μmol, 29.75 μL), the mixture was stirred at 20° C. for 10 min and a solution of N-(4-(2,7-diazaspiro[3.5]nonan-2-yl)piperidin-1-yl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (76 mg, crude, TFA) and DIPEA (55.18 mg, 426.97 μmol, 74.37 μL) in DMF (2 mL) was added and the resulting mixture was stirred at 20° C. for 1 h. LCMS showed starting material was consumed completely and a peak (48%) with desired mass. The reaction mixture was diluted with H$_2$O (12 mL) and extracted with EtOAc (12 mL×3). The organic layer was dried over Na$_2$SO$_4$, filtered and concentrated to afford product A which was purified by prep-HPLC (column: Unisil 3-100 C18 Ultra 150*50 mm*3 μm; mobile phase: [water (FA)-ACN]; B %: 5%-35%, 7 min) and lyophilization to afford product C. The aqueous phase was concentrated in vacuum which was purified by prep-HPLC (column: Unisil 3-100 C18 Ultra 150*50 mm*3 μm; mobile phase: [water (FA)-ACN]; B %: 6%-36%, 7 min) and lyophilization to afford product D. The product C and product D were combined and re-purified by prep-HPLC (column: Waters Xbridge 150*25 mm*5 μm; mobile phase: [water (NH$_4$HCO$_3$)-ACN]; B %: 28%-58%, 9 min) to afford 4-((7,7-difluoro-9-isopropyl-5-methyl-6-oxo-6,7,8,9-tetrahydro-5H-pyrimido[4,5-b][1,4]diazepin-2-yl)amino)-N-(4-(7-(3-(2,4-dioxotetrahydropyrimidin-1(2H)-yl)benzoyl)-2,7-diazaspiro[3.5]nonan-2-yl)piperidin-1-yl)-3-methoxybenzamide (3 mg, 3.45 μmol, 4.04% yield, 97% purity) as a white solid. MS (M+H)$^+$=844.3

$^1$H NMR (400 MHz, CD$_3$CN) δ=8.47 (d, J=8.4 Hz, 1H), 8.23 (s, 1H), 8.10-8.00 (m, 2H), 7.66 (s, 1H), 7.48-7.36 (m, 4H), 7.33 (t, J=1.7 Hz, 1H), 7.26-7.21 (m, 1H), 5.04-4.90 (m, 1H), 3.97 (s, 3H), 3.95-3.89 (m, 2H), 3.87-3.75 (m, 6H), 3.68-3.53 (m, 2H), 3.39-3.26 (m, 5H), 3.18 (d, J=11.5 Hz, 2H), 3.11-2.98 (m, 1H), 2.81 (t, J=10.8 Hz, 2H), 2.74 (t, J=6.7 Hz, 2H), 1.91-1.72 (m, 8H), 1.29 (s, 3H), 1.27 (s, 3H)

Example 48. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(9-(3-(2,4-dioxotetrahydropyrimidin-1(2H)-yl)benzoyl)-3,9-diazaspiro[5.5]undecan-3-yl)-3-methoxybenzamide (Compound 48)

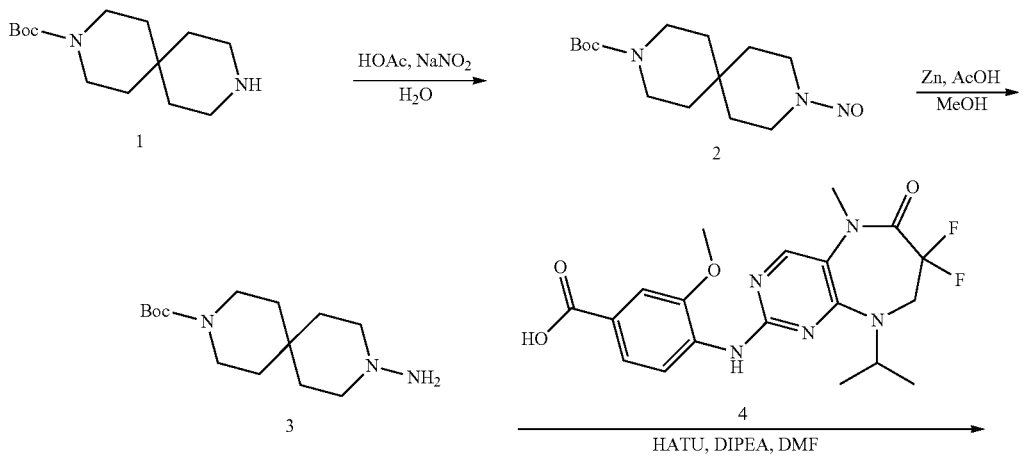

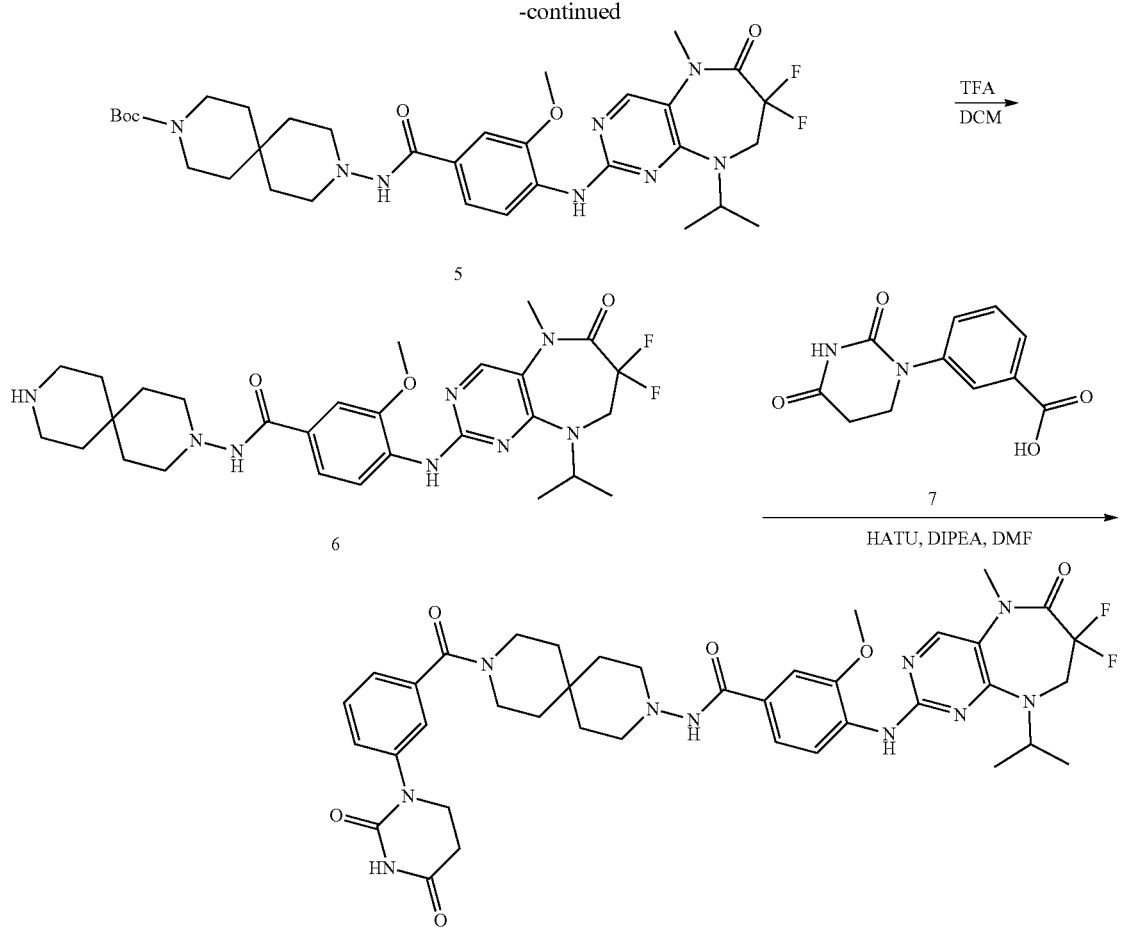

Compound 48

Step 1. Synthesis of tert-butyl 9-nitroso-3,9-diazaspiro[5.5]undecane-3-carboxylate (2)

To a solution of tert-butyl 3,9-diazaspiro[5.5]undecane-3-carboxylate (2 g, 7.86 mmol) in H$_2$O (20 mL) was added NaNO$_2$ (1.08 g, 15.73 mmol) at 0° C., then was added AcOH (1.42 g, 23.59 mmol, 1.35 mL) drop-wise at 0° C. and the resulting mixture was at 20° C. for 12 h. LCMS showed starting material was consumed completely and 90% peak with desired mass was detected. The reaction mixture was diluted with H$_2$O (100 mL) and extracted with EtOAc (100 mL×3). The organic layer was washed with brine (100 mL×3), dried over Na$_2$SO$_4$, filtered and concentrated to afford tert-butyl 9-nitroso-3,9-diazaspiro[5.5]undecane-3-carboxylate (1.8 g, 6.16 mmol, 78.37% yield, 97% purity) as a yellow oil. MS (M−56+H)$^+$=228.4

Step 2. Synthesis of tert-butyl 9-amino-3,9-diazaspiro[5.5]undecane-3-carboxylate (3)

To a solution of tert-butyl 9-nitroso-3,9-diazaspiro[5.5]undecane-3-carboxylate (1.8 g, 6.35 mmol) in MeOH (25 mL) was added Zn (2.16 g, 33.03 mmol) at 0° C., then AcOH (5.72 g, 95.28 mmol, 5.45 mL) was added drop-wise at 0° C. and the resulting mixture was at 20° C. for 3 h. LCMS showed 60% of starting material remained and 26% peak with desired mass was detected, and the mixture was at 20° C. for 12 h. LCMS showed starting material was consumed completely and 65% peak with desired mass was detected. The reaction mixture was diluted with MeOH (60 mL) and filtered. The filtrate was concentrated in vacuum to afford tert-butyl 9-amino-3,9-diazaspiro[5.5]undecane-3-carboxylate (7.5 g, crude) as a yellow oil. MS (M+H)$^+$=270.3

Step 3. Synthesis of tert-butyl 9-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-3,9-diazaspiro[5.5]undecane-3-carboxylate (5)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (400 mg, 949.22 μmol) in DMF (4 mL) were added HATU (397.02 mg, 1.04 mmol) and DIPEA (245.36 mg, 1.90 mmol, 330.68 μL), the mixture was stirred at 20° C. for 10 min and a solution of tert-butyl 9-amino-3,9-diazaspiro[5.5]undecane-3-carboxylate (1.25 g, crude) and DIPEA (613.40 mg, 4.75 mmol, 826.69 μL) in DMF (4 mL) was added and the resulting mixture was stirred at 20° C. for 1 h. LCMS showed starting material was consumed completely and peak with desired mass was detected. The reaction mixture was diluted with H$_2$O (20 mL) and extracted with EtOAc (20 mL×3). The organic layer was washed with brine (20 mL×3), dried over Na$_2$SO$_4$, filtered and concentrated. The residue was purified by flash silica gel chromatography (12 g SepaFlash Silica Flash Column, Eluent of 0~100% EtOAc/Petroleum ether to 0~12% Dichloromethane/Methanol gradient @ 100 mL/min) to afford product A (262 mg, 66% purity) and product B (351 mg, 19% purity). The two batches product were re-purified by prep-HPLC (column: Unisil 3-100 C18 Ultra 150*50 mm*3 µm; mobile phase: [water (FA)-ACN]; B %: 40%-70%, 7 min) and combined with lyophilization to afford tert-butyl 9-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-3,9-diazaspiro[5.5]undecane-3-carboxylate (62 mg, 91.24 µmol, 9.61% yield, 99% purity) as a white solid. MS (M+H)$^+$=673.2

Step 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(3,9-diazaspiro[5.5]undecan-3-yl)benzamide (6)

To a solution of tert-butyl 9-(4-((7,7-difluoro-9-isopropyl-5-methyl-6-oxo-6,7,8,9-tetrahydro-5H-pyrimido[4,5-b][1,4]diazepin-2-yl)amino)-3-methoxybenzamido)-3,9-diazaspiro[5.5]undecane-3-carboxylate (62 mg, 92.16 µmol) in DCM (2 mL) was added TFA (31.52 mg, 276.42 µmol, 20.47 µL) at 20° C. and the resulting mixture was stirred at 20° C. for 1 h. LCMS showed starting material was consumed completely and 96% peak with desired mass was detected. The reaction mixture was concentrated in vacuum to afford 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(3,9-diazaspiro[5.5]undecan-3-yl)benzamide (78 mg, crude, TFA) as a yellow oil. MS (M+H)$^+$=573.3

Step 5. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(9-(3-(2,4-dioxotetrahydropyrimidin-1(2H)-yl)benzoyl)-3,9-diazaspiro[5.5]undecan-3-yl)-3-methoxybenzamide (Compound 48)

To a solution of 3-(2,4-dioxohexahydropyrimidin-1-yl)benzoic acid (23 mg, 98.20 µmol) in DMF (1 mL) were added HATU (41.07 mg, 108.02 µmol) and DIPEA (25.38 mg, 196.41 µmol, 34.21 µL), the mixture was stirred at 20° C. for 10 min and a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxy-N-(3,9-diazaspiro[5.5]undecan-3-yl)benzamide (74.18 mg, crude, TFA) and DIPEA (50.77 mg, 392.81 µmol, 68.42 µL) in DMF (1 mL) was added and the resulting mixture was stirred at 20° C. for 1 h. LCMS showed starting material was consumed completely and 54% peak with desired mass was detected. The reaction mixture was diluted with H$_2$O (10 mL) and extracted with EtOAc (10 mL×3). The organic layer was dried over Na$_2$SO$_4$, filtered and concentrated. The residue was purified by prep-HPLC (column: Unisil 3-100 C18 Ultra 150*50 mm*3 µm; mobile phase: [water (FA)-ACN]; B %: 24%-54%, 7 min) and lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-(9-(3-(2,4-dioxotetrahydropyrimidin-1(2H)-yl)benzoyl)-3,9-diazaspiro[5.5]undecan-3-yl)-3-methoxybenzamide (19.7 mg, 23.47 µmol, 23.90% yield, 94% purity) as a white solid. MS (M+H)$^+$=789.4

$^1$H NMR (400 MHz, DMSO-d$_6$) δ=10.42 (s, 1H), 9.29 (s, 1H), 8.30 (d, J=8.3 Hz, 1H), 8.22 (s, 1H), 7.87 (s, 1H), 7.50-7.35 (m, 5H), 7.24 (d, J=7.5 Hz, 1H), 4.94-4.79 (m, 1H), 4.03 (t, J=13.5 Hz, 2H), 3.93 (s, 3H), 3.83 (t, J=6.6 Hz, 2H), 3.69-3.54 (m, 2H), 3.33-3.30 (m, 5H), 2.95-2.82 (m, 4H), 2.72 (t, J=6.6 Hz, 2H), 1.70-1.56 (m, 4H), 1.56-1.41 (m, 4H), 1.24 (d, J=6.7 Hz, 6H)

Example 49. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,4-dioxotetrahydropyrimidin-1(2H)-yl)benzoyl)piperazin-1-yl)methyl)piperidin-1-yl)-3-methoxybenzamide (Compound 49)

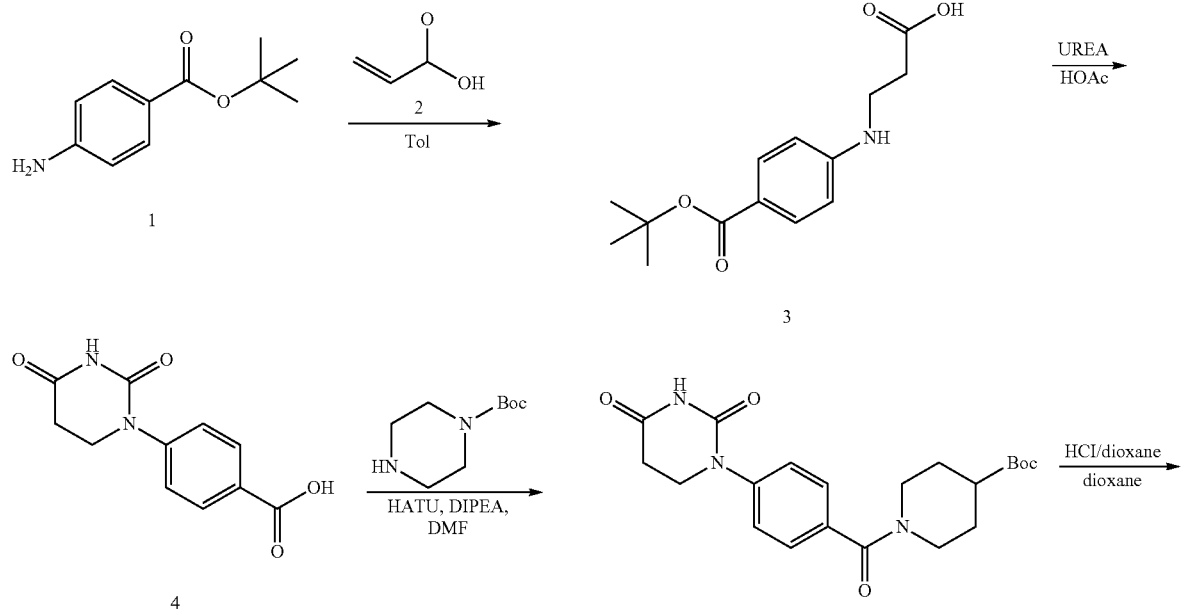

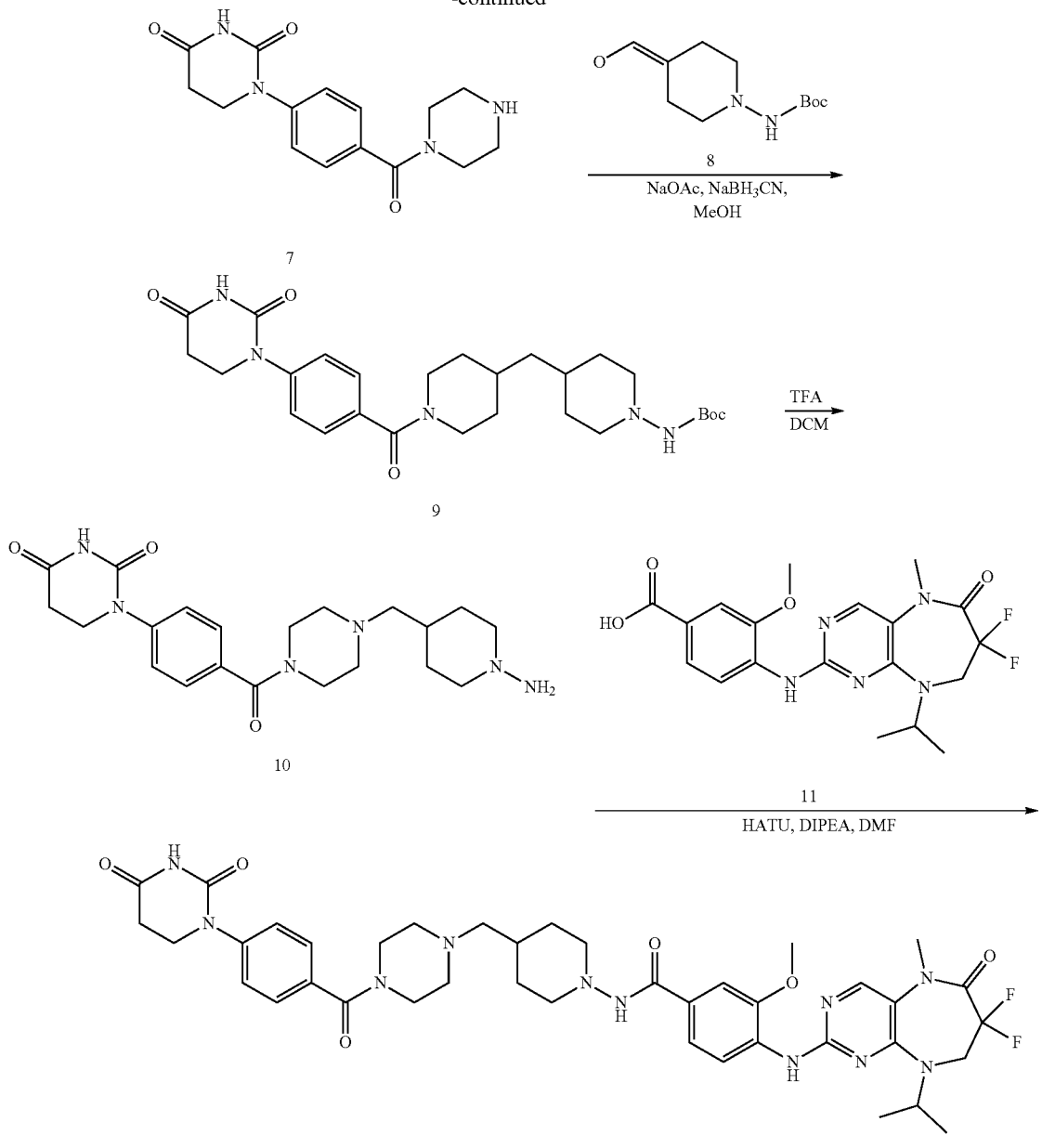

Compound 49

Step 1. Synthesis of 3-((4-(tert-butoxycarbonyl)phenyl)amino)propanoic Acid (3)

A mixture of tert-butyl 4-aminobenzoate (1 g, 5.17 mmol) and acrylic acid (410.21 mg, 5.69 mmol, 390.67 μL) in toluene (10 mL) was stirred at 100° C. for 16 h. LCMS showed a main peak with desired mass. The mixture was concentrated under reduced pressure. The residue was triturated with n-hexane (10 mL) at 20° C. for 10 min to afford 3-((4-(tert-butoxycarbonyl)phenyl)amino)propanoic acid (1 g, 3.77 mmol, 72.84% yield, 100% purity) as a yellow solid. MS (M−56+H)$^+$=266.1.

Step 2. Synthesis of 4-(2,4-dioxotetrahydropyrimidin-1(2H)-yl)benzoic Acid (4)

A mixture of 3-((4-(tert-butoxycarbonyl)phenyl)amino) propanoic acid (1 g, 3.77 mmol) and UREA (2.26 g, 37.69 mmol, 2.02 mL) in AcOH (10 mL) was stirred at 120° C. for 16 h. LCMS showed a main peak with desired mass. The mixture was concentrated under reduced pressure. The crude product was triturated with THF:MTBE ~1:1 (10 mL) at 20° C. for 10 min to afford 4-(2,4-dioxotetrahydropyrimidin-1 (2H)-yl)benzoic acid (700 mg, 2.63 mmol, 69.78% yield, 88% purity) as a yellow solid. MS (M−56+H)$^+$=235.0.

Step 3. Synthesis of tert-butyl 4-(4-(2,4-dioxotetrahydropyrimidin-1(2H)-yl)benzoyl)piperazine-1-carboxylate (6)

To a solution of 4-(2,4-dioxotetrahydropyrimidin-1(2H)-yl)benzoic acid (300 mg, 1.28 mmol) in DMF (8 mL) were added HATU (730.56 mg, 1.92 mmol) and DIPEA (496.65 mg, 3.84 mmol, 669.34 µL), and the mixture was stirred at 20° C. for 1 h. Then tert-butyl piperazine-1-carboxylate (285.27 mg, 1.28 mmol) was added and the resulting mixture was stirred at 20° C. for 16 h. LCMS showed a main peak with desired mass. The reaction mixture was diluted with $H_2O$ (30 mL), extracted with EtOAc (30 mL×3). The combined organic layers were washed with brine (50 mL×2), dried over $Na_2SO_4$, filtered. The filtrate was concentrated under reduced pressure. The residue was purified by flash silica gel chromatography (Biotage; 20 g SepaFlash Silica Flash Column, Eluent of 20~100% EtOAc/Petroleum ether @ 40 mL/min) followed by trituration with EA (10 mL) at 20° C. for 10 min to afford tert-butyl 4-(4-(2,4-dioxotetrahydropyrimidin-1(2H)-yl)benzoyl)piperazine-1-carboxylate (145 mg, 342.28 µmol, 26.72% yield, 95% purity) as a yellow solid. MS (M−56+H)$^+$=347.1.

Step 4. Synthesis of 1-(4-(piperazine-1-carbonyl)phenyl)dihydropyrimidine-2,4(1H,3H)-dione (7)

To a solution of tert-butyl 4-(4-(2,4-dioxotetrahydropyrimidin-1(2H)-yl)benzoyl)piperazine-1-carboxylate (145 mg, 360.30 µmol) in dioxane (2 mL) was added HCl/dioxane (4 M, 2 mL), the mixture was stirred at 20° C. for 0.5 h. LCMS showed a main peak with desired mass. The mixture was concentrated in vacuum to afford 1-(4-(piperazine-1-carbonyl)phenyl)dihydropyrimidine-2,4(1H,3H)-dione (120 mg, crude, HCl salt) as a white solid, which was used into the next step directly. MS (M+H)$^+$=303.2.

Step 5. Synthesis of tert-butyl (4-((4-(4-(2,4-dioxotetrahydropyrimidin-1(2H)-yl)benzoyl)piperazin-1-yl)methyl)piperidin-1-yl)carbamate (9)

To a solution of 1-(4-(piperazine-1-carbonyl)phenyl)dihydropyrimidine-2,4(1H,3H)-dione (120 mg, 354.20 µmol, HCl salt) in MeOH (2 mL) was added tert-butyl (4-formylpiperidin-1-yl)carbamate (161.72 mg, 708.41 µmol) and NaOAc (58.11 mg, 708.41 µmol), and the mixture was stirred at 20° C. for 0.5 h, then NaBH$_3$CN (66.78 mg, 1.06 mmol) was added and the resulting mixture was stirred at 20° C. for 2 h. LCMS showed a main peak with desired mass. The reaction mixture was diluted with $H_2O$ (10 mL), extracted with EtOAc (10 mL×3). The combined organic layers were washed with brine (20 mL×2), dried over $Na_2SO_4$, filtered. The filtrate was concentrated under reduced pressure. The residue was purified by flash silica gel chromatography (Biotage; 20 g SepaFlash Silica Flash Column, Eluent of 20~100% EtOAc/Petroleum ether to 10% Methanol/EtOAc gradient @ 40 mL/min) followed by prep-TLC (SiO$_2$, DCM:MeOH=10:1) to afford tert-butyl (4-((4-(4-(2,4-dioxotetrahydropyrimidin-1(2H)-yl)benzoyl)piperazin-1-yl)methyl)piperidin-1-yl)carbamate (162 mg, 280.17 µmol, 79.10% yield, 89% purity) as a white solid. MS (M+H)$^+$=515.1

Step 6. Synthesis of 1-(4-(4-((1-aminopiperidin-4-yl)methyl)piperazine-1-carbonyl)phenyl) dihydropyrimidine-2,4(1H,3H)-dione (10)

To a solution of tert-butyl (4-((4-(4-(2,4-dioxotetrahydropyrimidin-1(2H)-yl)benzoyl)piperazin-1-yl)methyl)piperidin-1-yl)carbamate (160 mg, 310.91 µmol) in DCM (5 mL) was added TFA (1.54 g, 13.51 mmol, 1 mL), the mixture was stirred at 20° C. for 1 h. LCMS showed a main peak with desired mass. The mixture was concentrated in vacuum to afford 1-(4-(4-((1-aminopiperidin-4-yl)methyl)piperazine-1-carbonyl)phenyl)dihydropyrimidine-2,4(1H,3H)-dione (160 mg, crude, TFA salt) as a brown oil, which was used into the next step directly. MS (M+H)$^+$=415.0.

Step 7. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,4-dioxotetrahydropyrimidin-1(2H)-yl)benzoyl)piperazin-1-yl)methyl)piperidin-1-yl)-3-methoxybenzamide (Compound 49)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (63.78 mg, 151.37 µmol) in DMF (3 mL) was added HATU (86.33 mg, 227.05 µmol) and DIPEA (58.69 mg, 454.10 µmol, 79.10 µL), the mixture was stirred at 20° C. for 0.5 h, 1-(4-(4-((1-aminopiperidin-4-yl)methyl)piperazine-1-carbonyl)phenyl)dihydropyrimidine-2,4(1H,3H)-dione (80 mg, 151.37 µmol, TFA salt) was added and the resulting mixture was stirred at 20° C. for 16 h. LCMS showed a main peak with desired mass. The reaction mixture was diluted with brine (10 mL), extracted with EtOAc (10 mL×3). The combined organic layers were washed with brine (20 mL×2), dried over $Na_2SO_4$, filtered. The filtrate was concentrated under reduced pressure. The residue was purified by prep-TLC (SiO$_2$, DCM:MeOH=10:1) and re-purified by reversed-phase HPLC (column: Waters Xbridge 150×25 mm×5 µm; mobile phase: [water (NH$_4$HCO$_3$)-ACN]; B %: 28%-58%, 9 min). The eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,4-dioxotetrahydropyrimidin-1(2H)-yl)benzoyl)piperazin-1-yl)methyl)piperidin-1-yl)-3-methoxybenzamide (7.0 mg, 8.30 µmol, 5.48% yield, 97% purity) as a white solid. MS (M+H)$^+$=818.4.

$^1$H NMR (400 MHz, DMSO-d$_6$) δ=10.45 (s, 1H), 9.27 (s, 1H), 8.29 (d, J=8.3 Hz, 1H), 8.21 (s, 1H), 7.88 (s, 1H), 7.45-7.36 (m, 6H), 4.93-4.80 (m, 1H), 4.09-3.98 (m, 2H), 3.93 (s, 3H), 3.83 (t, J=6.7 Hz, 2H), 3.70-3.53 (m, 2H), 3.32-3.31 (m, 5H), 3.04-2.98 (m, 2H), 2.79-2.70 (m, 4H), 2.42-2.33 (m, 4H), 2.25-2.15 (m, 2H), 1.80-1.68 (m, 2H), 1.59-1.45 (m, 1H), 1.30-1.20 (m, 8H).

Example 50. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,4-dioxotetrahydropyrimidin-1(2H)-yl)-3-methoxybenzoyl)piperazin-1-yl)methyl)piperidin-1-yl)-3-methoxybenzamide (Compound 50)
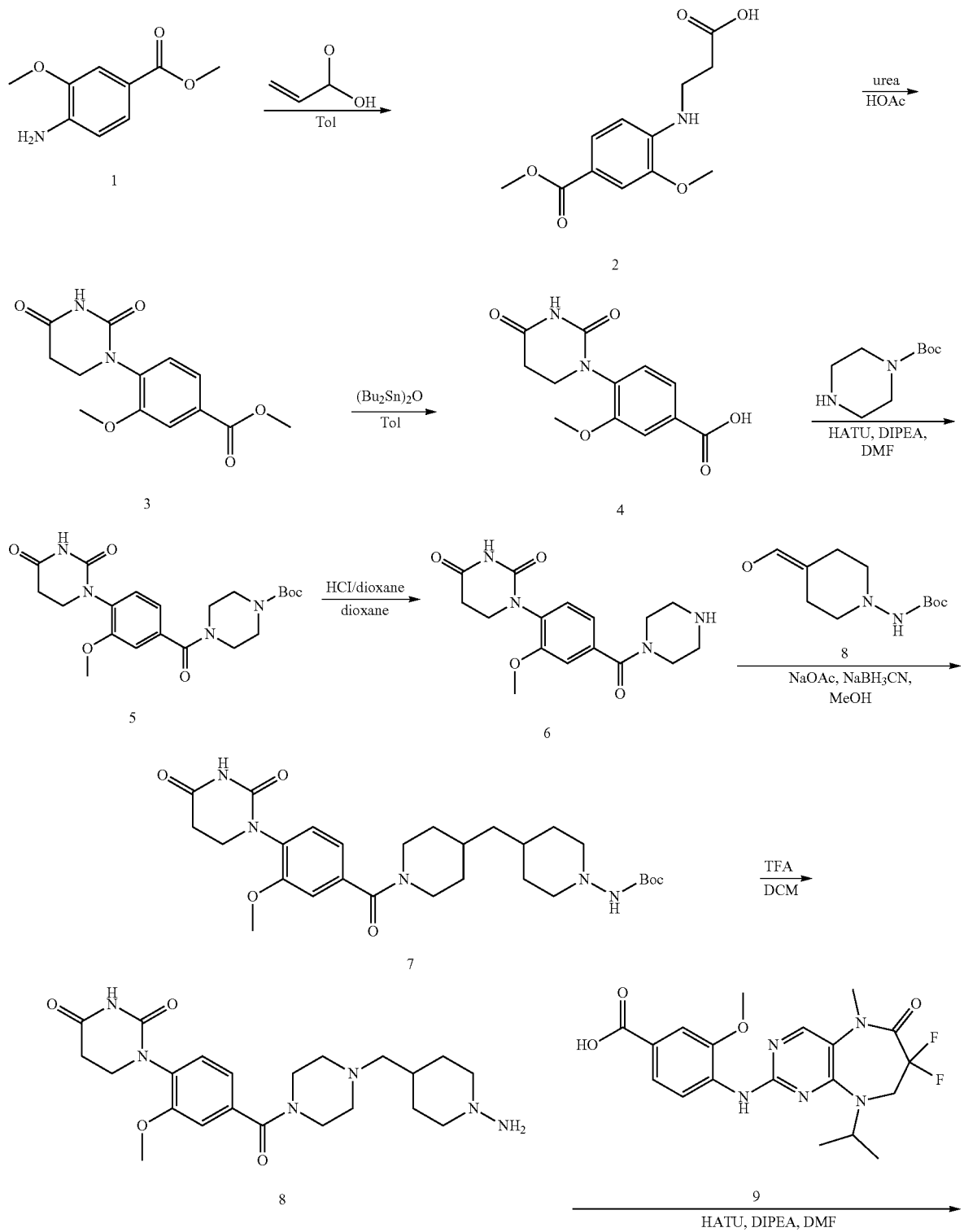

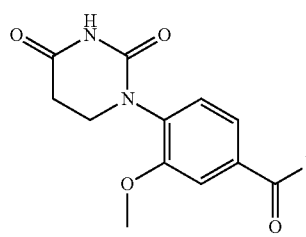

Compound 50

Step 1. Synthesis of 3-((2-methoxy-4-(methoxycarbonyl)phenyl)amino)propanoic Acid (2)

A mixture of methyl 4-amino-3-methoxybenzoate (1.8 g, 9.93 mmol) and acrylic acid (1.07 g, 14.90 mmol, 1.02 mL) in Tol (20 mL) was stirred at 100° C. for 16 h. LCMS showed a peak (84%) with desired mass. The mixture was concentrated under reduced pressure. The crude product was triturated with n-hexane (10 mL) at 20° C. for 10 min, the solid was collected and in vacuo to afford 3-((2-methoxy-4-(methoxycarbonyl)phenyl)amino)propanoic acid (2.5 g, 9.77 mmol, 98.37% yield, 99% purity) as a yellow solid. MS (M+H)$^+$=254.0

Step 2. Synthesis of methyl 4-(2,4-dioxotetrahydropyrimidin-1(2H)-yl)-3-methoxybenzoate (3)

To a solution of 3-((2-methoxy-4-(methoxycarbonyl)phenyl)amino)propanoic acid (2.5 g, 9.87 mmol) in AcOH (30 mL) was added UREA (5.93 g, 98.72 mmol, 5.29 mL), the mixture was stirred at 120° C. for 18 h. LCMS showed a peak (64%) with desired mass. The reaction mixture was concentrated under reduced pressure. The crude product was triturated with MTBE (10 mL) at 20° C. for 10 min, the solid was collected and in vacuo to afford methyl 4-(2,4-dioxotetrahydropyrimidin-1(2H)-yl)-3-methoxybenzoate (1 g, 3.56 mmol, 36.04% yield, 99% purity) as a white solid. MS (M+H)$^+$=279.0.

Step 3. Synthesis of 4-(2,4-dioxotetrahydropyrimidin-1(2H)-yl)-3-methoxybenzoic Acid (4)

To a solution of methyl 4-(2,4-dioxotetrahydropyrimidin-1(2H)-yl)-3-methoxybenzoate (500 mg, 1.80 mmol) in Tol. (10 mL) was added (Bu$_3$Sn)$_2$O (3.3 g, 5.54 mmol, 2.82 mL), the mixture was stirred at 110° C. for 16 h. LCMS showed a peak (45%) with desired mass. The mixture was poured into KF (2.5M, 20 mL), stirred at 20° C. for 0.5 h, then washed with EtOAc (10 mL), the EtOAc layer was discarded. The aqueous layer was adjusted to pH=6 by using 1 N HCl, extracted with EtOAc (3×20 mL), the combined organic layers was dried over Na$_2$SO$_4$, filtered and concentrated under reduced pressure to afford 4-(2,4-dioxotetrahydropyrimidin-1(2H)-yl)-3-methoxybenzoic acid (300 mg, crude) as a white solid. MS (M+H)$^+$=265.0

Step 4. Synthesis of tert-butyl 4-(4-(2,4-dioxotetrahydropyrimidin-1(2H)-yl)-3-methoxybenzoyl)piperazine-1-carboxylate (5)

To a solution of 4-(2,4-dioxotetrahydropyrimidin-1(2H)-yl)-3-methoxybenzoic acid (200 mg, 756.91 μmol) in DMF (2 mL) were added HATU (431.70 mg, 1.14 mmol) and DIPEA (293.47 mg, 2.27 mmol, 395.52 μL), the mixture was stirred at 20° C. for 0.5 h, tert-butyl piperazine-1-carboxylate (140.97 mg, 756.91 μmol) was added, and the mixture was stirred at 20° C. for 16 h. LCMS showed a peak (33%) with desired mass. The reaction mixture was diluted with H$_2$O (2 mL) and EtOAc (2 mL), filtered. The filter cake was dried in vacuum. The solid was triturated with MTBE (5 mL) at 20° C. for 10 min, the solid was collected and dried in vacuo to afford tert-butyl 4-(4-(2,4-dioxotetrahydropyrimidin-1(2H)-yl)-3-methoxybenzoyl)piperazine-1-carboxylate (190 mg, 404.19 μmol, 53.40% yield, 92% purity) as a yellow solid. MS (M-Boc+H)$^+$=332.9.

Step 5. Synthesis of 1-(2-methoxy-4-(piperazine-1-carbonyl)phenyl)dihydropyrimidine-2,4(1H,3H)-dione (6)

To a solution of tert-butyl 4-(4-(2,4-dioxotetrahydropyrimidin-1(2H)-yl)-3-methoxybenzoyl)piperazine-1-carboxylate (190 mg, 439.34 μmol) in dioxane (3 mL) was added HCl/dioxane (4 M, 109.83 μL), the mixture was stirred at 20° C. for 2 hr. LCMS showed a main peak with desired mass, the mixture was concentrated under vacuum to afford 1-(2-methoxy-4-(piperazine-1-carbonyl)phenyl)dihydropyrimidine-2,4(1H,3H)-dione (180 mg, crude) as a gray powder. MS (M+H)$^+$=333.1.

Step 6. Synthesis of tert-butyl (4-((4-(4-(2,4-dioxotetrahydropyrimidin-1(2H)-yl)-3-methoxybenzoyl)piperazin-1-yl)methyl)piperidin-1-yl)carbamate (7)

To a solution of 1-(2-methoxy-4-(piperazine-1-carbonyl)phenyl)dihydropyrimidine-2,4(1H,3H)-dione (140 mg, 379.59 μmol, HCl) in MeOH (7 mL) were added NaOAc (62.28 mg, 759.19 μmol) and tert-butyl (4-formylpiperidin-1-yl)carbamate (173.31 mg, 759.19 μmol), after stirring at 20° C. for 0.5 h, then NaBH$_3$CN (35.78 mg, 569.39 μmol) was added and the resulting mixture was stirred at 20° C. for 12 h. LCMS showed desired mass, the mixture was diluted with water (5 mL), extracted with EtOAc (5 mL×2). The aqueous layer was adjusted pH to 7~8 by NaHCO$_3$ solution, then extracted with EtOAc (5 mL×3), the combined organic layer was dried over Na$_2$SO$_4$, filtered and concentrated under vacuum to afford tert-butyl (4-((4-(4-(2,4-dioxotetrahydropyrimidin-1(2H)-yl)-3-methoxybenzoyl)piperazin-1-yl)methyl)piperidin-1-yl)carbamate (140 mg, crude) as a white powder. MS (M+H)$^+$=545.4

Step 7. Synthesis of 1-(4-(4-((1-aminopiperidin-4-yl)methyl)piperazine-1-carbonyl)-2-methoxyphenyl)dihydropyrimidine-2,4(1H,3H)-dione (8)

To a solution of tert-butyl (4-((4-(4-(2,4-dioxotetrahydropyrimidin-1(2H)-yl)-3-methoxybenzoyl)piperazin-1-yl)methyl)piperidin-1-yl)carbamate (80 mg, 146.89 μmol) in DCM (0.5 mL) was added TFA (100.49 mg, 881.31 μmol, 65.25 μL), the mixture was stirred at 20° C. for 1 hr. LCMS showed the desired mass, the mixture was concentrated under vacuum to afford 1-(4-(4-((1-aminopiperidin-4-yl)methyl)piperazine-1-carbonyl)-2-methoxyphenyl)dihydropyrimidine-2,4(1H,3H)-dione (85 mg, crude, TFA) as yellow oil. MS (M+H)$^+$=445.2.

Step 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,4-dioxotetrahydropyrimidin-1(2H)-yl)-3-methoxybenzoyl)piperazin-1-yl)methyl)piperidin-1-yl)-3-methoxybenzamide (Compound 50)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (60 mg, 142.38 μmol) in DMF (1 mL) were added HATU (81.21 mg, 213.58 μmol) and DIPEA (92.01 mg, 711.92 μmol, 124.00 μL), then 1-(4-(4-((1-aminopiperidin-4-yl)methyl)piperazine-1-carbonyl)-2-methoxyphenyl)dihydropyrimidine-2,4(1H,3H)-dione (79.53 mg, 142.38 μmol, TFA salt) was added and the resulting mixture was stirred at 20° C. for 16 hr. LCMS showed the starting material consumed completely and a peak with desired mass. The mixture was diluted with water (2 mL), extracted with EtOAc (2 mL×3). The organic layer was dried over Na$_2$SO$_4$, filtered and concentrated under vacuum. The crude product was purified by Prep-HPLC (column: Phenomenex Synergi Polar-RP 100*25 mm*4 μm; mobile phase: [water (TFA)-ACN]; B %: 23%-43%, 7 min) and Prep-HPLC (column: Waters Xbridge 150*25 mm*5 μm; mobile phase: [water (NH$_4$HCO$_3$)-ACN]; B %: 29%-59%, 9 min), the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,4-dioxotetrahydropyrimidin-1(2H)-yl)-3-methoxybenzoyl)piperazin-1-yl)methyl)piperidin-1-yl)-3-methoxybenzamide (13.5 mg, 15.83 μmol, 11.12% yield, 99.4% purity) as a white solid. MS (M+H)$^+$=848.5.

$^1$H NMR (400 MHz, DMSO-d$_6$) δ=10.36 (s, 1H), 9.27 (s, 1H), 8.30 (d, J=8.31 Hz, 1H), 8.22 (s, 1H), 7.88 (s, 1H), 7.46-7.42 (m, 2H), 7.32 (d, J=7.95 Hz, 1H), 7.10 (d, J=1.47 Hz, 1H), 6.98 (dd, J=7.89, 1.53 Hz, 1H), 4.88 (dt, J=13.36, 6.59 Hz, 1H), 4.04 (t, J=13.57 Hz, 2H), 3.93 (s, 3H), 3.84 (s, 3H), 3.60 (t, J=6.60 Hz, 4H), 3.33 (s, 3H), 3.31 (s, 2H), 3.01 (d, J=10.27 Hz, 2H), 2.75 (t, J=10.33 Hz, 2H), 2.69 (t, J=6.54 Hz, 2H), 2.45-2.32 (m, 4H), 2.20 (d, J=6.72 Hz, 2H), 1.76 (d, J=11.62 Hz, 2H), 1.51 (d, J=10.39 Hz, 1H), 1.25 (d, J=6.72 Hz, 8H).

Example 51. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(3-(2,4-dioxotetrahydropyrimidin-1(2H)-yl)-4-methoxybenzoyl)piperazin-1-yl)methyl)piperidin-1-yl)-3-methoxybenzamide (Compound 51)

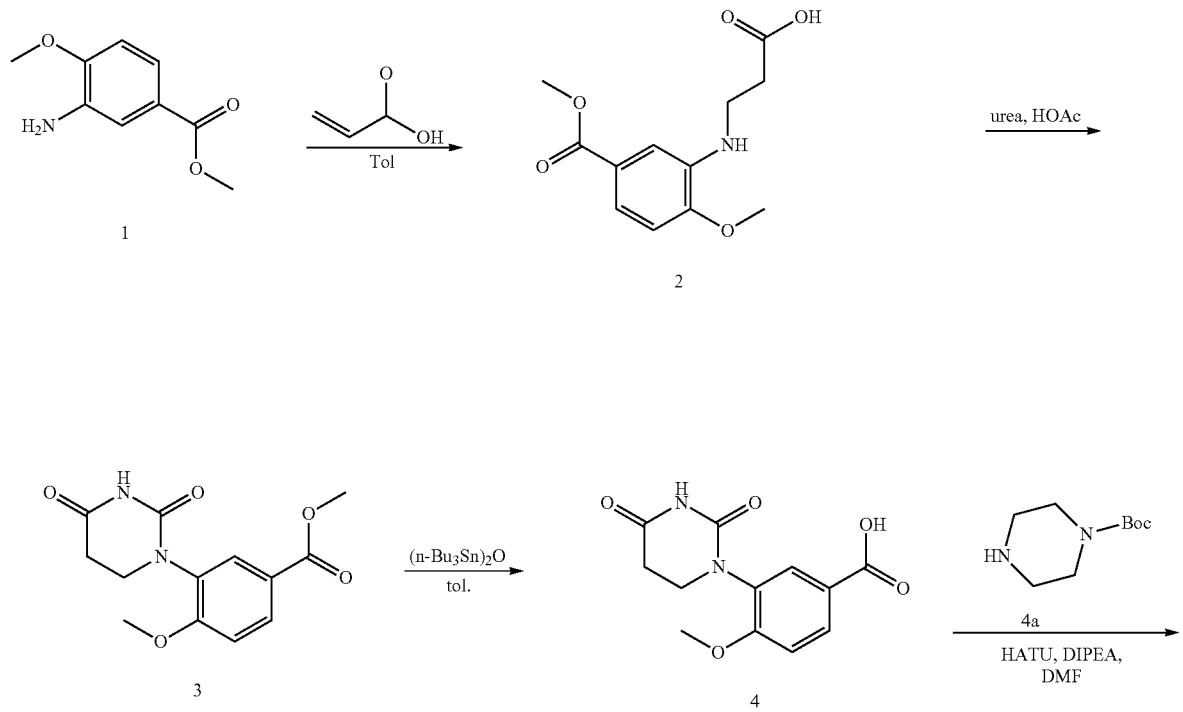

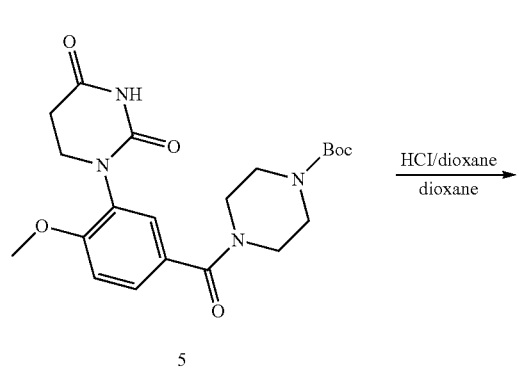
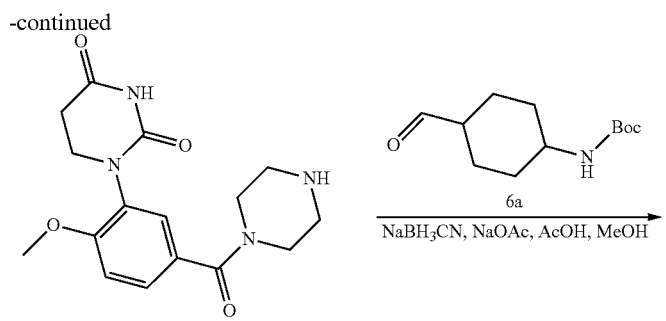
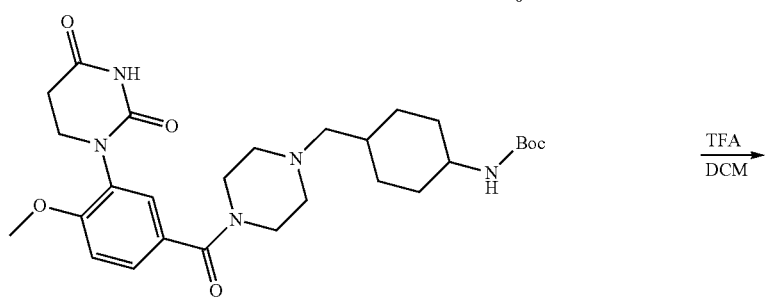
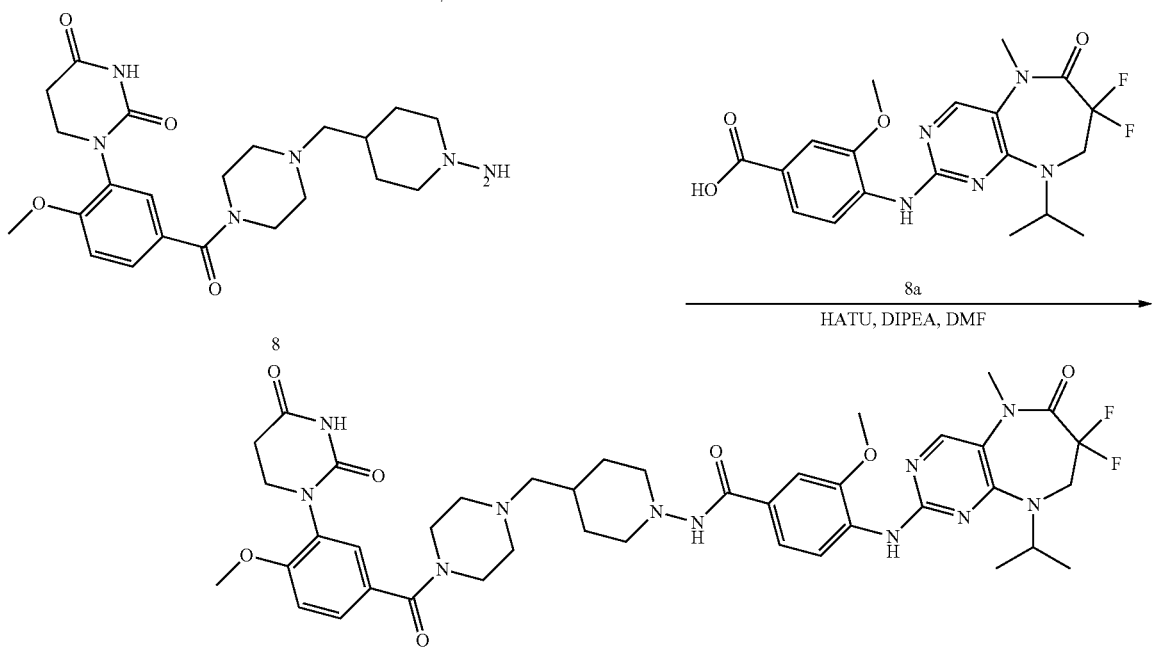

Compound 51

Step 1. Synthesis of 3-((2-methoxy-5-(methoxycarbonyl)phenyl)amino)propanoic Acid (2)

A mixture of acrylic acid (1.79 g, 24.84 mmol, 1.70 mL) and methyl 3-amino-4-methoxybenzoate (3 g, 16.56 mmol) in Tol. (40 mL) was stirred at 100° C. for 12 hr. LCMS showed a main peak with desired mass. The mixture solution was concentrated under reduced pressure. The crude product was triturated with Petroleum ether:EtOAc=8:1 (30 mL) and stirred for 0.5 h. Then the suspension was filtered. The filter cake was collected and dried to afford 3-((2-methoxy-5-(methoxycarbonyl)phenyl)amino)propanoic acid (3.6 g, 13.79 mmol, 83.28% yield, 97% purity) as a brown solid, which was used for the next step directly. MS (M+H)$^+$=254.0

Step 2. Synthesis of methyl 3-(2,4-dioxotetrahydropyrimidin-1(2H)-yl)-4-methoxybenzoate (3)

To a solution of 3-((2-methoxy-5-(methoxycarbonyl)phenyl)amino)propanoic acid (3.6 g, 14.22 mmol) in AcOH (30 mL) was added UREA (8.54 g, 142.15 mmol, 7.62 mL), the mixture was stirred at 120° C. for 12 hr. LCMS showed the starting material was consumed completely, and a main peak with desired mass. The mixture was poured into water (80 mL) and EtOAc (30 mL), then extracted with EtOAc (20 mL×3). The combined organic phase was washed with brine (10 mL×3), dried over $Na_2SO_4$, filtered and concentrated under reduced pressure. The crude product was triturated with Petroleum ether:EtOAc:Methanol=15:15:2 (32 mL) and stirred for 0.5 h. Then the suspension was filtered. The filter cake was collected and dried in vacuo to afford methyl 3-(2,4-dioxotetrahydropyrimidin-1(2H)-yl)-4-methoxybenzoate (2.8 g, 10.06 mmol, 70.79% yield, 100% purity) as a brown solid, which was used for the next step directly. MS $(M+H)^+$=279.0

Step 3. Synthesis of 3-(2,4-dioxotetrahydropyrimidin-1(2H)-yl)-4-methoxybenzoic Acid (4)

A mixture of methyl 3-(2,4-dioxotetrahydropyrimidin-1(2H)-yl)-4-methoxybenzoate (0.5 g, 1.80 mmol) and tributyl (tributylstannyloxy)stannane (6.51 g, 10.78 mmol, 5.56 mL) in toluene (5 mL) was stirred at 110° C. for 16 hr. LCMS showed the starting material was consumed completely, and a peak (44%) with desired mass. The mixture was poured into KF (2.5M, 30 mL) and washed with EtOAc (20 mL×2). The combined organic phase was discarded. The aqueous was adjusted the pH to 5 with 2M HCl aqueous solution, then extracted with EtOAc (30 mL×4). The combined organic layers were dried over $Na_2SO_4$ and concentrated to afford 3-(2,4-dioxotetrahydropyrimidin-1(2H)-yl)-4-methoxybenzoic acid (0.25 g, 936.67 μmol, 52.13% yield, 99% purity) as a white solid, which was used for the next step directly. MS $(M+H)^+$=265.0

Step 4. Synthesis of tert-butyl 4-(3-(2,4-dioxotetrahydropyrimidin-1(2H)-yl)-4-methoxybenzoyl)piperazine-1-carboxylate (5)

To a solution of 3-(2,4-dioxotetrahydropyrimidin-1(2H)-yl)-4-methoxybenzoic acid (370 mg, 1.40 mmol) in DMF (8 mL) were added HATU (638.91 mg, 1.68 mmol) and DIPEA (542.92 mg, 4.20 mmol, 731.69 μL), the mixture was stirred at 25° C. for 10 min, then tert-butyl piperazine-1-carboxylate (311.86 mg, 1.40 mmol) was added and the resulting mixture was stirred at 25° C. for 2 h. LCMS showed a peak (57%) with desired mass. The mixture was poured into water (80 mL) and extracted with EtOAc (20 mL×3). The combined organic phase was washed with brine (10 mL×3), dried over $Na_2SO_4$, filtered. The filtrate was concentrated under reduced pressure. The residue was purified by flash silica gel chromatography (12 g SepaFlash Silica Flash Column, Eluent of 0~100% EtOAc/Petroleum ether gradient @ 80 mL/min; Eluent of 0~50% Methanol/EtOAc @ 80 mL/min) to afford tert-butyl 4-(3-(2,4-dioxotetrahydropyrimidin-1(2H)-yl)-4-methoxybenzoyl)piperazine-1-carboxylate (480 mg, 932.32 μmol, 66.58% yield, 84% purity) as a brown solid, which was used for the next step directly. MS $(M-56+H)^+$=377.1

Step 5. Synthesis of 1-(2-methoxy-5-(piperazine-1-carbonyl)phenyl)dihydropyrimidine-2,4(1H,3H)-dione (6)

To a solution of tert-butyl 4-(3-(2,4-dioxotetrahydropyrimidin-1(2H)-yl)-4-methoxybenzoyl)piperazine-1-carboxylate (370 mg, 855.55 μmol) in dioxane (1 mL) was added HCl/dioxane (4 M, 10 mL) at 25° C. The mixture was stirred at 25° C. for 1 hr. LCMS showed the starting material was consumed completely. The mixture solution was concentrated under reduced pressure to afford 1-(2-methoxy-5-(piperazine-1-carbonyl)phenyl)dihydropyrimidine-2,4(1H,3H)-dione (315 mg, crude, HCl SALT) as a brown solid, which was used for the next step directly. MS $(M+H)^+$=333.1

Step 6. Synthesis of tert-butyl (4-((4-(3-(2,4-dioxotetrahydropyrimidin-1(2H)-yl)-4-methoxybenzoyl)piperazin-1-yl)methyl)piperidin-1-yl)carbamate (7)

A mixture of 1-(2-methoxy-5-(piperazine-1-carbonyl)phenyl)dihydropyrimidine-2,4(1H,3H)-dione (315 mg, 854.09 μmol, HCl) and AcONa (140.12 mg, 1.71 mmol) in MeOH (10 mL) was stirred at 25° C. for 0.5 hr, then tert-butyl (4-formylpiperidin-1-yl)carbamate (779.91 mg, 3.42 mmol) and AcOH (51.29 mg, 854.09 μmol, 48.89 μL) were added at 25° C. The mixture was stirred at 25° C. for 0.5 hr. In the end, $NaBH_3CN$ (107.35 mg, 1.71 mmol) was added at 25° C. and the resulting mixture was stirred at 25° C. for 12 h. LCMS showed the starting material was consumed completely, and a peak (3%) with desired mass. The reaction solution was concentrated. The crude product was dissolved in EtOAc (50 mL), washed with saturated $NaHCO_3$ (30 mL). The organic layer was dried over $Na_2SO_4$, filtered. The filtrate was concentrated under reduced pressure. The residue was purified by flash silica gel chromatography (4 g SepaFlash Silica Flash Column, Eluent of 0~100% EtOAc/Petroleum ether gradient to 0~50% Methanol/EtOAc gradient @ 60 mL/min) and re-purified by prep-HPLC (column: Unisil 3-100 C18 Ultra 150×50 mm×3 μm; mobile phase: [water (FA)-ACN]; B %: 1%-28%, 7 min), the eluent was lyophilized to afford tert-butyl (4-((4-(3-(2,4-dioxotetrahydropyrimidin-1(2H)-yl)-4-methoxybenzoyl)piperazin-1-yl)methyl)piperidin-1-yl)carbamate (80 mg, 145.42 μmol, 17.03% yield, 99% purity) as a yellow solid, which was used for the next step directly. MS $(M+H)^+$=545.2

Step 7. Synthesis of 1-(5-(4-((1-aminopiperidin-4-yl)methyl)piperazine-1-carbonyl)-2-methoxyphenyl)dihydropyrimidine-2,4(1H,3H)-dione (8)

To a solution of tert-butyl (4-((4-(3-(2,4-dioxotetrahydropyrimidin-1(2H)-yl)-4-methoxybenzoyl)piperazin-1-yl)methyl)piperidin-1-yl)carbamate (80 mg, 146.89 μmol) in DCM (2 mL) was added TFA (0.4 mL) at 25° C. and the resulting mixture was stirred at 25° C. for 1 hr. LCMS showed the starting material was consumed completely and a main peak with desired mass. The mixture solution was concentrated under reduced pressure to afford 1-(5-(4-((1-aminopiperidin-4-yl)methyl)piperazine-1-carbonyl)-2-methoxyphenyl)dihydropyrimidine-2,4(1H,3H)-dione (70 mg, crude, TFA salt) as yellow oil, which was used for the next step directly. MS $(M+H)^+$=445.1

Step 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(3-(2,4-dioxotetrahydropyrimidin-1(2H)-yl)-4-methoxybenzoyl)piperazin-1-yl)methyl)piperidin-1-yl)-3-methoxybenzamide (Compound 51)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (60 mg, 142.38 μmol) in DMF (2 mL) were added HATU (64.97 mg, 170.86 μmol)

and DIPEA (55.20 mg, 427.15 µmol, 74.40 µL). The mixture was stirred at 25° C. for 10 min. Then 1-(5-(4-((1-aminopiperidin-4-yl)methyl)piperazine-1-carbonyl)-2-methoxyphenyl)dihydropyrimidine-2,4(1H,3H)-dione (67.60 mg, 121.03 µmol, TFA salt) was added and the resulting mixture was stirred at 25° C. for 1 h. LCMS showed a peak (32%) with desired mass. The mixture was stirred at 25° C. for 12 h. LCMS showed a peak (~50%) with desired mass. The mixture solution was concentrated under reduced pressure. The residue was purified by flash silica gel chromatography (10 g SepaFlash Silica Flash Column, Eluent of 0~100% EtOAc/Petroleum ether gradient to 0~50% Methanol/EtOAc gradient @ 60 mL/min) and re-purified by prep-HPLC (column: Waters Xbridge 150×25 mm×5 µm; mobile phase: [water (NH$_4$HCO$_3$)-ACN]; B %: 29%-59%, 9 min), the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(3-(2,4-dioxotetrahydropyrimidin-1(2H)-yl)-4-methoxybenzoyl)piperazin-1-yl)methyl)piperidin-1-yl)-3-methoxybenzamide (36.9 mg, 42.65 µmol, 29.95% yield, 98% purity) as a white solid. MS (M+H)$^+$=848.2

$^1$H NMR (400 MHz, DMSO-d$_6$) δ=10.34 (s, 1H), 9.26 (s, 1H), 8.35-8.26 (m, 1H), 8.22 (s, 1H), 7.87 (s, 1H), 7.48-7.31 (m, 4H), 7.16 (d, J=8.5 Hz, 1H), 4.95-4.80 (m, 1H), 4.03 (br t, J=13.6 Hz, 2H), 3.93 (s, 3H), 3.85 (s, 3H), 3.66-3.40 (m, 6H), 3.35-3.32 (m, 2H), 3.29 (s, 3H), 3.00 (br d, J=10.0 Hz, 2H), 2.77-2.66 (m, 4H), 2.33 (br dd, J=1.9, 3.6 Hz, 2H), 2.19 (br d, J=7.0 Hz, 2H), 1.81-1.68 (m, 2H), 1.59-1.43 (m, 1H), 1.24 (br d, J=6.6 Hz, 8H).

Example 52. Synthesis of 4-((7,7-difluoro-9-isopropyl-5-methyl-6-oxo-6,7,8,9-tetrahydro-5H-pyrimido [4,5-b][1,4]diazepin-2-yl)amino)-N-(4-((4-(3-(2,4-dioxotetrahydropyrimidin-1(2H)-yl)benzoyl)piperazin-1-yl)methyl)piperidin-1-yl)-3-methoxybenzamide (Compound 52)

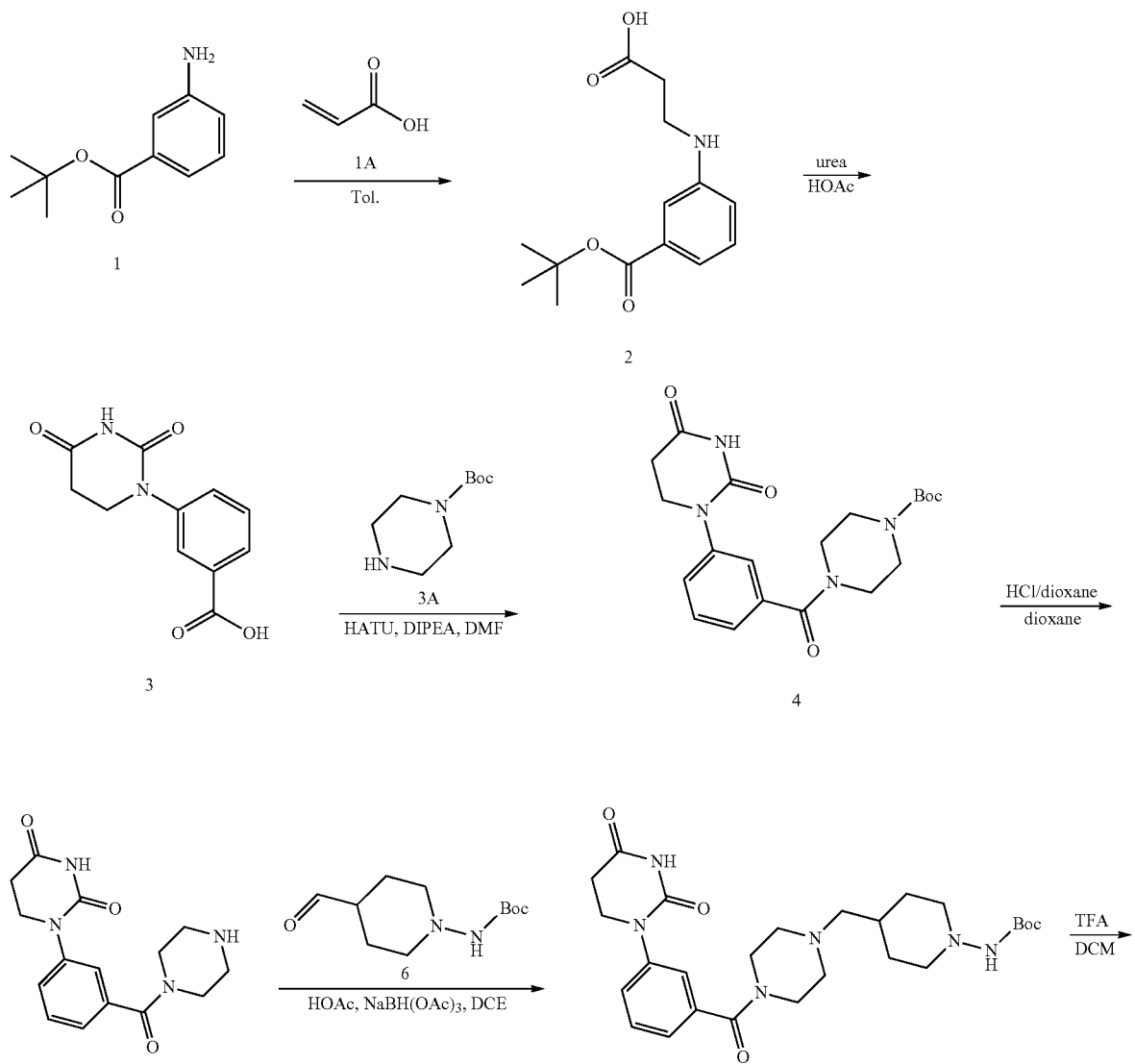

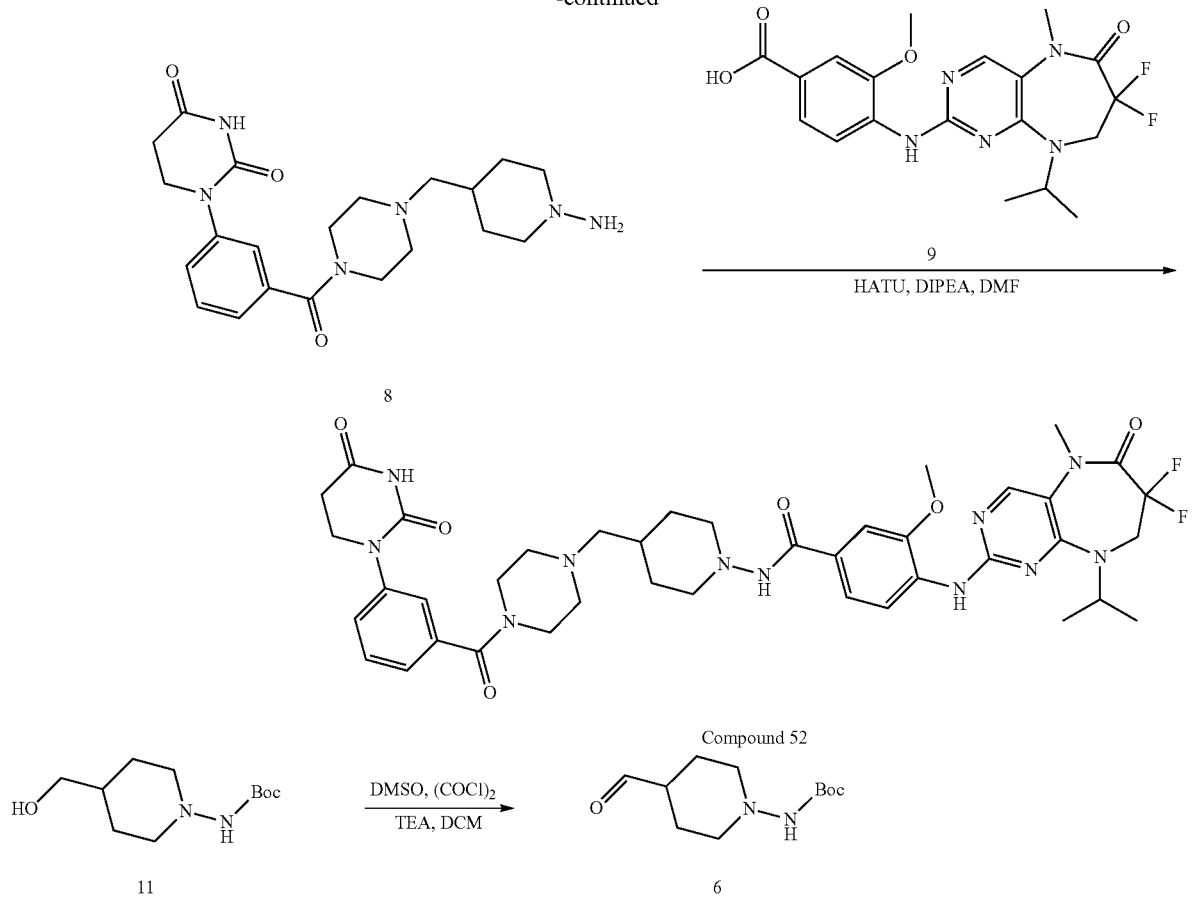

Step 1. Synthesis of 3-((3-(tert-butoxycarbonyl)phenyl)amino)propanoic Acid (2)

To a solution of tert-butyl 3-aminobenzoate (5 g, 25.87 mmol) in Tol. (50 mL) was added acrylic acid (1.86 g, 25.87 mmol, 1.78 mL). The mixture was stirred at 100° C. for 12 h. LCMS showed a peak (~87%) with desired mass. The mixture was concentrated under reduced pressure to afford 3-((3-(tert-butoxycarbonyl)phenyl)amino)propanoic acid (7 g, crude) as yellow oil. MS (M+H)$^+$=266.1.

Step 2. Synthesis of 3-(2,4-dioxotetrahydropyrimidin-1(2H)-yl)benzoic Acid (3)

To a solution of 3-((3-(tert-butoxycarbonyl)phenyl)amino)propanoic acid (7 g, 26.38 mmol) in HOAc (150 mL) was added urea (15.85 g, 263.85 mmol, 14.15 mL). The mixture was stirred at 120° C. for 12 h. LCMS showed a peak (~79%) with desired mass. The mixture was concentrated under reduced pressure. The residue was triturated with petroleum ether/EtOAc (500 mL, v/v=10:1). The filter cake was dried under reduced pressure to afford 3-(2,4-dioxotetrahydropyrimidin-1(2H)-yl)benzoic acid (5.6 g, 23.58 mmol, 89.35% yield, 98.6% purity) as a white solid. MS (M+H)$^+$=235.1.

Step 3. Synthesis of tert-butyl 4-(3-(2,4-dioxotetrahydropyrimidin-1(2H)-yl)benzoyl)piperazine-1-carboxylate (4)

To a solution of 3-(2,4-dioxotetrahydropyrimidin-1(2H)-yl)benzoic acid (2 g, 8.54 mmol) in DMF (15 mL) were added DIPEA (3.31 g, 25.62 mmol, 4.46 mL) and HATU (4.87 g, 12.81 mmol). Then tert-butyl piperazine-1-carboxylate (1.59 g, 8.54 mmol) was added to the mixture after 0.5 h. The mixture was stirred at 25° C. for 12 h. LCMS showed ~46% of desired mass was detected. The reaction mixture was diluted with water (100 mL) and extracted with EtOAc (100 mL×3). The combined organic layers were washed with saturated brine (150 mL), dried over anhydrous sodium sulfate, filtered and concentrated under reduced pressure to give a residue. The residue was purified by flash silica gel chromatography (ISCO; 40 g SepaFlash Silica Flash Column, Eluent of 0~60% petroleum ether:EtOAc/ethanol (v/v=1/1) gradient @ 80 mL/min) to give tert-butyl 4-(3-(2,4-dioxotetrahydropyrimidin-1(2H)-yl)benzoyl)piperazine-1-carboxylate (1 g, 2.06 mmol, 24.15% yield, 83% purity) as yellow oil. MS (M-tBu+H)$^+$=347.1.

Step 4. Synthesis of 1-(3-(piperazine-1-carbonyl)phenyl)dihydropyrimidine-2,4(1H,3H)-dione (5)

To a solution of tert-butyl 4-(3-(2,4-dioxotetrahydropyrimidin-1(2H)-yl)benzoyl)piperazine-1-carboxylate (1 g, 2.48 mmol) in dioxane (10 mL) was added HCl/dioxane (4 M, 15 mL). The mixture was stirred at 25° C. for 1 h. TLC (dichloromethane:methanol=10:1) indicated one new spot formed. The mixture was filtered. The filter cake was dried under reduced pressure to afford 1-(3-(piperazine-1-carbonyl)phenyl)dihydropyrimidine-2,4(1H,3H)-dione (430 mg, crude, HCl) as a yellow solid. MS (M+H)$^+$=303.1.

Step 5. Synthesis of tert-butyl (4-formylpiperidin-1-yl)carbamate (6)

To a solution of DMSO (678.53 mg, 8.68 mmol, 678.53 µL) in DCM (10 mL) was added a solution of oxalyl chloride (716.46 mg, 5.64 mmol, 494.11 µL) in DCM (5 mL) at −70° C. Then a solution of tert-butyl (4-(hydroxymethyl)piperidin-1-yl)carbamate (1 g, 4.34 mmol) in DCM (15 mL) was added to the mixture after 10 min at −70° C. The mixture was stirred for 20 min. Then TEA (2.20 g, 21.71 mmol, 3.02 mL) was added to the mixture at −70° C. Then the mixture was warmed to 20° C. and stirred for 30 min. TLC (dichloromethane:methanol=20:1) indicated one new spot formed. The reaction mixture was quenched with water (50 mL) and extracted with DCM (20 mL×3). The combined organic layers were washed with saturated brine (50 mL), dried over anhydrous sodium sulfate, filtered and concentrated under reduced pressure to give tert-butyl (4-formylpiperidin-1-yl)carbamate (640 mg, crude) as a yellow solid. MS (M+H)$^+$=229.1.

Step 6. Synthesis of tert-butyl (4-((4-(3-(2,4-dioxotetrahydropyrimidin-1(2H)-yl)benzoyl)piperazin-1-yl)methyl)piperidin-1-yl)carbamate (7)

To a solution of 1-(3-(piperazine-1-carbonyl)phenyl)dihydropyrimidine-2,4(1H,3H)-dione (427.41 mg, crude, HCl) in DCE (20 mL) were added tert-butyl (4-formylpiperidin-1-yl)carbamate (640 mg, 2.80 mmol), HOAc (336.71 mg, 5.61 mmol, 320.68 µL) and NaBH(OAc)$_3$ (1.19 g, 5.61 mmol). The mixture was stirred at 25° C. for 12 h. LCMS showed ~46% of desired mass was detected. The mixture was quenched with saturated sodium bicarbonate solution (30 mL) and then extracted with EtOAc (50 mL×3). The combined organic layers were washed with brine (50 mL), dried over anhydrous sodium sulfate, filtered and concentrated under reduced pressure to give a residue. The residue was purified by flash silica gel chromatography (ISCO; 40 g SepaFlash Silica Flash Column, Eluent of 0~60% petroleum ether:EtOAc/ethanol (v/v=1/1) gradient @ 80 mL/min) to afford tert-butyl (4-((4-(3-(2,4-dioxotetrahydropyrimidin-1(2H)-yl)benzoyl)piperazin-1-yl)methyl)piperidin-1-yl)carbamate (260 mg, 419.34 µmol, 14.96% yield, 83% purity) as yellow oil. MS (M+H)$^+$=515.4.

Step 7. Synthesis of 1-(3-(4-((1-aminopiperidin-4-yl)methyl)piperazine-1-carbonyl)phenyl)dihydropyrimidine-2,4(1H,3H)-dione (8)

To a solution of tert-butyl (4-((4-(3-(2,4-dioxotetrahydropyrimidin-1(2H)-yl)benzoyl)piperazin-1-yl)methyl)piperidin-1-yl)carbamate (150 mg, 291.48 µmol) in DCM (2 mL) was added TFA (4.62 g, 40.52 mmol, 3.00 mL). The mixture was stirred at 25° C. for 1 h. TLC (dichloromethane:methanol=10:1) indicated one new spot formed. The mixture was concentrated under reduced pressure to give 1-(3-(4-((1-aminopiperidin-4-yl)methyl)piperazine-1-carbonyl)phenyl)dihydropyrimidine-2,4(1H,3H)-dione (0.2 g, crude, TFA) as yellow oil. MS (M+H)$^+$=415.5

Step 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(3-(2,4-dioxotetrahydropyrimidin-1(2H)-yl)benzoyl)piperazin-1-yl)methyl)piperidin-1-yl)-3-methoxybenzamide (Compound 52)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (159.46 mg, 378.41 µmol) in DMF (5 mL) were added HATU (172.66 mg, 454.10 µmol) and DIPEA (195.63 mg, 1.51 mmol, 263.65 µL). Then 1-(3-(4-((1-aminopiperidin-4-yl)methyl)piperazine-1-carbonyl)phenyl)dihydropyrimidine-2,4(1H,3H)-dione (0.2 g, crude, TFA) was added to the mixture after 0.5 h. The mixture was stirred at 25° C. for 12 h. LCMS showed ~50% of desired mass was detected. The reaction mixture was diluted with water (30 mL) and extracted with EtOAc (30 mL×3). The combined organic layers were washed with brine (50 mL), dried over anhydrous sodium sulfate, filtered and concentrated under reduced pressure to give a residue. The residue was purified by flash silica gel chromatography (ISCO; 20 g SepaFlash Silica Flash Column, Eluent of 0~95% petroleum ether/EtOAc:ethanol (v/v=1/1) gradient @ 80 mL/min) and then prep-HPLC (column: Waters Xbridge 150×25 mm×5 µm; mobile phase: [water (NH$_4$HCO$_3$)-ACN]; B %: 25%-55%, 9 min) followed by lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(3-(2,4-dioxotetrahydropyrimidin-1(2H)-yl)benzoyl)piperazin-1-yl)methyl)piperidin-1-yl)-3-methoxybenzamide (36.3 mg, 43.94 µmol, 11.61% yield, 99% purity) as a white solid. MS (M+H)$^+$=818.3

$^1$H NMR (400 MHz, DMSO-d$_6$) δ=10.42 (s, 1H), 9.26 (s, 1H), 8.29 (d, J=8.3 Hz, 1H), 8.21 (s, 1H), 7.87 (s, 1H), 7.50-7.39 (m, 4H), 7.37 (s, 1H), 7.23 (d, J=7.3 Hz, 1H), 4.90-4.83 (m, 1H), 4.03 (t, J=13.6 Hz, 2H), 3.93 (s, 3H), 3.83 (t, J=6.6 Hz, 2H), 3.69-3.55 (m, 2H), 3.47-3.33 (m, 4H), 3.30 (s, 3H), 3.00 (d, J=10.3 Hz, 2H), 2.77-2.69 (m, 4H), 2.44-2.37 (m, 2H), 2.19 (d, J=7.0 Hz, 2H), 1.75 (d, J=11.0 Hz, 2H), 1.58-1.46 (m, 1H), 1.26-1.23 (m, 8H).

Example 53. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(1-(2,6-dioxopiperidin-3-yl)-1H-pyrazol-4-yl)piperazin-1-yl)ethyl)(methyl)amino)cyclohexyl)-3-methoxybenzamide (trans) (Compound 53)
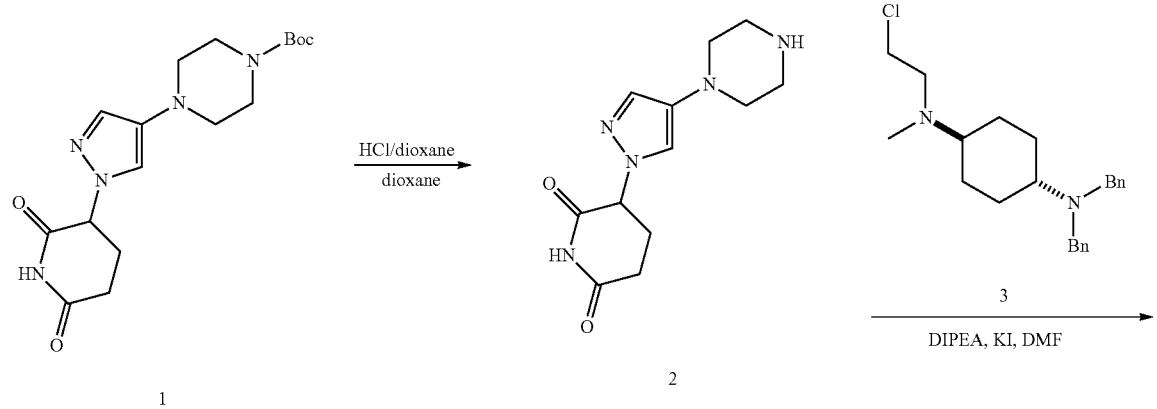
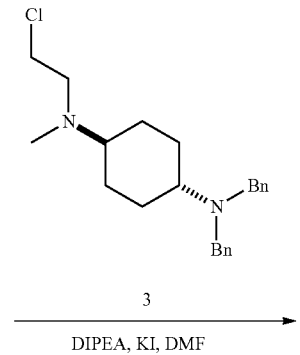
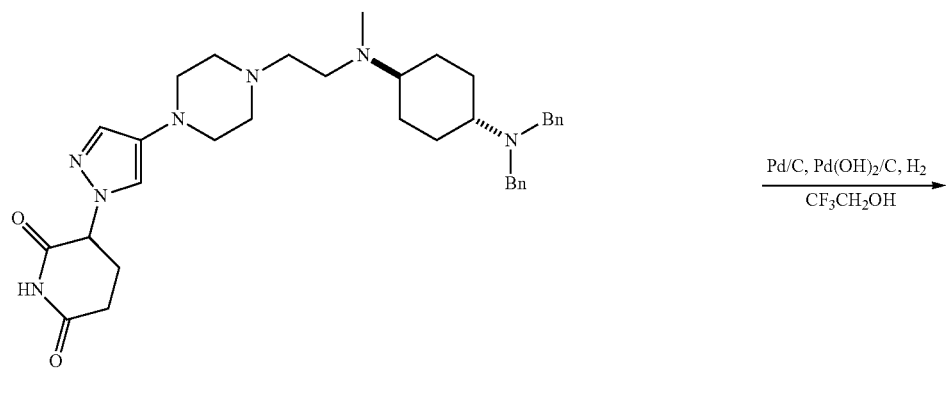
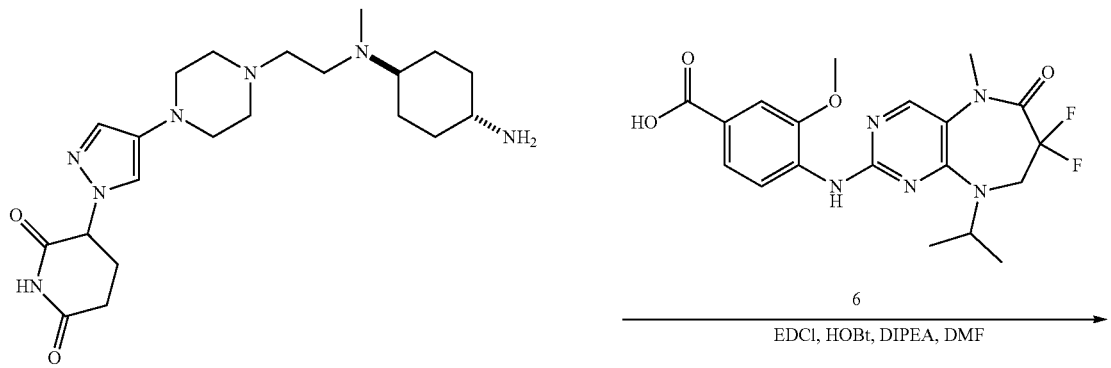

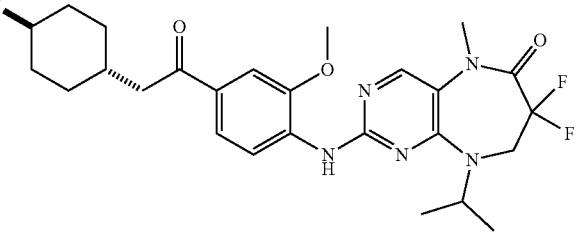
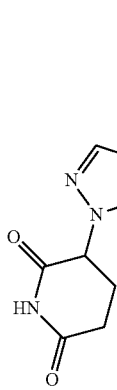

Compound 53

Step 1. Synthesis of 3-(4-(piperazin-1-yl)-1H-pyrazol-1-yl)piperidine-2,6-dione (2)

To a solution of tert-butyl 4-(1-(2,6-dioxopiperidin-3-yl)-1H-pyrazol-4-yl)piperazine-1-carboxylate (145 mg, 399.00 µmol) in dioxane (10 mL) was added HCl/dioxane (4 M, 10 mL), the mixture was stirred at 20° C. for 12 hr. LCMS showed main peak with the desired mass was detected and no peak with the starting material was remained. The reaction mixture was concentrated under reduced pressure to afford 3-(4-(piperazin-1-yl)-1H-pyrazol-1-yl)piperidine-2,6-dione (119 mg, crude, HCl salt) as a light yellow solid. MS (M+H)$^+$=264.1

Step 2. Synthesis of 3-(4-(4-(2-(((1r,4r)-4-(dibenzylamino)cyclohexyl)(methyl)amino) ethyl)piperazin-1-yl)-1H-pyrazol-1-yl)piperidine-2,6-dione (trans) (4)

To a solution of 3-(4-(piperazin-1-yl)-1H-pyrazol-1-yl)piperidine-2,6-dione (159 mg, 530.43 µmol, HCl) in DMF (4 mL) was added KI (19.08 mg, 114.94 µmol), (1r,4r)-N1,N1-dibenzyl-N4-(2-chloroethyl)-N4-methylcyclohexane-1,4-diamine (trans) (222.60 mg, 501.49 µmol, 2HCl salt) and DIPEA (471.91 mg, 3.65 mmol, 635.99 µL) at 25° C. The mixture was stirred at 50° C. for 16 h. LCMS showed a main peak with the desired mass. The mixture was filtered and the filtrate was purified by prep-HPLC (column: Phenomenex Synergi Polar-RP 100×25 mm×4 µm; mobile phase: [water (TFA)-ACN]; B %: 14%-34%, 7 min; Column Temp: 30° C.) and the eluent was lyophilized to afford 3-(4-(4-(2-(((1r,4r)-4-(dibenzylamino)cyclohexyl)(methyl)amino)ethyl)piperazin-1-yl)-1H-pyrazol-1-yl)piperidine-2,6-dione6-dione (trans) (240 mg, 337.17 µmol, 63.56% yield, TFA salt) as a light yellow solid. MS (M+H)$^+$=598.3

Step 3. Synthesis of 3-(4-(4-(2-(((1r,4r)-4-aminocyclohexyl)(methyl)amino)ethyl)piperazin-1-yl)-1H-pyrazol-1-yl)piperidine-2,6-dione (trans) (5)

To a solution of 3-(4-(4-(2-(((1r,4r)-4-(dibenzylamino)cyclohexyl)(methyl)amino)ethyl)piperazin-1-yl)-1H-pyrazol-1-yl)piperidine-2,6-dione (trans) (140 mg, 196.68 µmol, TFA) in CF$_3$CH$_2$OH (8 mL) was added Pd/C (30 mg, 10% purity) and Pd(OH)$_2$/C (30 mg, 20% purity) under N$_2$ atmosphere. Then the mixture was stirred at 20° C. for 40 hr under H$_2$ atmosphere (15 Psi). LCMS showed main peak with the desired mas. The reaction mixture was filtered and the filtrate was concentrated under reduced pressure to afford 3-(4-(4-(2-(((1r,4r)-4-aminocyclohexyl)(methyl)amino)ethyl)piperazin-1-yl)-1H-pyrazol-1-yl)piperidine-2,6-dione (trans) (104 mg, crude, TFA) as a light yellow oil. MS (M+H)$^+$=418.2

Step 4. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(1-(2,6-dioxopiperidin-3-yl)-1H-pyrazol-4-yl)piperazin-1-yl)ethyl)(methyl)amino)cyclohexyl)-3-methoxybenzamide (trans) (Compound 53)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (90 mg, 213.58 µmol) in DMF (2 mL) were added EDCI (70 mg, 365.15 µmol), HOBt (50 mg, 370.03 µmol), DIPEA (140.98 mg, 1.09 mmol, 190 µL) and 3-(4-(4-(2-(((1r,4r)-4-aminocyclohexyl)(methyl)amino)ethyl)piperazin-1-yl)-1H-pyrazol-1-yl)piperidine-2,6-dione (trans) (104 mg, 195.65 µmol, TFA) at 25° C. The mixture was stirred at 25° C. for 16 h under N$_2$ atmosphere. LCMS showed a main peak with the desired mass. The mixture was filtered and the filtrate was purified by prep-HPLC (column: Phenomenex Synergi Polar-RP 100×25 mm×4 µm; mobile phase: [water (TFA)-ACN]; B %: 19%-39%, 7 min; Column Temp: 30° C.) followed by lyophilization to afford 4-((7,7-difluoro-9-isopropyl-5-methyl-6-oxo-6,7,8,9-tetrahydro-5H-pyrimido[4,5-b][1,4]diazepin-2-yl)amino)-N-((1r,4r)-4-((2-(4-(1-(2,6-dioxopiperidin-3-yl)-1H-pyrazol-4-yl)piperazin-1-yl)ethyl)(methyl)amino)cyclohexyl)-3-methoxybenzamide (trans) (10.8 mg, 10.63 µmol, 4.98% yield, 92% purity, TFA salt) as a white solid. MS (M+H)$^+$=821.4

$^1$H NMR (400 MHz, DMSO-d$_6$) δ=11.04 (s, 1H), 8.30-8.25 (m, 1H), 8.25-8.17 (m, 3H), 7.61-7.39 (m, 3H), 7.33 (s, 1H), 5.26-5.19 (m, 1H), 4.91-4.85 (m, 1H), 4.14-4.03 (m, 2H), 3.93 (s, 3H), 3.86-3.78 (m, 1H), 3.74-2.89 (m, 16H), 2.85-2.74 (m, 4H), 2.70-2.55 (m, 2H), 2.21-2.14 (m, 1H), 2.07-1.95 (m, 4H), 1.75-1.63 (m, 2H), 1.50-1.39 (m, 2H), 1.24 (d, J=6.6 Hz, 6H).

Example 54. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(1-(2,6-dioxopiperidin-3-yl)-1H-pyrazol-3-yl)phenyl)piperidin-4-yl)methyl)-7-azaspiro[3.5]nonan-2-yl)-3-methoxybenzamide (Compound 54)
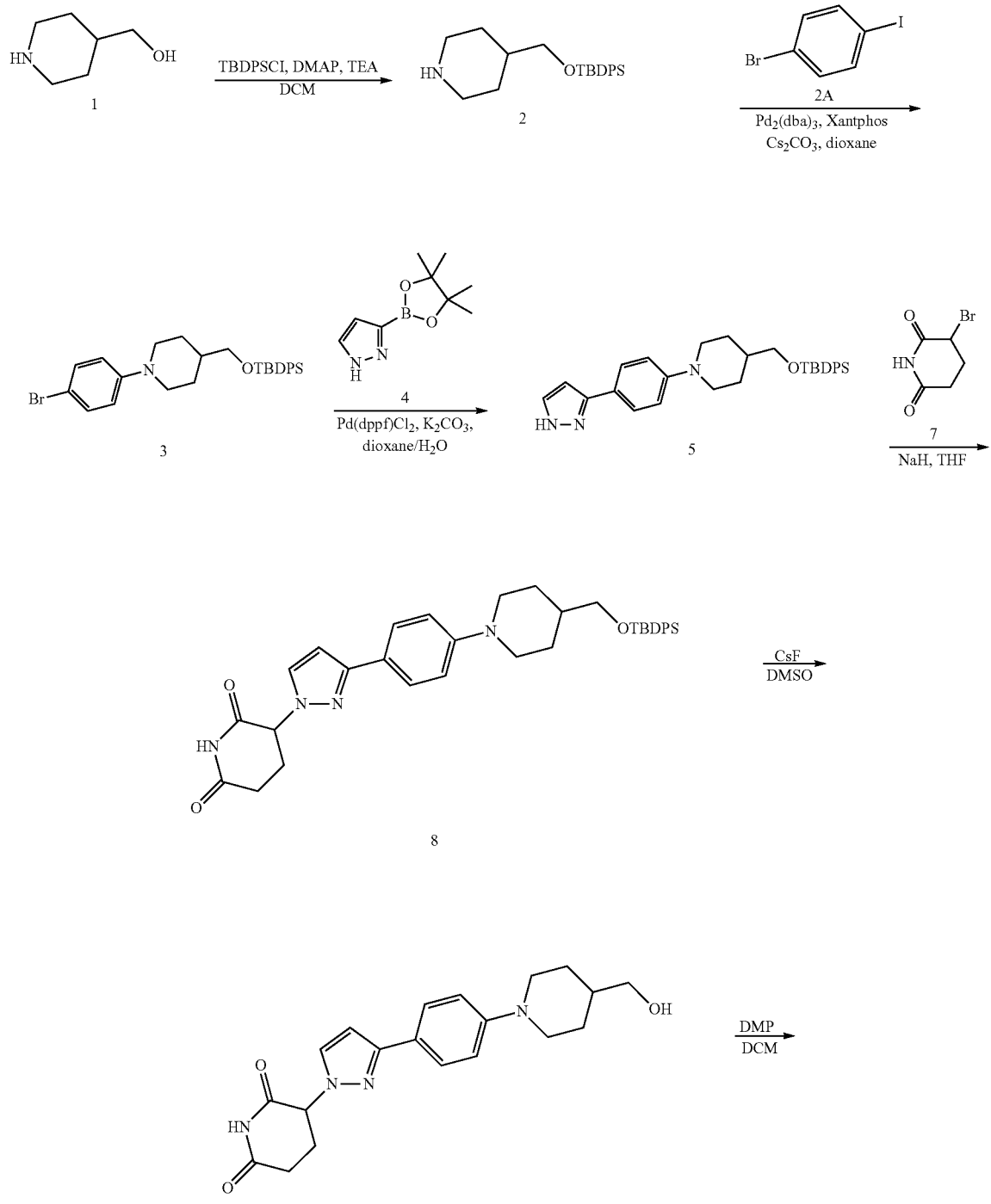

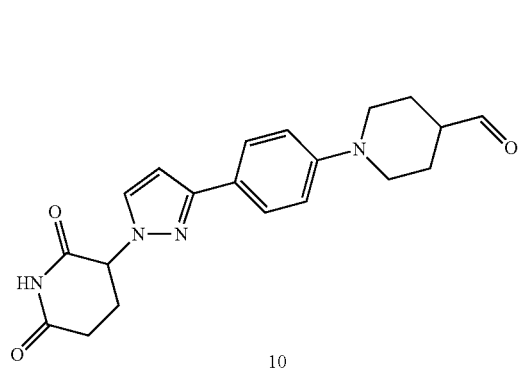

10

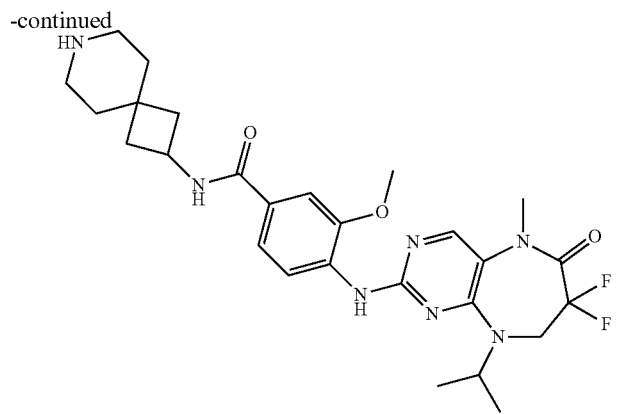

11

NaOAc, NaBH(OAc)₃, DCM

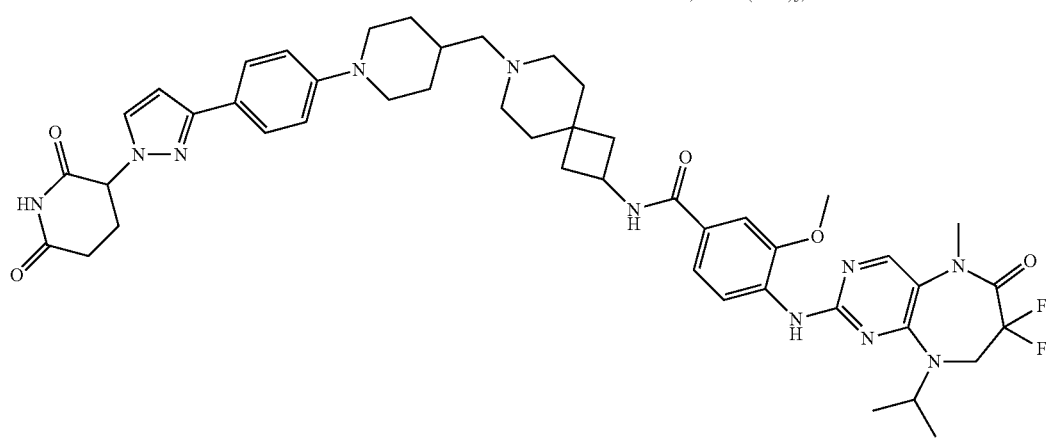

Compound 54

Step 1. Synthesis of 4-(((tert-butyldiphenylsilyl)oxy)methyl)piperidine (2)

To a solution of piperidin-4-ylmethanol (5 g, 43.41 mmol) in DCM (80 mL) was added TEA (7.27 g, 71.85 mmol, 10 mL) and DMAP (300 mg, 2.46 mmol), then TBDPSCl (18.19 g, 66.18 mmol, 17.00 mL) was added at 0° C.; The resulting mixture was stirred at 20° C. for 16 hr. LCMS showed piperidin-4-ylmethanol was consumed completely and a peak (55%) with desired mass. The reaction mixture was quenched by addition of water (100 mL) at 0° C., then extracted with DCM (80 mL×2). The combined organic layers were washed with brine (40 mL×3), dried over Na₂SO₄, filtered and concentrated under reduced pressure. The residue was purified by flash silica gel chromatography (Biotage; 40 g SepaFlash Silica Flash Column, Eluent of 20~100% EtOAc:Petroleum ether gradient, 60 mL/min) to afford 4-(((tert-butyldiphenylsilyl)oxy)methyl)piperidine (14.5 g, 41.01 mmol, 94.47% yield) as a white solid. MS (M+H)⁺=354.2

Step 2. Synthesis of 1-(4-bromophenyl)-4-(((tert-butyldiphenylsilyl)oxy)methyl)piperidine (3)

A mixture of 4-(((tert-butyldiphenylsilyl)oxy)methyl)piperidine (5 g, 14.14 mmol), 1-bromo-4-iodobenzene (4.40 g, 15.56 mmol), Pd₂(dba)₃ (1.25 g, 1.37 mmol), Xantphos (800.00 mg, 1.38 mmol), Cs₂CO₃ (15.00 g, 46.04 mmol) in dioxane (80 mL) was degassed and purged with N₂ for 3 times, the reaction mixture was stirred at 80° C. for 16 h under N₂ atmosphere. LCMS showed a peak (45%) with desired mass. The reaction mixture was filtered and the filtrate was concentrated under reduced pressure. The residue was purified by flash silica gel chromatography (Biotage; 40 g SepaFlash Silica Flash Column, Eluent of 0~10% EtOAc:Petroleum ether gradient, 60 mL/min) to afford 1-(4-bromophenyl)-4-(((tert-butyldiphenylsilyl)oxy) methyl)piperidine (4.5 g, 8.85 mmol, 62.57% yield) as a yellow oil. MS (M+H)⁺=508.3, 510.3

Step 3. Synthesis of 1-(4-(1H-pyrazol-3-yl)phenyl)-4-(((tert-butyldiphenylsilyl)oxy)methyl)piperidine (5)

A mixture of 1-(4-bromophenyl)-4-(((tert-butyldiphenylsilyl)oxy)methyl)piperidine (2.4 g, 4.72 mmol), 3-(4,4,5,5-tetramethyl-1,3,2-dioxaborolan-2-yl)-1H-pyrazole (1.4 g, 7.22 mmol), Pd(dppf)Cl₂ (360.00 mg, 492.00 μmol), K₂CO₃ (2.16 g, 15.63 mmol) in dioxane (30 mL) and H₂O (6 mL) was degassed and purged with N₂ for 3 times, then the mixture was stirred at 100° C. for 16 h under N₂ atmosphere. LCMS showed 27% of 1-(4-bromophenyl)-4-(((tert-butyldiphenylsilyl)oxy)methyl)piperidine remained and a peak (60%) with desired compound. The reaction mixture was diluted with H₂O (15 mL), then extracted with EtOAc (40 mL×2). The combined organic layers were washed with brine (30 mL×3), dried over $Na_2SO_4$, filtered and the filtrate was concentrated under reduced pressure. The residue was purified by flash silica gel chromatography (Biotage; 20 g SepaFlash Silica Flash Column, Eluent of 10~50% EtOAc: Petroleum ether gradient, 60 mL/min) to afford 1-(4-(1H-pyrazol-3-yl)phenyl)-4-(((tert-butyldiphenylsilyl)oxy) methyl)piperidine (2.1 g, 4.24 mmol, 89.77% yield) as a yellow oil. MS $(M+H)^+=496.4$ Step 4. Synthesis of 3-(3-(4-(4-(((tert-butyldiphenylsilyl)oxy)methyl)piperidin-1-yl)phenyl)-1H-pyrazol-1-yl)piperidine-2,6-dione (8)

To a solution of 1-(4-(1H-pyrazol-3-yl)phenyl)-4-(((tert-butyldiphenylsilyl)oxy)methyl)piperidine (1.2 g, 2.42 mmol) in THF (20 mL) was added NaH (240 mg, 6.00 mmol, 60% purity) at 0° C. The mixture was stirred at 0° C. for 0.5 h, then a solution of 3-bromopiperidine-2,6-dione (600.00 mg, 3.12 mmol) in THF (10 mL) was added at 0° C. and the resulting mixture was stirred at 20° C. for 3 hr. TLC (Petroleum ether:EtOAc=1:1) indicated 1-(4-(1H-pyrazol-3-yl)phenyl)-4-(((tert-butyldiphenylsilyl)oxy)methyl)piperidine was consumed completely and one new spot (Rf=0.22) was formed. The reaction mixture was quenched with $NH_4Cl$ (sat. aq, 20 mL) at 0° C., the resulting mixture was extracted with EtOAc (80 mL×2). The combined organic layers were washed with brine (100 mL×2), dried over anhydrous $Na_2SO_4$, filtered and the filtrate was concentrated under reduced pressure. The residue was purified by flash silica gel chromatography (Biotage; 20 g SepaFlash Silica Flash Column, Eluent of 10~50% EtOAc:Petroleum ether gradient, 60 mL/min) to afford 3-(3-(4-(4-(((tert-butyldiphenylsilyl)oxy)methyl)piperidin-1-yl)phenyl)-1H-pyrazol-1-yl)piperidine-2,6-dione (1.2 g, 1.98 mmol, 81.69% yield) as a light yellow solid. MS $(M+H)^+=607.1$ Step 5. Synthesis of 3-(3-(4-(4-(hydroxymethyl)piperidin-1-yl)phenyl)-1H-pyrazol-1-yl)piperidine-2,6-dione (9)

To a solution of 3-(3-(4-(4-(((tert-butyldiphenylsilyl)oxy)methyl)piperidin-1-yl)phenyl)-1H-pyrazol-1-yl)piperidine-2,6-dione (500 mg, 823.96 µmol) in DMSO (8 mL) was added CsF (200.00 mg, 1.32 mmol, 48.54 µL) at 20° C. Then the mixture was stirred at 20° C. for 12 hr. LCMS showed a peak (11%) with desired mass. The reaction mixture was diluted with $H_2O$ (10 mL), then extracted with EtOAc (50 mL×2). The combined organic layers were washed with brine (40 mL×3), dried over anhydrous $Na_2SO_4$, filtered. The filtrate was concentrated under reduced pressure. The residue was purified by flash silica gel chromatography (Biotage; 10 g SepaFlash Silica Flash Column, Eluent of 40~100% EtOAc:Petroleum ether gradient, 60 mL/min) to afford 3-(3-(4-(4-(hydroxymethyl)piperidin-1-yl)phenyl)-1H-pyrazol-1-yl)piperidine-2,6-dione (200 mg, 542.85 µmol, 65.88% yield) as a light yellow solid. MS $(M+H)^+=369.0$ Step 6. Synthesis of 1-(4-(1-(2,6-dioxopiperidin-3-yl)-1H-pyrazol-3-yl)phenyl)piperidine-4-carbaldehyde (10)

To a solution of 3-(3-(4-(4-(hydroxymethyl)piperidin-1-yl)phenyl)-1H-pyrazol-1-yl)piperidine-2,6-dione (150 mg, 407.13 µmol) in DCM (10 mL) was added DMP (270.00 mg, 636.58 µmol, 197.08 µL). The mixture was stirred at 20° C. for 2 hr. LCMS showed a peak (44%) with desired mass. The reaction mixture was concentrated under reduced pressure to afford 1-(4-(1-(2,6-dioxopiperidin-3-yl)-1H-pyrazol-3-yl)phenyl)piperidine-4-carbaldehyde (148 mg, crude) as a brown oil. MS $(M+H)^+=367.0$ Step 7. Synthesis of 4-((7,7-difluoro-9-isopropyl-5-methyl-6-oxo-6,7,8,9-tetrahydro-5H-pyrimido[4,5-b] [1,4]diazepin-2-yl)amino)-N-(7-((1-(4-(1-(2,6-dioxopiperidin-3-yl)-1H-pyrazol-3-yl)phenyl) piperidin-4-yl)methyl)-7-azaspiro[3.5]nonan-2-yl)-3-methoxybenzamide (Compound 54)

To a solution of 4-((7,7-difluoro-9-isopropyl-5-methyl-6-oxo-6,7,8,9-tetrahydro-5H-pyrimido[4,5-b][1,4]diazepin-2-yl)amino-3-methoxy-N-(7-azaspiro[3.5]nonan-2-yl)benzamide (150 mg, 258.59 µmol, HCl salt) in DCM (8 mL) was added 1-(4-(1-(2,6-dioxopiperidin-3-yl)-1H-pyrazol-3-yl)phenyl)piperidine-4-carbaldehyde (147.00 mg, 401.19 µmol) and NaOAc (100 mg, 1.22 mmol). The mixture was stirred at 25° C. for 1 hr. Then $NaBH(OAc)_3$ (240.00 mg, 1.13 mmol, was added and the resulting mixture was stirred at 25° C. for 15 hr. LCMS showed a peak (38%) with the desired mass. The reaction mixture was diluted with $H_2O$ (4 mL) at 0° C., then $NaHCO_3$ (sat. aq, 8 mL) was added to adjust pH=9 at 0° C., the resulting mixture was extracted with EtOAc (20 mL×3). The combined organic layers were washed with brine (20 mL×2), dried over anhydrous $Na_2SO_4$, filtered and the filtrate was concentrated under reduced pressure. The product was purified prep-HPLC (column: Unisil 3-100 C18 Ultra 150×50 mm×3 µm; mobile phase: [water (FA)-ACN]; B %: 13%-43%, 7 min; Column Temp: 30° C.), the eluents was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(1-(2,6-dioxopiperidin-3-yl)-1H-pyrazol-3-yl)phenyl) piperidin-4-yl)methyl)-7-azaspiro[3.5]nonan-2-yl)-3-methoxybenzamide (120 mg, 97.86 µmol, 37.84% yield, 91.5% purity, 2TFA salt) as a light yellow solid. MS $(M+H)^+=894.2$ $^1H$ NMR (400 MHz, $CD_3OD$) δ=8.15-8.10 (m, 2H), 7.87-7.79 (m, 2H), 7.77-7.69 (m, 1H), 7.61-7.54 (m, 2H), 7.38-7.29 (m, 2H), 6.72-6.67 (m, 1H), 5.41-5.31 (m, 1H), 5.16-5.10 (m, 1H), 4.60-4.50 (m, 1H), 4.16 (t, J=12.0 Hz, 2H), 4.02 (s, 3H), 3.86-3.76 (m, 2H), 3.64-3.50 (m, 2H), 3.41 (s, 3H), 3.30-3.21 (m, 2H), 3.19-3.08 (m, 3H), 3.04-2.96 (m, 1H), 2.94-2.81 (m, 2H), 2.81-2.67 (m, 1H), 2.59-2.51 (m, 1H), 2.47-2.30 (m, 2H), 2.29-2.20 (m, 1H), 2.15-1.93 (m, 8H), 1.74-1.61 (m, 2H), 1.35-1.29 (m, 6H).

About 80 mg product was diluted with DMF (2 mL) and adjust pH=7~8 with DIPEA (0.1 mL). Then the mixture was re-purified by prep-HPLC. (column: Waters Xbridge C18 150×50 mm×10 µm; mobile phase: [water ($NH_4HCO_3$)-ACN]; B %: 38%-68%, 10 min, Column Temp: 30° C.). The eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(7-((1-(4-(1-(2,6-dioxopiperidin-3-yl)-1H-pyrazol-3-yl)phenyl)piperidin-4-yl)methyl)-7-azaspiro[3.5]nonan-2-yl)-3-methoxybenzamide (18.2 mg, 18.69 µmol, 20.88% yield, 91.8% purity) as a light yellow solid. MS $(M+H)^+=894.2$ $^1H$ NMR (400 MHz, DMSO-$d_6$) δ=11.06 (s, 1H), 8.46-8.39 (m, 1H), 8.34-8.28 (m, 1H), 8.22 (s, 1H), 7.88 (s, 1H), 7.78 (d, J=2.2 Hz, 1H), 7.64-7.56 (m, 2H), 7.53-7.46 (m, 2H), 6.98-6.89 m, 2H), 6.64-6.57 (m, 1H), 5.41-5.33 (m, 1H), 4.93-4.84 (m, 1H), 4.44-4.35 (m, 1H), 4.09-3.99 (m, 2H), 3.94 (s, 3H), 3.77-3.67 (m, 2H), 3.31-3.28 (m, 5H), 2.86-2.76 (m, 1H), 2.71-2.61 (m, 4H), 2.28-2.21 (m, 3H), 2.18-2.10 (m, 4H), 1.84-1.74 (m, 4H), 1.66-1.51 (m, 5H), 1.27-1.22 (m, 6H), 1.20-1.13 (m, 2H).

Example 55. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2-(trifluoromethyl)phenyl)piperazin-1-yl)methyl)piperidin-1-yl)-3-methoxybenzamide (Compound 55)
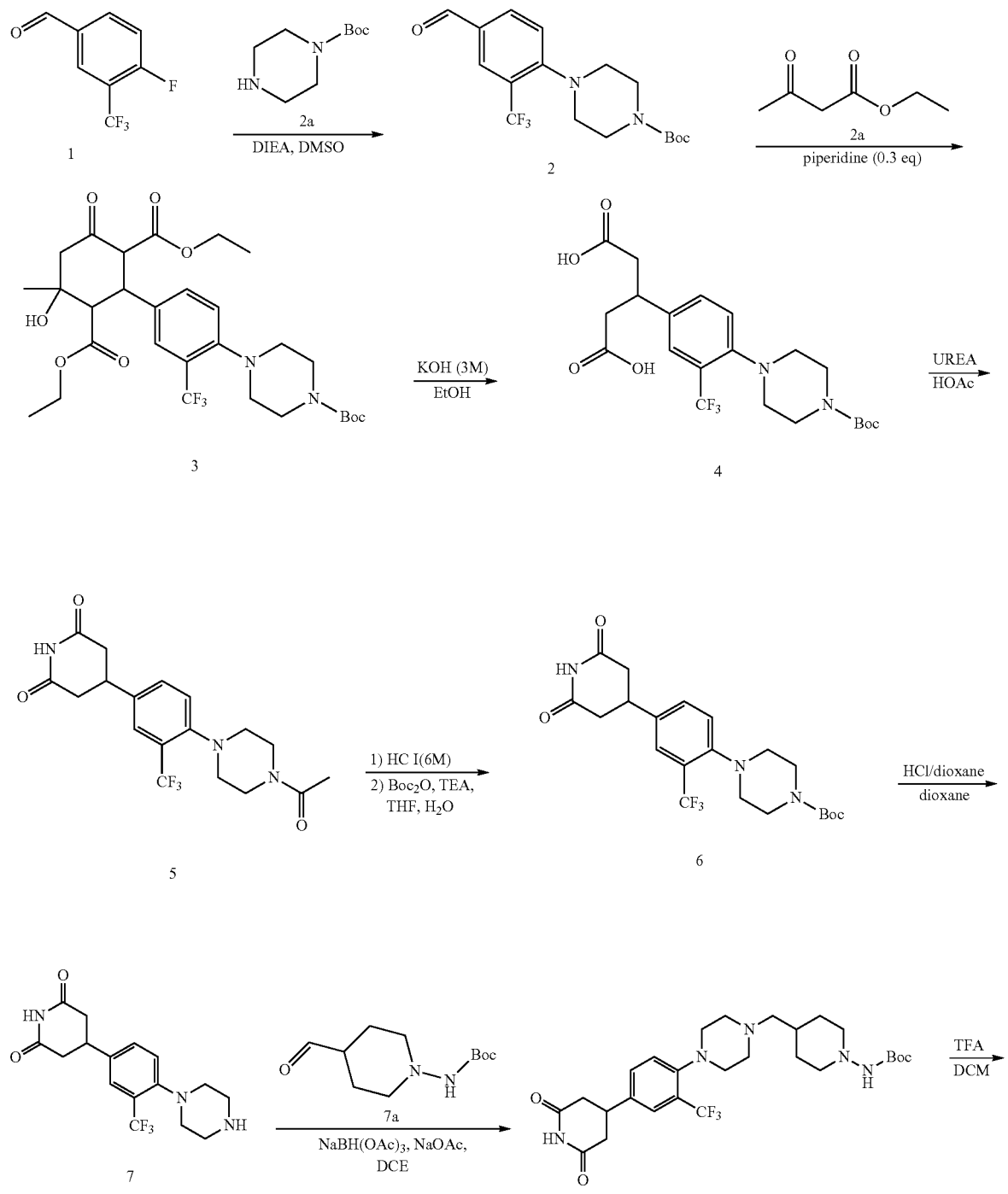

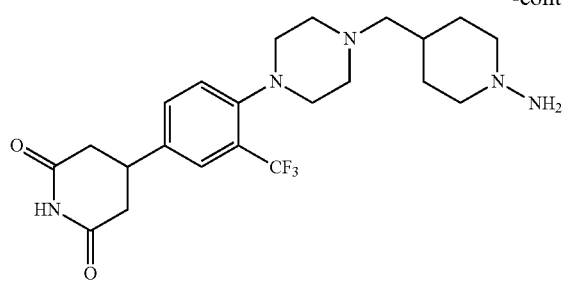

9

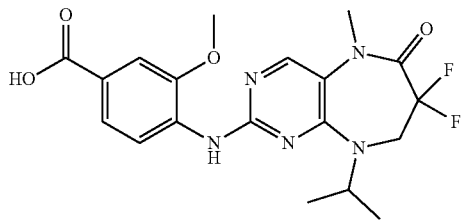

10
HATU, DIPEA, DMF →

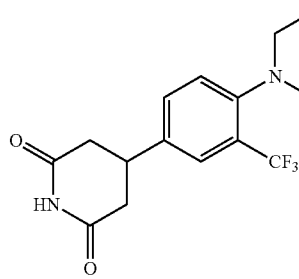

Compound 55

Step 1. Synthesis of tert-butyl 4-(4-formyl-2-(trifluoromethyl)phenyl)piperazine-1-carboxylate (2)

A mixture of tert-butyl piperazine-1-carboxylate (6.03 g, 27.07 mmol), 4-fluoro-3-(trifluoromethyl)benzaldehyde (4 g, 20.82 mmol, 2.84 mL) and DIPEA (6.73 g, 52.05 mmol, 9.07 mL) in DMSO (50 mL) was stirred at 100° C. for 16 hours. LCMS showed a peak (25%) with desired mass. TLC (petroleum ether:EtOAc=5:1; Rf=0.7) showed most of the starting material was remained. The mixture was stirred at 120° C. for another 16 hr. LCMS showed a peak (40%) with desired mass. The mixture was poured into water (150 mL) and extracted with EtOAc (30 mL×5). The combined organic phase was washed with brine (30 mL×3), dried over Na$_2$SO$_4$, filtered. The filtrate was concentrated under reduced pressure. The residue was purified by flash silica gel chromatography (45 g SepaFlash Silica Flash Column, Eluent of 0~15% EtOAc/Petroleum ether gradient @ 70 mL/min) to afford tert-butyl 4-(4-formyl-2-(trifluoromethyl)phenyl)piperazine-1-carboxylate (3.5 g, 9.38 mmol, 45.03% yield, 96% purity) as yellow oil, which was used for the next step directly. MS (M−56+H)$^+$=303.1

Step 2. Synthesis of diethyl 2-(4-(4-(tert-butoxycarbonyl)piperazin-1-yl)-3-(trifluoromethyl)phenyl)-4-hydroxy-4-methyl-6-oxocyclohexane-1,3-dicarboxylate (3)

To a solution of tert-butyl 4-(4-formyl-2-(trifluoromethyl)phenyl)piperazine-1-carboxylate (3.5 g, 9.77 mmol) in ethyl 3-oxobutanoate (7.63 g, 58.60 mmol, 7.40 mL) was added piperidine (249.49 mg, 2.93 mmol, 289.36 μL) and the mixture was stirred at 25° C. for 14 h. LCMS showed the starting material was consumed completely and a main peak (70%) with desired mass. The residue was purified by flash silica gel chromatography (80 g SepaFlash Silica Flash Column, Eluent of 0~35% EtOAc/Petroleum ether gradient @ 80 mL/min) to afford diethyl 2-(4-(4-(tert-butoxycarbonyl)piperazin-1-yl)-3-(trifluoromethyl)phenyl)-4-hydroxy-4-methyl-6-oxocyclohexane-1,3-dicarboxylate (6 g, crude) as yellow oil, which was used for the next step directly. MS (M+H)$^+$=601.4

Step 3. Synthesis of 3-(4-(4-(tert-butoxycarbonyl)piperazin-1-yl)-3-(trifluoromethyl)phenyl) pentanedioic Acid (4)

To a solution of diethyl 2-(4-(4-(tert-butoxycarbonyl)piperazin-1-yl)-3-(trifluoromethyl)phenyl)-4-hydroxy-4-methyl-6-oxocyclohexane-1,3-dicarboxylate (4.2 g, 6.99 mmol) in EtOH (40 mL) was added KOH (3 M, 11.65 mL) and the mixture was stirred at 80° C. for 2 h. LCMS showed the starting material was consumed completely and a peak (50%) with desired mass. The mixture was diluted with H$_2$O (100 mL) and concentrated to removed EtOH. The resulting mixture was filtered through a celite pad and the filter cake was discard. The filtrate was washed with EtOAc (20 mL×3). The aqueous layer was adjusted the pH=6 with 1 N HCl at 0° C. and extracted with EtOAc (30 mL×3). The combined organic layer was dried over Na$_2$SO$_4$, filtered and concentrated under reduced pressure, to afford 3-(4-(4-(tert-butoxycarbonyl)piperazin-1-yl)-3-(trifluoromethyl)phenyl) pentanedioic acid (2.3 g, 4.80 mmol, 68.58% yield, 96% purity) as a yellow solid, which was used for the next step directly. MS (M+H)$^+$=461.1

Step 4. Synthesis of 4-(4-(4-acetylpiperazin-1-yl)-3-(trifluoromethyl)phenyl)piperidine-2,6-dione (5)

To a solution of UREA (1.80 g, 29.97 mmol, 1.61 mL) in AcOH (20 mL) was added 3-(4-(4-(tert-butoxycarbonyl)piperazin-1-yl)-3-(trifluoromethyl)phenyl)pentanedioic acid (2.3 g, 5.00 mmol), the mixture was stirred at 120° C. for 12 hr. LCMS showed the starting material was consumed completely and a main peak with desired mass. The mixture solution was concentrated under reduced pressure to afford 4-(4-(4-acetylpiperazin-1-yl)-3-(trifluoromethyl)phenyl)piperidine-2,6-dione (2 g, crude) as brown oil, which was used for the next step directly. MS (M+H)+=384.0

Step 5. Synthesis of tert-butyl 4-(4-(2,6-dioxopiperidin-4-yl)-2-(trifluoromethyl)phenyl)piperazine-1-carboxylate (6)

A solution of 4-(4-(4-acetylpiperazin-1-yl)-3-(trifluoromethyl)phenyl)piperidine-2,6-dione (1.9 g, 4.96 mmol) in HCl (6 M, 16.52 mL) was stirred at 50° C. for 12 hr. LCMS showed the starting material was consumed completely. The reaction mixture was concentrated under reduced pressure. The residue was diluted with THF (50 mL) and $H_2O$ (50 mL), then TEA (12.54 g, 123.90 mmol, 17.25 mL) and $Boc_2O$ (4.33 g, 19.82 mmol, 4.55 mL) were added at 25° C., the mixture was stirred at 25° C. for 1 hr. LCMS showed a peak (36%) with desired mass. The mixture was extracted with EtOAc (40 mL×4). The combined organic phase was washed with brine (10 mL×3), dried over $Na_2SO_4$, filtered and concentrated under reduced pressure. The residue was purified by flash silica gel chromatography (25 g SepaFlash Silica Flash Column, Eluent of 0~50% EtOAc/Petroleum ether gradient @ 50 mL/min) to afford tert-butyl 4-(4-(2,6-dioxopiperidin-4-yl)-2-(trifluoromethyl)phenyl)piperazine-1-carboxylate (0.7 g, 1.59 mmol, 31.99% yield) as a yellow solid, which was used for the next step directly. MS (M+H)+=442.2

Step 6. Synthesis of 4-(4-(piperazin-1-yl)-3-(trifluoromethyl)phenyl)piperidine-2,6-dione (7)

To a solution of tert-butyl 4-(4-(2,6-dioxopiperidin-4-yl)-2-(trifluoromethyl)phenyl)piperazine-1-carboxylate (250 mg, 566.32 µmol) in dioxane (2 mL) was added HCl/dioxane (4 M, 10 mL) at 25° C. The resulting mixture was stirred at 25° C. for 0.5 hr. LCMS showed the starting material was consumed completely and a main peak with desired mass. The reaction mixture was concentrated under reduced pressure to afford 4-(4-(piperazin-1-yl)-3-(trifluoromethyl)phenyl)piperidine-2,6-dione (220 mg, crude, HCl salt) as a white solid, which was used for the next step directly. MS (M+H)+=342.2

Step 7. Synthesis of tert-butyl (4-((4-(4-(2,6-dioxopiperidin-4-yl)-2-(trifluoromethyl)phenyl) piperazin-1-yl)methyl)piperidin-1-yl)carbamate (8)

To a solution of 4-(4-(piperazin-1-yl)-3-(trifluoromethyl)phenyl)piperidine-2,6-dione (220 mg, 582.34 µmol, HCl salt) and tert-butyl (4-formylpiperidin-1-yl)carbamate (265.88 mg, 1.16 mmol) in DCE (3 mL) was added NaOAc (143.31 mg, 1.75 mmol) and the resulting mixture was stirred at 25° C. for 0.5 hr. Then NaBH(OAc)$_3$ (370.26 mg, 1.75 mmol) was added at 25° C. and the resulting mixture was stirred at 25° C. for 12 h. LCMS showed a peak (10%) with desired mass, and a peak (29%) with starting material. The crude product was dissolved in DCM (50 mL) and washed with saturated NaHCO$_3$ (30 mL). The organic layer was dried over Na$_2$SO$_4$, filtered and concentrated under reduced pressure. The residue was purified by flash silica gel chromatography (20 g SepaFlash Silica Flash Column, Eluent of 0~100% EtOAc/Petroleum ether gradient @ 70 mL/min; Eluent of 0~50% Methanol/EtOAc @ 70 mL/min), to afford tert-butyl (4-((4-(4-(2,6-dioxopiperidin-4-yl)-2-(trifluoromethyl)phenyl)piperazin-1-yl)methyl)piperidin-1-yl)carbamate (140 mg, crude) as a yellow solid, which was used for the next step directly. MS (M+H)+=554.1

Step 8. Synthesis of 4-(4-(4-((1-aminopiperidin-4-yl)methyl)piperazin-1-yl)-3-(trifluoromethyl)phenyl)piperidine-2,6-dione (9)

To a solution of tert-butyl (4-((4-(4-(2,6-dioxopiperidin-4-yl)-2-(trifluoromethyl)phenyl)piperazin-1-yl)methyl)piperidin-1-yl)carbamate (125 mg, 225.79 µmol) in DCM (2 mL) was added TFA (0.4 mL) at 25° C. The resulting mixture was stirred at 25° C. for 0.5 hr. LCMS showed a peak (16%) with mass of starting material and a peak (69%) with desired mass. The resulting mixture was stirred at 25° C. for another 1 hr. TLC (Dichloromethane:Methanol=10:1) showed the starting material was consumed completely and new spot was formed. The reaction mixture was concentrated under reduced pressure to afford 4-(4-(4-((1-aminopiperidin-4-yl)methyl)piperazin-1-yl)-3-(trifluoromethyl)phenyl)piperidine-2,6-dione (128 mg, crude, TFA salt) as brown oil, which was used for the next step directly. MS (M+H)+=454.3

Step 9. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2-(trifluoromethyl)phenyl)piperazin-1-yl)methyl)piperidin-1-yl)-3-methoxybenzamide (Compound 55)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (70 mg, 166.11 µmol) in DMF (2 mL) were added HATU (75.79 mg, 199.34 µmol) and DIPEA (64.41 mg, 498.34 µmol, 86.80 µL). The mixture was stirred at 25° C. for 10 min. Then 4-(4-(4-((1-aminopiperidin-4-yl)methyl)piperazin-1-yl)-3-(trifluoromethyl)phenyl)piperidine-2,6-dione (122.56 mg, 215.95 µmol, TFA salt) was added and the mixture was stirred at 25° C. for 1 h. LCMS showed the starting material was consumed completely and a peak (31%) with desired mass. The reaction mixture was concentrated under reduced pressure. The residue was purified by flash silica gel chromatography (4 g SepaFlash Silica Flash Column, Eluent of 0~100% EtOAc/Petroleum ether gradient @ 60 mL/min; Eluent of 0~50% Methanol/EtOAc @ 60 mL/min) followed by prep-HPLC (column: Waters Xbridge 150×25 mm×5 µm; mobile phase: [water (NH$_4$HCO$_3$)-ACN]; B %: 41%-71%, 8 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2-(trifluoromethyl)phenyl)piperazin-1-yl)methyl)piperidin-1-yl)-3-methoxybenzamide (28.5 mg, 30.93 µmol, 18.62% yield, 93% purity) as a brown solid. MS (M+H)+=857.5

$^1$H NMR (400 MHz, DMSO-d$_6$) δ=11.00-10.76 (m, 1H), 9.39-9.16 (m, 1H), 8.41-8.26 (m, 1H), 8.22 (s, 1H), 7.87 (s, 1H), 7.69-7.51 (m, 3H), 7.50-7.28 (m, 2H), 4.99-4.78 (m, 1H), 4.14-3.99 (m, 2H), 3.99-3.82 (m, 3H), 3.57-3.35 (m, 3H), 3.29 (br s, 3H), 3.02 (br d, J=8.1 Hz, 2H), 2.89-2.77 (m, 6H), 2.74 (br s, 2H), 2.65 (br d, J=17.0 Hz, 4H), 2.21 (br d, J=5.8 Hz, 2H), 1.83-1.72 (m, 2H), 1.60-1.47 (m, 1H), 1.24 (br d, J=6.4 Hz, 8H).

Example 56. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2-fluorophenyl)piperazin-1-yl)methyl)piperidin-1-yl)-3-methoxybenzamide (Compound 56)
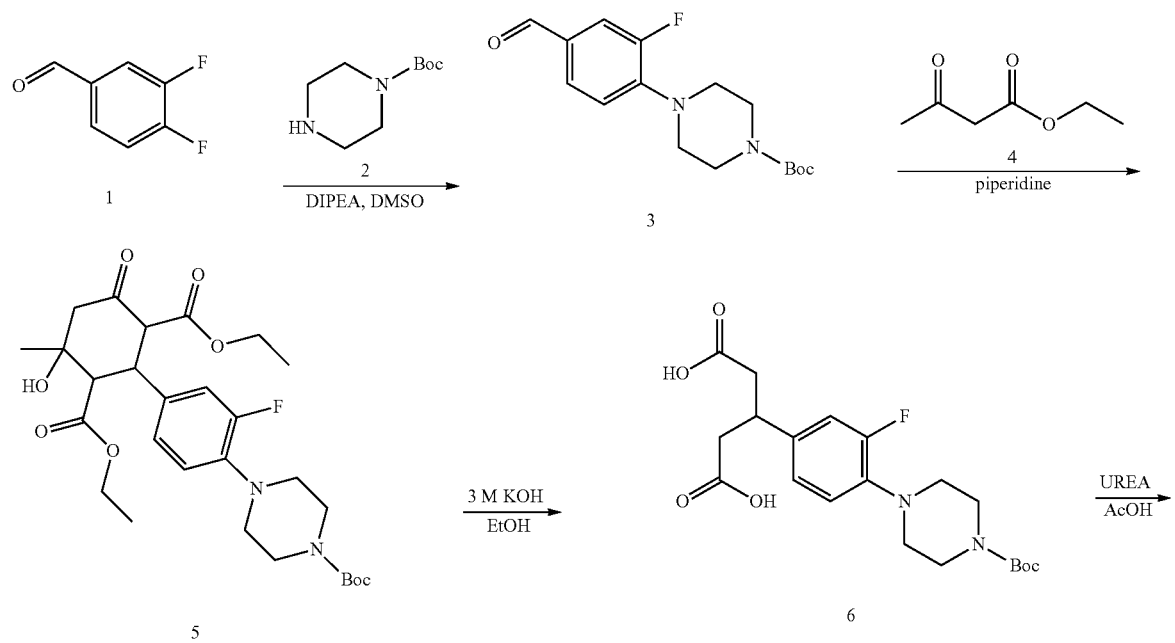
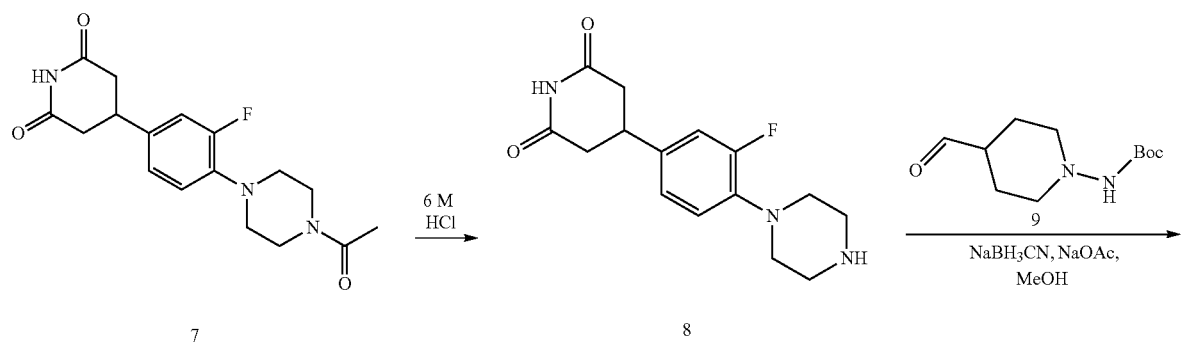
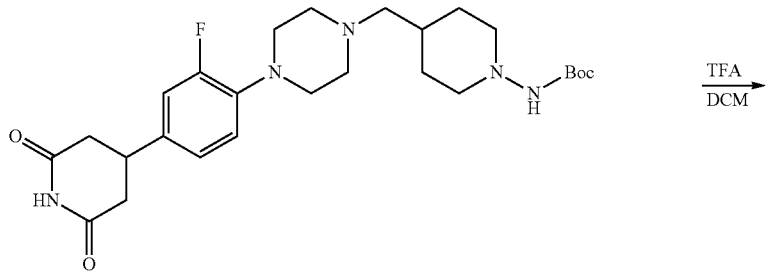

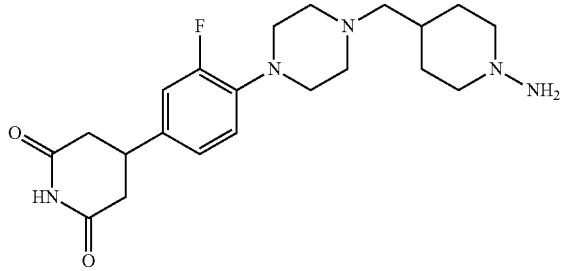

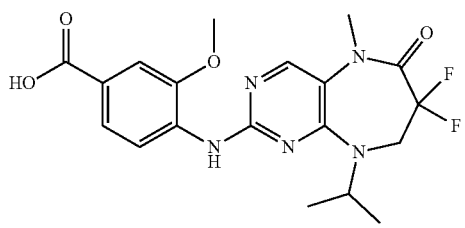

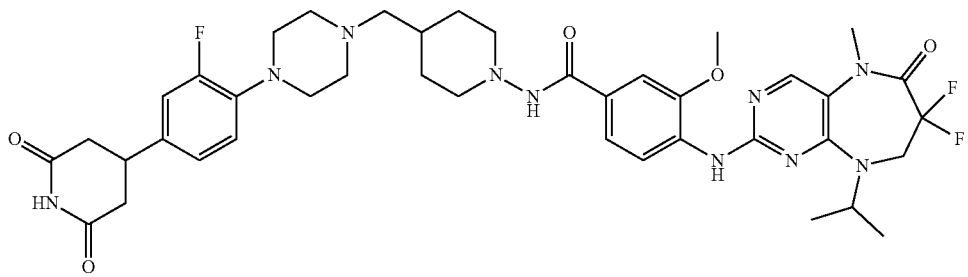

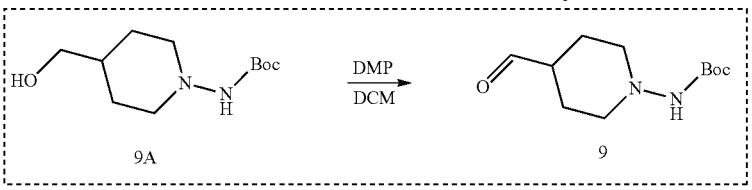

Step 1. Synthesis of tert-butyl 4-(2-fluoro-4-formylphenyl)piperazine-1-carboxylate (3)

To a solution of 3,4-difluorobenzaldehyde (9 g, 63.33 mmol, 6.87 mL) and tert-butyl piperazine-1-carboxylate (12.39 g, 66.50 mmol) in DMSO (90 mL) was added DIPEA (16.37 g, 126.67 mmol, 22.06 mL) and the mixture was stirred at 100° C. for 14 h. LCMS showed 89% of the desired mass. The mixture was diluted with H$_2$O (150 mL) and extracted with EtOAc (50 mL×3), the combined organic layer was washed with brine (50 mL×3), dried over Na$_2$SO$_4$ and filtered. The filtrate was concentrated under reduced pressure. The residue was purified by flash silica gel chromatography (120 g SepaFlash Silica Flash Column, Eluent of 10~20% EtOAc/Petroleum ether gradient @ 100 mL/min) to afford tert-butyl 4-(2-fluoro-4-formylphenyl)piperazine-1-carboxylate (18.1 g, 58.70 mmol, 92.68% yield, 100% purity) as yellow solid. MS (M+H)$^+$=309.1.

Step 2. Synthesis of diethyl 2-(4-(4-(tert-butoxycarbonyl)piperazin-1-yl)-3-fluorophenyl)-4-hydroxy-4-methyl-6-oxocyclohexane-1,3-dicarboxylate (5)

To a solution of tert-butyl 4-(2-fluoro-4-formylphenyl)piperazine-1-carboxylate (17.6 g, 57.08 mmol) in ethyl 3-oxobutanoate (44.60 g, 342.70 mmol, 43.3 mL) was added piperidine (1.47 g, 17.21 mmol, 1.7 mL) and the mixture was stirred at 20° C. for 14 h. LCMS showed tert-butyl 4-(2-fluoro-4-formylphenyl)piperazine-1-carboxylate remained and the desired mass was detected. The mixture was stirred at 20° C. for 14 h. LCMS showed 83% of the desired mass. The mixture was diluted with MTBE (150 mL) and stirred at 20° C. for 0.5 h. Then the mixture was filtered and the filter cake was washed with MTBE (100 mL). The filter cake was collected and dried under reduced pressure to afford diethyl 2-(4-(4-(tert-butoxycarbonyl)piperazin-1-yl)-3-fluorophenyl)-4-hydroxy-4-methyl-6-oxocyclohexane-1,3-dicarboxylate (19.2 g, crude) as a white solid. MS (M+H)$^+$=551.4.

Step 3. Synthesis of 3-(4-(4-(tert-butoxycarbonyl)piperazin-1-yl)-3-fluorophenyl)pentanedioic Acid (6)

To a solution of diethyl 2-(4-(4-(tert-butoxycarbonyl)piperazin-1-yl)-3-fluorophenyl)-4-hydroxy-4-methyl-6-oxocyclohexane-1,3-dicarboxylate (9.2 g, 16.71 mmol) in EtOH (90 mL) was added KOH (3 M, 27.85 mL) and the mixture was stirred at 80° C. for 14 h. LCMS showed 38% of the desired mass. The mixture was concentrated to remove EtOH. The crude was diluted with H$_2$O (100 mL) and washed with EtOAc (20 mL×3). The combined organic layer was washed with H$_2$O (20 mL), the aqueous layer was adjusted the pH=6 with 1 N HCl, then extracted with EtOAc (20 mL×3), the combined organic layer was washed with H$_2$O (20 mL), dried over Na$_2$SO$_4$ and filtered. The filtrate was concentrated under reduced pressure. The residue was purified by flash silica gel chromatography (40 g SepaFlash Silica Flash Column, Eluent of 70~100% EtOAc/Petroleum ether gradient @ 100 mL/min) to afford 3-(4-(4-(tert-butoxycarbonyl)piperazin-1-yl)-3-fluorophenyl)pentanedioic acid (3.05 g, 7.13 mmol, 42.70% yield, 96% purity) as a yellow solid. MS (M+H)$^+$=411.2.

Step 4. Synthesis of 4-(3-fluoro-4-(piperazin-1-yl)phenyl)piperidine-2,6-dione (8)

A solution of 3-(4-(4-(tert-butoxycarbonyl)piperazin-1-yl)-3-fluorophenyl)pentanedioic acid (7.17 g, 17.47 mmol) and UREA (5.25 g, 87.35 mmol, 4.68 mL) in AcOH (72 mL) was stirred at 120° C. for 14 h. LCMS showed a peak (85%) with mass of 4-(4-(4-acetylpiperazin-1-yl)-3-fluorophenyl)piperidine-2,6-dione. The mixture was concentrated under reduced pressure. HCl (6 M, 29.33 mL) was added and the resulting mixture was stirred at 50° C. for another 14 h. LCMS showed a peak (69%) with mass of 4-(3-fluoro-4-(piperazin-1-yl)phenyl)piperidine-2,6-dione. The mixture was concentrated under reduced pressure. The crude was purified by reversed-phase HPLC (Column 330 g Flash Column Welch Ultimate XB_C$_{18}$ 20-40 µm; 120 A Solvent for sample dissolution about 6.00 grams of sample dissolved in 100 mL of H$_2$O/MeCN Flow rate 100 mL/min Mobile phase MeCN/H$_2$O Gradient B % 0-5% 40 min; 5-95% 20 min Instrument TELEDYNE ISCO CombiFlash Rf$_{150}$) and the eluent was lyophilized to afford two batches of 4-(3-fluoro-4-(piperazin-1-yl)phenyl)piperidine-2,6-dione: batch 1: (2.3 g, 6.32 mmol, 36.15% yield, 90% purity, HCl salt) as a white solid and batch 2: 4-(3-fluoro-4-(piperazin-1-yl)phenyl)piperidine-2,6-dione (920 mg, 2.25 mmol, 12.85% yield, 80% purity, HCl salt) as a white solid. MS (M+H)$^+$=292.1

Step 5. Synthesis of tert-butyl (4-formylpiperidin-1-yl)carbamate (9)

To a solution of tert-butyl (4-(hydroxymethyl)piperidin-1-yl)carbamate (3.6 g, 15.63 mmol) in DCM (50 mL) was added DMP (9.95 g, 23.45 mmol, 7.26 mL) and the mixture was stirred at 20° C. for 1 h. LCMS showed a peak (59%) with desired mass and a peak (20%) with mass of the starting material. The mixture was diluted with MTBE (60 mL) and filtered. The filter cake was washed with MTBE (50 mL) and the filtrate was concentrated under reduced pressure to afford tert-butyl (4-formylpiperidin-1-yl)carbamate (5.8 g, crude) as yellow oil. MS (M+H)$^+$=229.3

Step 6. Synthesis of tert-butyl (4-((4-(4-(2,6-dioxopiperidin-4-yl)-2-fluorophenyl)piperazin-1-yl)methyl)piperidin-1-yl)carbamate (10)

To a solution of 4-(3-fluoro-4-(piperazin-1-yl)phenyl)piperidine-2,6-dione (1.5 g, 4.58 mmol, HCl salt) in MeOH (10 mL) was added NaOAc (376 mg, 4.58 mmol), then tert-butyl (4-formylpiperidin-1-yl)carbamate (4.70 g, 20.59 mmol) in MeOH (10 mL) was added and the mixture was stirred at 20° C. for 30 min. NaBH$_3$CN (863.31 mg, 13.74 mmol) was added and the mixture was stirred at 20° C. for 1 h. LCMS showed 28% of 4-(3-fluoro-4-(piperazin-1-yl)phenyl)piperidine-2,6-dione mass and 26% of the desired mass. A solution of tert-butyl (4-formylpiperidin-1-yl)carbamate (6.27 g, 27.46 mmol) in MeOH (10 mL) was added and the mixture was stirred at 20° C. for 1.5 h. NaBH$_3$CN (862.74 mg, 13.73 mmol) was added and the mixture was stirred at 20° C. for 14 h. LCMS showed the desired mass. The mixture was concentrated under reduced pressure. The residue was purified by flash silica gel chromatography (20 g SepaFlash Silica Flash Column, Eluent of 0~50% EtOH/EtOAc gradient @ 80 mL/min) and then purified by prep-HPLC (column: Phenomenex luna C18 150×40 mm×15 µm; mobile phase: [water (FA)-ACN]; B %: 8%-38%, 10 min) and the eluent was lyophilized to afford tert-butyl (4-((4-(4-(2,6-dioxopiperidin-4-yl)-2-fluorophenyl)piperazin-1-yl)methyl)piperidin-1-yl)carbamate (0.1 g, 198.57 µmol, 4.34% yield) as a white solid. MS (M+H)$^+$=504.3

Step 7. Synthesis of 4-(4-(4-((1-aminopiperidin-4-yl)methyl)piperazin-1-yl)-3-fluorophenyl)piperidine-2,6-dione (11)

To a solution of tert-butyl (4-((4-(4-(2,6-dioxopiperidin-4-yl)-2-fluorophenyl)piperazin-1-yl)methyl)piperidin-1-yl)carbamate (170 mg, 337.56 µmol) in DCM (2 mL) was added TFA (0.4 mL) and the mixture was stirred at 20° C. for 2 h. LCMS showed 73% of the desired mass and 19% of the starting material remained. Additional TFA (0.1 mL) was added and the mixture was stirred at 20° C. for 0.5 h. LCMS showed the starting material was consumed and 74% of the desired mass. The mixture was concentrated under reduced pressure to afford 4-(4-(4-((1-aminopiperidin-4-yl)methyl)piperazin-1-yl)-3-fluorophenyl)piperidine-2,6-dione (220 mg, crude, 2TFA) as yellow oil. MS (M+H)$^+$=404.3

Step 8. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2-fluorophenyl)piperazin-1-yl)methyl)piperidin-1-yl)-3-methoxybenzamide (Compound 56)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (170 mg, 403.42 µmol) and HATU (184.07 mg, 484.10 µmol) in DMF (3 mL) was added DIPEA (104.28 mg, 806.84 µmol, 140.54 µL) and the mixture was stirred at 20° C. for 30 min. Then a solution of 4-(4-(4-((1-aminopiperidin-4-yl)methyl)piperazin-1-yl)-3-fluorophenyl)piperidine-2,6-dione (220 mg, 461.78 µmol, 2TFA) and DIPEA (521.39 mg, 4.03 mmol, 702.68 µL) in DMF (2 mL) was added and the mixture was stirred at 20° C. for 2 h. LCMS showed the desired mass. The mixture was diluted with H$_2$O (20 mL) and extracted with EtOAc (10 mL×3). The combined organic layer was washed with brine (10 mL), dried over Na$_2$SO$_4$ and filtered. The filtrate was concentrated under reduced pressure. The crude was purified by prep-HPLC (column: Unisil 3-100 C18 µLtra 150×50 mm×3 µm; mobile phase: [water (FA)-ACN]; B %: 10%-40%, 7 min) followed by prep-HPLC (column: Waters Xbridge 150×25 mm×5 µm; mobile phase: [water (NH$_4$HCO$_3$)-ACN]; B %: 38%-68%, 8 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2-fluorophenyl)piperazin-1-yl)methyl)piperidin-1-yl)-3-methoxybenzamide (52.6 mg, 64.41 µmol, 15.97% yield, 98.8% purity) as a white solid. MS (M+H)$^+$=807.5

$^1$H NMR (400 MHz, DMSO-d$_6$) δ=10.87-10.83 (m, 1H), 9.31-9.26 (m, 1H), 8.33-8.28 (m, 1H), 8.22 (s, 1H), 7.88 (s, 1H), 7.46-7.40 (m, 2H), 7.12 (br d, J=13.4 Hz, 1H), 7.05-6.98 (m, 2H), 4.92-4.83 (m, 1H), 4.08-4.00 (m, 2H), 3.93 (s, 3H), 3.31-3.29 (m, 6H), 3.04-2.96 (m, 4H), 2.81-2.71 (m, 4H), 2.65-2.56 (m, 6H), 2.23-2.20 (m, 2H), 1.79-1.71 (m, 2H), 1.57-1.47 (m, 1H), 1.26-1.22 (m, 8H).

Example 57. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2,6-difluorophenyl)piperazin-1-yl)methyl)piperidin-1-yl)-3-methoxybenzamide (Compound 57)
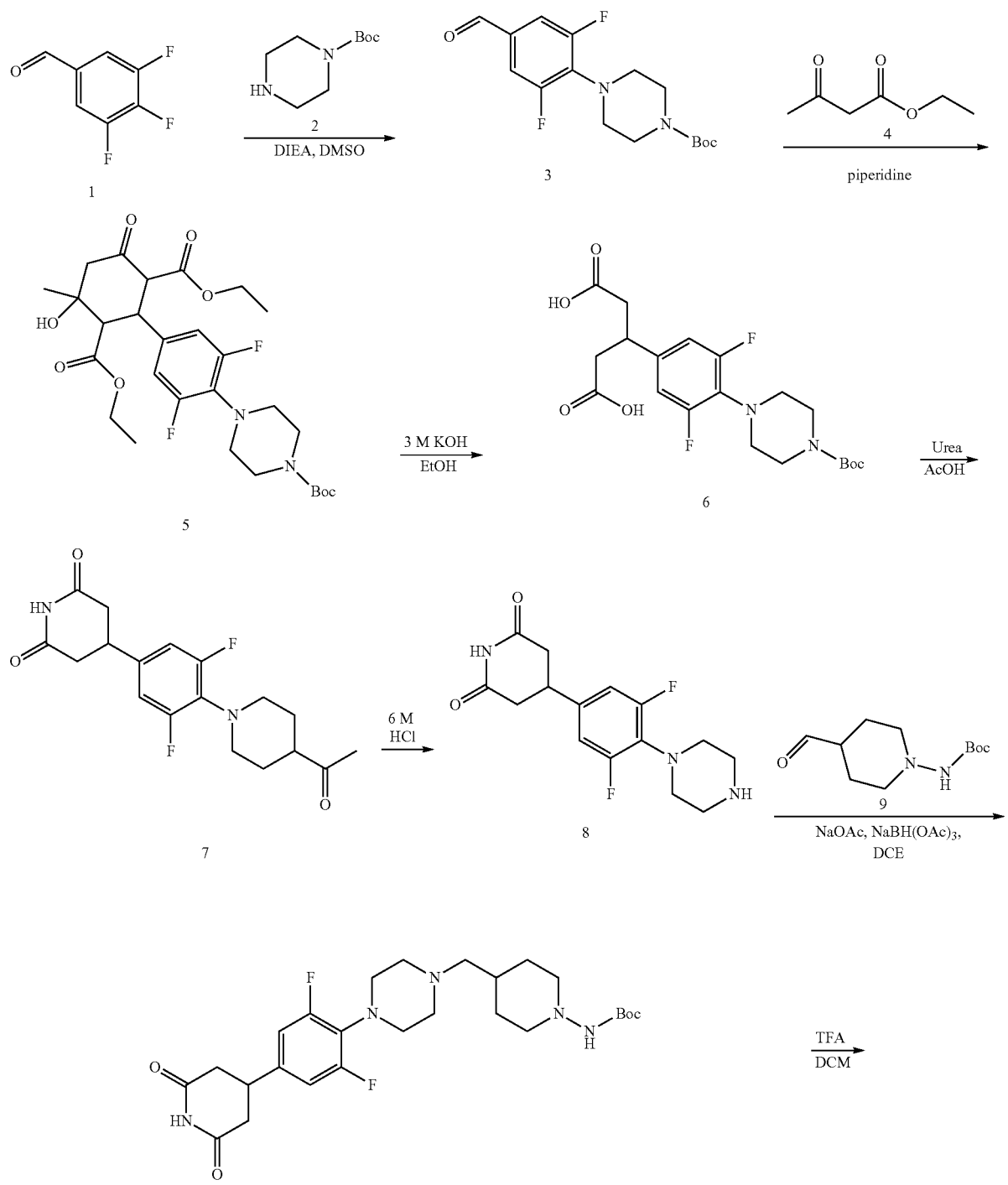

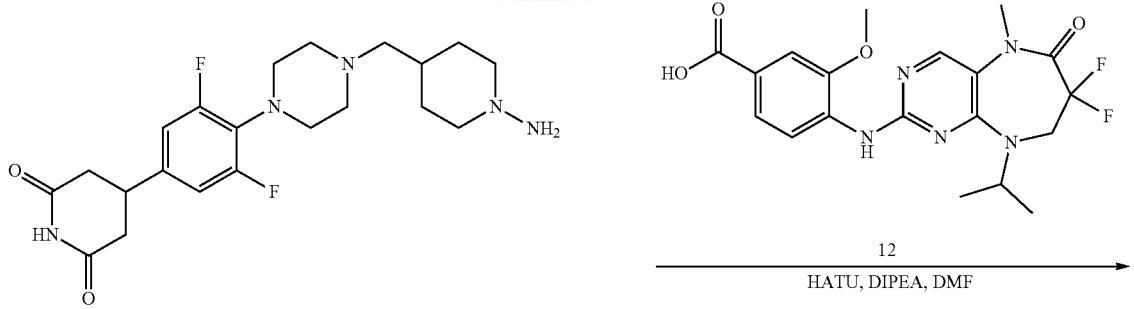

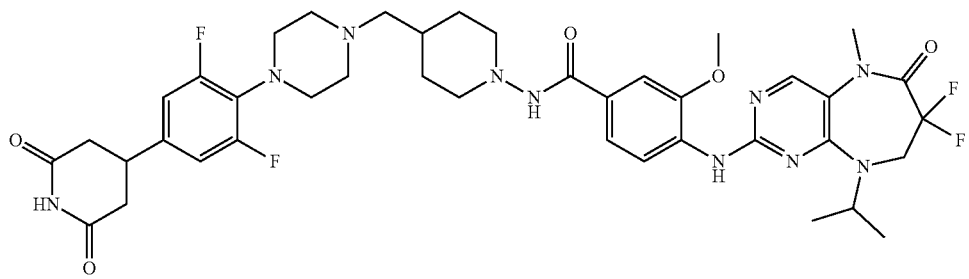

Compound 57

Step 1. Synthesis of tert-butyl 4-(2,6-difluoro-4-formylphenyl)piperazine-1-carboxylate (3)

To a solution of 3,4,5-trifluorobenzaldehyde (5 g, 31.23 mmol) and tert-butyl piperazine-1-carboxylate (6.11 g, 32.79 mmol) in DMSO (50 mL) was added DIPEA (12.11 g, 93.70 mmol, 16.32 mL) and the mixture was stirred at 100° C. for 14 h. LCMS showed 96% of the desired mass. The mixture was diluted with $H_2O$ (100 mL) and extracted with EtOAc (30 mL×3), the combined organic layer was washed with brine (30 mL×3), dried over $Na_2SO_4$ and filtered. The filtrate was concentrated under reduced pressure. The residue was purified by flash silica gel chromatography (80 g SepaFlash Silica Flash Column, Eluent of 15~20% EtOAc/Petroleum ether gradient @ 100 mL/min) to afford tert-butyl 4-(2,6-difluoro-4-formylphenyl)piperazine-1-carboxylate (9 g, 27.30 mmol, 87.42% yield, 99% purity) as a yellow solid. MS $(M-100+H)^+=227.0$

Step 2. Synthesis of diethyl 2-(4-(4-(tert-butoxycarbonyl)piperazin-1-yl)-3,5-difluorophenyl)-4-hydroxy-4-methyl-6-oxocyclohexane-1,3-dicarboxylate (5)

To a solution of tert-butyl 4-(2,6-difluoro-4-formylphenyl)piperazine-1-carboxylate (9 g, 27.58 mmol) in ethyl 3-oxobutanoate (21.53 g, 165.41 mmol, 20.9 mL) was added piperidine (707.00 mg, 8.30 mmol, 820 µL) and the mixture was stirred at 20° C. for 28 h. LCMS showed 82% of desired mass. The mixture was diluted with MTBE (60 mL) and stirred at 20° C. for 0.5 h. Then the mixture was filtered and the filter cake was washed with MTBE (50 mL). The filter cake was collected and dried under reduced pressure to afford diethyl 2-(4-(4-(tert-butoxycarbonyl)piperazin-1-yl)-3,5-difluorophenyl)-4-hydroxy-4-methyl-6-oxocyclohexane-1,3-dicarboxylate (10.67 g, crude) as a white solid. MS $(M+H)^+=569.3$

Step 3. Synthesis of 3-(4-(4-(tert-butoxycarbonyl)piperazin-1-yl)-3,5-difluorophenyl)pentanedioic Acid (6)

To a solution of diethyl 2-(4-(4-(tert-butoxycarbonyl)piperazin-1-yl)-3,5-difluorophenyl)-4-hydroxy-4-methyl-6-oxocyclohexane-1,3-dicarboxylate (5 g, 8.79 mmol) in EtOH (50 mL) was added KOH (3 M, 14.66 mL) and the mixture was stirred at 80° C. for 14 h. LCMS showed 76% of desired mass. The mixture was concentrated to remove EtOH. The crude was diluted with $H_2O$ (50 mL) and washed with EtOAc (20 mL×3), the combined organic layer was extracted with $H_2O$ (20 mL), the aqueous layer was adjusted the pH=6 with 1 N HCl. Then the aqueous layer was extracted with EtOAc (20 mL×3), the combined organic layer was washed with $H_2O$ (20 mL), dried over $Na_2SO_4$ and filtered. The filtrate was concentrated under reduced pressure. The residue was purified by flash silica gel chromatography (40 g SepaFlash Silica Flash Column, Eluent of 70~90% EtOAc/Petroleum ether gradient @ 80 mL/min) to afford 3-(4-(4-(tert-butoxycarbonyl)piperazin-1-yl)-3,5-difluorophenyl)pentanedioic acid (2.2 g, 5.14 mmol, 58.40% yield, 100% purity) as a yellow solid. MS $(M+H)^+=429.2$

Step 4. Synthesis of 4-(3,5-difluoro-4-(piperazin-1-yl)phenyl)piperidine-2,6-dione (8)

A solution of 3-(4-(4-(tert-butoxycarbonyl)piperazin-1-yl)-3,5-difluorophenyl)pentanedioic acid (2.2 g, 5.14 mmol) and UREA (1.54 g, 25.68 mmol, 1.38 mL) in AcOH (22 mL) was stirred at 120° C. for 14 h. LCMS showed a peak (87%) with mass of 4-(4-(4-acetylpiperazin-1-yl)-3,5-difluorophenyl)piperidine-2,6-dione. The mixture was concentrated under reduced pressure. HCl (6 M, 8.62 mL) was added and the mixture was stirred at 50° C. for 14 h. LCMS showed a peak (46%) with mass of 4-(4-(4-acetylpiperazin-1-yl)-3,5-difluorophenyl)piperidine-2,6-dione and a peak (36%) with mass of 4-(3,5-difluoro-4-(piperazin-1-yl)phenyl)piperidine-2,6-dione. Additional HCl (6 M, 8 mL) was added and the mixture was stirred at 50° C. for another 6 h. LCMS showed a peak (75%) with mass of 4-(3,5-difluoro-4-(piperazin-1-yl)phenyl)piperidine-2,6-dione. The mixture was concentrated under reduced pressure. The crude was purified by reversed-phase HPLC (Column 120 g Flash Column Welch Ultimate XB_$C_{18}$ 20-40 μm; 120 A Solvent for sample dissolution about 2.00 grams of sample dissolved in 40 mL of $H_2O$/MeCN; Flow rate 85 mL/min Mobile phase MeCN/$H_2O$ Gradient B % 0-30% 30 min; 30-100% 20 min; Instrument TELEDYNE ISCO CombiFlash $Rf_{150}$) and the eluent was lyophilized to afford 4-(3,5-difluoro-4-(piperazin-1-yl)phenyl)piperidine-2,6-dione (410 mg, 1.16 mmol, 22.63% yield, 98% purity, HCl salt) as a white solid. MS $(M+H)^+=310.1$ Step 5. Synthesis of tert-butyl (4-((4-(4-(2,6-dioxopiperidin-4-yl)-2,6-difluorophenyl)piperazin-1-yl)methyl)piperidin-1-yl)carbamate (10)

To a solution of 4-(3,5-difluoro-4-(piperazin-1-yl)phenyl)piperidine-2,6-dione (120 mg, 347.05 μmol, HCl salt) in DCE (4 mL) was added NaOAc (28.47 mg, 347.05 μmol), then a solution of tert-butyl (4-formylpiperidin-1-yl)carbamate (240.00 mg, 1.05 mmol) in DCE (4 mL) was added and the mixture was stirred at 20° C. for 30 min. NaBH(OAc)$_3$ (220.80 mg, 1.04 mmol) was added and the mixture was stirred at 20° C. for another 14 h. LCMS showed the desired mass was detected. The mixture was concentrated under reduced pressure. The residue was purified by flash silica gel chromatography (5 g SepaFlash Silica Flash Column, Eluent of 5~15% EtOAc/Petroleum ether gradient @ 50 mL/min) to afford tert-butyl (4-((4-(4-(2,6-dioxopiperidin-4-yl)-2,6-difluorophenyl)piperazin-1-yl)methyl)piperidin-1-yl)carbamate (90 mg, crude) as a yellow solid. MS $(M+H)^+=522.2$ Step 6. Synthesis of 4-(4-(4-((1-aminopiperidin-4-yl)methyl)piperazin-1-yl)-3,5-difluorophenyl)piperidine-2,6-dione (11)

To a solution of tert-butyl (4-((4-(4-(2,6-dioxopiperidin-4-yl)-2,6-difluorophenyl)piperazin-1-yl)methyl)piperidin-1-yl)carbamate (70 mg, 134.20 μmol) in DCM (0.7 mL) was added TFA (323.40 mg, 2.84 mmol, 210 μL) and the mixture was stirred at 20° C. for 1 h. LCMS showed 60% of desired mass was detected. The mixture was concentrated under reduced pressure to afford 4-(4-(4-((1-aminopiperidin-4-yl)methyl)piperazin-1-yl)-3,5-difluorophenyl)piperidine-2,6-dione (90 mg, crude, 2TFA salt) as yellow oil.

Step 7. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2,6-difluorophenyl)piperazin-1-yl)methyl)piperidin-1-yl)-3-methoxybenzamide (Compound 57)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (45 mg, 106.79 μmol) and HATU (48.72 mg, 128.15 μmol) in DMF (0.9 mL) was added DIPEA (29.68 mg, 229.64 μmol, 40 μL) and the mixture was stirred at 20° C. for 30 min. Then a solution of 4-(4-(4-((1-aminopiperidin-4-yl)methyl)piperazin-1-yl)-3,5-difluorophenyl)piperidine-2,6-dione (90.00 mg, 182.04 μmol, 2HCl salt) and DIPEA (138.02 mg, 1.07 mmol, 186.00 μL) in DMF (0.9 mL) was added and the mixture was stirred at 20° C. for 2 h. LCMS showed the desired mass was detected. The mixture was diluted with $H_2O$ (10 mL) and extracted with EtOAc (10 mL×3), the combined organic layer was washed with brine (10 mL), dried over $Na_2SO_4$ and filtered. The filtrate was concentrated under reduced pressure. The crude was purified by prep-TLC (Dichloromethane:Methanol=10:1) twice, the impure product was re-purified by prep-HPLC (column: Waters Xbridge 150×25 mm×5 μm; mobile phase: [water ($NH_4HCO_3$)-ACN]; B %: 43%-73%, 8 min) and the eluent was lyophilized to afford 4-((7,7-difluoro-9-isopropyl-5-methyl-6-oxo-6,7,8,9-tetrahydro-5H-pyrimido[4,5-b][1,4]diazepin-2-yl)amino)-N-(4-((4-(4-(2,6-dioxopiperidin-4-yl)-2,6-difluorophenyl)piperazin-1-yl)methyl)piperidin-1-yl)-3-methoxybenzamide (8.0 mg, 9.21 μmol, 8.63% yield, 95% purity) as a white solid. MS $(M+H)^+=825.4$
$^1$H NMR (400 MHz, DMSO-$d_6$) δ=10.95-10.86 (m, 1H), 9.36-9.25 (m, 1H), 8.35-8.27 (m, 1H), 8.25-8.18 (m, 1H), 7.92-7.85 (m, 1H), 7.47-7.40 (m, 2H), 7.14-7.05 (m, 1H), 7.05-7.01 (m, 1H), 4.94-4.83 (m, 1H), 4.08-4.00 (m, 2H), 3.90 (s, 3H), 3.31-3.29 (m, 6H), 3.11-3.07 (m, 2H), 3.05-2.97 (m, 2H), 2.81-2.74 (m, 4H), 2.65-2.61 (m, 6H), 2.23-2.13 (m, 2H), 1.83-1.72 (m, 2H), 1.57-1.47 (m, 1H), 1.32-1.18 (m, 8H).

Example 58. Synthesis of N-(4-((4-(2-chloro-4-(2,6-dioxopiperidin-4-yl)phenyl)piperazin-1-yl)methyl)piperidin-1-yl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (Compound 58)

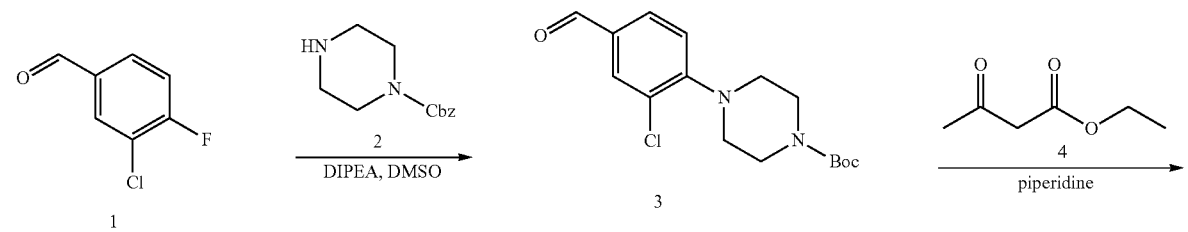

-continued
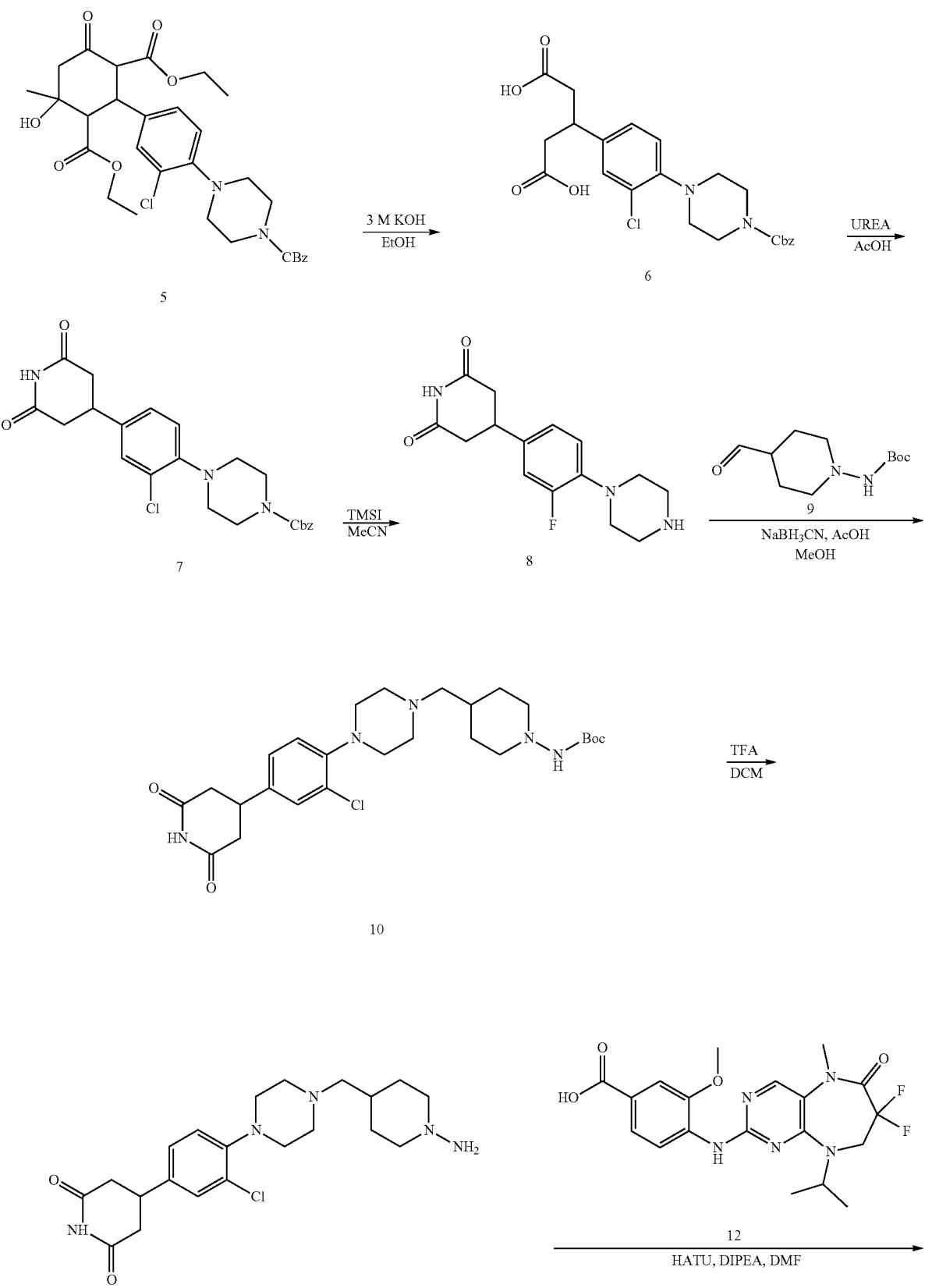

-continued

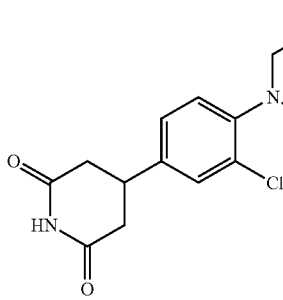 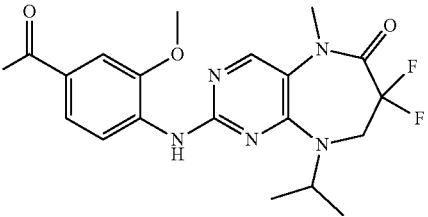

Compound 58

Step 1. Synthesis of benzyl 4-(2-chloro-4-formylphenyl)piperazine-1-carboxylate (3)

To a solution of 3-chloro-4-fluorobenzaldehyde (5 g, 31.53 mmol) and benzyl piperazine-1-carboxylate (7.29 g, 33.11 mmol, 6.40 mL) in DMSO (100 mL) was added DIPEA (12.22 g, 94.59 mmol, 16.48 mL) and the mixture was stirred at 100° C. for 14 h. LCMS showed 69% of the desired mass was detected. The mixture was diluted with $H_2O$ (100 mL) and extracted with EtOAc (30 mL×3), the combined organic layer was washed with brine (50 mL×3), dried over $Na_2SO_4$ and filtered. The filtrate was concentrated under reduced pressure. The residue was purified by flash silica gel chromatography (80 g SepaFlash Silica Flash Column, Eluent of 15~25% EtOAc/Petroleum ether gradient @ 100 mL/min) to afford benzyl 4-(2-chloro-4-formylphenyl)piperazine-1-carboxylate (8.79 g, 24.01 mmol, 76.14% yield, 98% purity) as yellow oil. MS $(M+H)^+=359.1$

Step 2. Synthesis of diethyl 2-(4-(4-((benzyloxy)carbonyl)piperazin-1-yl)-3-chlorophenyl)-4-hydroxy-4-methyl-6-oxocyclohexane-1,3-dicarboxylate (5)

To a solution of benzyl 4-(2-chloro-4-formylphenyl)piperazine-1-carboxylate (8.79 g, 24.50 mmol) in ethyl 3-oxobutanoate (18.54 g, 142.46 mmol, 18 mL) was added piperidine (629.41 mg, 7.39 mmol, 730 µL) and the mixture was stirred at 20° C. for 28 h. LCMS showed 69% of the desired mass. The mixture was concentrated under reduced pressure. The residue was purified by flash silica gel chromatography (120 g SepaFlash Silica Flash Column, Eluent of 40~60% EtOAc/Petroleum ether gradient @ 100 mL/min) to afford diethyl 2-(4-(4-((benzyloxy)carbonyl)piperazin-1-yl)-3-chlorophenyl)-4-hydroxy-4-methyl-6-oxocyclohexane-1,3-dicarboxylate (15.1 g, crude) as yellow oil. MS $(M+H)^+=601.1$

Step 3. Synthesis of 3-(4-(4-((benzyloxy)carbonyl)piperazin-1-yl)-3-chlorophenyl)pentanedioic Acid (6)

To a solution of diethyl 2-(4-(4-((benzyloxy)carbonyl)piperazin-1-yl)-3-chlorophenyl)-4-hydroxy-4-methyl-6-oxocyclohexane-1,3-dicarboxylate (15.1 g, 25.12 mmol) in EtOH (150 mL) was added KOH (3 M, 42 mL) and the mixture was stirred at 80° C. for 14 h. LCMS showed 36% of the desired mass. The mixture was concentrated to remove EtOH. The crude was diluted with $H_2O$ (100 mL) and the mixture was washed with EtOAc (30 mL×3), the combined organic layer was extracted with $H_2O$ (20 mL), the aqueous layer was adjusted the pH=6 with 1 N HCl, then extracted with EtOAc (30 mL×3), the combined organic layer was washed with $H_2O$ (20 mL), dried over $Na_2SO_4$ and filtered. The filtrate was concentrated under reduced pressure. The residue was purified by flash silica gel chromatography (40 g SepaFlash Silica Flash Column, Eluent of 60~80% EtOAc/Petroleum ether gradient @ 100 mL/min) to afford 3-(4-(4-((benzyloxy)carbonyl)piperazin-1-yl)-3-chlorophenyl)pentanedioic acid (4 g, 7.55 mmol, 30.06% yield, 87% purity) as a yellow solid. MS $(M+H)^+=461.2$.

Step 4. Synthesis of benzyl 4-(2-chloro-4-(2,6-dioxopiperidin-4-yl)phenyl)piperazine-1-carboxylate (7)

A solution of 3-(4-(4-((benzyloxy)carbonyl)piperazin-1-yl)-3-chlorophenyl)pentanedioic acid (1.5 g, 2.83 mmol, 87% purity) and UREA (850 mg, 14.15 mmol, 758.93 µL) in AcOH (15 mL) was stirred at 125° C. for 14 h. LCMS showed 93% of the desired mass was detected. The mixture was concentrated under reduced pressure. The crude was diluted with $H_2O$ (30 mL) and the mixture was stirred at 20° C. for 0.5 h. Then the mixture was filtered and the filter cake was washed with $H_2O$ (50 mL). The filter cake was collected and dried under reduced pressure to afford benzyl 4-(2-chloro-4-(2,6-dioxopiperidin-4-yl)phenyl)piperazine-1-carboxylate (1.2 g, 2.47 mmol, 87.28% yield, 91% purity) as a yellow solid. MS $(M+H)^+=441.9$

Step 5. Synthesis of 4-(3-chloro-4-(piperazin-1-yl)phenyl)piperidine-2,6-dione (8)

To a solution of benzyl 4-(2-chloro-4-(2,6-dioxopiperidin-4-yl)phenyl)piperazine-1-carboxylate (1.1 g, 2.49 mmol) in MeCN (10 mL) was added TMSI (1.99 g, 9.96 mmol, 1.36 mL) and the mixture was stirred at 20° C. for 1 h. LCMS showed the starting material was consumed and 50% of the desired mass. The mixture was quenched with ice water (30 mL) and washed with MTBE (10 mL×3), the combined organic layer was extracted with $H_2O$ (10 mL). The aqueous phase was lyophilized. The crude was purified by prep-HPLC (column: Phenomenex luna C18 150×40 mm×15 µm; mobile phase: [water (FA)-ACN]; B %: 1%-25%, 10 min) and the eluent was lyophilized to afford 4-(3-chloro-4-(piperazin-1-yl)phenyl)piperidine-2,6-dione (210 mg, 593.56 µmol, 23.85% yield, FA salt) as a white solid. MS $(M+H)^+=308.1$

Step 6. Synthesis of tert-butyl (4-((4-(2-chloro-4-(2,6-dioxopiperidin-4-yl)phenyl)piperazin-1-yl)methyl)piperidin-1-yl)carbamate (10)

To a solution of 4-(3-chloro-4-(piperazin-1-yl)phenyl)piperidine-2,6-dione (190 mg, 537.03 µmol, FA salt) and tert-butyl (4-formylpiperidin-1-yl)carbamate (360 mg, 1.58 mmol) in MeOH (4 mL) was added AcOH (31.50 mg, 524.55 μmol, 30 μL) and the mixture was stirred at 20° C. for 0.5 h. Then NaBH$_3$CN (101.33 mg, 1.61 mmol) was added and the resulting mixture was stirred at 20° C. for 2 h. LCMS showed the desired mass was detected. The mixture was quenched with NaHCO$_3$ (15 mL) and extracted with EtOAc (10 mL×3), the combined organic layer was washed with H$_2$O (10 mL×2), dried over Na$_2$SO$_4$ and filtered. The filtrate was concentrated under reduced pressure. The residue was purified by flash silica gel chromatography (5 g SepaFlash Silica Flash Column, Eluent of 0~15% MeOH/EtOAc gradient @ 50 mL/min) to afford tert-butyl (4-((4-(2-chloro-4-(2,6-dioxopiperidin-4-yl)phenyl)piperazin-1-yl)methyl)piperidin-1-yl)carbamate (200 mg, 353.80 μmol, 65.88% yield, 92% purity) as a white solid. MS (M+H)$^+$=520.2.

Step 7. Synthesis of 4-(4-(4-((1-aminopiperidin-4-yl)methyl)piperazin-1-yl)-3-chlorophenyl)piperidine-2,6-dione (11)

To a solution of tert-butyl (4-((4-(2-chloro-4-(2,6-dioxopiperidin-4-yl)phenyl)piperazin-1-yl)methyl)piperidin-1-yl)carbamate (0.1 g, 192.28 μmol) in DCM (1 mL) was added TFA (323.40 mg, 2.84 mmol, 210.00 μL) and the mixture was stirred at 20° C. for 1 h. LCMS showed 92% of the desired mass was detected. The mixture was concentrated under reduced pressure to afford 4-(4-(4-((1-aminopiperidin-4-yl)methyl)piperazin-1-yl)-3-chlorophenyl)piperidine-2,6-dione (120 mg, crude, 2TFA) as yellow oil. MS (M+H)$^+$=420.2

Step 8. Synthesis of N-(4-((4-(2-chloro-4-(2,6-dioxopiperidin-4-yl)phenyl)piperazin-1-yl)methyl)piperidin-1-yl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (Compound 58)

To a solution of 4-((7,7-difluoro-9-isopropyl-5-methyl-6-oxo-6,7,8,9-tetrahydro-5H-pyrimido[4,5-b][1,4]diazepin-2-yl)amino)-3-methoxybenzoic acid (60 mg, 142.38 μmol) and HATU (64.97 mg, 170.86 μmol) in DMF (1 mL) was added DIPEA (36.80 mg, 284.77 μmol, 49.60 μL) and the mixture was stirred at 20° C. for 15 min. Then a solution of 4-(4-(4-((1-aminopiperidin-4-yl)methyl)piperazin-1-yl)-3-chlorophenyl)piperidine-2,6-dione (120 mg, 185.19 μmol, 2TFA salt) and DIPEA (222.60 mg, 1.72 mmol, 0.3 mL) in DMF (1 mL) was added and the mixture was stirred at 20° C. for 1 h. LCMS showed the desired mass was detected. The mixture was diluted with H$_2$O (10 mL) and extracted with EtOAc (10 mL×3), the combined organic layer was washed with brine (10 mL×2), dried over Na$_2$SO$_4$ and filtered. The filtrate was concentrated under reduced pressure. The crude was purified by prep-HPLC (column: Waters Xbridge 150×25 mm×5 μm; mobile phase: [water (NH$_4$HCO$_3$)-ACN]; B %: 42%-72%, 8 min) and the eluent was lyophilized to afford N-(4-((4-(2-chloro-4-(2,6-dioxopiperidin-4-yl)phenyl)piperazin-1-yl)methyl)piperidin-1-yl)-4-((7,7-difluoro-9-isopropyl-5-methyl-6-oxo-6,7,8,9-tetrahydro-5H-pyrimido[4,5-b][1,4]diazepin-2-yl)amino)-3-methoxybenzamide (41.2 mg, 48.04 μmol, 33.74% yield, 96% purity) as a white solid. MS (M+H)$^+$=823.5

$^1$H NMR (400 MHz, DMSO-d$_6$) δ=10.87-10.81 (m, 1H), 9.27 (s, 1H), 8.32-8.27 (m, 1H), 8.22 (s, 1H), 7.87 (s, 1H), 7.47-7.41 (m, 2H), 7.38-7.36 (m, 1H), 7.26-7.20 (m, 1H), 7.16-7.10 (m, 1H), 4.96-4.82 (m, 1H), 4.09-3.98 (m, 2H), 3.93 (s, 3H), 3.42-3.34 (m, 3H), 3.30 (s, 3H), 3.04-2.99 (m, 2H), 2.98-2.94 (m, 2H), 2.84-2.73 (m, 4H), 2.69-2.63 (m, 2H), 2.61-2.57 (m, 4H), 2.25-2.19 (m, 2H), 1.81-1.72 (m, 2H), 1.59-1.48 (m, 1H), 1.28-1.20 (m, 8H).

Example 59. Synthesis of 4-((7,7-difluoro-9-isopropyl-5-methyl-6-oxo-6,7,8,9-tetrahydro-5H-pyrimido[4,5-b][1,4]diazepin-2-yl)amino)-N-(1-(1-(4-(2,6-dioxopiperidin-3-yl)-2-fluorophenyl)pyrrolidin-3-yl)piperidin-4-yl)-3-methoxybenzamide (Compound 59)

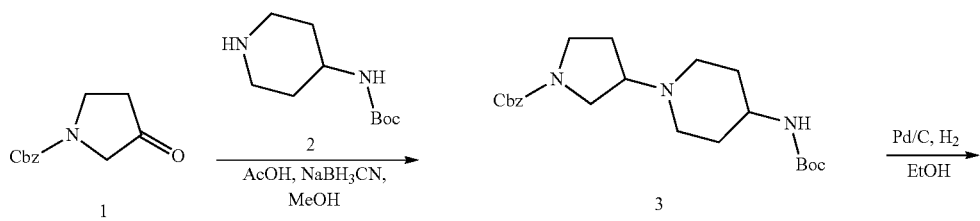

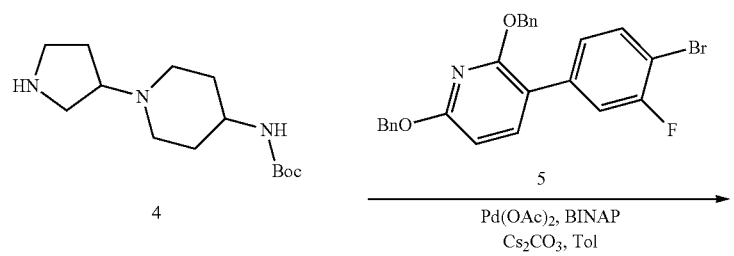

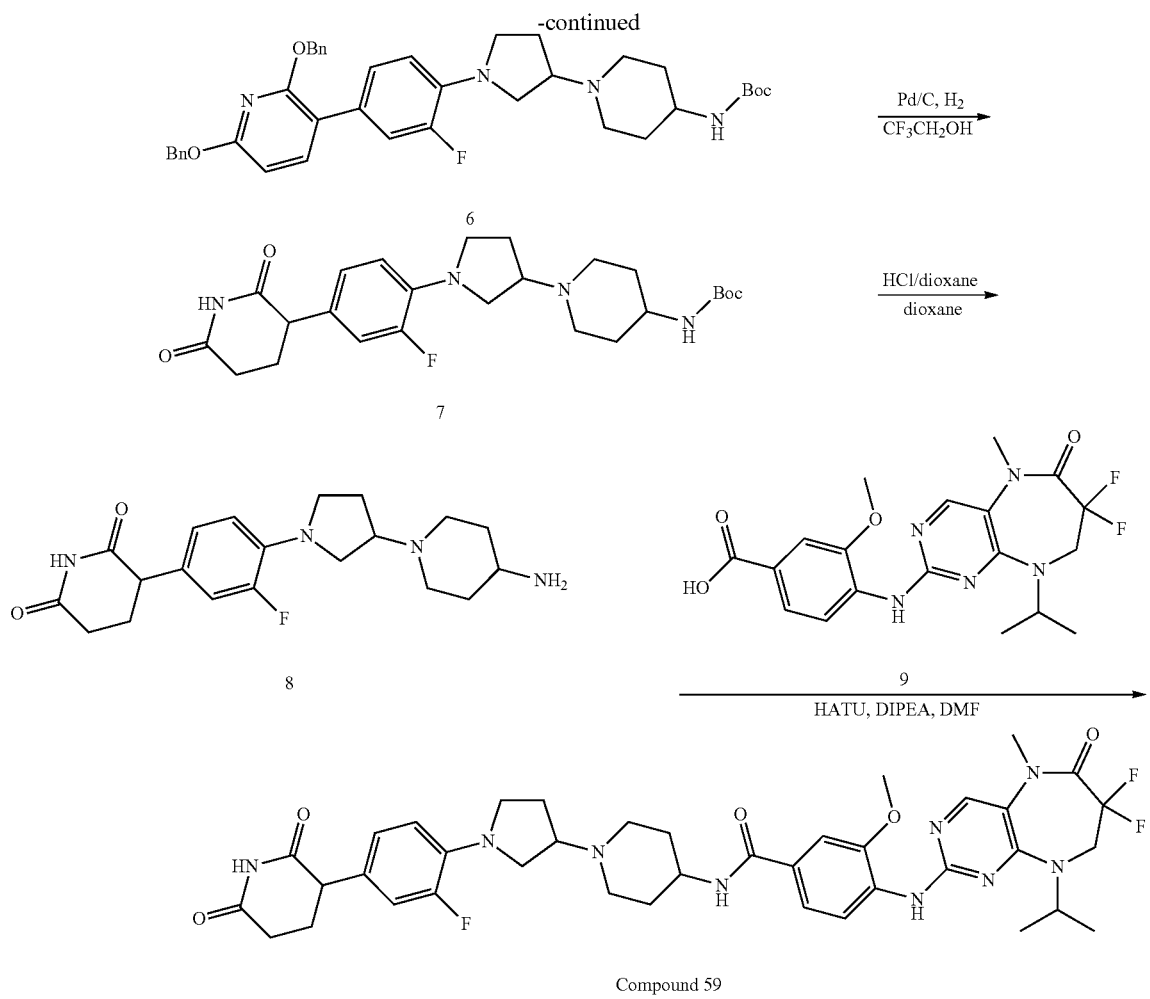

Compound 59

The compound 59 was synthesized by the method described in the scheme similar to the method described in the previous Examples.

MS (M+H)$^+$=778.9, $^1$H NMR (400 MHz, DMSO-d$_6$) δ=10.79 (s, 1H), 8.32 (d, J=8.8 Hz, 1H), 8.23 (s, 1H), 8.14 (br s, 1H), 7.89 (s, 1H), 7.54-7.46 (m, 2H), 7.01-6.84 (m, 2H), 6.79-6.67 (m, 1H), 4.95-4.83 (m, 1H), 4.05 (br t, J=13.3 Hz, 2H), 3.95 (s, 3H), 3.82-3.70 (m, 2H), 3.54-3.37 (m, 3H), 3.31 (s, 3H), 3.27-3.12 (m, 2H), 3.10-2.86 (m, 3H), 2.62-2.55 (m, 1H), 2.23-2.07 (m, 4H), 2.03-1.96 (m, 1H), 1.90-1.73 (m, 3H), 1.69-1.52 (m, 2H), 1.25 (d, J=6.7 Hz, 6H).

EXPERIMENTAL EXAMPLES

1. Western Blot Assay for PLK1
(1) Culture of HeLa Cell Line

The HeLa cell line was purchased from Korea Cell Line Bank (KCLB), Seoul, Korea. The passage in cell culture was maintained at P115 to P125.

For cell counting, cell counter (Thermo Fisher Scientific Inc., Catalog #AMQAX1000) and 0.4% trypan blue solution were used.

For cell culture, DMEM (Gibco, Cat. No. 1195-65; Lot. No. 2085318), FBS (Gibco, Cat. No. 16000-044; Lot. No. 2097593), Penicillin/Streptomycin (PS) (Gibco, Cat. No. 15140-122; Lot. No. 2058855), 100 mm$^2$ cell culture dish (SPL, Cat. No. 20100), 150 mm$^2$ cell culture dish (SPL, Cat. No. 20150), 12-well culture plate (SPL, Cat. No. 30012), PBS pH 7.4 (Gibco, Cat. No. 10010-023; Lot. No. 2085080), TrypLE™ Express (Gibco, Cat. No. 12605-010; Lot No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

(2) Treatment of Compounds of the Present Invention $2 \times 10^5$ cells were seeded for each well of a 12-well plate (SPL), and the cells were cultured in the culture medium in a total volume of 2 mL.

The compounds of Examples were completely dissolved in DMSO and used in the experiment, and thymidine was completely dissolved in DW and used in the experiment. For thymidine block, the products were treated with 2 mM of thymidine (Sigma-Aldrich Cat. No. T9250-5G) and then incubated for 24 hours.

For release and chemical treatment, the medium was suctioned and washed 3 times with 1×PBS. Complete media was added, followed by incubation for 4 hours in a CO$_2$ incubator. Each compound was diluted three folds from the highest concentration of 3 μM to the lowest concentration and then incubated for 6 hours again.

(3) Western Blotting

For SDS-PAGE and Western blotting, 1×RIPA lysis buffer (Rockland, Cat. No. MB-030-0050; Lot no. 39751), 100× Protease Inhibitor Cocktail (Quartett, Cat. No. PPI1015; Lot no. PCO50038424), Pierce™ BCA protein assay kit (ThermoScientific, Cat. No. 23225; Lot no. UC276876), albumin standard (ThermoScientific, Cat. No. 23209; Lot no. UB269561), 4-15% Mini-PROTEAN TGX stain-free gel (Bio-rad, Cat. No. 4568085; Lot no. L007041B), 10×Tris/Glycine/SDS buffer (Bio-rad, Cat. No. 1610732; Lot no. 10000044375B); 10×TBS (Bio-rad, Cat. No. 1706435; Lot no. 1000045140B), 10% Tween 20 (Cat. No. 1610781; Lot no. L004152B), Color protein standard broad range (NEB, Cat. No. P7719S; Lot no. 10040349), 4× Laemmli sample buffer (Bio-rad, Cat. No. 1610747; Lot no. L004133B), β-mercaptoethanol (Sigma-Aldrich, Cat. No. M3148; Lot no. 60-24-2), SuperBlock™ T20 (TBS) blocking buffer (ThermoScientific, Cat. No. 37536; Lot no. UC282578), 1 M sodium azide solution (Sigma-Aldrich, Cat. No. 08591-1 mL-F; Lot no. BCBV4989), α-Rabbit pAb to Ms IgG (abcam, Cat. No. ab97046; Lot no. GR3252115-1), α-Goat pAb to Rb IgG (CST, Cat. No. 7074S; Lot no. 28), α-GAPDH (abcam, Cat. No. ab8245; Lot no. GR3275542-2), α-PLK1 (CST, Cat. No. 208G4), α-BRD4 (CST, Cat. No. 13440S), ECL™ Prime western blotting reagents (GE Healthcare, Cat. No. RPN2232; Lot no. 17001655), Ponceau S solution (Sigma-Aldrich, Cat. No. P7170; Lot no. SLBV4112), Difco™ Skim milk (BD, Cat. No. 232100; Lot no. 8346795), and iBlot 2 NC Regular stacks (Invitrogen, Cat. No. IB23001; Lot no. 2NR110619-02) were used.

For cell harvesting, the cells were first separated from the plate using trypsin and then washed with the medium and PBS. Specifically, the medium was suctioned off and washed with 1 mL of PBS, and PBS was suctioned off. The cells were treated with 0.5 mL TrypLE™ Express at 37° C. for 7 minutes to separate the cells, and then 0.5 mL of complete medium was added to collect 1 mL of cell culture solution. Then, 1 mL of the cell collection solution was centrifuged at 8,000 rpm for 120 seconds, and the supernatant was removed. After washing with 0.2 mL of PBS, the PBS was removed.

For cell lysis, a lysis buffer was added and cell debris was removed to obtain a cell lysate. Specifically, the cells were treated with 70 μL of 1×RIPA buffer containing a protease inhibitor and incubated for 30 minutes on ice. Then, the cells were centrifuged at 4° C. and 15,000 rpm for 10 minutes to obtain a cell lysate.

Then, a standard curve was obtained using the BCA assay, and the protein mass in the lysate was quantified by substituting the curve equation. The mixture was incubated at 37° C. for 30 minutes using 20 μL of standard or sample solution, and 200 μL of BCA or Bradford solution, and measured at 562 nm absorbance. Samples were prepared by adding 4× sample buffer so that the quantity of protein added to each well was 15 μg.

Sodium dodecyl sulfate polyacrylamide gel electrophoresis (SDS-PAGE) was performed by setting a running time of 100 minutes at 120 V on a 4-15% Mini-PROTEAN TGX stain-free gel (15 well). Transferring was performed on iBlot 2 NC Mini stacks at P0 mode of the dry blotting system. After staining using Ponceau S solution, blocking was performed for 1 hour with a blocking buffer (Thermo). After washing with 1×TBS containing 0.05% Tween 20, the product was reacted at 4° C. for 16 hours with anti-PLK1 (CST) antibody (1:500), anti-BRD4 (Cell signaling) antibody (1:1000) or anti-GAPDH (abcam) antibody (1:10,000) in 1×TBS-T as a primary antibody. After washing three times for 10 minutes with 1×TBS containing 0.05% Tween20, the product was reacted at room temperature for 1 hour with anti-mouse antibody (abcam) (1:10000) or anti-rabbit antibody (CST) (1:5000) in 1×TBS-T as a secondary antibody. Then, after washing three times for 10 minutes with 1×TBS containing 0.05% Tween 20, the product was detected with an ECL working solution (1:1).

To analyze the results, an image analyzer (GE) was used to obtain final blot data. As a result, it was confirmed that all of the compounds of the present invention degraded PLK1 protein significantly.

2. Luciferase Assay for PLK1

(1) Preparation and Culture of HeLa LgBit (Plk1-HiBit KI) Cell Line

A HeLa cell line in which the LgBit vector was transfected and expressed stably was prepared. Then, after constructing gRNA and donor to express the HiBit amino acid sequence behind the C-terminal of the Plk1 gene, which was inherent in the cell, it was inserted into the cell together with a vector capable of expressing CRISPR/Cas9. Only the cells in which the insertion was completed and knock-in had progressed were selected, sub-cultured and used.

For cell culture, DMEM (Gibco, Cat. No. 11995-065; Lot. No. 2467189), FBS (Gibco, Cat. No. 16000-044; Lot. No. 2420173P), Penicillin/Streptomycin (PS) (Gibco, Cat. No. 15140-122; Lot. No. 2321114), 100 mm$^2$ cell culture dish (SPL, Cat. No. 20100), 150 mm$^2$ cell culture dish (SPL, Cat. No. 20150), 96-well culture plate (SPL, Cat. No. 30196), PBS pH 7.4 (Gibco, Cat. No. 10010-023; Lot. No. 2085080), TrypLE™ Express (Gibco, Cat. No. 12605-010; Lot. No. 2323417), Counting Chamber (Hematocytometer) (Marienfeld Superior, Cat. No. 0650010) and 0.4% Trypan Blue Solution (DYNEBIO, Cat. No. CBT3710; Lot. No. 20211201) were used.

(2) Treatment of Compounds of the Present Invention and Method of Luciferase Assay The compounds of Examples were completely dissolved in DMSO (Sigma-Aldrich Cat. No. D2438, Lot. No. RNBJ9566) and used in the experiment.

In the case of HeLa LgBit (Plk1-HiBit KI), the compounds were treated after being released after thymidine block, and the process was as follows. Thymidine (Sigma-Aldrich Cat. No. T9250-5G) was completely dissolved in DW and used in the experiment. For thymidine block, the products were treated with 2 mM of thymidine and then incubated for 24 hours. For release and chemical treatment, the medium was suctioned and washed with 1×PBS. TrypLE™ was added and incubated in 37° C. CO$_2$ incubator for 5 min. Cells neutralized by adding complete media were counted through a counter. For each well of a 96-well culture plate (SPL), 3.3×10$^4$ cells and a total medium volume of 150 μL were seeded and incubated in a CO$_2$ incubator.

Each cell line was incubated in a CO$_2$ incubator for 18 hours, and Endurazine was added to each well to make up 4% of the total volume. After adding the compound of the present invention in a 96-well white plate (SPL) to a concentration of 300 nM, the wavelength of the plate reader (BMG Labtech, CLARIOstar Plus) was set to 470-480 nM, and then the luminescence was tracked in real time. After 9 hours, the luminescence value was obtained and displayed as a bar graph through an Excel program.

The results are shown in Table 2 below and FIGS. 1 and 2.

TABLE 2

| Examplary Compound | Activity |
|---|---|
| Compound 1 | +++ |
| Compound 2 | ++ |
| Compound 3 | ++ |

TABLE 2-continued

| Examplary Compound | Activity |
|---|---|
| Compound 4 | ++ |
| Compound 5 | ++ |
| Compound 6 | ++ |
| Compound 7 | +++ |
| Compound 8 | ++ |
| Compound 9 | ++ |
| Compound 10 | ++ |
| Compound 11 | ++ |
| Compound 12 | ++ |
| Compound 13 | ++ |
| Compound 14 | ++ |
| Compound 15 | ++ |
| Compound 16 | ++ |
| Compound 17 | ++ |
| Compound 18 | ++ |
| Compound 19 | ++ |
| Compound 21 | ++ |
| Compound 22 | ++ |
| Compound 23 | +++ |
| Compound 24 | ++ |
| Compound 25 | ++ |
| Compound 26 | ++ |
| Compound 27 | ++ |
| Compound 28 | ++ |
| Compound 29 | ++ |
| Compound 30 | +++ |
| Compound 31 | +++ |
| Compound 32 | +++ |
| Compound 33 | ++ |
| Compound 34 | ++ |
| Compound 35 | ++ |
| Compound 36 | ++ |
| Compound 37 | ++ |
| Compound 38 | +++ |
| Compound 39 | ++ |
| Compound 40 | ++ |
| Compound 41 | ++ |
| Compound 42 | ++ |
| Compound 43 | +++ |
| Compound 44 | +++ |
| Compound 45 | +++ |
| Compound 46 | +++ |
| Compound 51 | + |
| Compound 54 | ++ |
| Compound 59 | ++ |

In Table 2, Activity represents the ratio of the luminescence value of each Exemplary Compound treatment group to DMSO treatment group (+++: <0.3, ++ <0.6, + <0.7).

3. Cell Viability Assay for H526 Cell Line (1) Culture of NCI-H526 Cell Line

The NCI-H526 (hereafter H526) cell line was purchased from Korea Cell Line Bank (KCLB, Seoul, Korea). For cell culture, RPMI 1640 (Gibco, Cat. No. 22400-089; Lot. No. 2277021), FBS (Gibco, Cat. No. 16000-044; Lot. No. 2351176P), Penicillin/Streptomycin (PS) (Gibco, Cat. No. 15140-122; Lot. No. 2321114), 75T cell culture flask (SPL, Cat. No. 71075), 175T cell culture flask (SPL, Cat. No. 71175), 96-well cell culture plate (SPL, Cat. No. 30096), PBS pH 7.4 (Gibco, Cat. No. 10010-023; Lot. No. 2085080), TrypLE™ Express (Gibco, Cat. No. 12605-010; Lot. No. 2323417), Counting Chamber (Hematocytometer)(Marienfeld Superior, Cat. No. 0650010), and 0.4% Trypan Blue Solution (DYNEBIO, Cat. No. CBT3710; Lot. No. 20211201) were used.

(2) Treatment of Compounds of the Present Invention and Method of Cell Viability Assay The compounds of Examples were completely dissolved in DMSO (Sigma-Aldrich Cat. No. D2438, Lot. No. RNBJ9566) and used in the experiment.

$3\times10^4$ cells were seeded for each well of a 96-well plate (SPL), and the cells were cultured in total volume of 150 μL. Each compound was diluted 3-folds from the highest concentration of 3000 nM to the lowest concentration of 0.46 nM. After treating the compound to each well to make the total volume of 200 μL, it was cultured in a $CO_2$ incubator (Thermo Fisher Science, Cat. No. 4111) for 5 days.

Then, after treating EZ-Cytox (DOGEN, Cat. NO. EZ-3000, Lot. No. DLS2109) 20 μL in each well, it was cultured in $CO_2$ incubator for 4 hours. The absorbance of the completely cultured sample was measured by setting the wavelength of a plate reader (BMG Labtech, CLARIOstar Plus) to 450 nM, and was measured after shaking for 3 minutes in a plate reader before measurement. The final measured value was arranged with Excel program, a graph was displayed through Prism-GraphPad program, and the $IC_{50}$ value was measured.

The results are shown in Table 3 below.

TABLE 3

| Cell Viability Assay for H526 cell line | |
|---|---|
| Examplary Compound | Activity |
| Compound 1 | B |
| Compound 2 | A |
| Compound 3 | C |
| Compound 4 | A |
| Compound 5 | D |
| Compound 6 | E |
| Compound 7 | A |
| Compound 9 | B |
| Compound 10 | B |
| Compound 11 | B |
| Compound 12 | B |
| Compound 13 | A |
| Compound 14 | B |
| Compound 15 | A |
| Compound 16 | C |
| Compound 17 | B |
| Compound 18 | C |
| Compound 19 | A |
| Compound 21 | B |
| Compound 22 | B |
| Compound 23 | A |
| Compound 24 | C |
| Compound 25 | D |
| Compound 26 | A |
| Compound 27 | A |
| Compound 28 | A |
| Compound 29 | A |
| Compound 30 | C |
| Compound 31 | A |
| Compound 32 | A |
| Compound 33 | A |
| Compound 35 | A |
| Compound 36 | A |
| Compound 38 | B |
| Compound 39 | B |
| Compound 40 | A |
| Compound 42 | A |
| Compound 43 | A |
| Compound 44 | A |

TABLE 3-continued

Cell Viability Assay for H526 cell line

| Examplary Compound | Activity |
|---|---|
| Compound 45 | A |
| Compound 46 | C |
| Compound 54 | A |

In Table 3, Activity represents $IC_{50}$ value of each Exemplary Compound treatment group to H526 cell line (A: <30 nM, B: <50 nM, C: <100 nM, D: <200 nM, E: <400 nM).

4. Cell Viability Assay for MRC-5 Cell Line (1) Culture of MRC-5 Cell Line

The MRC-5 cell line was purchased from Korea Cell Line Bank (KCLB), Seoul, Korea. Passage of cultured cells was maintained within P15.

For cell culture, MEM/EBSS (Hyclone, Cat. No. SH30024.01; Lot. No. AG29697698), FBS (Gibco, Cat. No. 16000-044; Lot. No. 2234018P), Penicillin/Streptomycin (PS) (Gibco, Cat. No. 15140-122; Lot. No. 2211099), 175T cell culture flask (SPL, Cat. No. 71175), 96-well cell culture plate (SPL, Cat. No. 30096), PBS pH 7.4 (Gibco, Cat. No. 10010-023; Lot. No. 2085080), TrypLE™ Express (Gibco, Cat. No. 12605-010; Lot. No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

(2) Treatment of Compounds of the Present Invention

MRC-5 cell line cultured in 175T cell culture flask was isolated using TrypLE™ Express. $6 \times 10^3$ cells were seeded for each well of a 96-well plate (SPL), and the cells were cultured in total volume of 150 μL.

The compounds of Examples were completely dissolved in DMSO (Sigma-Aldrich, Cat. No. D2438-50ML, Lot. No. RNBK6387) and used in the experiment. Each compound was diluted 3-folds from the highest concentration of 10000 nM to the lowest concentration of 1.52 nM. Each well was mixed with a medium and treated, and the volume was set to 50 μL, so that the total volume of each well was 200 μL. Then, it was cultured in 37° C. $CO_2$ incubator (Thermo Fisher Science, Cat. No. 4111, Lot. No. 300512709) for 5 days.

The following compounds were used as comparative examples, and the cell viability assay was performed in the same manner as in the compounds of Examples.

Comparative Example 1. Exemplary Compound Described in Mu et al. *BBRC,* 2020, 521(4): 833 (Comparative Compound 1)

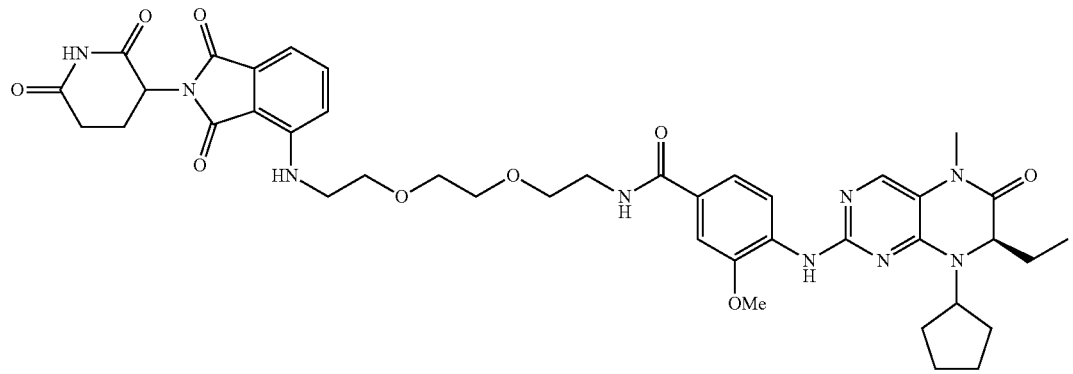 [SMILES: CC[C@@H]1C(=O)N(C)c2cnc(Nc3ccc(C(=O)NCCOCCOCCNc4cccc5c4C(=O)N(C4CCC(=O)NC4=O)C5=O)cc3OC)nc2N1C1CCCC1]

Comparative Example 2. BI2536 (Comparative Compound 2)

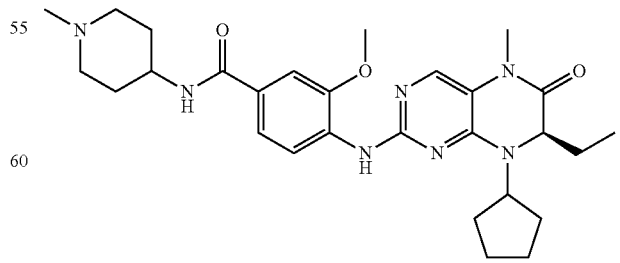

Comparative Example 3. Volasertib (Comparative Compound 3)

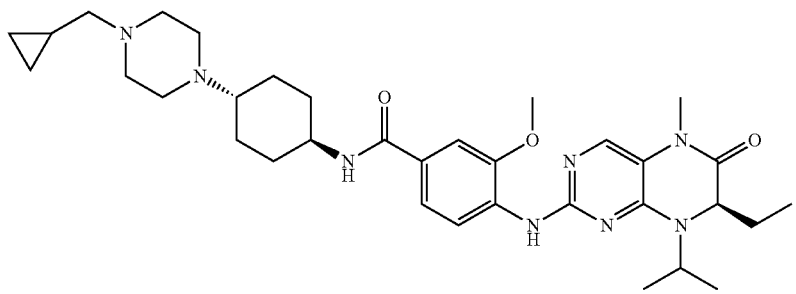 [SMILES: CC[C@@H]1C(=O)N(C)c2cnc(Nc3ccc(C(=O)N[C@H]4CC[C@H](N5CCN(CC6CC6)CC5)CC4)cc3OC)nc2N1C(C)C]

Comparative Example 4. TAK960 (Comparative Compound 4)

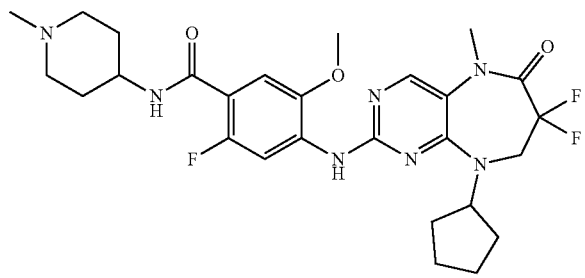 [SMILES: COc1cc(C(=O)NC2CCN(C)CC2)c(F)cc1Nc1ncc2c(n1)N(C1CCCC1)CC(F)(F)C(=O)N2C]

(3) Cytotoxicity Experiment

After treating EZ-Cytox (DOGEN, Cat. NO. EZ-3000, Lot. No. DLS2112) 20 μL in each well of completely cultured plate, it was cultured in 37° C. $CO_2$ incubator for 4 hours. The 96-well plate was placed in a plate reader (BMG Labtech, Clariostar Plus), mixed for 2 minutes, and absorbance was measured at 450 nM wavelength. The data were converted into graphs using the Prism (ver. 9) program.

The results are shown in Table 4 and Table 5 below.

TABLE 4

Cell Viability Assay for MRC-5 cell line

| Examplary Compound | Activity |
|---|---|
| Compound 1 | N.D |
| Compound 2 | N.D |
| Compound 3 | N.D |
| Compound 4 | N.D |
| Compound 5 | N.D |
| Compound 6 | 12316 |
| Compound 7 | 12980 |
| Compound 9 | 16622 |
| Compound 10 | 15563 |
| Compound 11 | N.D |
| Compound 12 | 24558 |
| Compound 13 | N.D |
| Compound 14 | 14673 |
| Compound 15 | 17734 |
| Compound 16 | N.D |
| Compound 17 | N.D |
| Compound 18 | N.D |
| Compound 19 | 13136 |
| Compound 21 | 12572 |
| Compound 22 | N.D |
| Compound 23 | N.D |

TABLE 4-continued

Cell Viability Assay for MRC-5 cell line

| Examplary Compound | Activity |
|---|---|
| Compound 25 | N.D |
| Compound 31 | N.D |
| Compound 32 | N.D |
| Compound 33 | N.D |
| Compound 35 | N.D |
| Compound 36 | N.D |
| Compound 38 | N.D |
| Compound 39 | 5804 |
| Compound 42 | N.D |
| Compound 43 | N.D |
| Compound 44 | N.D |
| Compound 45 | N.D |
| Compound 46 | N.D |
| Compound 54 | N.D |

In Table 4, Activity represents $IC_{50}$ value (nM) of each Exemplary Compound treatment group to MRC-5 cell line. N.D. (not determined) means that cytotoxicity did not appear until 10 μM. As a result, it was confirmed that all of the compounds of the present invention specifically exhibited a high level of cytotoxicity in cancer cell lines rather than normal cell lines.

TABLE 5

Cell Viability Assay for MRC-5 cell line

| Comparative Compound | Activity |
|---|---|
| Comparative Compound 1 | 106.6 |
| Comparative Compound 2 | 3085.4 |
| Comparative Compound 3 | 2939.3 |
| Comparative Compound 4 | 9152.5 |

In Table 5, Activity represents $IC_{50}$ value (nM) of each Comparative Compound treatment group to MRC-5 cell line. In particular, it was found that Comparative Compound 1, a known PROTAC compound, exhibited a high level of cytotoxicity in normal cell line, unlike the Exemplary Compounds of the present invention.

The invention claimed is:
1. A compound represented by the following Formula I:

Formula I or a pharmaceutically acceptable salt or stereoisomer thereof,
wherein:
$X_1$ is CH, —CH$_2$—, or N;
$X_2$ is CH, —CH$_2$—, or N;
ring U is phenylene or 5- or 6-membered heteroarylene;
  wherein the phenylene or 5- or 6-membered heteroarylene is linked to $X_1$ or $X_2$; and
  wherein the phenylene or 5- or 6-membered heteroarylene is optionally substituted with one or more independently selected $R_U$ substituents;
each $R_U$ is independently halo, $C_{1-4}$ alkyl, $C_{1-4}$ haloalkyl, $C_{1-4}$ aminoalkyl, $C_{1-4}$ hydroxyalkyl, or $OC_{1-4}$ alkyl;
$L_U$ is a bond, —(CH$_2$)$_x$—, —(CH$_2$)$_x$NH—, —(CH$_2$)$_x$O—, —C(O)—, or phenylene;
$L_1$ is a bond or heterocycloalkylene;
  wherein the heterocycloalkylene contains at least one nitrogen ring heteroatom; and
  wherein the heterocycloalkylene is optionally substituted with one or more substituents independently selected from halo, $C_{1-4}$ alkyl, $C_{1-4}$ haloalkyl, OH, $OC_{1-4}$ alkyl, or =O;
$L_2$ is —(CH$_2$)$_{y1}$—, —(CD$_2$)$_{y1}$-, —(CH$_2$)$_{y2}$—C(O)—(CH$_2$)$_{y3}$—, —(CH$_2$)$_{y2}$—NH—(CH$_2$)$_{y3}$—, or —(CH$_2$)$_{y2}$—N(C$_{1-4}$ alkyl)-(CH$_2$)$_{y3}$—;
$L_3$ is a bond, cycloalkylene, or heterocycloalkylene;
  wherein the heterocycloalkylene contains at least one nitrogen ring heteroatom; and
  wherein the cycloalkylene or heterocycloalkylene is optionally substituted with one or more substituents independently selected from halo, $C_{1-4}$ alkyl, or $C_{1-4}$ haloalkyl;
$L_P$ is —(CH$_2$)$_p$—NH—C(O)— or —(CH$_2$)$_p$—O—C(O)—, wherein the —C(O)— of $L_P$ is bonded to the ring bearing $R_6$;
p is 0, 1, or 2;
x is 0, 1, 2, 3, or 4;
$y_1$ is 0, 1, 2, 3, 4, 5, or 6;
$y_2$ is 0, 1, 2, 3, 4, 5, or 6;
$y_3$ is 0, 1, 2, 3, 4, 5, or 6;
z is 0, 1, 2, 3, 4, 5, or 6;
Y is CR$_7$ or N;
$R_6$ is halo, $C_{1-4}$ alkyl, $C_{1-4}$ haloalkyl, $C_{1-4}$ aminoalkyl, $C_{1-4}$ hydroxyalkyl, or $OC_{1-4}$ alkyl;
$R_7$ is H or halo;
$R_1$ is $C_{1-4}$ alkyl;
$R_2$ is H or $C_{1-4}$ alkyl; or
$R_1$ and $R_2$, taken together with the carbon and nitrogen atoms to which they are attached, form a 5- or 6-membered ring;
$R_3$ is H, halo, or $C_{1-4}$ alkyl;
$R_4$ is H, halo, or $C_{1-4}$ alkyl; or $R_3$ and $R_4$, taken together with the carbon atom to which they are attached, form a 3- to 6-membered ring; and
$R_5$ is $C_{1-4}$ alkyl.

2. The compound according to claim 1, or a pharmaceutically acceptable salt or stereoisomer thereof, wherein:
ring U is phenylene, pyrazolylene, pyridinylene, or pyrimidinylene;
  wherein the phenylene, pyrazolylene, pyridinylene, or pyrimidinylene is linked to $X_1$ or $X_2$; and
  wherein the phenylene, pyrazolylene, pyridinylene, or pyrimidinylene is optionally substituted with one or more independently selected $R_U$ substituents; and
each $R_U$ is independently halo, $C_{1-4}$ alkyl, $C_{1-4}$ haloalkyl, or $OC_{1-4}$ alkyl.

3. The compound according to claim 1, or a pharmaceutically acceptable salt or stereoisomer thereof, wherein:

is:

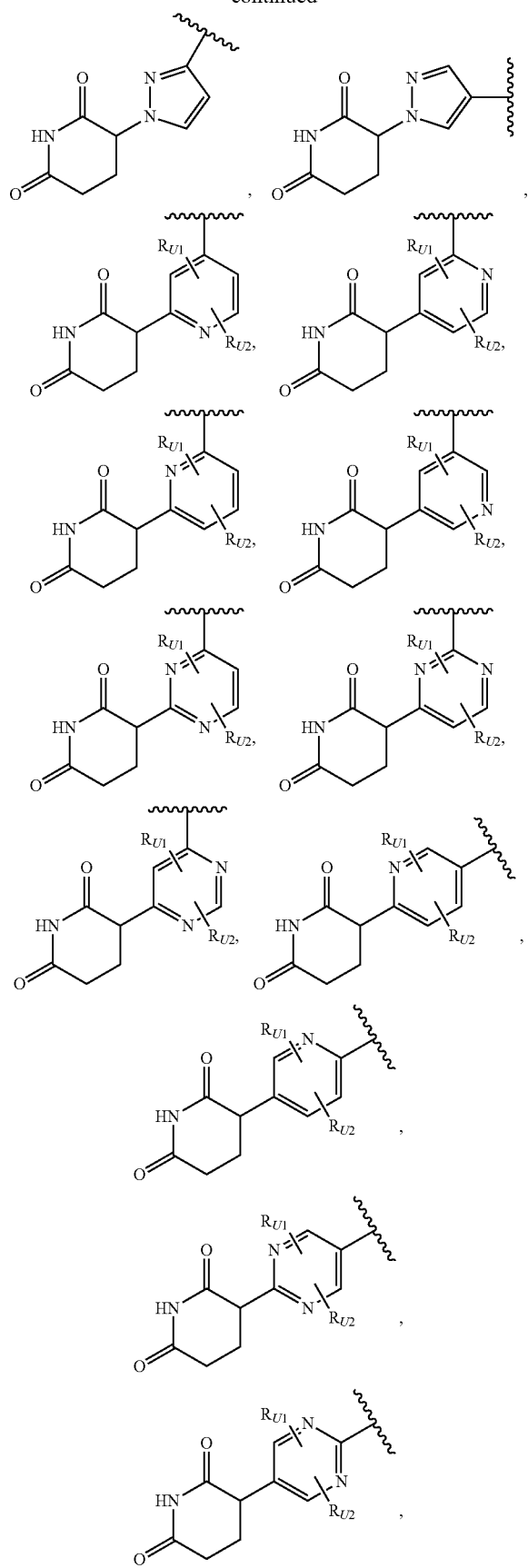
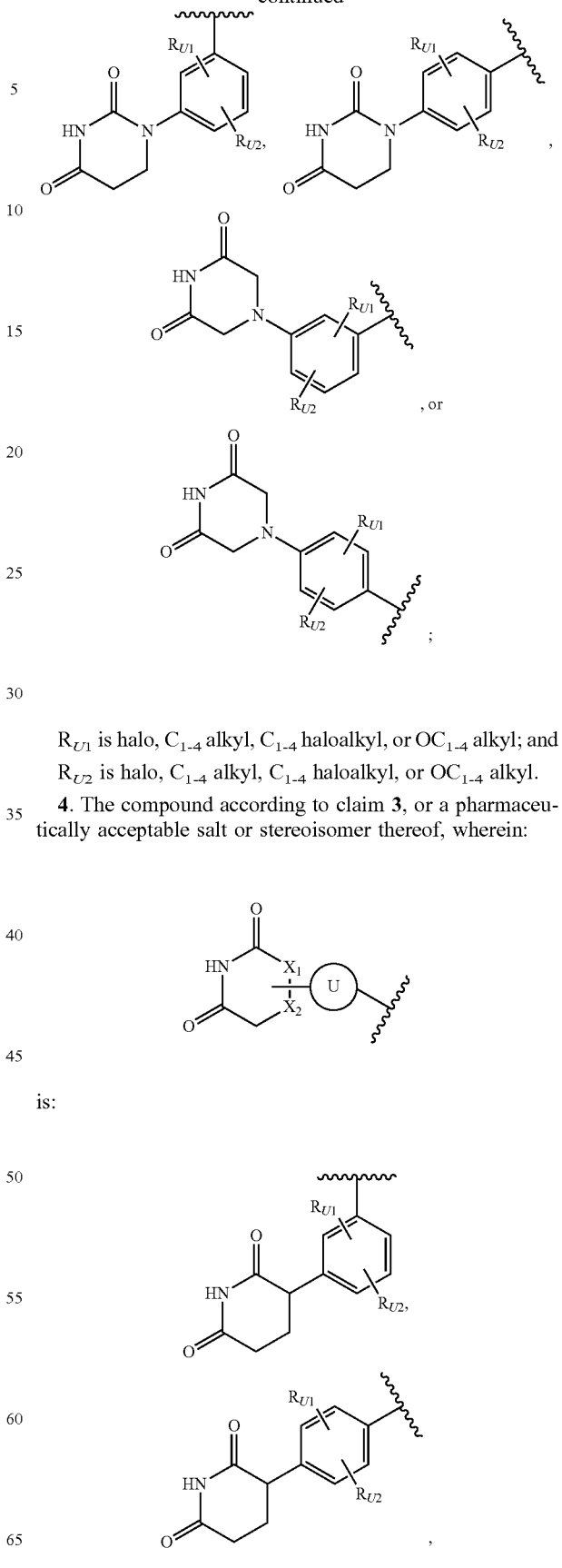
$R_{U1}$ is halo, $C_{1-4}$ alkyl, $C_{1-4}$ haloalkyl, or $OC_{1-4}$ alkyl; and $R_{U2}$ is halo, $C_{1-4}$ alkyl, $C_{1-4}$ haloalkyl, or $OC_{1-4}$ alkyl.
4. The compound according to claim 3, or a pharmaceutically acceptable salt or stereoisomer thereof, wherein:
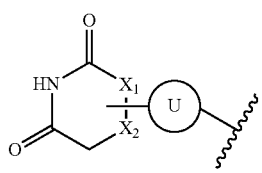
is:
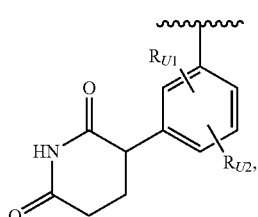
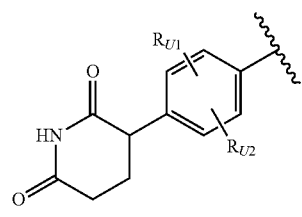

-continued

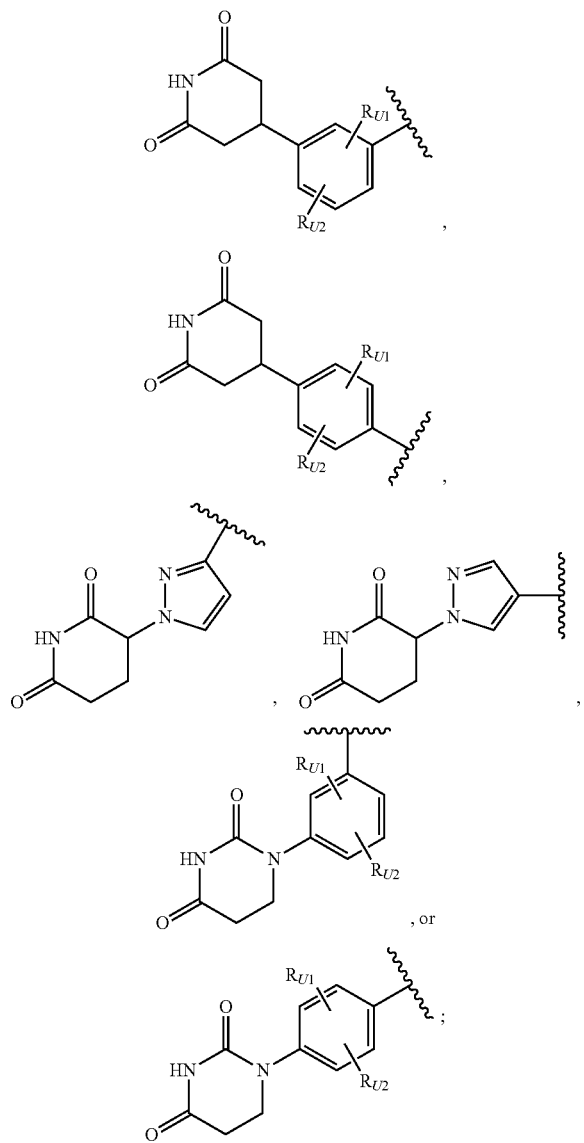

$R_{U1}$ is halo, $C_{1-4}$ alkyl, $C_{1-4}$ haloalkyl, or $OC_{1-4}$ alkyl; and
$R_{U2}$ is halo, $C_{1-4}$ alkyl, $C_{1-4}$ haloalkyl, or $OC_{1-4}$ alkyl.

5. The compound according to claim 1, or a pharmaceutically acceptable salt or stereoisomer thereof, wherein:

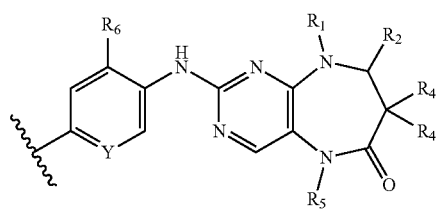

is:

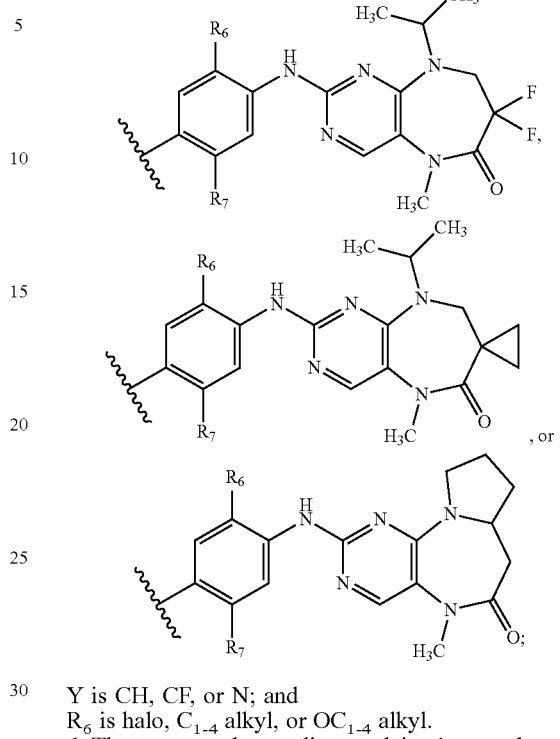

Y is CH, CF, or N; and
$R_6$ is halo, $C_{1-4}$ alkyl, or $OC_{1-4}$ alkyl.

6. The compound according to claim 1, or a pharmaceutically acceptable salt or stereoisomer thereof, wherein:
$L_U$ is a bond, —$(CH_2)_x$—, —$(CH_2)_xO$—, —C(O)—, or phenylene;
$L_1$ is a bond or 4- to 12-membered heterocycloalkylene;
 wherein the 4- to 12-membered heterocycloalkylene is monocyclic, bridged bicyclic, or spirocyclic;
 wherein the 4- to 12-membered heterocycloalkylene contains at least one nitrogen ring heteroatom;
 wherein the 4- to 12-membered heterocycloalkylene is bonded to $L_U$ or ring U via the nitrogen ring heteroatom; and
 wherein the 4- to 12-membered heterocycloalkylene is optionally substituted with one or more substituents independently selected from halo, $C_{1-4}$ alkyl, OH, or =O;
$L_2$ is —$(CH_2)_{y1}$—, —$(CH_2)_{y2}$—C(O)—$(CH_2)_{y3}$—, —$(CH_2)_{y2}$—NH—$(CH_2)_{y3}$—, or —$(CH_2)_{y2}$—N($C_{1-4}$ alkyl)-$(CH_2)_{y3}$—;
$L_3$ is a bond, 4- to 6-membered cycloalkylene or 4- to 12-membered heterocycloalkylene;
 wherein the 4- to 12-membered heterocycloalkylene is monocyclic, bridged bicyclic, or spirocyclic;
 wherein the 4- to 12-membered heterocycloalkylene contains at least one nitrogen ring heteroatom; and
 wherein the 4- to 6-membered cycloalkylene or 4- to 12-membered heterocycloalkylene is optionally substituted with one or more independently selected halo substituents;
$L_P$ is —$(CH_2)_p$—NH—C(O)— or —$(CH_2)_p$—O—C(O)—, wherein the —C(O)— of $L_P$ is bonded to the ring bearing $R_6$;
p is 0 or 1;
x is 0 or 1;
$y_1$ is 0, 1, 2, or 3;
$y_2$ is 0, 1, 2, or 3; and
$y_3$ is 0, 1, 2, or 3.

7. The compound according to claim 1, or a stereoisomer thereof, wherein the compound, or stereoisomer thereof, is selected from:
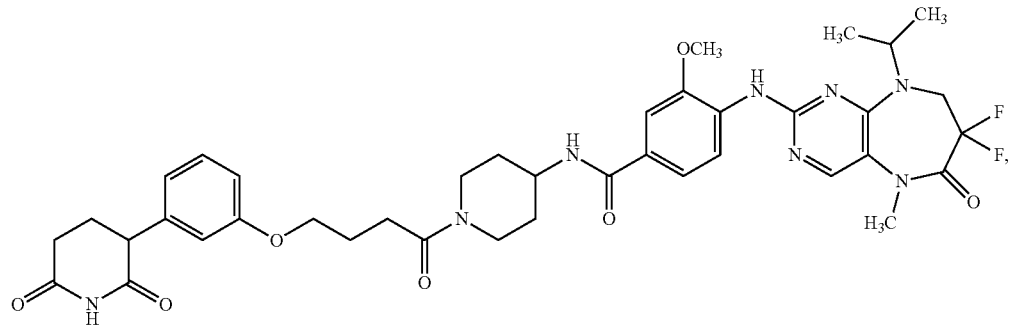
1
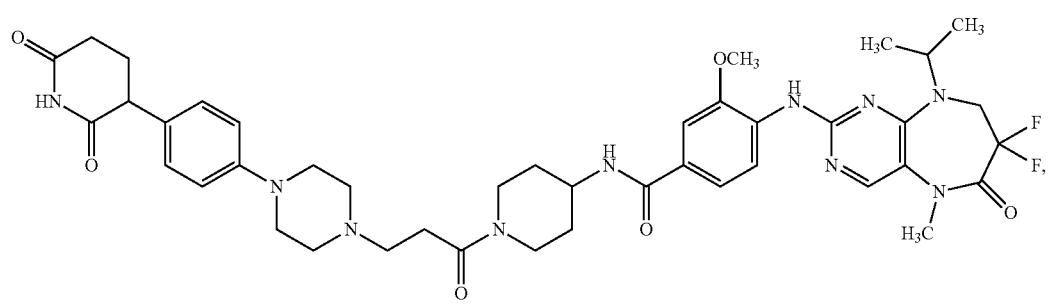
2
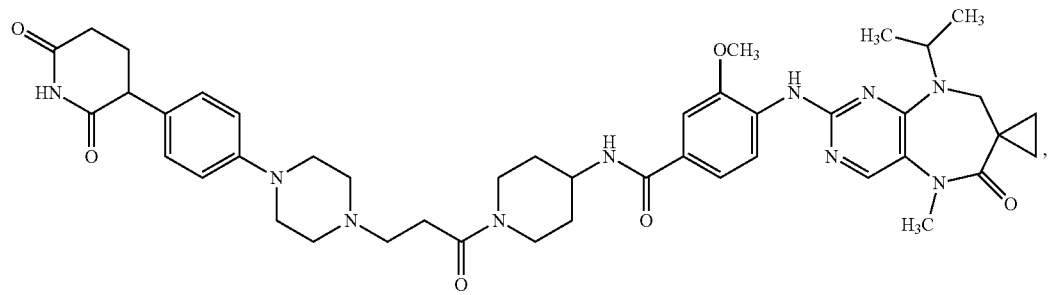
3
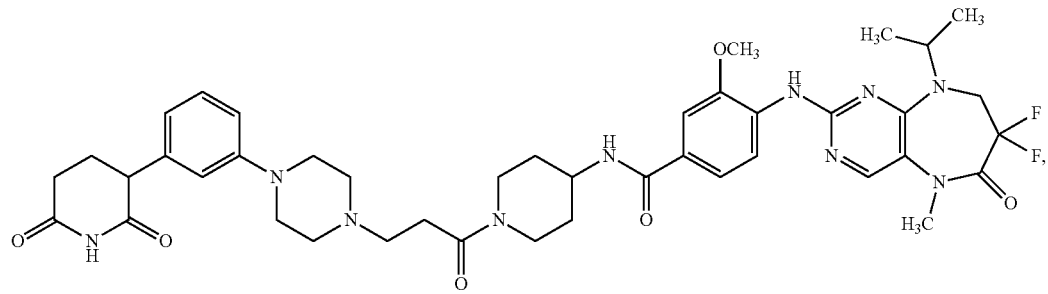
4
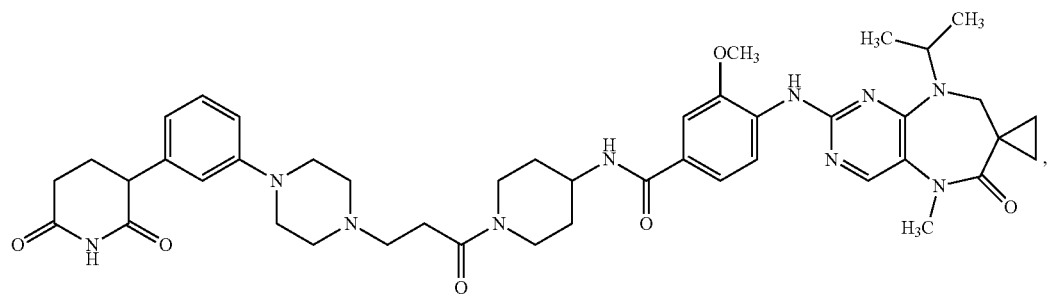
5

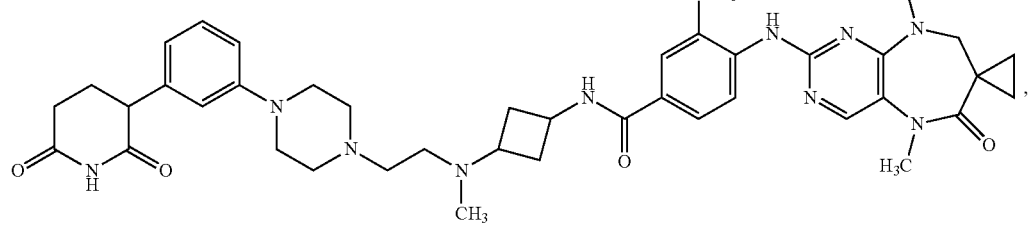
6
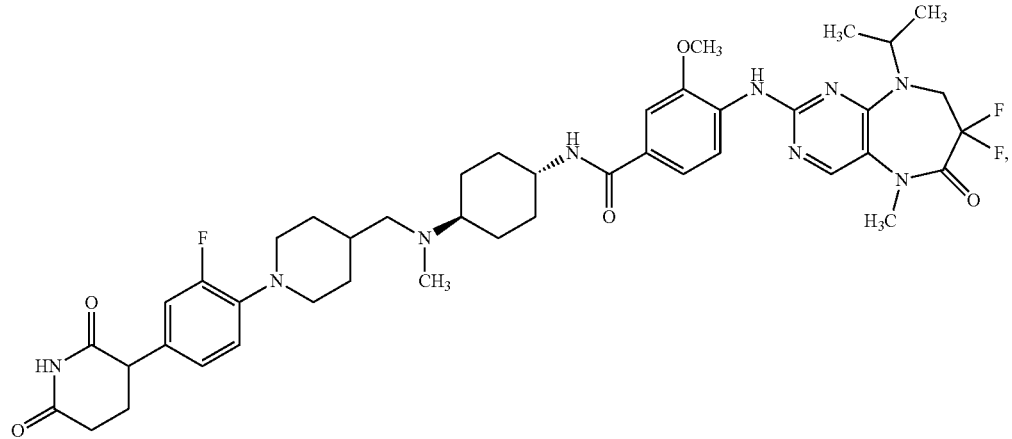
7
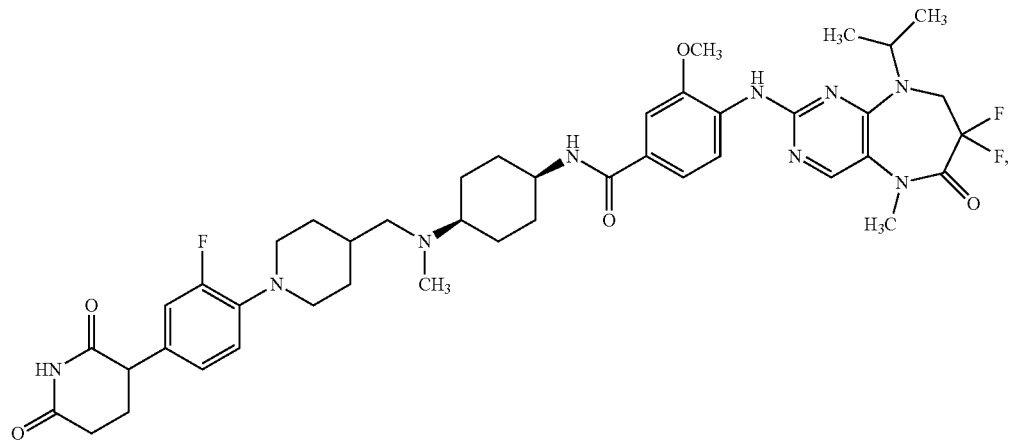
8
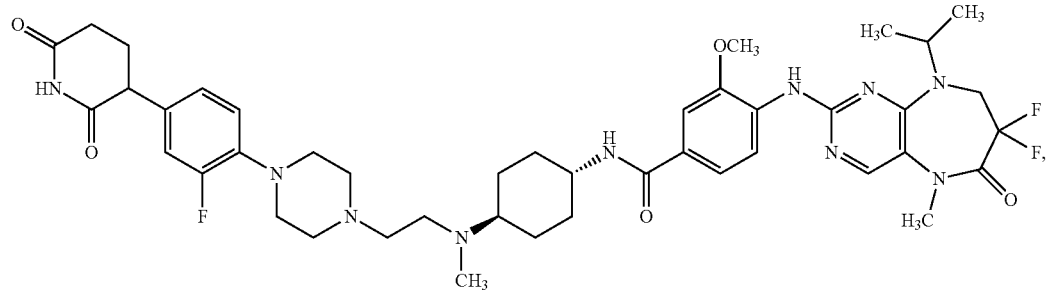
9

-continued
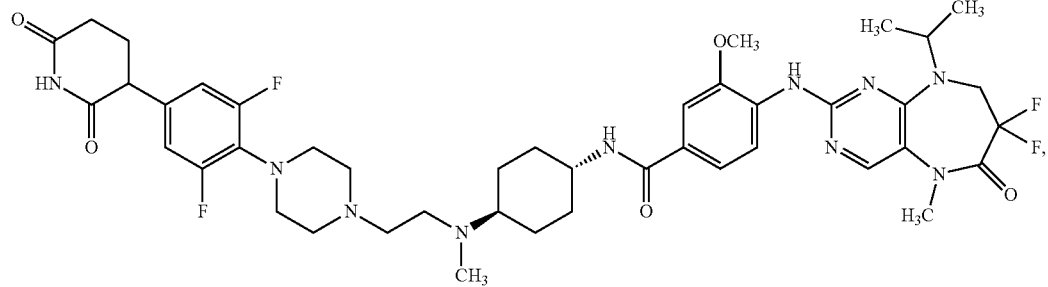
10
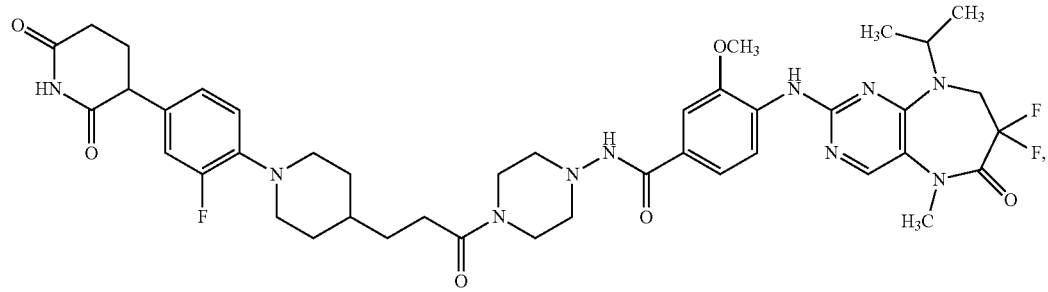
11
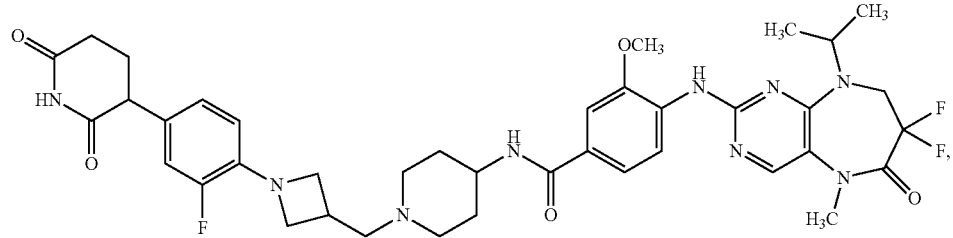
12
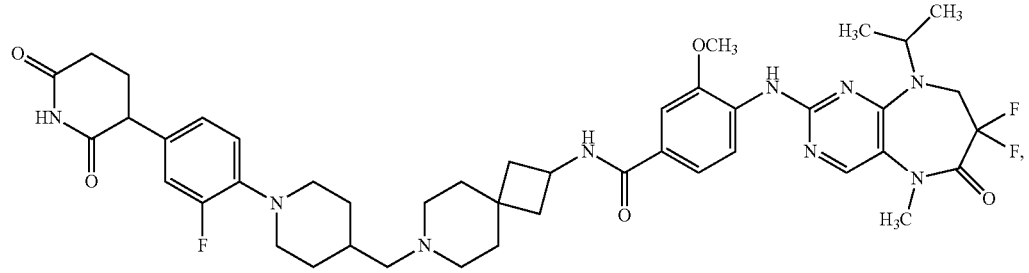
13
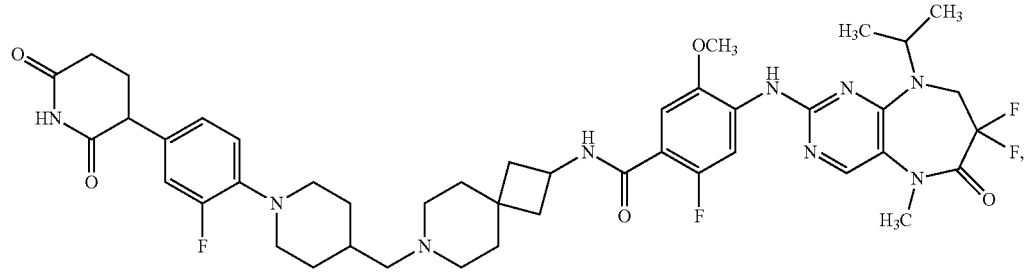
14

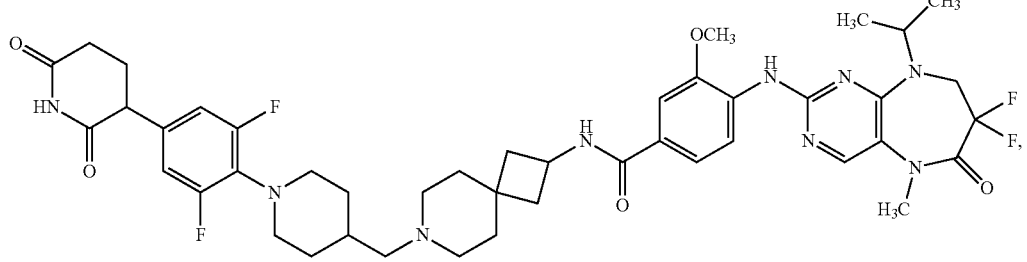
15
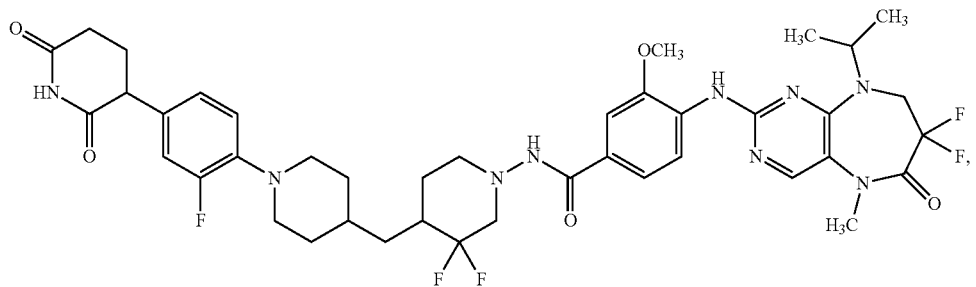
16
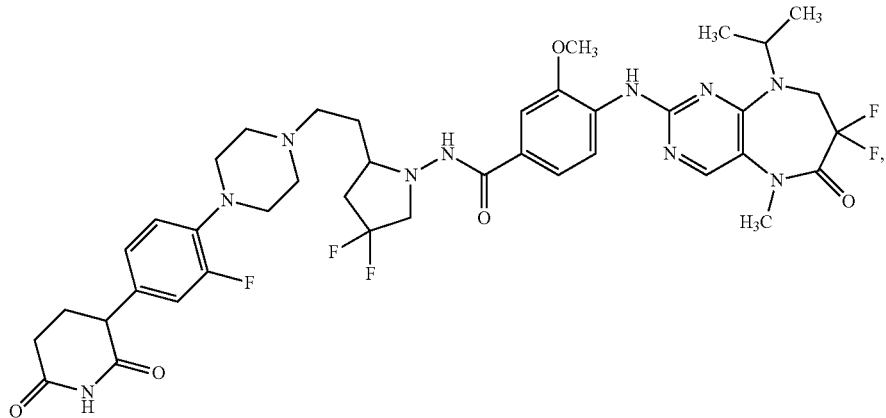
17
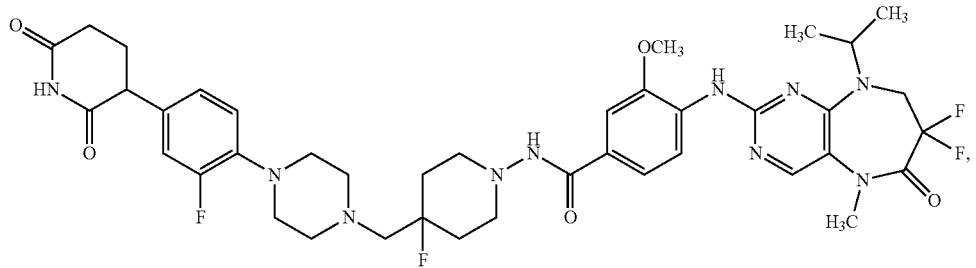
18
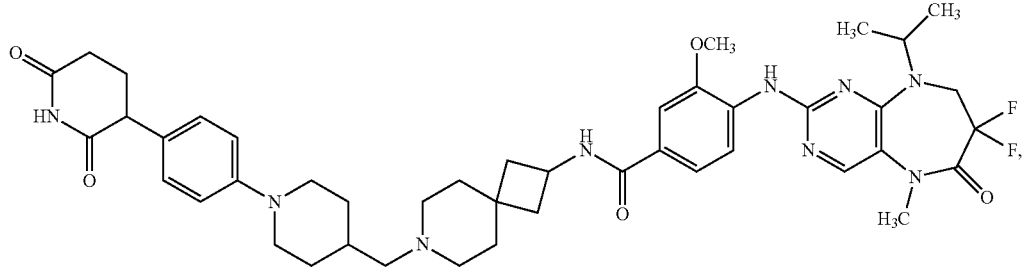
19

-continued
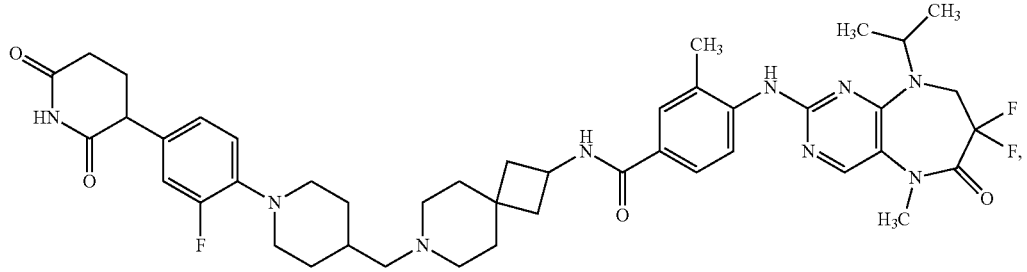
20
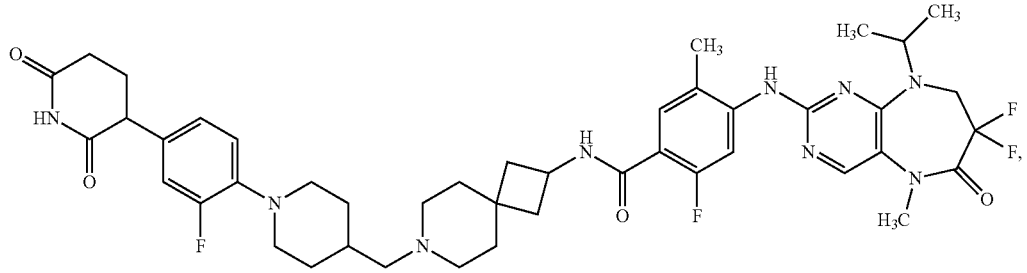
21
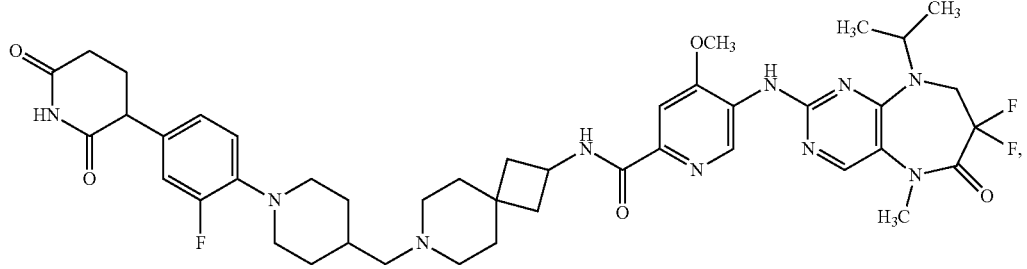
22
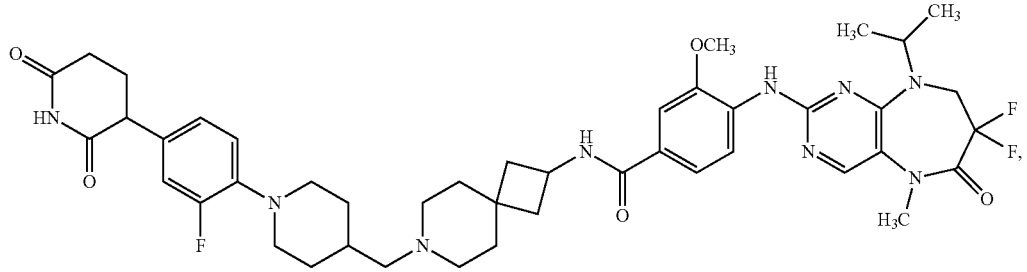
23
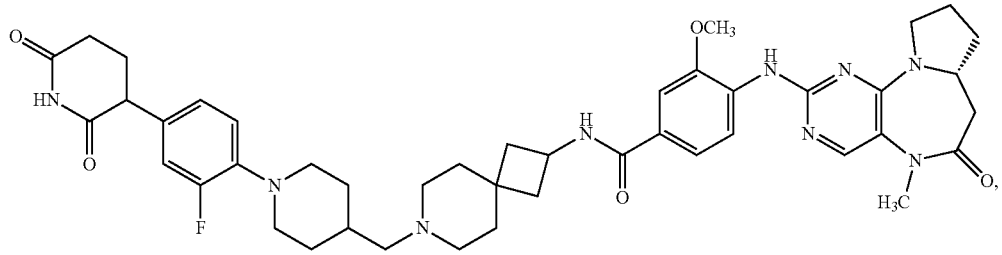
24

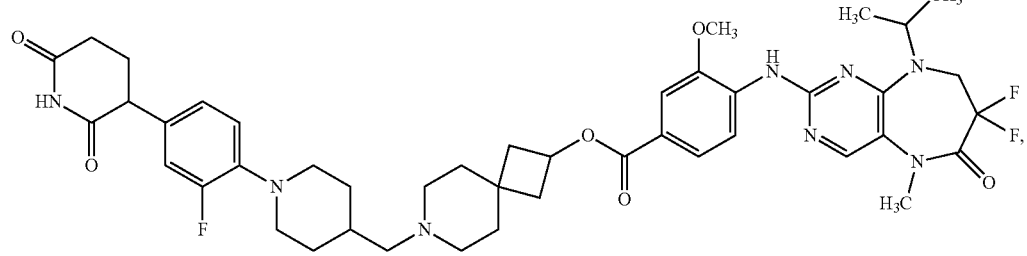
25
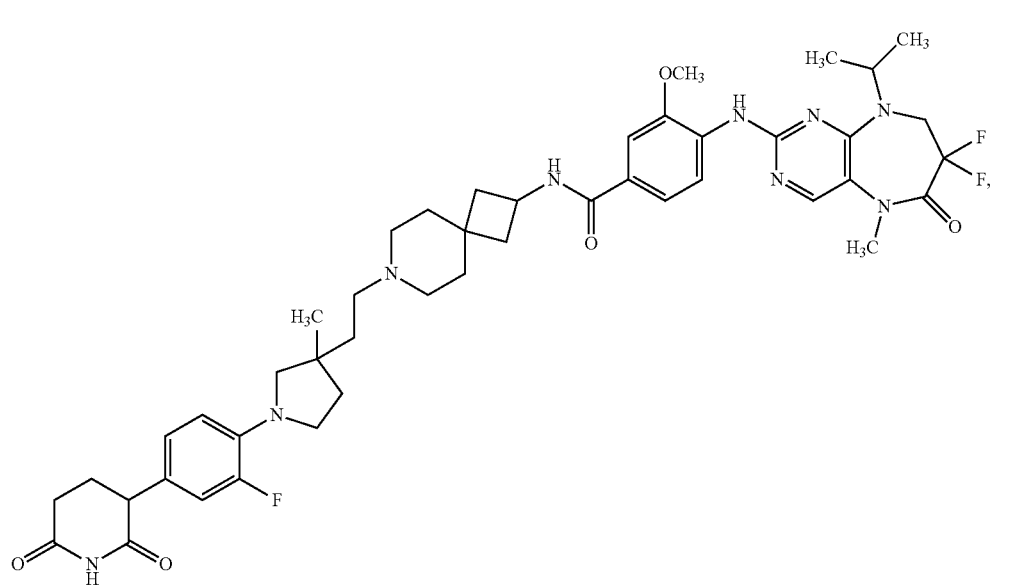
26
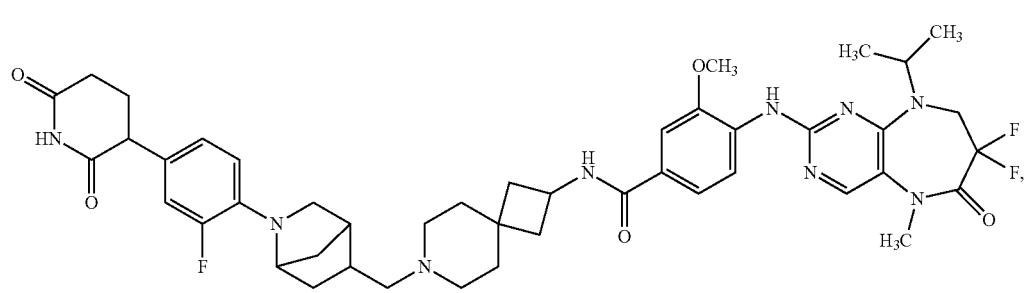
27
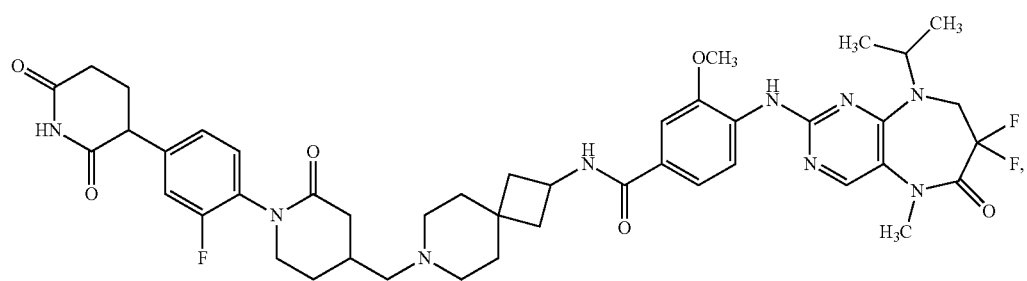
28

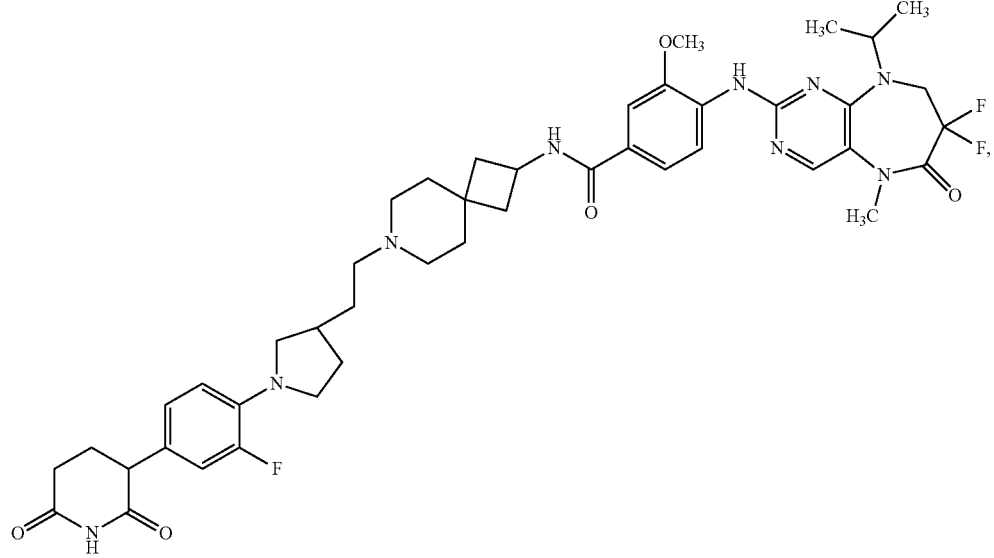
29
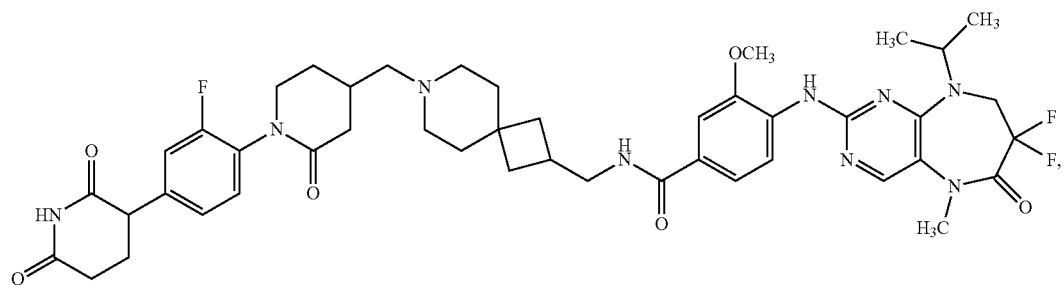
30
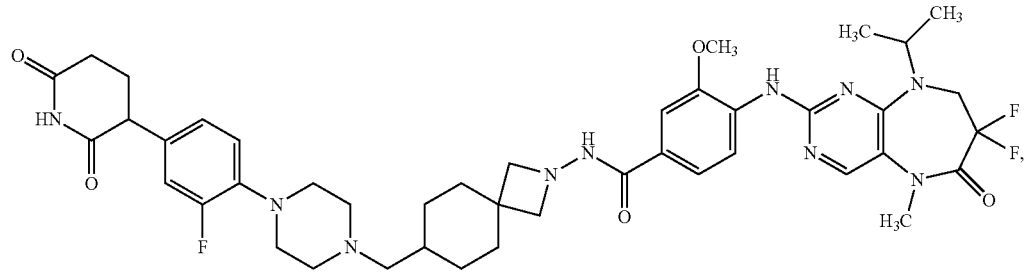
31
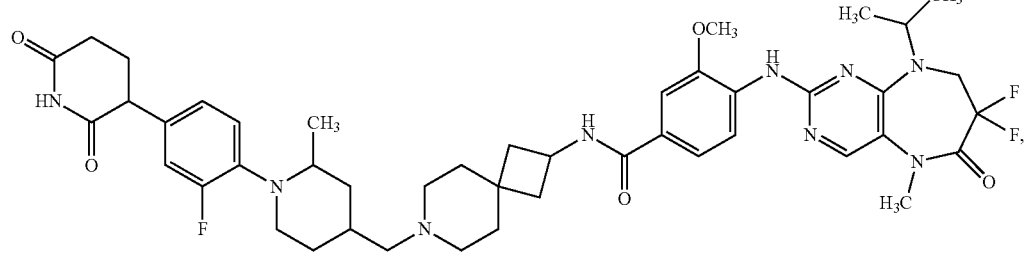
32

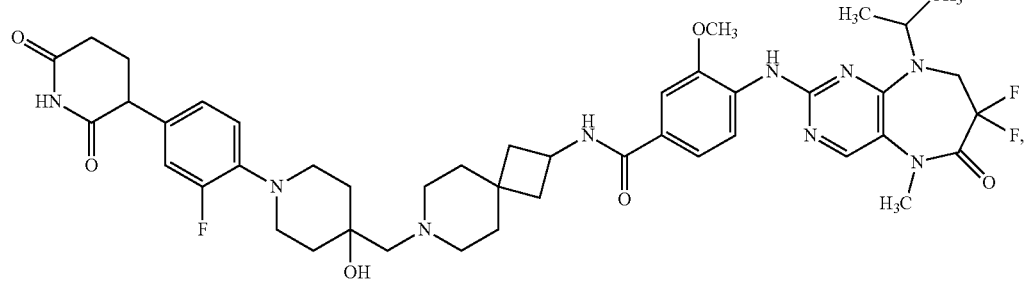
33
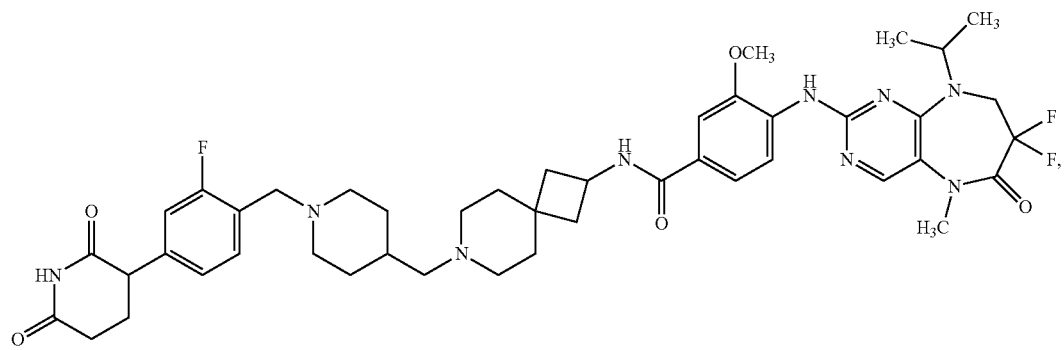
34
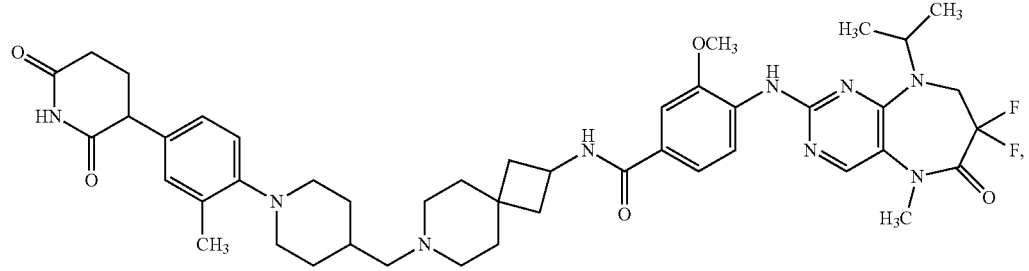
35
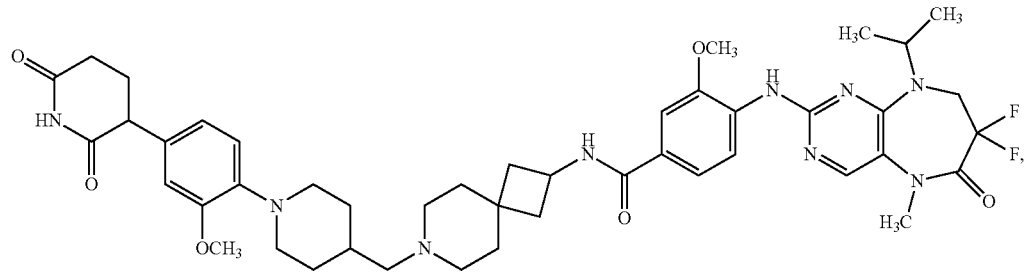
36
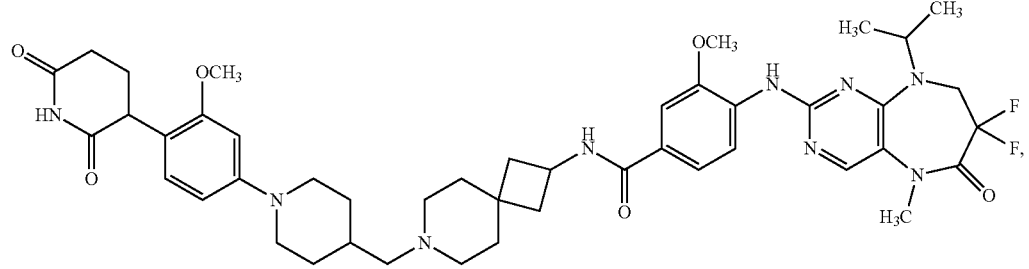
37

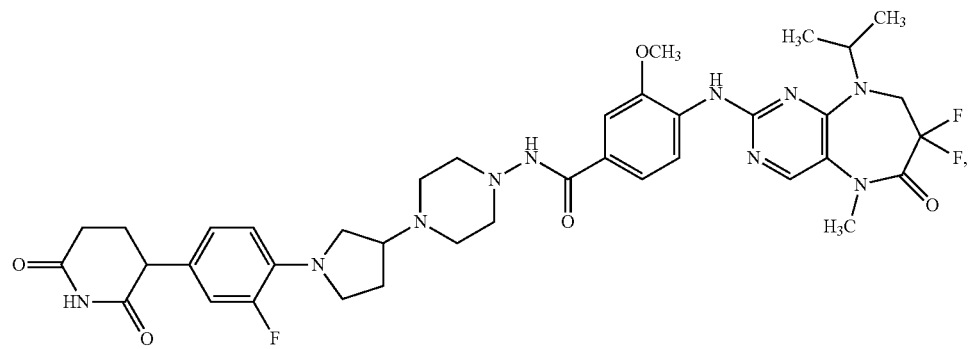
38
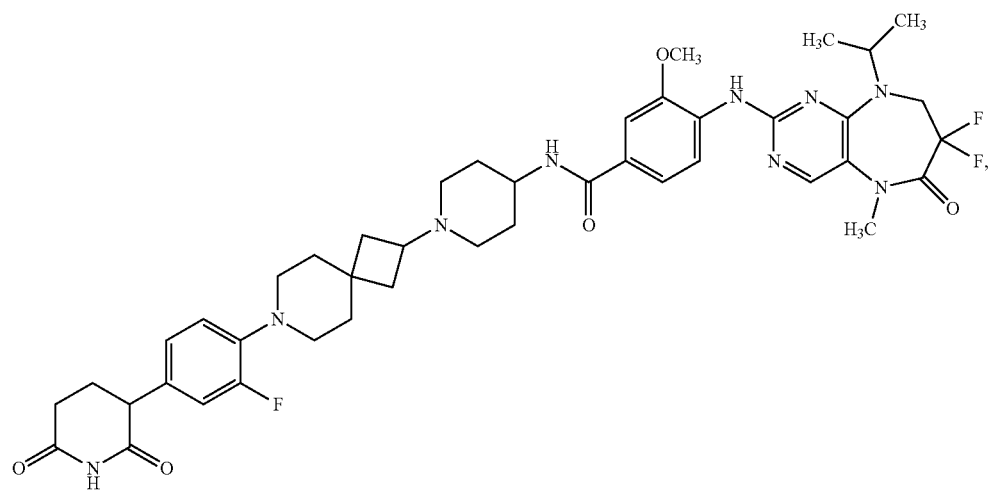
39
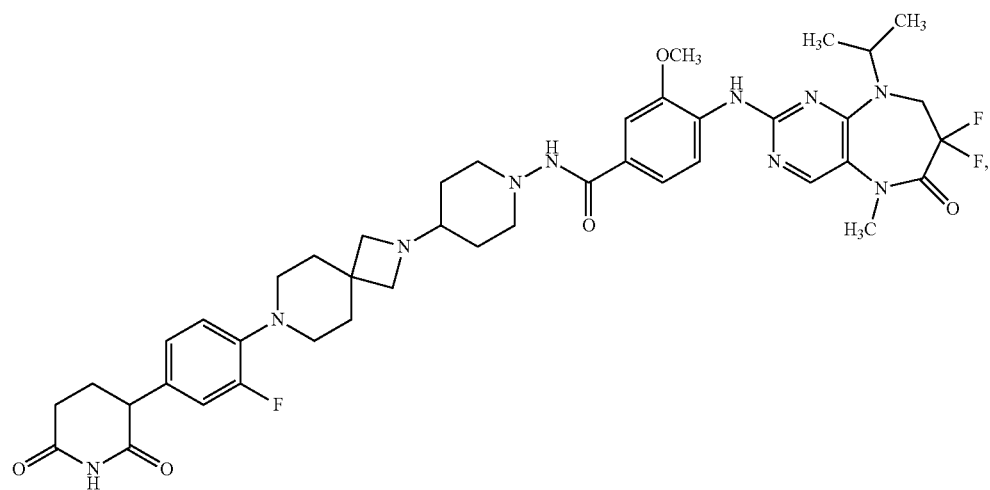
40

41
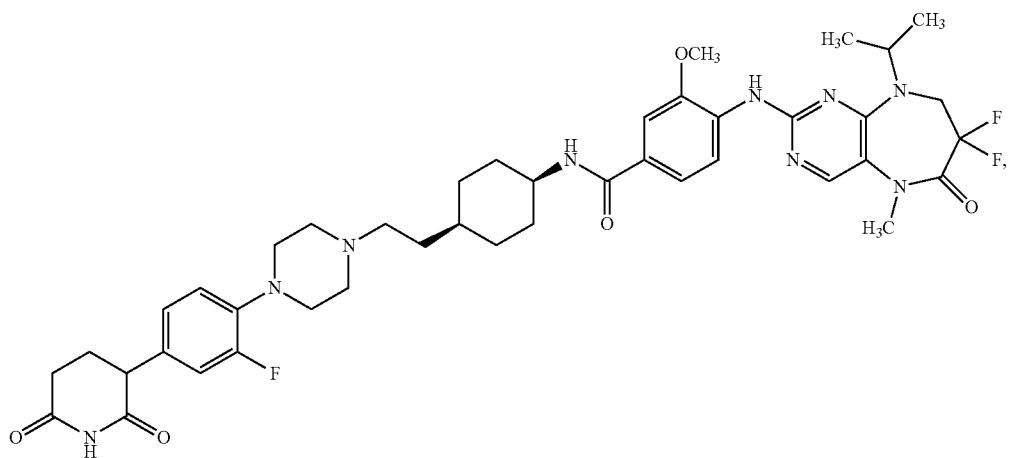
42
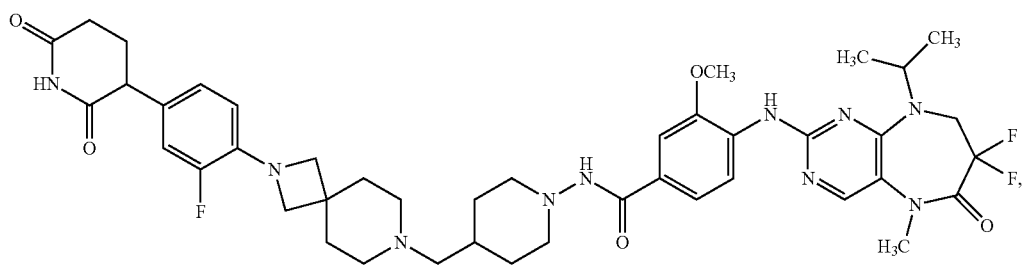
43
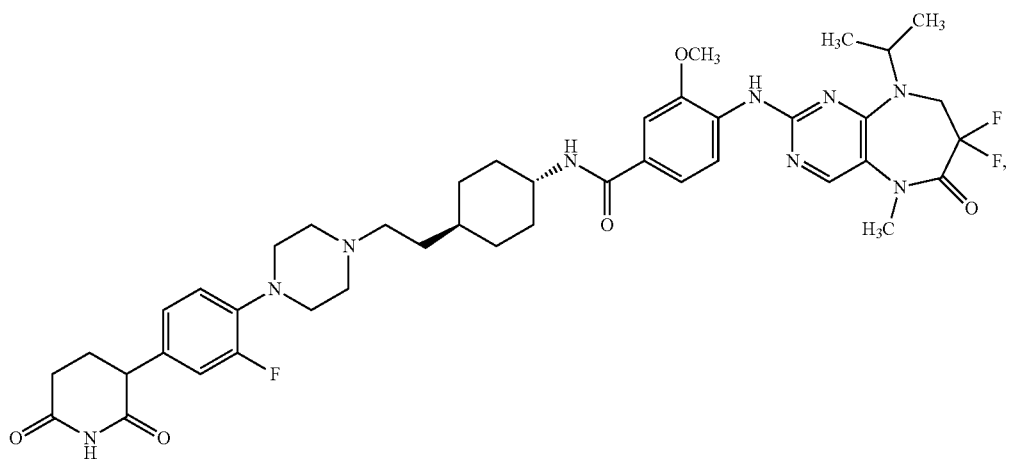
44
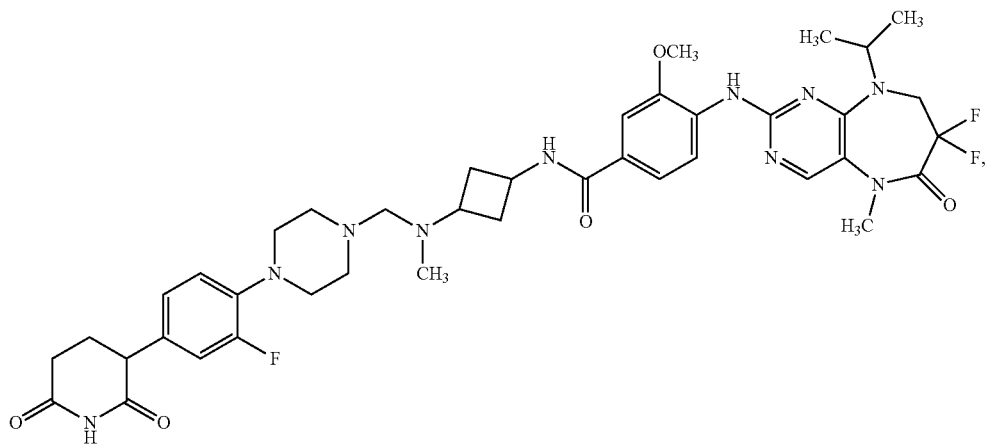

45
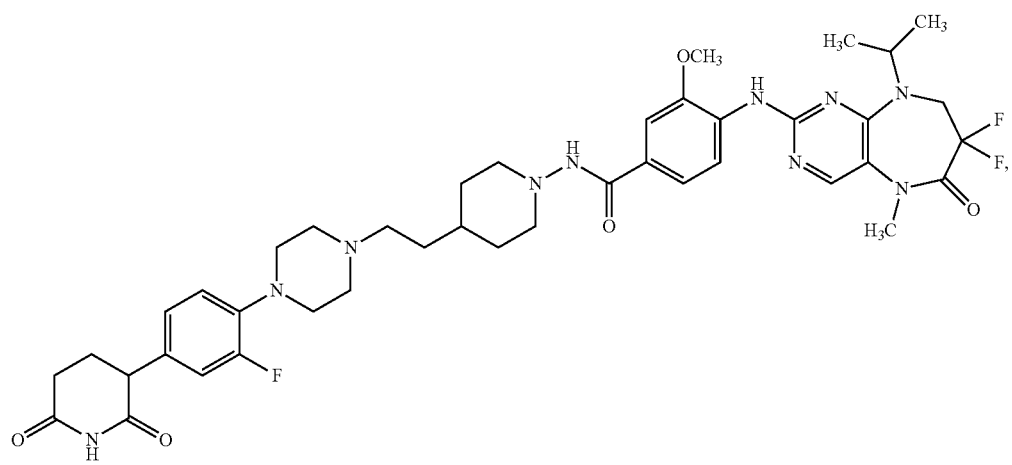
46
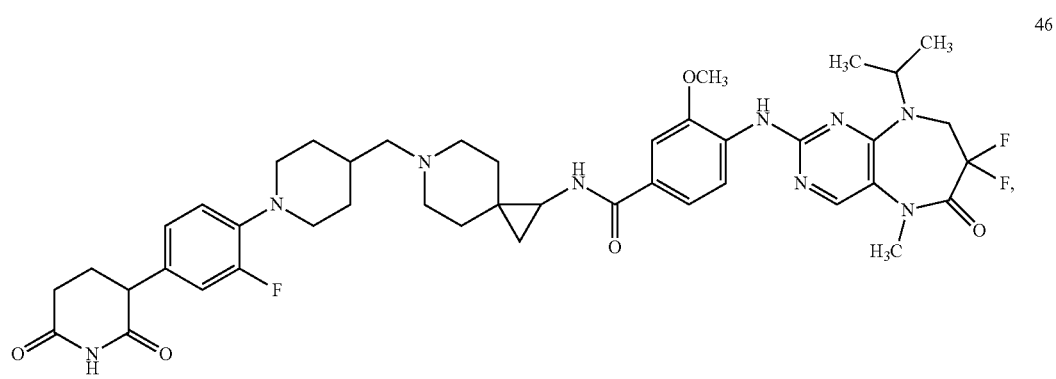
47
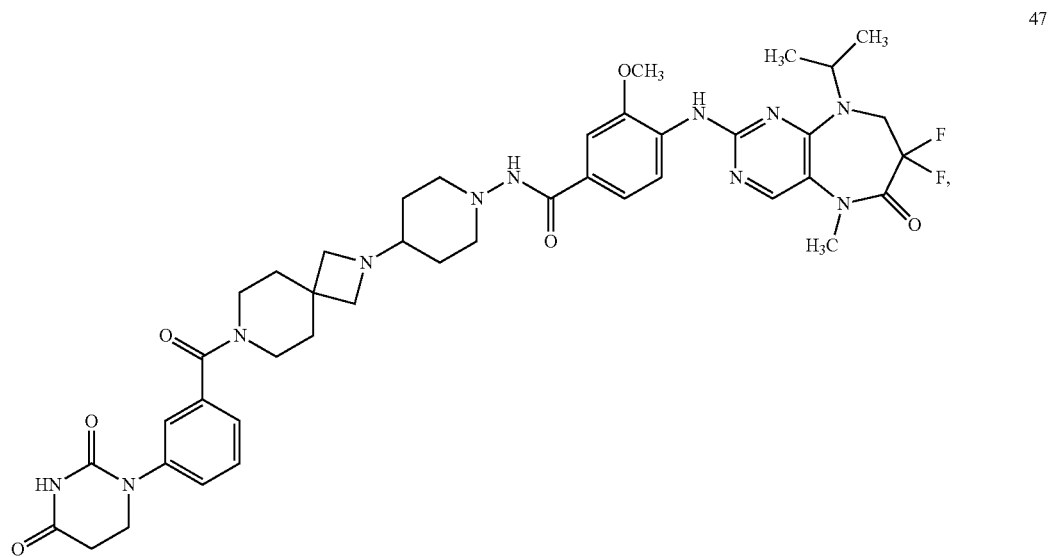

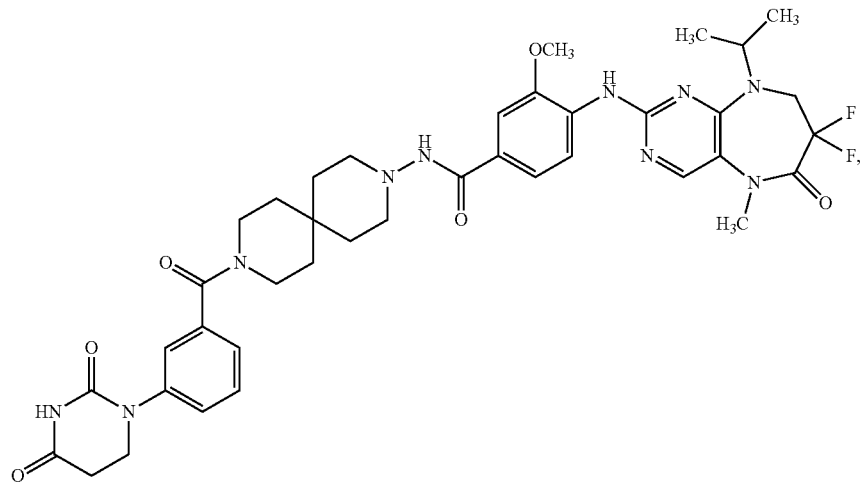
48
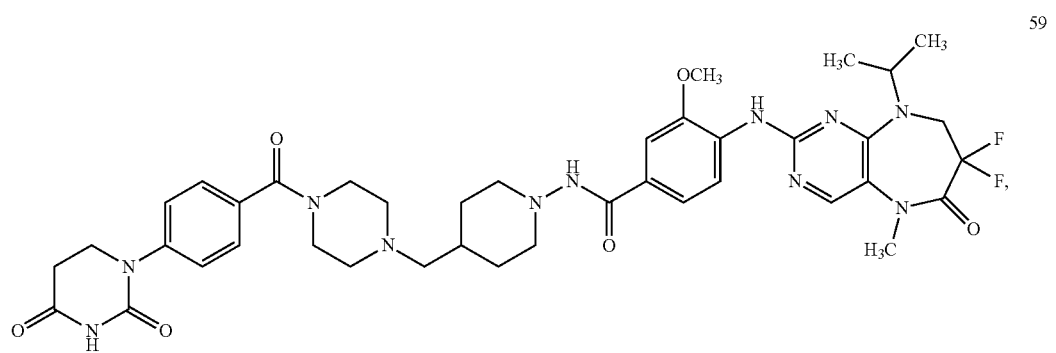
59
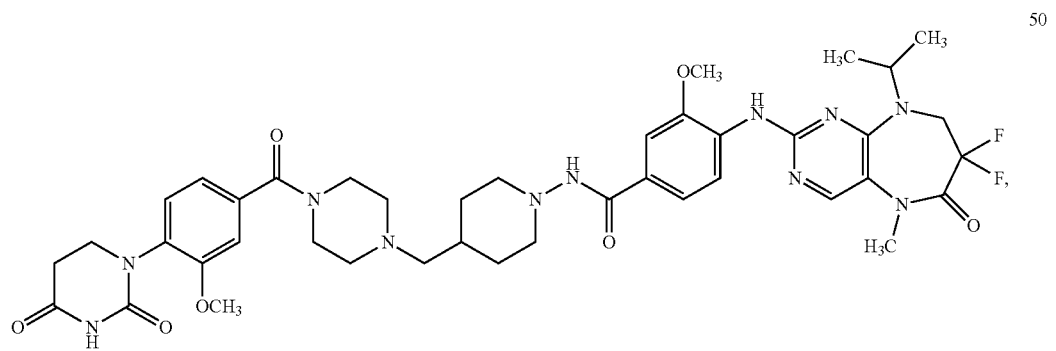
50
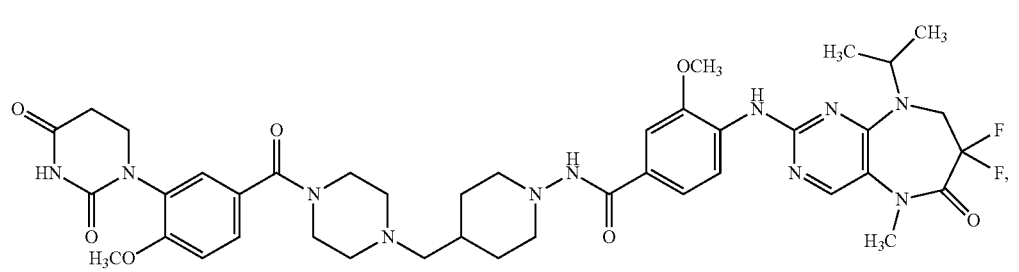
51

52
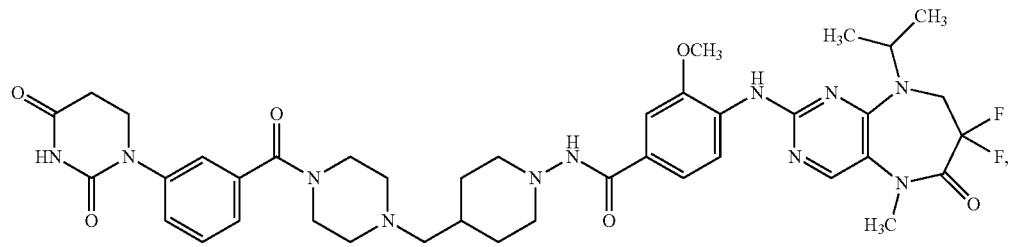
53
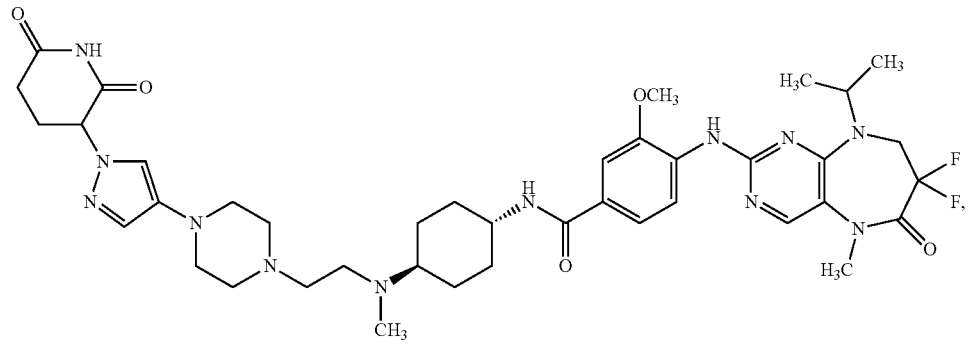
54
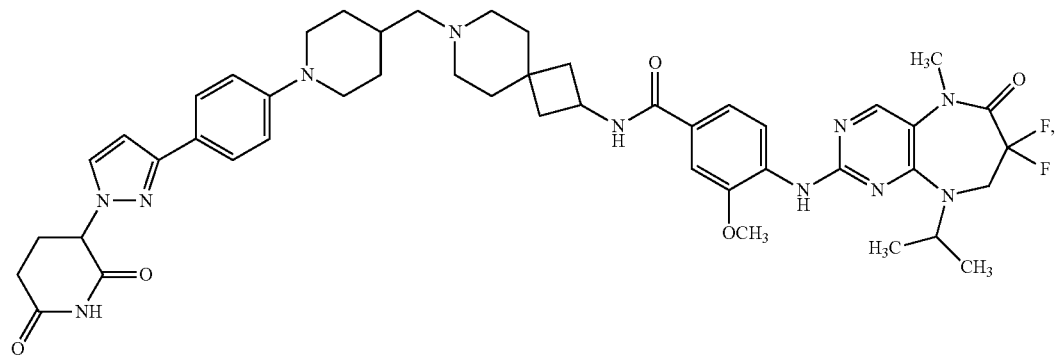
55
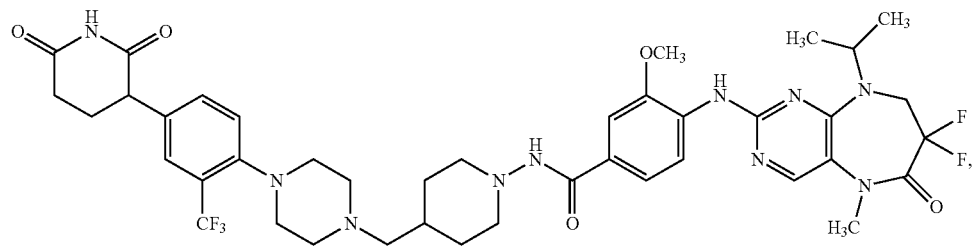
56
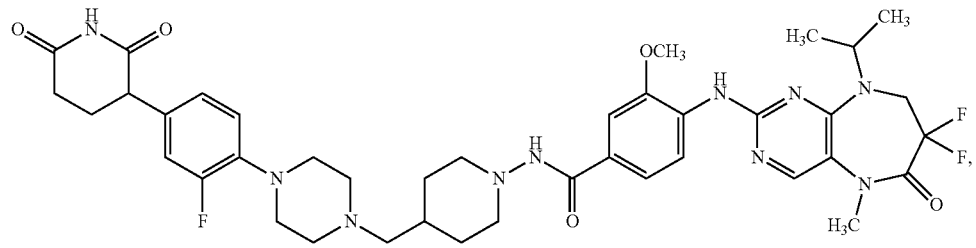

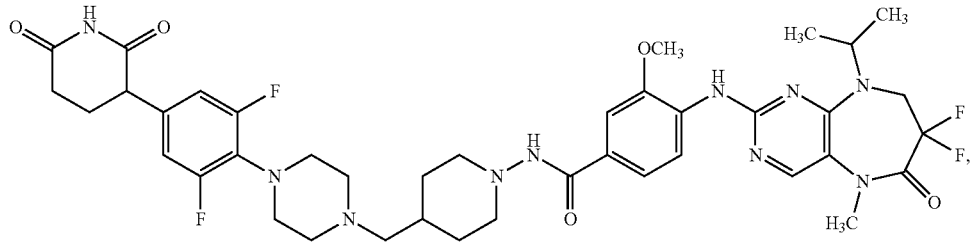

57

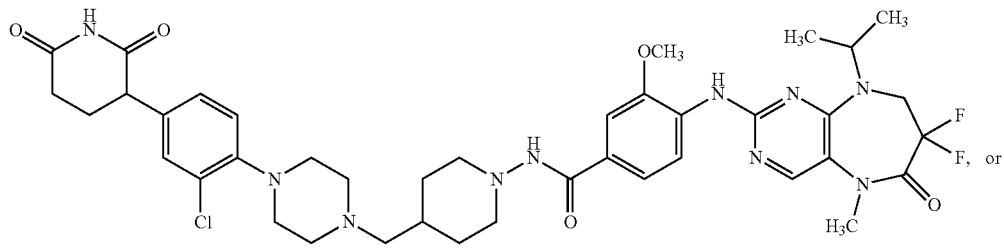

58

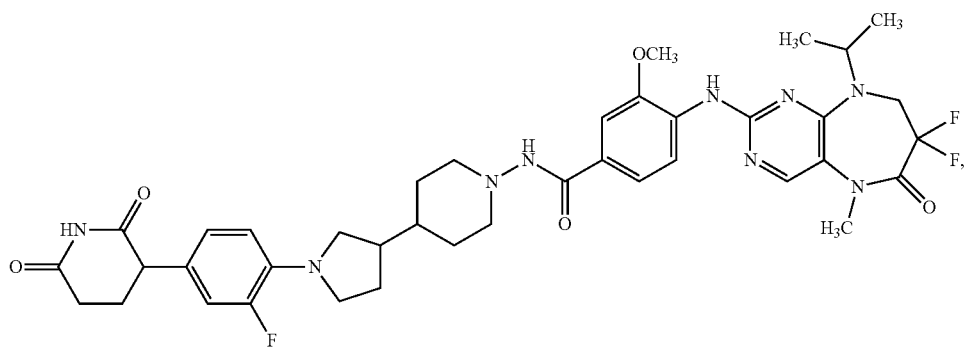

59 or a pharmaceutically acceptable salt thereof.

8. A pharmaceutical composition comprising a pharmaceutically acceptable carrier and a compound according to claim 1, or a pharmaceutically acceptable salt or stereoisomer thereof.

9. A method for inducing polo-like kinase 1 (PLK1) degradation in a subject, wherein the method comprises administering to the subject in need thereof a therapeutically effective amount of the pharmaceutical composition according to claim 8.

10. The method according to claim 9, wherein the subject has a PLK1-related disease selected from a benign tumor, a cancer, or a neurological disorder.

11. The method according to claim 10, wherein the benign tumor or the cancer is selected from acute leukemia, adrenal cancer, adrenocorticoid tumor, anal muscle cancer, Barrett's esophagus, bladder cancer, blood cancer, bone cancer, brain cancer, breast cancer, breast cyst, breast fibroadenoma, cervical cancer, cholangiocarcinoma, chronic leukemia, colon adenoma, colon cancer, colon polyp, colorectal cancer, endocrine cancer, endometrial cancer, esophageal cancer, gastric cancer, gastrointestinal cancer, glioblastoma, glioma, head and neck cancer, hepatocellular carcinoma, intraocular melanoma, kidney cancer, large cell lymphoma, liver cancer, liver tumor, lung adenocarcinoma, lymphocytic lymphoma, monoclonal gammopathy of undetermined significance (MGUS), monoclonal lymphocytosis, neuroblastoma, neuroendocrine cancer, neuroendocrine tumor, non-small cell lung cancer, osteosarcoma, ovarian cancer, pancreatic cancer, parathyroid cancer, peritoneal cancer, prostate cancer, rectal cancer, salivary gland cancer, skin cancer, skin melanoma, small cell lung cancer, small intestine cancer, soft tissue sarcoma, solid tumor, a squamous cell carcinoma, t cell leukemia, t cell lymphoma, thyroid cancer, urethral cancer, uterine cancer, or vulvar cancer, or a combination thereof.

12. The method according to claim 11, wherein the squamous cell carcinoma is lung squamous cell carcinoma.

13. The method according to claim 10, wherein the neurological disorder is selected from Alzheimer's disease, an axonal degeneration-related disorder following brain injury, an axonal degeneration-related disorder following spinal cord injury, a central nervous system disease, epilepsy, Huntington's disease, Lou Gehrig's disease, multiple sclerosis, nerve damage, a neurodegenerative disease, Parkinson's disease, senile dementia, or stroke, or a combination thereof.

* * * * *